US011993605B2

(12) United States Patent
Mohamed et al.

(10) Patent No.: US 11,993,605 B2
(45) Date of Patent: *May 28, 2024

(54) PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

(71) Applicant: AbbVie Inc., North Chicago, IL (US)

(72) Inventors: Mohamed-Eslam F. Mohamed, Gurnee, IL (US); Ahmed A. Othman, Libertyville, IL (US); Ben Klünder, Ludwigshafen (DE); Aileen L. Pangan, La Grange, IL (US); Jaclyn Kay Anderson, Gurnee, IL (US); Jeffrey W. Voss, Hudson, MA (US); Robert J. Padley, Highland Park, IL (US); Heidi S. Camp, Winnetka, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/176,664

(22) Filed: Mar. 1, 2023

(65) Prior Publication Data

US 2023/0312594 A1 Oct. 5, 2023

Related U.S. Application Data

(63) Continuation of application No. 18/093,222, filed on Jan. 4, 2023, which is a continuation of application No. 17/668,249, filed on Feb. 9, 2022, now abandoned, which is a continuation of application No. 17/527,717, filed on Nov. 16, 2021, now Pat. No. 11,365,198, which is a continuation-in-part of application No. 17/184,194, filed on Feb. 24, 2021, now abandoned, which is a continuation of application No. 16/656,237, filed on Oct. 17, 2019, now abandoned, which is a continuation of application No. 15/891,012, filed on Feb. 7, 2018, now abandoned, which is a continuation of application No. 15/295,561, filed on Oct. 17, 2016, now abandoned, said application No. 17/527,717 is a continuation-in-part of application No. 17/039,470, filed on Sep. 30, 2020, now abandoned.

(60) Provisional application No. 62/352,380, filed on Jun. 20, 2016, provisional application No. 62/301,537, filed on Feb. 29, 2016, provisional application No. 62/267,672, filed on Dec. 15, 2015, provisional application No. 62/242,797, filed on Oct. 16, 2015, provisional application No. 63/032,042, filed on May 29, 2020, provisional application No. 62/968,849, filed on Jan. 31, 2020, provisional application No. 62/927,548, filed on Oct. 29, 2019, provisional application No. 62/908,163, filed on Sep. 30, 2019.

(51) Int. Cl.
| | | |
|---|---|---|
| A61K 31/4985 | (2006.01) | |
| A61K 9/00 | (2006.01) | |
| A61K 47/12 | (2006.01) | |
| A61K 47/38 | (2006.01) | |
| C07D 487/14 | (2006.01) | |

(52) U.S. Cl.
CPC .......... *C07D 487/14* (2013.01); *A61K 9/0053* (2013.01); *A61K 31/4985* (2013.01); *A61K 47/12* (2013.01); *A61K 47/38* (2013.01); *C07B 2200/13* (2013.01)

(58) Field of Classification Search
CPC ............... C07D 487/14; A61K 9/0053; A61K 31/4985; A61K 47/12; A61K 47/38; C07B 2200/13
USPC ....................................................... 544/345
See application file for complete search history.

(56) References Cited

U.S. PATENT DOCUMENTS

| | | |
|---|---|---|
| 3,663,559 A | 5/1972 | Antoon et al. |
| 3,929,992 A | 12/1975 | Sehgal et al. |
| 4,053,474 A | 10/1977 | Treuner et al. |
| 5,212,310 A | 5/1993 | Thurkauf et al. |
| 5,266,698 A | 11/1993 | Shaw et al. |
| 5,521,173 A | 5/1996 | Venkatesan et al. |
| 5,605,690 A | 2/1997 | Jacobs et al. |
| 5,693,801 A | 12/1997 | Shaw et al. |
| 5,703,244 A | 12/1997 | Li et al. |
| 5,733,905 A | 3/1998 | Albright et al. |
| 5,736,540 A | 4/1998 | Albright et al. |
| 5,753,648 A | 5/1998 | Albright et al. |
| 5,763,137 A | 6/1998 | Deprez et al. |
| 5,840,888 A | 11/1998 | Shaw et al. |
| 5,990,109 A | 11/1999 | Chen et al. |

(Continued)

FOREIGN PATENT DOCUMENTS

| | | |
|---|---|---|
| CA | 2675288 A1 | 7/2008 |
| CN | 1762333 A | 4/2006 |

(Continued)

OTHER PUBLICATIONS

Song et al., "Treatment of active ankylosing spondylitis with abatacept: an open-label, 24-week pilot study," Annals of Rheumatic Diseases, 70(6): 1108-1110 (2011).

(Continued)

*Primary Examiner* — Kristin A Vajda
(74) *Attorney, Agent, or Firm* — WOMBLE BOND DICKINSON (US) LLP; Danielle L. Herritt; Scott R. Breining

(57) ABSTRACT

The present disclosure relates to processes for preparing (3S,4R)-3-ethyl-4-3H-imidazo[1,2-a]pyrrolo[2,3-e]pyrazin-8-yl)-N-(2,2,2-trifluoroethyl)pyrrolidine-1-carboxamide, solid state forms thereof, and corresponding pharmaceutical compositions, methods of treatment (including treatment of rheumatoid arthritis, ankylosing spondylitis, and psoriatic arthritis), kits, methods of synthesis, and products-by-process.

24 Claims, 88 Drawing Sheets

(56) References Cited

U.S. PATENT DOCUMENTS

| | | |
|---|---|---|
| 6,090,382 A | 7/2000 | Salfeld et al. |
| 6,120,778 A | 9/2000 | Simonnet |
| 6,245,801 B1 | 6/2001 | Bryans et al. |
| 6,262,241 B1 | 7/2001 | Cook et al. |
| 6,653,471 B2 | 11/2003 | Yohannes et al. |
| 6,949,562 B2 | 9/2005 | Yohannes et al. |
| 7,169,926 B1 | 1/2007 | Burgess et al. |
| 7,452,981 B2 | 11/2008 | Wijdenes et al. |
| 7,593,820 B2 | 9/2009 | Wilks et al. |
| 7,772,231 B2 | 8/2010 | Sheppard et al. |
| 7,834,024 B2 | 11/2010 | Li et al. |
| 7,902,197 B2 | 3/2011 | Elworthy et al. |
| 8,039,009 B2 | 10/2011 | Rastogi et al. |
| 8,168,624 B2 | 5/2012 | Agarwal et al. |
| 8,361,962 B2 | 1/2013 | Billedeau et al. |
| 8,367,689 B2 | 2/2013 | Bauer et al. |
| 8,426,411 B2 | 4/2013 | Wishart et al. |
| 8,637,529 B2 | 1/2014 | Woller et al. |
| 8,785,639 B2 | 7/2014 | Wishart et al. |
| 8,962,629 B2 | 2/2015 | Wishart et al. |
| 9,011,912 B2 | 4/2015 | Zu et al. |
| 9,365,579 B2 | 6/2016 | Wishart et al. |
| 9,879,018 B2 | 1/2018 | Mulhern et al. |
| 9,879,019 B2 | 1/2018 | Nordstroem et al. |
| 9,951,080 B2 | 4/2018 | Allian et al. |
| 9,963,459 B1 | 5/2018 | Jayanth et al. |
| 10,017,517 B2 | 7/2018 | Borchardt et al. |
| RE47,221 E | 2/2019 | Wishart et al. |
| 10,202,393 B2 | 2/2019 | Jayanth et al. |
| 10,202,394 B2 | 2/2019 | Jayanth et al. |
| 10,344,036 B2 | 7/2019 | Jayanth et al. |
| 10,519,164 B2 | 12/2019 | Jayanth et al. |
| 10,550,126 B2 | 2/2020 | Pangan et al. |
| 10,597,400 B2 | 3/2020 | Othman et al. |
| 10,730,883 B2 | 8/2020 | Allian et al. |
| 10,981,923 B2 | 4/2021 | Allian et al. |
| 10,981,924 B2 | 4/2021 | Jayanth et al. |
| 10,995,095 B2 | 5/2021 | Pangan et al. |
| 11,186,584 B2 | 11/2021 | Allian et al. |
| 11,198,697 B1 | 12/2021 | Allian et al. |
| 11,365,198 B2 | 6/2022 | Mohamed et al. |
| 11,512,092 B2 | 11/2022 | Allian et al. |
| 11,524,964 B2 | 12/2022 | Mohamed et al. |
| 11,535,624 B2 | 12/2022 | Othman et al. |
| 11,535,625 B2 | 12/2022 | Pangan et al. |
| 11,535,626 B2 | 12/2022 | Pangan et al. |
| 11,564,922 B2 | 1/2023 | Pangan et al. |
| 2003/0078277 A1 | 4/2003 | Hibi et al. |
| 2004/0023992 A1 | 2/2004 | Das et al. |
| 2005/0176796 A1 | 8/2005 | D'Alessio et al. |
| 2006/0160806 A1 | 7/2006 | Haviv et al. |
| 2006/0183758 A1 | 8/2006 | Beard et al. |
| 2006/0183779 A1 | 8/2006 | Brauns et al. |
| 2007/0232653 A1 | 10/2007 | Bachmann et al. |
| 2008/0070914 A1 | 3/2008 | Freyne et al. |
| 2009/0215724 A1 | 8/2009 | Dubois et al. |
| 2009/0215750 A1 | 8/2009 | Bamberg et al. |
| 2009/0215788 A1 | 8/2009 | Elworthy et al. |
| 2009/0264399 A1 | 10/2009 | Inoue et al. |
| 2009/0312338 A1 | 12/2009 | Wishart et al. |
| 2011/0021425 A1 | 1/2011 | Billedeau et al. |
| 2011/0190489 A1 | 8/2011 | Wishart et al. |
| 2011/0224190 A1 | 9/2011 | Huang et al. |
| 2011/0311474 A1 | 12/2011 | Wishart et al. |
| 2012/0015963 A1 | 1/2012 | Woller et al. |
| 2012/0034250 A1 | 2/2012 | Shirakami et al. |
| 2012/0330012 A1 | 12/2012 | Frank et al. |
| 2013/0072470 A1 | 3/2013 | Wishart et al. |
| 2013/0216497 A1 | 8/2013 | Wishart et al. |
| 2013/0295189 A1 | 11/2013 | Maier et al. |
| 2014/0140944 A1 | 5/2014 | Duccini et al. |
| 2014/0243312 A1 | 8/2014 | Brown et al. |
| 2014/0271842 A1 | 9/2014 | Herbig et al. |
| 2015/0118229 A1 | 4/2015 | Voss et al. |
| 2015/0210708 A1 | 7/2015 | Wishart et al. |
| 2016/0222020 A1 | 8/2016 | Wishart et al. |
| 2016/0326181 A1 | 11/2016 | Wishart et al. |
| 2017/0129902 A1 | 5/2017 | Allian et al. |
| 2017/0266289 A1 | 9/2017 | Lipari et al. |
| 2018/0057502 A1 | 3/2018 | Allian et al. |
| 2018/0162865 A1 | 6/2018 | Borchardt et al. |
| 2018/0186805 A1 | 7/2018 | Jayanth et al. |
| 2018/0291029 A1 | 10/2018 | Wishart et al. |
| 2018/0298016 A1 | 10/2018 | Pangan et al. |
| 2019/0023714 A1 | 1/2019 | Ayman et al. |
| 2019/0046527 A1 | 2/2019 | Thakkar et al. |
| 2020/0291040 A1 | 9/2020 | Allian et al. |
| 2021/0061813 A1 | 3/2021 | Wishart et al. |
| 2021/0361647 A1 | 11/2021 | Thakkar et al. |
| 2021/0363149 A1 | 11/2021 | Allian et al. |
| 2022/0233527 A1 | 7/2022 | Machado De Lacerda et al. |
| 2022/0281882 A1 | 9/2022 | Allian et al. |

FOREIGN PATENT DOCUMENTS

| | | |
|---|---|---|
| EA | 007415 B1 | 10/2006 |
| EP | 0423805 A2 | 4/1991 |
| EP | 0423805 B1 | 8/2000 |
| EP | 1097709 A2 | 5/2001 |
| EP | 1112253 B1 | 10/2004 |
| EP | 2123651 A1 | 11/2009 |
| EP | 2438909 A1 | 4/2012 |
| GB | 716327 A | 10/1954 |
| RU | 2158127 C2 | 10/2000 |
| RU | 2250904 C2 | 4/2005 |
| WO | 1991/010671 A1 | 7/1991 |
| WO | 199216553 | 10/1992 |
| WO | 1992/022552 A1 | 12/1992 |
| WO | 1993/022314 A1 | 11/1993 |
| WO | 1994/005665 A1 | 3/1994 |
| WO | 1994/011026 A2 | 5/1994 |
| WO | 1994/019351 A1 | 9/1994 |
| WO | 199519970 A1 | 7/1995 |
| WO | 1996/009304 A1 | 3/1996 |
| WO | 9822437 A1 | 5/1998 |
| WO | 9833782 A1 | 8/1998 |
| WO | 1999/045009 A1 | 9/1999 |
| WO | 0015611 A1 | 3/2000 |
| WO | 200015231 A1 | 3/2000 |
| WO | 0031606 A2 | 6/2000 |
| WO | 2003000695 A1 | 1/2003 |
| WO | 2003/031606 A2 | 4/2003 |
| WO | 2004032874 A2 | 4/2004 |
| WO | 2004/065378 A1 | 8/2004 |
| WO | 2004092126 A2 | 10/2004 |
| WO | 2004106293 A2 | 12/2004 |
| WO | 2005035524 A1 | 4/2005 |
| WO | 2005/110410 A2 | 11/2005 |
| WO | 2006002051 A1 | 1/2006 |
| WO | 2006010567 A1 | 2/2006 |
| WO | 2006015124 A2 | 2/2006 |
| WO | 2006058120 A1 | 6/2006 |
| WO | 2006069363 A2 | 6/2006 |
| WO | 2006/074984 A1 | 7/2006 |
| WO | 2006/074985 A1 | 7/2006 |
| WO | 2006107771 A2 | 10/2006 |
| WO | 2006122137 A1 | 11/2006 |
| WO | 2007007919 A2 | 1/2007 |
| WO | 2007/022268 A2 | 2/2007 |
| WO | 2007/035935 A1 | 3/2007 |
| WO | 2007061764 A2 | 5/2007 |
| WO | 2007/077949 A1 | 7/2007 |
| WO | 2007/079164 A2 | 7/2007 |
| WO | 2007143434 A2 | 12/2007 |
| WO | 2008019996 A2 | 2/2008 |
| WO | 2008021369 A2 | 2/2008 |
| WO | 2008/063287 A2 | 5/2008 |
| WO | 2008/084861 A1 | 7/2008 |
| WO | WO 2008/078091 | 7/2008 |
| WO | 2008/094602 A2 | 8/2008 |
| WO | 2008/112695 A2 | 9/2008 |
| WO | 2008121748 A2 | 10/2008 |
| WO | 2008124850 A1 | 10/2008 |
| WO | WO 2008/119792 | 10/2008 |

(56) References Cited

FOREIGN PATENT DOCUMENTS

| | | |
|---|---|---|
| WO | 2008135090 A1 | 11/2008 |
| WO | 2008139293 A1 | 11/2008 |
| WO | 2009/005675 A1 | 1/2009 |
| WO | 2009011705 A1 | 1/2009 |
| WO | WO 2009/047506 | 4/2009 |
| WO | 2009106443 A1 | 9/2009 |
| WO | 2009108827 A1 | 9/2009 |
| WO | 2009/152133 A1 | 12/2009 |
| WO | WO 2009/150240 | 12/2009 |
| WO | 2010003133 A2 | 1/2010 |
| WO | 2010099039 A1 | 9/2010 |
| WO | 2010117796 A2 | 10/2010 |
| WO | WO 2010/119284 | 10/2010 |
| WO | WO 2010/119285 | 10/2010 |
| WO | 201113082 A1 | 2/2011 |
| WO | 2011012540 A1 | 2/2011 |
| WO | 2011068881 A1 | 6/2011 |
| WO | 2011068899 A1 | 6/2011 |
| WO | 2011141791 A2 | 11/2011 |
| WO | 2011156543 A2 | 12/2011 |
| WO | 2012041814 A1 | 4/2012 |
| WO | 2013043826 A1 | 3/2013 |
| WO | 2013178752 A1 | 12/2013 |
| WO | 2014004863 A2 | 1/2014 |
| WO | WO 2014/015107 | 1/2014 |
| WO | WO 2014/128588 | 8/2014 |
| WO | 2014150289 A1 | 9/2014 |
| WO | WO 2014/147526 | 9/2014 |
| WO | WO 2014/174073 | 10/2014 |
| WO | 2015061665 A1 | 4/2015 |
| WO | 2016033308 A1 | 3/2016 |
| WO | 2016198983 A1 | 12/2016 |
| WO | 2017025849 A1 | 2/2017 |
| WO | 2017033093 A1 | 3/2017 |
| WO | 2017066775 A1 | 4/2017 |
| WO | 2017093857 A1 | 6/2017 |
| WO | 2017126488 A1 | 7/2017 |
| WO | 2017143014 A1 | 8/2017 |
| WO | 2018009566 A1 | 1/2018 |
| WO | 2018165581 A1 | 9/2018 |

OTHER PUBLICATIONS

Sornasse et al., "THU0181 Treatment with Upadacitinib Results in the Normalization of Key Pathobiologic Pathways in Patients with Rheumatoid Arthritis: Biomarker Results from the Phase 3 Select-Next and Select-Beyond Studies," Annals of Rheumatic Diseases, 78(Supp2): 365-366 (2019).
Stahl et al., Editors, Handbook of Pharmaceutical Salts: Properties, Selection, and Use (Wiley-VCR, Weinheim, Germany, 2002) (Table of Contents only).
Taylor et al., "Classification criteria for psoriatic arthritis: Development of new criteria from a large international study," Arthritis & Rheumatology, 54(8): 2665-2673 (2006).
Torgutalp et al., "Emerging treatment options for spondyloarthritis," Best Practice & Research Clinical Rheumatology, 32(3): 472-484 (2018).
Van Der Heijde et al., "Limited radiographic progression and sustained reductions in MRI inflammation in patients with axial spondyloarthritis: 4-year imaging outcomes from the RAPID-axSpA phase III randomized trial," Annals of Rheumatic Diseases, 0: 1-8 (2018) doi:10.1136/annrheumdis-2017-212377.
Van Der Heijde et al., "Efficacy and Safety of Upadacitinib in a Randomized Double-Blind, Placebo-Controlled, Multicenter Phase 2/3 Clinical Study of Patients with Active Ankylosing Spondylitis," ACR Meeting Abstract No. 2728. Arthritis Rheumatol., 71(10) (2019).
Van Der Heijde et al., "2016 update of the ASAS-EULAR management recommendations for axial spondyloarthritis," Annals of Rheumatic Diseases, 76(6): 978-991 (2017).
Van Der Heijde et al., "Efficacy and safety of filgotinib, a selective Janus kinase 1 inhibitor, in patients with active ankylosing spondylitis (TORTUGA): results from a randomised, placebo-controlled, phase 2 trial," Lancet, 392(10162): 2378-2387 (2018).
Van Der Heijde et al., "Ixekizumab, an interleukin-17A antagonist in the treatment of ankylosing spondylitis or radiographic axial spondyloarthritis in patients previously untreated with biological disease-modifying anti-rheumatic drugs (COAST-V): 16 week results of a phase 3 randomised, double-blind, active-controlled and placebo-controlled trial," Lancet 392(10163): 2441-2451 (2018).
Van Der Heijde et al., "Proposal of a linear definition of the Bath Ankylosing Spondylitis Metrology Index (BASMI) and comparison with the 2-step and 10-step definitions," Annals of Rheumatic Diseases, 67(4): 489-493 (2008).
Van Der Heijde et al., "Tofacitinib in patients with ankylosing spondylitis: a phase II, 16-week, randomised, placebo-controlled, dose-ranging study," Annals of Rheumatic Diseases, 76(8): 1340-1347 (2017).
Van Der Heijde et al., "Comparison of three methods for calculating the Bath Ankylosing Spondylitis Metrology Index in a randomized placebo-controlled study," Arthritis Care & Research, 64(12): 1919-1922 (2012).
Van Der Linden et al., "Evaluation of diagnostic criteria for ankylosing spondylitis," Arthritis and Rheumatism, 27(4): 361-368 (1984).
Veale et al., "The rationale for Janus kinase inhibitors for the treatment of spondyloarthritis," Rheumatology, 58(2): 197-205 (2019).
Ward et al., "American College of Rheumatology/Spondylitis Association of America/Spondyloarthritis Research and Treatment Network 2015 Recommendations for the Treatment of Ankylosing Spondylitis and Nomadiographic Axial Spondyloarthritis," Arthritis Rheumatol, 68(2): 282-298 (2016).
Zisman et al., "The juvenile psoriatic arthritis cohort in the CARRA registry: clinical characteristics, classification, and outcomes," Journal of Rheumatology, 44(3): 342-351 (2017).
Burmester, et al., "Safety and efficacy of upadacitinib in patients with rheumatoid arthritis and inadequate response to conventional synthetic disease-modifying anti-rheumatic drugs (SELECT-NEXT): a randomised, double-blind, placebo-controlled phase 3 trial," Lancet, 391(10139):2503-2512 (2018).
MedDRA, Medical Dictionary for Regulatory Activities (MedDRA, version 17.1), http://www.meddra.ond (2014).
Menet, C.J., et al., "Progress Toward JAK1-selective Inhibitors," Future Medicinal Chemistry 7(2):203-235, Future Science Ltd., England (2015).
Mikhaleva, M.A. and Mamaev, V.P., "XXXV. 6-Hydroxypyrazolo[3,4-d]Pyrimidines," Khimiya Geterotsiklicheskikh Soedinenii, No. 12, pp. 1696-1699, Latvian Institute of Organic Synthesis, Latvia (1972).
Mohamed, M-E., et al., "Assessment of the Effect of CYP3A Inhibition, CYP Induction, OATP1B Inhibition and Administration of High-Fat Meal on the Pharmacokinetics of the Potent and Selective JAK1 Inhibitor ABT-494," 2015 ACR/ARHP Annual Meeting, Abstract 2751, 2 pages.
Mohamed, M-E., et al., "Pharmacokinetics of ABT-494 with the Once-Daily Extended-Release Tablet Formulation Being Utilized in the Ongoing Rheumatoid Arthritis Phase 3 Trials," 2016 ACR/ARHP Annual Meeting, Abstract No. 1629, 2 pages.
Mohamed, M-E., et al., "Pharmacokinetics, Safety and Tolerability of the Selective JAK1 Inhibitor, ABT-494, in Healthy Volunteers and Subjects with Rheumatoid Arthritis," Annals of the Rheumatic Diseases 74(2):258, Abstract THU0176, BMJ Publishing Group Ltd., (2015).
Mohamed, M-E., et al., "Preferential Inhibition of IL-6 Relative To IL-7 Signaling Pathways by ABT-494: Exposure-Response Analysis of Ex-Vivo Data from Two Phase 1 Clinical Trials and Comparison to Tofacitinib," Annals of the Rheumatic Diseases 75(2):256, Abstract THU0195, BMJ Publishing Group Ltd., England (Jun. 2016).
Mohamed, M-E.F., et al., "Population Pharmacokinetics of ABT-494 in Healthy Subjects and in Subjects With Rheumatoid Arthritis: Combined Analysis of Phase I and II Trials," Clinical Pharmacology & Therapeutics 101(1):S79, Abstract PII-098, John Wiley & Sons, Inc., United States (Feb. 2017).
Mohamed-Eslam, F., et al., "Pharmacokinetics, Safety and Tolerability of ABT-494, a Novel Selective JAK 1 Inhibitor, in Healthy

(56) References Cited

OTHER PUBLICATIONS

Volunteers and Subjects with Rheumatoid Arthritis," Clinical Pharmacokinetics 55(12):1547-1558, Springer International, Switzerland (Jun. 2016).
Nakayamada, S., et al., "Chemical JAK Inhibitors for the Treatment of Rheumatoid Arthritis," Expert Opinion on Pharmacotherapy 17(16):2215-2225, Informa UK Limited, England (Oct. 2016).
Nakayamada, S., et al., "Recent Progress in JAK Inhibitors for the Treatment of Rheumatoid Arthritis," BioDrugs 30(5):407-419, Springer International, Switzerland (Aug. 2016).
Namour, F., "Pharmacokinetics and Pharmacokinetic/Pharmacodynamic Modeling of Filgotinib (GLPG0634), a Selective JAK1 Inhibitor, in Support of Phase IIB Dose Selection," Clinical pharmacokinetics 54(8):859-874, Springer Science+Business Media, Switzerland (2015).
Nayana, M.R.S., et al., "CoMFA and Docking Studies on Triazolopyridine Oxazole Derivatives as p38 MAP Kinase Inhibitors," European Journal of Medicinal Chemistry 43(6):1261-1269, Elsevier Masson SAS, France (2008).
Noble, M.E.M., et al., "Protein Kinase Inhibitors: Insights Into Drug Design From Structure," Science 303(5665):1800-1805, American Association for the Advancement of Science, United States (2004).
Norman, P., "Selective JAK Inhibitors in Development for Rheumatoid Arthritis," Expert Opinion on Investigational Drugs 23(8):1067-1077, Informa UK, Ltd., England (2014).
Olivera, P., et al., "Next Generation of Small Molecules in Inflammatory Bowel Disease," Gut 66(2):199-209, British Medical Assn, England (Feb. 2017).
Paulus, E.F. and Rivo, E., "1-Phenyl-3-carbethoxy-4-hydroxypyrroline," Acta Crystallographica C44:1242-1244, (1988).
Rochais, C., et al., "Synthesis of new dipyrrolo- and furopyrrolopyrazinones related to tripentones and their biological evaluation as potential kinases (CDKs1-5, GSK-3) inhibitors," Eur J Med Chem. 44(2):708-716, Elsevier Masson SAS, France (2009).
Rowe, et al., Editors, "Handbook of Phamlaceutical Excipients," 7th Ed., Pharmaceutical Press, 7 pages, 2012 (Table of Contents).
Rowe, R.C., et al., "Handbook of Pharmaceutical Excipients—7th Edition," Pharmaceutical Development and Technology, 18(2):544, Informa Healthcare USA, Inc., United States (2013).
Sahin, S. and Benet, L.Z., "The Operational Multiple Dosing Half-life: A Key to Defining Drug Accumulation in Patients and to Designing Extended Release Dosage Forms," Pharmaceutical Research 25(12):2869-2877, Kluwer Academic/Plenum Publishers, United States (2008).
Sandborn, W.J., "The Present and Future of Inflammatory Bowel Disease Treatment," Gastroenterology & Hepatology 12(7):438-441, Gastro-Hep Communications, United States (Jul. 2016).
Schram, K.H., et al., "Tricyclic nucleosides I. Synthesis of the new tricyclic ring system tetrazolo[1,5-c]pyrrolo[2,3-d]byrimidine and certain tetrazolo,5-c] pyrrolo[2,3-d] pyrimidine ribonucleosides," Journal of Heterocyclic Chemistry 12:1021-1023, Journal of Heterocyclic Chemistry, United States (1975).
Schwartz, D.M., et al., "Type I/II Cytokines, JAKs, and New Strategies for Treating Autoimmune Diseases," Nature Reviews. Rheumatology 12(1):25-36, Macmillan Publishers Limited, United States (Jan. 2016).
Scott, I.C and Scott, D., "Joint Counts in Inflammatory Arthritis," Clinical and Experimental Rheumatology 32(85):S7-S12, (2014).
Semerano, L., et al., "Developments with Investigational Janus Kinase Inhibitors for Rheumatoid Arthritis," Expert Opinion on Investigational Drugs 25(12):1355-1359, Informa UK Limited, England (Oct. 2016).
Semerano, L., et al., "Novel Immunotherapeutic Avenues for Rheumatoid Arthritis," Trends in Molecular Medicine 22(3):214-229, Elsevier Science Ltd., England (Mar. 2016).
Singh, J.A., et al., "2012 Update of the 2008 American College of Rheumatology Recommendations for the Use of Disease-Modifying Antirheumatic Drugs and Biologic Agents in the Treatment of Rheumatoid Arthritis," Arthritis Care & Research 64(5):625-639, John Wiley & Sons, United States (2012).

Sivaraman, P. and Cohen, S.B., "Malignancy and Janus Kinase Inhibition," Rheumatic Diseases Clinics of North America 43(1):79-93, Elsevier Inc., United States (Feb. 2017).
Smolen, J., et al., "EULAR recommendation for the management of rheumatoid arthritis with synthetic and biological disease-modifying antirheumatic drugs," Annals of the Rheumatic Diseases 69(6):964-975, BMJ, England (2010).
Smolen, J.S., et al., "Eular Reconnnendations for the Management of Rheumatoid Arthritis With Synthetic and Biological Disease-modifying Antirheumatic Drugs: 2013 Update," Annals of the Rheumatic Diseases 73(3):492-509, H.K. Lewis, England (2014).
Solomon, D.H. and Bucala, R.J., "The Enduring Value of Reporting Randomized Controlled Clinical Trials in Arthritis & Rheumatology: 2016 and Beyond," Arthritis & Rheumatology 68(12):2831-2833, American College of Rheumatology, United States (Aug. 2016).
Stahl, et al., Editors "IUPAC Handbook of Pharmaceutical Salts: Properties, Selection, and Use," Wiley-VCH, Weinheim, Geffilany, 5 pages (2002) (Table of Contents).
Stella, V.J., et al., "A Case for Prodrugs," in Prodrugs: Challenges and Rewards Part 1, p. 24, American Association of Pharmaceutical Sciences, United States (2007).
Strand, V., et al., "Sustained Benefit in Rheumatoid Arthritis Following One Course of Rituximab: Improvements in Physical Function Over 2 Years," Rheumatology 45(12):1505-1513, Mercury International, England (2006).
Trost, B.M., et al., "Palladium-catalyzed DYKAT of Vinyl Epoxides: Enantioselective Total Synthesis and Assignment of the Configuration of (+)-Broussonetine G," Angewandte Chemie 42(48):5987-5990, Wiley-VCH, Germany (2003).
Van Epps, S., et al., "Design and synthesis of tricyclic cores for kinase inhibition," Bioorg Med Chem Lett. 23(3):693-698, Elsevier Ltd., England (2013).
Van Vollenhoven, R.F., et al., "THU0178 Relationship Between NK Cell Count and Important Safety Events in Rheumatoid Arthritis Patients Treated with Tofacitinib," Annals of the Rheumatic Diseases 74(2):258-259, H.K. Lewis, England (2015).
Wang, G.T., et al., "Design, Synthesis, and Structural Analysis of Influenza Neuraminidase Inhibitors Containing Pyrrolidine Cores," Journal of Medicinal Chemistry 44(8):1192-1201, American Chemical Society, United States (2001).
Winthrop, K.L., "The Emerging Safety Profile of JAK Inhibitors in Rheumatic Disease," Nature Reviews. Rheumatology 13(4):234-243, Macmillan Publishers Limited, United States (Apr. 2017).
Wolff, M.E., "Some Considerations for Prodrug Design," in Burger's Medicinal Chemistry and Drug Discovery, Fifth Edition, vol. 1: Principles and Practices, pp. 975-977, John Wiley and Sons, United States (1995).
Woodworth, T., et al., "Standardizing Assessment and Reporting of Adverse Effects in Rheumatology Clinical Trials II: the Rheumatology Common Toxicity Criteria V.2.0.," The Journal of Rheumatology 34(6):1401-1414, Journal of Rheumatology Publishing Co, Canada (2007).
Wormser, H. C., "Synthesis of Azabiotin Analogs as Potential Cofactors for Biotin-dependent Enzymes," Journal of Pharmaceutical Sciences 59(12):1732-1737, Elsevier, United States (1970).
Stahl, P.H., et al., Chapters 7, 8, and 10 in Handbook of Pharmaceutical Salts, Stahl, P. H., et al., eds., pp. 161-189, 191-220, 237-247, 330-350, Verlag Helvetica Chimica Acta, Switzerland (2002)
AbbVie Announces Positive Phase 2 Study Results for Upadacitinib (ABT-494), an Investigational JAK1-Selective Inhibitor, in Crohn's Disease (May 9, 2017), accessed at https://news.abbvie.com/news/press-releases/abbvie-announces-positive-phase-2-study-results-for-upadacitinib-abt-494-an-investigational-jak1-selective-inhibitor-in-crohns-disease.htm, accessed on Dec. 18, 2017, 3 pages.
AbbVie's Upadacitinib (ABT-494) Meets All Primary and Ranked Secondary Endpoint in Phase 3 Study in Rheumatoid Arthritis (Jun. 7, 2017), accessed at https://news.abbvie.com/news/abbvies-upadacitinib-abt-494-meets-all-primary-and-ranked-secondary-endpoints-in-phase-3-study-in-rheumatoid arthritis.htm, accessed on Dec. 18, 2017, 4 pages.

(56) References Cited

OTHER PUBLICATIONS

AbbVie's Upadacitinib (ABT-494) Meets All Primary and Ranked Secondary Endpoint in Second Phase 3 Study in Rheumatoid Arthritis (Sep. 11, 2017), accessed at https://news.abbvie.com/alert-topics/immunology/abbvies-upadacitinib-abt-494-meets-all-primary-and-ranked-secondary-endpoints-in-second-phase-3-study-in-rheumatoid-arthritis.htm, accessed on Dec. 18, 2017, 4 pages.

AbbVie's Upadacitinib Granted Breakthrough Therapy Designation from the U.S. Food and Drug Administration for Atopic Dermatitis (Jan. 8, 2018), accessed at https://news.abbvie.com/news/abbvies-upadacitinib-granted-breakthrough-therapy-designation-from-food-and-drug-administration-for-atopic-dermatitis.htm, accessed on Aug. 1, 2018, 2 pages.

Amended Pleadings on Behalf of the Opponent in Opposition to Israel Patent Application 248466, mailed on Mar. 26, 2018, 12 pages.

Annex A—Relative IC50 Values for Compounds of Formula I(c), submitted in European Application No. EP10835061.2-1462, dated Nov. 7, 2014, cited as Document TM3 in Opposition to European Patent EP2506 716, mailed on Feb. 16, 2018, 10 pages.

Product Label: "SEPINEO P 600", XP002744402, accessed at http://gyermedhu/pdf/3664_Leaftet_Sepineo_P600_gb.pdf, accessed on Apr. 2008, pp. 1-2.

Bannister, M.J. and Freeman, S., "Adult-onset Atopic Dermatitis," Australasian Journal of Dermatology 41(4):225-228 (Nov. 2000).

Burmester, G.R., et al., "A Phase 3 Randomized, Placebo-Controlled, Double-Blind Study of Upadacitinib (ABT-494), a Selective JAK-1 Inhibitor, in Patients with Active Rheumatoid Arthritis with Inadequate Response to Conventional Synthetic Dmards," 2017 ACR/ARHP Annual Meeting, Abstract No. 1904, United States, 5 pages (2017).

Chamlin, S.L., et al., "The Price of Pruritus: Sleep Disturbance and Cosleeping in Atopic Dermatitis," Archives of Pediatrics & Adolescent Medicine 159(8):745-750, American Medical Association, United States (Aug. 2005).

Cotter, D.G., et al., "Emerging Therapies for Atopic Dermatitis: JAK Inhibitors," Journal of the American Academy of Dermatology 78(3S1):S53-S62, Mosby, United States (Mar. 2018).

Ellis, C.N., et al., "Understanding and Managing Atopic Dermatitis in Adult Patients," Seminars in Cutaneous Medicine and Surgery 31(3 Suppl):S18-S22, Frontline Medical Communications, United States (Sep. 2012).

Fraser, K.A., American Academy of Dermatology Annual Meeting: San Diego, CA, USA, Feb. 16-20, 2018, American Journal of Clinical Dermatology, vol. 19 (2), pp. 287-290 (Apr. 2018).

Genovese, M.C., "Long-Term Safety and Efficacy of Upadacitinib (ABT-494), an Oral JAK-1 Inhibitor in Patients with Rheumatoid Arthritis in an Open Label Extension Study," 2017 ACR/ARHP Annual Meeting, Abstract No. 509, 4 pages.

Goedken, E.R, et al., "Minimum Significant Ratio of Selectivity Ratios (MSRSR) and Confidence in Ratio of Selectivity Ratios (CRSR): Quantitative Measures for Selectivity Ratios Obtained by Screening Assays," Journal of Biomolecular Screening 17(7):857-867, Sage Publications, United States (Apr. 2012).

Grebien, F., et al., "Stat5 Activation Enables Erythropoiesis in the Absence of EpoR and Jak2," Blood 111(9):4511-4522, American Society of Hematology, United States (May 2008).

Guschin, D., et al., "A Major Role for the Protein Tyrosine Kinase JAL1 in the JAK/STAT Signal Transduction Pathway in Response to Interleukin-6," The EMBO Journal 14(7):1421-1429, Wiley Blackwell, England (Apr. 1995).

Hanifin, J.M. and Rajka, G., "Diagnostic Features of Atopic Dermatitis," Acta Dermatovener 60(92):44-47 (1980).

Hanifin, J.M., et al., "A Population-based Survey of Eczema Prevalence in the United States," Dermatitis 18(2):82-91, Lippincott Williams & Wilkins, United States (Jun. 2007).

Klunder, B., et al., "Exposure-Response Analyses of the Effect of Upadacitinib on ACR Responses in th Phase 2b Rheumatoid Arthritis Trials in Patients with Inadequate Response to Methotrxate or to Anti-Tumor Necrosis Factor Therapy," 2017 ACR/ ARHP Annual Meeting, Abstract No. 505, 4 pages (2017).

Merriam-Webster: Metabolite, accessed at https://www.merriam-webster.com/dictionary/metabolite, accessed on Dec. 2013.

Mohamed, M.E.F., et al., "ABT-494 Pharmacokinetics Following Administration of the Once-Daily Extended-Release Tablet Formulation Being Utilized in the Ongoing Rheumatoid Arthritis Phase 3 Trials," Annals of the Rheumatic Diseases, Abstract No. THU0177, 2 pages (Jun. 2017).

Mohamed, M.F., et al., "Assessment of Effect of CYP3A Inhibition, CYP Induction, OATP1B Inhibition, and High-fat Meal on Pharmacokinetics of the JAK1 Inhibitor Upadacitinib," British Journal of Clinical Pharmacology 83(10):2242-2248, Wiley-Blackwell, England (Oct. 2017).

Mohamed, M.E.F., et al., "ABT-494 Has no Effect on the QT Interval at the Doses Being Evaluated in Rheumatoid Arthritis Phase 3 Trials," Annals of the Rheumatic Diseases, Abstract No. AB0432, 1 page (Jun. 2017).

Mohamed, M.E.F., "Exposure-Response Analysis to Assess the Effect of ABT-494 on QT Interval and Utilization of a Non-Pharmacological Approach to Demonstrate ECG Assay Sensitivity," Clinical Pharmacology & Therapeutics 101(S1):S39, Abstract PI-076, John Wiley & Sons, Inc., United States (Feb. 2017).

Mohamed, M.E.F., et al., "Use of Early Clinical Trial Data to Support Thorough QT Study Waiver for Upadacitinib and Utility of Food Effect to Demonstrate ECG Assay Sensitivity," Clinical Pharmacology & Therapeutics, 7 pages, John Wiley & Sons, Inc., United States (Jul. 2017).

Mohamed, M.E.F., et al., "The Selective JAK1 Inhibitor Upadacitinib has no Effect on Pharmacokinetics of the Hormonal Contraceptives Levonorgesrel and Ethinylestradiol," 2017 ACR/ARHP Annual Meeting, Abstract No. 506, 4 pages (Sep. 2017).

Neubauer, H., et al., "JAK2 Deficiency Defines an Essential Developmental Checkpoint in Definitive Hematopoiesis," Cell 93(3):397-409, Cell Press, United States (May 1998).

Notice of Opposition for European Patent Application No. EP2506716, mailed on Feb. 16, 2018, 5 pages.

Nygaard, U., et al., "Emerging Treatment Options in Atopic Dermatitis: Systemic Therapies," Dermatology 233(5):344-357, Karger, Switzerland (2017).

Opposition Brief for European Patent Application No. EP2506716, mailed on Feb. 16, 2018, 16 pages.

Ortmann, R.A., et al., "Janus Kinases and Signal Transducers and Activators of Transcription: Their Roles in Cytokine Signaling, Development and Immunoregulation," Arthritis Research 2(1):16-32, BioMed Central Ltd, England (Dec. 1999).

AbbVie's Upadacitinib Meets All Primary and Ranked Secondary Endpoint including Superiority versus Adalimumab in Phase 3 Study in Rheumatoid Arthritis (Apr. 9, 2018), accessed at https://news.abbvie.com/article_print.cfm?article_id=11629, accessed on Aug. 1, 2018, 5 pages.

Response to Communication pursuant to Art. 94(3) EPC dated Jul. 12, 2016, submitted in European Application No. EP10835061.2-1462, cited as Document TM4 in Opposition to European Patent EP2506716, mailed on Feb. 16, 2018, 3 pages.

"Rituximab," in The Merck Index. 14th Ed., John Wiley & Sons, 2006; p. 1422.

Schwartz, D.M., et al., "JAK Inhibition as a Therapeutic Strategy for Immune and Inflammatory Diseases," Nature Reviews. Drug discovery 16(12):843-862, Nature Pub. Group, England (Dec. 2017).

Seppic: "How to use Sepineo P600 in a formulation", XP054976186, accessed at https://www.youtube.com/watch?v=SHiwvwnx1tA, access on Aug. 30, 2012, 1 page.

Silverberg, J.I. and Simpson, E.L., "Association Between Severe Eczema in Children and Multiple Comorbid Conditions and Increased Healthcare Utilization," Pediatric Allergy and Immunology 24(5):476-486, Blackwell Publishing, England (Aug. 2013).

Statement of Case in Opposition for Israel Patent Application 248466, mailed on Nov. 23, 2017, 4 pages.

Strand, V., et al., "Changes in Hemoglobin levels upon Treatment with ABT-494, a Selective JAK-1 Inhibitor and relation to baseline levels of C-Reactive Protein," THU0210, p. 283 (Jun. 2017).

(56) References Cited

OTHER PUBLICATIONS

Strand, V., et al., "Early Patient-Reported Outcomes and Clinical Outcomes with ABT-494 in Patients with Active Rheumatoid Arthritis who are Inadequate Responses to Methotrexate or Tumor Necrosis Factor Inhibitors: Post-Hoc Analysis of Phase 2 Randomized Controlled Trials," Annals of the Rheumatic Diseases, Abstract No. SAT0217, Jun. 2017, 1 page.
Strand, V., et al., "Economic Burden of Non-Responders to Biologic DMARD Treatments in Rheumatoid Arthritis," 2016 ACR/ARHP Annual Meeting, Abstract No. 2617, 2 pages (2016).
Strand, V., et al., "Patient-Reported Outcomes of Long-Term Upadacitinib Use in Patients with Rheumatoid Arthritis: Interim Analysis Results of a Phase 2, Open-Label Extension Study," 2017 ACR/ARHP Annual Meeting, Abstract No. 501, 3 pages (2017).
Torres, T., "Atopic Dermatitis: The New Therapeutic Revolution in Dermatology," Acta medica portuguesa 30(10):669-670, Lisboa, Portugal (Oct. 2017).
Voss, J., et al., "THU0127 Pharmacodynamics of A Novel JAK1 Selective Inhibitor in Rat Arthritis and Anemia Models and in Healthy Human Subjects," 2013 ACR/ARHP Annual Meeting, Abstract No. 2374, 4 pages.
Weiss, G. and Goodnough, L.T., "Anemia of Chronic Disease," The New England Journal of Medicine 352:1011-1023, Massachusetts Medical Society, United States (Mar. 2005).
Wermuth, C., et al., "Molecular Variations D Based on Isoteric Replacements," in The Practice of Medicinal Chemistry, Chapter 13, pp. 203-237, Academic Press, London (1996).
Williams, H.C. and Wuthrich, B., The Natural History of Atopic Dermatitis, Supplied by the British Library, pp. 41-59 (Apr. 2018).
Williams, H.C., "Atopic Dermatitis," The New England Journal of Medicine 352(22):2314-2324, Massachusetts Medical Society, United States (Jun. 2005).
Inami, M., "Small molecule drug development beyond biologics: Kinase inhibitors as an approach to autoimmune disease treatment," Folia Pharmacologica Japonica (2013) 142:63-67. With English certified language translation dated Jun. 17, 2019, 13 pages.
Kranz, H. et al., "Development of a single unit extended release formulation for ZK 811 752, a weakly basic drug," European Journal of Pharmaceutical Sciences 26 (2005) 47-53.
Search results of Upadacitinib in File Registry Database of STN® Search from Chemical Abstracts Service (CAS) conducted on May 4, 2020.
Caira, M.R., "Crystalline Polymorhism of Organic Compounds", Topics in Current Chemistry, v. 198, Chapter 3.1, p. 188, paragraph 2 (1998).
AbbVie's Upadacitinib (ABT-494) meets Primary Endpoint in Phase 2b Study in Atopic Dermatitis (Sep. 7, 2017), accessed at https://news.abbvie.com/news/abbvies-upadacitinib-abt-494-meets-primary-endpoint-in-phase-2b-study-in-atopic-dermatitis.htm, accessed on Dec. 18, 2017, 3 pages.
Declaration of Michael Friedman, dated Sep. 7, 2018, submitted in Response to Notice of Opposition in European Patent EP2506716, 15 pages.
RINVOQ™ (upadacitinib) Monotherapy Meets All Primary and Secondary Endpoints in Second Phase 3 Study for Atopic Dermatitis. Retrieved on Jul. 21, 2020. Retrieved from the Internet: [URL: https://news.abbvie.com/news/press-releases/rinvoq-upadacitinib-monotherapy-meets-all-primary-and-secondary-endpoints-in-second-phase-3-study-for-atopic dermatitis.htm], 5 pages.
Third Pivotal Phase 3 Study Shows RINVOQ™ (upadacitinib) Plus Topical Corticosteroids Improves Skin and Itch Symptoms in Atopic Dermatitis Patients, Retrieved on Jul. 28, 2020. Retrieved from the Internet: [URL: https://news.abbvie.com/news/press-releases/third-pivotal-phase-3-study-shows-rinvoq-upadacitinib-plus-topical-corticosteroids-improves-skin-and-itch-symptoms-in-atopic-dermatitis-patients.html], 5 pages.
Alamanos et al. "Epidemiology of psoriatic arthritis in northwest Greece, 1982-2001," J Rheumatol, 30(12):2641-2644 (2003).
Alten et al., "Examining patient preferences in the treatment of rheumatoid arthritis using a discrete-choice approach," Patient Prefer Adherence, 10: 2217-2228 (2016).
Aviel et al., "Juvenile Psoriatic Arthritis (JPsA): juvenile arthritis with psoriasis?" Pediatric Rheumatology, 11:11 (2013). https://doi.mg/10.-1186/1546-0096-•17-11.
Bozek et al., "The reliability of three psoriasis assessment tools: Psoriasis area and severity index, body surface area and physician global assessment," Advances in Clinical and Experimental Medicine, 26:851-856 (2017).
Coates et al., "Group for Research and Assessment of Psoriasis and Psoriatic Arthritis 2015 Treatment Recommendations for Psoriatic Arthritis," Arthritis & Rheumatology, 68(5): 1060-1071 (2016). https://doi.org/10.1002/art.39573.
Cohen et al., "THU0167 Safety Profile of Upadacitinib in Rheumatoid Arthritis: Integrated Analysis from the Select Phase 3 Clinical Program," Annals of the Rheumatic Diseases, 78: 357 (2019).
Cortese et al., "Secukinumab may be a valid treatment option in patients with CNS demyelination and concurrent ankylosing spondylitis: Report of two clinical cases," Multiple Sclerosis and Related Disorders, 35: 193-195 (2019).
Deodhar et al., "The Concept of Axial Spondyloarthritis," Arthritis & Rheumatology, 66(10): 2649-2656 (2014).
Deodhar et al., "Three Multicenter, Randomized, Double-Blind, Placebo-Controlled Studies Evaluating the Efficacy and Safety of Ustekinumab in Axial Spondyloarthritis," Arthritis and Rheumatology, 71(2): 258-270 (2019).
Deodhar et al., "Efficacy and Safety of Ixekizumab in the Treatment of Radiographic Axial Spondyloarthritis: Sixteen-Week Results From a Phase III Randomized, Double-Blind, Placebo-Controlled Trial in Patients With Prior Inadequate Response to or Intolerance of Tumor Necrosis Factor Inhibitors," Arthritis & Rheumatology, 71(4): 599-611.
Feld et al., "Axial disease in psoriatic arthritis and ankylosing spondylitis: a critical comparison," Nature Reviews, Rheumatology, 14(6): 363-371 (2018). doi: 10.1038/s41584-018-0006-8.
Feldman et al., "The Self-Administered Psoriasis Area and Severity Index Is Valid and Reliable," J; Investigative Dermatology, 106(1): 183-186 (1996).
Fleischmann et al., "Upadacitinib versus placebo or adalimumab in patients with rheumatoid arthritis and an inadequate response to methotrexate: results of a phase III, double-blind, randomized controlled trial," Arthritis & Rheumatology, 71(11): 1788-1800 (2019). [Epub ahead of print, 13 pages] doi: 10.1002/art.41032.
Fragoulis et al., "Inflammatory bowel diseases and spondyloarthropathies: From pathogenesis to treatment," World Journal of Gastroenterology, 25(18): 2162-2176 (2019).
Furst et al., "Targeting inflammatory pathways in axial spondyloarthritis," Arthritis Research and Therapy, 21: 135 (2019). https://doi.org/10.1186/s13075-019-1885-z.
Genovese et al., "Safety and efficacy of upadacitinib in patients with active rheumatoid arthritis refractory to biologic disease-modifying anti-rheumatic drugs (SELECT-BEYOND): a double-blind, randomised controlled phase 3 trial," Lancet, 391(10139): 2513-2524 (2018).
Ghoreschi et al., "Janus Kinases in immune cell signaling," Immunological Reviews, Special Issue: Kinases & Phosphatases of the Immune System, 228(1): 273-287 (2009).
Gladman et al., "Tofacitinib for Psoriatic Arthritis in Patients with an Inadequate Response to TNF Inhibitors," New England Journal of Medicine, 377(16): 1525-1536 (2017).
Glintborg et al., "Clinical response, drug survival and predictors thereof in 432 ankylosing spondylitis patients after switching tumour necrosis factor a inhibitor therapy: results from the Danish nationwide DANBIO registry," Annals of Rheumatic Diseases, 72(7): 1149-1155 (2013).
Gossec et al., "European League Against Rheumatism (EULAR) recommendations for the management of psoriatic arthritis with pharmacological therapies: 2015 update," Annals of Rheumatic Diseases, 75(3): 499-510 (2016).

(56) References Cited

OTHER PUBLICATIONS

Gracey et al., "IL-7 primes IL-17 in mucosal-associated invariant T (MAIT) cells, which contribute to the ThI 7-axis in ankylosing spondylitis," Annals of Rheumatic Diseases, 75(12): 2124-2132 (2016).
Ismail et al., "Exposure-Response Analysis for Upadacitinib Efficancy and Safety in Ankylosing Spondylitis—Analyses of the Select-Axis I Study," ACR Meeting Abstract No. 1492. Arthritis Rheumatology, 71(10) (2019).
Landewe et al., "Efficacy of certolizumab pegol on signs and symptoms of axial spondyloarthritis including ankylosing spondylitis: 24-week results of a double-blind randomised placebo-controlled Phase 3 study," Annals of Rheumatic Diseases, 73(1): 39-47 (2014).
Lauter, J., "Book Review of Hochberg et al, Multiple comparison procedures, John Wiley & Sons, Inc., 1987," in Biomedical Journal, 31, 1, 122 (1989).
Lie et al., "Effectiveness of switching between TNF inhibitors in ankylosing spondylitis: data from the NOR-DMARD register," Annals of Rheumatic Diseases, 70(1): 157-163 (2011).
Machado et al., "Ankylosing Spondylitis Disease Activity Score (ASDAS): 2018 update of the nomenclature for disease activity states," Annals of Rheumatic Diseases, 77(10): 1539-1540 (2018).
Maksymowych et al., "Spondyloarthritis research consortium of canada magnetic resonance imaging index for assessment of spinal inflammation in ankylosing spondylitis," Arthritis & Rheumatism (Arthritis Care & Research), 53(4): 502-509 (2005).
Mease et al. "Tofacitinib or Adalimumab versus Placebo for Psoriatic Arthritis," New England Journal of Medicine, 377(16): 1537-1550 (2017).
Mease et al. "Ixekizumab, an interleukin-17A specific monoclonal antibody, for the treatment of biologic-naive patients with active psoriatic arthritis: results from the 24-week randomised, double-blind, placebo-controlled and active (adalimumab)-controlled period of the phase III trial SPIRIT-PI," Annals of Rheumatic Diseases, 76(1):79-87 (2017).
Mease, P.J., "Inhibition of interleukin-I7, interleukin-23 and the THI 7 cell pathway in the treatment of psoriatic arthritis and psoriasis," Current Opinion in Rheumatology, 27(2): 127-133 (2015).
Nash et al., "Ixekizumab for the treatment of patients with active psoriatic arthritis and an inadequate response to tumour necrosis factor inhibitors: results from the 24-week randomised, double-blind, placebo-controlled period of the SPIRIT-P2 phase 3 trial," Lancet, 389(10086): 2317-2327 (2017).
Nestle et al., "Mechanisms of Disease, Psoriasis," New England Journal of Medicine, 361:496-509 (2009).
Perrotta et al., "Minimal Disease Activity and Remission in Psoriatic Arthritis Patients Treated with Anti-TNF-a Drugs," J Rheumatology, 43(2): 350-355 (2016).
Petty et al., "International League of Associations for Rheumatology classification of juvenile idiopathic arthritis: second revision, Edmonton, 2001," Journal of Rheumatology, 31(2): 390-392 (2004).
Poddubnyy et al., "Similarities and differences between nonradiographic and radiographic axial spondyloarthritis: a clinical, epidemiological and therapeutic assessment," Current Opinion in Rheumatology, 26(4): 377-383 (2014).
Poddubnyy et al., "Comparison of a high sensitivity and standard C reactive protein measurement in patients with ankylosing spondylitis and non-radiographic axial spondyloarthritis," Annals of Rheumatic Diseases, 69(7): 1338-1341 (2010).
RINVOQtm (upadacitinib) Meets Primary and All Ranked Secondary Endpoints in Phase 3 Study in Psoriatic Arthritis, AbbVie News Release, dated Oct. 31, 2019, retrieved from hitps:/inews.abbvie.com/article_print.cfm?article_id=1874.
Rudwaleit et al., "The development of Assessment of SpondyloArthritis international Society classification criteria for axial spondyloarthritis (part II): validation and final selection," Annals of Rheumatic Diseases, 68: 777-783 (2009).
Rudwaleit et al., "Effectiveness and safety of adalimumab in patients with ankylosing spondylitis or psoriatic arthritis and history of anti-tumor necrosis factor therapy," Arthritis Research & Therapy, 12: R117 (2010).
Saber et al., "Remission in psoriatic arthritis: is it possible and how can it be predicted?," Arthritis Research & Therapy, 12: R94 (2010).
Sandborn W.J., "State-of-the-Art: Immunosuppression and Biologic Therapy," Digestive Diseases, 28(3): 536-542 (2010).
Savolainen et al., J Rheumatol, "Total incidence and distribution of inflammatory joint diseases in a defined population: results from the Kuopio 2000 arthritis survey," 30(11): 2460-2468 (2003).
Sieper et al., "Axial spondyloarthritis," Lancet, 390(10089): 73-84 (2017).
Sieper et al., "The Assessment of SpondyloArthritis international Society (ASAS) handbook: a guide to assess spondyloarthritis," Annals of Rheumatic Diseases, 68 Suppl 2:iiI-44 (2009). doi: 10.I136/ard.2008.104018.
Sieper et al., "Secukinumab efficacy in anti-TNF-naive and anti-TNF-experienced subjects with active ankylosing spondylitis: results from the MEASURE 2 Study," Annals of Rheumatic Diseases, 76(3): 571-592 (2017).
Sieper et al., "Assessment of short-term symptomatic efficacy of tocilizumab in ankylosing spondylitis: results of randomised, placebo-controlled trials," Annals of Rheumatic Diseases, 73(1): 95-100 (2014).
Sieper et al., "Sarilumab for the treatment of ankylosing spondylitis: results of a Phase II, randomised, double-blind, placebo-controlled study (ALIGN)," Annals of Rheumatic Diseases, 74(6): 1051-1057 (2015).
Smolen et al., "Treating axial spondyloarthritis and peripheral spondyloarthritis, especially psoriatic arthritis, to target: 2017 update of recommendations by an international task force," Annals of Rheumatic Diseases, 77(1): 3-17 (2018).
Adamczyk, M., et al., "Synthesis of 3,7-dihydroimidazo[1,2a]pyrazine-3-ones and their Chemiluminescent Properties," Tetrahedron 59(41):8129-8142, Elsevier, England (2003).
Aletaha, D., et al., "2010 Rheumatoid Arthritis Classification Criteria: an American College of Rheumatology/european League Against Rheumatism Collaborative Initiative," Arthritis & Rheumatism 62(9):2569-2581, Wiley-Blackwell, United States (2010).
Allen., et al., Editors, "Ansel's Pharmaceutical Dosage Forms and Drug Delivery Systems," 9th Edition, Lippincott Williams & Wilkins, 2005 (8 pages, Table of Contents).
Anderson, J., et al., "Rheumatoid Arthritis Disease Activity Measures: American College of Rheumatology Recommendations for Use in Clinical Practice," Arthritis Care & Research 64(5):640-647, American College of Rheumatology, United States (2012).
Arnett, F.C., et al., "The American Rheumatism Association 1987 Revised Criteria for the Classification of Rheumatoid Arthritis," Arthritis and Rheumatism 31(3):315-324, Wiley-Blackwell, United States (1988).
Banerjee, S., et al., "JAK-STAT Signaling as a Target for Inflammatory and Autoimmune Diseases: Current and Future Prospects," Drugs 77(5):521-546, Springer International, Switzerland (Mar. 2017).
Banker, G.S. and Rhodes, C.T., "Prodrugs," in Modern Pharmaceutics, Third edition, p. 596, Marcel Dekker, Inc., United States (1996).
Baslund, B., et al., "Targeting Interleukin-15 in Patients With Rheumatoid Arthritis, A Proof-of-Concept Study," Arthritis & Rheumatism 52(9):2686-2692, American College of Rheumatology, United States (2005).
Bathon, J.M., et al., "A Comparison of Etanercept and Methotrexate in Patients with Early Rheumatoid Arthritis," The New England Journal of Medicine 343(22):1586-1593, Massachusetts Medical Society, United States (2000).
Bunnage, M.E., et al., "Asymmetric Synthesis of the cis- and trans-stereoisomers of 4-arninopyrrolidine-3-Carboxylic Acid and 4-aminotetrahydrofuran-3-carboxylic Acid," Organic & Biomolecular Chemistry 2(19):2763-2776, Royal Society of Chemistry, England (2004).
Burmester, G.R., et al., "Tofacitinib (CP-690,550) in Combination with Methotrexate in Patients with Active Rheumatoid Arthritis

(56) References Cited

OTHER PUBLICATIONS with an Inadequate Response to Tumour Necrosis Factor Inhibitors: A Randomised Phase 3 Trial.," Lancet 381(9865):451-460, Elsevier, England (2013).

Chaudhari, K., et al., "Rheumatoid Arthritis: Current and Future Trends," Nature Reviews. Drug Discovery 15(5):305-306, Macmillan Publishers Limited, England (May 2016).

Croasdell, G., "American College of Rheumatology/Association of Rheumatology Health Professionals—2015 Annual Meeting," Drugs of the Future 40(12):857-862, Prous Science S.A.U., United States (2015).

Dupre, et al., "An Improved Synthesis of Ethyl N-(methoxycarbonyl)-2,5-dihydro-IH-pyrrole-3-carboxylate," Journal of Organic Chemistry 56(9):3197-3198, (1991).

Dutta, S. and Reed, R.C., "Functional Half-Life is a Meaningful Descriptor of Steady-State Pharmacokinetics of an Extended-Release Formulation of a Rapidly Cleared Drug," Clinical Drug Investigation 26(12):681-690, Springer International, New Zealand (2006).

El-Nabi, H.A.A., et al., "1-Aryl-2-chloro-5-methoxy-1H-3-pyrrolecarbaldehyde as synthons for fused heterocycles: synthesis of pyrazolo[3,4-d]pyrrolo[2,3-b]pyridine derivatives," Journal of Chemical Research 5:325-327, Science Reviews Ltd., England (2004).

Farnia, et al., "Stille Reaction," Organic Reactions, L. Paquette et al., Editors, John Wiley & Sons, vol. 50, 1997 5 pages, 1997 (Table of Contents).

FDA, "Clinical Pharmacology and Biopharmaceutics Review(s)—Tofacitinib," Application No. 203214OrigIs000, Center for Drug Evaluation and Research, 181 pages (2011).

FDA, "Guidance for Industry Toxicity Grading Scale for Healthy Adult and Adolescent Volunteers Emolled in Preventive Vaccine Clinical Trials," Department of Health and Human Services, FDA, Center for Biologics Evaluation and Research, 10 pages (2007).

FDA, "Medical Review; Addendum to Primary Clinical Review—Tofacitinib," Application No. 203214OrigIs000, Center for Drug Evaluation and Research, 303 pages (2012).

Fleischmann, R.M., et al., "A Randomized, Double-blind, Placebo-controlled, Twelve-week, Dose-ranging Study of Decemotinib, an Oral Selective JAK-3 Inhibitor, as Monotherapy in Patients With Active Rheumatoid Arthritis," Arthritis and Rheumatology 67(2):334-343, Wiley, United States (2015).

Gennaro, A., Editor "Remington's Pharmaceutical Sciences", 18th Edition, Mack Publishing Co., 5 pages, 1990 (Table of Contents).

Genovese, M.C., et al., "Safety and Efficacy of ABT-494, a Novel Selective JAK1 Inhibitor, in Patients with Active Rheumatoid Arthritis with an Inadequate Response to Methotrexate," Annals of the Rheumatic Diseases 75(2):141-142, Abstract OP0223, BMJ Publishing Group, England (Jun. 2016).

Genovese, M.C., et al., "Efficacy and Safety of ABT-494, a Selective JAK-1 Inhibitor, in a Phase IIb Study in Patients With Rheumatoid Arthritis and an Inadequate Response to Methotrexate," Arthritis & Rheumatology 68(12):2857-2866, Wiley, United States (Dec. 2016).

Genovese, M.C., et al., "OP0029 Baricitinib, An Oral Janus Kinase (JAK)1/JAK2 Inhibitor, in Patients with Active Rheumatoid Arthritis (RA) and an Inadequate Response to TNF Inhibitors: Results of the Phase 3 RA-Beacon Study:," Annals of the Rheumatic Diseases 74(2):75.3-76, H.K. Lewis, England (2015).

Genovese, M.C., et al., "VX-509 (Decernotinib), an Oral Selective JAK-3 Inhibitor, in Combination with Methotrexate in Patients with Rheumatoid Arthritis," Arthritis & Rheumatology 68(1):46-55, Wiley, United States (2016).

Gilworth, G., et al., "Development of a Work Instability Scale for Rheumatoid Arthritis," Arthritis and Rheumatism 49(3):349-354, Wiley-Blackwell, United States (2003).

Graff, C., et al., "Characterization of ABT-494, a Second Generation JAK1 Selective Inhibitor," 2014 ACR/ARHP Annual Meeting, Abstract No. 1499, 3 pages.

Graul, A.I., et al., "The Year's New Drugs and Biologics 2015—Part II: Trends and highlights that Marked a Complicated Year," Drugs of Today 52(2):131-163, Prous Science S.A.U., United States (Feb. 2016).

Greene, et al., Editors, "Protective Groups in Organic Synthesis," 3rd Ed., John Wiley & Sons, NY, 52 pages, 1999 (Table of Contents, Abbreviations).

Hauser, M., et al., "Pyrazolono(3,4-d)pyrimidines. II. 6-Methylpyrazolono(3,4-d)pyrimidines and some reactions of pyrazolono(3,4-d)pyrimidines," The Journal of Organic Chemistry 26(2):451-455, American Chemical Society, United States (1960).

Hirahara, K., et al., "Targeting Cytokine Signaling in Autoimmunity: Back to the Future and Beyond," Current Opinion in Immunology 43:89-97, Elsevier Ltd., England (Dec. 2016).

Iwata, S. and Tanaka, Y., "Progress in Understanding the Safety and Efficacy of Janus Kinase Inhibitors for Treatment of Rheumatoid Arthritis," Expert Review of Clinical Immunology 12(10):1047-1057, Informa UK Limited, England (Jun. 2016).

Jacobson, K.A., "Comprehensive Organic Transformations: A Guide to Functional Group Preparations," 2nd ed. Richard C. Larock. Wiley New York, 1999, pp. 2583.

Jain, S., et al., "A Novel Synthesis of Dl(1-Methlazacycloalkeno)[2,3-b:2',3'-d]Pyridines Through Annulation on Lactam Acetals," Tetrahedron Letters 31(1):131-134, Pergamon Press PLC, Great Britain (1990).

Jenkins, et al., Editors, "Introduction to X-Ray Powder Diffractometry," John Wiley & Sons, 13 pages, 1996 (Table of Contents).

Jordan, V.C., "Tamoxifen: a most unlikely pioneering medicine," Nat Rev Drug Discov. 2(3):205-213, Nature Publishing Group, England (2003).

Kempson, J., et al., "Synthesis, initial SAR and biological evaluation of 1,6-dihydroimidazo[4,5-d]pyrrolo[2,3-b]pyridin-4-amine derived inhibitors of I?B kinase," Bioorg Med Chem Lett. <https://www.ncbi.nlm.nih.gov/pubmed?term=%22Bioorganic+%26+medicinal+chemistry+letters%22%5BJour%5D+AND+19%5Bvolume%5D+AND+2646%5Bpage%5D&cmd=detailssearch> 19(10):2646-2649, Elsevier Ltd., England (2009).

Kettle, J.G., et al., "Inhibitors of JAK-family Kinases: An Update on the Patent Literature 2013-2015, part 1," Expert Opinion on Therapeutic Patents 27(2):127-143, Informa UK Limited, England (Feb. 2017).

Keystone, E.C., et al., "Safety and Efficacy of Baricitinib at 24 Weeks in Patients with Rheumatoid Arthritis Who Have Had an Inadequate Response to Methotrexate," Annals of the Rheumatic Diseases 74(2):333-340, H.K. Lewis, England (2015).

Keystone, E.C., et al., "Certolizumab Pegol Plus Methotrexate Is Significantly More Effective Than Placebo Plus Methotrexate in Active Rheumatoid Arthritis: Findings of a Fifty-two-week, Phase III, Multicenter, Randomized, Double-blind, Placebo-controlled, Parallel-group Study," Arthritis & Rheumatology 58(11):3319-3329, Wiley, United States (2008).

Keystone, E.C., et al., "Radiographic, Clinical, and Functional Outcomes of Treatment With Adalimumab (a Human Anti-tumor Necrosis Factor Monoclonal Antibody) in Patients With Active Rheumatoid Arthritis Receiving Concomitant Methotrexate Therapy: a Randomized, Placebo-controlled, 52-week Trial," Arthritis and Rheumatism 50(5):1400-1411, Wiley-Blackwell, United States (2004).

Ko, et al., "N-Protecting Group Dependent Aromatization of 3-Pyrroline Systems to Pyrroles," Bulletin of the Korean Chemical Society 11(1):83-84, (1990).

Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Nov. 2016).

Kremer, J.M., et al., "Safety and Efficacy of ABT-494, a Novel Selective JAK1 Inhibitor, in Patients with Active Rheumatoid Arthritis and Inadequate Response or Intolerance to Anti-TNF Biologic Therapy," 2015 ACR/ARHP Annual Meeting, Abstract 14L, 4 pages.

(56) References Cited

OTHER PUBLICATIONS

Lam, S., "JAK Inhibitors: A Broadening Approach in Rheumatoid Arthritis," Drugs of Today 52(8):467-469, Prous Science S.A.U., United States (Aug. 2016).

Larock, R.C., Editor, "Comprehensive Organic Transformations, A Guide to Functional Group Preparations," 2nd edition, Wiley-VCH, 22 pages, 1999 (Table of Contents).

Larson, G.L., et al., "Ionic and Organometallic-Catalyzed Organosilane Reductions," Organic Reactions 71:1-737, (2008).

Ma, M.H., et al., "A Systematic Comparison of Combination DMARD Therapy and Tumour Necrosis Inhibitor Therapy With Methotrexate in Patients With Early Rheumatoid Arthritis," Rheumatology 49(1):91-98, Mercury International, England (2010).

Mangoni, A.A. and Jackson, S.H., "Age-related Changes in Pharmacokinetics and Pharmacodynamics: Basic Principles and Practical Applications," British Journal of Clinical Pharmacology 57(1):42900, Wiley-Blackwell, England (2004).

Dorwald, F.Z., "Side Reactions in Organic Synthesis: A Guide to Successful Synthesis Design," Weinheim: Wiley-VCH Verlag GmbH & Co_ KGaA, 2005.

Malemud, C.J, "Suppression of Autoimmune Arthritis by Small Molecule Inhibitors of the JAK/STAT Pathway," Pharmaceuticals (Basel) 3(5):1446-1455, MDPI, Switzerland (May 2010).

Milici, A.J., et al., "Cartilage Preservation by Inhibition of Janus Kinase 3 in Two Rodent Models of Rheumatoid Arthritis," Arthritis Research & Therapy 10(1):R14, BioMed Central, England (2008).

Response to Notice of Opposition, dated Sep. 10, 2018, submitted in European Patent EP2506716, 31 pages.

Roskoski, R Jr, "Janus Kinase (Jak) Inhibitors in the Treatment of Inflammatory and Neoplastic Diseases," Pharmacological Research 111:784-803, Elsevier, Netherlands (Sep. 2016).

Verstovsek, S, "Therapeutic Potential of JAK2 Inhibitors," Hematology American Society of Hematology Education Program 636-642, American Society of Hematology, United States (2009).

Mohamed, M.F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, ADIS Press, Switzerland (2016).

Abbvie, Press Release on Feb. 17, 2018, "AbbVie Presents New Late-Breaking Phase 2b Data on Upadacitinib in Atopic Dermatitis at the 2018 American Academy of Dermatology Annual Meeting", accessed at https://news.abbvie.com/article_print.cfm?article_id=11608, 3 pages.

AbbVie's Upadacitinib Shows Positive Results as Monotherapy in Phase 3 Rheumatoid Arthritis Study, Meeting All Primary and Key Secondary Endpoints, Dec. 2017, 5 pages.

Alabdulaai, M.K., et al., "The Role of JAK2 Abnormalities in Hematologic Neoplasms", Hematology Reviews 1(1):e10, PagePress, Italy (Mar. 2009).

Clinical Trials," A Phase 3, Randomized, Double-Blind Study Comparing Upadacitinib (ABT-494) to Placebo and to Adalimumab in Subjects With Moderately to Severely Active Rheumatoid Arthritis Who Are on a Stable Background of Methotrexate {MTX) and Who Have an Inadequate Response to MTX (MTX-IR)," Identifier NCT02629159 accessed at https://clinicaltrials_gov/ct2/show/ NCT02629159 accessed on Oct. 23, 2018, 10 pages.

Lin, TH, et aL, "Selective Functional Inhibition of JAK-3 Is Sufficient for Efficacy in Collagen-induced Arthritis in Mice," Arthritis and Rheumatism 62(8):2283-2293, Wiley-Blackwell, United States (Aug. 2010).

Clinical Trials, " A Phase 3, Randomized, Double-Blind Study Comparing Upadacitinib (ABT-494) Monotherapy to Methotrexate (MTX) in Subjects With Moderately to Severely Active Rheumatoid Arthritis With Inadequate Response to MTX," Identifier NCT02706951 accessed at https://clinicaltrials.gov/ct2/show/ NCT02706951 accessed on Oct. 23, 2018, 8 pages.

Parmentier, J.M., et al., "In Vitro and in Vivo Characterization of the JAKI Selectivity of upadacitinib (ABT-494)," BMC Rheumatology 2(23):16, BioMed Central, United Kingdom (2018).

Third Declaration of Michael Friedman, dated Oct. 23, 2018, submitted in U.S. Appl. No. 15/446,102, 41 pages.

Upadacitinib Meets All Primary and Ranked Secondary Endpoints Including Superiority Versus Adalimumab in Phase 3 Study in Rheumatoid Arthritis, [retrieved on Apr. 9, 2018]. Retrieved from the Internet: [URL http://www.prnewswire.com/news-releases/upadacitinib-meets-all-primary-and-ranked-secondary-endpoints-including-superiority-versus-adalimumab-in-phase-3-study-in-rheumatoid arthritis-300626157.html], accessed on Apr. 10, 2018, 5 pages.

Clinical Trials, "A Phase 2 Study, Multicenter, Open-Label Extension (OLE) Study in Rheumatoid Arthritis Subjects Who Have Completed a Preceding Phase 2 Randomized Controlled Trial (RCT) With Upadacitinib (ABT-494)," Identifier NCT02049138, accessed at https://clinicaltrials.gov/ct2/show/NCT02049138, accessed on Oct. 3, 2018, 10 pages.

Clinical Trials, "A Randomized, Double-Blind, Placebo-Controlled, Phase 2 Study to Investigate the Safety and Efficacy of ABT-494 With Background Methotrexate (MTX) in Subjects With Active Rheumatoid Arthritis (RA) Who Have Had an Inadequate Response to MTX Alone," Identifier NCT02066389, accessed at https://clinicaltrials.gov/ct2/show/NCT02066389, accessed on Oct. 11, 2018, 11 pages.

Clinical Trials, "A Study in Healthy Adult Volunteers and Adult Subjects With Rheumatoid Arthritis to Evaluate the Safety, Tolerability, and Pharmacokinetics After Multiple Dosing of ABT-494," Identifier NCT01741493, accessed at https://clinicaltrials.gov/ct2/show/NCT01741493, accessed on Sep. 27, 2018, 7 pages.

Clinical Trials, "A Randomized, Double-Blind, Placebo-Controlled, Phase 2 Study to Investigate the Safety and Efficacy of ABT-494 Given With Methotrexate (MTX) in Subjects With Moderately to Severely Active Rheumatoid Arthritis (RA) Who Have Had an Inadequate Response or Intolerance to Anti-TNF Biologic Therapy," Identifier NCT01960855, accessed at https://clinicaltrials.gov/ct2/show/NCT01960855, accessed on Sep. 13, 2018, 8 pages.

Clinical Trials, "A Multicenter, Randomized, Double-Blind, Placebo-Controlled Study of ABT-494 for the Induction of Symptomatic and Endoscopic Remission in Subjects With Moderately to Severely Active Crohn's Disease Who Have Inadequately Responded to or Are Intolerant to Immunomodulators or Anti-TNF Therapy," Identifier NCT02365649, accessed at https://clinicaltrials.gov/ct2/show/NCT02365649, accessed on Aug. 24, 2018, 7 pages.

Clinical Trials, "A Phase 3, Randomized, Double-Blind Study Comparing Upadacitinib (ABT-494) to Placebo in Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs" Identifier NCT02675426, accessed at https://clinicaltrials.gov/ct2/show/NCT02675426, accessed on Oct. 22, 2018, 9 pages.

Clinical Trials, "A Phase 3, Randomized, Double-Blind Study Comparing Upadacitinib (ABT-494) Once Daily Monotherapy to Methotrexate (MTX) Monotherapy in MTX-Naive Subjects With Moderately to Severely Active Rheumatoid Arthritis", accessed at https://clinicaltrials.gov/ct2/show/NCT02706873, accessed on Oct. 17, 2018, 9 pages.

Clinical Trials, "A Phase 3, Randomized, Double-Blind Study Comparing Upadacitinib (ABT-494) to Placebo on Stable Conventional Synthetic Disease-Modifying Anti-Rheumatic Drugs (csDMARDs) in Subjects With Moderately to Severely Active Rheumatoid Arthritis With Inadequate Response or Intolerance to Biologic DMARDs (bDMARDs)," Identifier NCT02706847, accessed at https://clinicaltrials.gov/ct2/show/NCT02706847, accessed on Oct. 23, 2018, 8 pages.

Klunder, B ., et al., "Population Pharmacokinetics of Upadacitinib in Healthy Subjects and Subjects with Rheumatoid Arthritis: Analyses of Phase I and II Clinical Trials," Clinical Pharmacokinetics, 57(8):977-988, Adis, part of Springer Science+Business Media, Switzerland (Aug. 2018).

Mohamed, M.F., et al., "Pharmacokinetics of Upadacitinib With the Clinical Regimens of the Extended-Release Formulation Utilized in

(56) References Cited

OTHER PUBLICATIONS

Rheumatoid Arthritis Phase 3 Trials," Clinical Pharmacology in Drug Development, 0(0):1-9, Wiley Periodicals, Inc., United States (Apr. 2018).
Clinical Trials, "A Phase 3 Randomized, Multicenter, Double-Blind Study to Evaluate the Safety of Upadacitinib in Combination With Topical Corticosteroids in Adolescent and Adult Subjects in Japan With Moderate to Severe Atopic Dermatitis," Identifier NCT03661138, accessed at https://clinicaltrials.gov/ct2/show/NCT03661138, accessed on Oct. 23, 2018, 10 pages.
Clinical Trials, "A Phase 2b/3, Randomized, Double-Blind Study Comparing Upadacitinib (ABT-494) to Placebo in Japanese Subjects With Moderately to Severely Active Rheumatoid Arthritis Who Are on a Stable Dose of Conventional Synthetic Disease-Modifying Anti-Rheumatic Drugs (csDMARDs) and Have an Inadequate Response to csDMARDs," Identifier NCT02720523, accessed at https://clinicaltrials.gov/ct2/show/NCT02720523, accessed on Oct. 23, 2018, 9 pages.
Clinical Trials, "A Phase 2, Multicenter, Open-Label Extension (OLE) Study to Observe the Long-Term Efficacy, Safety, and Tolerability of Repeated Administration of Upadacitinib (ABT-494) in Subjects With Crohn's Disease," Identifier NCT02782663, accessed at https://clinicaltrials.gov/ct2/show/NCT02782663 accessed on Oct. 23, 2018, 7 pages.
Clinical Trials,"A Multicenter, Randomized, Double-Blind, Placebo-Controlled Study to Evaluate the Safety and Efficacy of Upadacitinib (ABT-494) for Induction and Maintenance Therapy in Subjects With Moderately to Severely Active Ulcerative Colitis," Identifier NCT02819635, accessed at https://clinicaltrials.gov/ct2/show/NCT02819635, accessed on Oct. 23, 2018, 8 pages.
Clinical Trials, "A Phase 2b Multicenter, Randomized, Placebo-Controlled, Double-Blind Dose-Ranging Study to Evaluate ABT-494 (Upadacitinib) in Adult Subjects With Moderate to Severe Atopic Dermatitis," Identifier NCT02925117, accessed at https://clinicaltrials.gov/ct2/show/NCT02925117 accessed on Oct. 23, 2018, 9 pages.
Clinical Trials, "A Phase 3, Randomized, Double-Blind, Placebo-Controlled Study With Upadacitinib (ABT-494) in Subjects From China and Selected Countries With Moderately to Severely Active Rheumatoid Arthritis Who Have Had an Inadequate Response to Conventional Synthetic Disease-Modifying Anti-Rheumatic Drugs (csDMARDs)," Identifier NCT02955212, accessed at https://clinicaltrials.gov/ct2/show/NCT02955212 accessed on Oct. 23, 2018, 9 pages.
Clinical Trials, "A Phase 3 Multicenter, Long-Term Extension Study to Evaluate the Safety and Efficacy of Upadacitinib (ABT-494) in Subjects With Ulcerative Colitis," Identifier NCT03006068, accessed at https://clinicaltrials.gov/ct2/show/NCT03006068, accessed on Oct. 23, 2018, 8 pages.
Clinical Trials, "A Phase 3, Randomized, Active-Controlled, Double Blind Study Comparing Upadacitinib (ABT-494) to Abatacept in Subjects With Moderately to Severely Active Rheumatoid Arthritis With Inadequate Response or Intolerance to Biologic DMARDs (bDMARDs) on Stable Conventional Synthetic Disease Modifying Anti-Rheumatic Drugs (csDMARDs)," Identifier NCT03086343, accessed at https://clinicaltrials.gov/ct2/show/NCT03086343, accessed on Oct. 23, 2018, 8 pages.
Clinical Trials, "A Phase 3, Randomized, Double-Blind, Study Comparing Upadacitinib (ABT-494) to Placebo in Subjects With Active Psoriatic Arthritis Who Have a History of Inadequate Response to at Least One Biologic Disease Modifying Anti-Rheumatic Drug (bDMARD)," Identifier NCT03104374, accessed at https://clinicaltrials.gov/ct2/show/NCT03104374, accessed on Oct. 23, 2018, 10 pages.
Clinical Trials, "A Phase 3, Randomized, Double-Blind, Study Comparing Upadacitinib (ABT-494) to Placebo and to Adalimumab in Subjects With Active Psoriatic Arthritis Who Have a History of Inadequate Response to at Least One Non-Biologic Disease Modifying Anti-Rheumatic Drug (DMARD)—SELECT—PsA 1," Identifier NCT03104400, accessed at https://clinicaltrials.gov/ct2/show/NCT03104400, accessed on Oct. 23, 2018, 12 pages.

Clinical Trials, "A Multicenter, Randomized, Double-Blind, Placebo-Controlled Study Evaluating the Safety and Efficacy of Upadacitinib in Subjects With Active Ankylosing Spondylitis," Identifier NCT03178487, accessed at https://clinicaltrials.gov/ct2/show/NCT03178487, accessed on Oct. 23, 2018, 10 pages.
Clinical Trials, "A Multicenter, Randomized, Double-Blind, Placebo-Controlled Maintenance and Long-Term Extension Study of the Efficacy and Safety of Upadacitinib (ABT-494) in Subjects With Crohn's Disease Who Completed the Studies M14-431 or M14-433," Identifier NCT03345823, accessed at https://clinicaltrials.gov/ct2/show/NCT03345823, accessed on Oct. 23, 2018, 9 pages.
Clinical Trials,"A Multicenter, Randomized, Double-Blind, Placebo-Controlled Induction Study of the Efficacy and Safety of Upadacitinib (ABT-494) in Subjects With Moderately to Severely Active Crohn's Disease Who Have Inadequately Responded to or Are Intolerant to Biologic Therapy," Identifier NCT03345836, accessed at https://clinicaltrials.gov/ct2/show/NCT03345836, accessed on Oct. 23, 2018, 8 pages.
Clinical Trials, "A Phase 3 Randomized, Placebo-Controlled, Double-Blind Study to Evaluate Upadacitinib in Combination With Topical Corticosteroids in Adolescent and Adult Subjects With Moderate to Severe Atopic Dermatitis," Identifier NCT03568318, accessed at https://clinicaltrials.gov/ct2/show/NCT03568318, accessed on Oct. 23, 2018, 8 pages.
Clinical Trials, "A Phase 3 Randomized, Placebo-Controlled, Double-Blind Study to Evaluate Upadacitinib in Adolescent and Adult Subjects With Moderate to Severe Atopic Dermatitis," Identifier NCT03569293, accessed at https://clinicaltrials.gov/ct2/show/NCT03569293, accessed on Oct. 23, 2018, 9 pages.
Clinical Trials, "An Open-label Multiple Dose Study to Evaluate the Pharmacokinetics, Safety and Tolerability of Upadacitinib in Pediatric Subjects With Severe Atopic Dermatitis," Identifier NCT03646604, accessed at https://clinicaltrials.gov/ct2/show/NCT03646604, accessed on Oct. 23, 2018, 6 pages.
Clinical Trials, "A Multicenter, Randomized, Double-Blind, Placebo-Controlled Induction Study to Evaluate the Efficacy and Safety of Upadacitinib (ABT-494) in Subjects With Moderately to Severely Active Ulcerative Colitis," Identifier NCT03653026, accessed at https://clinicaltrials.gov/ct2/show/NCT03653026, accessed on Oct. 23, 2018, 8 pages.
Clinical Trials, "A Phase 2 Study to Investigate the Safety and Efficacy of ABBV-105 Given Alone or in Combination With Upadacitinib (ABBV-599 Combination) With a Background of Conventional Synthetic DMARDs in Subjects With Active Rheumatoid Arthritis With Inadequate Response or Intolerance to Biologic DMARDs," Identifier NCT03682705, accessed at https://clinicaltrials.gov/ct2/show/NCT03682705, accessed on Oct. 23, 2018, 10 pages.
Bissonnette, R., et al., "Topical tofacitinib for atopic dermatitis: a phase II a randomized trial," British Journal of Dermatology (2016) 175:902-911.
Guttman-Yassky, E., et al., "Baricitinib in adult patients with moderate-to-severe atopic dermatitis: A phase 2 parallel, double-blinded, randomized placebo-controlled multiple-dose study," J Am Acad Dermatol (2018) 80(4):913-921.
Levy, L.L., et al., "Treatment of recalcitrant atopic dermatitis with the oral Janus kinase inhibitor tofacitinib citrate," J Am Acad Dematol (2015) 73(3):395-398.
Vu, M., et al., "Oral tofacitinib: a promising treatment in atopic dermatitis, alopecia areata and vitiligo," Clinical and Experimental Dermatology (2017) 42:942-944.
Guttman-Yassky et al., "Upadacitinib in adults with moderate to severe atopic dermatitis: 16-week results from a randomized, placebo-controlled trial" J Allergy Clin Immunol, 2020, pp. 877-884.
RINVOQ™ (upadacitinib) Monotherapy Shows Improvement in Skin Clearance and Itch in First Phase 3 Study for Atopic Dermatitis Retrieved on Jun. 18, 2020. Retrieved from the Internet: [URL: https://news.abbvie.com/news/press-releases/rinvoq-upadacitinib-monotherapy-shows-improvement-in-skin-clearance-and-itch-in-first-phase-3-study-for-atopic-dermatitis.htm], 5 pages.
AbbVie News Release, "AbbVie's ABT-494 Meets Primary Endpoint in Two Phase 2 Studies in Rheumatoid Arthritis" (2015).

(56) References Cited

OTHER PUBLICATIONS

U.S. Appl. No. 18/174,736, filed Feb. 27, 2023, Pending, Not yet published.
U.S. Appl. No. 18/174,738, filed Feb. 27, 2023 Pending, Not yet published.
U.S. Appl. No. 18/176,850, filed Mar. 1, 2023, Pending, Not yet published.
U.S. Appl. No. 18/176,848, filed Mar. 1, 2023, Pending, Not yet published.
U.S. Appl. No. 18/176,647, filed Mar. 1, 2023, Pending, Not yet published.
U.S. Appl. No. 18/176,653, filed Mar. 1, 2023, Pending, Not yet published.
U.S. Appl. No. 18/176,651, filed Mar. 1, 2023, Pending, Not yet published.
U.S. Appl. No. 18/137,804, filed Apr. 21, 2023, Pending, Not yet published.
U.S. Appl. No. 18/140,653, filed Apr. 28, 2023, Pending, Not yet published.
U.S. Appl. No. 18/328,325, filed Jun. 2, 2023, Pending, Not yet published.
U.S. Appl. No. 18/328,350, filed Jun. 2, 2023, Pending, Not yet published.
U.S. Appl. No. 18/329,980, filed Jun. 6, 2023, Pending, Not yet published.
U.S. Appl. No. 18/329,986, filed Jun. 6, 2023, Pending, Not yet published.
U.S. Appl. No. 18/329,988, filed Jun. 6, 2023, Pending, Not yet published.
AbbVie, Morgan Stanley Health Care Conference, Sep. 10, 2014 (JAK 1 Inhibitors is use for the treatment of the rheumatoid arthritis).
Anderson et al., "Surgery in Ulcerative Colitis: Indication and Timing" Dig Dis (2009), 27(3), p. 335-340.
Badawy et al. "Microenvironmental pH Modulation in Solid Dosage Forms", Journal of Pharmaceutical Sciences, vol. 96, No. 5, May 2007.
Bao et al., The Involvement of the JAK-STAT Signaling Pathway in Chronic Inflammatory Skin Disease Atopic Dermatitis, 2:3, e24137, p. 1-8, Jul./Aug./Sep. 2013.
Bechman et al., "The new entries in the therapeutic armamentarium: The small molecule JAK Inhibitors", Pharmacological Research, Aug. 2019, 147, 1-10.
Bolourchian, "pH-independent release of propranolol hydrochloride from HPMC-based matrices using organic acids", DARU Journal of Pharmaceutical Sciences 16(3):136-142, Dec. 2008.
Danese et al., "JAK inhibition using tofacitinib for inflammatory bowel disease treatment: a hub for multiple inflammatory cytokines", Am J Physiol Gastrointest Liver Physiol, Published online Nov. 25, 2015.
Dvorackova, "The Effect of Acid pH Modifiers on the Release Characteristics of Weakly Basic Drug from Hydrophilic-Lipophilic Matrices", AAPS PharmSciTech, vol. 14, No. 4, Dec. 2013.
Eichenfield et al. "Guidelines of care for the management of atopic dermatitis", Journal of the American Academy of Dermatology, vol. 70, No. 2, Feb. 2014.
EMA, "Guideline on the pharmacokinetic and clinical evaluation of modified release dosage forms", published Nov. 2014.
FDA, "Guidance for Industry; Extended-Release Oral Dosage Forms: Development, Evaluation, and Application of In Vitro/In Vivo Correlations"; published Sep. 1997.
FDA, "Guidance for Industry; Rheumatoid Arthritis: Developing Drug Products for Treatment", published May 2013.
Fragoulis et al., "JAK-inhibitors. New players in the field of immune-mediated diseases, beyond rheumatoid arthritis", Rheumatology, Feb. 2019, 58, 143-154.
Gupta et al., "Evaluation of the Effect of Fluconazole and Ketoconazole on the Pharmacokinetics of Tofacitinib in Healthy Adult Subjects", Clinical Pharmacology in Drug Development, 2013, 3(1), 72-77.
Hanifin et al. "The eczema area and severity index (EASI): assessment of reliability in atopic dermatitis", Experimental Dermatology, 2001: 10: 11-18.
Hsu et al., "JAK Inhibitors: Treatment Efficacy and Safety Profile in Patients with Psoriasis", Journal of Immunology Research, 2014, 1-7.
Lamba et al., "Pharmacokinetics, Bioavailability and Safety of a Modified-Release Once-Daily Formulation of Tofacitinib in Healthy Volunteers", Poster 1478, ACR/ARHP Annual Meeting, Nov. 17, 2014.
Lamba et al., "Evaluating Pharmacokinetic Predictors of Tofacitinib Clinical Response in Rheumatoid Arthritis", Poster Abstract THU0192, Jun. 9, 2016, http://dx.doi.org/10.1136/annrheumdis-2016-eular.1696.
Lamba et al., "Pharmacokinetics, Bioavailability and Safety of a Modified Release Once Daily Formulation of Tofacitinib in Healthy Volunteers", Poster Abstract THU0143, Eular Jun. 12, 2014, 2014; Annals of the Rheumatic Diseases, 2014, 73(2), 228.
Lawendy et al. "The Effect of Mild and Moderate Hepatic Impairment on the Pharmacokinetics of Tofacitinib, an Orally Active Janus Kinase Inhibitor", Clinical Pharmacology in Drug Development, 2014, 3(6), 421-427.
NCT02281552: "A Multicenter, Randomized, Double-Blind, Parallel-Group, Phase 3 Study to Demonstrate Non-Inferiority for the Efficacy of a Once Daily Dose of Tofacitinib Modified Release Tablet to a Twice Daily Dose of the Immediate Release Tablet in Adult Patients with Rheumatoid Arthritis on Background Methotrexate", Final Protocol Amendment, Aug. 13, 2015.
Nokhodchi et al., "The role of oral controlled release matrix tablets in drug delivery systems", BioImpacts, 2012, 2(4), 175-187.
Novosad et al., "Beyond TNF inhibition: the expanding pipeline of biologic therapies for inflammatory disease and their associated infectious sequelae", Clinical infectious disease advance access, Feb. 27, 2014, 1-38.
O'Shea et al., "Janus kinase inhibitors in autoimmune disease", Annual Rheumatoid disease, 2013, 72, iill1-ii115.
Remington: The Science and Practice of Pharmacy. 22nd Ed. Linda A. Felton. Pharmaceutical Press, 2012.
Rudwaleit et al., "Atopic disorders in ankylosing spondylitis and rheumatoid arthritis", Ann Rheum Dis., Nov. 2002; 61(11): 968-974.
Saini et al. "Effect of Medication Dosing Frequency on Adherence in Chronic Diseases", Am J Manag Care, Jun 1;15(6):e22-33.2009.
Schmitt et al., Assessment of clinical signs of atopic dermatitis: a systematic review and recommendation, J Allergy Clin Immunol 2013; 132(6): 1337-1347.
Siepe et al., "Strategies for the design of hydrophilic matrix tablets with controlled microenvironmental pH", Int J Pharm Jun. 19, 2006;316(1-2): 14-20.
Siepe et al., "Microenvironmental pH and microviscosity inside pH-controlled matrix tablets: An EPR imaging study", J Control Release May 1, 2006;112(1):72-8.
Siepe et al., "Assessment of Tailor-Made HPMC-Based Matrix Minitablets Comprising a Weakly Basic Drug Compound", Drug Dev Ind Pharm Jan. 2008;34(1):46-52.
Singh et al., "Use of Clinical Disease Activity Index Score for Assessment of Disease Activity in Rheumatoid Arthritis Patients: An Indian Experience", Arthritis (2011).
Streubel et al., "pH-independent release of a weakly basic drug from water- insoluble and -soluble matrix tablets", J Control Release Jun. 1, 20005;67(1): 101-10.
Timmins et al., Ed., "Hydrophilic Matrix Tablets for Oral Controlled Release", In: AAPS vol. 16, 2014, Springer.
Van der Heijde et al., "Efficacy and safety of upadacitinib in patients with active ankylosing spondylitis (SELECT-AXIS 1): a multicentre, randomised, double-blind, placebo-controlled, phase 2/3 trial", The Lancet, Elsevier, Amsterdam, NL, Nov. 2019, 394 (10214), 2108-2117.
Varma et al., "Influence of micro-environmental pH on the gel layer behavior and release of a basic drug from various hydrophilic matrices", J Control Release Mar. 21, 2005; 103(2):499-510.
Vippagunta et al., "Crystalline Solids", Advanced Drug Delivery Reviews 48 (2001) 3-26.

(56) References Cited

OTHER PUBLICATIONS

Walpole et al., "The weight of nations: an estimation of adult human biomass", BMC Public Health 2012, 12:439, pp. 1-6.
Zalte et al., "Review on Sustained Release Matrix Tablet", International Journal of Pharmacy and Biological Sciences, Dec. 2013, 3(4), 17-29.
Zhang et al., "A Randomized, Placebo-Controlled Study of the Pharmacokinetics, Pharmacodynamics, and Tolerability of the Oral JAK2 Inhibitor Fedratinib (SAR302503) in Healthy Volunteers", The Journal of Clinical Pharmacology, 2013, 54(4) 415-421.

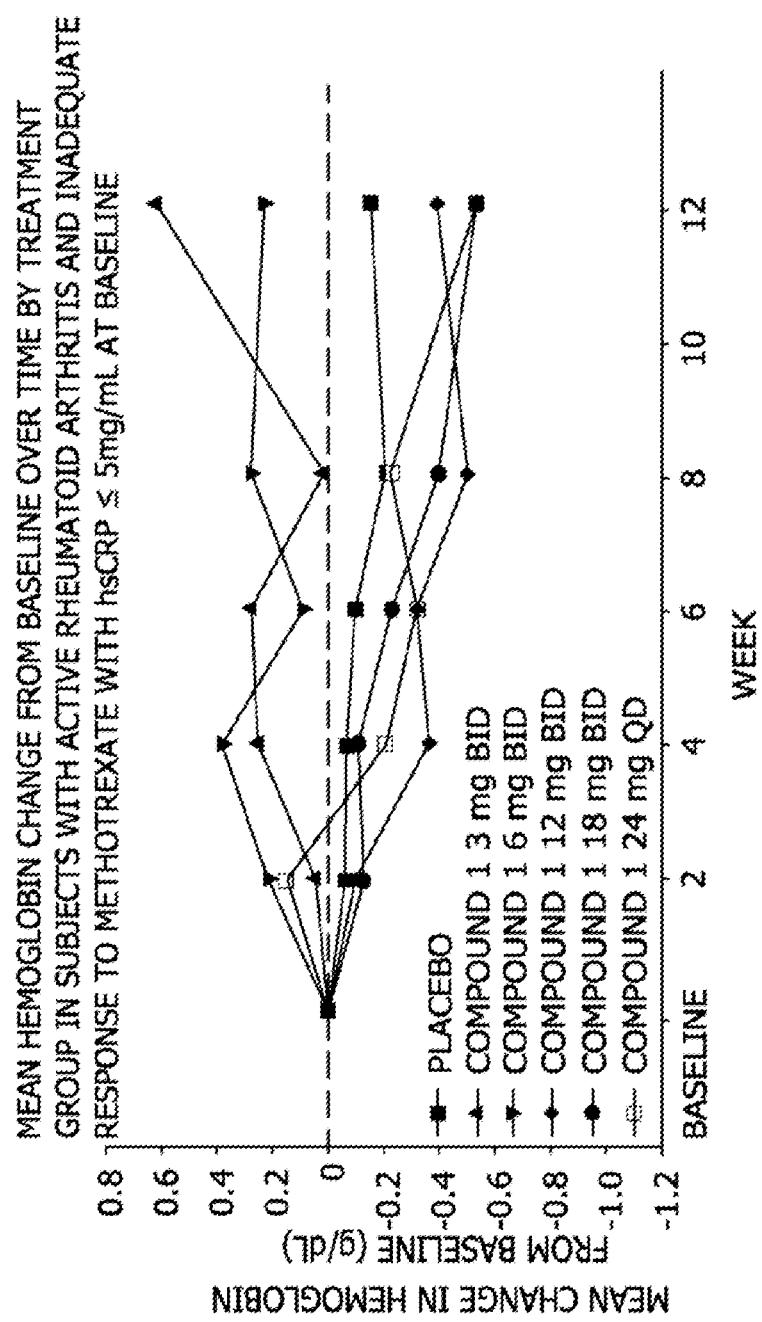

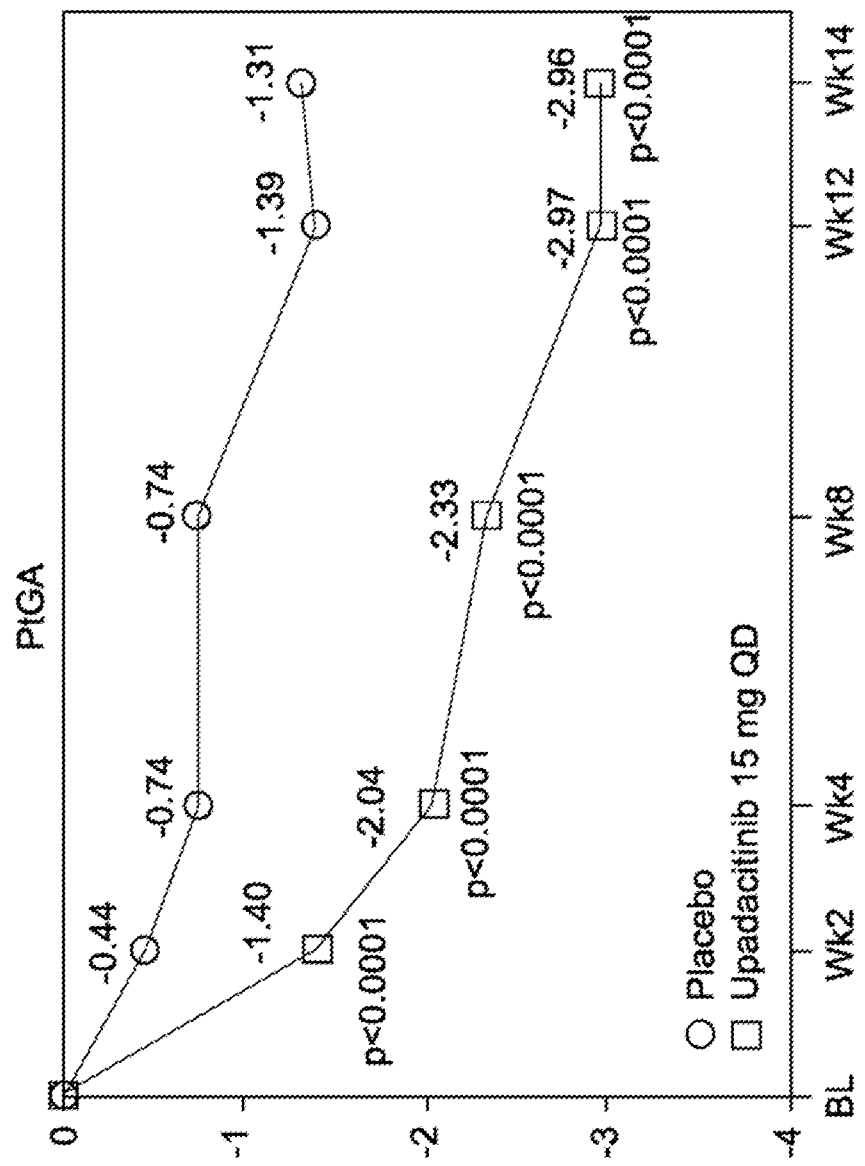

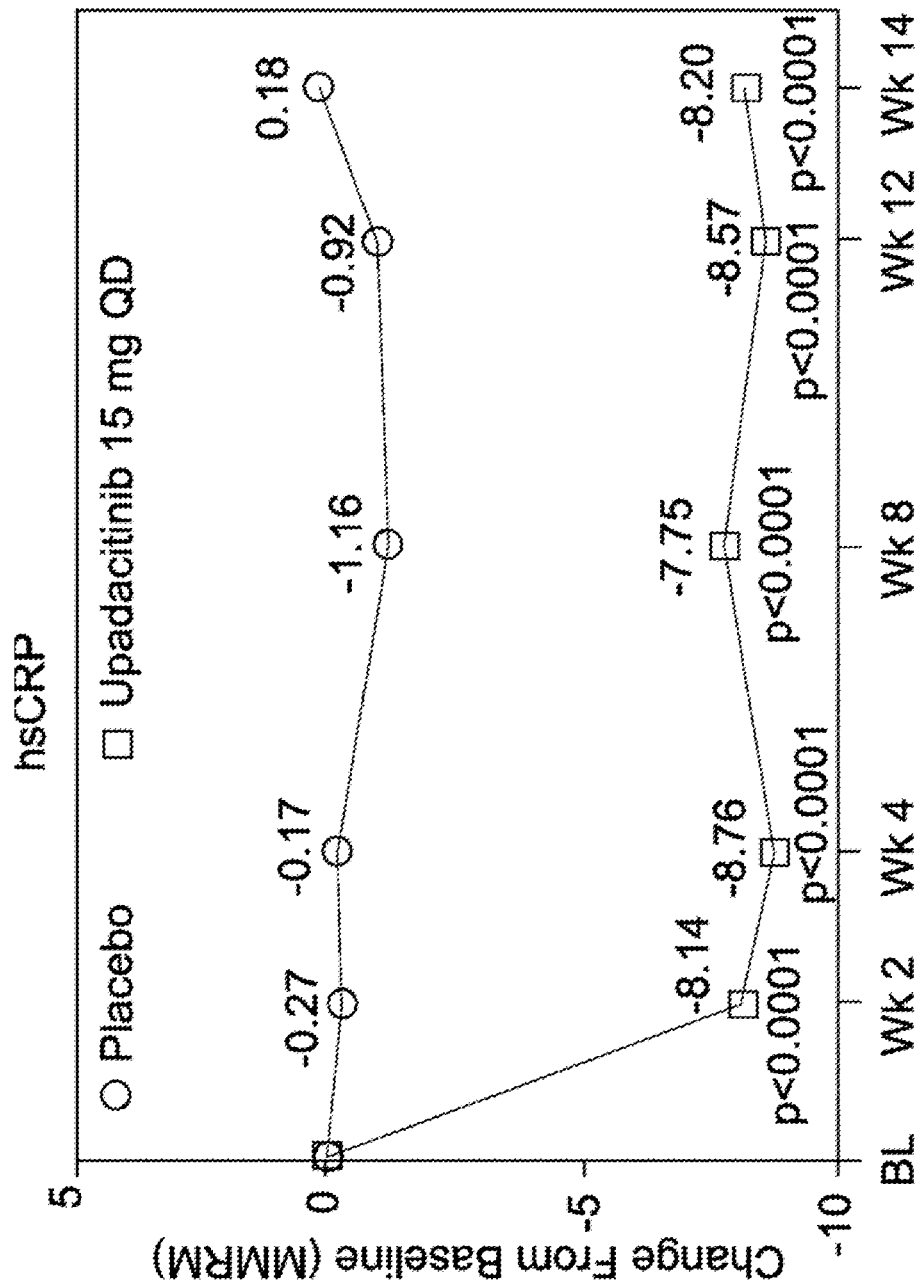

PROCESSES FOR THE PREPARATION OF (3S,4R)-3-ETHYL-4-(3H-IMIDAZO[1,2-A] PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

CROSS-REFERENCE TO RELATED APPLICATIONS

This application is a continuation of U.S. patent application Ser. No. 18/093,222, filed Jan. 4, 2023, which is a continuation of U.S. patent application Ser. No. 17/668,249, filed Feb. 9, 2022, which is a continuation of U.S. patent application Ser. No. 17/527,717, filed Nov. 16, 2021, now U.S. Pat. No. 11,365,198, issued Jun. 21, 2022, which is a continuation-in-part of U.S. patent application Ser. No. 17/184,194, filed Feb. 24, 2021, which is a continuation of U.S. patent application Ser. No. 16/656,237, filed Oct. 17, 2019, which is a continuation of U.S. patent application Ser. No. 15/891,012, filed Feb. 7, 2018, which is a continuation of U.S. patent application Ser. No. 15/295,561, filed Oct. 17, 2016, and which claims the benefit of U.S. Provisional Application No. 62/242,797, filed Oct. 16, 2015; and claims the benefit of U.S. Provisional Application No. 62/267,672, filed Dec. 15, 2015; and claims the benefit of U.S. Provisional Application No. 62/301,537, filed Feb. 29, 2016; and claims the benefit of U.S. Provisional Application No. 62/352,380, filed Jun. 20, 2016; all of which are herein incorporated by reference in their entirety and for all purposes. The '717 application is also a continuation-in-part of U.S. patent application Ser. No. 17/039,470, filed Sep. 30, 2020, which claims priority to U.S. Provisional Patent Application No. 63/032,042, filed on May 29, 2020; U.S. Provisional Patent Application No. 62/968,849, filed Jan. 31, 2020; U.S. Provisional Patent Application No. 62/927,548, filed Oct. 29, 2019; and U.S. Provisional Patent Application No. 62/908,163, filed Sep. 30, 2019, all of which are herein incorporated by reference in their entirety and for all purposes.

FIELD OF THE INVENTION

The present disclosure relates to: (a) processes for the preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (referred to herein as "Compound 1"), (b) intermediates used in the preparation of Compound 1 and processes for preparing the intermediates; (c) solid state forms of Compound 1, (d) pharmaceutical compositions comprising one or more solid state forms of Compound 1, and, optionally, one or more additional therapeutic agents; (e) methods of treating Janus kinase-associated conditions (including rheumatoid arthritis) by administering one or more solid state forms of Compound 1 to a subject in need thereof; (f) kits comprising a first pharmaceutical composition comprising a solid state form of Compound 1, and, optionally, a second pharmaceutical composition comprising one or more additional therapeutic agents; (g) methods for the preparation of solid state forms of Compound 1; and (h) solid state forms of Compound 1 prepared in accordance with such methods.

BACKGROUND OF THE INVENTION (3S,4R)-3-ethyl-4-(3H-imidazo[1,2-a]pyrrolo[2,3-e]pyrazin-8-yl)-N-(2,2,2-trifluoroethyl)pyrrolidine-1-carbox-amide ("Compound 1") was first disclosed in International Application WO2011/068881A1, which is herein incorporated by reference in its entirety. The compound has activity as a Janus kinase ("JAK") inhibitor, particularly as a JAK-1 inhibitor. Clinical trials are ongoing to evaluate the use of the compound to treat rheumatoid arthritis.

The isolation and commercial-scale preparation of a solid state form of Compound 1 and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges that are discussed in greater detail below. Accordingly, there is a current need for one or more solid state forms of Compound 1 that have an acceptable balance of these properties and can be used in the preparation of pharmaceutically acceptable solid dosage forms.

Additionally, currently known processes for the preparation of Compound 1 involve the use of particularly hazardous reagents, such as trimethylsilyldiazomethane or diazomethane, and do not produce a crystalline product. There is thus also a need for a process for preparing Compound 1, and pharmaceutically acceptable salts thereof, that avoids the use of particularly hazardous reagents, and can produce a crystalline product and crystalline intermediates.

Additionally, sustained peak plasma concentrations can theoretically be achieved by means of sustained release matrix systems. However, when such systems are made of hydrophilic polymers, such as HPMC, they seldom provide pH independent drug release of pH-dependent soluble drugs, and they are normally incapable of attaining zero-order release except for practically insoluble drugs. Unexpectedly, is has been discovered that when tartaric acid is used as a pH-modifier in such a system, it allows Compound 1 to be released at a steady rate regardless of the pH of the environment.

In an unexpected finding, it was discovered that as a tablet containing the hydrophilic polymer matrix system erodes, Compound 1 reacts with the HPMC, creating a thicker gel layer which slows the release of Compound 1 from the tablet. The resulting gel layer provided an environment suitable for Compound 1 to dissolve.

Axial spondyloarthritis (axSpA) encompasses a spectrum of inflammatory involvement of the axial skeleton. Based on the Assessment of SpondyloArthritis International Society (ASAS) axSpA criteria, the disease can be further divided into 2 categories by radiographic findings: ankylosing spondylitis (AS), and an "early" form of axial SpA, referred to as non-radiographic axial spondyloarthritis (nr-axSpA). Patients with nr-axSpA and AS share common epidemiological, genetic, and clinical disease characteristics, including with regard to disease activity, and similar response to treatment. See, e.g., Poddubnyy and Sieper, *Curr Opin Rheumatol*. (2014) 26:377-383.

Per international treatment recommendations, nonsteroidal anti-inflammatory drugs (NSAIDs) are the first-line therapy in axSpA. See, e.g., van der Heijde D et al., *Ann Rheum Dis*. (2017) 76:978-991; Ward et al., *Arthritis Rheumatol*. (2016) 68:282-298. After failure of two NSAIDs given over a maximum of four weeks, biologic disease-modifying anti-rheumatic drugs (bDMARDs) are the next recommended treatment option. In axSpA, conventional synthetic disease-modifying anti-rheumatic drugs (csDMARDs) and long-term corticosteroids are not efficacious and therefore not recommended for treatment of axial symptoms. See, e.g., van der Heijde D et al., *Ann Rheum Dis*.

(2017) 76:978-991. Furthermore, only approximately 45% to 50% of patients show an Assessment of SpondyloArthritis International Society 40 (ASAS40) response and only approximately 15% to 20% achieve a state of remission in biologic-naïve patients, and response rates are even less in axSpA patients who had an inadequate response to bDMARDs. See, e.g., Sieper and Poddubnyy, *Lancet* (2017) 390:73-84; Sieper et al., *Ann Rheum Dis.* (2017) 76:571-592; Rudwaleit et al., *Arthritis Res Ther.* (2010) 12:R117; Deodhar et al., *Arthritis Rheumatol.* (2019) 71:599-611. To date, other than NSAIDs, there have been no oral targeted therapies approved for the treatment of ankylosing spondylitis (AS) or non-radiographic axSpA.

Psoriatic Arthritis (PsA) is a chronic systemic inflammatory disease classified as a sub-type of spondyloarthritis (SpA) and characterized by the association of arthritis and psoriasis. The course of PsA is usually characterized by flares and remissions. Left untreated, patients with PsA can have persistent inflammation, progressive joint damage, disability, and a reduced life expectancy. Initial treatment of the musculoskeletal symptoms is composed of nonsteroidal anti-inflammatory drugs (NSAIDs) and local corticosteroid injections, while topical therapies are used for the initial treatment of psoriasis. For subjects who experience lack of efficacy or toxicity with these measures, systemic therapy with non-biologic disease modifying anti-rheumatic drugs (non-biologic DMARDs) (e.g., methotrexate [MTX], leflunomide [LEF], sulfasalazine [SSZ]) and ciclosporin A, followed by anti-tumor necrosis factor (TNF) therapy in subjects who do not respond adequately, is recommended. Other biologic therapies (e.g., IL-12/23 or IL-17 inhibitors) are also recommended as alternatives to anti-TNF inhibitors in selected PsA subjects. See, e.g., Gossec et al., *Ann Rheum Dis.* (2016) 75:499-510; Coates et al., *Arthritis Rheumatol.* (2016) 68:1060-71. However, despite the beneficial results achieved with currently available biologic agents, approximately 40% of patients do not have at least 20% improvement in American College of Rheumatology (ACR) scores and only 58% to 61% of patients with PsA who receive them are able to achieve clinical remission after 1 year of treatment, with only approximately 43% achieving sustained remission for at least 1 year. See, e.g., Gossec et al., *Ann Rheum Dis.* (2016) 75:499-510; Alamanos et al., *J Rheumatol.* (2003) 30:2641-2644; Savolainen et al., *J Rheumatol.* (2003) 30:2460-8; Sandborn, *Dig Dis.* (2010) 28:536-42; Saber et al., *Arthritis Res Therapy* (2010) 12: R94; Perrotta et al., *J Rheumatol.* (2016) 43:350-5.

Thus, there continues to remain a clear medical need for additional therapeutic options for the treatment of non-radiographic axial spondyloarthritis (nr-axSpA), ankylosing spondylitis (AS), psoriatic arthritis (PsA), and psoriasis (PsO), including PsO as a skin manifestation of PsA.

SUMMARY OF THE INVENTION

In another aspect, the present disclosure relates to pharmaceutical compositions comprising one or more solid state forms of Compound 1, and, optionally, one or more additional therapeutic agents.

In another aspect, the present disclosure relates to methods of treating a JAK-associated condition (such as rheumatoid arthritis) in a human subject suffering from or susceptible to such a condition comprising administering to the subject a therapeutically effective amount of a solid state form of Compound 1. In another aspect, the disclosure relates to a pharmaceutical composition comprising a therapeutically effective amount of a solid state form of Compound 1 as described in the present disclosure, for use in treatment of a JAK-associated condition (such as rheumatoid arthritis) in a subject, particularly in a human subject suffering from or susceptible to the condition.

In another aspect, the present disclosure relates to methods of treating rheumatoid arthritis, wherein the term "rheumatoid arthritis" includes juvenile rheumatoid arthritis, juvenile idiopathic arthritis, ankylosing spondylitis disease, Sjogren's syndrome, psoriatic arthritis.

In another aspect, the present disclosure relates to methods of treating inflammatory bowel disease, wherein the term "inflammatory bowel disease" includes Crohn's disease, pediatric Crohn's disease and ulcerative colitis.

In another aspect, the present disclosure relates to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis and systemic lupus erythematosus in a human subject suffering from or susceptible to such a condition, the method comprising administering to the subject a therapeutically effective amount a solid state form of Compound 1. In another aspect, the disclosure relates to a pharmaceutical composition comprising a therapeutically effective amount of a solid state form of Compound 1 as described in the present disclosure, for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition.

In another aspect, the present disclosure relates to methods of treating a JAK-associated condition (such as rheumatoid arthritis) in a human subject suffering from or susceptible to such a condition comprising administering to the subject a solid state form of Compound 1, in combination with one or more additional therapeutic agents (e.g., a therapeutic agent for treating rheumatoid arthritis that is not a JAK inhibitor). In another aspect, the disclosure relates to a pharmaceutical composition comprising a solid state form of Compound 1, as described in the present disclosure, in combination with one or more additional therapeutic agents (e.g., a therapeutic agent for treating rheumatoid arthritis that is not a JAK inhibitor), for use in treatment of a JAK-associated condition (such as rheumatoid arthritis) in a subject, particularly in a human subject suffering from or susceptible to the condition.

In another aspect, the present disclosure relates to a method of treating moderate to severely active rheumatoid arthritis, the method comprising administering a therapeutically effective amount of Compound 1 in one or more forms as disclosed herein to a subject suffering from or susceptible to the condition. In a particular aspect, such a method may comprise administering 7.5 mg once daily or 15 mg once daily, or 30 mg once daily, or 45 mg once daily of the Compound 1, in one or more forms as disclosed herein, to the subject. In this or another particular aspect, the subject may be administered the Compound 1 in Freebase Form C. In this or yet another particular aspect, the subject may have an inadequate response to methotrexate. In this or yet another particular aspect, the subject may have an inadequate response to biologics medicines approved for rheumatoid arthritis. In this or yet another particular aspect, the subject may have not previously been administered biologics medicines approved for rheumatoid arthritis.

In another aspect, the present disclosure relates to a method of treating an adult subject having moderate to severely active rheumatoid arthritis, the method comprising administering to the subject: a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent. In one embodiment, the present disclosure is directed to a pharmaceutical composition for use in treating an adult subject having moderate to severely active rheumatoid arthritis, the use comprising administering the pharmaceutical composition to the subject, wherein the pharmaceutical composition comprises a) about 7.5 mg of Compound 1 freebase, or a pharmaceutically acceptable salt thereof, or a crystalline hydrate or a crystalline anhydrate of Compound 1 in an amount sufficient to deliver to the subject about 7.5 mg of Compound 1 freebase equivalent; or b) about 15 mg of Compound 1 freebase, or a pharmaceutically acceptable salt thereof, or a crystalline hydrate or a crystalline anhydrate of Compound 1 in an amount sufficient to deliver to the subject about 15 mg of Compound 1 freebase equivalent; or c) about 30 mg of Compound 1 freebase, or a pharmaceutically acceptable salt thereof, or a crystalline hydrate or a crystalline anhydrate of Compound 1 in an amount sufficient to deliver to the subject about 30 mg of Compound 1 freebase equivalent; or d) about 45 mg of Compound 1 freebase, or a pharmaceutically acceptable salt thereof, or a crystalline hydrate or a crystalline anhydrate of Compound 1 in an amount sufficient to deliver to the subject about 45 mg of Compound 1 freebase equivalent.

In another embodiment, the present disclosure relates to a method of treating structural damage associated with rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened. In one embodiment, the disclosure relates to a pharmaceutical composition for use in treating structural damage associated with rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; such that the structural damage in the adult subject is inhibited or lessened.

In another aspect, the disclosure is directed to a method of treating moderate to severely active rheumatoid arthritis in an adult subject, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating. In one embodiment, the disclosure is directed to a pharmaceutical composition for use in treating moderate to severely active rheumatoid arthritis in an adult subject, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg per day of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg per day of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg per day of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg per day of Compound 1 freebase equivalent; wherein the subject has symptoms selected from the group consisting of at least 6 swollen joints, at least 6 tender joints, and combinations thereof prior to treating.

In another aspect, the disclosure is directed to a method of reducing signs and symptoms of rheumatoid arthritis in an adult subject with moderately to severely active rheumatoid arthritis, the method comprising administering to the subject: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent. In one embodiment, the disclosure is directed to a pharmaceutical composition for use in reducing signs and symptoms of rheumatoid arthritis in an adult subject with moderately to severely active rheumatoid arthritis, the use comprising administering the pharmaceutical composition to the subject, wherein the pharmaceutical composition comprises: a) about 7.5 mg per day of Compound 1 freebase or a pharmaceutically acceptable salt thereof, or a crystalline hydrate or crystalline anhydrate of Compound 1 in an amount sufficient to deliver to the subject about 7.5 mg of Compound 1 freebase equivalent; or b) about 15 mg per day of Compound 1 freebase or a pharmaceutically acceptable salt thereof, or a crystalline hydrate or crystalline anhydrate of Compound 1 in an amount sufficient to deliver to the subject about 15 mg of Compound 1 freebase equivalent; or c) about 30 mg per day of Compound 1 freebase or a pharmaceutically acceptable salt thereof, or a crystalline hydrate or crystalline anhydrate of Compound 1 in an amount sufficient to deliver to the subject about 30 mg of Compound 1 freebase equivalent; or d) about 45 mg per day of Compound 1 freebase or a pharmaceutically acceptable salt thereof, or a crystalline hydrate or crystalline anhydrate of Compound 1 in an amount sufficient to deliver to the subject about 45 mg of Compound 1 freebase equivalent.

In another aspect, the present disclosure relates to kits comprising one or more pharmaceutical compositions comprising a solid state form of Compound 1. The kit optionally can comprise another pharmaceutical composition comprising one or more additional therapeutic agents and/or instructions, for example, instructions for using the kit.

In another aspect, the present disclosure relates to methods for the preparation of a solid state form of Compound 1.

In another aspect, the present disclosure relates to solid state forms of Compound 1 prepared in accordance with such methods.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of Compound 1 freebase, or a crystalline hydrate of Compound 1 in an amount sufficient to deliver to the subject about 7.5 mg, or about 15 mg, or about 30 mg, or about 45 mg of Compound 1 freebase equivalent. In this or another particular aspect, the hydrate may be a hemihydrate. In this or another aspect, the hemihydrate may be Freebase Hydrate Form C. In this or yet another particular aspect, the subject may have an inadequate response or tolerance to one or more disease-modifying antirheumatic drugs (DMARDS), such as methotrexate. In this or yet another particular aspect, the subject may have not previously been administered DMARDS. In this or yet another particular aspect, the subject may further be administered one or more DMARD.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of Compound 1 freebase or a crystalline hydrate of Compound 1 in an amount sufficient to deliver to the subject about 7.5 mg, or about 15 mg, or about 30 mg, or about 45 mg per day of Compound 1 freebase equivalent, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg per day of Compound 1 freebase or a crystalline hydrate of Compound 1 in an amount sufficient to deliver to the subject about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 15 mg per day of Compound 1 freebase or a crystalline hydrate of Compound 1 in an amount sufficient to deliver to the subject about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 30 mg per day of Compound 1 freebase or a crystalline hydrate of Compound 1 in an amount sufficient to deliver to the subject about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 45 mg per day of Compound 1 freebase or a crystalline hydrate of Compound 1 in an amount sufficient to deliver to the subject about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a method of treating an adult subject having moderate to severely active rheumatoid arthritis, the method comprising administering to the subject about 7.5 mg, or about 15 mg, or about 30 mg, or about 45 mg of a crystalline hydrate of Compound 1. In this or another particular aspect, the hydrate may be a hemihydrate. In this or another aspect, the hemihydrate may be Freebase Hydrate Form C.

In another aspect, the present disclosure relates to a method of treating structural damage associated with rheumatoid arthritis in an adult subject, the method comprising administering to the subject about 7.5 mg, or about 15 mg, or about 30 mg, or about 45 mg per day of a crystalline hydrate of Compound 1, such that the structural damage in the adult subject is inhibited or lessened. In this or another particular aspect, the hydrate may be a hemihydrate. In this or another aspect, the hemihydrate may be Freebase Hydrate Form C.

In another aspect, the present disclosure relates to a method of treating moderate to severely active rheumatoid arthritis in an adult subject, the method comprising administering to the subject about 7.5 mg, or about 15 mg, or about 30 mg, or about 45 mg per day of a crystalline hydrate of Compound 1, wherein the subject has symptoms selected from the group consisting of at least 6 swollen joints, at least 6 tender joints, and combinations thereof prior to treating. In this or another particular aspect, the hydrate may be a hemihydrate. In this or another aspect, the hemihydrate may be Freebase Hydrate Form C.

In another aspect, the present disclosure relates to a method of reducing signs and symptoms of rheumatoid arthritis in an adult subject with moderately to severely active rheumatoid arthritis, the method comprising administering to the subject about 7.5 mg, or about 15 mg, or about 30 mg, or about 45 mg per day of a crystalline hydrate of Compound 1. In this or another particular aspect, the hydrate may be a hemihydrate. In this or another aspect, the hemihydrate may be Freebase Hydrate Form C.

In another aspect, the present disclosure is directed to an extended release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

The present disclosure addresses the above needs and provides methods for treating axial spondyloarthritis (axSpA), including non-radiographic axSpA (nr-axSpA) and ankylosing spondylitis (AS), and for treating psoriatic arthritis (PsA) and psoriasis (PsO), including PsO as a skin manifestation of PsA.

The below recited Embodiments 1-77 set forth certain aspects of the methods as described herein.

Embodiment 1: In certain aspects, provided is a method of treating active ankylosing spondylitis (AS) in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an Assessment of SpondyloArthritis International Society 40 (ASAS40) response within 14 weeks of administration of the first dose.

Embodiment 2: The method of Embodiment 1, wherein when the method is used to treat a population of subjects, at least 10%, at least 15%, at least 20%, at least 25%, at least 30%, at least 35%, at least 40%, or at least 45% of the subjects in the treated population achieve an ASAS40 response within 14 weeks of administration of the first dose. In certain embodiments of the method of Embodiment 1, wherein when the method is used to treat a population of subjects, a statistically significant population of the subjects in the treated population achieves an ASAS40 response within 14 weeks of administration of the first dose.

Embodiment 3: The method of Embodiment 1 or 2, wherein the subject or subjects in the treated population suffering from active AS at baseline further achieve within 14 weeks of administration of the first dose at least one result selected from the group consisting of:
a. improvement from baseline in Ankylosing Spondylitis Disease Activity Score (ASDAS);
b. improvement from baseline in magnetic resonance imaging (MRI) Spondyloarthritis Research Consortium of Canada (SPARCC) score for spine (MRI-Spine SPARCC);
c. ASAS partial remission (PR);
d. Bath Ankylosing Spondylitis Disease Activity Index 50 (BASDAI50) response;
e. improvement from baseline in Bath Ankylosing Spondylitis Functional Index (BASFI);
f. ASDAS low disease activity (LDA);
g. ASDAS inactive disease (ID);
h. ASDAS major improvement (MI); and
i. ASDAS clinically important improvement (CII).

In certain embodiments of the method of Embodiment 1 or 2, when the method is used to treat a population of subjects, at least 10%, at least 15%, at least 20%, at least 25%, at least 30%, at least 35%, at least 40%, or at least 45% of the subjects in the treated population achieve at least one of these results within 14 weeks of administration of the first dose. In other embodiments of the method of Embodiment 1 or 2, when the method is used to treat a population of subjects, a statistically significant population of subjects in the treated population achieves at least one result within 14 weeks of administration of the first dose.

Embodiment 4: The method of Embodiment 3, wherein the subject or subjects in the treated population suffering from active AS at baseline further achieve within 14 weeks of administration of the first dose each result.

Embodiment 5: The method of any one of Embodiments 1-4, wherein the subject or subjects in the treated population fulfill the 1984 modified New York Criteria for ankylosing spondylitis at baseline.

Embodiment 6: The method of any one of Embodiments 1-5, wherein the subject or subjects in the treated population fulfill the 2009 ASAS classification criteria at baseline.

Embodiment 7: The method of any one of Embodiments 1-6, wherein the subject or subjects in the treated population meet at least one criteria at baseline selected from the group consisting of:
a. a Bath Ankylosing Spondylitis Disease Activity Index (BASDAI) score ≥4;
b. an Ankylosing Spondylitis Disease Activity Score (ASDAS) of ≥2.1; and
c. a Patient's Assessment of Total Back Pain (Total Back Pain score) of ≥4 based on a 0-10 numerical rating scale.

Embodiment 8: The method of any one of Embodiments 1-7, wherein the subject or subjects in the treated population are biologic disease-modifying anti-rheumatic drug (bDMARD) naïve at baseline.

Embodiment 9: The method of any one of Embodiments 1-7, wherein the subject or subjects in the treated population have had an inadequate response or intolerance to a biologic disease-modifying anti-rheumatic drug (bDMARD) at baseline.

Embodiment 10: The method of Embodiment 9, wherein prior to administration of the first dose, the subject or subjects in the treated population have been administered one bDMARD, and discontinued use of the bDMARD due to intolerance or lack of efficacy.

Embodiment 11: The method of Embodiment 10, wherein the bDMARD is a tumor necrosis factor (TNF) inhibitor or an interleukin (IL)-17 inhibitor.

Embodiment 12: The method of any one of Embodiments 1-11, wherein the subject or subjects in the treated population have had an inadequate response or intolerance to at least two NSAIDs, intolerance to NSAIDS, and/or contraindication for NSAIDs at baseline.

Embodiment 13: In other aspects, provided is a method of treating active non-radiographic axial spondyloarthritis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an ASAS40 response within 14 weeks of administration of the first dose. In certain embodiments, when the method is used to treat a population of subjects, at least 10%, at least 15%, at least 20%, at least 25%, at least 30%, at least 35%, at least 40%, or at least 45% of the subjects in the treated population achieve an ASAS40 response within 14 weeks of administration of the first dose. In certain embodiments, a statistically significant population of subjects in the treated population achieve an ASAS40 response within 14 weeks of administration of the first dose.

Embodiment 14: In yet other aspects, provided is a method of treating active non-radiographic axial spondyloarthritis in a subject in need thereof, the method comprising orally administering to the subject once a day for at least 52 weeks a dose of upadacitinib freebase, or a pharmaceutically acceptable salt thereof, in an amount sufficient to deliver 15 mg of upadacitinib freebase equivalent, wherein the subject achieves an ASAS40 response within 52 weeks of administration of the first dose. In certain embodiments, when the method is used to treat a population of subjects, at least 10%, at least 15%, at least 20%, at least 25%, at least 30%, at least 35%, at least 40%, or at least 45% of the subjects in the treated population achieve an ASAS40 response within 52 weeks of administration of the first dose. In certain embodiments, a statistically significant population of subjects in the treated population achieves an ASAS40 response within 52 weeks of administration of the first dose.

Embodiment 15: The method of Embodiment 13 or 14, wherein the subject or subjects in the treated population fulfill at baseline the 2009 ASAS classification criteria for axial spondyloarthritis, but does not meet the radiologic criteria of the 1984 modified New York criteria for ankylosing spondylitis.

Embodiment 16: The method of Embodiment 13 or 14, wherein the subject or subjects in the treated population meet at least one criteria at baseline selected from the group consisting of:
a. Bath Ankylosing Spondylitis Disease Activity Index (BASDAI) score of ≥4;
b. an Ankylosing Spondylitis Disease Activity Score (ASDAS) of ≥2.1;
c. a Patient's Assessment of Total Back Pain (Total Back Pain score) of ≥4 based on a 0-10 numerical rating scale; and
d. an objective sign of inflammatory activity selected from the group consisting of:
i. an objective sign of active inflammation on MRI of sacroiliac (SI) joints, and
ii. high-sensitivity C reactive protein >upper limit of normal (ULN).

Embodiment 17: The method of any one of Embodiments 13-16, wherein the subject or subjects in the treated population are bDMARD naïve at baseline.

Embodiment 18: The method of any one of Embodiments 13-16, wherein the subject or subjects in the treated population have had an inadequate response or intolerance to a bDMARD at baseline.

Embodiment 19: The method of Embodiment 18, wherein prior to administration of the first dose, the subject or subjects in the treated population have been administered one bDMARD, and discontinued use of the bDMARD due to intolerance or lack of efficacy.

Embodiment 20: The method of Embodiment 19, wherein the bDMARD is a tumor necrosis factor (TNF) inhibitor or an interleukin (IL)-17 inhibitor.

Embodiment 21: The method of any one of Embodiments 13-20, wherein the subject or subjects in the treated population have had an inadequate response or intolerance to at least 2 NSAIDs, has an intolerance to NSAIDS, and/or has a contraindication for NSAIDs at baseline.

Embodiment 22: The method of any one of Embodiments 13-21, wherein the subject or subjects in the treated population achieve within 14 weeks of administration of the first dose at least one additional result selected from the group consisting of:
  a. improvement from baseline in Ankylosing Spondylitis Disease Activity Score (ASDAS);
  b. improvement from baseline in magnetic resonance imaging (MRI) Spondyloarthritis Research Consortium of Canada (SPARCC) score for SI joints (MRI-SI joints SPARCC);
  c. ASAS partial remission (PR);
  d. Bath Ankylosing Spondylitis Disease Activity Index (BASDAI) 50 response;
  e. improvement from baseline in Bath Ankylosing Spondylitis Functional Index (BASFI);
  f. improvement from baseline in Ankylosing Spondylitis Quality of Life (ASQoL);
  g. improvement from baseline in ASAS Health Index (HI);
  h. improvement from baseline in Maastricht Ankylosing Spondylitis Enthesitis Score (MASES); and
  i. improvement from baseline in Linear Bath Ankylosing Spondylitis Metrology Index ($BASMI_{lin}$).

In certain embodiments of the method of any one of Embodiments 13-21, wherein when the method is used to treat a population of subjects, at least 10%, at least 15%, at least 20%, at least 25%, at least 30%, at least 35%, at least 40%, or at least 45% of the subjects in the treated population achieve at least one result within 14 weeks of administration of the first dose. In certain embodiments of the method of any one of Embodiments 13-21, wherein when the method is used to treat a population of subjects, a statistically significant population of subjects in the treated population achieves at least one result within 14 weeks of administration of the first dose.

Embodiment 23: In yet other aspects, provided is a method of treating active psoriatic arthritis (PsA) in a subject in need thereof, the method comprising orally administering to the subject once a day for at least 12 weeks a dose of upadacitinib freebase, or a pharmaceutically acceptable salt thereof, in an amount sufficient to deliver 15 mg of upadacitinib freebase equivalent, wherein the subject achieves an American College of Rheumatology 20% (ACR20) response within 12 weeks of administration of the first dose.

Embodiment 24: In still yet other aspects, provided is a method of treating active psoriatic arthritis (PsA) in a subject in need thereof, the method comprising orally administering to the subject once a day for at least 12 weeks a dose of upadacitinib freebase, or a pharmaceutically acceptable salt thereof, in an amount sufficient to deliver 30 mg of upadacitinib free base equivalent, wherein the subject achieves an American College of Rheumatology 20% (ACR20) response within 12 weeks of administration of the first dose.

Embodiment 25: The method of Embodiment 23 or 24, wherein when the method is used to treat a population of subjects, at least 10%, at least 15%, at least 20%, at least 25%, at least 30%, at least 35%, at least 40%, or at least 45% of the subjects in the treated population achieve an ACR20 response within 12 weeks of administration of the first dose. In other embodiments of the method of Embodiment 23 or 24, when the method is used to treat a population of subjects, a statistically significant population of subjects in the treated population achieves an ACR20 response within 12 weeks of administration of the first dose.

Embodiment 26: The method of any one of Embodiments 23-25, wherein the subject or subjects in the treated population suffering from active PsA at baseline further achieve at least one result selected from the group consisting of:
  a. improvement from baseline in Health Assessment Questionnaire—Disability Index (HAQ-DI) within 12 weeks of administration of the first dose;
  b. achieve Static Investigator Global Assessment (sIGA) of Psoriasis of 0 or 1 and at least a 2-point improvement from baseline at within 16 weeks of administration of the first dose (for subjects with baseline sIGA≥2);
  c. achieve Psoriasis Area Severity Index (PASI) 75 response within 16 weeks of administration of the first dose (for subjects with ≥3% BSA psoriasis at baseline);
  d. improvement from baseline in Sharp/van der Heijde Score (SHS) within 24 weeks of administration of the first dose;
  e. achieve Minimal Disease Activity (MDA) within 24 weeks of administration of the first dose;
  f. improvement from baseline in Leeds Enthesitis Index (LEI) within 24 weeks of administration of the first dose, preferably wherein the improvement is a resolution of enthesitis (LEI=0) within 24 weeks of administration of the first dose (for subjects with baseline presence of enthesitis (LEI>0));
  g. achieve ACR 20 response within 12 weeks of administration of the first dose (non-inferiority of upadacitinib vs adalimumab);
  h. improvement from baseline in 36-Item Short Form Health Survey (SF-36) within 12 weeks of administration of the first dose; and
  i. improvement from baseline in Functional Assessment of Chronic Illness Therapy-Fatigue (FACIT-F) Questionnaire within 12 weeks of administration of the first dose.

In certain embodiments, wherein when the method of Embodiments 23-25 is used to treat a population of subjects, at least 10%, at least 15%, at least 20%, at least 25%, at least 30%, at least 35%, at least 40%, or at least 45% of the subjects in the treated population achieve at least one result within 14 weeks of administration of the first dose. In other embodiments, wherein when the method of Embodiments 23-25 is used to treat a population of subjects, a statistically significant population of subjects in the treated population achieve at least one result within 14 weeks of administration of the first dose.

Embodiment 27: The method of Embodiment 26, wherein the subject or subjects in the treated population suffering from active PsA at baseline further achieve each result.

Embodiment 28: The method of anyone of Embodiments 23-27, wherein the subject or subjects in the treated population suffering from active PsA at baseline further achieve at least one result selected from the group consisting of:
  a. ACR 20 response and superiority over adalimumab (40 mg every other week) within 12 weeks of administration of the first dose; and
  b. improvement from baseline in Leeds Dactylitis Index (LDI) within 24 weeks of administration of the first dose, preferably wherein the improvement is a resolution of dactylitis (LDI=0) within 24 weeks of administration of the first dose (for subjects with baseline presence of dactylitis (LDI>0)).

In certain embodiments of Embodiment 28, wherein when the method is used to treat a population of subjects, at least 10%, at least 15%, at least 20%, at least 25%, at least 30%, at least 35%, at least 40%, or at least 45% of the subjects in the treated population achieve at least one result within 14 weeks of administration of the first dose. In other embodiments of Embodiment 28, wherein when the method is used to treat a population of subjects, a statistically significant population of subjects in the treated population achieve at least one result within 14 weeks of administration of the first dose.

Embodiment 29: The method of Embodiment 28, wherein the subject or subjects in the treated population suffering from active PsA further achieve ACR 20 response and superiority over adalimumab (40 mg every other week) within 12 weeks of administration of the first dose. In certain embodiments of Embodiment 29, a statistically significant population of subjects in the treated population achieves an ACR20 response and superiority over adalimumab within 12 weeks of administration of the first dose. In certain embodiments of Embodiment 29, at least 10%, at least 15%, at least 20%, at least 25%, at least 30%, at least 35%, at least 40%, or at least 45% of the subjects in the treated population achieve an ACR20 response and superiority over adalimumab within 12 weeks of administration of the first dose.

Embodiment 30: The method of Embodiment 29, wherein the subject or subjects in the treated population suffering from active PsA are orally administered once a day for at least 12 weeks a dose of upadacitinib freebase, or a pharmaceutically acceptable salt thereof, in an amount sufficient to deliver 30 mg of upadacitinib freebase equivalent.

Embodiment 31: The method of any one of Embodiments 23-30, wherein the subject or subjects in the treated population achieve an ACR 50% response (ACR50) within 12 weeks of administration of the first dose. In certain embodiments of Embodiment 31, a statistically significant population of subjects in the treated population achieves an ACR50 response within 12 weeks of administration of the first dose. In certain embodiments of Embodiment 31, at least 10%, at least 15%, at least 20%, at least 25%, at least 30%, at least 35%, at least 40%, or at least 45% of subjects in the treated population achieve an ACR50 response within 12 weeks of administration of the first dose.

Embodiment 32: The method of any one of Embodiments 23-30, wherein the subject or subjects in the treated population achieve an ACR 70% response (ACR70) within 12 weeks of administration of the first dose. In certain embodiments of Embodiment 32, a statistically significant population of subjects in the treated population achieves an ACR70 response within 12 weeks of administration of the first dose. In certain embodiments of Embodiment 32, at least 10%, at least 15%, at least 20%, at least 25%, at least 30%, at least 35%, at least 40%, or at least 45% of the subjects in the treated population achieve an ACR70 response within 12 weeks of administration of the first dose.

Embodiment 33: The method of any one of Embodiments 23-32, wherein the subject or subjects in the treated population fulfill the Classification Criteria for Psoriatic Arthritis (CASPAR) criteria at baseline.

Embodiment 34: The method of claim of any one of Embodiments 23-33, wherein the subject or subjects in the treated population have at least one criteria selected from the group consisting of ≥3 tender joints (based on 68 joint counts) and ≥3 swollen joints (based on 66 joint counts) at baseline.

Embodiment 35: The method of Embodiment 34, wherein the subject or subjects in the treated population have ≥5 tender joints (based on 68 joint counts) and ≥5 swollen joints (based on 66 joint counts) at baseline.

Embodiment 36: The method of any one of Embodiments 23-35, wherein the subject or subjects in the treated population have at least one criteria selected from the group consisting of ≥1 erosion on x-ray as determined by central imaging review, and hs-CRP>laboratory defined upper limit of normal (ULN) at baseline.

Embodiment 37: The method of any one of Embodiments 23-36, wherein the subject or subjects in the treated population have a diagnosis of active plaque psoriasis, or the subject has a documented history of plaque psoriasis at baseline.

Embodiment 38: The method of any one of Embodiments 23-36, wherein the subject or subjects in the treated population have had an inadequate response or intolerance to at least one biologic disease-modifying anti-rheumatic drug (bDMARD) at baseline.

Embodiment 39: The method of Embodiment 38, wherein the subject or subjects in the treated population have discontinued all bDMARDs prior to administration of the first dose.

Embodiment 40: The method of any one of Embodiments 23-36, wherein the subject or subjects in the treated population have had an inadequate response or intolerance to previous or concurrent treatment with at least one non-biologic DMARD, or an intolerance to or contraindication for non-biologic DMARDs at baseline.

Embodiment 41: The method of any one of Embodiments 23-40, wherein the subject or subjects in the treated population have moderately to severely active psoriatic arthritis at baseline.

Embodiment 42: In yet other aspects, provided is a method of treating active psoriasis in a subject in need thereof, the method comprising orally administering to the subject once a day for at least 16 weeks a dose of upadacitinib freebase, or a pharmaceutically acceptable salt thereof, in an amount sufficient to deliver 15 mg of upadacitinib freebase equivalent, wherein the subject achieves a Psoriasis Area Severity Index (PASI) 75 response within 16 weeks of administration of the first dose.

Embodiment 43: In yet other aspects, provided is a method of treating active psoriasis in a subject in need thereof, the method comprising orally administering to the subject once a day for at least 16 weeks a dose of upadacitinib freebase, or a pharmaceutically acceptable salt thereof, in an amount sufficient to deliver 30 mg of upadacitinib freebase equivalent, wherein the subject achieves a Psoriasis Area Severity Index (PASI) 75 response within 16 weeks of administration of the first dose.

Embodiment 44: The method of Embodiment 42 or 43, wherein when the method is used to treat a population of subjects, a portion of the subjects in the treated population achieve a PASI 75 response within 16 weeks of administration of the first dose. In certain embodiments of Embodiment 44, at least 10%, at least 15%, at least 20%, at least 25%, at least 30%, at least 35%, at least 40%, or at least 45% of the subjects in the treated population achieve a PASI 75 response within 16 weeks of administration of the first dose. In other embodiments of Embodiment 44, a statistically significant population of the subjects in the treated population achieve a PASI 75 response within 16 weeks of administration of the first dose.

Embodiment 45: The method of any one of Embodiments 1-44 or 46-77, wherein the subject is an adult subject, or the subjects in the treated population are adult subjects.

Embodiment 46: The method of any one of Embodiments 1-12, wherein the ASAS40 response is maintained or improved after Week 14 by continuing to administer the daily dose. In one aspect, the ASAS40 response is maintained or improved up to and including Week 64.

Embodiment 47: The method of any one of Embodiments 1-12, wherein the subject or subjects in the treated population further achieve ASAS40 within 2 weeks of administration of the first dose.

Embodiment 48: The method of any one of Embodiments 1-12, wherein the subject or subjects in the treated population further achieved ASAS40 within 2 weeks of administration of the first dose, and wherein the ASAS40 is maintained or improved after Week 14 by continuing to administer the daily dose.

Embodiment 49: In another aspect, provided is a method of treating active ankylosing spondylitis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves ASAS partial remission (PR), ASDAS low disease activity (LDA), ASDAS inactive disease (ID), ASDAS major improvement (MI), and/or ASDAS clinically important improvement (CII) within 14 weeks of administration of the first dose.

Embodiment 50: The method of Embodiment 49, wherein when the method is used to treat a population of subjects, a portion of the subjects in the treated population achieve ASAS partial remission (PR), ASDAS low disease activity (LDA), ASDAS inactive disease (ID), ASDAS major improvement (MI), and/or ASDAS clinically important improvement (CII) within 14 weeks of administration of the first dose. In certain embodiments of Embodiment 50, at least 10%, at least 15%, at least 20%, at least 25%, at least 30%, at least 35%, at least 40%, or at least 45% of the subjects in the treated population achieve ASAS partial remission (PR), ASDAS low disease activity (LDA), ASDAS inactive disease (ID), ASDAS major improvement (MI), and/or ASDAS clinically important improvement (CII) within 14 weeks of administration of the first dose. In certain embodiments of Embodiment 50, a statistically significant population of subjects in the treated population achieves ASAS partial remission (PR), ASDAS low disease activity (LDA), ASDAS inactive disease (ID), ASDAS major improvement (MI), and/or ASDAS clinically important improvement (CII) within 14 weeks of administration of the first dose.

Embodiment 51: The method of Embodiment 49 or 50, wherein the subject or subjects in the treated population further achieve within 14 weeks of administration of the first dose each result.

Embodiment 52: The method of any one of Embodiments 49-51, wherein the subject or subjects in the treated population fulfill the 1984 modified New York Criteria for ankylosing spondylitis at baseline.

Embodiment 53: The method of any one of Embodiments 49-51, wherein the subject or subjects in the treated population fulfill the 2009 ASAS classification criteria at baseline.

Embodiment 54: The method of any one of Embodiments 49-53, wherein the subject or subjects in the treated population meet at least one criteria at baseline selected from the group consisting of:
  a. a Bath Ankylosing Spondylitis Disease Activity Index (BASDAI) score ≥4;
  b. an Ankylosing Spondylitis Disease Activity Score (ASDAS) of ≥2.1; and
  c. a Patient's Assessment of Total Back Pain (Total Back Pain score) of ≥4 based on a 0-10 numerical rating scale.

Embodiment 55: The method of any one of Embodiments 49-54, wherein the subject or subjects in the treated population are biologic disease-modifying anti-rheumatic drug (bDMARD) naïve at baseline.

Embodiment 56: The method of any one of Embodiments 49-55, wherein the subject or subjects in the treated population have had an inadequate response or intolerance to a biologic disease-modifying anti-rheumatic drug (bDMARD) at baseline.

Embodiment 57: The method of Embodiments 56, wherein prior to administration of the first dose, the subject or subjects in the population have been administered one bDMARD, and discontinued use of the bDMARD due to intolerance or lack of efficacy.

Embodiment 58: The method of Embodiments 57, wherein the bDMARD is a tumor necrosis factor (TNF) inhibitor or an interleukin (IL)-17 inhibitor.

Embodiment 59: The method of any one of Embodiments 49-58, wherein the subject or subjects in the population have had an inadequate response or intolerance to at least two NSAIDs, intolerance to NSAIDS, and/or contraindication for NSAIDs at baseline.

Embodiment 60: The method of any one of Embodiments 49-59, wherein the ASAS partial remission (PR), ASDAS low disease activity (LDA), ASDAS inactive disease (ID), ASDAS major improvement (MI), and/or ASDAS clinically important improvement (CII) is maintained or improved after Week 14 by continuing to administer the daily dose.

Embodiment 61: The method of any one of Embodiments 49-60, wherein the subject or subjects in the treated population further achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose. In certain embodiments of Embodiment 61, a statistically significant population of subjects in the treated population achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose. In certain embodiments of Embodiment 61, at least 10%, at least 15%, at least 20%, at least 25%, at least 30%, at least 35%, at least 40%, or at least 45% of the subjects in the treated population achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose.

Embodiment 62: The method of any one of Embodiments 2341, wherein the ACR score is maintained or improved after Week 12 by continuing to administer the daily dose.

Embodiment 63: The method of any one of Embodiments 2341 or 62, wherein the subject or subjects in the treated population further achieve ACR20 within 2 weeks of administration of the first dose.

Embodiment 64: The method of any one of Embodiments 42-44, wherein the subject or subjects in the treated population achieve a Psoriasis Area Severity Index (PASI) 90 response within 16 weeks of administration of the first dose.

Embodiment 65: The method of any one of Embodiments 42-44 or 64, wherein the PASI response is maintained or improved after Week 16 by continuing to administer the daily dose.

Embodiment 66: In another aspect, provided is a method of treating active psoriatic arthritis in a subject in need thereof, the method comprising orally administering to the subject once a day for at least 24 weeks a dose of upadacitinib freebase, or a pharmaceutically accept thereof, in an amount sufficient to deliver 15 mg of upadacitinib freebase equivalent, wherein the subject achieves Minimal Disease Activity (MDA) within 24 weeks of administration of the first dose.

Embodiment 67: In another aspect, provided is a method of treating active psoriatic arthritis in a subject in need thereof, the method comprising orally administering to the subject once a day for at least 24 weeks a dose of upadacitinib freebase, or a pharmaceutically acceptable salt thereof, in an amount sufficient to deliver 30 mg of upadacitinib freebase equivalent, wherein the subject achieves Minimal Disease Activity (MDA) within 24 weeks of administration of the first dose.

Embodiment 68: The method of Embodiment 66 or 67, wherein when the method is used to treat a population of subjects, a portion of the subjects in the treated population achieve Minimal Disease Activity (MDA) within 24 weeks of administration of the first dose. In certain embodiments of Embodiment 68, a statistically significant population of the subjects in the treated population achieve Minimal Disease Activity (MDA) within 24 weeks of administration of the first dose. In certain embodiments of Embodiment 68, at least 10%, at least 15%, at least 20%, at least 25%, at least 30%, at least 35%, at least 40%, or at least 45% of the subjects in the treated population achieve Minimal Disease Activity (MDA) within 24 weeks of administration of the first dose.

Embodiment 69: The method of any one of Embodiments 66-68, wherein the subject or subjects in the treated population further achieve a Psoriasis Area Severity Index (PASI) response selected from a PASI 75 response, a PASI 90 response, and a PASI 100 response, within 16 weeks of administration of the first dose, and the PASI response is maintained or improved after Week 16 by continuing to administer the daily dose. In certain embodiments of Embodiment 69, a statistically significant population of subjects in the treated population achieve a PASI 75 response, a PASI 90 response, and a PASI 100 response within 16 weeks of administration of the first dose. In certain embodiments of Embodiment 69, at least 10%, at least 15%, at least 20%, at least 25%, at least 30%, at least 35%, at least 40%, or at least 45% of the subjects in the treated population achieve a PASI 75 response, a PASI 90 response, and a PASI 100 response within 16 weeks of administration of the first dose.

Embodiment 70: The method of any one of Embodiments 23-42, wherein the subject or subjects in the treated population achieve a Psoriasis Area Severity Index (PASI) 75 response within 16 weeks of administration of the first dose. In certain embodiments of Embodiment 70, a statistically significant population of subjects in the treated population achieve a PASI 75 response within 16 weeks of administration of the first dose. In certain embodiments of Embodiment 70, at least 10%, at least 15%, at least 20%, at least 25%, at least 30%, at least 35%, at least 40%, or at least 45% of the subjects in the treated population achieve a PASI 75 response within 16 weeks of administration of the first dose.

Embodiment 71: The method of any one of Embodiments 23-42 or 70, wherein the subject or subjects in the treated population achieve a Psoriasis Area Severity Index (PASI) 90 response within 16 weeks of administration of the first dose.

Embodiment 72: The method of any one of Embodiments 23-42 or 70-71, wherein the subject or subjects in the treated population achieve a Psoriasis Area Severity Index (PASI) 100 response within 16 weeks of administration of the first dose.

Embodiment 73: In another aspect, provided is a method of treating active psoriatic arthritis in a subject in need thereof, the method comprising orally administering to the subject once a day for at least 16 weeks a dose of upadacitinib freebase, or a pharmaceutically acceptable salt thereof, in an amount sufficient to deliver 15 mg of upadacitinib freebase equivalent, wherein the subject achieves a Psoriasis Area Severity Index (PASI) 75 response within 16 weeks of administration of the first dose.

Embodiment 74: In another aspect, provided is a method of treating active psoriatic arthritis in a subject in need thereof, the method comprising orally administering to the subject once a day for at least 16 weeks a dose of upadacitinib freebase, or a pharmaceutically acceptable salt thereof, in an amount sufficient to deliver 30 mg of upadacitinib free base equivalent, wherein the subject achieves a Psoriasis Area Severity Index (PASI) 75 response within 16 weeks of administration of the first dose.

Embodiment 75: The method of Embodiment 73 or 74, wherein when the method is used to treat a population of subjects, a portion subjects in the treated population achieve a PASI 75 response within 16 weeks of administration of the first dose. In certain embodiments of Embodiment 75, a statistically significant population of subjects in the treated population achieve a PASI 75 response within 16 weeks of administration of the first dose. In certain embodiments of Embodiment 75, at least 10%, at least 15%, at least 20%, at least 25%, at least 30%, at least 35%, at least 40%, or at least 45% of the subjects in the treated population achieve a PASI 75 response within 16 weeks of administration of the first dose.

Embodiment 76: The method of any one of Embodiments 73-75, wherein the subject or subjects in the treated population achieve a Psoriasis Area Severity Index (PASI) 90 response within 16 weeks of administration of the first dose.

Embodiment 77: The method of any one of Embodiments 73-76, wherein the subject or subjects in the treated population achieve a Psoriasis Area Severity Index (PASI) 100 response within 16 weeks of administration of the first dose.

BRIEF DESCRIPTION OF THE DRAWINGS

FIGS. 9A-9C show the mean change in hemoglobin from baseline overtime by treatment group in all subjects (FIG. 9A), subjects with hsCRP≤5 mg/mL at baseline (FIG. 9B), and subjects with hsCRP>5 mg/mL at baseline (FIG. 9C) following administration of placebo or various doses of Compound 1 to subjects with active rheumatoid arthritis and inadequate response to methotrexate (safety population with observed data (no imputation of missing values)).

FIG. 12A depicts the ASAS20, ASAS40, ASAS PR, and BASDAI50 Responses at Week 14; FIG. 12B depicts the change from Baseline in SPARCC MRI Spine and SI Joint Scores at Week 14; and FIG. 12C depicts other Multiplicity-Controlled Key Secondary Efficacy Endpoints at Week 14. The results demonstrate the study met its primary endpoint, with statistically significantly more patients treated with upadacitinib freebase versus placebo achieving ASAS40 response at Week 14 (48/93 [51.6%] vs 24/94 [25.5%]; p=0.0003) with a treatment difference (95% CI) of 26.1% (12.6-39.5%). All endpoints were multiplicity controlled, except for ASAS20 and SPARCC MRI ST joint. The multiplicity-controlled secondary endpoints were tested in a sequential manner: ASDAS, SPARCC MRI Spine, group of endpoints tested by Hochberg procedure (BASDAI50, ASQoL, ASAS PR, BASFI, BASMI, MASES, and WPAI), and ASAS HI. For FIGS. 12L-12N, Asterisk (*) indicates P<0.001. Asterisk () P<0.01; and Asterisk (*)

P<0.05. For other Figures. Asterisk (*) indicates statistically significant in multiplicity-controlled analysis, otherwise nominal p values are shown. Accounting for multiplicity adjustment, change from baseline to Week 14 in ASDAS (FIG. 12C), SPARCC MRI spine (FIG. 12B), and BASFI (FIG. 12C) and proportion of patients who achieved BASDAI50 (FIG. 12A) and ASAS PR (FIG. 12A) were statistically significant for upadacitinib freebase versus placebo. FIGS. 12D-12K depict the time course of the ASAS40 (FIG. 12D), ASAS20 (FIG. 12E), ASAS partial remission (PR) (FIG. 12F), BASDAI50 Responses (FIG. 12G), ASDAS inactive disease (ID) (FIG. 12H), ASDAS low disease activity (LDA) (FIG. 12I), ASDAS major improvement (MI) (FIG. 12J), and ASDAS clinically important improvement (CII) (FIG. 12K) up to and including Week 64. At week 14, the placebo group was rescued and administered 15 mg upadacitinib free base (Placebo→Upadacitinib 15 mg QD). Patients who switched from placebo to upadacitinib at week 14 showed a similar efficacy response compared with those who received continuous upadacitinib free base from Day 0. The data suggests upadacitinib 15 mg QD, showing achievement of efficacy at Week 14, and sustaining or even improving upon this efficacy up to and including Week 64, will help to address an unmet need for patients with AS (as well as in patients with non-radiographic axial spondyloarthritis (nr-axSpA)), especially in those patients who have active disease and have inadequately responded to NSAIDs. A significantly higher proportion of patients receiving upadacitinib versus placebo achieved ≥30/6 (FIG. 12L) and ≥50% reduction (FIG. 12M) in Patient's Global Assessment of pain (PtPain) as early as week 2, and ≥70% reduction (FIG. 12N) as early as week 4, and efficacy achieved was sustained thereafter. Patients who switched from placebo to open-label upadacitinib at week 14 generally reached the same level of pain reduction after week 14 as those initially randomized to upadacitinib. MASES assessment includes patients with baseline enthesitis; WPAI assessment includes patients currently employed; SPARCC MRI assessment population as pre-specified in the statistical analysis plan (baseline included MRI data ≤3 days after first dose of study drug, and Week 14 included MRI data up to first dose of Period 2 study drug). ASAS20=Assessment of SpondyloArthritis international Society 20 response. ASAS40=Assessment of SpondyloArthritis international Society 40 response. ASQoL=Ankylosing Spondylitis Quality of Life score, ASDAS=Ankylosing Spondylitis Disease Activity Score. BASDAI50=50% improvement from baseline in Bath Ankylosing Spondylitis Disease Activity Index. BASFI=Bath Ankylosing Spondylitis Functional Index. BASMI=Bath Ankylosing Spondylitis Metrology Index. HI=Health Index. MASES=Maastricht Ankylosing Spondylitis Enthesitis Score. MRI=magnetic resonance imaging. MMRM=mixed model for repeated measures. NRI=non-responder imputation. AO=As Observed. PR=partial remission. QD=once daily. SI, sacroiliac. SPARCC=Spondyloarthritis Research Consortium of Canada. WPAI=Work Productivity and Activity Impairment.

FIGS. 13A-13E depict data for ASAS domains (ASAS40, PtGA, Back Pain, BASFI, and Inflammation) measured at Weeks 2, 4, 8, 12, and 14 in the Phase 2/3 Ankylosing Spondylitis (SELECT-AXIS 1) clinical trial. A significant difference for upadacitinib freebase versus placebo in ASAS40 (FIG. 13A) and the mean change for each of its four individual domains (FIGS. 13B-13E) was observed as early as the first post-baseline visit (Week 2), and this difference was maintained consistently through Week 14, with Week 14 achieving a statistically significant difference in multiplicity-controlled analysis. Back pain defined on a numerical rating scale (0-10) based on the following question, "What is the amount of back pain that you experienced at any time during the last week? Inflammation is defined as mean of Questions 5 and 6 of the BASDAI. BASDAI=Bath Ankylosing Spondylitis Disease Activity Index. BASFI=Bath Ankylosing Spondylitis Functional Index. BL=baseline. LSM=least squares mean. MMRM=mixed model for repeated measures. NRI=non-responder imputation. PtGA=Patient Global Assessment of disease activity. QD=once daily.

FIGS. 17A-17D depict the least squares mean (LSM) change from baseline in individual ASDAS components over time in the Phase 2/3 Ankylosing Spondylitis (SELECT-AXIS 1) clinical trial. Improvement in the mean ASDAS (FIG. 16B) and the individual ASDAS components (FIGS. 17A-17D) was seen as early as Week 2 with continued improvement up to Week 14 with upadacitinib freebase. Spinal pain=BASDAI Question 2. Peripheral pain/swelling=BASDAI Question 3. Duration of morning stiffness=BASDAI Question 6, ASDAS=Ankylosing Spondylitis Disease Activity Index. BL=baseline. hsCRP=high-sensitivity C-reactive protein. MMRM=mixed model for repeated measures. PtGA=Patient Global Assessment of disease activity. QD=once daily.

FIG. 19A, Part 1, describes the testing sequence of the adequately powered ranked secondary endpoints in PsA symptoms and radiographic progression. FIG. 19B, Part 2, describes the testing sequence of additional ranked secondary endpoints including superiority tests versus adalimumab. Part 2 endpoints are tested only after statistical significance of all Part 1 endpoints are achieved.

FIG. 20A depicts the time course of the ACR20 response and associated 95% confidence interval (CI) up to and including Week 24. Response rate (%) with 95% CI is presented by visit. Nominal p-value <0.05 for both UPA doses vs placebo for all visits. UPA=upadacitinib freebase; ADA=adalimumab; QD=once daily; EOW=every other week. Symbols: ***, P<0.001 for upadacitinib vs. placebo; ###, P<0.001 for upadacitinib vs, adalimumab; ζζζ, P<0.001 for non-inferiority upadacitinib vs, adalimumab. Additional key secondary efficacy results include: patients achieving ACR50 response (FIG. 20B); patients achieving ACR70 response (FIG. 20C); patients achieving Minimal Disease Activity (MDA) (FIG. 20D); patients achieving Non-inferiority of Upadacitinib versus Adalimumab in ACR20 at Week 12 (FIG. 20E); patients achieving LS mean change from baseline over 24 weeks in core components of the ACR criteria: tender joint count (TJC68) (FIG. 20F), swollen joint count (SJC66) (FIG. 20G), Physician's global assessment of disease activity (PhGA) (FIG. 20H), patient's global assessment of disease activity (PtGA) (FIG. 20I), Pain (PtPain) (score of 0 indicates "no pain" and a score of 10 indicates "worst possible pain") (FIG. 20J), and high-sensitivity C-reactive protein (hs-CRP) (FIG. 20K); proportion of patients achieving Psoriasis Area Severity Index PASI 75 (FIG. 20L), PASI 9) (FIG. 20M), and PASI 100 (FIG. 20N) over 24 weeks, wherein after week 16 assessments were performed and patients were able to use concomitant treatments specifically for psoriasis per investigator judgment; proportions of patients achieving Static Investigator Global Assessment (sIGA) over 24 weeks (FIG. 20O); change from baseline over 24 weeks in Self-Assessment of Psoriasis Symptoms (SAPS) (FIG. 20P); patients achieving change from baseline over 24 weeks in health assessment questionnaire disability index (HAQ-DI) (FIG. 20Q) and SF-36 Physical Component Summary Score (the PCS is one of two summary scores calculated from the eight SF-36 domains. A linear algorithm is applied to calculate the PCS which has normative mean value of 50, with higher scores indicating better outcomes) (FIG. 20R); patients achieving change from baseline over 24 weeks in Functional Assessment of Chronic Illness Therapy-Fatigue (FACIT-F) (the FACIT-F score ranges from 0-52, with higher scores indicating less fatigue) (FIG. 20S); patients achieving change from baseline over 24 weeks in Morning Stiffness (Mean of BASDAI Questions 5 and 6) (FIG. 20T), Morning Stiffness Severity (BASDAI Question 5) (FIG. 20U), and Morning Stiffness Duration (BASDAI Question 6) (FIG. 20V); Proportion of Patients with Resolution of Enthesis Over 24 Weeks by Leeds Enthesitis Indices (LEI) (FIG. 20W), by Spondyloarthritis Research Consortium of Canada (SPARCC) (FIG. 20X), and Proportion of Patients with Resolution of Dactylitis by Leeds Dactylitis Index (LDI) (FIG. 20Y); patients achieving change from baseline at Week 24 in radiographic endpoints (mTSS=modified total Sharp/van der Heijde Score. JSN=joint space narrowing score) (FIG. 20Z); and proportion of patients with no radiographic progression mTSS≤0.0 ((FIG. 20AA) and mTSS≤0.5 at Week 24 (FIG. 20BB). A significantly higher proportion of patients receiving upadacitinib freebase (15 mg QD or 30 mg QD) versus placebo achieved ≥30% and ≥50% reduction in Patient's Global Assessment of pain (PtPain) as early as week 2, and efficacy achieved was sustained thereafter (see FIGS. 20CC and 20DD). A significantly higher proportion of patients receiving upadacitinib freebase versus placebo achieved ≥70% reduction in PtPain as early as week 2 (30 mg QD upadacitinib) or as early as week 4 (15 mg QD upadacitinib), and efficacy achieved was sustained thereafter (see FIG. 20EE). Symbols: *, statistically significant at 0.05 level (UPA 15 mg QD); ζ, statistically significant at 0.05 level (UPA 30 mg QD); #, statistically significant at 0.05 level (ADA 40 mg EOW);***, P<0.001 for upadacitinib vs. placebo; ###, P<0.001 for upadacitinib vs, adalimumab; ζζζ, P<0.001 for non-inferiority upadacitinib vs, adalimumab; PBO=placebo; ADA=adalimumab; UPA=upadacitinib freebase; EOW=every other week; QD=once daily; CI=confidence interval.

FIG. 22A depicts the time course up to and including Week 24 of the primary endpoint ACR20. Response rate (%) with 95% CI is presented by visit. Nominal p-value <0.05 for both UPA doses vs placebo for all visits. UPA=upadacitinib freebase. Symbols: *=p≤0.05 for comparison of upadacitinib 15 mg QD versus placebo; #=p≤0.05 for comparison of upadacitinib 30 mg QD versus placebo; †=significant in the multiplicity-controlled analysis. Additional key secondary efficacy results include: patients achieving ACR50 response (FIG. 22B); patients achieving ACR70 response (FIG. 22C); proportion of patients achieving Minimal Disease Activity (MDA) over 24 weeks (FIG. 22D); patients achieving change in baseline in Leeds Enthesitis Index (LEI) (FIG. 22E); patients achieving resolution of enthesitis (LEI=0) (FIG. 22F); proportion of patients with resolution of enthesitis over 24 weeks by Spondyloarthritis Research Consortium of Canada (SPARCC) (FIG. 22G); patients achieving change in baseline in Leeds Dactylitis Index (LDI) (FIG. 22H); patients achieving resolution of dactylitis (LDI=0) (FIG.

Figure 22B:
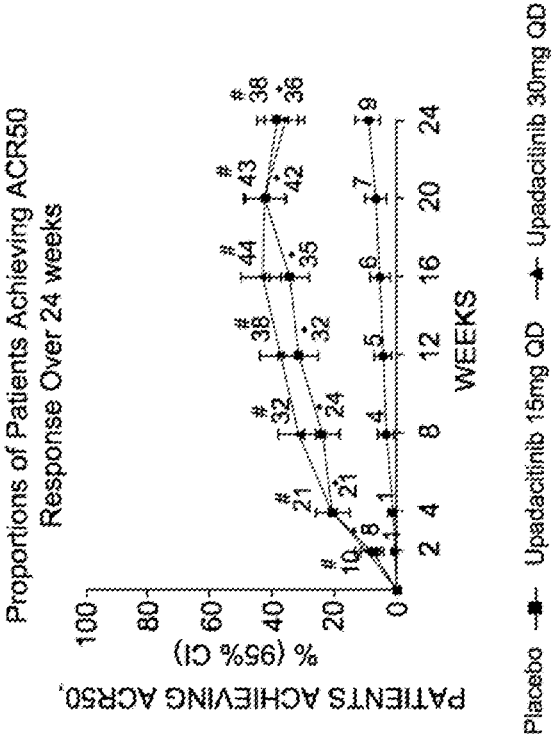
FIGS. 22A-22DD provides a summary of primary and key secondary efficacy results for the SELECT-PSA2 (PsA bDMARD-IR) Phase 3 clinical trial.
Figure 22A:
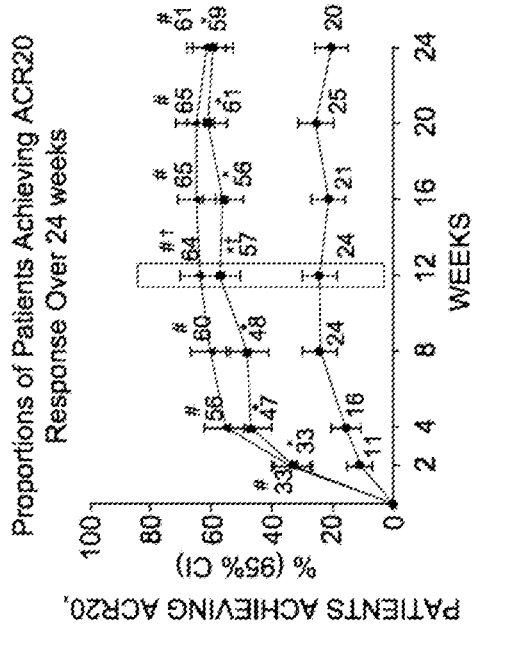
Figure 22D:
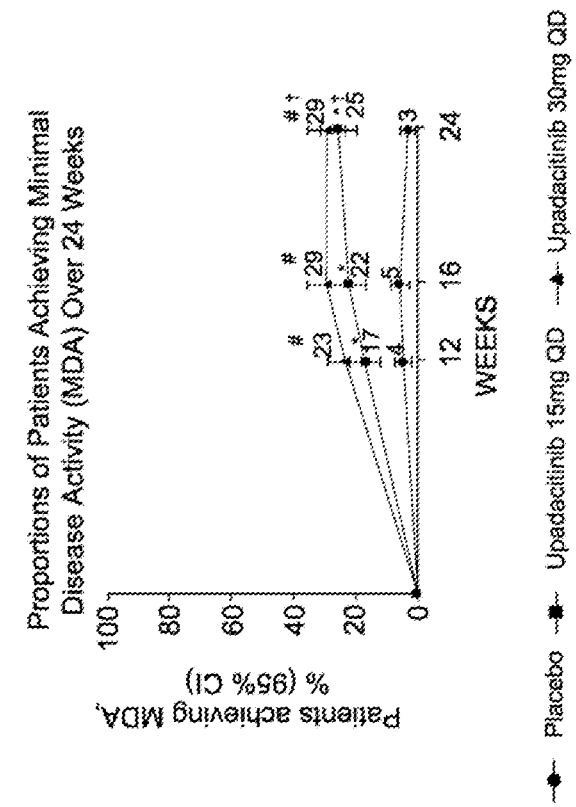
Figure 22C:
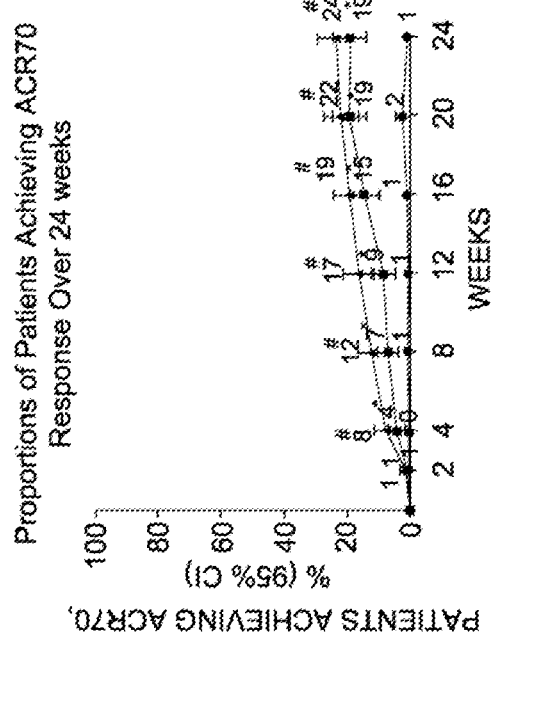
Figure 22E:
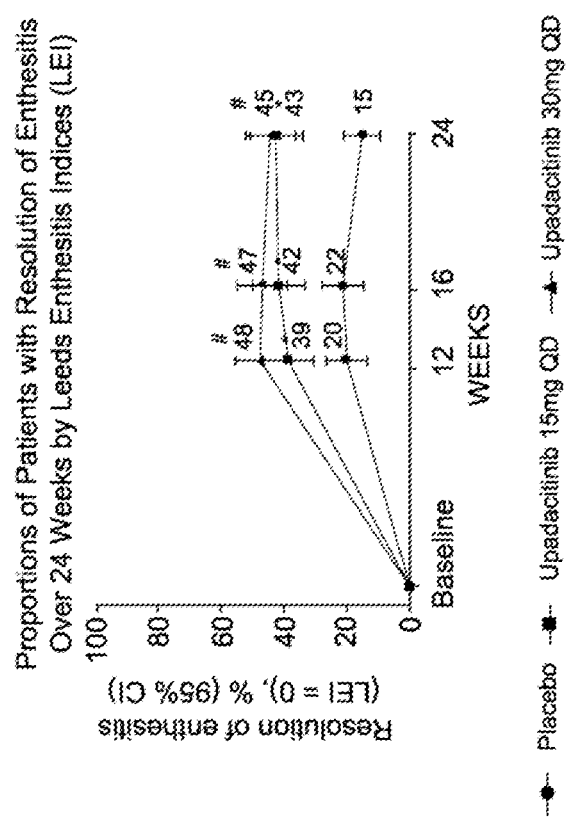
Figure 22F:
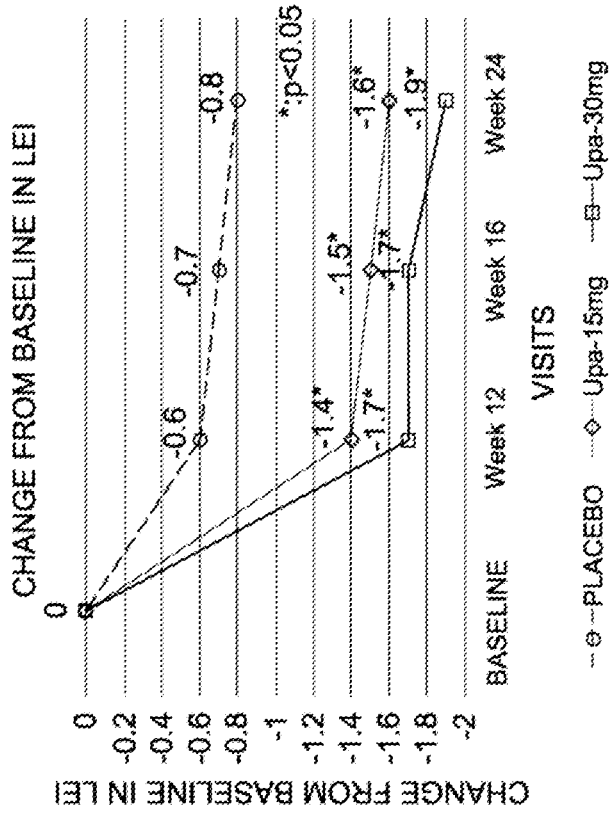
Figure 22H:
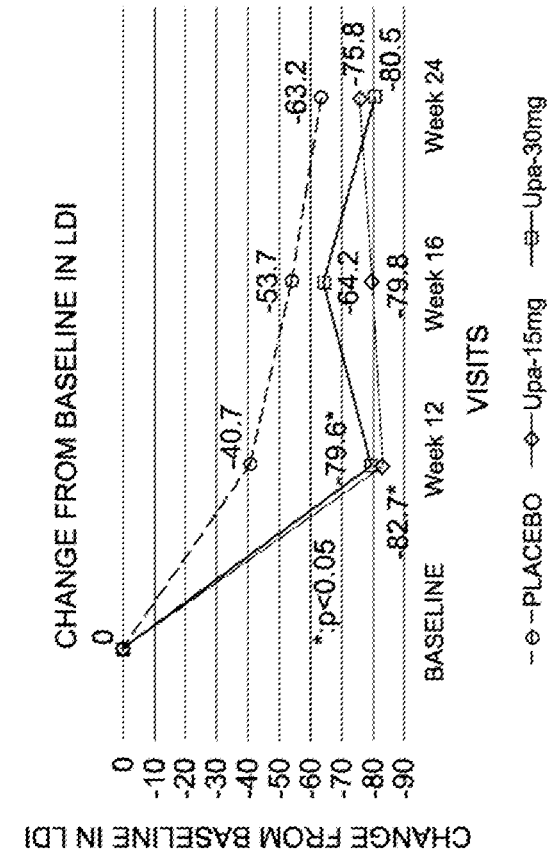
Figure 22G:
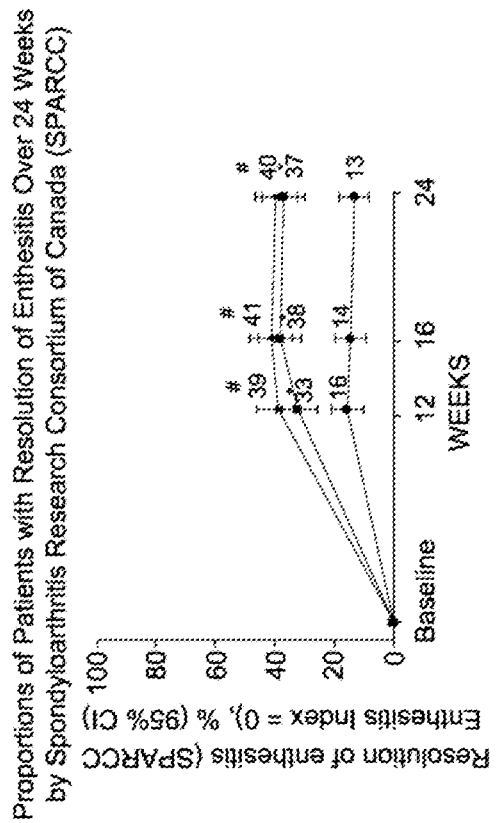
Figure 22J:
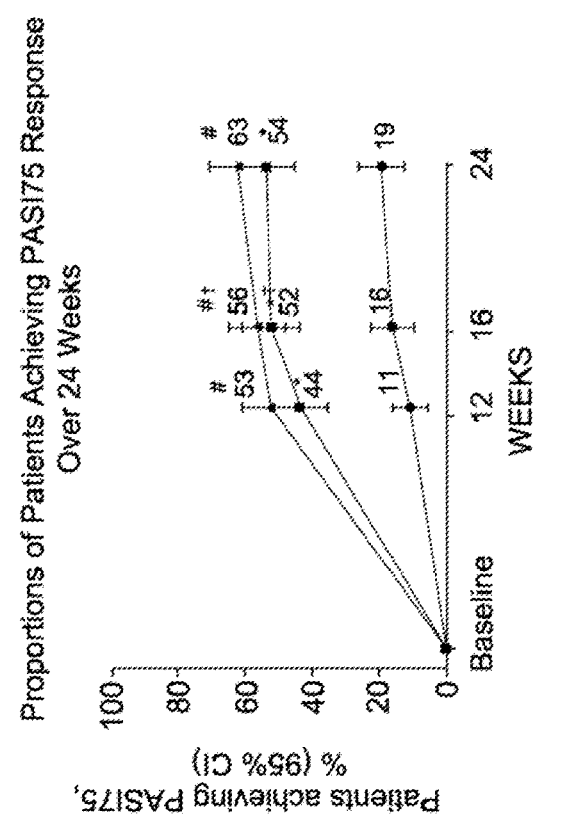
Figure 22I:
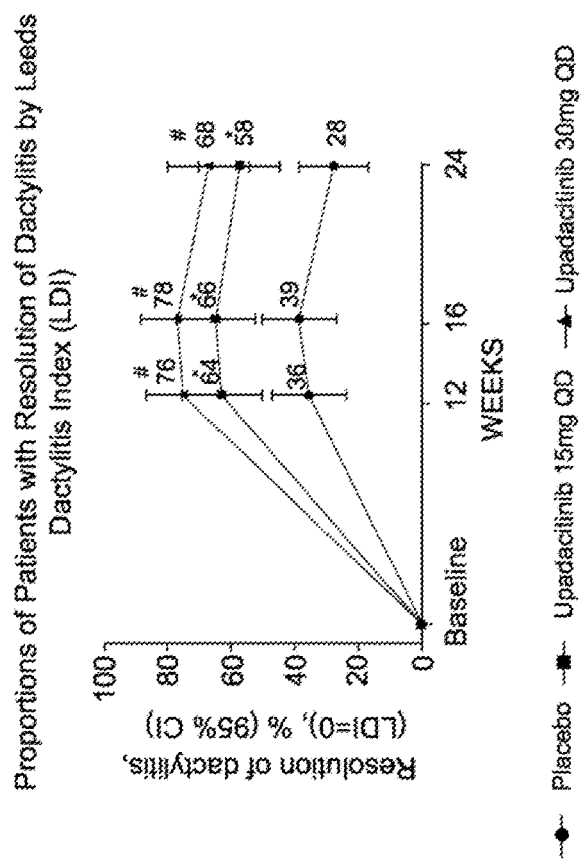
Figure 22K:
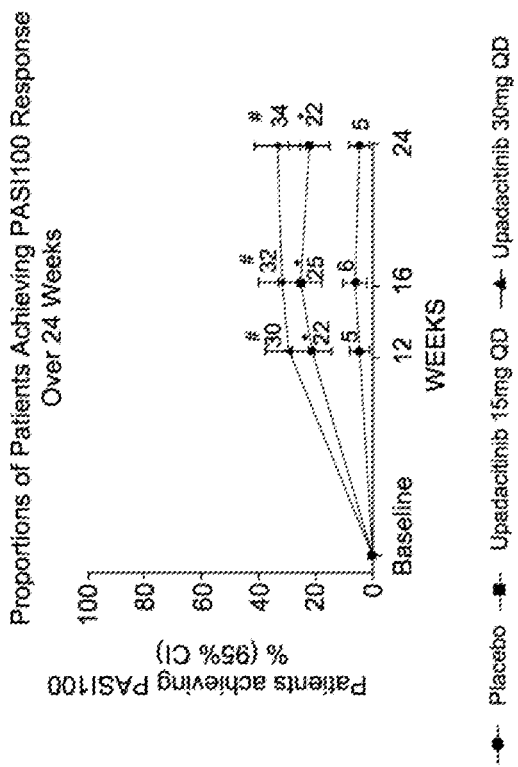
Figure 22L:
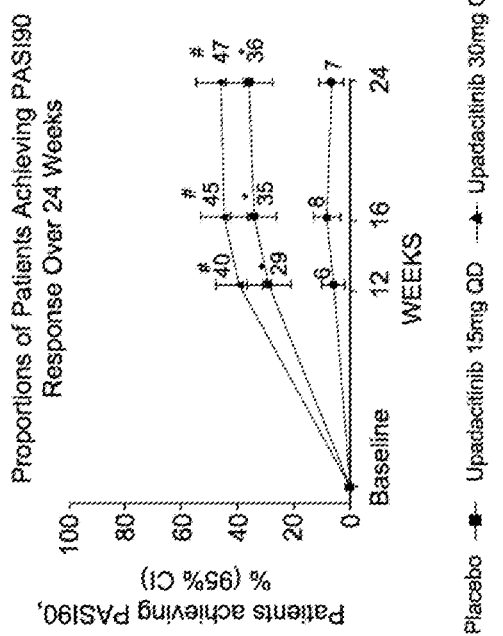
Figure 22N:
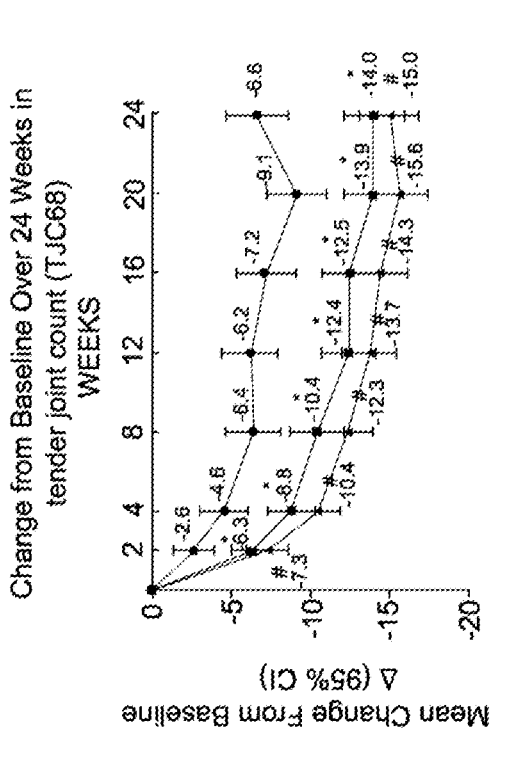
Figure 22M:
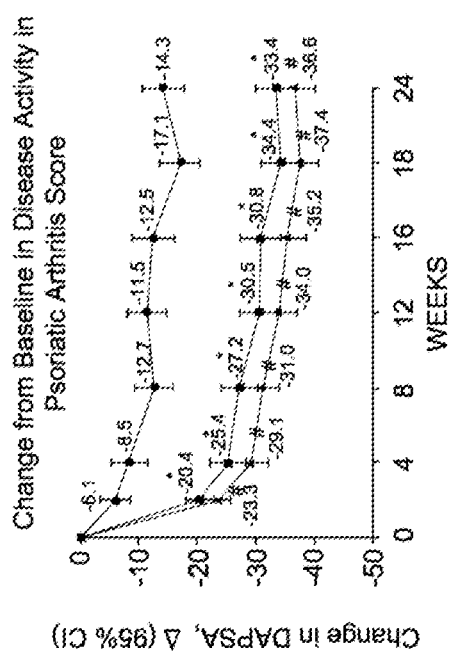
Figures 22O, 22P:
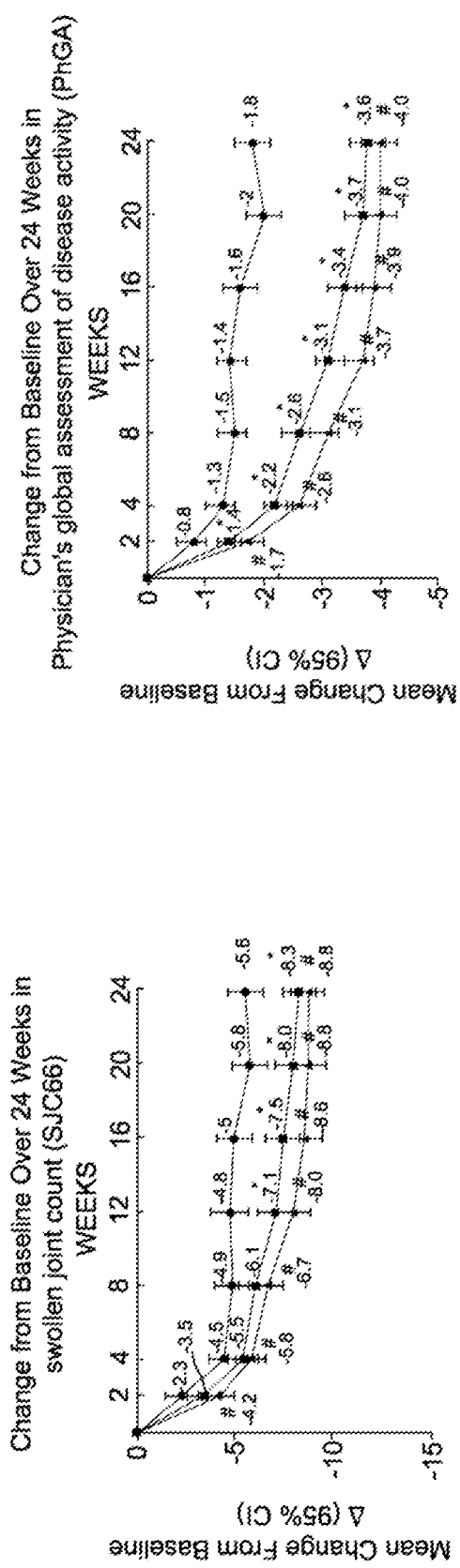
Figure 22Q:
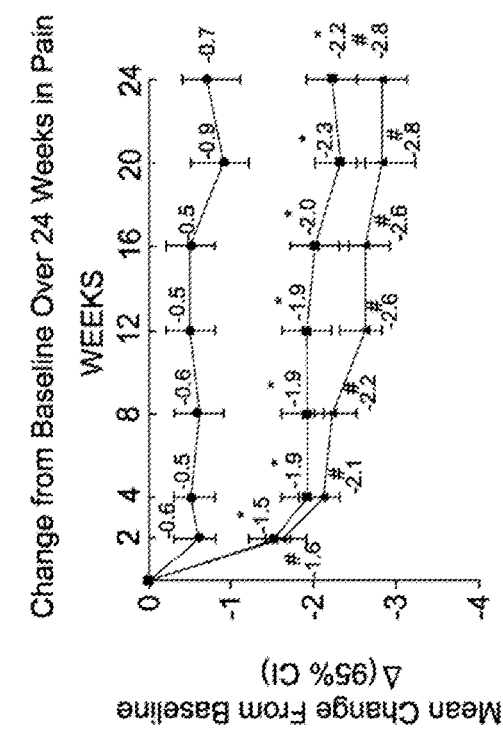
Figure 22R:
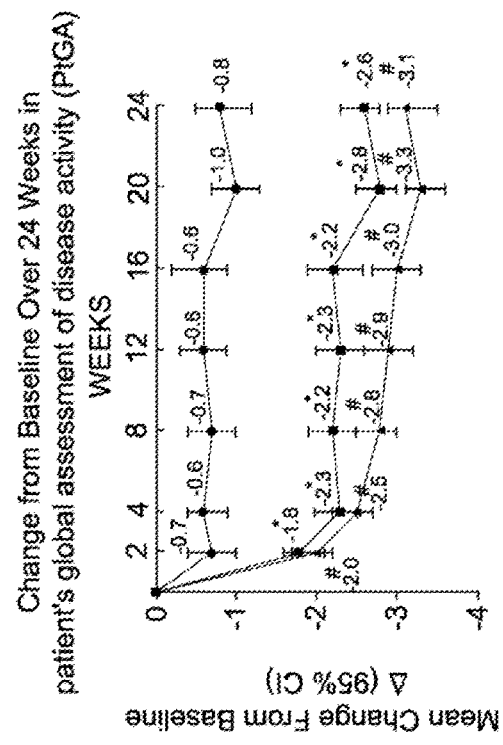
Figure 22S:
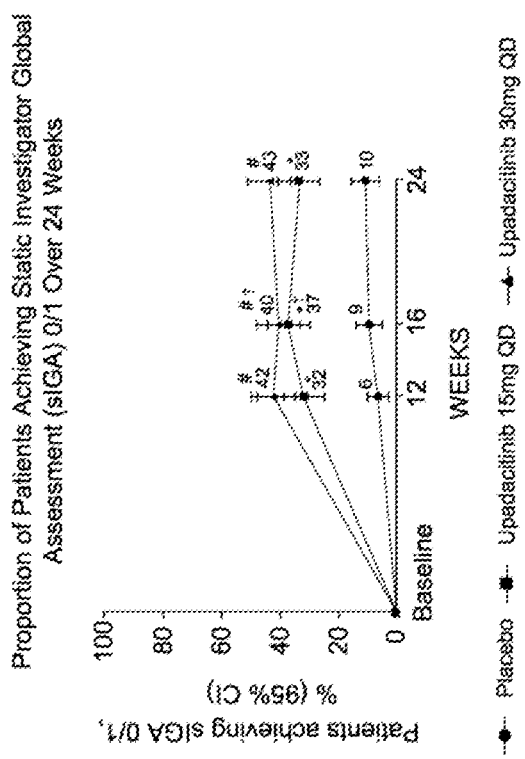
Figure 22T:
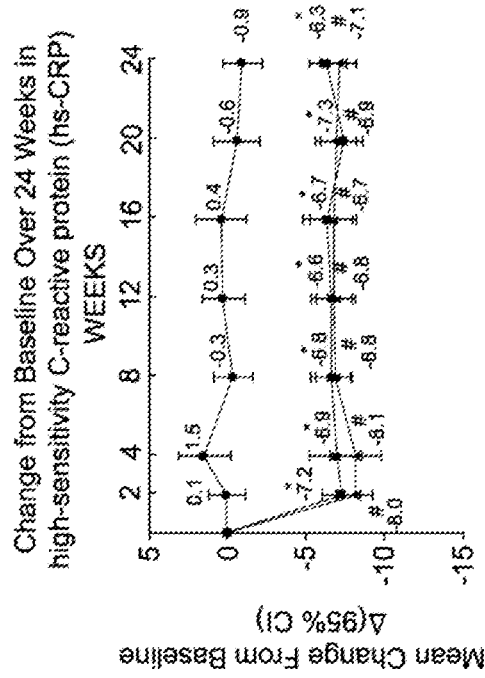
Figure 22V:
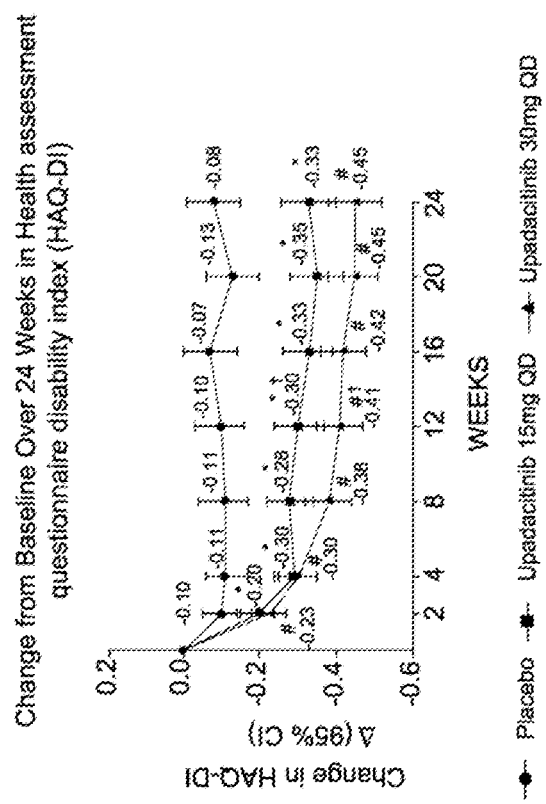
Figure 22U:
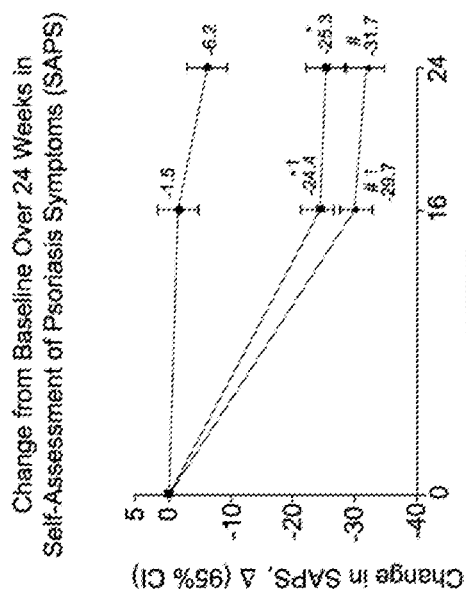
Figure 22W:
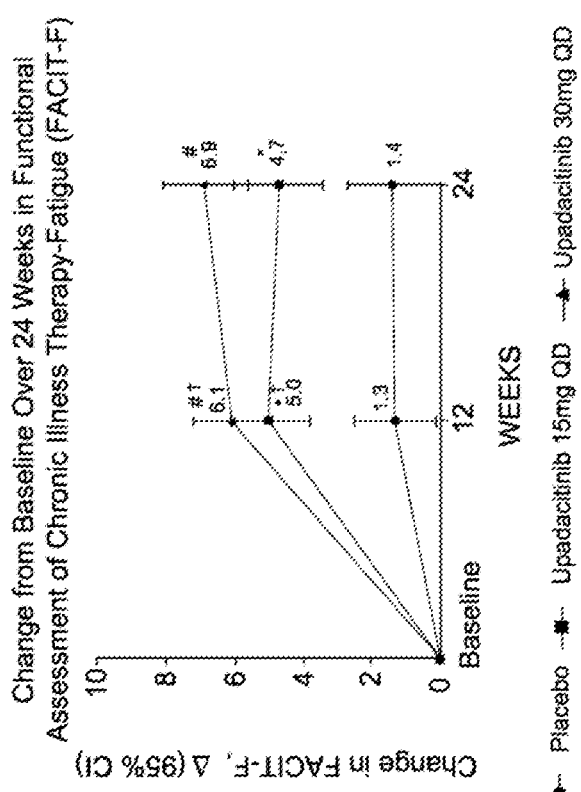
Figure 22X:
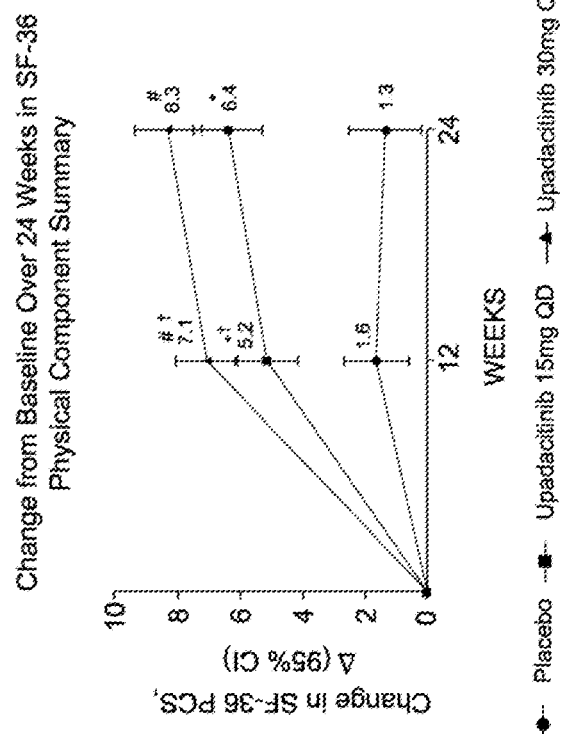
Figures 22Y, 22Z:
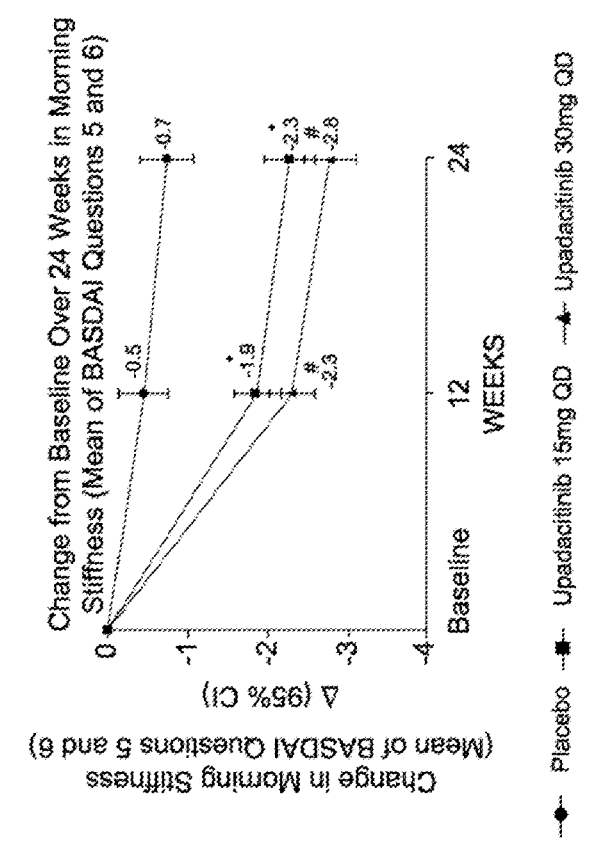
Figure 22A:
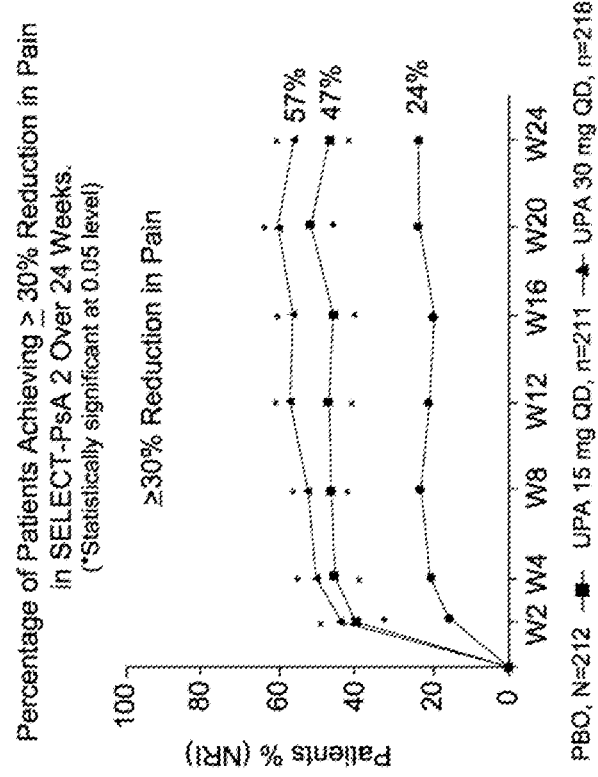
Figure 22B:
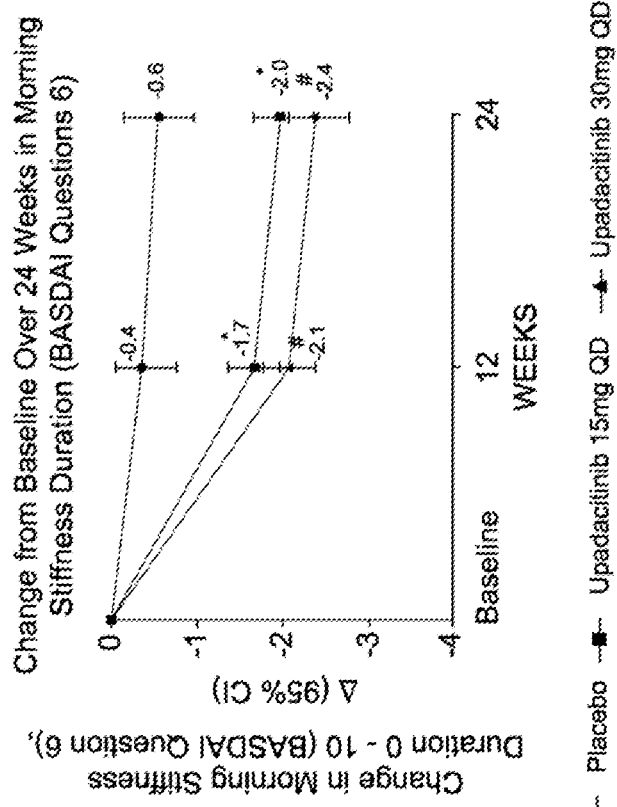
Figure 22C:
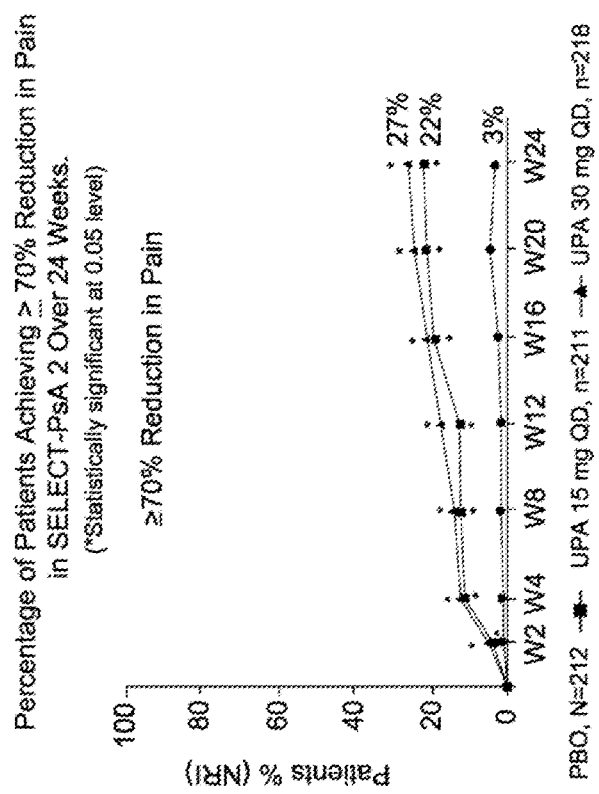
Figure 22D:
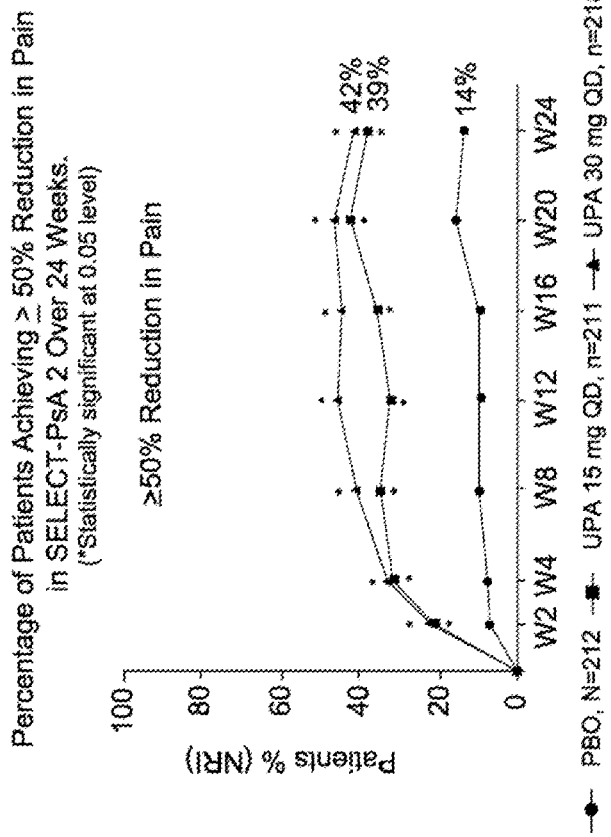

22I); proportion of patients achieving Psoriasis Area Severity Index PASI 75 (FIG. 22J), PASI 90 (FIG. 22K), and PASI 100 Response (FIG. 22L) over 24 weeks; patients achieving change from baseline in disease activity in psoriatic arthritis (DAPSA) score (FIG. 22M); patients achieving change from baseline over 24 weeks in core components of the ACR criteria; tender joint count (TJC68) (FIG. 22N), swollen joint count (SJC66) (FIG. 22O), physician's global assessment of disease activity (PhGA) (FIG. 22P), patient's global assessment of disease activity (PtGA) (FIG. 22Q), Pain (PtPain) (a score of 0 indicates "no pain" and a score of 10 indicates "worst possible pain") (FIG. 22R), high-sensitivity C-reactive protein (hs-CRP) (FIG. 22S); proportions of patients achieving static investigator global assessment (sIGA) 0/1 over 24 weeks (FIG. 22T); patients achieving change from baseline over 24 weeks in self-assessment of psoriasis symptoms (SAPS) (FIG. 22U); patients achieving change from baseline over 24 weeks in health assessment questionnaire disability index (HAQ-DI) (FIG. 22V); patients achieving change from baseline over 24 weeks in SF-36 Physical Component Summary (FIG. 22W); patients achieving change from baseline over 24 weeks in Functional Assessment of Chronic Illness Therapy-Fatigue (FACIT-F) (the FACIT-F score ranges from 0-52, with higher scores indicating less fatigue) (FIG. 22X); patients achieving change from baseline over 24 weeks in morning stiffness (mean of BASDAI Questions 5 and 6) (FIG. 22Y); patients achieving change from baseline over 24 weeks in morning stiffness severity (BASDAI Question 5) (FIG. 22Z); and patients achieving change from baseline over 24 weeks in morning stiffness duration (BASDAI Question 6) (FIG. 22AA). A significantly higher proportion of patients receiving upadacitinib freebase (15 mg QD or 30 mg QD) versus placebo achieved ≥30%, ≥50%, and ≥70% reduction in Patient's Global Assessment of pain (PtPain) as early as week 2, and efficacy achieved was sustained thereafter (see FIGS. 22BB-22DD). UPA=upadacitinib; PBO=placebo; QD=once daily; NRI=non-responder imputation.

Figure 23:
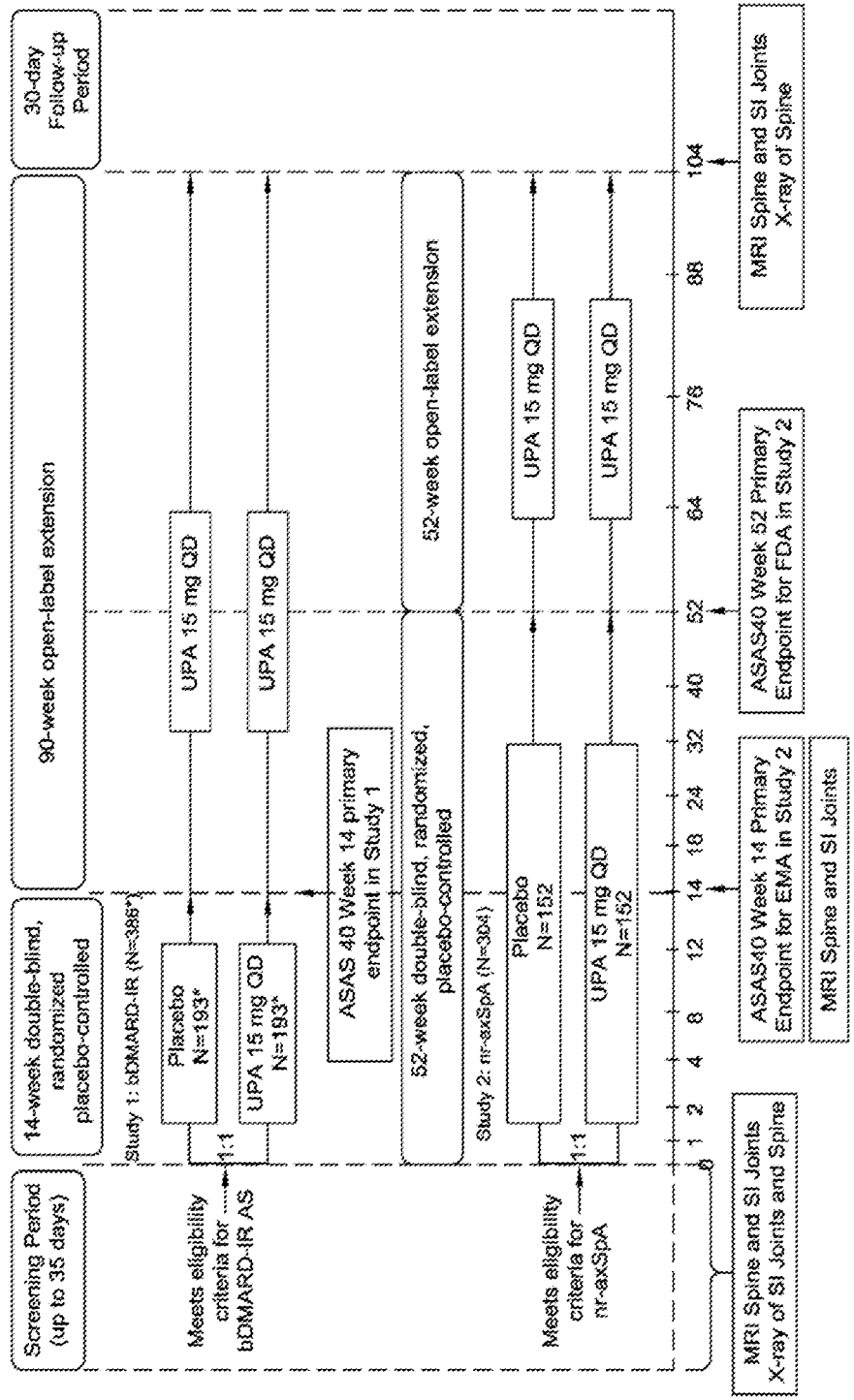

FIG. 23 depicts the Phase 3 study design for the treatment of AS and nr-AxSpA subjects. AS=ankylosing spondylitis; ASAS=Assessment of Spondylo Arthritis International Society; bDMARD-IR=biologic disease-modifying antirheumatic drug inadequate responder; EMA=European Medicines Agency; FDA=Food and Drug Administration; MRI=magnetic resonance imaging; nr-axSpA=non-radiographic axial spondyloarthritis; QD=once daily; SI=sacroiliac; UPA=upadacitinib freebase.

DETAILED DESCRIPTION OF THE INVENTION

This written description uses examples to disclose the invention and also to enable any person skilled in the art to practice the invention, including making and using any of the disclosed solid state forms or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "subject" refers to a human subject.

The terms "treating" and "treatment" refer to ameliorating, suppressing, eradicating, reducing the severity of, decreasing the frequency of incidence of, preventing, reducing the risk of, slowing the progression of damage caused by or delaying the onset of the condition or improving the quality of life of a patient suffering from the condition.

The abbreviation "% CV" refers to the coefficient of variation, expressed as a percent. % CV is calculated according to the following equation: % CV=(SD/x)*10, wherein x is the mean value and SD is the standard deviation.

As used herein, the term "entry into a use environment" means contact of a formulation of the disclosure with the gastric fluids of the subject to whom it is administered, or with a fluid intended to simulate gastric fluid.

The abbreviation "MTX" refers to methotrexate.

Clinical Endpoint Definitions

American College of Rheumatology (ACR) Criteria

ACR criteria is a composite measurement calculated based on the improvement over a set of core measurements. ACR20 is defined as at least 20% improvement (compared to baseline values) in tender and swollen joint counts (TJC and SJC) and at least 20% improvement in 3 of the remaining 5 core set measures (subject assessment of pain, subject global assessment of disease activity, physician global assessment of disease activity, subject assessment of physical function and acute phase reactant hsCRP). ACR50 and ACR70 are similarly defined with at least 50% and 70% improvement, respectively. A subject will be classified as an ACR20 (ACR50, or ACR70) responder, if the following conditions are met:

1. ≥20% (50%, or 70%) improvement from baseline in tender joint count (TJC68) and
2. ≥20% (50%, or 70%) improvement from baseline in swollen joint count (SJC66) and
3. ≥20% (50%, or 70%) improvement from baseline in at least 3 of the following 5:
   a. Patient's Global Assessment of Pain (Pt Pain)
   b. Patient's Global Assessment of Disease Activity (PtGA)
   c. Physician's Global Assessment of Disease Activity (PGA)

d. Patient's self-assessment of physical function (i.e., measured by Health Assessment Questionnaire HAQ-DI score)
e. Acute-phase reactant value high-sensitivity CRP (hsCRP)

Assessment of SpondyloArthritis International Society (ASAS), ASAS20, ASAS40, ASAS-PR, and ASAS 5/6 Responses.

Domains used for the ASAS responses are as follows:
a. Patient's Global Assessment—Represented by the PtGA-disease activity (NRS score 0-10)
b. Pain—Represented by the Patient's Assessment of Total Back Pain (Total Back Pain, NRS score 0-10)
c. Function—Represented by the BASFI (NRS score 0-10)
d. Inflammation—Represented by the mean of the 2 morning stiffness-related BASDAI (mean of Questions 5 and 6 of the BASDAI NRS score 0-10)

ASAS20 Response: Improvement of ≥20% and absolute improvement of ≥1 unit (on a scale of 0 to 10; 0=no pain and 10=worst possible pain) from Baseline in ≥3 of the above 4 domains above, with no deterioration (defined as a worsening of ≥20% and a net worsening of ≥1 unit) in the potential remaining domain.

ASAS40 Response: Improvement of ≥40% and absolute improvement of ≥2 units (on a scale of 0 to 10; 0=no pain and 10=worst possible pain) from Baseline in ≥3 of the above 4 domains above, with no deterioration (defined as a net worsening of >0 units) in the potential remaining domain.

ASAS partial remission (PR): an absolute score of ≤2 units (on a scale of 0 to 10; 0=no pain and 10=worst possible pain) from Baseline for each of the 4 domains above.

ASAS 5/6 Response: Improvement of ≥20% from Baseline in 5 out of the following 6 domains: BASFI, Patient's Assessment of Total Back Pain, PtGA-disease activity, inflammation (mean of Questions 5 and 6 of the BASDAI]), lateral lumbar flexion from BASMI, and hs-CRP.

ASAS Health Index (HI)

The ASAS HI is a linear composite measure with a dichotomous response option: "I agree" and "I do not agree" to a listing of 17 Questions. Each statement on the ASAS HI is given a score of "1"="I agree" or "0"="I do not agree." The total sum of the ASAS HI ranges from 0-17, with a lower score indicating a better health status. Questions 7 and 8 are not applicable to all patients. For those patients who ticked the response "not applicable," the sum score is analyzed based on n=16 or n=15 respectively. A total score can be analyzed if no more than 20% of the data (i.e., 3 Questions) are missing. The total score is calculated as follows for respondents with up to a maximum of three missing responses: Sum·score=x/(17−m)*17, where x is the Question summation score and m is the number of missing Questions and m≤3. Cases with more than three missing responses (m>3) cannot be allocated a total score and the total score will be set as missing. The 17 ASAS Health Index Questions are as follows:

1. Pain sometimes disrupts my normal activities.
2. I find it hard to stand for long.
3. I have problems running.
4. I have problems using toilet facilities.
5. I am often exhausted.
6. I am less motivated to do anything that requires physical effort.
7. I have lost interest in sex.
8. I have difficulty operating the pedals in my car.
9. I am finding it hard to make contact with people.
10. I am not able to walk outdoors on flat ground.
11. I find it hard to concentrate.
12. I am restricted in traveling because of my mobility.
13. I often get frustrated.
14. I find it difficult to wash my hair.
15. I have experienced financial changes because of my rheumatic disease.
16. I sleep badly at night.
17. I cannot overcome my difficulties.

Ankylosing Spondylitis Disease Activity Score (ASDAS)

Parameters used for the calculation of ASDAS:
1. Patient's Assessment of Total Back Pain (BASDAI Question 2 NRS score 0-10),
2. Duration of morning stiffness (BASDAI Question 6 NRS score 0-10),
3. Patient global assessment of disease activity (PtGA NRS score 0-10),
4. Peripheral pain/swelling (BASDAI Question 3 NRS score 0-10), and
5. high-sensitivity C reactive protein (hsCRP) (in mg/mL) or erythrocyte sedimentation rate (ESR).

Calculation of ASDAS:

$$ASDAS_{hs\text{-}CRP}\ 0.121 \times \text{total back pain} + 0.110 \times \text{PtGA} + 0.073 \times \text{peripheral-pain/swelling} + 0.058 \times \text{duration of morning stiffness} + 0.579 \times \text{Ln(hs-CRP+1)}.$$

$$ASDAS_{ESR} = 0.113 \times \text{patient global} + 0.293 \times \sqrt{ESR} + 0.086 \times \text{peripheral pain/swelling} + 0.069 \times \text{duration of morning stiffness} + 0.079 \times \text{total back pain}.$$

To calculate observed ASDAS scores, the observed component value will be calculated first. Then the components will be included in the calculation per the ASDAS formula. If any observed component is missing in a window, then the observed ASDAS score will be missing.

When the conventional CRP is below the limit of detection or when the high sensitivity CRP is <2 mg/L, the constant value of 2 mg/L should be used to calculate ASDAS-CRP.

ASDAS score is categorized by the following ASDAS Disease Activity States:

ASDAS Inactive Disease (ID): ASDAS<1.3
ASDAS Moderate Disease: 1.3≤ASDAS<2.1
ASDAS Low Disease Activity (LDA): ASDAS<2.1
ASDAS High Disease: 2.1≤ASDAS<3.5
ASDAS Very High Disease: ASDAS>3.5
ASDAS Response categories are defined as follows:
ASDAS Major Improvement (MI) (a change from baseline ≤−2.0; ≥2-point decrease from baseline)
ASDAS Clinically Important Improvement (CII) (a change from baseline ≤−1.1; (≥1.1-point decrease from baseline)

Ankylosing Spondylitis Quality of Life Questionnaire (ASQoL)

Each of the 18 statements on the ASQoL (provided below) is given a score of "1" (yes) or "0" (no). Concepts measured include activities of daily life, emotional functioning, pain, fatigue, and sleep problems. A score of "1" is given where the Question is affirmed (with a "yes" answer), indicating adverse QoL. All Question scores are summed to give a total score or index. Scores can range from 0 (good QoL) to 18 (poor QoL), with higher scores equaling worsening functioning. Cases with more than three missing responses (i.e., more than 20%) cannot be allocated a total score. For cases with between one and three missing responses, the total score is calculated as follows: T=18x/18−m where: T is the total score, x is the total score for the Questions affirmed and m is the number of missing Questions.

1. My condition limits the places I can go
2. I sometimes feel like crying
3. I have difficulty dressing
4. I struggle to do jobs around the house
5. It's impossible to sleep
6. I am unable to join in activities with my friends/family
7. I am tired all the time
8. I have to keep stopping what I am doing to rest
9. I have unbearable pain
10. It takes a long time to get going in the morning
11. I am unable to do jobs around the house
12. I get tired easily
13. I often get frustrated
14. The pain is always there
15. I feel I miss out on a lot
16. I find it difficult to wash my hair
17. My condition gets me down
18. I worry about letting people down Bath Ankylosing Spondylitis Disease Activity Index (BASDAI), BASDAI 50 Response, and the Morning Stiffness Score The BASDAI consists of a 1 through 10 scale (1 being no problem and 10 being the worst problem) and is used to answer 6 questions pertaining to the 5 symptoms: Fatigue, Spinal pain, Joint pain/swelling, Areas of localized tenderness (also called enthesitis, or inflammation of tendons and ligaments), Morning stiffness duration, and Morning stiffness severity. A lower score indicates less disease activity.

The six BASDAI Questions (Components) are as follows:
Q1. How would you describe the overall level of fatigue/tiredness you have experienced?
Q2. How would you describe the overall level of AS neck, back or hip pain you have had?
Q3. How would you describe the overall level of pain/swelling in joints, other than neck, back or hips you have had?
Q4. How would you describe the overall level of discomfort you have had from any areas tender to touch or pressure?
Q5. How would you describe the overall level of morning stiffness you have had from the time you wake up?
Q6. How long does your morning stiffness last from the time you wake up?

Questions 1 through 5 have responses that can range from 0 (none) to 10 (very severe); Question 6 have response range from 0 (0 hr) to 10 (2 or more hrs), with 5 representing 1 hr.

Scoring of the BASDAI: BASDAI will be reported 0 to 10. The score has a maximum value of 10 and is calculated as follows:

$$\text{BASDAI Score} = 0.2(Q1+Q2+Q3+Q4+Q5/2+Q6/2)$$

If one of the 5 Questions (Questions 1-Question 4, inflammation) is missing, then the score is the mean of the 4 non-missing Questions (total of 4 non-missing Questions divided by 4). If more than 1 of the 5 Questions is missing, then the BASDAI score is missing. Question 5 and Question 6 jointly constitute Question 5 (inflammation). If both Questions 5 and 6 are missing, and questions 1 through 4 are non-missing, then only one Question will be considered missing. The BASDAI score can still be calculated as the mean of Questions 1-4. However, if, for example, both Question 6 and Question 1 are missing, then 2 Questions will be considered missing, as the inflammation calculation would be incomplete. The BASDAI score would then be considered missing in this case.

A BASDAI 50 response is a categorical response based on BASDAI that represents an at least 50% improvement from baseline in BASDAI.

The Morning Stiffness Score is the average of BASDAI Questions 5 and 6, and it ranges from 0-10.

A "change from baseline in BASDAI and BASDAI Questions (Components), including change from baseline in mean of Question 5 and 6 of the BASDAI" means (1) a change from baseline from the BASDAI Score, (2) a change from baseline in all of the BASDAI Questions, and (3) a change from baseline of the mean of Questions 5 and 6 (which represent inflammation).

Bath Ankylosing Spondylitis Functional Index (BASFI)

The BASFI consists of the following 10 questions, assessing ability to perform activities such as dressing, bending, reaching, turning, and climbing steps, each with a response ranging from 0 (easy) to 10 (impossible);
1. Putting on your socks or tights without help or aids (e.g., sock-aid).
2. Bending forward from the waist to pick up a pen from the floor without an aid.
3. Reaching up to a high shelf without help or aids (e.g., helping hand).
4. Getting up out of an armless dining room chair without using your hands or any other help.
5. Getting up off the floor without help from lying on your back.
6. Standing unsupported for 10 minutes without discomfort.
7. Climbing 12 to 15 steps without using a handrail or walking aid. One foot on each step.
8. Looking over your shoulder without turning your body.
9. Doing physically demanding activities (e.g., physiotherapy, exercises, gardening, or sports).
10. Doing a full day's activities whether at home or at work.

See, e.g., Sieper et al., Ann Rheum Dis (2009) 68 (Suppl II): ii1-ii44. doi:10.1136/ard.2008.104018.

Scoring of BASFI. The BASFI score will be derived based on the average of Questions 1 through 10. If up to 2 Questions are missing, corresponding scores will be replaced with the mean of the remaining non-missing Questions. If 3 or more Questions are missing, BASFI will be considered missing.

Bath Ankylosing Spondylitis Metrology Linear Index (BASMI$_{lin}$)

The Linear BASMI (BASMI$_{lin}$) composite score will be calculated using the BASMI components. The table below presents the components of BASMI$_{lin}$ and assessment ranges for score.

TABLE 1

| Components of BASMI$_{lin}$ | 0 | Between 0 and 10 | 10 |
| --- | --- | --- | --- |
| Lateral Lumbar flexion (cm) | A ≥ 21.1 | (21.1 − A)/2.1 | A ≤ 0.1 |
| Tragus to wall distance (cm) | A ≤ 8 | (A − 8)/3 | A ≥ 38 |
| Lumbar flexion (modified Schober) (cm) | A ≥ 7.4 | (7.4 − A)/0.7 | A ≤ 0.4 |
| Intermalleolar distance (cm) | A ≥ 124.5 | (124.5 − A)/10 | A ≤ 24.5 |
| Cervical rotation (°) | A ≥ 89.3 | (89.3 − A)/8.5 | A ≤ 4.3 |

BASMI$_{lin}$ = Assessment measurements for tragus to wall, cervical rotation and lateral lumbar flexion are the means of the left and right measurement;
A = assessment measurement Scores for each assessment range from 0 to 10, and the BASMI$_{lin}$ total score will be the average of the 5 assessment scores. If 1 Question is missing, the BASMI$_{lin}$ will be calculated as the mean of remaining 4 Questions. Hence, the range of the BASMI$_{lin}$ total score should be between 0 and 10. If 2 or more Questions are missing, then the BASMI$_{lin}$ score will be considered missing. See e.g., van der Heijde et al., *Arth. Care & Res.* (2012) 64:1919-1922 and van der Heijde et al., *Ann Rheum Dis* (2008) 67:489-93.

Body Surface Area—Psoriasis (BSA-PS)

The subject's right or left hand should be selected as the measuring device. For purposes of clinical estimation, the total surface of the palm plus five digits will be assumed to be approximately equivalent to 1%. Measurement of the total area of involvement is aided by imagining if scattered plaques were moved so that they were next to each other and then estimating the total area involved. See, e.g., See, e.g., Bozek and Reich, *Adv. Clin. Exp. Med.* (2017) 26:851-856.

Disease Activity in Psoriatic Arthritis (DAPSA) Score

DAPSA is a continuous endpoint that measures the disease activity in psoriatic arthritis. DAPSA consists of five components: Tender Joint Count 68, Swollen Joint Count 66, Patient's Global Assessment of Pain (Pt Pain) (0-10 NRS), PtGA of Disease Activity (0-10 NRS), and hsCRP (in mg/dL). Calculation of the DAPSA score is as follows: DAPSA=SJC66+ TJC68+Pt Pain (0-10 NRS)+PtGA (0-10 NRS)+hsCRP (in mg/dL)

To calculate observed DAPSA scores, the observed component value will be calculated first. Then the components will be included in the calculation per the DAPSA formula. If any observed component is missing in a window, then the observed DAPSA score will be missing.

Disease Activity Score (DAS28)

DAS28 (CRP) and DAS28 (ESR) are composite indices to assess disease activity in PsA using high-sensitivity c-reactive protein lab value (hsCRP) or erythrocyte sedimentation rate (ESR) measurement, respectively. The DAS28 provides a score between 0 and 10, indicating arthritis disease activity at the time of measurement. DAS28 (CRP) and DAS28 (ESR) are calculated based on Tender Joint Count, Swollen Joint Count, PtGA of Disease Activity (0-100), and hsCRP (in mg/L) or ESR (mm/hr). As PtGA of Disease Activity is collected with the scale of 0-10 NRS, the variable needs to be multiplied by 10 before being used the DAS28 formula. To calculate observed DAS28 scores, the observed component value will be calculated first. Then the components will be included in the calculation per the DAS formula selected. If any observed component is missing in a window, then the observed DAS28 score will be missing. Calculation of DAS28 (CRP) and DAS28 (ESR) are provided by the following equations:

$$DAS28(CRP)=0.56\times\sqrt{(TJC28)}+0.28\times\sqrt{(SJC28)}+0.36\times \ln(hsCRP+1)+0.014\times PtGA+0.96$$

$$DAS28(ESR)=0.56\times\sqrt{(TJC28)}+0.28\times\sqrt{(SJC28)}+0.70\times \ln(ESR)+0.014\times PtGA$$

where $\sqrt{}$ is square root and ln is natural log; TJC28 refers to the Subject's total Tender Joint Count out of the provided 28 evaluated joints; SJC28 refers to the Subject's total Swollen Joint Count out of the provided 28 evaluated joints; hsCRP unit in the DAS28 (CRP) equation is expressed as mg/L; ESR unit in the DAS28 (ESR) equation is expressed as mm/hr; and PtGA refers to the Patient's Global Assessment of Disease Activity.

TABLE 2

Anatomical Joints for DAS28 (CRP) Calculation

| Shoulder | Elbow | Wrist | Thumb Interphalangeal |
|---|---|---|---|
| Metacarpophalangeal I | Metacarpophalangeal II | Metacarpophalangeal III | Metacarpophalangeal IV |
| Metacarpophalangeal V | Proximal Interphalangeal II | Proximal Interphalangeal III | Proximal Interphalangeal IV |
| Proximal Interphalangeal V | Knee | | |

Leeds Dactylitis Index (LDI), Dactylitis Count and Tender Dactylitis Count

The Dactylitis scores will be the presence of Dactylitis at baseline, the Dactylitis Count (out of subjects with baseline presence of Dactylitis) ("total dactylitis count" or "tender dactylitis count") and the resolution of Dactylitis (out of subjects with baseline presence of Dactylitis). The presence of Dactylitis at baseline is defined as the following: at least one affected and tender digit with circumference increase over reference digit ≥10%. The Dactylitis Count will be calculated as the number of digits (hands and feet) with presence of dactylitis, and ranges from 0 to 20.

The Leeds Dactylitis Index (LDI) is a score based on finger circumference and tenderness, assessed and summed across all dactylitic digits. The assessment should begin with visual inspection of the hands and feet. For each pair of digits in which one or both digits appear dactylitic, the circumference of the affected digits (both right and left side) is assessed using a dactylometer. Additionally, the affected digit pairs are assessed for tenderness by squeezing the digital shaft mid-way between the metacarpophalangeal and proximal interphalangeal joints and is recorded as tenderness, yes or no. Tenderness should not be assessed by squeezing the joint lines. For each of 20 digits of a subject, a digit final score needs to be calculated first. For an unaffected digit, the digit final score is set to be 0. For an affected digit, the digit final score is calculated as (A/B−1)*100*C if A/B≥1.1, and digit finals score=0 if A/B<1.1, where A denotes the circumference of the digit, B the reference circumference, and C the tenderness score. The reference circumference can be either the circumference of the unaffected contralateral digit if available, or from a reference table if otherwise. For any digit without an available dactylometer measurement the standard reference value will be utilized in calculation of the LDI. LDI is the sum of the digit final scores over all 20 digits. The proportion of subjects with Resolution of Dactylitis is defined as the proportion of subjects with LDI=0. Digits injected with corticosteroid will be considered non-evaluable for 90 days from the time of the injection. If a digit is missing and its contralateral digit is dactylitic, "digit absent" will be recorded for the missing digit.

Enthesitis Scoring: Spondyloarthritis Research Consortium of Canada (SPARCC) Enthesitis Index, Leeds Enthesitis Index (LEI), Total Enthesitis Count, and Maastricht Ankylosing Spondylitis Enthesitis Score (MASES)

For the Spondyloarthritis Research Consortium of Canada (SPARCC) Enthesitis Index, 16 sites are evaluated as indicated in rows 1-8 in the table below. Tenderness on examination is recorded as either present (coded as 1), absent (coded as 0), or not assessed (NA) for each site. The SPARCC enthesitis index is calculated by taking the sum of the scores from the 16 sites. The SPARCC score ranges from 0 to 16.

The Leeds Enthesitis Index evaluates enthesitis at the 6 entheseal sites indicated in rows 2, 7 and 9 in the table below. Tenderness on examination is recorded as either present (coded as 1), absent (coded as 0), or not assessed (NA) for each of the 6 sites. The LEI is calculated by taking the sum of the scores from the 6 sites. The LEI ranges from 0 to 6.

The Total Enthesitis Count is calculated by taking the sum of the tenderness scores from all 18 sites in the table below.

The proportion of subjects with resolution of enthesitis sites included in the LEI is defined as the proportion of subjects with LEI=0; the proportion with resolution of the SPARCC Enthesitis Index and of the total enthesitis count are similarly defined (score=0).

TABLE 3

| | Tenderness in Left | | | Tenderness in Right | | |
|---|---|---|---|---|---|---|
| | Present | Absent | NA | Present | Absent | NA |
| 1 Medial epicondyle | | | | | | |
| 2 Lateral epicondyle | | | | | | |
| 3 Supraspinatus insertion into the greater tuberosity of humerus | | | | | | |
| 4 Greater trochanter | | | | | | |
| 5 Quadriceps insertion into superior border of patella | | | | | | |
| 6 Patellar ligament insertion into inferior pole of patella or tibial tubercle | | | | | | |
| 7 Achilles tendon insertion into calcaneum | | | | | | |
| 8 Plantar fascia insertion into calcaneum | | | | | | |
| 9 Medial femoral condyle | | | | | | |

Present = 1; Absent = 0; NA = Not assessed

The Maastricht Ankylosing Spondylitis Enthesitis Score (MASES) will be measured to assess the presence (1) or absence (0) of enthesitis at 13 different sites (first costochondral joint left/right, seventh costochondral joint left/right, posterior superior iliac spine left/right, anterior superior iliac spine left/right, iliac crest left/right, fifth lumbar spinous process, and proximal insertion of Achilles tendon left/right), noting the subjects' responses, yielding a total score ranging 0-13. If one or more locations are missing, the score will be calculated using available data. If all locations are missing, then MASES is set to be missing.

EuroQoL-5D (EQ-5D-5L)

The EQ-5D-5L questionnaire is one of the most commonly used questionnaires to measure health-related quality of life. It consists of a questionnaire and a visual analogue scale (VAS). The self-assessment questionnaire measures 5 dimensions of health status (mobility, self-care, usual activities, pain/discomfort, and anxiety/depression). The AS subject is asked to grade their own current level of function in each dimension into 1 of 3 degrees of disability (severe, moderate, or none). The PsA subject is asked to grade their own current level of function in each dimension into 5 levels per dimension (no problems, slight problems, moderate problems, severe problems, and extreme problems corresponding to Level 1 to Level 5 respectively) and includes the EQ Visual Analogue Scale (EQ VAS). The 5 dimensions of health status are converted into a single index value. Using the VAS, subjects record perceptions of current perceived health status with a grade ranging from 0 (the worst possible health status) to 100 (the best possible health status).

FACIT-Fatigue Questionnaire (FACIT-F)

The FACIT Fatigue Questionnaire is a 13-Question tool that measures an individual's level of fatigue during their usual daily activities over the past week. The level of fatigue is measured on a four point scale (4=not at all fatigued to 0=very much fatigued). The Fatigue scale ranges from 0 to 52, with higher scores indicating less fatigue. Question score for each Question is calculated by either subtracting from 4 or adding 0 depending on whether it is a reversal Question or not. FACIT Fatigue Scale is then calculated by adding up all Question scores, multiplying by 13 and dividing by the number of Questions answered. If less than 7 Questions are answered, the scale will not be computed.

1. I feel fatigued
2. I feel weak all over
3. I feel listless ("washed out")
4. I feel tired
5. I have trouble starting things because I am tired
6. I have trouble finishing things because I am tired
7. I have energy
8. I am able to do my usual activities
9. I need to sleep during the day
10. I am too tired to eat
11. I need help doing my usual activities
12. I am frustrated by being too tired to do the things I want to do
13. I have to limit my social activity because I am too tired Health Assessment Questionnaire Disability Index (HAQ DI)

HAQ-DI is a self-reported patient outcome measurement. It is calculated as the mean of the scores from 8 following categories with a range 0-3: Dressing and Grooming. Rising, Eating, Walking, Hygiene, Reach, Grip, and Activities. Higher scores reflect greater disability. The maximum score for all the questions in each category is considered as the score for the category. The HAQ-DI takes into account the subject's use of aids or devices or assistance in the scoring algorithm for a disability category. For each category there is an AIDS OR DEVICES companion variable that is used to record the type of assistance, if any, a subject uses for his/her usual activities. If aids or devices and/or assistance from another person are checked for a category, the score for this category is set to 2 (much difficulty), if the original score is 0 (no difficulty) or 1 (some difficulty). The HAQ-DI is then calculated by summing the adjusted categories scores and dividing by the number of categories answered. The HAQ-DI cannot be calculated if the subject does not have scores for at least 6 categories.

High-Sensitivity C Reactive Protein (hs-CRP)

C-reactive protein (CRP), which is measured in blood plasma, is an acute phase protein that appears in blood circulation in response to inflammation, and serves as a biomarker for systemic inflammation. However, routine methods of CRP detection (turbidimetric, nephelometric) demonstrated poor sensitivity in detecting concentrations of CRP below 6-10 mg/litre. See, e.g., Poddubnyy et al., Ann. Rheum. Dis. (2010) 69:1338-1341.

The high-sensitivity C-reactive protein (hs-CRP) assay is a more precise measurement than routine CRP. Several different tests may be used to measure the hs-CRP normal range versus abnormal value for the subject to be treated; thus the upper limit of normal (ULN) will be determined by the laboratory for the hs-CRP test used and may differ from laboratory to laboratory.

Health Resource Utilization (HRU) Questionnaire for PsA

The HRU questionnaire contains three questions regarding health care utilization in the following categories: unscheduled health care professional visits, emergency room visits, and hospital admissions. The data gathered from the HRU questionnaire will be used to calculate the individual cumulative number of utilizations per unit of time (e.g., subject-year) under observation in each variable (i.e., the number of unscheduled PsA-related health care professional visits, the number of emergency room visits, the number of hospital admissions and the total number of days in hospital) as follows: (i) time under observation for a subject will be defined as "date of last visit with non-missing HRU—date of baseline visit." and (ii) the number of utilizations after baseline will be summed up for each subject.

Joint Count Assessment: SJC and TJC

Swollen Joint Count Assessment (SJC or SJC66): An assessment of 66 joints will be done by physical examination. The joints to be examined for swelling are the same as those examined for tenderness, except the hip joints are excluded. Joint swelling will be classified as present ("1"), absent ("0"), replaced ("9"), or no assessment ("NA"). Joints injected with corticosteroid will be considered non-evaluable for 90 days from the time of the injection. The range for SJC66 will be 0 to 66.

Tender Joint Count Assessment (TJC or TJC68): An assessment of 68 joints will be done for tenderness by pressure manipulation on physical examination. Joint pain/tenderness will be classified as: present ("1"), absent ("0"), replaced ("9"), or no assessment ("NA"). Joints injected with corticosteroid will be considered non-evaluable for 90 days from the time of the injection. The range for TJC68 will be 0 to 68.

Anatomical joints are evaluated for swelling and tenderness at every study visit. The 34 anatomical joints in the below table are assessed in this study for both the left and right side of the body.

TABLE 4

Anatomical Joints Assessed for Calculation of Tender and Swollen Joint Counts (TJC68 and SJC66)

| Temporo-mandibular | Sterno-clavicular | Acromio-clavicular | Shoulder |
|---|---|---|---|
| Elbow | Wrist | Metacarpo-phalangeal I | Metacarpo-phalangeal II |
| Metacarpo-phalangeal III | Metacarpo-phalangeal IV | Metacarpo-phalangeal V | Thumb Interphalangeal |
| Proximal Inter-phalangeal II | Proximal Inter-phalangeal III | Proximal Inter-phalangeal IV | Proximal Inter-phalangeal V |
| Distal Inter-phalangeal II | Distal Inter-phalangeal III | Distal Inter-phalangeal IV | Distal Inter-phalangeal V |
| Hip[a] | Knee | Ankle | Tarsus |
| Metatarso-phalangeal I | Metatarso-phalangeal II | Metatarso-phalangeal III | Metatarso-phalangeal IV |
| Metatarso-phalangeal V | Great Toe/Hallux | Inter-phalangeal II | Inter-phalangeal III |
| Inter-phalangeal IV | Inter-phalangeal V | | |

[a]Hip joints are not assessed for swelling.

Modified Stoke Ankylosing Spondylitis Spine Score (mSASSS)

The mSASSS is a scoring method that measure radiographic progression in the spine of patients with ankylosing spondylitis. The mSASSS has a range of 0 to 72, which is derived from scoring the anterior site of the lumbar spine from the lower border of T12 to the upper border of S1 and the anterior site of the cervical spine from the lower border of C2 to the upper border of T1 as either 0 (normal), 1 (erosion, sclerosis, or squaring), 2 (syndesmophyte), 3 (bridging syndesmophyte), or NA vertebral body not evaluable. X-ray of spinal films will be analyzed for radiographic progression (from Baseline to the follow-up timepoint).

Modified Psoriatic Arthritis Response Criteria (Modified PsARC)

The modified PsARC is a PsA-specific composite responder index. To achieve response, a subject must achieve 2 of the following 4 Questions, one of which has to be a Tender Joint Count 68 or Swollen Joint Count 66, and no worsening of any measure: ≥30% improvement in TJC68; ≥30% improvement in SJC66; Improvement in PtGA of Disease Activity NRS; Improvement in PGA of Disease Activity NRS.

Patient's Assessment of Nocturnal Back Pain (Nocturnal Back Pain), Patient's Assessment of Total Back Pain (Total Back Pain score), and Patient's Global Assessment of Pain (Pt Pain or "Pain") Numerical Rating Scales (NRS)

Pain will be measured using 0-10 numerical rating scale (NRS) scale Questions for Nocturnal Back Pain NRS (0=no pain and 10=worst possible pain), Total Back Pain (0=no pain and 10=severe pain), and Pain (i.e., overall pain) (0=no pain and 10=severe pain).

ASAS (e.g., ASAS20, ASAS40, ASAS PR) assesses the Patient's Assessment of Total Back Pain (Total Back Pain score) using the above described scoring method. For ASDAS, Patient's Assessment of Total Back Pain assesses total back pain by answering BASDAI Question 2.

Psoriatic Arthritis Disease Activity Score (PASDAS)

PASDAS is a continuous scale of combined joint, dactylitis and enthesitis assessments, physician and patient global assessments for arthritis, SF36-PCS, and hsCRP measurements. PASDAS is calculated based on the following equation:

$$= (((0.18\sqrt{(PGA)}) + 0.159\sqrt{(PtGA)} - 0.253\sqrt{(SF36\text{-}PCS)} + 0.101 \ln(SJC66+1) + 0.048 \ln(TJC68+1) + 0.23 \ln(LEI+1) + 0.37 \ln(\text{Tender Dactylitis Count}+1) + 0.102 \ln(hsCRP+1) + 2)*1.5$$

wherein $\sqrt{}$ is square root and ln is natural log; PtGA is on the scale of 0-10; PGA is on the scale of 0-100 (as PtGA and PGA are collected with the scale of 0-10 NRS, their values need to be multiplied by 10 before being used in the PASDAS formula); SF36-PCS is the physical component scale in the SF36 instrument; the unit for hsCRP is mg/L; and LEI ranges from 0 to 6.

Psoriasis Area Severity Index (PASI)

The PASI is a measure of psoriasis severity. Four anatomic sites—head, upper extremities, trunk, and lower extremities—are assessed for erythema, induration and desquamation using a 5-point scale (0=no symptoms; 1=slight; 2=moderate; 3=marked; 4=very marked). Based on the extent of lesions in a given anatomic site, the area affected is assigned a numerical value (0=no involvement; 1=<10%; 2=10%-29%; 3=30%-49%; 4=50%-69%; 5=70%-89%; 6=90%-100%). Since the head, upper extremities, trunk and lower extremities correspond to approximately 10, 20, 30 and 40% of body surface area, respectively; the PASI score is calculated using the formula:

$$= 0.1(E_h + I_h + D_h)A_h + 0.2(E_u + I_u + D_u)A_u + 0.3(E_t + I_t + D_t)A_t + 0.4(E_l + I_l + D_l)A_l$$

where E, I, D, and A denote erythema, induration, desquamation, and area, respectively, and h, u, t, and l denote head, upper extremities, trunk, and lower extremities, respectively.

PASI scores range from 0.0 to 72.0 with the highest score representing complete erythroderma of the severest possible degree. Typically scores of 3 or less represent mild disease, scores over 3 and up and including 15 represent moderate disease and scores over 15 are considered to be associated with severe disease. If a Question is missing, PASI is not scored. PASI 75 (PASI 50, PASI 90, PASI 100) response is achieved if there is at least a 75% (50%, 90%, 100%) reduction in PASI score (≥PASI 75/50/90/100 response) at a visit relative to the Baseline PASI score. See, e.g., Feldman et al., *J Invest Dermatol.* 1996; 106(1):183-6.

Self-Assessment of Psoriasis Symptoms (SAPS)

The Self-Assessment of Psoriasis Symptoms (SAPS) contains 11 symptom-focused Questions, as provided below. Each Question is scored from 0 to 10, with 0 being least severe and 10 being most severe. The total score is generated by summing the 11 Questions. The total score ranges from 0 to 110.

1. Over the past 24 hours, what was the worst pain you experienced in the areas affected by psoriasis?
2. Over the past 24 hours, what was the worst itching you experienced in the areas affected by psoriasis?
3. Over the past 24 hours, what was the worst redness you experienced in the areas affected by psoriasis?
4. Over the past 24 hours, what was the worst scaling you experienced in the areas affected by psoriasis?
5. Over the past 24 hours, what was the worst flaking (scales falling off your skin) you experienced in the areas affected by psoriasis?
6. Over the past 24 hours, what was the worst bleeding you experienced in the areas affected by psoriasis?
7. Over the past 24 hours, what was the worst burning you experienced in the areas affected by psoriasis?
8. Over the past 24 hours, what was the worst stinging you experienced in the areas affected by psoriasis?
9. Over the past 24 hours, what was the worst tenderness you experienced in the areas affected by psoriasis?
10. Over the past 24 hours, what was the worst pain you experienced due to skin cracking in the areas affected by psoriasis?
11. Over the past 24 hours, what was the worst joint pain you experienced due to psoriasis?

Sharp/Van Der Heijde Score (SHS) Score (Equivalent to the Modified Total Sharp Score, mTSS)

Radiographic outcomes will be assessed and scored according to Sharp's method (van der Heijde modification for PsA). To obtain the total SHS score, scores for erosions and JSN in both the hands and feet will be added together. The range of scores is summarized below. A finding of No Radiographic Progression of PsA is no change or improvement from baseline in SHS (≤0).

TABLE 5

Range of Total SHS Score, Erosion Score and Joint Space Narrowing

|  | Hands | Feet | Total (Hands and Feet) |
|---|---|---|---|
| Erosion Score Range | 0-200 | 0-120 | 0-320 |
| Joint Space Narrowing Range | 0-160 | 0-48 | 0-208 |
| Total SHS Range for Erosion and JSN | 0-360 | 0-168 | 0-528 |

Erosion Assessment. Erosions will be assessed in each hand (20 locations per hand) and foot (6 locations per foot). The locations assessed in the SHS method include: 4 Distal inter-phalangeal joints (2-5); 5 Metacarpo-Phalangeal Joints (1-5); 4 Proximal Inter-Phalangeal Joints (2-5); Inter-Phalangeal Joint of the thumb; Proximal first Metacarpal Bone; Radius Bone; Ulnar Bone; Trapezium and Trapezoid (as one unit; multangular); Navicular Bone; Lunate Bone; 5 Metatarso-phalangeal joints (1-5); Inter-phalangeal joint of the first toe.

Joint Space Narrowing Assessment. Joint space narrowing (JSN) will be assessed in each hand (20 locations per hand) and foot (6 locations per foot). The locations assessed in the SHS method include: 4 Distal inter-phalangeal joints (2-5); 4 Proximal inter-phalangeal joints (2-5); 5 Metacarpo-phalangeal joints (1-5); Interphalangeal Joint of thumb (IP); 3 Carpo-metacarpal joints (3-5); Radio-carpal joint; Multangular-navicular joint; Capitate-navicular-lunate joint; 5 Metatarso-phalangeal joints; Inter-phalangeal joint of first toe.

For each Joint and Bone assessed, scores range as follows: Erosions: 0-5 (hands/wrists) or 0-10 (feet) to characterize the extent of erosions (where 0 denotes no erosion); Joint Space Narrowing: 0-4 to characterize the extent of Joint Space Narrowing (JSN) (where 0 denotes no narrowing).

SpondyloArthritis Research Consortium of Canada (SPARCC) Assessment for Spine (MRI SPARCC—Spine or MRI-Spine SPARCC) and Sacroiliac (SI) Joints (MRI SPARCC—Joints or MRI-SI Joints SPARCC)

SPARCC scores for spine and sacroiliac (SI) joints are calculated by adding up the dichotomous outcomes from evaluations of the presence, depth and intensity of bone marrow edema lesions of the spine and SI joints, respectively.

In the MRI SPARCC score of Spine, the entire spine is evaluated for active inflammation (bone marrow edema) using the Short-TI Inversion Recovery (STIR) image sequence. 23 discovertebral units (DVUs) are assessed, and the six most severely affected DVUs are selected and used to calculate the MRI Spine SPARCC score. For each of the six DV Us, 3 consecutive sagittal slices are assessed in four quadrants in order to evaluate the extent of inflammation in all three dimensions.

1. Each quadrant is scored for presence of increased signal on STIR (1=increased signal; 0=normal signal)
2. Presence, on each of the sagittal slices, of a lesion exhibiting high signal intensity (comparable to cerebrospinal fluid) in any disco-vertebral unit is given an additional score of 1.
3. Slices that included a lesion demonstrating continuous increased signal of depth ≥1 cm extending from the endplate are to be scored as +1 per slice.

The maximum possible score for any individual slice is 6, with a maximum score for all 6 discovertebral units being 108.

The MRI SPARCC score of SI joints is conducted on 6 consecutive slices of the STIR image sequence. All lesions within the iliac bone and within the sacrum up to the sacral foramina are to be scored. The SI joint is divided into 4 quadrants: upper iliac, lower iliac, upper sacral and lower sacral. Each consecutive slice is scored separately for the right and left joint in all four quadrants as follows:

1. Each quadrant is scored for presence of increased signal on STIR (1=increased signal; 0=normal signal)
2. Joints that include a lesion exhibiting intense signal on the STIR sequence are scored as +1 per slice.
3. Joints that included a lesion demonstrating continuous increased signal of depth ≥1 cm from the articular surface are be scored as +1 per slice.

The maximum possible score for any individual slice is 12, with a maximum score for all 6 slices being 72.

Static Investigator Global Assessment of Psoriasis (sIGA)

The sIGA is a 5-point score ranging from 0 to 4, based on assessment of the average elevation, erythema, and scaling of all psoriatic lesions. The assessment is considered "static" which refers to the patient's disease state at the time of the assessments, without comparison to any of the patient's previous disease states, whether at baseline or at a previous visit. A lower score indicates less severe psoriasis (0=clear, 1=almost clear, 2=mild, 3=moderate and 4=severe). A binary clinical endpoint for the PsA-1 and PsA-2 clinical studies based on sIGA is the proportion of subjects achieving a sIGA score of 0 or 1 and at least a 2-point improvement from baseline. This endpoint is calculated among the subjects with baseline sIGA score ≥2.

Work Productivity and Activity Impairment Questionnaire for Psoriatic Arthritis (WPAI-PsA) and Axial Spondyloarthritis (WPAI-Axial SpA)

The Work Productivity and Activity Impairment Questionnaire (WPAI) was developed to measure the effect of overall health and specific symptoms on productivity at work and outside of work. It consists of 6 questions. A lower WPAI score indicates an improvement. The 4 main impairment scores (S1 to S4) are expressed as percent impairment based on the 6 questions.

S0. Employment: defined below

S1. Absenteeism: Percent work time missed due to PsA or Axial SpA:

$$100 \times \left[\frac{Q2}{Q2+Q4}\right]$$

S2. Presenteeism: Percent impairment while working due to PsA or Axial SpA:

$$100 \times \left[\frac{Q5}{10}\right]$$

S3. Percent overall work impairment due to PsA or Axial SpA:

$$100 \times \left[\frac{Q2}{Q2+Q4} + \left\{1 - \frac{Q2}{Q2+Q4}\right\} \times \frac{Q5}{10}\right]$$

4 Percent activity impairment due to PsA or Axial SpA:

$$100 \times \left[\frac{Q6}{10}\right]$$

S5. Did subject miss work (defined below). This is needed to derive the proportion of subjects who missed work.

When calculating the WPAI scores, the following computational notes should be followed.

Define Employment as a binary YES or NO variable where YES corresponds to "Employed" and NO corresponds to "Not Employed."

A subject will be considered "employed" at a given visit if Q1=YES or Q2>0 or Q4>0.

A subject will be considered "unemployed" at a given visit if Q1=NO and no positive hours recorded under Q2 and Q4 (i.e., if Q1=NO AND Q2≤0 AND Q4≤0, then UNEMPLOYED).

Employment status for a subject will be considered "missing" at a given visit if Q1=missing and no positive hours recorded under Q2 and Q4.

If a subject is "unemployed" or employment status is "missing," then S1, S2, and S3 will be set to "missing."

If Q2=0 and Q4=0 or missing then Q2/(Q2+Q4)=missing (i.e., S1=missing).

If Q2=0 and Q4=0, then set S3 to missing.

If Q2 is missing or Q4 is missing, then set S1 and S3 to missing.

If Q4=missing, then DO NOT set Q5=missing.

If Q5 is missing, then apply the following rules:

If Q2>0, Q4=0, and Q5=missing, then S3=100%.

If Q2=0, Q4>0, and Q5=missing, then S3 is missing.

If Q2>0, Q4>0, and Q5=missing, then S3 is missing.

Determine if a subject missed work (based on Q2) in order to analyze the proportion of subjects who missed work:

Create a binary (yes or no) "missed work" variable.

A subject will be considered as yes to missed work if Q2 is greater than 0.

If Q2=missing, then MISSED WORK=missing.

If Q2>0, then MISSED WORK="yes."

If Q2=0, then MISSED WORK="no."

Therefore, the proportion of subjects who missed work will be counted based on the number of subjects with MISSED WORK=YES.

36-Item Short Form Health Survey (Form SF-36)

The 36-Item Short Form, Version 2 (SF-36v2) (Quality Metric) health survey consists of 36 general health questions. It has 2 components: physical and mental. For each component, a transformed summary score is calculated using 8 sub domains: physical functioning, role-physical, bodily pain, general health, vitality, social functioning, role-emotional, and mental health. The range is from 0 to 100, with higher scores indicating better outcomes. The coding and scoring for the SF-36 will use the software provided by the vendor.

Additional Definitions

A "subject" means a human. The terms "patient" and "subject" are used interchangeably herein.

An "adult subject" means a subject 18 years or older.

A "juvenile" or "pediatric" subject means a subject 1 to <18 years old. Juvenile subjects to be treated are subjects diagnosed with juvenile AS (JAS), juvenile PsA (JPsA), and/or juvenile PsO (JPsO) and in need of treatment as determined by a physician ("active juvenile AS" and "active juvenile PsA", "active juvenile PsO", respectively). Juvenile AS may be classified per International League of Associations for Rheumatology (ILAR) (defining 7 discrete categories of arthritis starting before the age of 18 years: systemic arthritis, oligoarthritis, polyarthritis (rheumatoid factor [RF]-negative), polyarthritis (RF-positive), PsA, enthesitis-related JIA (or juvenile enthesitis-related arthritis [ERA]), and undifferentiated arthritis). See, e.g., Petty el al., *J Rheumatol.* (2004)31:390-2. Juvenile PsA may be classified per pediatric International League of Associations for Rheumatology (ILAR) and/or adult criteria [Classification criteria for Psoriatic Arthritis (CASPAR)]. See e.g., Aviel et al., *Pediatric Rheumatology* (2013) 11:11; Zisman et al., *J. Rheum.* (2017) 44:342-351.

The "2009 ASAS classification criteria" for the classification of a subject with axial spondyloarthritis (axial SpA, or axSpA) is described in Rudwaleit et al., *Ann. Rheum. Dis.* (2009) 68:777-783. The criteria require chronic back pain (≥3 months) in the subject and age at onset <45 years, with the subject also having the following conditions (1) the presence of sacroiliitis by radiography or by magnetic resonance imaging (MRI) plus at least one SpA feature ("imaging arm") or (2) the presence of human leukocyte antigen (HLA) B27 plus at least two SpA features ("clinical arm"). Sacroiliitis on imaging refers to active (acute) inflammation on MRI highly suggestive of sacroiliitis associated with SpA, or definite radiographic sacroiliitis. SpA features are selected from the group consisting of inflammatory back pain, arthritis, enthesitis (heel), uveitis, dactylitis, psoriasis, Crohn's disease or ulcerative colitis, good response to NSAISs (24-48 hours after a full dose of an NSAID the back pain is not present any more or is much better), family history for SpA, positive HLA-B27, and elevated C-reactive protein (above the upper normal limit in the presence of back pain, and after exclusion of other reasons for elevation). See also Deodhar et al., *Arth. & Rheum.* (2014) 66:2649-2656.

The "1984 modified New York criteria" for the classification of a subject with ankylosing spondylitis (AS), is described in van der Linden et al., Arthritis *and Rheumatism* (1984) 27:361-368, and has two components: diagnosis and grading; the diagnosis component further has two criteria: clinical and radiologic. The clinical criteria require: (i) low back pain and stiffness for more than 3 months which improves with exercise, but is not relieved by rest; (ii) limitation of motion of the lumbar spine in both the sagittal and frontal planes, and (iii) limitation of chest expansion relative to normal values corrected for age and sex. The radiologic criterion requires sacroiliitis grade >2 bilaterally or sacroiliitis grade 3-4 unilaterally. The grading component requires: (i) definite ankylosing spondylitis if the radiologic criterion is associated with at least 1 clinical criterion; and (ii) probable ankylosing spondylitis if 3 clinical criteria are present, and the radiologic criterion is present without any signs or symptoms satisfying the clinical criteria. See also Deodhar et al., *Arth. & Rheum.* (2014) 66:2649-2656.

The term "axial Spondyloarthritis" (axial SpA or axSpA) encompasses both "ankylosing spondylitis" (AS) and "non-radiographic axial spondyloarthritis" (nr-axial SpA, or nr-axSpA). A subject with "active axial Spondyloarthritis" (active axSpA) means a subject with a clinical diagnosis of active AS or active nr-axial SpA, and in need of treatment as determined by a physician.

A subject with "active ankylosing spondylitis" (active AS) means a subject with a clinical diagnosis of AS and in need of treatment as determined by a physician. In certain embodiments, the subject diagnosed as suffering from AS is further classified (e.g., in the United States) as fulfilling the 1984 modified New York Criteria for AS and/or as fulfilling the 2009 ASAS classification criteria. In certain embodiments, the subject with a high disease activity of AS has a Bath Ankylosing Spondylitis Disease Activity Index score ≥4 and/or ASDAS≥2.1 and/or a Patient's Assessment of Total Back Pain (Total Back Pain score)≥4 based on a 0-10 numerical rating scale at baseline. See, e.g., van der Heijde et al., Ann Rheum Dis. (2017)76:978-991; Sieper and Poddubnyy, Lancet (2017) 73-84.

A subject with "active non-radiographic axial spondyloarthritis" (active nr-axial SpA or active nr-axSpA) means a subject with a clinical diagnosis of nr-axial SpA and in need of treatment as determined by a physician. In certain embodiments, the subject diagnosed as suffering from nr-axial SpA is further classified (e.g., in the United States) as fulfilling the 2009 ASAS classification criteria for axSpA but not meeting the radiologic criterion of the 1984 modified New York criteria for AS. In certain embodiments, the subject with high disease activity of nr-axial SpA has a Bath Ankylosing Spondylitis Disease Activity Index score ≥4 and/or an ASDAS≥2.1 and/or a Patient's Assessment of Total Back Pain Score (Total Back Pain score)≥4 based on a 0-10 numerical rating scale at baseline; and an objective sign of inflammatory activity selected from the group consisting of (i) an objective sign of active inflammation on MRI of SI joints or (ii) hsCRP>upper limit of normal (ULN) at baseline. See, e.g., van der Heijde et al., Ann Rheum Dis. (2017) 76:978-991 Sieper el al. Ann. Rheum. Dis. (2009) 68 Suppl 2:ii1-44. doi: 10.1136/ard.2008.104018; Van der Heijde et al. Ann Rheum Dis. (2017) 76:978-991; Sieper and Poddubnyy, Lancet (2017) 73-84.

The "CASPAR criteria" (Classification criteria for Psoriatic Arthritis (see, e.g., Taylor et al., Arthritis and Rheumatism (2006) 54:2665-2673)) requires the subject to have inflammatory articular disease (joint, spine, or entheseal) with ≥3 points from the following 5 categories at baseline:

1. Evidence of current psoriasis, a personal history of psoriasis, or a family history of psoriasis (one of the following).
   a. Current psoriasis is defined as psoriatic skin or scalp disease present today as judged by a rheumatologist or dermatologist. Current psoriasis is assigned a score of 2; all other features are assigned a score of 1.
   b. A personal history of psoriasis is defined as a history of psoriasis that may be obtained from a patient, family physician, dermatologist, rheumatologist, or other qualified health care provider.
   c. A family history of psoriasis is defined as a history of psoriasis in a first- or second-degree relative according to a patient report.
2. Typical psoriatic nail dystrophy including oncolysis, pitting, and hyperkeratosis observed on current physical examination.
3. A negative test result for the presence of rheumatoid factor by any method except latex but preferably by enzyme-linked immunosorbent assay or nephelometry, according to the local laboratory reference range.
4. Either current dactylitis, defined as swelling of an entire digit, or a history of dactylitis recorded by a rheumatologist.
5. Radiographic evidence of juxta articular new bone formation, appearing as ill-defined ossification near joint margins (but excluding osteophyte formation) on plain radiographs of the hand or foot.

A subject with "active psoriatic arthritis" (active PsA) means a subject with a clinical diagnosis of PsA and in need of treatment as determined by a physician. In certain embodiments, the subject diagnosed as suffering from PsA is further classified (e.g., in the United States) as fulfilling the Classification Criteria for PsA (CASPAR) criteria at baseline. In certain embodiments, the subject may have ≥3 tender joints (based on 68 joint counts) and ≥3 swollen joints (based on 66 joint counts) at baseline. In certain embodiments, the subject may have ≥5 tender joints (based on 68 joint counts) and ≥5 swollen joints (based on 66 joint counts) at baseline. In certain embodiments, the subject may have ≥3% Body Surface Area with Psoriasis (BSA-PS). In certain embodiments, subjects with Minimal Disease Activity (responders and non-responders) for PsA are excluded. "Active PsA" includes subjects who are, as determined by a physician, functioning normally while suffering from active PsA and subjects who are not, as determined by a physician, functioning normally while suffering from active PsA. For example, a subject with psoriasis on the abdomen may be considered to be manifesting active PsA but able to function normally, while a subject with psoriasis on the face may be considered to be manifesting active PsA but not able to function normally (e.g., due to emotional distress). "Moderately to severely active PsA" is a subset of "active PsA" and involves the determination by a physician that the subject is not able to function normally while suffering from active PsA.

A subject with "active psoriasis" (active PsO) means a subject with a clinical diagnosis of PsO and in need of treatment as determined by a physician. In certain embodiments, the active psoriasis is active plaque psoriasis. In certain embodiments, the subject has a documented history of plaque psoriasis. "Active PsO" includes subjects who are, as determined by a physician, functioning normally while suffering from active PsO and subjects who are not, as determined by a physician, functioning normally while suffering from active PsO. For example, a subject with psoriasis on the abdomen may be considered to be manifesting active PsO but able to function normally, while a subject with psoriasis on the face may be considered to be manifesting active PsO but not able to function normally (e.g., due to emotional distress). "Moderately to severely active PsO" is a subset of "active PsO" and involves the determination by a physician that the subject is not able to function normally while suffering from active PsO. In certain embodiments, the subject may have >3% Body Surface Area with Psoriasis (BSA-PS) at baseline.

The abbreviation "AS" refers to ankylosing spondylitis.

A result being achieved "within X weeks" of administration of the first dose of the JAK1 inhibitor wherein X is a integer greater than 0 (e.g., 1, 2, 4, 6, 8, 10, 12, 14, 16, 18, 20, 22, 24, 52, . . . 64 weeks, etc.) means the result occurs within the time frame beginning at the time of the administration of the first dose (Week 0) of the JAK1 inhibitor, and ending on and including the last day of the given specified week. A measurement or score used to determine if a result is achieved "at week X" (e.g., at week 1, 2, 4, 6, 8, 10, 12, 14, 16, 18, 20, 22, 24, 52, . . . 64 weeks, etc.) may be taken at any point during, as well as on and including the first and last day, of given week X for the subject.

The abbreviation "axSpA" refers to axial spondyloarthritis.

The abbreviations "bDMARDs" and "biologic DMARDs" refer to biologic Disease Modifying Anti-Rheumatic Drugs. Examples of bDMARDs include, but are not limited to, biologic tumor necrosis factor inhibitors (e.g., adalimumab, etanercept) and interleukin (IL)-17 inhibitors (e.g., secukinumab, ixekizumab).

The term "bDMARD-IR" refers to a subject who is a bDMARD inadequate responder, bDMARD-IR subjects include those who have had an inadequate response to treatment with at least one bDMARD, or who have an intolerance to or contraindication for bDMARDs. Subjects who are bDMARD-IR include subjects who have discontinued treatment with at least one bDMARD due to intolerance or lack of efficacy.

The term "bDMARD naïve" refers to a subject who has not had prior exposure to any biologic therapy, including any bDMARD, that may potentially have a therapeutic impact on the disorder or condition that is being treated.

The term "baseline" or "BL" refers to the time immediately before first dosing with the JAK1 inhibitor. Baseline measurements (i.e., on the "Baseline Visit" or on the "Screening Visit") are collected prior to administration of the first dose of the JAK1 inhibitor (i.e., upadacitinib freebase or a pharmaceutically acceptable salt thereof), and may include a measurement taken the day of but prior to first dosing with the JAK1 inhibitor.

The term "change from baseline" for a particular score or measurement means the score or measurement has improved (e.g., demonstrating a positive clinical effect in the subject or population of subjects) as compared to the score or measurement taken at baseline.

The abbreviation "CII" means Clinically Important Improvement.

The phrase "concomitant administration" or "concomitant treatment" when referencing a therapy in addition to administration of the JAK1 inhibitor means the additional therapy is occurring at baseline and/or during treatment with the JAK1 inhibitor.

The abbreviations "DMARDs" and "non-biologic DMARDs" refer to non-biologic Disease Modifying Anti-Rheumatic Drugs. Non-biologic DMARDs include, but are not limited to, methotrexate (MTX), sulfasalazine (SSZ), leflunomide (LEF), apremilast, hydroxychloroquine (HCQ), bucillamine, and iguratimod. "Non-biologic DMARDs" and "conventional-synthetic disease modifying anti-rheumatic drugs" (csDMARDs) are used interchangeably herein.

The term "DMARD-IR" or "non-biologic DMARD-IR" refers a subject who is a non-biologic DMARD inadequate responder. DMARD-IR subjects include those who have had an inadequate response to treatment with at least one non-biologic DMARD, or who have an intolerance to or contraindication for non-biologic DMARDs.

The abbreviation "EMA" means European Medicines Agency.

The abbreviation "FDA" means Food and Drug Administration.

The abbreviation "hsCRP" means high-sensitivity C-reactive protein.

The abbreviation "ID" means Inactive Disease.

The phrase "improving physical function" in a subject with active PsA means an improvement in activities or tasks compared to baseline.

"In need of treatment" or "in need of treatment . . . as determined by a physician" refers to the physician's opinion that, at baseline, the condition is not sufficiently well-controlled, such as by other medical management (e.g., by other therapy or therapies previously administered to treat the condition).

The phrase "inhibiting the progression of structural damage" or "preventing structural progression" in a subject with active PsA means demonstrating prevention of bony changes on x-ray compared to baseline.

"JAK1 inhibitor" refers to the compound upadacitinib ((3S,4R)-3-ethyl-4-(3H-imidazo[1,2-a]pyrrolo[2,3-e]pyrazin-8-yl)-N-(2,2,2-trifluoroethyl)pyrrolidine-1-carboxamide) freebase or a pharmaceutically acceptable salt thereof. Solid state forms of the JAK1 inhibitor are further described herein.

The abbreviation "LDA" means low disease activity.

The abbreviation "MI" means major improvement.

The abbreviation "MRI" means magnetic resonance imaging.

A result is considered "non-inferior" (NI) as compared to adalimumab if administration of the JAK1 inhibitor preserves at least 50% of the placebo-subtracted adalimumab effect.

The abbreviation "nr-axSpA" refers to non-radiographic axial spondyloarthritis.

The abbreviation "NRI" means non-responder imputation.

The abbreviation "NSAIDs" refers to non-steroidal anti-inflammatory drugs. Examples NSAIDs include, but are not limited to, traditional NSAIDs (e.g., ibuprofen) and salicylates (e.g., aspirin).

The term "pharmaceutically acceptable" (such as in the recitation of a "pharmaceutically acceptable salt" or a "pharmaceutically acceptable diluent") refers to a material that is compatible with administration to a human subject. e.g., the material does not cause an undesirable biological effect. Examples of pharmaceutically acceptable salts are described in "Handbook of Pharmaceutical Salts: Properties. Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methane sulfonic acid, ethane sulfonic acid, p-toluene sulfonic acid, citric acid, fumaric acid, maleic acid, succinic acid, benzoic acid, salicylic acid, lactic acid, mono-malic acid, mono oxalic acid, tartaric acid such as mono tartaric acid (e.g., (+) or (−)-tartaric acid or mixtures thereof), amino acids (e.g., (+) or (−)-amino acids or mixtures thereof), and the like. These salts can be prepared by methods known to those skilled in the art.

A "population of subjects" refers to the group of subjects participating in a clinical trial, with all subjects suffering from the same disease or symptom to be treated, wherein the clinical trial comprises a treatment arm (a subgroup of the subjects treated with the JAK1 inhibitor), and a placebo arm (a subgroup of the subjects not treated with the JAK1 inhibitor). When used in connection with the treatment of a population of subjects, the phrase "at least X % of the subjects in the treated population achieve" a particular response refers to the placebo corrected X % response (subjects treated—subjects not treated).

The abbreviation "PR" means partial remission.

The abbreviation "PsA" refers to psoriatic arthritis.

The abbreviation "PsO" refers to psoriasis. Psoriasis includes psoriasis as a skin manifestation of PsA.

The abbreviation "QD" means once daily.

The phrase "reducing signs and symptoms" means an improvement in disease activity, function, and/or quality of life compared to baseline.

The abbreviation "SI" means sacroiliac.

"Statistically significant" means when observed p value <alpha for a given hypothesis testing. The pre-specified significance level, alpha, is the probability of rejecting the null hypothesis given that it is true. Alpha is also called type I error or false positive rate. It is usually set at or below 0.05. The observed p value is the probability, under the null hypothesis, of observing an effect of the same magnitude or more extreme. When observed p value <alpha, the null hypothesis is rejected, and statistical significance is claimed. In a multiplicity-controlled analysis, when the adjusted p value <alpha, the result is statistically significant. In the fixed sequence of a multiplicity-controlled analysis, statistical significance can be claimed for a lower ranked endpoint only if the previous endpoint in the sequence meets the requirements of statistical significance.

A result is considered "superior" as compared to adalimumab if the multiplicity adjusted p value for the null hypothesis testing of the treatment difference between the JAK1 inhibitor and adalimumab is less than pre-specified significance level.

"Total spinal ankylosis" refers to bridging syndesmophytes (fusion) in a total sum of ≥5 segments of the C2-T1 or T12-S1 spine (e.g., 2 segments fused in the cervical and 3 segments fused in the lumbar spine would be considered positive for total spinal ankylosis).

The terms "treating", "treatment", and "therapy" and the like, as used herein, are meant to include but not limited to alleviation or relief of one or more symptoms of the condition from which the subject is suffering (i.e., axial spondyloarthritis (axSpA) (e.g., non-radiographic axSpA (nr-axSpA), ankylosing spondylitis (AS)), psoriatic arthritis (PsA), psoriasis (PsO)), including the slowing or cessation of the progression of the condition, such as slowing or cessation of the progression of structural damage associated with the condition, the structural progression of the condition, and/or improving the physical function of a subject suffering from the condition.

The term "upadacitinib freebase" refers to freebase (non-salt, neutral) forms of upadacitinib. Examples of upadacitinib freebase solid state forms include amorphous upadacitinib freebase and crystalline freebases of upadacitinib, such as crystalline freebase solvates, crystalline freebase hydrates, crystalline freebase hemihydrates, and crystalline freebase anhydrates of upadacitinib. Specific examples of upadacitinib freebase solid state forms include but are not limited to Amorphous Upadacitinib Freebase, Upadacitinib Freebase Solvate Form A, Upadacitinib Freebase Hydrate Form B, Upadacitinib Freebase Hydrate Form C (which is a hemihydrate), and Upadacitinib Freebase Anhydrate Form D, each as described in WO 2017/066775 and WO 2018/165581.

The term "upadacitinib freebase equivalent" refers to the amount of the neutral upadacitinib freebase (active ingredient) administered, and not including any coformer (e.g., solvent or water molecule(s)) of a solvate or hydrate (including hemihydrate), and not including any pharmaceutically acceptable salt counter anions of a pharmaceutically acceptable salt. For example, 15.4 mg of crystalline upadacitinib freebase hemihydrate (which includes ½ of a water conformer molecule per upadacitinib freebase molecule) delivers 15 mg of upadacitinib freebase equivalent, while 30.7 mg of crystalline upadacitinib freebase hemihydrate (which includes ½ of a water conformer molecule per upadacitinib freebase molecule) delivers 30 mg of upadacitinib freebase equivalent.

II. Methods of Treatment

The present disclosure also relates to methods of treating a JAK-associated condition in a subject, particularly a human subject suffering from or susceptible to the condition, comprising administering to the subject a therapeutically effective amount of Compound 1 freebase or a pharmaceutically acceptable salt thereof or one or more solid state forms of Compound 1 as described in the present disclosure. Another aspect of the disclosure relates to Compound 1 freebase or a pharmaceutically acceptable salt thereof or one or more solid state forms of Compound 1 as described in the present disclosure for use in treatment of a JAK-associated condition in a subject, particularly in a human subject suffering from or susceptible to the condition, the use comprising administering to the subject a therapeutically effective amount of Compound 1 freebase or a pharmaceutically acceptable salt thereof or one or more solid state forms of Compound 1. In one aspect, the condition is a JAK-1-associated condition. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of immunomodulation, inflammation, and proliferative disorders (such as cancer) in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of immunomodulation, inflammation, and proliferative disorders (such as cancer) in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Anhydrate Form D. In another aspect, the solid state form is the Freebase Hydrate Form B. In another aspect, the solid state form is the Freebase Hydrate Form C. In another aspect, the solid state form is the Tartrate Hydrate.

In one embodiment, the present disclosure relates to methods of treating a condition selected from the group consisting of rheumatoid arthritis, multiple sclerosis, experimental allergic encephalomyelitis, systemic lupus erythematosus. Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis. POEMS syndrome, and chronic fatigue syndrome in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune hemolytic anemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopenia in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of an ocular condition, systemic inflammatory response syndrome, juvenile rheumatoid arthritis, systemic onset juvenile rheumatoid arthritis, type III hypersensitivity reactions, type IV hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune hemolytic anemia, rheumatoid arthritis associated interstitial lung disease, systemic lupus erythematosus associated lung disease, dermatomyositis/polymyositis associated lung disease, Sjögren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjögren's syndrome, and autoimmune thrombocytopenia in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition, the use comprising administering to the subject a therapeutically effective amount of Compound 1 freebase or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis. Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating arthritis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of arthritis in a subject, particularly in a human subject suffering from or susceptible to arthritis, the use comprising administering to the subject a therapeutically effective amount of Compound 1 freebase or a pharmaceutically acceptable salt thereof or a solid state form of Compound 1. In one aspect, the arthritis is selected from the group consisting of rheumatoid arthritis, juvenile idiopathic arthritis, and psoriatic arthritis. In another aspect, the arthritis is rheumatoid arthritis. In another aspect, the arthritis is juvenile idiopathic arthritis. In another aspect, the arthritis is psoriatic arthritis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a spondyloarthropathy in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of spondyloarthropathy, particularly in a human subject suffering from or susceptible to spondyloarthropathy, the use comprising administering to the subject a therapeutically effective amount of Compound 1 freebase or a pharmaceutically acceptable salt thereof or a solid state form of Compound 1. In one aspect, the spondyloarthropathy is ankylosing spondylitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a gastrointestinal condition in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a gastrointestinal condition, particularly in a human subject suffering from or susceptible to a gastrointestinal condition, the use comprising administering to the subject a therapeutically effective amount of Compound 1 freebase or a pharmaceutically acceptable salt thereof or a solid state form of Compound 1. In one aspect, the gastrointestinal condition is selected from the group consisting of Crohn's disease and ulcerative colitis. In another aspect, the gastrointestinal condition is Crohn's disease. In another aspect, the gastrointestinal condition is ulcerative colitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a skin condition, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a skin condition, particularly in a human subject suffering from or susceptible to a skin condition, the use comprising administering to the subject a therapeutically effective amount of Compound 1 freebase or a pharmaceutically acceptable salt thereof or a solid state form of Compound 1. In one aspect, the skin condition is selected from the group consisting of psoriasis, plaque psoriasis, nail psoriasis, and hidradenitis suppurativa. In another aspect, the skin condition is psoriasis. In another aspect, the skin condition is plaque psoriasis. In another aspect, the skin condition is nail psoriasis. In another aspect, the skin condition is hidradenitis suppurativa. In another aspect, the skin condition is atopic dermatitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

The therapeutically effective dose level for any particular subject will depend upon the specific situation and can depend upon a variety of factors including the type, age, weight, sex, diet, and condition of the subject being treated; the severity of the pathological condition; activity of the specific compound employed; the specific composition employed; the age, body weight, general health, sex and diet of the subject; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The total daily dose of the solid state form (administered in single or divided doses) typically is from about 0.001 to about 100 mg/kg, or from about 0.001 to about 30 mg/kg, or from about 0.001 to about 15 mg/kg. In another embodiment, the total daily dose is from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

In one embodiment, the daily dose of the solid state form administered to the subject is from about 0.01 mg to about 3000 mg. In one aspect, the daily dose is from about 0.1 mg to about 1000 mg. In another aspect, the daily dose is from is from about 1 mg to about 500 mg. In another aspect, the daily dose is from about 1 mg to about 250 mg. In another aspect, the daily dose is from about 1 mg to about 100 mg. In another aspect, the daily dose is from about 1 mg to about 50 mg. In another aspect, the daily dose is from about 1 mg to about 45 mg. In another aspect, the daily dose is from about 1 mg to about 30 mg. In another aspect, the daily dose is from about 1 mg to about 25 mg. In another aspect, the daily dose is from about 1 mg to about 24 mg. In another aspect, the daily dose is from about 1 mg to about 15 mg. In another aspect, the daily dose is from about 1 mg to about 7.5 mg. In another aspect, the daily dose is from about 25 mg to about 50 mg. In another aspect, the daily dose is from about 1 mg to about 10 mg. In another aspect, the daily dose is from about 10 mg to about 20 mg. In another aspect, the daily dose is from about 20 mg to about 30 mg. In another aspect, the daily dose is from about 30 mg to about 40 mg. In another aspect, the daily dose is from about 7.5 mg to about 45 mg. In another aspect, the daily dose is from about 15 mg to about 30 mg. In another aspect, the daily dose is about 3 mg. In another aspect, the daily dose is about 6 mg. In another aspect, the daily dose is about 7.5 mg. In another aspect, the daily dose is about 12 mg. In another aspect, the daily dose is about 15 mg. In another aspect, the daily dose is about 18 mg. In another aspect, the daily dose is about 24 mg. In another aspect, the daily dose is about 30 mg. In another aspect, the daily dose is about 36 mg. In another aspect, the daily dose is about 45 mg.

In one embodiment, a dose of about 3 mg, about 6 mg, about 12 mg, or about 24 mg per unit dosage form (e.g., per tablet or capsule) of a solid state form of Compound 1 is administered orally BID (twice daily) in equal amounts (e.g., twice a day, about 3 mg each time) to a human subject.

In one embodiment, the disclosure relates to a method of treating a subject having rheumatoid arthritis, the method comprising administering to the subject about 3 mg, per unit dosage form (e.g., per tablet or capsule) of a solid state form of Compound 1 orally BID (twice daily) in equal amounts (e.g., twice a day, about 3 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 3 mg, per unit dosage form (e.g., per tablet or capsule) of a solid state form of Compound 1 orally BID (twice daily) in equal amounts (e.g., twice a day, about 3 mg each time).

In one embodiment, the disclosure relates to a method of treating a subject having rheumatoid arthritis, the method comprising administering to the subject about 6 mg, per unit dosage form (e.g., per tablet or capsule) of a solid state form of Compound 1 orally BID (twice daily) in equal amounts (e.g., twice a day, about 6 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 6 mg, per unit dosage form (e.g., per tablet or capsule) of a solid state form of Compound 1 orally BID (twice daily) in equal amounts (e.g., twice a day, about 6 mg each time).

In one embodiment, the disclosure relates to a method of treating a subject having rheumatoid arthritis, the method comprising administering to the subject about 12 mg, per unit dosage form (e.g., per tablet or capsule) of a solid state form of Compound 1 orally BID (twice daily) in equal amounts (e.g., twice a day, about 12 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 12 mg, per unit dosage form (e.g., per tablet or capsule) of a solid state form of Compound 1 orally BID (twice daily) in equal amounts (e.g., twice a day, about 12 mg each time).

In one embodiment, the disclosure relates to a method of treating a subject having rheumatoid arthritis, the method comprising administering to the subject about 24 mg, per unit dosage form (e.g., per tablet or capsule) of a solid state form of Compound 1 orally BID (twice daily) in equal amounts (e.g., twice a day, about 24 mg each time). In another aspect, the present disclosure relates a solid state form of Compound 1 for use in treating rheumatoid arthritis in a subject, particularly in a human subject suffering from or susceptible to rheumatoid arthritis, the use comprising administering to the subject about 24 mg, per unit dosage form (e.g., per tablet or capsule) of a solid state form of Compound 1 orally BID (twice daily) in equal amounts (e.g., twice a day, about 24 mg each time).

In another embodiment, the methods or uses comprise administering orally QD (once daily) to a human subject a dose of about 7.5 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 7.5 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 7.5 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 15 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 15 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 15 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 24 mg of Compound 1 freebase or a pharmaceutically acceptable salt thereof. The 24 mg QD dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously.

In another embodiment, the methods or uses comprise administering orally QD (once daily) to a human subject a dose of about 24 mg of a solid state form of Compound 1. In one embodiment, the methods or uses comprise administering orally QD (once daily) to a human subject a solid state form of Compound 1 in an amount sufficient to deliver 24 mg of Compound 1 freebase equivalent to the subject. The 24 mg QD dose of the solid state form of Compound 1 may be administered as either a single dosage form comprising about 24 mg per unit dosage form (e.g., per tablet or capsule) of the solid state form of Compound 1, or two dosage forms comprising about 12 mg per unit dosage form (e.g., per tablet or capsule) of the solid state form of Compound 1 administered simultaneously. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 30 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 30 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 30 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 36 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 36 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 36 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 45 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 45 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 45 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In certain embodiments, Compound 1 freebase or a pharmaceutically acceptable salt thereof and/or solid state forms thereof can be used to treat rheumatoid arthritis (RA), including reducing signs and symptoms of RA, inducing a major clinical response, inhibiting the progression of or treating structural damage associated with RA, and improving physical function in adult subjects, such as adult subjects with moderately to severely active RA. In one embodiment, Compound 1 freebase or a pharmaceutically acceptable salt thereof and/or solid state forms thereof are used to treat RA in adult subjects. In one embodiment, Compound 1 freebase or a pharmaceutically acceptable salt thereof and/or solid state forms thereof are used to reduce signs and symptoms of RA in adult subjects. In one embodiment, Compound 1 freebase or a pharmaceutically acceptable salt thereof and/or solid state forms thereof induce a major clinical response in adult subjects with RA. In one embodiment. Compound 1 freebase or a pharmaceutically acceptable salt thereof and/or solid state forms thereof are used to inhibit the progression of structural damage associated with RA in adult subjects. In one embodiment, Compound 1 freebase and/or solid state forms thereof are used to treat structural damage associated with RA in adult subjects. In one embodiment, Compound 1 freebase or a pharmaceutically acceptable salt thereof and/or solid state forms thereof are used to improve physical function in adult subjects. In one embodiment, the adult subjects have RA. In another embodiment, the adult subjects have moderately to severely active RA.

Compound 1 freebase or a pharmaceutically acceptable salt thereof or solid state forms thereof may be used alone, or in combination with methotrexate or other non-biologic disease-modifying anti-rheumatic drugs (DMARDs), and/or in combination with anti-TNFα biological agents, such as TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™ tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept).

Patients having active rheumatoid arthritis (RA) may be diagnosed according to 1987-revised American College of Rheumatology (ACR) classification criteria or the 2010 ACR/EULAR criteria. In certain embodiments, RA may be diagnosed based on patients having at least 6 swollen and 6 tender joints. In certain embodiments, patients treatable with Compound 1 or solid state forms thereof may include those who have failed therapy with at least one (e.g., at least one but no more than four) DMARDs and/or have inadequate response to methotrexate, adalimumab, infliximab, etanercept, or other anti-TNFα biological agents, or non-anti-TNF biologics.

In certain embodiments, Compound 1 freebase or a pharmaceutically acceptable salt thereof or solid state forms thereof halt disease progression, and/or relieves at least a symptom of the disease, which may be detected or monitored by X-ray results, including radiographic progression of joint damage.

In certain embodiments, therapeutic efficacy can be measured by improvements in ACR20, ACR50, and/or ACR70, either in individual patients or a population of patients in need of treatment. In certain embodiments, statistically significant improvement (as compared placebo or untreated control) over a treatment period (e.g., 1 week, 2 weeks, 4 weeks, 6 weeks, 8 weeks, 12 weeks, 2 months, 3 months, 6 months, 1 year, 2 years, 5 years, 10 years or more) in one or more of the ACR criteria is achieved. Statistical significance is manifested by a p value of less than 0.05, or less than 0.01.

Components of the ACR responses are well known in the art, and may include the median number of tender joints, the median number of swollen joints, physician global assessment such as one measured by visual analog scale (VAS), patient global assessment such as one measured by visual analog scale, pain such as one measured by visual analog scale, disability index of the Health Assessment Questionnaire (HAQ-DI score), and C-reactive protein (CRP) (mg/dL).

In certain embodiments, an ACR20 response is determined based on a 20% or greater improvement in tender joint count (TJC) and swollen joint count (SJC) and greater than or equal to 3 of the 5 measures of Patient's Assessment of Pain (VAS), Patient's Global Assessment of Disease Activity (VAS), Physician's Global Assessment of Disease Activity (VAS), HAQ-DI, or high sensitivity C-reactive protein (hsCRP). In some embodiments, an ACR50 response is determined based on a 50% or greater improvement in TJC and SJC and greater than or equal to 3 of the 5 measures of Patient's Assessment of Pain (VAS), Patient's Global Assessment of Disease Activity (VAS), Physician's Global Assessment of Disease Activity (VAS), HAQ-DI, or hsCRP. An ACR70 response is determined based on a 70% or greater improvement in TJC and SJC and greater than or equal to 3 of the 5 measures of Patient's Assessment of Pain (VAS). Patient's Global Assessment of Disease Activity (VAS), Physician's Global Assessment of Disease Activity (VAS), HAQ-DI, or hsCRP. In certain embodiments, the ACR20, ACR50, or ACR70 response occurs by week 12 of treatment.

In certain embodiments, a DAS28 (disease activity score based on the 28 joints examined) score is determined as a composite score derived from four of the following measures: examination of joints for swelling and tenderness, global scores of pain and overall status, blood markers of inflammation (e.g. ESR (erythrocyte sedimentation rate) and CRP (C reactive protein), referred to herein as DAS28 (CRP)), questionnaires (e.g. the HAQ (health assessment questionnaire) which assess function) and X-rays and other imaging techniques such as ultrasound and MRI.

In certain embodiments, structural joint damage can be assessed radiographically and expressed as change in Total Sharp Score (TSS) and its components, the erosion score and Joint Space Narrowing (JSN) score, for example, at week 12 compared to baseline, or at week 24 as compared to baseline.

In certain embodiments, improvement in signs and symptoms of the disease can be measured by patient physical function response, such as disability index of Health Assessment Questionnaire (HAQ-DI), and/or the health-outcomes as assessed by The Short Form Health Survey (SF 36). In one embodiment, improvement in signs and symptoms of the disease is measured by HAQ-DI, including the minimal clinically important difference (MCID) of −0.22. Improvement can also be measured by one or both of Physical Component Summary (PCS) and the Mental Component Summary (MCS). Improvements can further be measured by Work Instability Scale for RA (RA-WIS) (see Gilworth et al., Arthritis & Rheumatism (Arthritis Care & Research) 49(3): 349-354, 2003, incorporated by reference).

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 7.5 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 7.5 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 7.5 mg, per unit dosage form (e.g., per tablet or capsule) of a solid state form of Compound 1 orally QD (once daily). In one embodiment, the solid state form delivers about 7.5 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 15 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 15 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 15 mg, per unit dosage form (e.g., per tablet or capsule) of a solid state form of Compound 1 orally QD (once daily). In one embodiment, the solid state form delivers about 15 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 24 mg of Compound 1 freebase or a pharmaceutically acceptable salt thereof orally QD (once daily). The 24 mg dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 24 mg of a solid state form of Compound 1 orally QD (once daily). In one embodiment, the method comprising administering to the subject a solid state form of Compound 1 orally QD (once daily) in an amount sufficient to deliver 24 mg of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 24 mg of a solid state form of Compound 1 orally QD (once daily). In one embodiment, the solid state form delivers about 24 mg of Compound 1 freebase equivalent to the subject. The 24 mg dose of the solid state form of Compound 1 may be administered as either a single dosage form comprising about 24 mg per unit dosage form (e.g., per tablet or capsule) of the solid state form of Compound 1, or two dosage forms comprising about 12 mg per unit dosage form (e.g., per tablet or capsule) of the solid state form of Compound 1 administered simultaneously. In one embodiment, the solid state form is the Freebase Hydrate Form B. In one embodiment, the solid state form is the Freebase Hydrate Form C.

In one embodiment, the solid state form is the Tartrate Hydrate. In one embodiment, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 30 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 30 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 30 mg, per unit dosage form (e.g., per tablet or capsule) of a solid state form of Compound 1 orally QD (once daily). In one embodiment, the solid state form delivers about 30 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 36 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 36 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 36 mg, per unit dosage form (e.g., per tablet or capsule) of a solid state form of Compound 1 orally QD (once daily). In one embodiment, the solid state form delivers about 36 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of Compound 1 freebase or a pharmaceutically acceptable salt thereof orally QD (once daily). In another aspect, the present disclosure relates to Compound 1 freebase or a pharmaceutically acceptable salt thereof for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of Compound 1 freebase or a pharmaceutically acceptable salt thereof orally QD (once daily). In one embodiment, the subject has moderately to severely active rheumatoid arthritis. In one embodiment, the subject is an adult.

In one embodiment, the disclosure relates to a method of treating rheumatoid arthritis in a subject, the method comprising administering to the subject, particularly a human subject suffering from or susceptible to rheumatoid arthritis, about 45 mg, per unit dosage form (e.g., per tablet or capsule) of a solid state form of Compound 1 orally QD (once daily). In one embodiment, the method comprising administering to the subject a solid state form of Compound 1 orally QD (once daily) in an amount sufficient to deliver 45 mg, per unit dosage form (e.g., per tablet or capsule) of Compound 1 freebase equivalent to the subject. In another aspect, the present disclosure relates to a solid state form of Compound 1 for use in treatment of rheumatoid arthritis in a subject, particularly in a human subject suffering from or susceptible to rheumatoid arthritis, the use comprising administering to the subject about 45 mg, per unit dosage form (e.g., per tablet or capsule) of a solid state form of Compound 1 orally QD (once daily). In one embodiment, the solid state form delivers about 45 mg, per unit dosage form (e.g., per tablet or capsule) of Compound 1 freebase equivalent to the subject. In one embodiment, the solid state form is the Freebase Hydrate Form B. In one embodiment, the solid state form is the Freebase Hydrate Form C. In one embodiment, the solid state form is the Tartrate Hydrate. In one embodiment, the solid state form is the Freebase Anhydrate Form D. In one embodiment, the subject has moderately to severely active rheumatoid arthritis. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB. In one embodiment, the subject is an adult.

In one embodiment, the disclosure relates to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid state form of Compound 1. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule) of Compound 1 freebase equivalent. In one embodiment, the method comprises administering to the subject about 7.5 mg or about 15 mg or about 30 mg or about 45 mg, per unit dosage form (e.g., per tablet or capsule) of Compound 1 (freebase), or a pharmaceutically acceptable salt thereof or a solid state form of Compound 1. In one embodiment, the Compound 1 (freebase) or a pharmaceutically acceptable salt thereof or the solid state form of Compound 1 is administered to the subject orally QD (once daily). In another aspect, the disclosure relates to Compound 1 freebase or a pharmaceutically acceptable salt thereof or a solid state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the solid state form is the Freebase Solvate Form A. In another aspect, the solid state form is the Hydrochloride Solvate form AA. In one embodiment, the solid state form is the Hydrochloride Solvate Form BB. In one embodiment, the solid state form is the Hydrochloride Solvate Form CC. In one embodiment, the solid state form is the L-Maleate Form AAA. In one embodiment, the solid state form is the L-Maleate Form BBB. In one embodiment, the Compound 1 (freebase) or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or a solid state form of Compound 1 orally QD (once daily).

In one embodiment, the subject having moderate to severely active rheumatoid arthritis has, prior to treatment, at least one of the following identifying characteristics: at least 6 swollen joints (based on 66 joint counts), at least 6 tender joints (based on 68 joint counts), high-sensitivity C-reactive protein (hsCRP) greater than the upper limit of normal (ULN), or positive test results for both rheumatoid factor (RF) and anti-cyclic citrullinated peptide (CCP). In one embodiment, the subject having moderate to severely active rheumatoid arthritis has, prior to treatment, at least 6 swollen joints (based on 66 joint counts) and at least 6 tender joints (based on 68 joint counts). Methods for assessing tender and swollen joints are known, and described in, for example, Scott, et al., Clinical and Experimental Rheumatology, 2014, Vol. 32 (Supp. 85), S7-S12.

Thus, in another embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject a therapeutically effective amount of Compound 1 (freebase), or a pharmaceutically acceptable salt thereof or a solid state form of Compound 1 (e.g., a crystalline hydrate or a crystalline anhydrate) as described herein, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 or about 15 mg or about 30 mg or about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg or about 15 mg or about 30 mg or about 45 mg, per unit dosage form (e.g., per tablet or capsule) of a solid state form of Compound 1. In another aspect, the disclosure relates to Compound 1 freebase or a pharmaceutically acceptable salt thereof or a solid state form of Compound 1 (e.g., a crystalline hydrate or crystalline anhydrate), as described in the present disclosure, for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject a therapeutically effective amount of Compound 1 freebase or a pharmaceutically acceptable salt thereof or a solid state form of Compound 1. In one embodiment, the therapeutically effective amount of the solid state form of Compound 1 delivers to the subject about 7.5 mg or about 15 mg or about 30 mg or about 45 mg per unit dosage form (e.g., per tablet or capsule) of Compound 1 (freebase equivalent) or a solid state form of Compound 1 orally QD (once daily). In one embodiment, the Compound 1 (freebase) or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is administered to the subject orally QD (once daily). In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is Tartrate Hydrate. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 15 mg, per unit dosage form (e.g., per tablet or capsule), per day of Compound 1 (freebase), or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 30 mg, per unit dosage form (e.g., per tablet or capsule), per day of Compound 1 (freebase), or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the present disclosure is directed to a method of treating moderate to severely active rheumatoid arthritis in an adult subject, particularly in a human subject suffering from or susceptible to moderate to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent, wherein the subject has symptoms selected from the group consisting of at least 6 swollen joints, at least 6 tender joints, and combinations thereof prior to treating. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in treatment of moderate to severely active rheumatoid arthritis in an adult subject, particularly in a human subject suffering from or susceptible to moderate to severely active rheumatoid arthritis, wherein the subject has symptoms selected from the group consisting of at least 6 swollen joints, at least 6 tender joints, and combinations thereof prior to treating, the use comprising administering to the subject about 45 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the symptoms result from the progression of structural damage assessed by radiograph.

In one embodiment, the adult subject receiving the treatment achieves an ACR20 response after treatment. In one embodiment, the adult subject achieves an ACR20 response after treatment for at least twelve weeks (e.g., at week 12 of treating). In another embodiment, the adult subject receiving the treatment achieves an ACR50 response after treatment. In one embodiment, the adult subject achieves an ACR50 response after treatment for at least twelve weeks (e.g., at week 12 of treating), or after at least twenty-four weeks (e.g., at week 24). In another embodiment, the adult subject receiving the treatment achieves an ACR70 response after treatment. In one embodiment, the adult subject achieves an ACR70 response after treatment for at least twelve weeks (e.g., at week 12 of treating). In certain embodiments, the adult subject achieves an ACR20 response, an ACR50 response, and/or an ACR70 response following treatment for at least twelve weeks (e.g., at week 12 of treating).

In one embodiment, the adult subject receiving the treatment achieves an ACR20 response after treatment for at least 8 weeks (e.g., at week 8 of treating). In another embodiment, the adult subject receiving the treatment achieves an ACR20 response after treatment for at least 6 weeks (e.g., at week 6 of treating). In another embodiment, the adult subject receiving the treatment achieves an ACR20 response after treatment for at least 4 weeks (e.g., at week 4 of treating). In another embodiment, the adult subject receiving the treatment achieves an ACR20 response after treatment for at least 2 weeks (e.g., at week 2 of treating).

In one embodiment, the adult subject receiving the treatment achieves an ACR50 response after treatment for at least 8 weeks (e.g., at week 8 of treating). In another embodiment, the adult subject receiving the treatment achieves an ACR50 response after treatment for at least 6 weeks (e.g., at week 6 of treating). In another embodiment, the adult subject receiving the treatment achieves an ACR50 response after treatment for at least 4 weeks (e.g., at week 4 of treating). In another embodiment, the adult subject receiving the treatment achieves an ACR50 response after treatment for at least 2 weeks (e.g., at week 2 of treating).

In one embodiment, the adult subject receiving the treatment achieves an ACR70 response after treatment for at least 8 weeks (e.g., at week 8 of treating). In another embodiment, the adult subject receiving the treatment achieves an ACR70 response after treatment for at least 6 weeks (e.g., at week 6 of treating). In another embodiment, the adult subject receiving the treatment achieves an ACR70 response after treatment for at least 4 weeks (e.g., at week 4 of treating).

In one embodiment, the adult subject receiving the treatment achieves a change in DAS28 score after treatment. In one embodiment, the change in DAS score is a decrease in DAS28(CRP) after treatment, as compared to baseline (i.e., DAS28(CRP) prior to treatment). In one embodiment, the adult subject achieves a decrease in DAS28 score as compared to baseline after treatment for at least twelve weeks (e.g., at week 12 of treating). In one embodiment, the adult subject achieves a decrease in DAS28(CRP) as compared to baseline after treatment for at least 12 weeks (e.g., at week 12 of treating). In another embodiment, the adult subject achieves a decrease in DAS28(CRP) as compared to baseline after treatment for at least 8 weeks (e.g., at week 8 of treating). In another embodiment, the adult subject achieves a decrease in DAS28(CRP) as compared to baseline after treatment for at least 6 weeks (e.g., at week 6 of treating). In another embodiment, the adult subject achieves a decrease in DAS28(CRP) as compared to baseline after treatment for at least 4 weeks (e.g., at week 4 of treating). In another embodiment, the adult subject achieves a decrease in DAS28(CRP) as compared to baseline after treatment for at least 2 weeks (e.g., at week 2 of treating).

In another embodiment, the adult subject receiving the treatment achieves a low disease activity (LDA) score or clinical remission after treatment. In one embodiment, the LDA score or clinical remission is measured as a DAS28 score (in particular. DAS28(CRP)) of 3.2 or less. In another embodiment, the LDA score or clinical remission is measured as a DAS28(CRP) of less than 2.6. In another embodiment, the LDA score or clinical remission is assessed using Clinical Disease Activity Index (CDAI) criteria. In one embodiment, the adult subject achieves a CDAI score of 10 or less after treatment. In another embodiment, the adult subject achieves a CDAI score of 2.8 or less after treatment. In one embodiment, the adult subject achieves the LDA score or clinical remission after treatment for at least 12 weeks (e.g., at week 12 of treating). In one embodiment, the adult subject achieves the LDA score or clinical remission after treatment for at least 8 weeks (e.g., at week 8 of treating). In one embodiment, the adult subject achieves the LDA score or clinical remission after treatment for at least 6 weeks (e.g., at week 6 of treating). In one embodiment, the adult subject achieves the LDA score or clinical remission after treatment for at least 4 weeks (e.g., at week 4 of treating). In one embodiment, the adult subject achieves the LDA score or clinical remission after treatment for at least 2 weeks (e.g., at week 2 of treating).

In one embodiment, the adult subject receiving the treatment achieves a change in mean modified Total Sharp Score (mTSS). In one embodiment, the adult subject receiving the treatment achieves a change in mTSS after treatment for at least twelve weeks (e.g., at week 12 of treating), or after treatment for at least twenty-four weeks (e.g., at week 24 of treating). In one embodiment, mTSS may be determined by scoring x-rays of the hand/wrist and feet joints for erosions and joint space narrowing. The erosion score and narrowing score are added to determine the total score.

In one embodiment, the adult subject receiving the treatment achieves a change in HAQ-DI score. In one embodiment, the adult subject receiving the treatment achieves a change in HAQ-DI score after treatment for at least twelve weeks (e.g., at week 12 of treating).

In one embodiment, the adult subject receiving the treatment achieves a change in Short Form 36 (SF-36) physical component score (PCS). In one embodiment, the adult subject receiving the treatment achieves a change in SF-36 PCS after treatment for at least twelve weeks (e.g., at week 12 of treating). SF-36 is a 36 item participant questionnaire with questions relating to participant health and daily activities.

In one embodiment, the adult subject receiving the treatment achieves a clinical remission (CR). In one embodiment, the adult subject receiving the treatment achieves a CR after treatment for at least twelve weeks (e.g., at week 12 of treating). In one embodiment, CR is determined based on DAS28 C-Reactive Protein (DAS28(CRP)) response rate. In one embodiment, CR is a DAS28(CRP) score of less than 2.6.

In one embodiment, the adult subject receiving the treatment achieves a change in functional assessment of chronic illness therapy (FACIT-F). In one embodiment, the adult subject receiving the treatment achieves a change in FACIT-F after treatment for at least twelve weeks (e.g., at week 12 of treating). FACIT-F is a participant questionnaire with 13 indexes rated on a 5 point scale. The indexes relate to the participant's level of fatigue during the past seven days.

In one embodiment, the adult subject receiving the treatment achieves a change in work instability score for rheumatoid arthritis (RA-WIS). In one embodiment, the adult subject receiving the treatment achieves a change in RA-WIS after treatment for at least twelve weeks (e.g., at week 12 of treating). RA-WIS is a participant questionnaire containing 23 questions relating to the participant's functioning in their work environment.

In one embodiment, the adult subject receiving the treatment achieves a change in morning stiffness severity. In one embodiment, the adult subject receiving the treatment achieves a change in morning stiffness severity after treatment for at least twelve weeks (e.g., at week 12 of treating). Morning stiffness severity is determined by the Patient's Assessment of Severity and Duration of Morning Stiffness questionnaire.

In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent to the subject, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves an ACR70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 24 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 30 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves an ACR70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, the adult subject is a subject who has had an inadequate response or intolerance to one or more disease-modifying antirheumatic drugs (DMARDs). In one embodiment, the DMARD is a conventional synthetic DMARD (csDMARD). In another embodiment, the DMARD is a biologic DMARD (bDMARD). Examples of csDMARDs include, but are not limited to, methotrexate (MTX), sulfasalazine, hydroxychloroquine, chloroquine, leflunomide, and azathioprine. Examples of bDMARDs include, but are not limited to, tocilizumab such as ACTEMRA™, etanercept such as p75TNFR1gG (ENBREL™ brand etanercept), adalimumab (such as HUMIRA™ brand adalimumab), and golimumab such as SIMPONI™ (golimumab). In one embodiment, the csDMARD is MTX. In one embodiment, the bDMARD is an anti-TNF biologic. An inadequate response or intolerance to one or more DMARDs can be measured using any of the indices described herein (e.g., failure to achieve an ACR20 response). In one embodiment, a subject having an inadequate response to a DMARD is a subject who does not achieve reduced disease activity, does not achieve an improvement in physical function, exhibits no evidence of stopping disease progression, or who experiences disease relapse after treatment with the DMARD. In one embodiment, a subject having an inadequate response to a DMARD is a subject who does not achieve an ACR20 response after treatment with the DMARD. In one embodiment, a subject having an inadequate tolerance (intolerance) to a DMARD is a subject who experiences toxicity or complicating co-morbidities after treatment with the DMARD.

In one embodiment, the adult subject is a subject who has had an inadequate response to stable methotrexate therapy. In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject received a supplement of folic acid for at least four weeks prior to treatment. In another embodiment, the adult subject is administered a supplement of folic acid during treatment.

In one embodiment, the adult subject is a subject who has had an inadequate response or intolerance to at least one anti-TNF therapy. Anti-TNF biologic agents are described elsewhere herein, and include TNF antagonists such as chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept). In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject has been treated with at least one anti-TNF biologic agent for at least three months prior to treatment with Compound 1. In another embodiment, the adult subject received a supplement of folic acid for at least four weeks prior to treatment. In another embodiment, the adult subject is administered a supplement of folic acid during treatment In certain embodiments, the adult subject, who has had an inadequate response or tolerance to one or more DMARDS (including methotrexate and/or an anti-TNF biologic agent), achieves an ACR20 response, an ACR50 response, an ACR70 response, and/or a decrease in DAS28(CRP) as compared to baseline following treatment for at least twelve weeks (e.g., at week 12 of treating), and/or following treatment for at least 8 weeks (e.g., at week 8 of treating), and/or following treatment for at least 6 weeks (e.g., at week 6 of treating), and/or following treatment for at least 4 weeks (e.g., at week 4 of treating), and/or following treatment for at least 2 weeks (e.g., at week 2 of treating).

For instance, in one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 7.5 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In one embodiment, the method or use comprises administering to the subject about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent, wherein the subject has had an inadequate response or intolerance to one or more DMARDS, and the subject achieves a decrease in DAS28 (CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 15 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 24 mg, per unit dosage form (e.g., per tablet or capsule), of Compound 1 (freebase), or a pharmaceutically acceptable salt thereof or a solid state form of Compound 1 in an amount sufficient to deliver to the subject about 24 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 24 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In another embodiment, the subject achieves an ACR50 response at week 2 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In one embodiment, the method or use comprises administering to the subject about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 30 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 20 response at week 12 of treating. In another embodiment, the subject achieves an ACR20 response at week 8 of treating. In another embodiment, the subject achieves an ACR20 response at week 6 of treating. In another embodiment, the subject achieves an ACR20 response at week 4 of treating. In another embodiment, the subject achieves an ACR20 response at week 2 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 50 response at week 12 of treating. In another embodiment, the subject achieves an ACR50 response at week 8 of treating. In another embodiment, the subject achieves an ACR50 response at week 6 of treating. In another embodiment, the subject achieves an ACR50 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves an ACR 70 response at week 12 of treating. In another embodiment, the subject achieves an ACR70 response at week 8 of treating. In another embodiment, the subject achieves an ACR70 response at week 6 of treating. In another embodiment, the subject achieves an ACR70 response at week 4 of treating. In one embodiment, the method or use comprises administering to the subject about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent, wherein the subject has had an inadequate response or intolerance to one or more DMARDS, and the subject achieves a decrease in DAS28(CRP) as compared to baseline at week 12 of treating. In another embodiment, the subject achieves a decrease in DAS28(CRP) as compared to baseline at week 8 of treating. In another embodiment, the subject achieves a decrease in DAS28(CRP) as compared to baseline at week 6 of treating. In another embodiment, the subject achieves a decrease in DAS28(CRP) as compared to baseline at week 4 of treating. In another embodiment, the subject achieves a decrease in DAS28(CRP) as compared to baseline at week 2 of treating. In one embodiment, the method or use comprises administering about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, the adult subject is also administered a csDMARD or a bDMARD in a combination therapy, as described hereinafter. In certain embodiments, the DMARD is MTX. In certain embodiments, the adult subject receiving the combination therapy achieves an ACR20 response, an ACR50 response, an ACR70 response, and/or a decrease in DAS28(CRP) as compared to baseline following treatment. In particular embodiments, the adult subject receiving the combination therapy achieves an ACR20 response, an ACR50 response, an ACR70 response, and/or a decrease in DAS28(CRP) as compared to baseline at week 12 of treating, and/or at week 8 of treating, and/or at week 6 of treating, and/or at week 4 of treating, and/or at week 2 of treating. In one embodiment, the adult subject receiving the combination therapy is administered about 7.5 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg, per unit dosage form (e.g., per tablet or capsule), of Compound 1 freebase equivalent. In one embodiment, the adult subject receiving the combination therapy is administered about 15 mg, per unit dosage form (e.g., per tablet or capsule), of Compound 1 (freebase), or a pharmaceutically acceptable salt thereof or a solid state form of Compound 1 in an amount sufficient to deliver to the subject about 15 mg, per unit dosage form (e.g., per tablet or capsule), of Compound 1 freebase equivalent. In one embodiment, the adult subject receiving the combination therapy is administered about 30 mg, per unit dosage form (e.g., per tablet or capsule), of Compound 1 (freebase), or a pharmaceutically acceptable salt thereof or a solid state form of Compound 1 in an amount sufficient to deliver to the subject about 30 mg, per unit dosage form (e.g., per tablet or capsule), of Compound 1 freebase equivalent. In one embodiment, the adult subject receiving the combination therapy is administered about 45 mg, per unit dosage form (e.g., per tablet or capsule), of Compound 1 (freebase), or a pharmaceutically acceptable salt thereof or a solid state form of Compound 1 in an amount sufficient to deliver to the subject about 45 mg, per unit dosage form (e.g., per tablet or capsule), of Compound 1 freebase equivalent. In one embodiment, the method comprises administering about 7.5 mg or about 15 mg or about 30 mg or about 45 mg, per unit dosage form (e.g., per tablet or capsule), of the solid state form to the subject. In one embodiment, the Compound 1 (freebase) or a pharmaceutically acceptable salt thereof or the solid state form is in a once daily extended release formulation. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In another embodiment, any of the methods of treating an adult subject having moderate to severely active rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the present disclosure relates to a method of treating structural damage associated with rheumatoid arthritis in an adult subject, particularly in a human subject suffering from or susceptible to structural damage associated with rheumatoid arthritis. The method comprises administering to the subject a therapeutically effective amount of Compound 1 (freebase), or a pharmaceutically acceptable salt thereof or a solid state form of Compound 1 (e.g., a crystalline hydrate or a crystalline anhydrate) as described herein, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg or about 15 mg or about 30 mg or about 45 mg, per unit dosage form (e.g., per tablet or capsule) of a solid state form of Compound 1, such that the structural damage in the adult subject is inhibited or lessened. In one embodiment, the Compound 1 (freebase) or a pharmaceutically acceptable salt thereof or the solid state form of Compound 1 is administered to the subject orally QD (once daily). In one embodiment, the structural damage is selected from the group consisting of loss of bone and/or cartilage, bone erosion, joint space narrowing as measured by radiography, and combinations thereof. In one embodiment, the structural damaged is inhibited or lessened when the structural damage is reduced by at least 20%, or at least 25%, or at least 30%, or at least 50%. In other embodiments, structural damage is inhibited or lessened when there is no further radiographic progression of the structural damage. In certain embodiments, structural joint damage can be assessed radiographically and expressed as change in Total Sharp Score (TSS) and its components, the erosion score and Joint Space Narrowing (JSN) score, for example, at week 12 compared to baseline. In another aspect, the disclosure relates to a solid state form (and in particular a crystalline hydrate) of Compound 1, as described in the present disclosure, for use in treatment of structural damage associated with rheumatoid arthritis in an adult subject, particularly in a human subject suffering from or susceptible to rheumatoid arthritis. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the stolid state form is Tartrate Hydrate. In one embodiment, the Compound 1 (freebase) or a pharmaceutically acceptable salt thereof or the crystalline hydrate is in a once daily extended release formulation. In one embodiment, the Compound 1 (freebase) or a pharmaceutically acceptable salt thereof or the crystalline hydrate is in a once daily extended release formulation, and the formulation delivers about 7.5 mg or about 15 mg or about 30 mg or about 45 mg per unit dosage form (e.g., per tablet or capsule) of Compound 1 (freebase equivalent) orally QD (once daily).

In another aspect, the disclosure relates to Compound 1 freebase or a pharmaceutically acceptable salt thereof or a solid state form of Compound 1 (e.g., a crystalline hydrate or crystalline anhydrate), as described in the present disclosure for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject a therapeutically effective amount of Compound 1 freebase or a pharmaceutically acceptable salt thereof or a solid state form of Compound 1. In one embodiment, the solid state form is a crystalline hydrate. In one embodiment, the crystalline hydrate is Freebase Hydrate Form B. In one embodiment, the crystalline hydrate is a hemihydrate. In one embodiment, the hemihydrate is Freebase Hydrate Form C. In one embodiment, the solid state form is a crystalline anhydrate. In one embodiment, the crystalline anhydrate is Freebase Anhydrate Form D. In one embodiment, the Compound 1 (freebase) or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or a solid state form of Compound 1 orally QD (once daily).

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent, such that the structural damage in the adult subject is inhibited or lessened. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 15 mg, per unit dosage form (e.g., per tablet or capsule), per day of Compound 1 (freebase), or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent, such that the structural damage in the adult subject is inhibited or lessened. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 30 mg, per unit dosage form (e.g., per tablet or capsule), per day of Compound 1 (freebase), or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent, such that the structural damage in the adult subject is inhibited or lessened. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In one embodiment, the present disclosure is directed to a method of treating structural damage associated with rheumatoid arthritis in an adult subject, particularly in a human subject suffering from or susceptible to structural damage associated with rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent, such that the structural damage in the adult subject is inhibited or lessened. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1, for use in treatment of structural damage associated with rheumatoid arthritis in an adult subject, particularly in a human subject suffering from or susceptible to structural damage associated with rheumatoid arthritis, such that the structural damage in the adult subject is inhibited or lessened, the use comprising administering to the subject 45 mg, per unit dosage form (e.g., per tablet or capsule) of Compound 1 freebase or a pharmaceutically acceptable salt thereof or a solid state form of Compound 1.

In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the structural damage is selected from the group consisting of loss of bone and/or cartilage, bone erosion, joint space narrowing as measured by radiography, and combinations thereof.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject a therapeutically effective amount of Compound 1 (freebase), or a pharmaceutically acceptable salt thereof or a solid state form of Compound 1 (e.g., a crystalline hydrate or a crystalline anhydrate) as described herein. In one embodiment, the method comprises administering to the subject about 7.5 mg or about 15 mg or about 30 mg or about 45 mg, per unit dosage form (e.g., per tablet or capsule), per day of Compound 1 (freebase) or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the method comprises administering to the subject about 7.5 mg or about 15 mg or about 30 mg or about 45 mg, per unit dosage form (e.g., per tablet or capsule) of a solid state form of Compound 1. In one embodiment, the Compound 1 (freebase) or a pharmaceutically acceptable salt thereof or the solid state form of Compound 1 is administered to the subject orally QD (once daily). In another aspect, the disclosure relates to Compound 1 freebase or a pharmaceutically acceptable salt thereof or a solid state form (and in particular a crystalline hydrate) of Compound 1, as described in the present disclosure, for use in reducing signs and symptoms of rheumatoid arthritis in an adult subject, particularly in a human subject suffering from or susceptible to moderate to severely active rheumatoid arthritis, the use comprising administering to the subject a therapeutically effective amount of Compound 1 freebase or a pharmaceutically acceptable salt thereof or a solid state form (and in particular a crystalline hydrate) of Compound 1. In one embodiment, the Compound 1 freebase or a pharmaceutically acceptable salt thereof or the solid state form of Compound 1 is in a once daily extended release formulation. In one embodiment, the formulation delivers about 7.5 mg or about 15 mg or about 30 mg or about 45 mg per unit dosage form (e.g., per tablet or capsule) of Compound 1 (freebase equivalent) or the solid state form of Compound 1 to the subject orally QD (once daily). In one embodiment, the solid state form is a crystalline hydrate. In one embodiment, the crystalline hydrate is the Freebase Hydrate Form B. In one embodiment, the crystalline hydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 7.5 mg, per unit dosage form (e.g., per tablet or capsule), per day of Compound 1 (freebase), or a pharmaceutically acceptable salt thereof or a solid state form of Compound 1 in an amount sufficient to deliver to the subject about 7.5 mg, per unit dosage form (e.g., per tablet or capsule), per day of Compound 1 freebase equivalent. In one embodiment, the method comprises administering to the subject about 7.5 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 7.5 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 7.5 mg per unit dosage form (e.g., per tablet or capsule) of Compound 1 (freebase equivalent) or the solid state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 15 mg, per unit dosage form (e.g., per tablet or capsule), per day of Compound 1 (freebase) or a pharmaceutically acceptable salt thereof or a solid state form of Compound 1 in an amount sufficient to deliver to the subject about 15 mg, per unit dosage form (e.g., per tablet or capsule), per day of Compound 1 freebase equivalent. In one embodiment, the method comprises administering to the subject about 15 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject, about 15 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or the solid state form of Compound 1 is administered orally QD (once daily). In one embodiment, the Compound 1 (freebase) or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 15 mg per unit dosage form (e.g., per tablet or capsule) of Compound 1 (freebase equivalent) or the solid state form of Compound 1 orally QD (once daily) to the subject.

In another embodiment, the present disclosure is directed to a method of reducing signs and symptoms of rheumatoid arthritis in an adult subject, particularly in a human subject suffering from or susceptible to moderately to severely active rheumatoid arthritis. The method comprises administering to the subject about 30 mg, per unit dosage form (e.g., per tablet or capsule), per day of Compound 1 (freebase) or a pharmaceutically acceptable salt thereof or a solid state form of Compound 1 in an amount sufficient to deliver to the subject about 30 mg, per unit dosage form (e.g., per tablet or capsule), per day of Compound 1 freebase equivalent. In one embodiment, the method comprises administering to the subject about 30 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 30 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is a hemihydrate. In one embodiment, the hemihydrate is Freebase Hydrate Form C. In one embodiment, the crystalline hydrate is the Freebase Hydrate Form B. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 (freebase) or the crystalline hydrate is in a once daily extended release formulation. In one embodiment, the Compound 1 (freebase) or a pharmaceutically acceptable salt thereof or the solid state form of Compound 1 is in a once daily extended release formulation, and the formulation delivers about 30 mg per unit dosage form (e.g., per tablet or capsule) of Compound 1 (freebase equivalent) or the solid state form of Compound 1 orally QD (once daily) to the subject.

In one embodiment, the present disclosure is directed to a method of reducing the signs and symptoms of rheumatoid arthritis in an adult subject, particularly in a human subject suffering from or susceptible to moderately to severely active rheumatoid arthritis, the method comprising administering to the subject about 45 mg, per unit dosage form (e.g., per tablet or capsule), per day of Compound 1 (freebase), or a pharmaceutically acceptable salt thereof or a solid state form of Compound 1 in an amount sufficient to deliver to the subject about 45 mg, per unit dosage form (e.g., per tablet or capsule), per day of Compound 1 freebase equivalent. In one embodiment, the method comprises administering to the subject about 45 mg, per unit dosage form (e.g., per tablet or capsule), per day of a solid state form of Compound 1. In another aspect, the disclosure relates to Compound 1 freebase or a pharmaceutically acceptable salt thereof or a solid state form of Compound 1 for use in reducing signs and symptoms of rheumatoid arthritis in an adult subject, particularly in a human subject suffering from or susceptible to moderate to severely active rheumatoid arthritis, the use comprising administering to the subject about 45 mg, per unit dosage form (e.g., per tablet or capsule) of Compound 1 freebase or a pharmaceutically acceptable salt thereof or a solid state form of Compound 1. In one embodiment, the solid state form is a crystalline hydrate. In one embodiment, the crystalline hydrate is the Freebase Hydrate Form B. In one embodiment, the crystalline hydrate is a hemihydrate. In one embodiment, the hemihydrate is the Freebase Hydrate Form C. In one embodiment, the solid state form is a crystalline anhydrate. In one embodiment, the crystalline anhydrate is the Freebase Anhydrate Form D. In one embodiment, the solid state form is the Tartrate Hydrate. In one embodiment, the Compound 1 freebase or a pharmaceutically acceptable salt thereof or the solid state form of Compound 1 is administered orally QD (once daily). In one embodiment, the Compound 1 freebase or a pharmaceutically acceptable salt thereof or the solid state form of Compound 1 is in a once daily extended release formulation. In one embodiment, the Compound 1 (freebase) or a pharmaceutically acceptable salt thereof or the solid state form of Compound 1 is in a once daily extended release formulation, and the formulation delivers about 45 mg per unit dosage form (e.g., per tablet or capsule) of Compound 1 (freebase equivalent) or the solid state form of Compound 1 orally QD (once daily) to the subject.

In another aspect, the disclosure relates to a solid state form (and in particular a crystalline hydrate) of Compound 1, as described in the present disclosure, for use in reducing signs and symptoms of rheumatoid arthritis in an adult subject, particularly in a human subject suffering from or susceptible to rheumatoid arthritis.

In another embodiment, any of the methods of reducing signs and symptoms of rheumatoid arthritis described herein may further comprises alleviating at least one symptom selected from the group consisting of bone erosion, cartilage erosion, inflammation, and vascularity. In another embodiment, the arthritis is further treated by alleviating at least one symptom selected from the group consisting of joint distortion, swelling, joint deformation, ankyloses on flexion, and severely impaired movement.

In another embodiment, the Compound 1 freebase or a pharmaceutically acceptable salt thereof and/or solid state forms of Compound 1 used in any of the methods set forth herein may be administered to the subject in a once daily extended release solid oral dosage form. In particular, in one embodiment, the methods comprise once daily administration to the subject of an extended release (e.g., modified release) solid oral dosage form comprising the Compound 1 freebase or a pharmaceutically acceptable salt thereof or the solid state form of Compound 1, and a pharmaceutically acceptable polymeric carrier substantially contributing to the modification of the release of the Compound 1 freebase or a pharmaceutically acceptable salt thereof or the solid state form of Compound 1. In one aspect, the dosage form sustains release of the Compound 1 freebase or a pharmaceutically acceptable salt thereof or the solid state form of Compound 1 for from about 4 hours to about 24 hours following entry of the dosage form into a use environment. In one embodiment, the dosage form has a release rate of not more than about 60% after passage of about 4 hours following entry of the dosage form into a use environment. The term "entry into a use environment" refers to contact of the dosage form with gastric fluids of the subject to whom it is administered. As used herein, the term "release rate" refers to the percentage of the active ingredient (e.g., Compound 1 or a solid state form of Compound 1) in the dosage form that is released in the given time period, and under the specified conditions. In one embodiment, the dosage form comprises about 7.5 mg or about 15 mg or about 30 mg or about 45 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the dosage form comprises about 7.5 mg or about 15 mg or about 30 mg or about 45 mg, per unit dosage form (e.g., per tablet or capsule), per day of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the pharmaceutically acceptable polymeric carrier is a release control polymer, as set forth herein.

Thus, in one aspect, the dosage form sustains release of the Compound 1 freebase or a pharmaceutically acceptable salt thereof or the solid state form of Compound 1 for from about 4 hours to about 24 hours. In one embodiment, the dosage form releases the active ingredient (i.e., Compound 1 or a solid state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising once daily administration to a subject suffering from or susceptible to the condition, of an extended release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the use comprising once daily administration to a subject suffering from or susceptible to the condition, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another embodiment, the disclosure is directed to a method of treating an adult subject having moderate to severely active rheumatoid arthritis, the method comprising once daily administration to the subject, particularly a human subject suffering from or susceptible to rheumatoid arthritis, of an extended release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In another aspect, the disclosure is directed to an extended release solid oral dosage form comprising Compound 1 freebase or a pharmaceutically acceptable salt thereof or a solid state form of Compound 1 for use in treating an adult subject having moderate to severely active rheumatoid arthritis, the use comprising once daily administration to the subject, particularly a subject suffering from or susceptible to moderately to severely active rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase or a pharmaceutically acceptable salt thereof, or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment. In one embodiment, the subject has symptoms selected from the group consisting of at least 6 swollen joints, at least 6 tender joints, and combinations thereof prior to treating.

In one embodiment, the disclosure is directed to a method of treating structural damage associated with rheumatoid arthritis in an adult subject, the method comprising once daily administration to the subject, particularly a human subject suffering from or susceptible to rheumatoid arthritis, of an extended release solid oral dosage form comprising about 7.5 mg, or about 15 mg, or about 30 mg, or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase or a pharmaceutically acceptable salt thereof equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in treating structural damage associated with rheumatoid arthritis in an adult subject, the use comprising once daily administration to the subject, particularly a subject suffering from or susceptible to structural damage associated with rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In one embodiment, the disclosure is directed to a method of reducing signs and symptoms of rheumatoid arthritis in an adult subject, the method comprising once daily administration to the subject, particularly a human subject suffering from or susceptible to moderately to severely active rheumatoid arthritis, of an extended release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 1000% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in reducing signs and symptoms associated with rheumatoid arthritis in an adult subject, the use comprising once daily administration to the subject, particularly a subject suffering from or susceptible to rheumatoid arthritis, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In the foregoing methods, in one embodiment, the pharmaceutically acceptable polymeric carrier comprises a release control polymer. In one embodiment, the release control polymer is hydroxypropylmethyl cellulose. In one embodiment, the dosage form comprises a pH modifier. In one embodiment, the pH modifier is tartaric acid. In one embodiment, the dosage form comprises from about 10 w/w % to about 35 w/w % tartaric acid. In one embodiment, the dosage form comprises about 10 w/w % tartaric acid. In one embodiment, the dosage form comprises about 20 w/w % tartaric acid. In one embodiment, the dosage form comprises about 30 w/w % tartaric acid.

In another embodiment the methods of the present disclosure further comprise administering Compound 1 or a solid state form thereof for at least 8 weeks. In another embodiment, the methods of the present disclosure comprise administering Compound 1 or a solid state form thereof for at least 12 weeks.

In another embodiment, the present disclosure relates to the use of a solid state form of Compound 1 for treating a condition as described in the various embodiments of the present disclosure.

In another embodiment, the present disclosure relates to a solid state form of Compound 1 for use in treatment of a condition as described in the various embodiments of the present disclosure.

III. Combination Therapy and Fixed-Dose Combinations

The present disclosure further relates to (i) methods of treatment and uses as previously described that further comprise the administration of one or more additional therapeutic agents (i.e., combination therapies), and (ii) pharmaceutical compositions as previously described that further comprise one or more additional therapeutic agents (i.e., fixed-dose combinations). When administered to a subject in combination with one or more additional therapeutic agents, the solid state form of Compound 1 and the additional therapeutic agent(s) can be administered as separate dosage forms or as a single dosage form comprising the solid state form of Compound 1 and the additional therapeutic agent(s). If administered as a separate dosage form, the additional therapeutic agent may be administered either simultaneously with, or sequentially with, the dosage form comprising the solid state form of Compound 1.

For example, the solid state forms of the present disclosure may be administered in a pharmaceutically acceptable form either alone or in combination with one or more additional agents that modulate a mammalian immune system or with anti-inflammatory agents. These agents may include but are not limited to cyclosporin A (e.g., SAND-IMMUNE® or NEORAL®), rapamycin, FK-506 (tacrolimus), leflunomide, deoxyspergualin, mycophenolate (e.g., CELLCEPT®), azathioprine (e.g., IMURAN®), daclizumab (e.g., ZENAPAX®), OKT3 (e.g., ORTHO-CLONE®), AtGam, aspirin, acetaminophen, aminosalicylate, ciprofloxacin, corticosteroid, metronidazole, probiotic, tacrolimus, ibuprofen, naproxen, piroxicam, and anti-inflammatory steroids (e.g., prednisolone or dexamethasone). In certain embodiments, the one or more additional agents are selected from the group consisting of aspirin, acetaminophen, aminosalicylate, ciprofloxacin, corticosteroid, cyclosporine, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, penicillamine, sulfasalazine, leflunomide, tocilizumab, anakinra, abatacept, certolizumab pegol, golimumab, vedolizumab, natalizumab, ustekinumab, rituximab, efalizumab, belimumab, etanercept, infliximab, adalimumab, and immune modulator (e.g., activator) for CD4+CD25+ Treg cells.

Non-limiting examples of therapeutic agents for rheumatoid arthritis with which a compound of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L). Combinations of therapeutic agents may interfere at different points in the autoimmune and subsequent inflammatory cascade. Such examples may include TNF antagonists like chimeric, humanized or human TNF antibodies, adalimumab (such as HUMIRA™ brand adalimumab), infliximab such as CA2

(REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11.

The solid state form may also be combined with nonbiologic DMARDS or other agents, such as methotrexate, 6-mercaptopurine, azathioprine sulphasalazine, mesalamine, olsalazine chloroquinone/hydroxychloroquine, penicillamine aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide. NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, and 6-mercaptopurines. The solid state form may also be combined with methotrexate.

Non-limiting examples of therapeutic agents for inflammatory bowel disease (IBD) with which the solid state form can be combined may include (but are not limited to) the following: budesonide; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinylimidazole compounds, antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as TNFα or IL-1 (e.g., NIK, IKK, or MAP kinase inhibitors); IL-1β converting enzyme inhibitors; TNFα converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g., IL-4, IL-10, IL-11, IL-13 and TGFβ). The solid state form may also be combined with methotrexate.

Examples of therapeutic agents for Crohn's disease with which the solid state form can be combined include the following: TNF antagonists, for example, anti-TNF antibodies, adalimumab (such as HUMIRA™ brand adalimumab), infliximab such as CA2 (REMICADE™ brand infliximab), certolizumab pegol such as CIMZIA™, golimumab such as SIMPONI™ (golimumab), CDP 571, TNFR-Ig constructs, etanercept such as p75TNFRIgG (ENBREL™ brand etanercept) and lenercept such as p55TNFRIgG (Lenercept™) inhibitors and PDE4 inhibitors.

The solid state form can be combined with corticosteroids, for example, budesonide and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis (MS) with which the solid state form can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of the invention can be combined with antibodies to cell surface molecules such as CD2, CD3, CD4, CD8, CD19, CD20, CD25, CD28, CD30, CD40, CD45, CD69, CD80, CD86, CD90 or their ligands. The solid state form may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFβ). Examples of therapeutic agents for multiple sclerosis in which a compound of the invention can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The solid state form may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis (AS) with which the solid state form can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

Non-limiting examples of therapeutic agents for psoriasis (Ps, such as moderate to severe plaque psoriasis) with which the solid state form can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, ustekinumab, and adalimumab (such as HUMIRA™ brand adalimumab).

Non-limiting examples of therapeutic agents for psoriatic arthritis (PsA) with which the solid state form can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab (such as HUMIRA™ brand adalimumab), and efalizumab.

Examples of therapeutic agents for SLE (Lupus) with which the solid state form can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budesonide, dexamethasone; cytotoxics, for example, azathioprine, cyclophosphamide, mycophenolate mofetil, methotrexate; inhibitors of PDE4 or purine synthesis inhibitor, for example CELLCEPT®. The solid state form may also be combined with agents such as sulfasalazine, 5-aminosalicylic acid, olsalazine, IMURAN® and agents which interfere with synthesis, production or action of proinflammatory cytokines such as IL-1, for example, caspase inhibitors like IL-1β converting enzyme inhibitors and IL-1ra. The solid state form may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The solid state form can be combined with IL-1I or anti-cytokine antibodies, for example, fontolizumab (anti-IFNg antibody), or anti-receptor receptor antibodies, for example, anti-IL-6 receptor antibody and antibodies to B-cell surface molecules. The solid state form may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

The solid state form may also be combined with an immune modulator for CD4+CD25+ Treg cells. Treg cells are essential for maintaining normal immune homeostasis. In patients with autoimmune diseases, reduced numbers or functional impairment of Treg cells has been observed, leading to loss of this finely-tuned mechanism. A humanized agonistic monoclonal antibody, BT-061, binds to a unique epitope of human CD4, and induces Treg-specific signaling events that lead to their functional activation. Pre-clinical data using isolated Treg cells and rheumatoid arthritis synovial fluid indicate that BT-061 leads to suppression of CD4+ and CD8+ T effector cell proliferation, reduction of the expression of pro-inflammatory cytokines, and increase in the production of the anti-inflammatory cytokine TGFβ. Thus similar immune modulators for CD4+CD25+ Treg cells can also be co-administered with a compound of the invention for treating any of the inflammatory disease/disorder, or an autoimmune disease/disorder described herein, including but not limited to rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, or atopic dermatitis. In certain embodiments, the combination treats rheumatoid arthritis, Crohn's disease, psoriasis, or psoriatic arthritis, including moderately to severely active rheumatoid arthritis, Crohn's disease, psoriasis, or psoriatic arthritis. In certain embodiments, the rheumatoid arthritis, Crohn's disease, psoriasis, or psoriatic arthritis patient being treated has inadequately responded to or has discontinued therapy due to loss of response to or intolerance to a first line therapy (such as a DMARD, including methotrexate) or an anti-TNF, therapy.

In certain embodiments, the immune modulator has one or more (or all) of the following properties: (1) activates a subset of CD4+ T cells comprising CD4+CD25+ regulatory T cells (Treg), or CD4+CD25+ Treg cells; (2) binds only to a special epitope of the human CD4 antigen (such as the IgG-like C2 type 1 domain of CD4), which said epitope of human CD4 may be bound by a mouse IgG1 anti-CD4 monoclonal antibody B-F5 or a humanized version thereof, such as the BT-061 hB-F5 antibody tregalizumab as described in U.S. Pat. No. 7,452,981 (incorporated herein by reference, including all sequences of the VH and VL chains disclosed therein); (3) provides an activation signal to naturally occurring Treg cells but does not activate conventional T cells (e.g., CD4+ T cells that are not activated in (1), CD8+ cytotoxic T cells, etc.); and (4) is not a depleting anti-CD4 antibody that depletes CD4+ T cells, and/or does not appreciably trigger ADCC or CDC.

VI. Pharmaceutical Compositions

The present disclosure further relates, in part, to compositions comprising Compound 1 or a pharmaceutically acceptable salt thereof, or one or more solid state forms of Compound 1. Although the solid state form may be administered alone or in the form of a pharmaceutical composition, administration generally will be in the form of a pharmaceutical composition. In some embodiments, the composition comprises Compound 1 or a pharmaceutically acceptable salt thereof or a solid state form of Compound 1 in association with a pharmaceutically acceptable carrier. The preferred composition depends on the method of administration, and typically comprises one or more conventional pharmaceutically acceptable carriers, adjuvants, and/or vehicles (together referred to as "excipients"). Such compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise pH modifiers, such as sodium citrate; magnesium or calcium carbonate or bicarbonate; tartaric acid, fumaric acid, citric acid, succinic acid, malic acid, and phosphoric acid and combinations thereof. Tablets and pills additionally can be prepared with enteric coatings.

In one embodiment, the pharmaceutical composition is a tablet dosage form. In one aspect, the tablet is coated with a pharmaceutically acceptable polymer.

In one embodiment, tablet is a controlled-release formulation, such as an extended release tablet dosage form (also referred to herein as a modified release or sustained release formulation). Such formulations permit the sustained release of the active ingredient over an extended period of time, as compared to immediate release solid dosage forms, which permit the release of most or all of the active ingredient over a short period of time (e.g., typically around 60 minutes or less). In one aspect, the tablet comprises an active ingredient and at least one additive selected from the group consisting of a release control polymer, a filler, a glidant, a lubricant (e.g., for use in compacting the granules), a pH modifier, a surfactant, and combinations thereof. In one aspect, the tablet comprises an active ingredient, a release control polymer, a filler, a glidant, and a lubricant. In one aspect, the tablet comprises an active ingredient, a release control polymer, a filler, a glidant, a lubricant, and a pH modifier.

In certain embodiments, the release control polymer will be a hydrophilic polymer. Examples of suitable release control polymers include, but are not limited to a cellulose derivative with a viscosity of between 1000 and 150,000 mPA-s, hydroxypropylmethyl cellulose (e.g., Hypromellose 2208 or controlled release grades of hydroxypropylmethyl cellulose, including the E, F, and K series), copolymers of acrylic acid crosslinked with a polyalkenyl polyether (e.g., Carbopol® polymers), hydroxypropyl cellulose, hydroxyethyl cellulose, non-ionic homopolymers of ethylene oxide (e.g., Polyox™), water soluble natural gums of polysaccharides (e.g., xanthan gum, alginate, locust bean gum, etc.), crosslinked starch, polyvinyl acetates, polyvinylpyrrolidone, mixtures of polyvinyl acetates and polyvinyl pyrrolidone, and combinations thereof. In one embodiment, the release control polymer is selected from the group consisting of hydroxypropylmethyl cellulose, copolymers of acrylic acid crosslinked with a polyalkenyl polyether (e.g., Carbopol® polymers), and combinations thereof. Examples of suitable fillers ("bulking agents") include, but are not limited to, microcrystalline cellulose (e.g., Avicel® PH 101; Avicel, PH 102;), mannitol (e.g., Pearlitol® 100 SD or Pearlitol® 200 SD), lactose, sucrose, sorbitol, and the like. In one embodiment, the filler is selected from the group consisting of microcrystalline cellulose, mannitol, and combinations thereof. Examples of suitable glidants include, but are not limited to, silicone dioxide (e.g., colloidal silicon dioxide), calcium silicate, magnesium silicate, talc, and combinations thereof. In one embodiment, the glidant is colloidal silicone dioxide. Examples of suitable lubricants include, but are not limited to, polyethylene glycol (e.g., having a molecular weight of from 1000 to 6000), magnesium stearate, calcium stearate, sodium stearyl fumarate, talc, and the like. In one embodiment, the lubricant is magnesium stearate. Examples of suitable pH modifiers include, but are not limited to, organic acids, such as tartaric acid, citric acid, succinic acid, fumaric acid; sodium citrate; magnesium or calcium carbonate or bicarbonate; and combinations thereof. In one embodiment, the pH modifier is tartaric acid. Examples of suitable surfactants include sodium lauryl sulfate.

In one embodiment, the pharmaceutical composition comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w %, about 20 w/w %, about 25 w/w % or about 30 w/w % pH modifier. In one embodiment, the pH modifier is tartaric acid.

IV. Pharmacokinetic Parameters 15 mg Dosage Formulations

In certain embodiments, the methods of the present disclosure comprise administering to an adult subject (e.g., a human subject) Compound 1 (freebase), or a pharmaceutically acceptable salt thereof, or a crystalline hydrate of Compound 1 in an amount sufficient to deliver to the subject 15 mg of Compound 1 freebase equivalent. In one embodiment, the freebase or the hydrate is in a once daily extended release formulation.

Unless otherwise indicated, the following pharmacokinetic parameters are achieved after administration of a single 15 mg dose the Compound 1 (freebase) or a pharmaceutically acceptable salt thereof or the crystalline hydrate (e.g., Freebase Hydrate Form C) to the adult subject, or after administration of a sufficient number of once-daily 15 mg doses to achieve a steady-state. By a single 15 mg dose, it is meant a single dosage unit containing an amount of freebase or pharmaceutically acceptable salt or crystalline hydrate sufficient to deliver to the subject 15 mg of Compound 1 freebase equivalent. In one embodiment, the single dosage unit is a once daily extended release formulation.

30 mg Dosage Formulations

In certain embodiments, the methods of the present disclosure comprise administering to an adult subject (e.g., a human subject) 30 mg of Compound 1 (freebase), or a pharmaceutically acceptable salt thereof or a crystalline hydrate of Compound 1 in an amount sufficient to deliver to the subject 30 mg of Compound 1 freebase equivalent. In one embodiment, the freebase or the hydrate is in a once daily extended release formulation.

Unless otherwise indicated, the following pharmacokinetic parameters are achieved after administration of a single 30 mg dose the Compound 1 (freebase) or a pharmaceutically acceptable salt thereof or the crystalline hydrate (e.g., Freebase Hydrate Form C) to the adult subject, or after administration of a sufficient number of once-daily 30 mg doses to achieve a steady-state. By a single 30 mg dose, it is meant a single dosage unit containing an amount of freebase or pharmaceutically acceptable salt or crystalline hydrate sufficient to deliver to the subject 30 mg of Compound 1 freebase equivalent. In one embodiment, the single dosage unit is a once daily extended release formulation.

VIII. Extended Release Tablets

In one embodiment, the Compound 1 (freebase) or a pharmaceutically acceptable salt thereof or the crystalline hydrate used in the methods of the present disclosure is in a once daily extended release formulation. In one embodiment, the Compound 1 (freebase) or a pharmaceutically acceptable salt thereof or the crystalline hydrate is in a once daily extended release formulation, and the formulation delivers about 7.5 mg or about 15 mg or about 30 mg or about 45 mg per unit dosage form (e.g., per tablet or capsule) of Compound 1 (freebase equivalent) orally QD (once daily). In one particular embodiment, the crystalline hydrate is Freebase Hydrate Form C.

In one embodiment, the Compound 1 (freebase) or a pharmaceutically acceptable salt thereof or the crystalline hydrate is in a once daily extended release formulation, and the formulation delivers 7.5 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 3 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 15 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 6 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 30 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 12 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 45 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 18 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

V. Ankylosing Spondylitis

Ankylosing Spondylitis (AS) is a chronic, inflammatory rheumatic disease primarily affecting the axial skeleton, characterized by chronic back pain (including nocturnal back pain), morning stiffness, enthesitis, peripheral arthritis, and extra-articular manifestations. The "early" form of this disease (non-radiographic axial spondyloarthritis (nr-axSpA)) shares many of AS disease characteristics.

Due to the longstanding debilitating nature of AS, irreversible structural damage often occurs, negatively impacting patients' lives. No cure for AS exists, thus the primary goal of treatment is to maximize patients' quality of life through controlling the signs and symptoms of disease, preventing structural damage, and maintaining physical function, ideally by achieving sustained clinical remission or, at minimum, low disease activity. Nonsteroidal anti-inflammatory drugs (NSAIDs) are the first-line treatment for AS, followed by biologic disease-modifying antirheumatic drugs (bDMARDs), such as tumor necrosis factor (TNF) inhibitors or interleukin-17 (IL-17) inhibitors, in patients who do not sufficiently respond to NSAIDs. TNF inhibitors and IL-17 inhibitors are efficacious in some patients with AS, but there are still patients for whom neither of these approved therapies address individual treatment goals. AS is a difficult disease to treat, as shown based on low efficacy achieved with IL-6 inhibitors tocilizumab and sarilumab, as well as IL-12/23 inhibitor ustekinumab and T cell blockade inhibitor abatacept. See, e.g., Sieper et al., Ann. Rheum. Dis. 2014 73:95-100, Sieper et al., Ann. Rheum. Dis. 2015 74:1051-1057; Deodhar et al., Arthritis and Rheumatology 2019 71:258-270, and Song et al., Ann. Rheum. Dis. 2011 70:1108-1110.

The JAK family is composed of 4 members: JAK1, 2, 3, and tyrosine kinase 2 (Tyk2). These cytoplasmic tyrosine kinases act in tandem to activate the Signal Transducer and Activator of Transcription (STAT) that transduce cytokine-mediated signals and are associated with multiple membrane cytokine receptors such as common gamma-chain (CGC) receptors and the glycoprotein 130 trans-membrane proteins. JAK3 and JAK1 are components of the CGC cytokine receptor complexes that are responsible for the signaling of the inflammatory cytokines IL-2, -4, -7, -9, -15 and -21; whereas IL-12 and IL-23 signal through JAK2 and Tyk2. See Ghoreschi, et al., Immunol Rev. (2009), 228:273-87. Propagation of these signals is important in the amplification of inflammatory responses in axial spondyloarthritis (axSpA). Upadacitinib, a JAK inhibitor engineered for increased selectivity for JAK1 over JAK2, JAK3, and tyrosine kinase 2, has been investigated for the treatment of bDMARD-naïve patients with AS who had an inadequate response to non-steroidal anti-inflammatory drugs (NSAIDs) in the randomized, placebo-controlled phase 2/3 SELECT-AXIS 1 study. See Example 2, herein. A second study (SELECT-AXIS-2) is underway, expanding the scope of enrollment to non-radiographic axial spondyloarthritis (nr-axSpA) patients and AS bDMARD-IR patients. See Example 3.

The SELECT-AXIS 1 met its primary endpoint of significantly greater achievement of Assessment of SpondyloArthritis International Society (ASAS40) response at Week 14, as well as several disease activity measures (ASDAS, BASDAI, ASAS, and their components), inflammation (based on MRI of spine and sacroiliac joints as well as hsCRP), physical function (BASFI), quality of life (ASQoL, ASAS HI), and other aspects of disease (BASMI, MASES), reflecting significant improvement in outcomes for upadacitinib versus placebo. Furthermore, a review of the placebo corrected data for upadacitinib at Week 14, biologics Ixekizumab and Adalimumab at Week 16, and JAK small molecule inhibitors Tofacitinib and Filgotinib at Week 12 for key primary and secondary endpoints, while not a head to head comparison, suggests that upadacitinib 15 mg QD shows decided promise for the more difficult to achieve endpoints ASAS PR, ASDAS ID, and ASDAS LDA versus the other two JAK small molecule inhibitors, with a remarkable efficacy only comparable to that demonstrated with the biologics. See Example 2, and van der Heijde et al. Lancet (2018) 392: 2441-2451, van der Heijde D. et al. Ann. Rheum. Dis. (2017) 1-8; van der Heijde et al. Lancet (2018) 2378-2387. Furthermore, this efficacy, once achieved at Week 14, was sustained or improved over time, with long term efficacy in these difficult to achieve endpoints (including ASDAS major improvement (MI) and ASDAS clinically important improvement (CII)), sustained or improved up to and including Week 64. In patients who switched from placebo to upadacitinib at Week 14, a similar speed of onset and magnitude of efficacy response was observed up to and including Week 64 compared with those who received continuous upadacitinib starting at Week 0. Based on the results of phase 2/3 study SELECT-AXIS 1 and the consistent safety data from other upadacitinib clinical trials, the benefit-risk profile of upadacitinib in AS (particularly compared to the risk profile of other small molecule JAK inhibitors), and viewed in the context of the benefit-risk of TNF inhibitors and IL-17 inhibitors, presents a promising oral targeted treatment option for patients with AS, especially for those AS (as well as nr-axSpA patients) who have active disease and inadequate response to NSAIDs.

VI. Psoriatic Arthritis

Psoriatic arthritis (PsA) is a systemic inflammatory disease with heterogeneous clinical manifestations such as plaque psoriasis, arthritis, dactylitis, and enthesitis, and is interrelated with AS, as it shares genetic and clinical features (e.g., axial involvement with back pain, peripheral arthritis or enthesitis, genetic association with HLA-B27 as well as presence of extra-articular manifestations). Multiple cytokines such as IL-1, -6, -12, -17, -20, and -23 are thought to be involved in the activation and proliferation of epidermal keratinocytes in psoriatic lesions. See e.g., Nestle, et al., N. Engl. J. Med. (2009) 361:496-509. The IL-17/IL-23 cytokine axis is also thought to be important in PsA pathogenesis. See e.g., Mease, Curr. Opin. Rheumatol. (2015) 27:127-33. Thus, blockade of JAK1 could inhibit the response of central cytokine signals thought to be important in the pathogenesis of PsA. Current treatment guidelines for PsA vary, recommending conventional synthetic disease-modifying anti-rheumatic drugs (DMARDs) such as methotrexate as initial therapy, followed by biologic DMARDs or targeted synthetic DMARDs, such as tofacitinib, or TNFi initially, followed by other approved therapies. While multiple therapeutic choices are available, additional options are needed in order to reach the more difficult to achieve endpoints, such as achievement of minimal disease activity (MDA), as well as treatment of the psoriasis as a skin manifestation of PsA, with achievement of PASI 75 or PASI 90. The JAK1 inhibitor upadacitinib has been investigated for the treatment of patients with active Psoriatic Arthritis and a previous inadequate response to at least one non-biologic Disease Modifying Anti-Rheumatic Drug (non-biologic DMARD) (SELECT PSA1) or previous inadequate response to at least one biologic Disease Modifying Anti-Rheumatic Drug (bDMARD) (SELECT PSA2). See Examples 4 and 5. In these two trials, greater efficacy was demonstrated for once daily upadacitinib 15 mg and 30 mg versus placebo for clinical manifestations of psoriatic arthritis including musculoskeletal symptoms (peripheral arthritis, enthesitis, dactylitis, and spondylitis), psoriasis, physical function, pain, fatigue, and quality of life. Efficacy was observed as early as week 2. Furthermore, a review of the placebo corrected data for upadacitinib and the JAK small molecule inhibitor Tofacitinib (approved for the lower (5 mg BID) dose in the treatment of PsA) for key primary and secondary endpoints, while not a head to head comparison, suggests that upadacitinib 15 mg QD and 30 mg QD shows decided promise for the more difficult to achieve endpoints of minimal disease activity (MDA), as well as psoriasis endpoints PASI 75 or PASI 90, as well as certain ACR components (e.g., ACR20/50/70). See Examples 4 and 5, as well as Gladman et al., New England Journal of Medicine (2017) 377:1525-1536 and Mease P et. al., N Engl J Med (2017) 377:1537-1550. Furthermore, it was observed that this efficacy, once achieved, was sustained or improved over time during the course of the daily treatment.

Thus, in one aspect, provided is a method for treating various spondyloarthritic and psoriatic conditions, including types of axial spondyloarthritis (axSpA), psoriatic arthritis (PsA), and psoriasis (PsO) by administering the JAK1 inhibitor, upadacitinib free base or a pharmaceutically acceptable salt, to a subject in need thereof. In various aspects, provided is a method for treating active non-radiographic axSpA (nr-axSpA), methods for treating active ankylosing spondylitis (AS), and methods for treating active psoriatic arthritis (PsA) and active psoriasis (PsO), including PsO as a skin manifestation of PsA.

In one embodiment, the JAK1 inhibitor useful in the methods disclosed herein is upadacitinib freebase. Upadacitinib freebase solid state forms include amorphous upadacitinib freebase and crystalline freebases of upadacitinib. Crystalline freebases of upadacitinib include those selected from the group consisting of crystalline freebase solvates of upadacitinib, crystalline freebase hydrates of upadacitinib (e.g., crystalline freebase hemihydrates of upadacitinib), and crystalline freebase anhydrates of upadacitinib. In one embodiment, the crystalline freebase of upadacitinib is a crystalline freebase hemihydrate of upadacitinib. In one embodiment, the crystalline freebase of upadacitinib is Upadacitinib Freebase Hydrate Form C (which is a hemihydrate) as described in WO 2018/165581 and WO 2017/066775. Other specific examples of solid state forms of the JAK1 inhibitor suitable for use in the methods disclosed herein include those selected from the group consisting of Amorphous Upadacitinib Freebase, Upadacitinib Freebase Solvate Form A, Upadacitinib Freebase Hydrate Form B, Upadacitinib Freebase Anhydrate Form D, and Upadacitinib Tartrate Hydrate, each as described in WO 2018/165581 and WO 2017/066775.

VII. Methods of Treating Axial Spondyloarthritis

Provided herein are methods of treating axial spondyloarthritis (axSpA). In a particular aspect, provided are methods of treating active axSpA, which encompasses treating subjects with active ankylosing spondylitis (AS) and active non-radiographic axial spondyloarthritis (nr-axSpA), comprising administering orally once a day a dose of the JAK1 inhibitor, upadacitinib freebase, or a pharmaceutically acceptable salt thereof, to a subject in need thereof in certain amounts and/or at certain intervals. In one aspect, the JAK1 inhibitor is upadacitinib freebase. In one aspect, the JAK1 inhibitor is administered orally once a day in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

Disease activity/severity for axSpA may be measured using a variety of indexes, including the Assessment of SpondyloArthritis International Society (ASAS) responses (e.g., ASAS20, ASAS40, ASAS partial remission (PR). ASAS5/6); the Ankylosing Spondylitis Disease Activity Score (ASDAS), ASDAS low disease activity (LDA), ASDAS inactive disease (ID), ASDAS major improvement (MI), ASDAS clinically important improvement (CII), the magnetic resonance imaging (MRI) Spondyloarthritis Research Consortium of Canada (SPARCC) score for spine (MRI-Spine SPARCC); the MRI SPARCC score for sacroiliac (SI) joints (MRI-SI joints SPARCC); the Bath Ankylosing Spondylitis Disease Activity Index (BASDAI); a BASDAI 50 (BASDAI50) response; the Bath Ankylosing Spondylitis Functional Index (BASFI); the Ankylosing Spondylitis Quality of Life Questionnaire (ASQoL); the ASAS Health Index (HI); the Maastricht Ankylosing Spondylitis Enthesitis Score (MASES) (enthesitis); the Linear Bath Ankylosing Spondylitis Metrology Index (BASMIlin) (mobility); the Work Productivity and Activity Impairment Questionnaire—Axial Spondyloarthritis (WPAI-Axial SpA); high-sensitivity C-reactive protein levels (hsCRP); the Functional Assessment of Chronic Illness Therapy-Fatigue (FACIT-F) Questionnaire; the Insomnia Severity Index (ISI); the Modified Stroke Ankylosing Spondylitis Spine Score (mSASSS); the Patient's Assessment of Total Back Pain (Total Back Pain score); the Patient's Assessment of Nocturnal Back Pain (Nocturnal Back Pain); the Patient's Global Assessment of Pain (Pt Pain); the Physician's Global Assessment of Disease Activity (PGA-Disease Activity); Inflammation (mean of Questions 5 and 6 of the BASDAI); Patient's Assessment of Total Back Pain (Question 2 of BASDAI); Peripheral pain/swelling (Question 3 of BASDAI); duration of morning stiffness (Question 6 of BASDAI); Patient's Global Assessment of Disease Activity (PtGA); tender joint count (TJC68) and swollen joint count (SJC66); resolution of dactylitis; total dactylitis count; EuroQoL-5D-5L (EQ-5D-5L) Questionnaire; 36-Item Short Form Health Survey (SF-36); Physical Activity Assessment, and NSAID score. These indexes are described in detail in the Clinical Endpoint Definitions and Examples.

In one aspect, provided is a method of treating axSpA, including active axSpA, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer the daily dose. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer the daily dose. In one aspect, the subject achieves an ASAS40 response within 52 weeks of administration of the first dose of the JAK1 inhibitor (including at week 52). In one aspect, the subject achieves an ASAS40 response within 52 weeks of administration of the first dose of the JAK1 inhibitor (including at week 52), and the response is maintained or improved after week 52 by continuing to administer the daily dose. In one aspect, the subject achieves an ASAS40 response within 2 weeks, within 4 weeks, within 8 weeks, within 12 weeks, within 14 weeks, within 18 weeks, within 24 weeks, within 32 weeks, within 40 weeks, and/or within 52 weeks of administration of the first dose of the JAK1 inhibitor (including at week 2, week 4, week 8, week 12, week 14, week 18, week 24, week 32, week 40, and/or week 52). In one embodiment, the subject achieves an ASAS40 response within 2 weeks of administration of the first dose (including at week 2) and maintains the ASAS40 response until at least 14 weeks after administration of the first dose (e.g., until at least week 14). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 18 weeks, for at least 24 weeks, for at least 32 weeks, for at least 40 weeks, and/or for at least 52 weeks. In one embodiment, the JAK1 inhibitor is administered orally once a day for at least 14 weeks. In one aspect, the JAK1 inhibitor is administered orally once a day for at least 52 weeks.

In another aspect, provided is a method of treating axSpA, including active axSpA, comprising administering the JAK1 inhibitor to a subject in need thereof in certain amounts and/or at certain intervals as described herein, wherein the subject achieves an ASAS40 response at a certain interval as described herein, and additionally achieves at least one of the results set forth hereinafter for treatment of ankylosing spondylitis (AS) and/or non-radiographic axial spondyloarthritis (nr-axSpA) following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

In another aspect, provided is a method of treating axSpA, including active axSpA, in a population of subjects in need thereof, the method comprising administering a dose of the JAK1 inhibitor to the subjects in certain amounts and/or at certain intervals as described herein, wherein a portion of subjects in the treated population achieve an ASAS40 response following administration of the JAK1 inhibitor (e.g., a statistically significant population of the subjects in the treated population, and/or at least 10%, at least 15%, at least 20%, at least 25%, at least 30%, at least 35%, at least 40%, or at least 45% of the subjects in the treated population achieve the response). In one aspect, the subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the response is maintained or improved after week 14 by continuing to administer a daily dose of the JAK1 inhibitor to the subjects. In one aspect, subjects in the treated population achieve an ASAS40 response within 52 weeks of administration of the first dose of the JAK1 inhibitor (including at week 52). In one aspect, subjects in the treated population achieve an ASAS40 response within 52 weeks of administration of the first dose of the JAK1 inhibitor (including at week 52), and the response is maintained or improved after week 52 by continuing to administer a daily dose of the JAK1 inhibitor to the subjects. In one aspect, the subjects in the treated population achieve an ASAS40 response within 2 weeks of administration of the first dose of the JAK1 inhibitor (including at week 2). In one aspect, subjects in the treated population achieve an ASAS40 response within 2 weeks of administration of the first dose of the JAK1 inhibitor (including at week 2), and the response is maintained or improved after week 2 by continuing to administer a daily dose of the JAK1 inhibitor to the subjects. In one aspect, subjects in the treated population achieve at least one of the results set forth hereinafter for treatment of ankylosing spondylitis (AS) and/or non-radiographic axial spondyloarthritis (nr-axSpA) following administration of the JAK1 inhibitor (e.g., a statistically significant population of subjects in the treated population, and/or at least 10%, at least 15%, at least 20%, at least 25%, at least 30%, at least 35%, at least 40%, or at least 45% of the subjects in the treated population achieve at least one of the results). In one aspect, the JAK1 inhibitor is upadacitinib freebase. In one aspect, a dose of the JAK1 inhibitor is administered to the population in an amount sufficient to deliver 15 mg of upadacitinib freebase equivalent. In one aspect, the JAK1 inhibitor is administered to the subjects orally once a day for at least 14 weeks. In one aspect, the JAK1 inhibitor is administered to the subjects orally once a day for at least 52 weeks.

Further provided are methods of reducing the signs and symptoms of axSpA. In one aspect, provided is a method of reducing the signs and symptoms of axSpA, including active axSpA, comprising administering a dose of the JAK1 inhibitor to a subject in need thereof in certain amounts and/or at certain intervals. In one aspect, the JAK1 inhibitor is upadacitinib freebase or a pharmaceutically acceptable salt thereof. In one aspect, the JAK1 inhibitor is administered in an amount sufficient to deliver 15 mg of upadacitinib freebase equivalent. In one aspect, the JAK1 inhibitor is administered once a day for 14 weeks. In one aspect, the JAK1 inhibitor is administered once a day for 52 weeks.

In one aspect, the signs and symptoms of axSpA, including active axSpA, are reduced following administration of the JAK1 inhibitor when the subject achieves, within 14 weeks of administration of the first dose of the JAK1 inhibitor (including at week 14), at least one result selected from the group consisting of: an ASAS40 response; a change (improvement) from baseline in ASDAS; a change (improvement) from baseline in MRI SPARCC score for spine (MRI-Spine SPARCC); ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); a change (improvement) from baseline in BASMIlin (mobility); a change (improvement) from baseline in WPAI-Axial SpA; and a change (improvement) from baseline in MRI SPARCC score for SI joints (MRI-SI joints SPARCC); or when the subject achieves, within 52 weeks of administration of the first dose of the JAK1 inhibitor (including at week 52), an ASAS40 response. In one aspect, the subject achieves the response within 14 weeks of administration of the first dose of the JAK1 inhibitor (including at week 14), and the response is maintained or improved after week 14 by continuing to administer a daily dose of the JAK1 inhibitor. In another aspect, the subject achieves the response within 52 weeks of administration of the first dose of the JAK1 inhibitor (including at week 52), and the response is maintained or improved after week 52 by continuing to administer a daily dose of the JAK1 inhibitor. In one aspect, the subject achieves the response within 2 weeks of administration of the first dose of the JAK1 inhibitor (including at week 2), and the response is maintained or improved after week 2 by continuing to administer a daily dose of the JAK1 inhibitor.

For any of the methods of treating axSpA and/or methods for reducing the signs and symptoms of axSpA described herein, the subject and/or subjects in the treated population i) may be biologic disease-modifying anti-rheumatic drug (bDMARD) naïve or ii) may have had an inadequate response or intolerance to a bDMARD (bDMARD-IR) at baseline. In certain embodiments, the subject (or subjects in the treated population) may have had a prior inadequate response to, intolerance to, or contraindication to NSAIDs at baseline.

VIII. Methods of Treating Ankylosing Spondylitis (AS)

Further provided are methods of treating ankylosing spondylitis (AS). For example, in one aspect, provided is a method of treating AS, including active AS, comprising administering orally once a day a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR Disease activity/severity for AS may be measured using a variety of indexes, including those set forth above for the treatment of axSpA. In one particular aspect, provided is a method of treating AS, including active AS, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR. In one aspect, the subject is an adult.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer a daily dose of the JAK1 inhibitor. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer a daily dose of the JAK1 inhibitor. In one aspect, the subject achieves an ASAS40 response within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one aspect, the subject achieves an ASAS 40 response within 14 weeks of administration of the first dose of the JAK1 inhibitor (including at week 14), and the ASAS40 response is maintained or improved until at least 64 weeks after administration of the first dose (e.g., up to and including week 64). In one embodiment, the subject achieves an ASAS 40 response within 2 weeks of administration of the first dose (including at week 2), and maintains or improves the ASAS40 response until at least 14 weeks after administration of the first dose (e.g., until at least week 14). In one embodiment, the subject achieves an ASAS 40 response within 2 weeks of administration of the first dose of the JAK1 inhibitor (including at week 2), and the ASAS40 response is maintained or improved until at least 64 weeks after administration of the first dose (e.g., up to and including week 64). In one aspect, the subject alternately or additionally achieves within 14 weeks of administration of the first dose of the JAK1 inhibitor (including at week 14) at least one additional result selected from the group consisting of: ASAS partial remission (PR); BASDAI50 response; change (improvement) from baseline in MRI SPARCC score for spine (MRI-Spine SPARCC); change (improvement) from baseline in ASDAS; change (improvement) from baseline in BASFI; ASDAS low disease activity (LDA); ASDAS inactive disease (ID); ASDAS major improvement (MI); and ASDAS clinically important improvement (CII). In one aspect, the subject achieves the result within 14 weeks of administration of the first dose of the JAK1 inhibitor (including at week 14), and the result is maintained or improved after week 14 by continuing to administer a daily dose of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, and/or for at least 104 weeks. In one embodiment, the JAK1 inhibitor is administered orally once a day for at least 14 weeks.

Further provided are methods of treating AS, including active AS, in a subject in need thereof, comprising administering orally once a day a dose of a JAK1 inhibitor to a subject in need thereof in certain amounts and/or at certain intervals as described herein, wherein the subject achieves ASAS partial remission (PR), ASDAS low disease activity (LDA), ASDAS inactive disease (ID), ASDAS major improvement (MI), and/or ASDAS clinically important improvement (CII) following administration of the JAK1 inhibitor. In one embodiment, the subject achieves ASAS PR, ASDAS LDA, ASDAS ID, ASDAS MI, and/or ASDAS CII within 14 weeks of administration of the first dose of the JAK1 inhibitor (including at week 14). In one embodiment, the subject achieves each result (e.g., ASAS PR, ASDAS LDA, ASDAS ID, ASDAS MI, and ASDAS CII) within 14 weeks of administration of the first dose of the JAK1 inhibitor (including at week 14). In one aspect, the subject achieves ASAS PR, ASDAS LDA, ASDAS ID, ASDAS MI, and/or ASDAS CII within 2 weeks of administration of the first dose of the JAK1 inhibitor (including at week 2). In one aspect, the subject achieves ASAS PR, ASDAS LDA, ASDAS ID, ASDAS MI, and/or ASDAS CII within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one aspect, the subject achieves ASAS PR, ASDAS LDA, ASDAS ID, ASDAS MI, and/or ASDAS CII within 14 weeks of administration of the first dose of the JAK1 inhibitor (including at week 14), and the response is maintained or improved after week 14 by continuing to administer a daily dose of the JAK1 inhibitor. In one aspect, the subject achieves ASAS PR, ASDAS LDA, ASDAS ID, ASDAS MI, and/or ASDAS CII within 2 weeks of administration of the first dose of the JAK1 inhibitor (including at week 2), and the response is maintained or improved after week 2 by continuing to administer the daily dose of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, and/or for at least 104 weeks. In one embodiment, the JAK1 inhibitor is administered orally once a day for at least 14 weeks. In one aspect, the subject is bDMARD naïve. In one aspect, the subject is bDMARD-IR. In one aspect, the subject is an adult.

In one aspect, provided is a method of treating AS, including active AS, in a population of subjects in need thereof, the method comprising administering a dose of the JAK1 inhibitor to the subjects in certain amounts and/or at certain intervals as described herein, wherein a portion of subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve an ASAS40 response following administration of the JAK1 inhibitor. In one aspect, subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the response is maintained or improved after week 14 by continuing to administer a daily dose of the JAK1 inhibitor. In one aspect, subjects in the treated population achieve an ASAS40 response within 2 weeks of administration of the first dose of the JAK1 inhibitor (including at week 2). In one aspect, subjects in the treated population of the subjects achieve an ASAS40 response within 2 weeks of administration of the first dose of the JAK1 inhibitor (including at week 2), and the response is maintained or improved after week 2 by continuing to administer a daily dose of the JAK1 inhibitor. In one aspect, subjects in the treated population achieve an ASAS40 response within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one embodiment, subjects in the treated population achieve an ASAS 40 response within 14 weeks of administration of the first dose of the JAK1 inhibitor (including at week 14), and the ASAS40 response is maintained or improved until at least 64 weeks after administration of the first dose (e.g., up to and including week 64). In one embodiment, subjects in the treated population achieve an ASAS 40 response within 2 weeks of administration of the first dose (including at week 2), and maintains or improves the ASAS40 response until at least 14 weeks after administration of the first dose (e.g., until at least week 14). In one aspect, subjects in the treated population alternately or additionally achieve within 14 weeks of administration of the first dose of the JAK1 inhibitor (including at week 14) at least one additional result selected from the group consisting of ASAS partial remission (PR); BASDAI50 response; change (improvement) from baseline in MRI SPARCC score for spine (MRI-Spine SPARCC); change (improvement) from baseline in ASDAS; change (improvement) from baseline in BASFI; ASDAS low disease activity (LDA); ASDAS inactive disease (ID); ASDAS major improvement (MI); and ASDAS clinically important improvement (CII). In one aspect, subjects in the treated population achieve the result within 14 weeks of administration of the first dose of the JAK1 inhibitor (including at week 14), and the result is maintained or improved after week 14 by continuing to administer a daily dose of the JAK1 inhibitor. In certain embodiments, for any of the aforementioned results achieved, a statistically significant population of the subjects in the treated population, and/or at least 10%, at least 15%, at least 20%, at least 25%, at least 30%, at least 35%, at least 40%, or at least 45% of the subjects in the treated population, achieve the result. In one aspect, the JAK1 inhibitor is upadacitinib freebase. In one aspect, a dose of the JAK1 inhibitor is administered to the population in an amount sufficient to deliver 15 mg of upadacitinib freebase equivalent. In one aspect, the JAK1 inhibitor is administered to the population orally once a day for at least 14 weeks. In one aspect, the subjects in the population are bDMARD naïve. In one aspect, the subjects in the population are bDMARD-IR.

Further provided are methods of treating AS, including active AS, in a population of subjects in need thereof, the method comprising administering orally once a day a dose of the JAK1 inhibitor to a subject in need thereof in certain amounts and/or at certain intervals as described herein, wherein a portion of the subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve ASAS partial remission (PR), ASDAS low disease activity (LDA), ASDAS inactive disease (ID), ASDAS major improvement (MI), and/or ASDAS clinically important improvement (CII) following administration of the JAK1 inhibitor. In one aspect, subjects in the treated population achieve ASAS PR, ASDAS LDA, ASDAS ID, ASDAS MI, and/or ASDAS CII within 14 weeks of administration of the first dose of the JAK1 inhibitor (including at week 14). In one aspect, subjects in the treated population achieve each result (e.g., ASAS PR, ASDAS LDA, ASDAS ID, ASDAS MI, and ASDAS CII) within 14 weeks of administration of the first dose of the JAK1 inhibitor (including at week 14). In one aspect, subjects in the treated population achieve ASAS PR, ASDAS LDA, ASDAS ID, ASDAS MI, and/or ASDAS CII within 2 weeks of administration of the first dose of the JAK1 inhibitor (including at week 2). In one aspect, subjects in the treated population achieve ASAS PR, ASDAS LDA, ASDAS ID, ASDAS MI, and/or ASDAS CII within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one aspect, subjects in the treated population achieve ASAS PR, ASDAS LDA, ASDAS ID, ASDAS MI, and/or ASDAS CII within 14 weeks of administration of the first dose of the JAK1 inhibitor (including at week 14), and the response is maintained or improved after week 14 by continuing to administer the daily dose of the JAK1 inhibitor. In one aspect, subjects in the treated population achieve ASAS PR, ASDAS LDA, ASDAS ID, ASDAS MI, and/or ASDAS CII within 2 weeks of administration of the first dose of the JAK1 inhibitor (including at week 2), and the response is maintained or improved after week 2 by continuing to administer the daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve the result. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, and/or for at least 104 weeks. In one embodiment, the JAK1 inhibitor is administered orally once a day for at least 14 weeks. In one aspect, the subjects in the population are bDMARD naïve. In one aspect, the subjects in the population are bDMARD-IR. In one aspect, the subjects are adults.

Further provided are methods of reducing the signs and symptoms of AS. In one aspect, provided is a method of reducing the signs and symptoms of AS, including active AS, the method comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR In one aspect of a method of reducing the signs and symptoms of AS, including active AS, wherein the subject achieves within 14 weeks of administration of the first dose of the JAK1 inhibitor (including at week 14), at least one result selected from the group consisting of, an ASAS40 response; a change (improvement) from baseline in ASDAS; a change (improvement) from baseline in MRI-Spine SPARCC; ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); a change (improvement) from baseline in BASMIlin (mobility); and a change (improvement) from baseline in WPAI-Axial SpA. In certain embodiments, for any of the aforementioned results achieved, a statistically significant population of the subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the subject (or subjects in the treated population) achieve the result or results within 14 weeks of administration of the first dose of the JAK1 inhibitor (including at week 14), and the result (or results) is maintained or improved after week 14 by continuing to administer a daily dose of the JAK1 inhibitor.

In another aspect, the subject has (or subjects in the treated population have) active AS at baseline. In one aspect, the subject (or subjects in the treated population) fulfills the 1984 modified New York Criteria for AS at baseline. In another aspect, the subject (or subjects in the treated population) fulfills the 2009 ASAS classification criteria at baseline. In yet another aspect, the subject (or subjects in the treated population) fulfills the 1984 modified New York Criteria for AS and the 2009 ASAS classification criteria at baseline. In one embodiment, the subject (or subjects in the treated population) meets at least one criteria selected from the group consisting of: (i) a BASDAI score ≥4; (ii) an ASDAS of ≥2.1; and (iii) a Patient's Assessment of Total Back Pain (Total Back Pain score) of ≥4 (based on a 0-10 numerical rating scale) at baseline. In one embodiment, the subject (or subjects in the treated population) has both a BASDAI score ≥4 and a Patient's Assessment of Total Back Pain (Total Back Pain score) of ≥4 at baseline. In another embodiment, the subject (or subjects in the treated population) has both a BASDAI score ≥4 and an ASDAS of ≥2.1 at baseline. In certain embodiments, the subject (or subjects in the treated population) has (i) a BASDAI score ≥4; (ii) an ASDAS of ≥2.1; and (iii) a Patient's Assessment of Total Back Pain (Total Back Pain score) of ≥4 (based on a 0-10 numerical rating scale) at baseline. In one aspect, the subject (or subjects in the treated population) does not have total spinal ankylosis at baseline. In one aspect, the subject (or subjects in the treated population) is an adult subject. In another aspect, the subject (or subjects in the treated population) is a juvenile subject.

In one aspect, the subject (or subjects in the treated population) is bDMARD naïve at baseline. Exemplary bDMARDs include, but are not limited to, a biologic tumor necrosis factor inhibitor (e.g., adalimumab, etanercept) and interleukin IL)-17 inhibitors (e.g., secukinumab, ixekizumab).

In one aspect, the subject (or subjects in the treated population) is bDMARD naïve at baseline, and further has had i) an inadequate response or intolerance to at least two NSAIDs (e.g., over at least a four-week period at the maximum recommended or tolerated doses); ii) intolerance to NSAIDs; and/or iii) contraindication for NSAIDs, as determined by a physician. Examples of NSAIDs include, but are not limited to, traditional NSAIDs (e.g., ibuprofen) and salicylates (e.g., aspirin).

In certain aspects, the subject (or subjects in the treated population) to be treated is bDMARD naïve at baseline, has had an inadequate response or intolerance to at least two NSAIDS (as described above), or an intolerance to or contraindication for NSAIDS, and is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include:
1) Concomitant administration of non-biologic DMARDs, including methotrexate (MTX), leflunomide (LEF), sulfasalazine (SSZ), and/or hydroxychloroquine (HCQ). In one embodiment, the subject is on a stable dose of MTX (≤25 mg/week), SSZ (≤3 g/day), hydroxychloroquine (≤400 mg/day), and/or leflunomide (≤20 mg/day) for at least 28 days prior to baseline. In some embodiments, a combination of up to two background non-biologic DMARDs is allowed, except the combination of MTX and leflunomide. In one embodiment, the subject has not received any non-biologic DMARDs (other than MTX, LEF, SSZ, and/or HCQ), thalidomide, or apremilast within 28 days or five half-lives (whichever is longer) prior to baseline.
2) Concomitant administration of oral corticosteroids. In one embodiment, the subject is on a stable dose of prednisone (≤10 mg/day), or oral corticosteroid equivalents, for at least 14 days prior to baseline.
3) Concomitant administration of NSAIDs, tramadol, a combination of acetaminophen and codeine or hydrocodone, and/or non-opioid analgesics. In one embodiment, the subject is on stable dose(s) for at least 14-days prior baseline.

In another aspect, the subject (or subjects in the treated population) is bDMARD-IR at baseline. In one aspect, the subject has had an inadequate response or intolerance to a bDMARD at baseline. Subjects who are bDMARD-IR include those subjects who have had prior exposure to one bDMARD (either 1 tumor necrosis factor (TNF) inhibitor (e.g., adalimumab, etanercept) or 1 interleukin (IL)-17 inhibitor (e.g., secukinumab, ixekizumab)), and have discontinued the bDMARD due to either intolerance or lack of efficacy (e.g., as determined by a physician). In one embodiment, the subject (or subjects in the treated population) has not had prior exposure to a second bDMARD, if the reason for discontinuation was not due to lack of efficacy. In one embodiment, the subject (or subjects in the treated population) has not discontinued both a TNF inhibitor and an IL-17 inhibitor due to lack of efficacy.

In certain embodiments, the subject (or subjects in the treated population) has discontinued the bDMARD prior to receiving the first dose of the JAK1 inhibitor for:
≥4 weeks for etanercept;
≥8 weeks for adalimumab, infliximab, certolizumab, golimumab, abatacept, tocilizumab, and ixekizumab;
≥12 weeks for ustekinumab;
≥16 weeks for secukinumab;
≥1 year for rituximab or ≥6 months if B cells have returned to pre-treatment level or normal reference range (central lab) if pre-treatment levels are not available; or
≥12 weeks or at least 5 times the mean terminal elimination half-life, whichever is longer, for other bDMARDs.

In one aspect, the subject (or subjects in the treated population) is bDMARD-IR a baseline, and further has had i) an inadequate response or intolerance to at least two NSAIDs (e.g., over at least a four week period at the maximum recommended or tolerated doses); ii) intolerance to NSAIDs; and/or iii) contraindication for NSAIDs. In one aspect, the subject (or population of subjects) is bDMARD-IR, and has had an inadequate response to at least two NSAIDS or intolerance to and/or contraindication for NSAIDs. Examples of NSAIDs include, but are not limited to, traditional NSAIDs (e.g., ibuprofen) and salicylates (e.g., aspirin).

In certain aspects, the subject (or subjects in the treated population) to be treated is bDMARD-IR at baseline, has had an inadequate response or intolerance to at least two NSAIDS (as described above), and/or an intolerance to NSAIDs and/or contraindication for NSAIDS, and is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include.
1) Concomitant administration of non-biologic DMARDs, including methotrexate (MTX), leflunomide, sulfasalazine (SSZ), hydroxychloroquine, chloroquine, and/or apremilast. In one embodiment, the subject is on a stable dose of MTX (≤25 mg/week), SSZ (≤3 g/day), hydroxychloroquine (≤400 mg/day), chloroquine (≤400 mg/day); leflunomide (≤20 mg/day), or apremilast (≤60 mg/day)), for at least 28 days prior to baseline. In some embodiments, a combination of up to two background non-biologic DMARDs is allowed, except the combination of MTX and leflunomide.
2) Concomitant administration of oral corticosteroids. In one embodiment, the subject is on a stable dose of prednisone (≤10 mg/day), or oral corticosteroid equivalents, for at least 14 days prior to baseline.
3) Concomitant administration of NSAIDs, tramadol, a combination of acetaminophen/paracetamol and codeine or combination of acetaminophen/paracetamol and hydrocodone, and/or non-opioid analgesics. In one embodiment, the subject is on stable dose(s) for at least 14 days prior to baseline.

In one embodiment, the subject (or subjects in the treated population) is bDMARD-IR at baseline, has not been exposed to any JAK inhibitor, and has not had any of the following treatments/conditions within the specified time frame prior to baseline:
1) Intra-articular joint injections, spinal/paraspinal injection(s), or parenteral administration of corticosteroids within 28 days prior to baseline (not including inhaled or topical corticosteroids);
2) Any other non-biologic DMARDs (other than those mentioned above for concomitant treatment), including thalidomide, within 28 days or 5 half-lives (whichever is longer) of the drug prior to baseline;
3) Opioid analgesics (except for combination of acetaminophen/paracetamol and codeine or combination of acetaminophen/paracetamol and hydrocodone) within 14 days prior to the Baseline Visit:
4) No live vaccine within 28 days (or longer if required locally) prior to the first dose of JAK1 inhibitor, or have expected need of live vaccination during treatment with the JAK1 inhibitor, including at least 30 days (or longer if required locally) after the last dose of the JAK1 inhibitor;
5) No systemic use of known strong cytochrome P450 3A (CYP3A) inhibitors during administration of the JAK1 inhibitor, or strong CYP3A inducers 30 days prior to administration of the JAK1 inhibitor through the end of treatment;
6) Herbal therapies or other traditional medicines with unknown effects on CYP3A during treatment;
7) Investigational drug of chemical or biologic nature within a minimum of 30 days or 5 half-lives of the drug (whichever is longer) prior to the first dose of the JAK1 inhibitor; or
8) History of an allergic reaction or significant sensitivity to constituents of the JAK1 inhibitor (and its excipients) and/or other products in the same class.

In one embodiment, the subject (or subjects in the treated population) is bDMARD naïve or bDMARD-IR, and has not been previously exposed to any JAK inhibitor at baseline.

In one aspect of the methods of treating AS described herein, the subject (or subjects in the treated population) is bDMARD naïve at baseline, and achieves an ASAS40 response within 14 weeks of administration of the first dose (including at week 14). In another embodiment, the subject (or subjects in the treated population) is bDMARD naïve at baseline, and achieves an ASAS40 response within 2 weeks of administration of the first dose (including at week 2). In one embodiment, the subject (or subjects in the treated population) is bDMARD naïve at baseline, and achieves an ASAS40 response within 2 weeks of administration of the first dose (including at week 2) and maintains the ASAS40 response until at least 14 weeks after administration of the first dose (i.e., including until at least week 14). In one aspect, the subject (or subjects in the treated population) further achieves ASAS PR, ASDAS LDA, ASDAS ID, ASDAS MI, and/or ASDAS CII within 2 weeks of administration of the first dose (including at week 2). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and achieves within 14 weeks of administration of the first dose (including at week 14) an improvement of ≥40% and absolute improvement of ≥2 units (on a scale of 0 to 10) from baseline in each of the following 4 (ASAS40) domains:
a) Patient Global Assessment of disease activity (PtGA) as assessed on a numeric rating scale (NRS 0-10);
b) Patient's Assessment of Total Back Pain (Total Back Pain score) as assessed on a numeric rating scale (NRS 0-10);
c) Bath Ankylosing Spondylitis Functional Index (BASFI); and
d) inflammation, as represented by the mean of Questions 5 and 6 of the Bath Ankylosing Spondylitis Disease Activity Index (BASDAI).

In one embodiment, the above described improvements are achieved within 2 weeks of administration of the first dose (including at week 2). In one embodiment, the improvements are achieved within 14 weeks of administration of the first dose (including at week 14). In certain embodiments, a statistically significant population of subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration of the first dose (including at week 14) at least one result selected from the group consisting of: a) a change (improvement) from baseline in ASDAS (CRP); b) a change (improvement) from baseline in MRI SPARCC score for spine (MRI-Spine SPARCC); c) ASAS partial remission (PR); d) BASDAI50 response; e) a change (improvement) from baseline in BASFI; f) change from baseline in ASQoL; g) a change (improvement) from baseline in ASAS Health Index (HI); h) a change (improvement) from baseline in MASES (i.e., for subjects with baseline enthesitis); i) a change (improvement) from baseline in BASMIlin (mobility); and j) a change (improvement) from baseline in WPAI-Axial SpA. In one embodiment, the subject achieves the result within 2 weeks of administration of the first dose (including at week 2). In one embodiment, the subject achieves the result within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration (including at week 14) of the first dose at least one result selected from the group consisting of: a) a change (improvement) from baseline in ASDAS; b) a change (improvement) from baseline in MRI SPARCC score for spine (MRI-Spine SPARCC); c) ASAS partial remission (PR); d) BASDAI50 response; and e) a change (improvement) from baseline in BASFI. In one embodiment, each of the results are achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration of the first dose (including at week 14) at least one result selected from the group consisting of: k) ASAS 20 response; and l) a change (improvement) from baseline in MRI SPARCC score for sacroiliac (SI) joints (MRI-SI joints SPARCC). In one embodiment, each of the results are achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves at least one result selected from the group consisting of: m) ASAS20 response; n) ASAS40 response; o) ASAS PR; p) ASAS 5/6 response; q) ASDAS Inactive Disease (based on ASDAS (CRP) and ASDAS (ESR)); r) ASDAS Low Disease; s) ASDAS Major Improvement (based on ASDAS (CRP) and ASDAS (ESR)); t) ASDAS Clinically Important Improvement (based on ASDAS (CRP) and ASDAS(ESR); u) change (improvement) from baseline in ASAS HI; v) change (improvement) from baseline in ASDAS(CRP) and ASDAS (ESR); w) change (improvement) from baseline in ASQoL; x) change (improvement) from baseline in BASDAI; y) change (improvement) from baseline in BASFI; z) change (improvement) from baseline in BASMIlin; aa) change (improvement) from baseline in C-reactive protein (CRP); bb) change (improvement) from baseline in FACIT-F; cc) change (improvement) from baseline in ISI; dd) change (improvement) from baseline in MASES (in subjects with baseline MASES>0); ee) change (improvement) from baseline in mASSS (with conventional radiograph); ff) change (improvement) from baseline in MRI SPARCC score of SI joints; gg) change (improvement) from baseline in MRI SPARCC score of spine; hh) change (improvement) from baseline in Patient's Assessment of Total Back Pain score (Total Back Pain score); ii) change (improvement) from baseline in Patient's Assessment of Nocturnal Back Pain (Nocturnal Back Pain); jj) change (improvement) from baseline in Patient's Global Assessment of Pain (Pt Pain); kk) change (improvement) from baseline in Physician's Global Assessment of Disease Activity (PGA-Disease Activity); ll) change (improvement) from baseline in inflammation, as represented by the change (improvement) from baseline in the mean of Questions 5 and 6 of the BASDAI; mm) change (improvement) from baseline in the Patient's Assessment of Total Back Pain, as represented by a change (improvement) from baseline in question 2 of BASDAI; nn) change (improvement) from baseline in peripheral pain/swelling, as represented by a change (improvement) in baseline in question 3 of BASDAI; oo) change (improvement) from baseline in duration of morning stiffness, as represented by a change (improvement) in baseline in question 6 of BASDAI; pp) change (improvement) from baseline in Patient's Global Assessment of Disease Activity (PtGA); qq) change (improvement) from baseline in TJC68 and SJC66; rr) change (improvement) from baseline in WPAI-Axial SpA; ss) resolution (improvement) of dactylitis in subjects with baseline presence of dactylitis; and tt) change (improvement) from baseline in total dactylitis count in subjects with baseline presence of dactylitis. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration (including at week 14) of the first dose at least one result selected from the group consisting of: q) ASDAS Inactive Disease; r) ASDAS Low Disease, s) ASDAS Major Improvement; and t) ASDAS Clinically Important Improvement. In one embodiment, each of the results are achieved within 14 weeks of administration of the first dose (including at week 14). In certain embodiments, for any of the aforementioned results achieved, a statistically significant population of subjects in the treated population and/or at least 10%, at least 15%, at least 20%, at least 25%, at least 30%, at least 35%, at least 40%, or at least 45% of the subjects in the treated population, achieved at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves at least one result selected from the group consisting of: ASDAS Inactive Disease, ASDAS Moderate Disease, ASDAS Low Disease Activity (LDA), ASDAS High Disease, ASDAS Very High Disease, ASDAS Major Improvement, and ASDAS Clinically Important Improvement. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and achieves an ASAS40 response within 14 weeks of administration of the first dose (including at week 14). In another embodiment, the subject is bDMARD-IR at baseline, and achieves an ASAS40 response within 2 weeks of administration of the first dose (including at week 2). In one embodiment, the subject achieves an ASAS40 response within 2 weeks of administration of the first dose (including at week 2) and maintains the ASAS40 response until at least 14 weeks after administration of the first dose (i.e., including until at least week 14). In one aspect, the subject (or population of subjects)

further achieves ASAS PR, ASDAS LDA, ASDAS ID, ASDAS MI, and/or ASDAS CII within 2 weeks of administration of the first dose (including at week 2). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieved the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves within 14 weeks of administration (including at week 14) of the first dose at least one result selected from the group consisting of: a) change (improvement) from baseline in ASDAS; b) change (improvement) from baseline in MRI SPARCC score for spine (MRI-Spine SPARCC); c) ASAS partial remission (PR); d) BASDAI 50 response; e) change (improvement) from baseline in BASFI; f) change (improvement) from baseline in ASQoL; g)
change (improvement) from baseline in ASAS Health Index (HI); h) change (improvement) from baseline in MASES (enthesitis); and i) change (improvement) from baseline in BASMIlin (mobility). In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves at least one result selected from the group consisting of: j) ASAS 20 response; and k) change (improvement) from baseline in MRI SPARCC score for SI joints (MRI-SI joints SPARCC). In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves at least one result selected from the group consisting of: l) ASAS20 response; m) ASAS40 response; n) ASAS PR; o) ASDAS Inactive Disease; p) ASDAS Low Disease; q) ASDAS Major Improvement; r) ASDAS Clinically Important Improvement; s) discontinuation of opioids among subjects with opioid use at baseline; t) change (improvement) from baseline in ASAS HI; u) change (improvement) from baseline in ASDAS; v) change (improvement) from baseline in ASQoL; w) change (improvement) from baseline in BASDAI and BASDAI Questions, including change (improvement) from baseline in mean of question 5 and 6 of the BASDAI; x) change (improvement) from baseline in BASFI; y) change (improvement) from baseline in BASMIlin; z) change (improvement) from baseline in high sensitivity C-reactive protein (hsCRP); aa) change (improvement) from baseline in FACIT-F; bb) change (improvement) from baseline in EuroQoL-5D-5L (EQ-5D-5L); cc) change (improvement) from baseline in MASES; dd) change (improvement) from baseline in mSASSS (with conventional radiograph); ee) change (improvement) from baseline in MRI SPARCC score of SI joints; ff) change (improvement) from baseline in MRI SPARCC score of spine; gg) change (improvement) from baseline in Patient's Assessment of Total Back Pain score (Total Back Pain score); hh) change (improvement) from baseline in Patient's Assessment of Nocturnal Back Pain (Nocturnal Back Pain); ii) change (improvement) from baseline in Patient's Global Assessment of Pain (Pt Pain); jj) change (improvement) from baseline in Physician's Global Assessment of Disease Activity (PGA-Disease Activity); kk) change (improvement) from baseline in Patient's Global Assessment of Disease Activity (PtGA); ll) change (improvement) from baseline in SF-36; mm) change (improvement) from baseline in TJC68 and SJC66; nn) change (improvement) from baseline in WPAI-Axial SpA; oo) change (improvement) from baseline in Change of NSAID score; and pp) change (improvement) from baseline in Physical Activity Assessment. In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

IX. Methods of Treating Non-Radiographic Axial Spondyloarthritis (Nr-axSpA)

Further provided are methods of treating non-radiographic axial spondyloarthritis (nr-axSpA). In one aspect, provided are methods of treating active nr-axSpA, comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

Disease activity/severity for nr-axSpA may be measured using a variety of indexes, including those set forth above for the treatment of axSpA. In one particular aspect, provided is a method of treating nr-axSpA, including active nr-axSpA, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer a daily dose of the JAK1 inhibitor. In one aspect, the subject achieves an ASAS40 response within 52 weeks of administration of the first dose of the JAK1 inhibitor (including at week 52). In one aspect, the subject achieves an ASAS40 response within 52 weeks of administration of the first dose of the JAK1 inhibitor (including at week 52), and the response is maintained or improved after week 52 by continuing to administer a daily dose of the JAK1 inhibitor. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer a daily dose of the JAK1 inhibitor. In one aspect, the subject achieves an ASAS40 response within 2 weeks, within 4 weeks, within 8 weeks, within 12 weeks, within 14 weeks, within 18 weeks, within 24 weeks, within 32 weeks, within 40 weeks, and/or within 52 weeks of administration of the first dose of the JAK1 inhibitor (including at week 2, week 4, week 8, week 12, week 14, week 18, week 24, week 32, week 40, and/or week 52). In one embodiment, the subject achieves an ASAS 40 response within 2 weeks of administration of the first dose (including at week 2), and maintains the ASAS40 response until at least 14 weeks after administration of the first dose (e.g., until at least week 14). In one embodiment, the subject achieves an ASAS 40 response within 2 weeks of administration of the first dose (including at week 2), and maintains the ASAS40 response until at least 52 weeks after administration of the first dose (e.g., until at least week 52). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 18 weeks, for at least 24 weeks, for at least 32 weeks, for at least 40 weeks, and/or for at least 52 weeks. In one embodiment, the JAK1 inhibitor is administered orally once a day for at least 14 weeks. In one aspect, the JAK1 inhibitor is administered orally once a day for at least 52 weeks.

In one aspect, provided is a method of treating nr-axSpA, including active nr-axSpA, in a population of subjects in need thereof, the method comprising administering a dose of the JAK1 inhibitor to the subjects in certain amounts and/or at certain intervals as described herein, wherein a portion of the subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve an ASAS40 response following administration of the JAK1 inhibitor. In one aspect, subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the result is maintained or improved after week 14 by continuing to administer a daily dose of the JAK1 inhibitor. In one aspect, subjects in the treated population achieve an ASAS40 response within 52 weeks of administration of the first dose of the JAK1 inhibitor (including at week 52). In one aspect subjects in the treated population achieve an ASAS40 response within 52 weeks of administration of the first dose of the JAK1 inhibitor (including at week 52), and the result is maintained or improved after week 52 by continuing to administer a daily dose of the JAK1 inhibitor. In one aspect, the JAK1 inhibitor is upadacitinib freebase. In one aspect, a dose of the JAK1 inhibitor is administered to the subjects in an amount sufficient to deliver 15 mg of upadacitinib freebase equivalent. In one aspect, the JAK1 inhibitor is administered to the subjects orally once a day for at least 14 weeks. In one aspect, the JAK1 inhibitor is administered to the subjects orally once a day for at least 52 weeks. In one aspect, the subjects in the population are bDMARD naïve. In one aspect, the subjects in the population are bDMARD-IR.

Further provided are methods of reducing the signs and symptoms of nr-axSpA. In one aspect, provided is a method of reducing the signs and symptoms of active nr-axSpA, in particular methods comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

In one aspect of a method of reducing the signs and symptoms of nr-axSpA, including active nr-axSpA, the subject (or subjects in the treated population) achieves within 14 weeks of administration of the first dose of the JAK1 inhibitor (including at week 14), at least one result selected from the group consisting of, an ASAS40 response; a change (improvement) from baseline in ASDAS; a change (improvement) from baseline in MRI-Spine SPARCC; ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); and a change (improvement) from baseline in BASMIlin (mobility); or the subject achieves within 52 weeks of administration of the first dose of the JAK1 inhibitor (including at week 52) an ASAS40 response. In one aspect, the subject (or subjects in the treated population) achieves the result within 14 weeks of administration of the first dose of the JAK1 inhibitor (including at week 14), and the result is maintained or improved after week 14 by continuing to administer a daily dose of the JAK1 inhibitor. In one aspect, the subject (or subjects in the treated population) achieves the result within 52 weeks of administration of the first dose of the JAK1 inhibitor (including at week 52), and the result is maintained or improved after week 52 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect, the subject (or population of subjects) in need of treatment has active nr-axSpA at baseline. In one aspect, the subject (or subjects in the treated population) fulfills the 2009 ASAS classification criteria for axSpA, but does not meet the radiologic criteria of the 1984 modified New York Criteria for AS at baseline. In one embodiment, the subject (or subjects in the treated population) meets at least one criteria at baseline selected from the group consisting of: (i) a BASDAI score $\geq 4$; (ii) an ASDAS of $\geq 2.1$; (iii) a Patient's Assessment of Total Back Pain (Total Back Pain score) of $\geq 4$ (based on a 0-10 numerical rating scale); and (iv) an objective sign of inflammatory activity selected from the group consisting of: a) an objective sign of active inflammation on MRI of sacroiliac (SI) joints; and b) high-sensitivity C reactive protein (hsCRP)>upper limit of normal (ULN). In one aspect, the subject meets criteria (i), (ii), (iii), and (iv). In one aspect, the subject (or subjects in the treated population) is an adult subject. In another aspect, the subject (or subjects in the treated population) is a juvenile subject.

In one aspect, the subject (or subjects in the treated population) is bDMARD naïve at baseline. Exemplary bDMARDs include, but are not limited to, a biologic tumor necrosis factor inhibitor (e.g., adalimumab, etanercept) and interleukin (IL)-17 inhibitors (e.g., secukinumab, ixekizumab).

In another aspect, the subject (or subjects in the treated population) is bDMARD-IR at baseline. In one aspect, the subject (or subjects in the treated population) has had an inadequate response or intolerance to a bDMARD. Subjects who are bDMARD-IR include those subjects who have had prior exposure to one bDMARD (either 1 tumor necrosis factor (TNF) inhibitor (e.g., adalimumab, etanercept) or 1 interleukin (IL)-17 inhibitor (e.g., secukinumab, ixekizumab)), and have discontinued the bDMARD due to either intolerance or lack of efficacy (e.g., as determined by a physician). In one embodiment, the subject (or subjects in the treated population) has not had prior exposure to a second bDMARD, if the reason for discontinuation was not due to lack of efficacy. In one embodiment, the subject (or subjects in the treated population) has not discontinued both a TNF inhibitor and an IL-17 inhibitor due to lack of efficacy. In certain embodiments, the subject (or subjects in the treated population) has discontinued the bDMARD prior to receiving the first dose of the JAK1 inhibitor for:

$\geq 4$ weeks for etanercept;
$\geq 8$ weeks for adalimumab, infliximab, certolizumab, golimumab, abatacept, tocilizumab, and ixekizumab;
$\geq 12$ weeks for ustekinumab;
$\geq 16$ weeks for secukinumab;
$\geq 1$ year for rituximab or $\geq 6$ months if B cells have returned to pre-treatment level or normal reference range (central lab) if pre-treatment levels are not available; or
$\geq 12$ weeks or at least 5 times the mean terminal elimination half-life, whichever is longer, for other bDMARDs.

In one aspect, the subject (or subjects in the treated population) further has had i) an inadequate response or intolerance to at least two NSAIDs (e.g., over at least a four week period at the maximum recommended or tolerated doses); ii) intolerance to NSAIDs; and/or iii) contraindication for NSAIDs at baseline. Examples of NSAIDs include, but are not limited to, traditional NSAIDs (e.g., ibuprofen) and salicylates (e.g., aspirin).

In certain aspects, the subject (or population of subjects) to be treated is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include:

1) Concomitant administration of non-biologic DMARDs, including methotrexate (MTX), leflunomide, sulfasalazine (SSZ), hydroxychloroquine, chloroquine, or apremilast. In one embodiment, the subject is on a stable dose of MTX ($\leq 25$ mg/week), SSZ ($\leq 3$ g/day), hydroxychloroquine ($\leq 400$ mg/day), chloroquine ($\leq 400$ mg/day); leflunomide ($\leq 20$ mg/day), or apremilast ($\leq 60$ mg/day)), for at least 28 days prior to baseline. In some embodiments, a combination of up to two background non-biologic DMARDs is allowed, except the combination of MTX and leflunomide.
2) Concomitant administration of oral corticosteroids. In one embodiment, the subject is on a stable dose of prednisone ($\leq 10$ mg/day), or oral corticosteroid equivalents, for at least 14 days prior to baseline.
3) Concomitant administration of NSAIDs, tramadol, a combination of acetaminophen/paracetamol and codeine or combination of acetaminophen/paracetamol and hydrocodone, and/or non-opioid analgesics. In one embodiment, the subject is on stable dose(s) for at least 14 days prior to baseline.

In one embodiment, the subject (or subjects in the treated population) has not been previously exposed to any JAK inhibitor at baseline.

In one aspect of the methods of treating nr-axSpA described herein, the subject (or subjects in the treated population) alternately or additionally achieves within 14 weeks of administration of the first dose (including at week 14) at least one result selected from the group consisting of: a) a change (improvement) from baseline in ASDAS; b) a change (improvement) from baseline in MRI SPARCC score for SI joints (MRI-SI joints SPARCC); c) ASAS partial remission (PR); d) BASDAI50 response; e) a change (improvement) from baseline in BASFI f) change (improvement) from baseline in ASQoL; g) a change (improvement) from baseline in ASAS Health Index (HI); h) a change (improvement) from baseline in MASES (enthesitis); and i) a change (improvement) from baseline in BASMIlin (mobility); In one embodiment, the subject achieves the result within 2 weeks of administration of the first dose (including at week 2). In one embodiment, the subject achieves each of the results within 14 weeks of administration of the first dose (including at week 14). In certain embodiments, for any of the aforementioned results achieved, the result (or results) is maintained or improved after week 2 or week 14 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating nr-axSpA described herein, the subject (or subjects in the treated population) alternately or additionally achieves within 14 weeks of administration of the first dose (including at week 14) at least one result selected from the group consisting of: j) ASAS 20 response; and k) a change (improvement) from baseline in MRI SPARCC score for spine (MRI-Spine SPARCC). In one embodiment, each of the results is achieved within 14 weeks of administration of the first dose (including at week 14). In certain embodiments, for any of the aforementioned results achieved, the result (or results) is maintained or improved after week 14 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating nr-axSpA described herein, the subject (or subjects in the treated population) alternately or additionally achieves at least one result selected from the group consisting of: l) ASAS20 response; m) ASAS40 response; n) ASAS PR; o) ASDAS Inactive Disease; p) ASDAS Low Disease; q) ASDAS Major Improvement; r) ASDAS Clinically Important Improvement; s) discontinuation of opioids among subjects with opioid use at baseline; t) change (improvement) from baseline in ASAS HI; u) change (improvement) from baseline in ASDAS; v) change (improvement) from baseline in ASQoL; w) change (improvement) from baseline in BASDAI and BASDAI Questions, including change (improvement) from baseline in mean of questions 5 and 6 of the BASDAI; x) change (improvement) from baseline in BASFI; y) change (improvement) from baseline in BASMIlin; z) change (improvement) from baseline in high sensitivity C-reactive protein (hsCRP); aa) change (improvement) from baseline in FACIT-F; bb) change (improvement) from baseline in EQ-5D-5L; cc) change (improvement) from baseline in MASES; dd) change (improvement) from baseline in mASSS (with conventional radiograph); ee) change (improvement) from baseline in MRI SPARCC score of SI joints; ff) change (improvement) from baseline in MRI SPARCC score of spine; gg) change (improvement) from baseline in Patient's Assessment of Total Back Pain score (Total Back Pain score); hh) change (improvement) from baseline in Patient's Assessment of Nocturnal Back Pain (Nocturnal Back Pain); ii) change (improvement) from baseline in Patient's Global Assessment of Pain (Pt Pain); jj) change (improvement) from baseline in Physician's Global Assessment of Disease Activity (PGA-Disease Activity); kk) change (improvement) from baseline in Patient's Global Assessment of Disease Activity (PtGA); ll) change (improvement) from baseline in SF-36; mm) change (improvement) from baseline in TJC68 and SJC66; nn) change (improvement) from baseline in (WPAI-Axial SpA); and oo) change (improvement) from baseline in Change of NSAID score. In certain embodiments, for any of the aforementioned results achieved, the result (or results) is maintained or improved after the result (or results) is achieved by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

X. Methods of Treating Psoriatic Arthritis (PsA) and Psoriasis (PsO)

Further provided are methods of treating psoriatic arthritis (PsA) and psoriasis (PsO), including PsO as a skin manifestation of PsA.

In one aspect, provide are methods of treating active PsA comprising administering a dose of the JAK1 inhibitor to a subject in need thereof in certain amounts and/or at certain intervals as described herein. In one aspect, the JAK1 inhibitor is upadacitinib freebase. In one aspect, the JAK 1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR. In one aspect, the subject is an adult.

Disease activity/severity for PsA may be measured using a variety of indexes, including the American College of Rheumatology response rates (e.g., ACR20, ACR50, ACR70); the Health Assessment Questionnaire—Disability Index (HAQ-DI); the Static Investigator Global Assessment of Psoriasis (sIGA); the Psoriasis Area Severity Index (PASI) (including PASI 75, PASI 90, and PASI 100); the Sharp/van der Heijde Score (SHS); Minimal Disease Activity (MDA) assessment; Leeds Enthesitis Index (LEI); Leeds Dactylitis Index (LDI); the 36-Item Short Form Health Survey (SF-36); the Patient's Global Assessment of Pain Numerical Rating Scale (NRS); the Functional Assessment of Chronic Illness Therapy-Fatigue (FACIT-F) Questionnaire; the Self-Assessment of Psoriasis Symptoms (SAPS) Questionnaire; tender joint count (TJC68); swollen joint count (SJC66); the Physician's Global Assessment of Disease Activity Numeric Rating Scale (PGA-Disease Activity NRS) (numerical rating scale); the Patient's Global Assessment of Disease Activity (PtGA); high-sensitivity C Reactive Protein levels (hsCRP); dactylitis count; resolution of dactylitis; resolution of enthesitis sites included in the LEI; Spondyloarthritis Research Consortium of Canada (SPARCC) Enthesitis Index; resolution of enthesitis sites included in the SPARCC Enthesitis Index; total enthesitis count; resolution of enthesitis; Body Surface Area with Psoriasis (BSA-PS); Modified Psoriatic Arthritis Response Criteria (PsARC); Disease Activity Score 28 (DAS28) (CRP); DAS28 (Erythrocyte Sedimentation Rate (ERS)); Psoriatic Arthritis Disease Activity Score (PASDAS); Disease Activity in Psoriatic Arthritis (DAPSA) score; EuroQoL-5D-5L (EQ-5D-5L) Questionnaire; Work Productivity and Activity Impairment Questionnaire-Psoriatic Arthritis (WPAI-PsA); Health Resource Utilization (HRU) Questionnaire; the Bath Ankylosing Spondylitis Disease Activity Index (BASDAI); BASDAI 50 response; Morning Stiffness (mean of BASDAI Questions 5 and 6); and Ankylosing Spondylitis Disease Activity Score (ASDAS). These indexes are described in detail in the Clinical Endpoint Definitions and Examples.

In one particular aspect, provided is a method of treating PsA, including active PsA, comprising administering a dose of the JAK1 inhibitor to a subject in need thereof in certain amounts and/or at certain intervals as described herein, wherein the subject achieves an American College of Rheumatology 20% (ACR20) response following administration of the JAK1 inhibitor. In one embodiment, the subject achieves an ACR 50% (ACR50) response following administration of the JAK1 inhibitor. In one embodiment, the subject achieves an ACR 70% (ACR70) response following administration of the JAK1 inhibitor. In one aspect, the subject achieves an ACR20, ACR50, or ACR70 response within 12 weeks of administration of the first dose of the JAK1 inhibitor (including at week 12). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR.

In another aspect, provided is a method of treating PsA, including active PsA, in a population of subjects in need thereof, the method comprising administering a dose of the JAK 1 inhibitor to the subjects in certain amounts and/or at certain intervals as described herein, wherein a portion of subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve an ACR20, ACR50, or ACR70 response following administration of the JAK1 inhibitor. In one aspect, subjects in the treated population achieve an ACR20, ACR50, or ACR70 response within 12 weeks of administration of the first dose of the JAK1 inhibitor (including at week 12). In one aspect, the JAK1 inhibitor is upadacitinib freebase. In one aspect, a dose of the JAK1 inhibitor is administered to the subjects in an amount sufficient to deliver 15 mg of upadacitinib freebase equivalent. In one aspect, a dose of the JAK1 inhibitor is administered to the subjects in an amount sufficient to deliver 30 mg of upadacitinib freebase equivalent. In one aspect, the JAK1 inhibitor is administered to the subjects orally once a day for at least 12 weeks.

In certain embodiments, the subject (or subjects in the treated population) achieve an ACR20 response within 12 weeks of administration of the first dose of the JAK1 inhibitor (including at week 12). In certain embodiments, the ACR20 response is maintained or improved after Week 12 by continuing to administer a daily dose of the JAK1 inhibitor. In certain embodiments, the subject (or subjects in the treated population) achieves an ACR20 response within 2 weeks of administration of the first dose (including at week 2). In certain embodiments, the subject (or subjects in the treated population) achieves an ACR20 response within 2 weeks of administration of the first dose of the JAK1 inhibitor (including at week 2), and the ACR20 response is maintained or improved after Week 2 by continuing to administer a daily dose of the JAK1 inhibitor. In certain embodiments, the subject (or subjects in the treated population) suffering from active PsA at baseline further achieve at least one result selected from the group consisting of: (a) change (improvement) from baseline in Health Assessment Questionnaire—Disability Index (HAQ-DI) within 12 weeks of administration of the first dose (including at week 12); (b) achieve Static Investigator Global Assessment (sIGA) of Psoriasis of 0 or 1 and at least a 2-point improvement from baseline at within 16 weeks of administration of the first dose (for subjects with baseline sIGA≥2) (including at week 16); (c) achieve Psoriasis Area Severity Index (PASI) 75 response within 16 weeks of administration of the first dose (for subjects with ≥3% BSA psoriasis at baseline) (including at week 16); (d) change (improvement) from baseline in Sharp/van der Heijde Score (SHS) within 24 weeks of administration of the first dose (including at week 24); (e) achieve Minimal Disease Activity (MDA) within 24 weeks of administration of the first dose (including at week 24); (f) change (improvement) from baseline in Leeds Enthesitis Index (LET) within 24 weeks of administration of the first dose, preferably wherein the change (improvement) is a resolution of enthesitis (LEI=0) within 24 weeks of administration of the first dose (for subjects with baseline presence of enthesitis (LEI>0)) (including at week 24); (g) achieve ACR 20 response within 12 weeks of administration of the first dose (non-inferiority of upadacitinib vs adalimumab) (including at week 12); (h) change (improvement) from baseline in 36-Item Short Form Health Survey (SF-36) within 12 weeks of administration of the first dose (including at week 12); and (i) change (improvement) from baseline in Functional Assessment of Chronic Illness Therapy-Fatigue (FACIT-F) Questionnaire within 12 weeks of administration of the first dose (including at week 12). In certain embodiments, the subject (or subjects in the treated population) suffering from active PsA at baseline further achieve each result. In certain embodiments, the subject (or subjects in the treated population) suffering from active PsA at baseline further achieve at least one result selected from the group consisting of: (j) ACR 20 response and superiority over adalimumab (40 mg every other week) within 12 weeks of administration of the first dose (including at week 12); and (k) change (improvement) from baseline in Leeds Dactylitis Index (LDI) within 24 weeks of administration of the first dose, preferably wherein the change (improvement) is a resolution of dactylitis (LDI=0) within 24 weeks of administration of the first dose (for subjects with baseline presence of dactylitis (LDI>0)) (including at week 24). In certain embodiments, the subject (subjects in the treated population) suffering from active PsA at baseline further achieve ACR 20 response and superiority over adalimumab (40 mg every other week) within 12 weeks of administration of the first dose (including at week 12). In one aspect, the subject (or subjects in the treated population) are non-biologic DMARD-IR at baseline. In one aspect, the subject (or subjects in the treated population) are bDMARD-IR at baseline. In one aspect, the result is maintained or improved after week 12, week 16, and/or week 24 by continuing to administer a daily dose of the JAK1 inhibitor. In one aspect, the subject (or subjects in the treated population) further achieves a Psoriasis Area Severity Index (PASI) 75 response within 16 weeks of administration of the first dose (including at week 16). In one aspect, the subject (or subjects in the treated population) further achieves a PASI 90 response within 16 weeks of administration of the first dose (including at week 16). In one aspect, the subject (or subjects in the treated population) further achieves a PASI 100 response within 16 weeks of administration of the first dose (including at week 16). In one aspect the PASI response (e.g., the PASI 75, PASI 90, or PASI 100 response) is maintained or improved after week 16 by continuing to administer a daily dose of the JAK1 inhibitor. In certain embodiments, for any of the aforementioned results achieved, the result (or results) is maintained or improved after the result (or results) is achieved by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

Further provided are methods of reducing the signs and symptoms of PsA in a subject in need thereof. In one aspect, provided is a method of reducing the signs and symptoms of PsA, including active PsA, comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR.

In another aspect, provided is a method of treating PsA, including active PsA, in a subject in need thereof, comprising administering a dose of the JAK1 inhibitor to the subject in certain amounts and/or at certain intervals as described herein, wherein the subject achieves Minimal Disease Activity (MDA) following administration of the JAK1 inhibitor. In one aspect, the JAK1 inhibitor is upadacitinib freebase, or a pharmaceutically acceptable salt thereof. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 24 weeks. In one aspect, the subject achieves MDA within 24 weeks of administration of the first dose of the JAK1 inhibitor (including at week 24). In one aspect, the subject achieves MDA within 24 weeks of administration of the first dose of the JAK1 inhibitor (including at week 24), and the MDA is maintained or improved after week 24 by continuing to administer a daily dose of the JAK1 inhibitor. In one aspect, the subject further achieves a Psoriasis Area Severity Index (PASI) response selected from a PASI 75 response, a PASI 90 response, and a PASI 100 response, within 16 weeks of administration of the first dose. In one aspect, the PASI 75, PASI 90, and/or PASI 100 response is maintained or improved after Week 16 by continuing to administer the daily dose of the JAK1 inhibitor. In one aspect, the subject is non-biologic DMARD-IR. In one aspect, the subject is bDMARD-IR.

In another aspect, provided is a method of treating PsA, including active PsA, in a population of subjects in need thereof, the method comprising administering a dose of the JAK1 inhibitor to the subjects in certain amounts and/or at certain intervals as described herein, wherein a portion of subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve Minimal Disease Activity (MDA) following administration of the JAK1 inhibitor. In one aspect, the JAK1 inhibitor is upadacitinib freebase, or a pharmaceutically acceptable salt thereof. In one aspect, a dose of the JAK1 inhibitor is administered to the subjects in an amount sufficient to deliver 15 mg of upadacitinib freebase equivalent. In one aspect, a dose of the JAK1 inhibitor is administered to the subjects in an amount sufficient to deliver 30 mg of upadacitinib freebase equivalent. In one aspect, the JAK1 inhibitor is administered to the subjects orally once a day for at least 24 weeks. In one aspect, subjects in the treated population achieve MDA within 24 weeks of administration of the first dose of the JAK1 inhibitor (including at week 24). In one aspect, subjects in the treated population achieve MDA within 24 weeks of administration of the first dose of the JAK1 inhibitor (including at week 24), and the MDA is maintained or improved after week 24 by continuing to administer a daily dose of the JAK 1 inhibitor. In one aspect, subjects in the treated population further achieve a Psoriasis Area Severity Index (PASI) response selected from a PASI 75 response, a PASI 90 response, and a PASI 100 response, within 16 weeks of administration of the first dose. In one aspect, the PASI 75, PASI 90, and/or PASI 100 response is maintained or improved after Week 16 by continuing to administer the daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In one aspect, the subjects in the treated population are non-biologic DMARD-IR at baseline. In one aspect, the subjects in the treated population are bDMARD-IR at baseline.

In one aspect, the subject (or subjects in the treated population) achieves an ACR20, ACR50, or ACR70 response within 12 weeks of administration (including at week 12) of the first dose of the JAK1 inhibitor. In one aspect, the subject (or subjects in the treated population) achieves an ACR20, ACR50, or ACR70 response within 12 weeks of administration (including at week 12) of the first dose of the JAK1 inhibitor, and the response is maintained or improved after week 12 by continuing to administer a daily dose of the JAK1 inhibitor. In one aspect, the subject (or subjects in the treated population) achieves an ACR20, ACR50, or ACR70 response within 2 weeks of administration of the first dose of the JAK1 inhibitor (including at week 2). In one aspect, the subject (or subjects in the treated population) achieves an ACR20, ACR50, or ACR70 response within 2 weeks of administration of the first dose of the JAK1 inhibitor (including at week 2), and the response is maintained or improved after week 12 by continuing to administer a daily dose of the JAK1 inhibitor. In one aspect, the subject (or subjects in the treated population) achieves an ACR20, ACR50, or ACR70 response within 2 weeks, within 4 weeks, within 8 weeks, within 12 weeks, within 16 weeks, within 20 weeks, within 24 weeks, within 28 weeks, within 32 weeks, within 36 weeks, within 44 weeks, and/or within 56 weeks of administration of the first dose of the JAK1 inhibitor (including at week 2, at week 4, at week 8, at week 12, at week 16, at week 20, at week 24, at week 28, at week 32, at week 36, at week 44, and/or at week 56). In one embodiment, the subject (or subjects in the treated population) achieves an ACR20, ACR50, or ACR70 response within 2 weeks of administration of the first dose (including at week 2), and maintains the ACR20, ACR50, or ACR70 response until at least 12 weeks after administration of the first dose (e.g., until at least week 12). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 2 weeks, for at least 4 weeks, for at least 8 weeks, for at least 12 weeks, at least 16 weeks, for at least 20 weeks, for at least 24 weeks, for at least 28 weeks, for at least 32 weeks, for at least 36 weeks, for at least 44 weeks, and/or for at least 56 weeks. In one embodiment, the JAK1 inhibitor is administered orally once a day for at least 12 weeks. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of a method of reducing the signs and symptoms of PsA, including active PsA, the subject (or subjects in the treated population) achieves at least one result selected from the group consisting of: an ACR20 response within 12 weeks of administration of the first dose of the JAK1 inhibitor (including at week 12); a change (improvement) from baseline in HAQ-DI within 12 weeks of administration of the first dose of the JAK1 inhibitor (including at week 12); a sIGA of 0 or 1 and at least a 2 point improvement from baseline within 16 weeks of administration of the first dose of the JAK1 inhibitor (including at week 16); PASI 75 response (for subjects with ≥3% Body Surface Area psoriasis at baseline) within 16 weeks of administration of the first dose of the JAK 1 inhibitor (including at week 16); a change (improvement) from baseline in SHS within 24 weeks of administration of the first dose of the JAK1 inhibitor (including at week 24); Minimal Disease Activity within 24 weeks of administration of the first dose of the JAK1 inhibitor (including at week 24); a change (improvement) from baseline in LEI within 24 weeks of administration of the first dose of the JAK1 inhibitor (including at week 24); a change (improvement) from baseline in LDI within 24 weeks of administration of the first dose of the JAK1 inhibitor (including at week 24); a change (improvement) from baseline in SF-36 within 12 weeks of administration of the first dose of the JAK1 inhibitor (including at week 12); change (improvement) from baseline in Patient's Global Assessment of Pain (Pt Pain) (numerical rating scale) within 12 weeks of administration of the first dose of the JAK1 inhibitor (including at week 12); change (improvement) from baseline in FACIT-F within 12 weeks of administration of the first dose of the JAK1 inhibitor (including at week 12); change (improvement) from baseline in SAPS Questionnaire within 16 weeks of administration of the first dose of the JAK1 inhibitor (including at week 16); ACR50 or ACR70 response within 12 weeks of administration of the first dose of the JAK1 inhibitor (including at week 12); and ACR20 response within 2 weeks of administration of the first dose of the JAK1 inhibitor (including at week 2). In one aspect, the result is maintained or improved after week 2, week 12, week 16, or week 24 by continuing to administer a daily dose of the JAK 1 inhibitor. In certain embodiments, for any of the aforementioned results achieved, a statistically significant population of subjects in the treated population, and/or at least 10%, at least 15%, at least 20%, at least 25%, at least 30%, at least 35%, at least 4(0%, or at least 45% of the subjects in the treated population, achieve at least one result.

Further provided are methods of inhibiting the progression of structural damage of PsA in a subject in need thereof. In one aspect, provided is a method of inhibiting the progression of structural damage of PsA, including active PsA, comprising administering a dose of the JAK1 inhibitor to a subject in need thereof in certain amounts and/or at certain intervals as described herein. In one aspect, the JAK1 inhibitor is upadacitinib freebase. In one aspect, the JAK 1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR.

Further provided are methods of improving physical function in a subject in need thereof. In one aspect, provided is a method of improving physical function of PsA, including active PsA, comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR.

Further provided are methods of preventing structural progression of PsA in a subject in need thereof. In one aspect, provided is a method of preventing structural progression of PsA, including active PsA, comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver 30 mg of upadacitinib freebase equivalent. In one aspect, the JAK1 inhibitor is administered orally once a day for at least 12 weeks. In one aspect, the subject is non-biologic DMARD-IR. In one aspect, the subject is bDMARD-IR.

In one aspect, the subject (or population of subjects) in need of treatment has active PsA at baseline. In one aspect, the subject (or population of subjects) in need of treatment and with active PsA at baseline further have moderately to severely active psoriatic arthritis at baseline, as determined by a physician. In one aspect, the subject (or subjects in the treated population) has a clinical diagnosis of PsA with symptoms onset at least six months prior to baseline. In one aspect, the subject (or subjects in the treated population) fulfills the Classification Criteria for PsA (CASPAR) criteria at baseline. In one embodiment, the subject (or subjects in the treated population) meets at least one criteria selected from the group consisting of: (i)≥3 tender joints (based on 68 joint counts); and (ii)≥3 swollen joints (based on 66 joint counts) at baseline. In one aspect the subject (or subjects in the treated population) has ≥3 tender joints (based on 68 joint counts); and (ii)≥3 swollen joints (based on 66 joint counts) at baseline. In certain embodiments, the subject (or subjects in the treated population) may have ≥5 tender joints (based on 68 joint counts) and ≥5 swollen joints (based on 66 joint counts) at baseline. In one aspect, the subject (or subjects in the treated population) meets at least one criteria selected from the group consisting of ≥1 erosion on x-ray as determined by central imaging review, and hs-CRP>laboratory defined upper limit of normal (ULN), at baseline. In one aspect, the subject (or subjects in the treated population) does not have Minimal Disease Activity (responders and non-responders) for PsA at baseline. In one aspect, the subject (or subjects in the treated population) has a diagnosis of active plaque psoriasis or a documented history of plaque psoriasis (e.g., as determined by a physician) at baseline. In one aspect, the subject (or subjects in the treated population) is an adult subject. In another aspect, the subject (or subjects in the treated population) is a juvenile subject.

In one aspect, the subject (or subjects in the treated population) is non-biologic DMARD-IR at baseline. In one aspect, the subject (or subjects in the treated population) has had an inadequate response or intolerance to treatment with a non-biologic DMARD. Subjects who are non-biologic DMARD-IR include those subjects who have an intolerance to or contraindication for non-biologic DMARDs (e.g., as determined by a physician), or who have had an inadequate response (i.e., a lack of efficacy after a minimum 12-week duration of therapy) to previous or concomitant treatment with at least one non-biologic DMARD at maximally tolerated dose or up to a dose set forth as follows:
  i) methotrexate (MTX): ≤25 mg/week, or ≥15 to ≤25 mg/week, or ≥10 mg/week in subjects who are intolerant of MTX at doses ≥12.5 mg/week after complete titration;
  ii) sulfasalazine (SSZ): ≤3000 mg/day;
  iii) leflunomide (LEF): ≤20 mg/day;
  iv) apremilast: ≤60 mg/day;
  v) hydroxychloroquine (HCQ): ≤400 mg/day;
  vi) bucillamine: ≤300 mg/day; or
  vii) iguratimod: ≤50 mg/day)
for ≥12 weeks and at stable dose for ≥4 weeks prior to the baseline. In one aspect, the subject has not been exposed to any additional non-biologic DMARDs.

In certain aspects, the subject (or population of subjects) to be treated is non-biologic DMARD-IR and is further receiving at least one additional therapy. Suitable additional therapies include:
  1) Stable doses of non-biologic DMARDs. In one aspect, the subject is receiving a concomitant DMARD treatment at baseline. In one aspect, the subject is on ≤2 non-biologic DMARDs (except the combination of MTX and leflunomide). Suitable doses for MTX, SSZ, LEF, apremilast, HCQ, bucillamine, and iguratimod are set forth above. In one aspect, the subject is not on any non-biologic DMARD other than MTX, SSZ, LEF, apremilast, HCQ, bucillamine, iguratimod, or the combination of MTX and LEF. In one embodiment, the subject is not receiving concomitant treatment of any non-biologic DMARD other than MTX, SSZ, leflunomide, apremilast, HCQ, bucillamine, or iguratimod.
  2) Stable doses of NSAIDs, acetaminophen/paracetamol, low-potency opiates (tramadol or combination of acetaminophen and codeine or hydrocodone), oral corticosteroids (equivalent to prednisone ≤10 mg/day), or inhaled corticosteroids for stable medical conditions. In one embodiment, the subject has been receiving stable doses of such additional therapies for ≥1 week prior to baseline.

In one aspect, the subject (or population of subjects) to be treated is non-biologic DMARD-IR, and may discontinue treatment with at least one non-biologic DMARD prior to baseline in order to comply with the concomitant administration of non-biologic DMARD protocols set forth above (e.g., concomitant administration of ≤2 non-biologic DMARDs (not including the combination of MTX and leflunomide), selected from MTX, SSZ, leflunomide, apremilast, HCQ, bucillamine, and iguratimod) at stable doses. In one embodiment, the subject has discontinued the treatment with the non-biologic DMARD prior to baseline for:
  ≥8 weeks for LEF if no elimination procedure was followed, or adheres to an elimination procedure (i.e., 11 days with cholestyramine, or 30 day washout with activated charcoal or as per local label); or
  ≥4 weeks for all other non-biologic DMARDs.

In another aspect, the subject (or subjects in the treated population) is bDMARD-IR at baseline. In one aspect, the subject (or subjects in the treated population) has had an inadequate response or intolerance to a bDMARD. Subjects who are bDMARD-IR include those subjects who have had prior exposure to at least one bDMARD prior to baseline and have had an inadequate response due to lack of efficacy after a minimum 12-week duration of therapy, or who are intolerance to treatment with at least 1 bDMARD. In one aspect, the subject (or subjects in the treated population) has discontinued all bDMARDs prior to baseline. In certain embodiments, the subject (or subjects in the treated population) has discontinued the bDMARD prior to receiving the first dose of the JAK1 inhibitor for:
  ≥4 weeks for etanercept;
  ≥8 weeks for adalimumab, infliximab, certolizumab, golimumab, abatacept, tocilizumab, and ixekizumab;
  ≥12 weeks for ustekinumab;
  ≥16 weeks for secukinumab; or
  ≥1 year for rituximab or ≥6 months if B cells have returned to pre-treatment level or normal reference range (central lab) if pre-treatment levels are not available.

In certain aspects, the subject (or population of subjects) to be treated is bDMARD-IR, and is further receiving at least one additional therapy. Additional therapies include but are not limited to concomitant administration of non-biologic DMARDs and/or NSAIDs, corticosteroids, and combinations thereof. Suitable additional therapies for use in combination with the methods of described herein include:
  1) Concomitant administration of <2 non-biologic DMARDs (not including the combination of MTX and leflunomide), selected from methotrexate (MTX), sulfasalazine (SSZ), leflunomide, apremilast, hydroxychloroquine (HCQ), bucillamine, and iguratimod. In one embodiment, the subject is on a stable dose of MTX (≤25 mg/week), SSZ (≤3000 mg/day), leflunomide (LEF) (≤20 mg/day), apremilast (≤60 mg/day), HCQ (≤400 mg/day), bucillamine (≤300 mg/day) or iguratimod (≤50 mg/day) for ≥12 weeks and for ≥4 weeks prior to the baseline. In one embodiment, the subject is not receiving concomitant treatment of any non-biologic DMARD other than MTX, SSZ, leflunomide, apremilast, HCQ, bucillamine, or iguratimod.
  2) Concomitant administration of stable doses of NSAIDs, acetaminophen/paracetamol, low-potency opiates (tramadol or combination of acetaminophen and codeine or hydrocodone), oral corticosteroids (equivalent to prednisone ≤10 mg/day), or inhaled corticosteroids at a stable dose for >1 weeks prior to the baseline.

In one aspect, the subject (or population of subjects) to be treated is bDMARD-IR and has received previous treatment with at least one non-biologic DMARD. In one embodiment, such a subject may discontinue treatment with at least one non-biologic DMARD prior to baseline in order to comply with the concomitant administration of non-biologic DMARD protocols set forth above (e.g., concomitant administration of ≤2 non-biologic DMARDs (not including the combination of MTX and leflunomide), selected from MTX, SSZ, leflunomide, apremilast, HCQ, bucillamine, and iguratimod) at stable doses. In one embodiment, the subject has discontinued the treatment with the non-biologic DMARD prior to baseline for:

≥8 weeks for LEF if no elimination procedure was followed, or adheres to an elimination procedure (i.e., 11 days with cholestyramine, or 30 day washout with activated charcoal or as per local label); or ≥4 weeks for all other non-biologic DMARDs.

In one aspect, the subject (or subjects in the treated population) is bDMARD-IR or non-biologic DMARD-IR at baseline, and has discontinued all opiates (except for tramadol, or combination of acetaminophen and codeine or hydrocodone) at least 1 week prior to baseline. In one aspect, the subject (or subjects in the treated population) is bDMARD-IR or non-biologic DMARD-IR at baseline, and has not been previously exposed to any JAK inhibitor. In one aspect, the subject (or subjects in the treated population) is bDMARD-IR or non-biologic DMARD-IR at baseline, and is not receiving current treatment (i.e., treatment at the time of administration of the JAK 1 inhibitor) with >2 non-biologic DMARDs, or treatment with a DMARD other than MTX, SSZ, LEF, apremilast, HCQ, bucillamine or iguratimod, or use of MTX in combination with LEF at baseline. In one embodiment, the subject (or subjects in the treated population) is non-biologic DMARD-IR or bDMARD-IR, and does not have a history of fibromyalgia, any arthritis with onset prior to age 17 years, or a current diagnosis of inflammatory joint disease other than PsA (including, but not limited to, rheumatoid arthritis, gout, overlap connective tissue diseases, scleroderma, polymyositis, dermatomyositis, and systemic lupus erythrematosus).

In one aspect of the methods of treating PsA described herein, the subject (or subjects in the treated population) is non-biologic DMARD-IR at baseline, and alternately or additionally achieves at least one result selected from the group consisting of: a) change (improvement) from baseline in HAQ-DI within 12 weeks of administration of the first dose (including at week 12); b) sIGA of 0 or 1 and at least a 2-point improvement from baseline within 16 weeks of administration of the first dose (including at week 16); c) PASI 75 response within 16 weeks of administration of the first dose (including at week 16) (for subjects with ≥3% Body Surface Area (BSA) psoriasis at baseline); d) change (improvement) from baseline in SHS within 24 weeks of administration of the first dose (including at week 24); e) Minimal Disease Activity (MDA) within 24 weeks of administration of the first dose (including at week 24); f) change (improvement) from baseline in LEI within 24 weeks of administration of the first dose (including at week 24); g) change (improvement) from baseline in LDI within 24 weeks of administration of the first dose (including at week 24); h) change (improvement) from baseline in SF-36 within 12 weeks of administration of the first dose (including at week 12); i) change (improvement) from baseline in Patient's Global Assessment of Pain (Pt Pain) Numerical Rating Scale (NRS) within 12 weeks of administration of the first dose (including at week 12); j) change (improvement) from baseline in FACIT-F Questionnaire within 12 weeks of administration of the first dose (including at week 12); and k) change (improvement) from baseline in SAPS Questionnaire within 16 weeks of administration of the first dose (including at week 16). In one aspect, the result is maintained or improved after week 12, week 16, or week 24 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating PsA described herein, the subject (or subjects in the treated population) is non-biologic DMARD-IR and may alternately or additionally achieve a result that is non-inferior or superior to the result achieved by administration of adalimumab. In one aspect, the result is superior or non-inferior to the result achieved when a subject is administered 40 mg doses of adalimumab every other week for 12 weeks. Examples of suitable formulations of adalimumab are described in Example 1. In one aspect, the subject achieves within 12 weeks of administration of the first dose (including at week 12) at least one result selected from the group consisting of: i) ACR20 that is non-inferior as compared to adalimumab; ii) ACR20 response that is superior as compared to adalimumab; change (improvement) from baseline in Patient's Global Assessment of Pain (Pt Pain) Numerical Rating Scale (NRS) that is superior as compared to adalimumab; iv) change (improvement) from baseline in HAQ-DI that is superior as compared to adalimumab. In one aspect, the result (or results) is maintained or improved after the result (or results) is achieved by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating PsA described herein, the subject (or subjects in the treated population) is non-biologic DMARD-IR at baseline, and alternately or additionally achieves least one result selected from the group consisting of: l) ACR50 or ACR70 response rate within 12 weeks of administration of the first dose (including at week 12); and m) ACR20 response rate within 2 weeks of administration of the first dose (including at week 2). In one aspect, the result is maintained or improved after week 2 or week 12 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating PsA described herein, the subject (or subjects in the treated population) is non-biologic DMARD-IR at baseline, and alternately or additionally achieves at least one result selected from the group consisting of: n) no radiographic progression, as demonstrated by change (improvement) in baseline in SHS of ≤0; o) change (improvement) from baseline in at least one individual components of ACR response selected from the group consisting of: (i) change (improvement) from baseline in Tender Joint Count (TJC68) (0-68); (ii) change (improvement) from baseline in Swollen Joint Count (SJC66) (0-66); (iii) change (improvement) from baseline in Physician Global Assessment-Disease Activity (PGA-Disease Activity) Numerical Rating Scale (NRS); (iv) change (improvement) from baseline in Patient's Global Assessment (PtGA)-Disease Activity Numerical Rating Scale (NRS); (v) change (improvement) from baseline in Patient's Global Assessment of Pain (Pt Pain) Numerical Rating Scale (NRS); (vi) change (improvement) from baseline in HAQ-DI; and (vii) change (improvement) from baseline in hs-CRP; p) ACR20, ACR5, or ACR70 response; q) change (improvement) from baseline in LDI; r) change (improvement) from baseline in dactylitis count; s) resolution of dactylitis; t) change (improvement) from baseline in LEI; u) resolution of enthesitis sites included in the LEI; v) change (improvement) from baseline in SPARCC Enthesitis Index; w) resolution of enthesitis sites included in the SPARCC Enthesitis Index; x) change (improvement) from baseline in total enthesitis count; y) resolution of enthesitis; z) PASI 75, PSA 90, or PSA 100 response in subjects with ≥3% Body Surface Area (BSA) psoriasis at baseline; aa) sIGA score of 0 or 1 and at least a 2-point improvement from baseline; bb) Body Surface Area with Psoriasis (BSA-PS); cc) change (improvement) from baseline in PsARC; dd) change (improvement) from baseline in DAS28 (CRP); ee) change (improvement) from baseline in DAS28 (ESR); ff) change (improvement) from baseline in PASDAS; gg) change (improvement) from baseline in DAPSA score; hh) change (improvement) from baseline in SF-36; ii) change (improvement) from baseline in FACIT-F Questionnaire; jj) change (improvement) from baseline in EQ-5D-5L Questionnaire; kk) change (improvement) from baseline in WPAI-PsA Questionnaire; ll) change (improvement) from baseline in HRU Questionnaire; mm) change (improvement) from baseline in SAPS Questionnaire; nn) change (improvement) from baseline in BASDAI; oo) BASDAI 50 response rate; pp) change (improvement) from baseline in Morning stiffness, measured as mean of BASDAI Questions 5 and 6; qq) change (improvement) from baseline in ASDAS; rr) ASDAS Inactive Disease, ss) ASDAS Major Improvement; tt) ASDAS Clinically Important Improvement; and uu) clinically meaningful improvement in HAQ-DI (≥0.35). In one aspect, the result (or results) is maintained or improved after achieving the result (or results) by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating PsA described herein, the subject (or subjects in the treated population) is bDMARD-IR at baseline, and alternately or additionally achieves least one result selected from the group consisting of: a) change (improvement) from baseline in HAQ-DI within 12 weeks of administration of the first dose (including at week 12); b) sIGA of Psoriasis of 0 or 1 and at least a 2-point improvement from baseline within 16 weeks of administration of the first dose (including at week 16); c) PASI 75 response within 16 weeks of administration of the first dose (including at week 16) for subjects with ≥3% Body Surface Area (BSA) psoriasis at baseline; d) Minimal Disease Activity (MDA) within 24 weeks of administration of the first dose (including at week 24); e) change (improvement) from baseline in SF-36 within 12 weeks of administration of the first dose (including at week 12); f) change (improvement) from baseline in FACIT-F Questionnaire within 12 weeks of administration of the first dose (including at week 12); and g) change (improvement) from baseline in SAPS Questionnaire within 16 weeks of administration of the first dose (including at week 16). In one aspect, the result is maintained or improved after week 12, week 16, or week 24 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating PsA described herein, the subject (or subjects in the treated population) is bDMARD-IR at baseline, and alternately or additionally achieves at least one result selected from the group consisting of: h) ACR50 or ACR70 response within 12 weeks of administration of the first dose (including at week 12); and i) ACR20 response within 2 weeks of administration of the first dose (including at week 2). In one aspect, the result is maintained or improved after week 2 or week 12 by continuing to administer a daily dose of the JAK1 inhibitor. In certain embodiments, for any of the aforementioned results achieved, a statistically significant population of subjects in the treated population, and/or at least 10%, at least 15%, at least 20r/o, at least 25%, at least 30%, at least 35%, at least 40%, or at least 45% of the subjects in the treated population, achieve at least one result.

In one aspect of the methods of treating PsA described herein, the subject (or subjects in the treated population) is bDMARD-IR at baseline, and alternately or additionally achieves at least one result selected from the group consisting of: j) change (improvement) from baseline in at least one individual component of an ACR response selected from the group consisting of: (i) change (improvement) from baseline in Tender Joint Count (TJC68) (0-68); (ii) change (improvement) from baseline in Swollen Joint Count (SJC66) (0-66); (iii) change (improvement) from baseline in Physician Global Assessment—Disease Activity (PGA-Disease Activity) Numerical Rating Scale (NRS); (iv) change (improvement) from baseline in Patient's Global Assessment (PtGA)-Disease Activity Numerical Rating Scale (NRS); (v) change (improvement) from baseline in Patient's Global Assessment of Pain (Pt Pain) Numerical Rating Scale (NRS); (vi) change (improvement) from baseline in Health Assessment Questionnaire—Disability Index (HAQ-DI); and (vii) change (improvement) from baseline in High-Sensitivity C Reactive Protein (hs-CRP); k) ACR20, ACR50, or ACR70 response rate; l) change (improvement) from baseline in LDI; m) change (improvement) from baseline in dactylitis count; n) resolution of dactylitis; n) change (improvement) from baseline in LEI; o) resolution of enthesitis sites included in the LEI; p) change (improvement) from baseline in SPARCC Enthesitis Index; q) resolution of enthesitis sites included in the SPARCC Enthesitis Index; r) change (improvement) from baseline in total enthesitis count; s) resolution of enthesitis; t) PASI 75, PASI 90, or PASI 100 response in subjects with ≥3% Body Surface Area (BSA) psoriasis at baseline; u) sIGA score of 0 or 1 and at least a 2-point improvement from baseline; v) Body Surface Area with Psoriasis (BSA-PS); w) change (improvement) from baseline in PsARC; x) change (improvement) from baseline in DAS28 (CRP); y) change (improvement) from baseline in DAS28 (ESR); z) change (improvement) from baseline in PASDAS; aa) change (improvement) from baseline in DAPSA score; bb) change (improvement) from baseline in SF-36; cc) change (improvement) from baseline in FACIT-F Questionnaire; dd) change (improvement) from baseline in EQ-5D-5L Questionnaire; ee) change (improvement) from baseline in WPAI-PsA Questionnaire; ff) change (improvement) from baseline in HRU Questionnaire; gg) change (improvement) from baseline in SAPS Questionnaire; hh) change (improvement) from baseline in BASDAI; ii) BASDAI 50 response; jj) change (improvement) from baseline in Morning stiffness, measured as mean of BASDAI Questions 5 and 6; kk) change (improvement) from baseline in ASDAS; ll) ASDAS Inactive Disease; mm) ASDAS Major Improvement; nn) ASDAS Clinically Important Improvement; and oo) clinically meaningful improvement in HAQ- DI (≥0.35). In one aspect, the result (or results) is maintained or improved after achieving the result (or results) by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In another aspect, provided is a method of treating active PsA in a subject in need thereof, the method comprising orally administering to the subject once a day for at least 16 weeks a dose of upadacitinib freebase, or a pharmaceutically acceptable salt thereof, in an amount sufficient to deliver 15 mg of upadacitinib freebase equivalent, wherein the subject achieves a Psoriasis Area Severity Index (PASI) 75 response within 16 weeks of administration of the first dose (including at week 16). In certain embodiments, the subject achieves a PASI 90 response within 16 weeks of administration of the first dose (including at week 16). In certain embodiments, the subject achieves a PASI 100 response within 16 weeks of administration of the first dose (including at week 16). In certain embodiments, the PASI response (e.g., the PASI 75, PASI 90, and/or PASI 100 response) is maintained or improved after week 16 by continuing to administer a daily dose of the upadacitinib freebase, or a pharmaceutically acceptable salt thereof. In one aspect, the subject is non-biologic DMARD-IR. In one aspect, the subject is bDMARD-1R.

In yet other aspects, provided is a method of treating active PsA in a subject in need thereof, the method comprising orally administering to the subject once a day for at least 16 weeks a dose of upadacitinib freebase, or a pharmaceutically acceptable salt thereof, in an amount sufficient to deliver 30 mg of upadacitinib freebase equivalent, wherein the subject achieves a Psoriasis Area Severity Index (PASI) 75 response within 16 weeks of administration of the first dose (including at week 16). In certain embodiments, the subject achieves a PASI 90 response within 16 weeks of administration of the first dose (including at week 16). In certain embodiments, the subject achieves a PASI 100 response within 16 weeks of administration of the first dose (including at week 16). In certain embodiments, the PASI response (e.g., the PASI 75, PASI 90, and/or PASI 100 response) is maintained or improved after week 16 by continuing to administer a daily dose of the upadacitinib freebase, or a pharmaceutically acceptable salt thereof. In one aspect, the subject is non-biologic DMARD-IR. In one aspect, the subject is bDMARD-IR.

In yet another aspect, provided is a method of treating active PsA in a population of subjects in need thereof, the method comprising administering a dose of upadacitinib freebase, or a pharmaceutically acceptable salt thereof, to the subjects according to the methods described herein, wherein a portion of the subjects in the treated population (e.g., a statistically significant population of the subjects in the treated population and/or at least 10%, at least 15%, at least 20%, at least 25%, at least 30%, at least 35%, at least 40r, or at least 45% of the subjects in the treated population) achieve a PASI 75 response within 16 weeks of administration of the first dose (including at week 16). In certain embodiments, subjects in the treated population achieve a PASI 90 response within 16 weeks of administration of the first dose (including at week 16). In certain embodiments, subjects in the treated population achieve a PASI 100 response within 16 weeks of administration of the first dose (including at week 16). In certain embodiments, the PASI response (e.g., the PASI 75, PASI 90, and/or PASI 100 response) is maintained or improved after week 16 by continuing to administer a daily dose of the JAK1 inhibitor. In one aspect, the upadacitinib freebase, or a pharmaceutically acceptable salt thereof, is administered in an amount sufficient to deliver 15 mg of upadacitinib freebase equivalent. In one aspect, the upadacitinib freebase, or a pharmaceutically acceptable salt thereof, is administered in an amount sufficient to deliver 30 mg of upadacitinib freebase equivalent. In one aspect, the upadacitinib freebase, or a pharmaceutically acceptable salt thereof, is administered orally once a day for at least 16 weeks. In one aspect, the subjects in the treated population are non-biologic DMARD-IR at baseline. In one aspect, the subject in the treated population are bDMARD-IR at baseline.

In certain embodiments, the subject (or subjects in the treated population) with active PsA at baseline is an adult subject. In another aspect, the subject (or subjects in the treated population) with active PsA at baseline is a juvenile subject. In certain embodiments, the subject (or subjects in the treated population) has >3% Body Surface Area with Psoriasis at baseline.

Further provided are methods of treating psoriasis (PsO), including PsO as a skin manifestation of PsA.

For example, in one aspect, provided is a method of treating active psoriasis in a subject in need thereof, the method comprising orally administering to the subject once a day for at least 16 weeks a dose of upadacitinib freebase, or a pharmaceutically acceptable salt thereof, in an amount sufficient to deliver 15 mg of upadacitinib freebase equivalent, wherein the subject achieves a Psoriasis Area Severity Index (PASI) 75 response within 16 weeks of administration of the first dose (including at week 16). In certain embodiments, the subject achieves a PASI 90 response within 16 weeks of administration of the first dose (including at week 16). In certain embodiments, the subject achieves a PASI 100 response within 16 weeks of administration of the first dose (including at week 16). In certain embodiments, the PASI response (e.g., PASI 75, PASI 90, or PASI 100 response) is maintained or improved after Week 16 by continuing to administer a daily dose of the upadacitinib freebase, or a pharmaceutically acceptable salt thereof.

In yet other aspects, provided is a method of treating active psoriasis in a subject in need thereof, the method comprising orally administering to the subject once a day for at least 16 weeks a dose of upadacitinib freebase, or a pharmaceutically acceptable salt thereof, in an amount sufficient to deliver 30 mg of upadacitinib freebase equivalent, wherein the subject achieves a Psoriasis Area Severity Index (PASI) 75 response within 16 weeks of administration of the first dose (including at week 16). In certain embodiments, the subject achieves a PASI 90 response within 16 weeks of administration of the first dose (including at week 16). In certain embodiments, the subject achieves a PASI 100 response within 16 weeks of administration of the first dose (including at week 16). In certain embodiments, the PASI response (e.g., PASI 75, PASI 90, or PASI 100 response) is maintained or improved after Week 16 by continuing to administer the daily dose of the upadacitinib freebase, or a pharmaceutically acceptable salt thereof.

In yet another aspect, provided is a method of treating active psoriasis in a population of subjects in need thereof, the method comprising administering a dose of upadacitinib freebase, or a pharmaceutically acceptable salt thereof, to the subjects according to the above methods, wherein a portion of the subjects in the treated population (e.g., a statistically significant population of the subjects in the treated population and/or at least 10%, at least 15%, at least 20%, at least 25%, at least 30%, at least 35%, at least 40%, or at least 45% of the subjects in the treated population) achieve a PASI 75 response within 16 weeks of administration of the first dose (including at week 16). In certain embodiments, subjects in the treated population achieve a PASI 90 response within 16 weeks of administration of the first dose (including at week 16). In certain embodiments, subjects in the treated population achieve a PASI 100 response within 16 weeks of administration of the first dose (including at week 16). In certain embodiments, the PASI response (e.g., PASI 75, PASI 90, or PASI 100 response) is maintained or improved after Week 16 by continuing to administer the daily dose of the upadacitinib freebase, or a pharmaceutically acceptable salt thereof. In one aspect, the upadacitinib freebase, or a pharmaceutically acceptable salt thereof, is administered in an amount sufficient to deliver 15 mg of upadacitinib freebase equivalent. In one aspect, the upadacitinib freebase, or a pharmaceutically acceptable salt thereof, is administered in an amount sufficient to deliver 30 mg of upadacitinib freebase equivalent. In one aspect, the upadacitinib freebase, or a pharmaceutically acceptable salt thereof, is administered orally once a day for at least 16 weeks. In one aspect, the subjects in the treated population are non-biologic DMARD-IR at baseline. In one aspect, the subject in the treated population are bDMARD-IR at baseline.

In certain embodiments, the subject (or subjects in the treated population) with active psoriasis at baseline is an adult subject. In another aspect, the subject (or subjects in the treated population) with active psoriasis at baseline is a juvenile subject. In certain embodiments, the subject (or subjects in the treated population) has >3% Body Surface Area with Psoriasis at baseline.

In certain embodiments, the active psoriasis is a skin manifestation of PsA. For example, in certain embodiments, the subject (or subjects in the treated population) in need thereof have active PsA.

EXAMPLES

Examples 1-4: Extended Release Tablets

The Freebase Hydrate Form C and Amorphous Freebase solid state forms of Compound 1 were formulated into 24 mg extended release tablets according to the formulations set forth in Table 6.

TABLE 6

Extended Release Tablets (no pH modifier)

| Component | Function | Ex. 1 (ER1) (mg) | Ex. 2 (ER2) (mg) | Ex .3 (ER3) (mg) | Ex. 4 (mg) |
|---|---|---|---|---|---|
| Freebase Hydrate Form C | Active | 24.0 | 24.0 | 24.0 | — |
| Amorphous Freebase | Active | — | — | — | 24.0 |
| Microcrystalline cellulose (Avicel ® PH 102) | Filler | 351.4 | 303.4 | 303.4 | 303.4 |
| HPMC (Methocel ® K100 Premium LVCRLH) | Release control polymer | 96.0 | 96.0 | — | — |
| HPMC (Methocel® K4M Premiam CR) | Release control polymer | — | 48.0 | 144.0 | 144.0 |
| Colloidal silicon dioxide | Glidant | 3.8 | 3.8 | 3.8 | 3.8 |
| Magnesium stearate impalpable powder | Lubricant | 4.8 | 4.8 | 4.8 | 4.8 |
| Uncoated weight of tablet | | 480.0 | 480.0 | 480.0 | 480.0 |

The formulations were prepared by combining and blending the active, microcrystalline cellulose, hydroxypropyl methyl cellulose (HPMC), and colloidal silicone dioxide. The blend was milled using a Mobil Mill fitted with a 610-micron screen. The magnesium stearate was screened through mesh #30 and was added to the bin and blended.

The lubricated granulation was compressed into 480 mg weight tablets using a rotary tablet press. The tablets may optionally be coated with any suitable film coating.

The effect of solid state form on the dissolution profile of the tablets was evaluated. In particular, the dissolution profile of the Example 3 (containing Freebase Hydrate Form C as active) and Example 4 (containing Amorphous Freebase as active) tablets was evaluated at pH 6.8 (representative of the pH in the lower intestine). The dissolution test was carried out using the following dissolution parameters and conditions:

Apparatus: USP Dissolution Apparatus 2 and fraction collector
Medium: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours. Other samples may be taken at other times, as appropriate.
Sample Volume: 1.5 mL obtained automatically, without media replacement.

The medium used for the study was a 0.05 M sodium phosphate buffer solution, pH 6.8 f 0.05. The medium was prepared using an acid stage medium (0.1 N hydrochloric acid solution) and a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The medium was prepared by mixing 500 mL of the acid stage medium and 400 mL of buffer stage concentrate in an appropriate size container or directly in the dissolution vessel and adjusting the pH with 1 N phosphoric acid or 1 N sodium hydroxide, if the pH was not within 6.8±0.05.

For the dissolution test, one tablet each was added to a dissolution vessel containing 900 mL of the 0.05 M sodium phosphate buffer solution maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % of the labelled amount of active released (% LA Released) was calculated. The formulation containing Freebase Hydrate Form C (Example 3) as the active showed a slower rate of dissolution than the formulation containing Amorphous Freebase (Example 4) as the active at pH 6.8.

The dissolution profile of formulations comprising Freebase Hydrate Form C as an active was further evaluated at pH 6.8 and in a dual pH system. In particular, the dissolution profile of the Example 1 (ER1), Example 2 (ER2), and Example 3 (ER3) tablets at pH 6.8 was carried out as described above. The dissolution profile of the Examples 1-3 tablets was also carried out in a dual pH system using the following dissolution parameters and conditions:

Apparatus: USP Dissolution Apparatus 2 and fraction collector
Medium: Acid Stage: 500 mL of Acid Stage Medium (0.1 N hydrochloric acid solution)
  Buffer Stage: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: Acid Stage: 1 Hour
  Buffer Stage: 2, 4, 6, 8, 10, 12, 16, and 20 Hours.
  Other samples may be taken at other times, as appropriate.
Sample Volume: Acid: 1.5 mL obtained automatically, without media replacement.

The acid stage medium is a 0.1 N hydrochloric acid solution. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1N sodium hydroxide, if the pH was not within 6.8±0.05.

For the dissolution test, one tablet each was added to a dissolution vessel containing 500 mL of a 0.1 N hydrochloric acid solution maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, maintained at 37° C. The dissolution test was continued, with the paddles remaining at a speed of 75 RPM. The sample filtrate was the sample preparation.

For the analysis of the sample, conventional liquid chromatography methods were utilized, wherein the % relative standard deviation (RSD) of peak areas was calculated for each set of six standard injections.

After the initial release at the low pH (representative of the pH in the stomach), release of the drug is slowed at the higher pH (representative of the pH in the lower intestine). Therefore, in order to achieve the desired bioavailability, a formulation which allowed pH independent release was required.

Examples 5-12: Extended Release Tablets

The Freebase Hydrate Form C solid state form of Compound 1 was formulated into 15 mg, 24 mg, or 30 mg extended release tablets according to the formulations set forth in Table 7 using direct compression.

TABLE 7

Extended Release Tablets (tartaric acid pH modifier)

| Component | Function | Ex. 5 (mg) (ER7) | Ex. 6 (mg) | Ex. 7 (mg) | Ex. 8 (mg) (ER8) | Ex. 9 (mg) (ER4) | Ex. 10 (mg) (ER4, no mannitol) | Ex. 11 (mg) (ER5) | Ex. 12 (mg) (ER6) |
|---|---|---|---|---|---|---|---|---|---|
| Freebase Hydrate Form C | Active | 15.4[a] | 15.4[a] | 15.4[a] | 30.7[b] | 24.6[c] | 24.6[c] | 24.6[c] | 24.6[c] |
| Microcrystalline cellulose (Avicel ® PH 102) | Filler | 162.4 | 162.4 | 162.4 | 147.1 | 158.0 | 210.6 | 282.6 | 258.6 |
| Mannitol (Pearlitol ® 100 SD) | Filler | 52.6 | 52.4 | — | 52.6 | 52.7 | — | — | — |
| Mannitol (Pearlitol ® 200 SD) | Filler | — | — | 52.4 | — | — | — | — | — |
| Tartaric acid | pH modifier | 144.0 | 144.0 | 144.0 | 144.0 | 144.0 | 144.0 | 96.0 | 96.0 |
| HPMC (Hypromellose 2208) | Release control polymer | 96.0 | — | — | 96.0 | — | — | — | — |
| HPMC (Methocel ® K4M Premium CR) | Release control polymer | — | 96.0 | 96.0 | — | 96.0 | 96.0 | — | — |
| Carbopol ® 71G | Release control polymer | — | — | — | — | — | — | 48.0 | 72.1 |
| Carbopol ® 971P | Release control polymer | — | — | — | — | — | — | 24.0 | 24.0 |
| Colloidal silicon dioxide | Glidant | 2.4 | 2.4 | 2.4 | 2.4 | — | — | — | — |
| Magnesium stearate impalpable powder | Lubricant | 7.2 | 7.2 | 7.2 | 7.2 | 4.8 | 4.8 | 4.8 | 4.8 |
| Uncoated weight of tablet | | 480.0 | 479.8 | 479.8 | 480.0 | 480.1 | 480.0 | 480.0 | 480.1 |
| Opadry ® II Yellow (PVA based) | Film coat | 14.40 | — | — | 14.40 | — | — | — | — |
| Total weight of tablet | | 494.39 | — | — | 494.43 | — | — | — | — |

[a] Provides 15 mg of Compound 1 freebase equivalent.
[b] Provides 30 mg of Compound 1 freebase equivalent.
[c] Provides 24 mg of Compound 1 freebase equivalent.

The formulations were prepared by first milling the tartaric acid through a Fitz mill Model M5A, fitted with a 1512-0027 screen. The Freebase Hydrate Form C, microcrystalline cellulose, mannitol (when present), milled tartaric acid, release control polymer, and colloidal silicone dioxide (when present) were combined and blended. The blend was milled using a Mobil Mill fitted with a 610- or 1397-micron screen. The magnesium stearate was screened through mesh #30 and was then added to the bin and blended. The lubricated granulation was compressed into about 480 mg weight tablets using a rotary tablet press.

The Example 5 and 8 tablets were coated using a film coater, which sprayed a solution containing the Opadry® II Yellow film coat and purified water until 14.40 mg of coating had been applied to the tablets.

The dissolution profile of the Example 9 (ER4, 24 mg active), Example 10 (ER4, no mannitol, 24 mg active), Example 11 (ER5, 24 mg active), and Example 12 (ER6, 24 mg active) tablets was evaluated at pH 1.2, at pH 6.8, and in a dual pH system. The pH 6.8 study was performed as described above for Examples 3 and 4. For the dual pH study, an acid stage medium of 0.05 M sodium phosphate solution, pH 3.5 t 0.05, was prepared by dissolving about 41.4 g of sodium phosphate, monobasic, monohydrate in about 4 L of water, measuring the pH and adding phosphoric acid, 85%, dropwise as needed to adjust to the target pH. The mixture was diluted to 6 L with water and mixed. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

The dissolution test was carried out using the following dissolution parameters and conditions:
Apparatus: USP Dissolution Apparatus 2 and fraction collector
Medium: Acid Stage: 500 mL of Acid Stage Medium
Buffer Stage: 900 mL of 50 mM sodium phosphate buffer solution, pH 6.8
Temperature: 37° C.±0.5° C.
RPM: 75 RPM t 4%
Filter: 35 µm PE filter, or equivalent, for automatic sampling
Sampling Times: Acid Stage: 1 Hour
Buffer Stage: 2, 4, 6, 8, 10, 12, 16, and 20 Hours.
Other samples may be taken at other times, as appropriate.
Sample Volume: Acid and Buffer Stage: 1.5 mL obtained automatically, without media replacement.

For the dissolution test, one tablet each was added to a dissolution vessel containing 500 mL of the acid stage medium, maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, and then the mixture was maintained at 37° C. The dissolution test was continued, with the paddles remaining at a speed of 75 RPM. The sample filtrate was the sample preparation.

For the pH 1.2 study, the dissolution test was carried out using the following dissolution parameters and conditions:

Apparatus: USP Dissolution Apparatus 2 and fraction collector
Medium: 500 mL of Acidic Medium, pH 1.2
Temperature: 37° C.±0.5° C.
RPM: 75 RPM±4%
Filter: 35 µm PE filter, or equivalent, for automatic sampling
Sampling Times: 1, 2, 4, 6, 8, 10, 12, 16, and 20 Hours.
Other samples may be taken at other times, as appropriate.
Sample Volume: 1.5 mL obtained automatically, without media replacement.

For this study, an acidic medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH of 1.2. The mixture was diluted to 6 L with water and mixed.

For the dissolution test, one tablet each was added to a dissolution vessel containing 500 mL of the acidic medium, maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % relative standard deviation (RSD) of peak areas was calculated for each set of six standard injections. The results shown that pH independence is achieved in the once daily formulations.

The dissolution profile of the Example 5 (ER7), Example 8 (ER8), and Example 9 (ER4) tablets were evaluated in a dual pH system, as described above. The formulations provide an extended release profile of 80-100% over a period of about 8-10 hours.

The formulations of Examples 5 and 8-12 all exhibited pH independent release of the active ingredient. In contrast, after the initial release at the low pH, release of the active is slowed at the higher pH for the formulations of Examples 1-3. Without wishing to be bound to any particular theory, it is believed that the inclusion of tartaric acid as a pH modifier in the Example 5 and 8-12 formulations contributed to the pH independent release observed for these tablets.

Example 13: Extended Release Tablet

The Freebase Hydrate Form C solid state form of Compound 1 was formulated into a 7.5 mg extended release tablet according to the formulation set forth in Table 8.

TABLE 8

Extended Release Tablets (tartaric acid pH modifier)

| Component | Function | Ex. 34 (mg) (ER9) |
|---|---|---|
| Freebase Hydrate Form C* | Active | 7.678[a] |
| Microcrystalline cellulose (Avicel® PH 102) | Filler | 170.1 |
| Mannitol (Pearlitol® 100 SD) | Filler | 52.62 |
| Tartaric acid (crystalline) | pH modifier | 144.0 |
| HPMC (Hypromellose 2208) | Release control polymer | 96.0 |
| Colloidal silicon dioxide | Glidant | 2.4 |
| Magnesium stearate | Lubricant | 7.2 |
| Uncoated weight of tablet | | 479.998 |
| Opadry ® II Yellow | Film coat | 14.40 |
| Purified water | Processing aid | n/a |
| Total weight of tablet | | 494.398 |

[a]Provides 7.5 mg of Compound 1 freebase equivalent.

The formulation was prepared by first milling the tartaric acid through a Fitz mill Model M5A, fitted with a 1512-0027 screen. The Freebase Hydrate Form C, microcrystalline cellulose, mannitol, milled tartaric acid, release control polymer, and colloidal silicone dioxide were combined and blended. The blend was milled using a Mobil Mill fitted with a 610-micron screen. The magnesium stearate was screened through mesh #30 and was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Examples 14-19: Extended Release Tablets

The Freebase Hydrate Form C solid state form of Compound 1 was formulated into 15 mg or 30 mg extended release tablets according to the formulations set forth in Table 9. The tablets were prepared using a wet granulation process, and were compressed into tablets having a core weight of about 480 mg.

rystalline cellulose filler were added to a granulator, and mixed. Water was sprayed to granulate. The granulated material was then dried and milled using a comill fitted with a 610-micron screen. The milled granulation was then added to the extragranular tablet components other than magnesium stearate, and sieved using a comill fitted with a 1397-micron screen, followed by blending. The magnesium stearate was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Example 20: Evaluation of the Effect of Organic Acids on Dissolution Profile of Extended Release Tablets In this example, the effect of various organic acid pH modifiers (e.g., tartaric acid, citric acid, succinic acid, and

TABLE 9

Extended Release Tablets (tartaric acid pH modifier)

| Component | Function | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
|---|---|---|---|---|---|---|---|
| Tablet Core (Intragranular) | | | | | | | |
| Freebase Hydrate Form C | Active | 30.7[a] | 30.7[a] | 30.7[a] | 15.46[b] | 15.4[b] | 15.45[b] |
| Microcrystalline cellulose (Avicel® PH 101) | Filler | 79.9 | 79.9 | 79.9 | 40.0 | 40.0 | 40.0 |
| HPMC (Hypromellose 2208) | Release control polymer | 9.5 | 9.5 | 9.5 | 4.8 | 4.8 | 4.8 |
| Tablet Core (Extragranular) | | | | | | | |
| Microcrystalline cellulose (Avicel® PH 102) | Filler | 67.2 | 67.2 | 67.2 | 122.5 | 122.5 | 122.5 |
| Mannitol | Filler | 52.6 | 100.6 | 148.6 | 52.6 | 100.6 | 148.6 |
| Tartaric acid (crystalline) | pH modifier | 144.0 | 96.0 | 48.0 | 144.0 | 96.0 | 48.0 |
| HPMC (Hypromellose 2208) | Release control polymer | 86.5 | 86.5 | 86.5 | 91.2 | 91.2 | 91.2 |
| Colloidal silicon dioxide/silica | Glidant | 2.4 | 2.4 | 2.4 | 2.4 | 2.4 | 2.4 |
| Magnesium stearate | Lubricant | 7.2 | 7.2 | 7.2 | 7.2 | 7.2 | 7.2 |
| Uncoated weight of tablet | | 480.0 | 480.0 | 480.0 | 480.1 | 480.1 | 480.1 |
| Opadry® II Yellow[c] | Film coat | 14.4 | 14.4 | 14.4 | 14.4 | 14.4 | 14.4 |
| Total weight of tablet | | 494.4 | 494.4 | 494.4 | 494.5 | 494.5 | 494.5 |

[a] Provides 30 mg of Compound 1 freebase equivalent.
[b] Provides 15 mg of Compound 1 freebase equivalent.
[c] Film coat weight is approximate.

The formulation was prepared by first milling the tartaric acid through a Fitz mill Model M5A, fitted with a 1512-0027 screen. The intragranular portion of the hydroxypropylmethyl cellulose release control polymer, the Freebase Hydrate Form C, and intragranular portion of the microcfumaric acid) on the release rate of Freebase Hydrate Form C from 24 mg once-daily extended release (ER) tablets was evaluated. Freebase Hydrate Form C was formulated into 24 mg extended release tablets according to the formulations set forth in Table 10.

TABLE 10

Extended Release Tablets

| Component | Function | Tartaric acid | | Citric acid | | Succinic acid | | Fumaric acid | |
|---|---|---|---|---|---|---|---|---|---|
| | | A | B | C | D | E | F | G | H |
| Freebase Hydrate Form C | Active | 24.6 | 24.6 | 24.6 | 24.6 | 24.6 | 24.6 | 24.6 | 24.6 |
| Microcrystalline cellulose (Avicel ® PH102) | Filler | 306.6 | 306.6 | 306.6 | 306.6 | 306.6 | 306.6 | 306.6 | 306.6 |
| HPMC (Methocel ® K4M) | Release control polymer | 96.0 | — | 96.0 | — | 96.0 | — | 96.0 | — |
| Carbopol ® 71G | Release control polymer | — | 96.0 | — | 96.0 | — | 96.0 | — | 96.0 |
| Organic acid | pH modifier | 48.0 | 48.0 | 48.0 | 48.0 | 48.0 | 48.0 | 48.0 | 48.0 |
| Magnesium stearate | Lubricant | 4.8 | 4.8 | 4.8 | 4.8 | 4.8 | 4.8 | 4.8 | 4.8 |
| Total | | 480.0 | 480.0 | 480.0 | 480.0 | 480.0 | 480.0 | 480.0 | 480.0 |

The formulations were prepared by first milling the organic acid through a Fitz mill Model M5A, fitted with a 1512-0027 screen. The active, microcrystalline cellulose, milled organic acid, and release control polymer, were combined and blended. The blend was milled using a Mobil Mill fitted with a 610-micron screen. The magnesium stearate was screened through mesh #30 and was added to the bin and blended. The lubricated granulation was compressed into 480 mg weight tablets using a rotary tablet press.

The effect of the organic acids on the dissolution profile of the tablets was evaluated at pH 1.2 and pH 6.8. The dissolution tests were carried out using the dissolution parameters and conditions as described above in Examples 3 and 4 and 9-12. For analysis of the sample, conventional liquid chromatography methods were utilized, wherein the % of the labelled amount of active released (% LA Released) was calculated. The results show that organic acids improved dissolution rate at high pH, with tartaric acid showing the best improvement. The formulations comprising the control release polymer Carbopol® with tartaric acid provided near linear release at pH 6.8.

Example 21: Gel pH Measurements for Tablets with Different Amounts of Tartaric Acid To measure the pH of the environment created when Compound 1 reacts with HPMC, the following experiment was performed.

The Freebase Hydrate Form C solid state form of Compound 1 was formulated into 30 mg extended release tablets according to the formulations set forth in Table 11A. The tablets were prepared using a wet granulation process, as described in Examples 14-19.
Dissolution media of 0.01 N HCl (pH 2) and 113 mM sodium phosphate buffer (pH 6.8) was prepared at 37° C. One tablet was added to 500 mL of 0.01 N HC media and stirred at 75 rpm at 37° C. for one hour in a Vankel VK 7010 dissolution bath. Then 400 mL of sodium phosphate buffer was added. The solution was stirred an additional three hours. The tablet was removed, rinsed with water and dried using laboratory tissues. The gel that formed on the tablet was separated from the dry core for pH measurement. This procedure was repeated three times for each formulation. The pH of the gel formed on the tablets is set forth in Table 11B.
Table 11A: Formulations

| Component | Formulation 1 | Formulation 2 | Formulation 3 | Formulation 4 | Formulation 5 |
|---|---|---|---|---|---|
| | Intragranular | | | | |
| | mg/tab | mg/tab | mg/tab | mg/tab | mg/tab |
| Freebase Hydrate Form C | 30.71 | 30.71 | 30.71 | 30.71 | 30.71 |
| HPMC (Methocel ® K4M) | 3.920 | 3.920 | 3.920 | 3.920 | 3.920 |
| Microcrystalline cellulose (Avicel ®) PH102) | 30.71 | 30.71 | 30.71 | 30.71 | 30.71 |
| | extragranular | | | | |
| Microcrystalline cellulose (Avicel ® PH102) | 116.4 | 164.4 | 188.4 | 212.4 | 260.4 |
| Tartaric Acid (milled) | 144.0 | 96.00 | 72.00 | 48.00 | 0.00 |
| Mannitol (Pearlitol ® 100SD) | 52.62 | 52.62 | 52.62 | 52.62 | 52.62 |
| HPMC (Methocel ® K4M) | 92.08 | 92.08 | 92.08 | 92.08 | 92.08 |
| Colloidal silicon dioxide | 2.400 | 2.400 | 2.400 | 2.400 | 2.400 |
| Magnesium Stearate | 7.200 | 7.200 | 7.200 | 7.200 | 7.200 |
| Total | 480.04 | 480.04 | 480.04 | 480.04 | 480.04 |

TABLE 11B pH Results

| Formulation | % Tartaric Acid | $1^{st}$ tablet | $2^{nd}$ tablet | $3^{rd}$ tablet | Average |
|---|---|---|---|---|---|
| 1 | 30 | 2.63 | 2.68 | 2.81 | 2.71 |
| 2 | 20 | 3.17 | 3.09 | 3.23 | 3.16 |
| 3 | 15 | 3.42 | 3.94 | 3.65 | 3.67 |
| 4 | 10 | 3.88 | 3.67 | 3.77 | 3.77 |
| 5 | 0 | 6.26 | 6.21 | 6.55 | 6.34 |

Example 22: Evaluation of the In Vivo Pharmacokinetic Profile of 15 mg Extended Release Tablets (Fasting)

The pharmacokinetic profile of the 15 mg once-daily extended release (ER) tablets prepared in Example 5 was evaluated, and compared to that of a 12 mg immediate-release (IR) capsule comprising Tartrate Hydrate as the active.

Healthy human subjects (n=11) were administered a single dose of the 12 mg IR capsule (Regimen A) and the 15 mg ER (once-daily) tablet from Example 5 (Regimen B) under fasting conditions in a randomized, two-period, cross-over study design. Subjects were administered Regimen A in the first study period and Regimen B in the second study period, or administered Regimen B in the first study period and Regimen A in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 12A.

TABLE 12A

Mean (% CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
| --- | --- | --- | --- |
| $C_{max}$ | ng/mL | 64.6 (16) | 26.0 (37) |
| $T_{max}$[a] | hours | 1.0 (0.5-1.5) | 3.0 (1.0-40) |
| $t_{1/2}$[b] | hours | 9.2 (119) | 12.5 (90) |
| $AUC_t$ | ng · h/mL | 231 (15) | 227 (26) |
| $AUC_{inf}$ | ng · h/mL | 234 (15) | 242 (26) |

[a]Median (minimum, maximum)
[b]Harmonic mean (pseudo-% CV)
[c]Data in parentheses is coefficient of variance of the PK parameter (% CV), unless otherwise indicated.

As can be seen from this data, the 15 mg ER tablet provided a lower $C_{max}$, and comparable AUC to the 12 mg IR capsule under fasting conditions.

The relative bioavailability for a single dose of the once-daily (ER) tablet formulation (Regimen B) relative to the IR capsule formulation (Regimen A) was also determined based on analysis of the natural logarithms of $C_{max}$ and AUC. The results are summarized in Table 12B below.

TABLE 12B

Relative Bioavailability and 90% Confidence Intervals for Bioequivalence Assessment

| | Relative Bioavailability | |
| --- | --- | --- |
| PK Parameter | Point Estimate | 90% Confidence Interval |
| $C_{max}$ | 0.373 | 0.312-0.446 |
| $AUC_t$ | 0.939 | 0.869-1.013 |
| $AUC_{inf}$ | 0.992 | 0.909-1.082 |

For Regimen B versus Regimen A, the point estimates for the ratios of $AUC_t$ and $AUC_{inf}$ were near unity, and the 90% confidence intervals were within the 0.86-1.09 range.

Example 23: Evaluation of the In Vivo Pharmacokinetic Profile of 30 mg Extended Release Tablets (Fasting)

The pharmacokinetic profile of the 30 mg once daily extended release (ER) tablets prepared in Example 8 was evaluated, and compared to that of a 24 mg dose of an immediate release (IR) capsule comprising Tartrate Hydrate as the active.

Healthy human subjects (n=12) were administered a single 24 mg dose (two 12 mg IR capsules) (Regimen C) and the 30 mg ER (once daily) tablet from Example 8 (Regimen D) under fasting conditions in a randomized, two-period, cross-over study design. Half the subjects were administered Regimen C in the first study period and Regimen D in the second study period, while the other half were administered Regimen D in the first study period and Regimen C in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 13A.

TABLE 13A

Mean (% CV)[c] Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
| --- | --- | --- | --- |
| $C_{max}$ | ng/mL | 176 (37) | 63.7 (33) |
| $T_{max}$[a] | hours | 0.5 (0.5-1.5) | 2.0 (1.5-4.0) |
| $t_{1/2}$[b] | hours | 9.9 (52) | 10.8 (67) |

TABLE 13A-continued

Mean (% CV)[c] Pharmacokinetic
Parameters for Compound 1 Following Administration of
30 mg ER Tablet and 24 mg Dose (2 × 12 mg)
IR Capsule Formulations Under Fasting Conditions

| PK Parameter | Units | Regimen C (IR Capsules, 24 mg) | Regimen D (ER Tablet, 30 mg) |
|---|---|---|---|
| $AUC_t$ | ng · h/mL | 520 (25) | 477 (27) |
| $AUC_{inf}$ | ng · h/mL | 524 (25) | 491 (27) |

[a]Median (minimum-maximum)
[b]Harmonic mean (pseudo % CV)

As can be seen from this data, the 30 mg ER tablet provided a lower $C_{max}$ and comparable AUC to the 24 mg dose IR capsule (2×12 mg) under fasting conditions.

The relative bioavailability for a single dose of the once-daily (ER) tablet formulation (Regimen D) relative to the IR capsule formulations (Regimen C) was also determined based on analysis of the natural logarithms, of $C_{max}$ and AUC The results are summarized in Table 13B below.

TABLE 13B

Relative Bioavailability and 90% Confidence Intervals for Bioequivalence Assessment

| | PK Value | | Relative Bioavailability | |
|---|---|---|---|---|
| PK Paramenter | Regimen D | Regimen C (reference) | Point Estimate | 90% Confidence Interval |
| $C_{max}$ | 63.7 | 176 | 0.368 | 0.326-0.415 |
| $AUC_t$ | 477 | 520 | 0.912 | 0.828-1.004 |
| $AUC_{inf}$ | 491 | 524 | 0.933 | 0.845-1.029 |

For Regimen D versus Regimen C, the point estimates for the ratios of $AUC_t$ and $AUC_{inf}$ were near unity, and the 90% confidence intervals were within the 0.82-1.03 range.

Example 24: Comparison of the In Vivo Pharmacokinetic Profile of 30 mg Extended Release Tablets Under Fasting Versus Fed Conditions The pharmacokinetic profile of the 30 mg extended release tablets prepared in Example 8 after a high-fat meal was evaluated, and compared to the pharmacokinetic profile of the 30 mg extended release tablets under fasting conditions (see Example 23).

Following completion of the Example 23 study, the healthy human subjects (n=12) were administered single doses of the 30 mg ER (once daily) tablet from Example 8 after a high-fat meal (Regimen E). Serial blood samples were collected from each subject prior to dosing and for 72 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter, and compared to the pharmacokinetic parameters for the 30 mg tablets administered under fasting conditions (see Example 23, Regimen D). The results are summarized in Table 14A.

TABLE 14A

Mean (% CV)[c]
Pharmacokinetic Parameters for Compound 1 Following Administration of
30 mg ER Tablet Under Fasting Conditions or After a High-Fat Meal

| PK Parameter | Units | Regimen D (Fasting) | Regimen E (After High-Fat Meal) |
|---|---|---|---|
| $C_{max}$ | ng/mL | 63.7 (33) | 76.8 (39) |
| $T_{max}$[a] | hours | 2.0 (1.5-4.0) | 4.0 (1.5-8.0) |
| $t_{1/2}$[b] | hours | 0.8 (67) | 11.9 (51) |
| $AUC_t$ | ng · h/mL | 477 (27) | 564 (26) |
| $AUC_{inf}$ | ng · h/mL | 491 (27) | 577 (27) |

[a]Median (minimum-maximum)
[b]Harmonic mean (pseudo-CV %)
[c]Data in parentheses is coefficient of variance of the PK parameter (% CV), unless otherwise indicated.

The relative bioavailability for a single dose of the once-daily (ER) 30 mg tablet formulation after a high-fat meal (Regimen E) relative to the bioavailability of the ER 30 mg tablet under fasting conditions (Regimen D) was also determined based on analysis of the natural logarithms of $C_{max}$ and AUC. The results are summarized in Table 14B below.

TABLE 14B

Relative Bioavailability, and 90% Confidence
Intervals for Bioequivalence Assessment

| | PK Value | | Relative Bioavailability | |
|---|---|---|---|---|
| PK Paramenter | Regimen E (after high-fat meal) | Regimen D (fasting) | Point Estimate | 90% Confidence interval |
| $C_{max}$ | 76.8 | 63.7 | 1.197 | 1.027-1.395 |
| $AUC_t$ | 564 | 477 | 1.184 | 1.042-1.344 |
| $AUC_{inf}$ | 577 | 491 | 1.171 | 1.035-1.326 |

As can be seen from Tables 14A and 14B, there is no clinically meaningful food effect for the 30 mg ER tablets. Administration following a high-fat meal increased the Compound 1 mean AUC and $C_{max}$ by 17% and 20%, respectively.

As can be seen from Tables 14A and 141B, there is no clinically meaningful food effect for the 30 mg ER tablets. Administration following a high-fat meal increased the Compound 1 mean AUC and $C_{max}$ by 17% and 20%, respectively.

Example 25: Observed Steady State Exposures for 15 mg and 30 mg Extended Release Tablets Under Non-Fasting Conditions The steady state pharmacokinetic profile of the 15 mg once daily extended release (ER) tablets (prepared in Example 5) and the 30 mg once daily ER tablets (prepared in Example 8) was evaluated.

Healthy human subjects (n=24) were assigned to one of two regimens. Subjects in Regimen F (n=12) were administered the 15 mg ER tablet from Example 5 once daily for seven days under non-fasting conditions. Subjects in Regimen G (n=12) were administered the 30 mg ER tablet from Example 8 once daily for seven days under non-fasting conditions. On days one and seven, serial blood samples were collected from each subject prior to the daily dosing and up to 24 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

The results are summarized in Table 15A.

Example 26: Observed Steady State Exposures for 15 mg Extended Release Tablets and 6 mg Immediate Release Capsules Under Fasting Conditions The steady state pharmacokinetic profile of the 15 mg once daily extended release (ER) tablets (prepared in Example 5) under fasting conditions was evaluated, and compared to that of a 6 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=62) were administered the 15 mg ER tablet from Example 5 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma

TABLE 15A

Mean (% CV)[e] Pharmacokinetic Parameters for Compound 1 Following Administration of 15 mg ER Tablet or 30 mg ER Tablet QD for Seven Days (Non-Fasting)

| PK Parameter | Units | Regimen F (15 mg ER Tablet) | | Regimen G (30 mg ER Tablet) | |
| --- | --- | --- | --- | --- | --- |
| | | Day 1 | Day 7 | Day 1 | Day 7 |
| $C_{max}$ | ng/mL | 36.8 (26) | 36.0 (24) | 74.3 (32) | 79.5 (40) |
| $T_{max}$[a] | hours | 4.0 (3.0-6.0) | 4.0 (2.0-6.0) | 40 (2.0-6.0) | 4.0 (1.5-6.0) |
| $AUC_{24}$ | ng · h/mL | 305 (24) | 317 (21) | 517 (30) | 582 (30) |
| $C_{24}$ | ng/mL | 2.42 (45) | 3.22 (46) | 4.27 (48) | 5.25 (44) |
| $C_{trough}$ | ng/mL | — | 2.96 (35) | — | 5.02 (42) |
| $C_{min,ss}$ | ng/mL | — | 2.80 (41) | — | 4.62 (38) |
| Fluctuation Index | % | 291 (14) | 251 (14) | 345 (14) | 306 (17) |
| $t_{1/2}$[b] | hours | — | 9.43 (76) | — | 10.4 (44) |
| $C_{max}$ to $C_{24}$ ratio | | 17 (7.8-44) | 13 (5.6-35) | 17 (9.9-38) | 14 (7.0-30) |
| $C_{max}$/Dose | (ng/mL)/mg | 2.46 (26) | 2.40 (24) | 2.48 (32) | 2.65 (40) |
| $C_{trough}$/Dose | (ng/mL)/mg | 0.16 (45) | 0.21 (46) | 0.14 (48) | 0.18 (44) |
| $AUC_{24}$/Dose | (ng · h/mL)/mg | 20.3 (24) | 21.2 (21) | 17.2 (30) | 19.4 (30) |
| $R_{AUC}$[c] | | — | 1.02 (0.91-1.40) | — | 1.16 (0.92-1.31) |
| $R_{Cmax}$[d] | | — | 1.00 (0.84-1.26) | — | 1.02 (0.82-1.40) |

[a] Median (minimum-maximum)

[b] Harmonic mean (pseudo-% CV)

[c] $R_{AUC}$ = $AUC_{24}$Day 7/$AUC_{24}$Day 1; median (range)

[d] $R_{Cmax}$ = $C_{max}$Day 7/$C_{max}$Day 1; median (range)

[e] Data in parentheses is the coefficient of variance of the PK parameter (% CV), unless otherwise indicated As can be seen from this data, the observed steady state $C_{max}$ and $AUC_{24}$ following 15 mg QD and 30 mg QD administration are generally consistent with the single dose and food-effect results obtained in Examples 45-47. The bioavailability of the 15 mg and 30 mg ER tablets is 70% to 80% relative to the same dose of IR capsules.

samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

The results are summarized in Table 16A.

TABLE 16A

Mean (% CV)[e] Pharmacokinetic Parameters for Compound 1 Following Administration of 6 mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
|---|---|---|---|---|---|
| | | Day 1 | Day 7 | Day 1 | Day 7 |
| $C_{max}$ | ng/mL | 36.5 (25) | 33.9 (26) | 31.7 (40) | 31.9 (35) |
| $T_{max}$[a] | hours | 1.0 (1.0-13) | 1.0 (0.5-14) | 3.0 (1.5-6.0) | 2.5 (1.5-4.0) |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/mL | 3.2 (36) | 3.6 (23) | 1.9 (42) | 3.1 (37) |
| $C_{min}$ | ng/mL | — | 2.7 (26) | — | 3.1 (37) |
| Fluctuation Index | % | 303 (13) | 259 (13) | 299 (22) | 246 (21) |
| $t_{1/2}$[b] | hours | — | 14.7 (77) | — | 10.3 (76) |
| $C_{max}$ to $C_{24}$ ratio[a] | — | 12 (7.7-19) | 8.8 (7.4-13) | 22 (5.8-43) | 12 (4.2-20) |
| $C_{max}$ to $C_{min}$ ratio[a] | — | — | 13 (8.3-18) | — | 12 (4.2-20) |
| $AUC_{24}$/Dose | (ng · h/mL)/mg | 24.8 (23) | 24.0 (22) | 16.6 (29) | 18.6 (26) |
| $R_{AUC}$[c] | — | — | 1.02 (0.88-1.09) | — | 1.11 (0.87-1.99) |
| $R_{Cmax}$[d] | — | — | 0.97 (0.68-1.17) | — | 1.01 (0.65-3.01) |

[a]Median (minimum-maximum)
[b]Harmonic mean (pseudo-% CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for the once-daily (ER) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{24}$. The results are summarized in Table 16B below.

TABLE 16B

Relative Bioavailability Estimates and 90% Confidence Intervals for 15 mg QD Tablets Relative to 6 mg BID Capsules at Steady State under Fasting Conditions

| PK Parameter | Relative Bioavailability | |
|---|---|---|
| | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state $C_s$ was approximately 1 for the 15 mg QD tablet relative to the 6 mg BID capsules.

The pre-morning dose trough concentration ($C_{trough}$) for the 6 mg BID capsules and 15 mg QD tablets was determined prior to the morning dose on Days 2-8. At steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 27: Observed Steady State Exposures for 30 mg Extended Release Tablets and 12 mg Immediate Release Capsules Under Fasting Conditions The steady state pharmacokinetic profile of the 30 mg once daily extended release (ER) tablets (prepared in Example 8) under fasting conditions was evaluated, and compared to that of a 12 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg ER tablet from Example 8 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

The results are summarized in Table 17A. The mean plasma concentration of Compound 1 at each time point measured for each of the two regimens is set forth in FIG. 22.

TABLE 17A

Mean (% CV)[e] Pharmacokinetic Parameters for Compound 1 Following Administration of 12 mg BID (IR) Capsules and 30 mg QD (ER) Tablets for Seven Days (Fasting Conditions)

| PK Parameter | Units | Regimen M (12 mg IR Capsules (BID)) | | Regimen N (30 mg ER Tablet (QD)) | |
|---|---|---|---|---|---|
| | | Day 1 | Day 7 | Day 1 | Day 7 |
| $C_{max}$ | ng/mL | 80.8 (23) | 73.9 (19) | 65.7 (22) | 68.2 (30) |
| $T_{max}$[a] | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/mL | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/mL | — | 3.8 (58) | — | 3.8 (43) |
| Fluctuation Index | % | 388 (15) | 317 (14) | 349 (12) | 291 (17) |
| $t_{1/2}$[b] | hours | — | 7.3 (60) | — | 14.4 (64) |
| $C_{max}$ to $C_{24}$ ratio[a] | — | 15 (5.4-20) | 12 (5.9-16) | 29 (13-38) | 17 (4.1-33) |
| $C_{max}$ to $C_{min}$ ratio[a] | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}$[c] | — | — | 1.08 (0.97-1.18) | — | 1.11 (0.79-1.67) |
| $R_{Cmax}$[d] | — | — | 0.98 (0.65-1.18) | — | 1.03 (0.40-1.82) |

[a]Median (minimum-maximum)
[b]Harmonic mean (pseudo-% CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for a single dose of the once-daily (ER) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 17B below.

TABLE 17B

Relative Bioavailability Estimates and 90% Confidence Intervals for 30 mg QD Tablets Relative to 12 mg BID Capsules at Steady State under Fasting Conditions

| | Relative Bioavailability | |
|---|---|---|
| PK Parameter | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

The ratio of steady-state AUC for the 30 mg QD tablets relative to the 12 mg BID capsules was approximately 1, with the 90% confidence intervals within the equivalence boundaries. The steady-state $C_{min}$ for the 30 mg QD tablet was approximately 13% lower than for the 12 mg BID capsules. Outliers with high $C_{min}$ in the 12 mg BID dose may have contributed to this difference.

The pre-morning dose trough concentration ($C_{trough}$) for the 12 mg BID capsules and 30 mg QD tablets was determined prior to the morning dose on Days 2-8. The results show that, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 28: Comparison of AM vs. PM Pharmacokinetic Profile Following Administration of 6 mg or 12 mg Immediate Release Capsules Under Fasting Conditions The pharmacokinetic profile of the 6 mg immediate release (IR) twice daily (BID) capsules and the 12 mg IR twice daily capsules was determined on Day 7 of Regimen K (Example 26) and Regimen M (Example 27), respectively, after administration of the morning (AM dose) and evening (PM dose). The results are summarized in Table 18.

TABLE 18

Mean (% CV)[b] Pharmacokinetic Parameters for Compound 1 Following Administration of AM and PM Doses of 6 mg and 12 mg Immediate Release Capsules on Day 7 (Fasting Conditions)

| PK Parameter | Units | Regimen K (6 mg IR Capsules) | | Regimen M (12 mg IR Capsules) | |
|---|---|---|---|---|---|
| | | AM Dose | PM Dose[c] | AM Dose | PM Dose[c] |
| $C_{max}$ | ng/mL | 33.6 (28) | 24.4 (22) | 73.9 (19) | 46.0 (26) |
| $T_{max}$[a] | hours | 1 (0.5-1.5) | 2 (1.0-3.0) | 1 (0.5-1.5) | 3 (1.0-4.0) |
| $AUC_{12}$ | ng · h/mL | 152 (26) | 153 (19) | 290 (19) | 244 (19) |
| $C_{12}$ | ng/mL | 2.76 (24) | 3.63 (23) | 4.1 (55) | 6.94 (37) |
| $C_{max}$/$C_{12}$ | — | 12.3 (23) | 6.9 (22) | 18.0 (30) | 7.4 (39) |

[a]Median (Minimum-Maximum)
[b]Data in parentheses is the coefficient of variance of the PK parameter (% CV), unless otherwise indicated
[c]The PM dose was administered 3 hours after starting dinner and 4 hours before a snack.

Example 29: Evaluation of the In Vivo Pharmacokinetic Profile of 30 mg Extended Release Tablets The pharmacokinetic profiles of the 30 mg once-daily extended release (ER) tablets that were prepared in Examples 14 (ER10, 30% tartaric acid), 15 (ER11, 20% tartaric acid), and 16 (ER 12, 10% tartaric acid) using wet granulation were evaluated, and compared to that of the 30 mg ER tablet that was prepared in Example 8 (ER8, 30% tartaric acid) using direct compression (no wet granulation). The effect of a high-fat meal on the Example 14, 15, and 16 formulations was also evaluated.

Healthy human subjects (n=36) were administered a single dose of the 30 mg ER (once daily) tablet from Example 8 (ER8). Example 14 (ER10), Example 15 (ER 11), and Example 16 (ER12) under fasting conditions or after a high-fat meal (non-fasting), in an open-label, randomized, four-period, incomplete crossover study. Doses in the four periods were separated by at least four days. Dosing regimens were as set forth below in Table 19A.

TABLE 19A

| Regimen | Dose | Formulation | Fasting/Non-Fasting |
|---|---|---|---|
| A | Single 30 mg | Example 8 (ER8) | Fasting |
| B | Single 30 mg | Example 14 (ER10) | Fasting |
| C | Single 30 mg | Example 14 (ER10) | Non-Fasting |
| D | Single 30 mg | Example 15 (ER11) | Fasting |
| E | Single 30 mg | Example 15 (ER11) | Non-Fasting |
| F | Single 30 mg | Example 16 (ER12) | Fasting |
| G | Single 30 mg | Example 16 (ER12) | Non-Fasting |

Serial blood samples were collected from each subject prior to dosing and for 72 hours after dosing in each study period. Upon collection, the samples were promptly placed in an ice bath, and within 1 hour after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

Bioavailability Under Fasting Conditions

The results for administration under fasting conditions are summarized in Table 19B.

The relative bioavailability for a single dose of the three once-daily (ER) tablet formulations prepared using wet granulation (Regimens B, D, and F) relative to the ER tablet prepared via direct compression (no wet granulation) (Regimen A) was also determined based on analysis of the natural logarithms of $C_{max}$, $AUC_t$, and $AUC_{inf}$. The results are summarized in Table 19C below.

TABLE 19C

Bioavailability for Three Compound 1 Once-Daily Formulations Prepared Using Wet Granulation (30 mg; ER10, ER11, ER12) Relative to a Formulation Prepared Via Direct Compression (30 mg, ER8) under Fasting Conditions

| Regimens | PK Paramenter | Relative Bioavailability Point Estimate | 90% Confidence Interval |
|---|---|---|---|
| Regimen B (ER10) | $C_{max}$ | 1.024 | 0917-1.143 |
| vs. | $AUC_t$ | 0.990 | 0.933-1.049 |
| Regimen A (ER8) | $AUC_{inf}$ | 0.976 | 0.918-1.037 |
| Regimen D (ER11) | $C_{max}$ | 1.063 | 0.952-1.187 |
| vs. | $AUC_t$ | 0.985 | 0.929-1.044 |
| Regimen A (ER8) | $AUC_{inf}$ | 0.977 | 0.919-1.038 |
| Regimen F (ER12) | $C_{max}$ | 1.034 | 0.926-1.154 |
| vs. | $AUC_t$ | 0.958 | 0.904-1.016 |
| Regimen A (ER8) | $AUC_{inf}$ | 0.958 | 0.901-1.018 |

As can be seen from this data, all three of the 30 mg tablets prepared using wet granulation (ER10, ER11, and ER12) were bioequivalent under fasting conditions to the tablet prepared via direct compression (no wet granulation).

Effect of a High-Fat Meal on Example 37 Formulation (ER10)

The effect of a high-fat meal on the pharmacokinetic parameters of the Example 14 (ER10, 30 mg active, 30% tartaric acid) formulation is summarized in Table 19D.

TABLE 19D

Mean (% CV)[c] Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
|---|---|---|---|
| $C_{max}$ | ng/mL | 55.8 (27) | 76.3 (30) |
| $T_{max}$[a] | hours | 3.0 (1.0-4.0) | 4.0 (1.5-8.0) |

TABLE 19B

Mean (% CV)[c] Pharmacokinetic Parameters for Compound 1 Following Administration of a Single 30 mg Dose of Various Compound 1 Once-Daily Formulations Prepared Using Wet Granulation Compared to Administration of a Single 30 mg Dose of a Compound 1 Once-Daily Formulation Prepared Via Direct Compression Under Fasting Conditions

| PK Parameter | Units | Regimen A (ER8) (n = 36) | Regimen B (ER10) (n = 24) | Regimen D (ER11) (n = 24) | Regimen F (ER12) (n = 24) |
|---|---|---|---|---|---|
| $C_{max}$ | ng/mL | 57.0 (33) | 55.8 (27) | 61.0 (25) | 58.6 (34) |
| $T_{max}$[a] | hours | 2.5 (1.0-4.0) | 3.0 (1.0-4.0) | 2.0 (1.0-4.0) | 2.0 (1.0-4.0) |
| $AUC_t$ | ng · h/mL | 495 (24) | 473 (24) | 487 (22) | 481 (23) |
| $AUC_{inf}$ | ng · h/mL | 513 (26) | 484 (24) | 499 (22) | 495 (23) |
| $t_{1/2}$[b] | hours | 9.2 (61) | 10.1 (50) | 9.0 (61) | 9.3 (63) |

[a]Median (minimum-maximum)
[b]Harmonic mean (pseudo-% CV)
[c]Data in parentheses is coefficient of variance of the PK parameter (% CV), unless otherwise indicated.

TABLE 19D-continued

Mean (% CV)[c] Pharmacokinetic Parameters for Compound 1
Following Administration of Single 30 mg Dose of the Once-
Daily Tablet Formulation ER10 under Fasting Conditions
and After High-Fat Meal

| PK Parameter | Units | Regimen B (ER10, fasting) (n = 24) | Regimen C (ER10, high fat meal) (n = 12) |
|---|---|---|---|
| $AUC_t$ | ng · h/mL | 473 (24) | 605 (23) |
| $AUC_{inf}$ | ng · h/mL | 484 (24) | 609 (23) |
| $t_{1/2}$[b] | hours | 10.1 (50) | 9.1 (35) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 14 formulation (ER10) administered after a high-fat meal relative to administration under fasting conditions was also determined based on analysis of the natural logarithms of $C_{max}$, $AUC_t$, and $AUC_{inf}$. The results are summarized in Table 19E below.

TABLE 19E

Bioavailability of Single Dose of the 30 mg Once-Daily Tablet ER10
Administered after High-Fat Meal Relative to under Fasting Conditions

| | | Relative Bioavailability | |
|---|---|---|---|
| | PK Parameter | Point Estimate | 90% Confidence Interval |
| Regimen C (ER10, high-fat meal) vs. Regimen B (ER10, fasting) | $C_{max}$ | 1.322 | 1.134-1.541 |
| | $AUC_t$ | 1.296 | 1.194-1.405 |
| | $AUC_{inf}$ | 1.278 | 1.174-1.392 |

As can be seen from this data, a high-fat meal increased the $C_{max}$ and $AUC_{inf}$ for the ER10 formulation (30 mg active, 30% tartaric acid) by about 32% and 28%, respectively.

Effect of a High-Fat Meal on Example 38 Formulation (ER11)

The effect of a high-fat meal on the pharmacokinetic parameters of the Example 15 (ER11, 30 mg, 20% tartaric acid) formulation is summarized in Table 19F.

TABLE 19F

Mean (% CV)[c] Pharmacokinetic Parameters for Compound 1
Following Administration of Single 30 mg Dose of the Once-
Daily Tablet Formulation ER11 under Fasting Conditions
and After High-Fat Meal

| PK Parameter | Units | Regimen D (ER11, fasting) (n = 24) | Regimen E (ER11, high fat meal) (n = 12) |
|---|---|---|---|
| $C_{max}$ | ng/ml | 61.0 (25) | 82.2 (33) |
| $T_{max}$[a] | hours | 2.0 (1.0-4.0) | 4.0 (3.0-8.0) |
| $AUC_t$ | ng · h/mL | 487 (22) | 648 (24) |
| $AUC_{inf}$ | ng · h/mL | 499 (22) | 657 (24) |
| $t_{1/2}$[b] | hours | 9.0 (61) | 9.7 (53) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 15 formulation (ER11) administered after a high-fat meal relative to administration under fasting conditions was also determined based on analysis of the natural logarithms of $C_{max}$, $AUC_t$, and $AUC_{inf}$. The results are summarized in Table 19G below.

TABLE 19G

Bioavailability of Single Dose of the 30 mg Once-Daily Tablet ER11
Administered after High-Fat Meal Relative to under Fasting Conditions

| | | Relative Bioavailability | |
|---|---|---|---|
| | PK Parameter | Point Estimate | 90% Confidence Interval |
| Regimen E (ER11, high-fat meal) vs. Regimen D (ER11, fasting) | $C_{max}$ | 1.343 | 1.153-1.563 |
| | $AUC_t$ | 1.305 | 1.204-1.415 |
| | $AUC_{inf}$ | 1.285 | 1.181-1.398 |

As can be seen from this data, a high-fat meal increased the $C_{max}$ and $AUC_{inf}$ for the ER11 formulation (30 mg active, 20% tartaric acid) by about 34% and 29% respectively, which was a similar food effect as that observed for the Example 14 (ER10) tablet.

Effect of a High-Fat Meal on Example 16 Formulation (ER12)

The effect of a high-fat meal on the pharmacokinetic parameters of the Example 16 (ER12, 30 mg active, 10% tartaric acid) formulation is summarized in Table 19H.

TABLE 19H

Mean (% CV)[c] Pharmacokinetic Parameters for
Compound 1 Following Administration of Single 30 mg
Dose of the Once-Daily Tablet Formulation
ER12 under Fasting Conditions and After High-Fat Meal

| PK Parameter | Units | Regimen E (ER12, fasting) (n = 24) | Regimen G (ER12, high fat meal) (n = 12) |
|---|---|---|---|
| $C_{max}$ | ng/mL | 58.6 (34) | 84.2 (33) |
| $T_{max}$[a] | hours | 2.0 (1.0-4.0) | 4.0 (4.0-6.0) |
| $AUC_t$ | ng · h/mL | 481 (23) | 615 (24) |
| $AUC_{inf}$ | ng · h/mL | 495 (23) | 622 (23) |
| $t_{1/2}$[b] | hours | 9.3 (63) | 11.7 (91) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 16 formulation (ER12) administered after a high-fat meal relative to administration under fasting conditions was also determined based on analysis of the natural logarithms of $C_{max}$, $AUC_t$, and $AUC_{inf}$. The results are summarized in Table 19I below.

TABLE 19I

Bioavailability of Single Dose of the 30 mg Once-Daily Tablet ER12
Administered after High-Fat Meal Relative to under Fasting Conditions

| | | Relative Bioavailability | |
|---|---|---|---|
| | PK Parameter | Point Estimate | 90% Confidence Interval |
| Regimen G (ER12, high-fat meal) vs. Regimen F (ER12, fasting) | $C_{max}$ | 1.527 | 1.314-1.774 |
| | $AUC_t$ | 1.295 | 1.196-1.402 |
| | $AUC_{inf}$ | 1.272 | 1.171-1.381 |

As can be seen from this data, a high-fat meal increased the $C_{max}$ and $AUC_{inf}$ for the ER12 formulation (30 mg active, 10% tartaric acid) by about 53% and 27%, respectively.

Example 30: Predicted Pharmacokinetic Parameters for 15 mg Extended Release Tablets The mean pharmacokinetic parameters under fasting conditions for the once daily (QD) 15 mg extended release tablets prepared in Examples 17 (ER13), 18 (ER14), and 19 (ER15) using wet granulation were extrapolated from the single dose data obtained in Example 29 for the Examples 14 (ER10), 15 (ER11), and 16 (ER12) formulations, respectively, under fasting conditions. The results are set forth in Table 20A.

TABLE 20A

Predicted Mean Pharmacokinetic Parameters under Fasting Conditions for Compound 1 Following Administration of Single 15 mg Once-Daily Formulations (Extrapolated from Single-Dose Profiles in Example 52 for 30 mg Doses)

| PK Parameters | Units | Single 15 mg Dose (ER 13) | Single 15 mg dose (ER14) | Single 15 mg dose (ER15) |
| --- | --- | --- | --- | --- |
| $C_{max}$ | ng/mL | 27.9 | 30.5 | 29.3 |
| $T_{max}^a$ | h | 3.0 | 2.0 | 2.0 |
| $AUC_{inf}$ | ng · h/mL | 242 | 250 | 248 |

$^a$Median (minimum-maximum)

Example 31: Preliminary Data from Phase 1 Study in Healthy Volunteers and Patients with Rheumatoid Arthritis Compound 1 has been studied in 2 Phase 1 studies, first in human single ascending dose study (Study M13-401, described in WO 2015/061665, and referred to herein as Study 1), and then in a multiple ascending dose study (Study M13-845, also generally referred to in WO 2015/061665, and referred to herein as Study 2).

In Study 1, a total of 42 healthy volunteers received a single dose of Compound 1. In Study 2, a total of 32 healthy volunteers received multiple doses of Compound 1 for 14 days (Study 2, Part 1). In addition, 14 patients with RA were enrolled and completed the double-blind Part 2 of Study 2. The study was designed as a multiple-dose, randomized, multicenter trial, with the primary objective as assessing the safety, tolerability, and PK of multiple ascending doses of Compound 1 in healthy adult volunteers and to assess the safety, tolerability, and PK of multiple doses of Compound 1 in patients with RA who are on a stable methotrexate regimen.

Details of Study 1 and Study 2 and results obtained therefrom are provided below.

Study 1—Single-Dose Escalation in Healthy Subjects

Study 1 was a single-dose escalation evaluation of Compound 1. Study 1 was designed as a single-site, randomized, double-blind, placebo-controlled study. Fifty-six subjects in general good health were randomized to receive single doses of Compound 1 immediate release capsules comprising Tartrate Hydrate (1, 3, 6, 12, 24, 36, and 48 mg) or placebo in a 3:1 ratio with 8 subjects in each dose level. Study drug was administered following at least 10 hours of fasting. The study was conducted at PPD Development (Austin. TX). Subjects were confined to the study site and supervised for approximately 8 consecutive days. Study protocol and informed consent were approved by RCRC institutional review board (IRB) (Austin, TX).

Study 2—Multiple-Dose Escalation

In Study 2, multiple twice-daily (BID) doses of immediate release capsules comprising Tartrate Hydrate were administered to healthy subjects (Part 1) or to subjects with rheumatoid arthritis (RA) receiving stable doses of methotrexate (Part 2). Both evaluations followed randomized, double-blind, placebo-controlled designs. Part 1 was conducted at PPD Development (Austin, TX) and Part 2 was conducted at two sites: Aspen Clinical Research (Orem, UT) and Altoona Center for Clinical Research (Duncansville, PA). Study protocol and informed consents were approved by RCRC IRB (Austin, TX) and Quorum Review IRB (Seattle, WA).

Study 2—Part 1—Multiple-Dose Escalation in Healthy Subjects

The objective of Part 1 of the multiple-dose study was to characterize the pharmacokinetics, safety, and tolerability of multiple oral doses of Compound 1 immediate release capsules comprising Tartrate Hydrate in healthy subjects. Four escalating dosing regimens (3, 6, 12, and 24 mg Compound 1 or matching placebo twice daily for 13 consecutive days and once in the morning on Day 14) were evaluated. Study drug was administered approximately 30 minutes after a standard breakfast (in the morning) or a snack (in the evening). Forty-four healthy subjects participated in this part of the study with 11 subjects per dose group (8:3 Compound 1:placebo ratio). Subjects were confined to the study site and supervised for approximately 18 days.

Study 2—Part 2—Multiple-Dose Evaluation in Subjects with RA

The objective of Part 2 of the multiple dose study was to assess the pharmacokinetics, safety, and tolerability of multiple oral doses of Compound 1 immediate release capsules comprising Tartrate Hydrate in subjects with mild to moderate RA who were on stable methotrexate treatment. This evaluation was designed to enroll approximately 32 subjects randomized in a 1:1:1:1 ratio to one of four parallel twice-daily regimens (6, 12, and 24 mg Compound 1 and placebo). Subjects received study drug for 26 consecutive days (Study Days 3 through 28) and a single morning dose of study drug on Study Day 29. Compound 1 was administered following breakfast for the morning dose and dinner or snack for the evening dose. Subjects were on methotrexate therapy for at least 3 months and on a stable dose of 10 to 25 mg/week of methotrexate for at least 4 weeks prior to the first dose of study drug administered on Study Day 3 and continued their weekly stable dose of methotrexate on Study Days 1, 8, 15, 22 and 29. Subjects were confined to the study site for a total of 10 days—from Day 1 to Day 4 and from Day 27 to Day 31.

Study Participants

Subjects underwent screening procedures within 30 days prior to the initial administration of study drug. Subjects signed a written informed consent prior to the initiation of any screening or study-specific procedures. Subjects were eligible for study participation if they were men or women between 18 and 55 years of age (Study 1 and Study 2—Part 1) or 18 to 75 years of age (Study 2—Part 2); judged to be in good general health based upon the results of medical history, laboratory profile, physical examination, chest x-ray, and 12-lead electrocardiogram (ECG); and their body mass index (BMI) was within 19 to 29 kg/m² (Study 1 and Study 2—Part 1) or within 19 to 39 kg/m² (Study 2—Part 2) at screening. Subjects were considered eligible to participate in Study 2—Part 2 if they had diagnosis of RA based on the 2010 American College of Rheumatology/European League against Rheumatism criteria ≥6 months, have been on methotrexate therapy ≥3 months (and folate or equivalent for at least 2 weeks prior to Study Day 1), on a stable methotrexate dose of 10 to 25 mg/week for at least 4 weeks prior to the first dose of study drug administered on Study Day 3.

In both studies, subjects were excluded if they had any clinically significant abnormalities, infection, major febrile illness, hospitalization, or had any clinically relevant surgical procedure within 30 days prior to the first dose of study drug; had positive test result for hepatitis A virus immunoglobulin M, hepatitis B surface antigen, or hepatitis C virus antibody, or HIV antibodies at Screening; had history or evidence of active or latent tuberculosis; had history of diabetes or lymphoproliferative disease or evidence of immunosuppression (except for use of methotrexate in Study 2—Part 2); or had clinically significant findings at Screening as determined by the principal investigator. Additionally, subjects in Study 2—Part 2 were excluded if they had a history of acute inflammatory joint disease of different origin other than RA or had current or expected need for oral intake of >10 mg prednisone/day or equivalent corticosteroid therapy.

Pharmacokinetic Sampling

In healthy subjects, serial blood samples were collected over 72 hours after single dosing (Study 1) or over 12 hours after the first dose (Study Day 1) and over 72 hours after the last dose (Study Day 14) of study drug (Study 2—Part 1). In subjects with RA, serial blood samples were collected over 48 hours on Study Day 1 for methotrexate assay, over 12 hours following the first Study drug dose on Study Day 3 for Compound 1 assay, over 12 hours following the morning Study drug dose on Study Day 28 for Compound 1 assay, and over 48 hours following the last Study drug dose on Study Day 29 for Compound 1 and methotrexate assays. Pre-dose trough samples were collected prior to the morning dose on Study Days 5, 6, 7, 13, and 14 in Study 2—Part 1 to assess attainment of steady state.

Urine for Compound 1 assay was collected over a 12-hour interval after the last dose was administered on Study Day 14 in Study 2—Part 1 and on Study Days 28 and 29 in Study 2—Part 2. Urine for methotrexate assay was collected for 48 hours on Study Day 1 and Study Day 29.

Plasma and urine concentrations of Compound 1 and methotrexate were determined using validated liquid chromatography method with mass spectrometric detection methods. The lower limits of quantitation (LLOQ) for Compound 1 and methotrexate in plasma were established at 0.0503 ng/mL and 1.00 ng/mL, respectively. The LLOQ for Compound 1 and methotrexate in urine were established at 1.01 ng/mL and 0.0500 pg/mL, respectively. Samples quantified below the LLOQ were reported as zero. For Compound 1 assays, inter-run variability (measured as % coefficient of variation [% CV]) was ≤9.5% for plasma ≤8.4% for urine and the mean absolute bias was ≤6.7% for plasma and ≤5.9% for urine. For methotrexate assay, inter-run variability (% CV) was ≤3.9% for plasma and ≤5.2% for urine and the mean absolute bias was ≤5.4% in plasma and ≤13.1% in urine.

Pharmacokinetic Analyses

Compound 1 and methotrexate pharmacokinetic parameters were determined using non-compartmental analyses with Phoenix software (Version 6.3, Certara. Princeton. NJ. USA). Calculated pharmacokinetic parameters included the maximum observed plasma concentration ($C_{max}$), time to $C_{max}$ ($T_{max}$), trough plasma concentration ($C_{trough}$), the apparent terminal phase elimination rate constant ($\beta$), the terminal phase elimination half-life ($t_{1/2}$), the area under the plasma concentration-time curve (AUC) [from time 0 to time of the last measurable concentration ($AUC_t$), from time 0 to infinity ($AUC_\infty$) for single dosing, and over a 12-hour dosing interval ($AUC_{0-12}$, or $AUC_{12,ss}$) for multiple dosing and the apparent oral clearance (CL/F). Compound 1 functional half-life ($t_{1/2}F$) following multiple dosing was calculated as $\ln(2)/(\ln[C_{max}/C_{trough}]/\tau)$ at steady state, where r is the 12-hour dosing interval (Dutta et al., *Clin. Drug Investig.*, 2006, Vol. 26(12), pp. 681-690). The accumulation ratio ($R_{ac}$) was calculated as the ratio of Compound 1 $AUC_{0-12}$ on Day 14 to Day 1 (Study 2—Part 1) or Day 28 to Day 3 (Study 2—Part 2). The percentage of Compound 1 dose recovered unchanged in urine ($f_e$ %) at steady state was calculated as the amount of Compound 1 recovered in urine over the 0 to 12-hour interval (Au, $_{0-12}$), divided by the administered dose and multiplied by 100. Renal clearance (CLr) was calculated as Au, $_{0-12}/AUC_{0-12}$ at steady state. Methotrexate $f_e$ % was calculated as the amount of methotrexate recovered in urine over the 0 to 48-hour interval (Au, $_{0-48}$), divided by the administered dose and multiplied by 100. CLr of methotrexate was calculated as Au, $_{0-48}/AUC_{0-48}$. The effect of co-administration of methotrexate on Compound 1 exposure was assessed from the ratios of Compound 1 $AUC_{0-12}$ and $C_{max}$ on Study Day 29 to Study Day 28. The effect of Compound 1 on methotrexate exposure was assessed from the ratios of methotrexate $AUC_\infty$ and $C_{max}$ on Study Day 29 to Study Day 1.

Safety and Tolerability Assessment

Safety was evaluated based on assessments of adverse events, vital signs, physical examination, laboratory metrics, and 12-lead electrocardiogram (ECG). All subjects who received at least one dose of study drug were included in the safety analyses. Subjects who were administered placebo were pooled into a single group within each study or study part. Laboratory test values and vital signs measurements that were above or below the reference range were identified. Subjects were followed-up for a total of 7 days in Study 1, 35 days in Study 2—Part 1, and 57 days in Study 2—Part 2. In healthy subjects, clinical adverse events were graded as described in the Guidance for Industry Toxicity Grading Scale for Healthy Adult and Adolescent Volunteers Enrolled in Preventive Vaccine Clinical Trials (September 2007). In subjects with RA, the severity of adverse events was rated by the investigator as mild (transient and easily tolerated by the subject), moderate (causes subject discomfort and interrupts the subject's usual activities), or severe (causes considerable interference with the subject's usual activities and may be incapacitating or life-threatening). One subject in Study 2—Part 2 was randomized to the placebo arm, but received Compound 1 in error on Study Days 10 to 16. Therefore, this subject was included with the Compound 1 cohort for safety assessments Statistical Analyses Dose proportionality for Compound 1 in healthy subjects was tested using the natural logarithms of dose-normalized $C_{max}$ and AUC following single dosing (Study 1) or for steady-state dose-normalized $C_{max}$, $C_{trough}$, and AUC following multiple dosing (Study 2—Part 1) assessments. Attainment of steady-state following multiple doses in healthy volunteers was assessed by testing the logarithmic transformation of Compound 1 morning pre-dose concentrations for Study Days 5, 6, 7, 13, and 14 by repeated measures analysis. Statistical analyses were performed using SAS software (Version 9.3; SAS institute Inc., Cary, NC, USA).

Results

Demographics and Subject Disposition

A total of 56 healthy subjects were enrolled in and completed the single-dose evaluation (Study 1) and 44 healthy subjects were enrolled in and completed the multiple-dose evaluation (Study 2—Part 1). Enrollment in the multiple-dose evaluation in subjects with RA (Study 2—Part 2) was discontinued early due to slow recruitment rate and 14 subjects with RA were actually enrolled and completed this evaluation. No early withdrawals occurred in any of the three evaluations. A summary of demographic data is presented in Table 21A.

Compound 1 pre-dose concentration on Study Day 13 and Study Day 14, indicating that steady-state was achieved by Study Day 13. At steady-state, the median accumulation ratios for Compound 1 $AUC_{0-12}$ were approximately 1.0 over the evaluated dose range (Table 21-C).

In the single dose evaluation, 1 mg dose group was excluded from the statistical analyses for $AUC_\infty$ as the majority of samples collected at the terminal phase were below the limit of quantitation for all subjects. There was no statistically significant difference in dose-normalized $C_{max}$ between the highest (48 mg) and the lowest (1 mg) dose of Compound 1, and there was no statistically significant trend

TABLE 21A

Baseline Demographics of Study Participants

| | Study 1 | | Study 2 - Part 1 | | Study 2 - Part 2 | |
|---|---|---|---|---|---|---|
| | Compound 1 N = 42 | Placebo N = 14 | Compound 1 N = 32 | Placebo N = 12 | Compound 1 N = 11 | Placebo N = 3 |
| Mean Age, years ± SD | 31.0 ± 9.8 | 32.4 ± 8.6 | 33.3 ± 9.9 | 30.7 ± 5.0 | 59.3 ± 8.3 | 58.7 ± 14.3 |
| Mean Weight, kg ± SD | 74.7 ± 10.1 | 74.3 ± 8.8 | 74.1 ± 9.9 | 78.4 ± 13.6 | 78.5 ± 14.9 | 62.5 ± 6.9 |
| Mean Height, cm ± SD | 171 ± 8.9 | 171 ± 10.2 | 172 ± 7.9 | 177 ± 6.2 | 171 ± 7.3 | 165 ± 9.9 |
| Sex, number (%) | 35 males (83.3%), 7 females (16.7%) | 11 males (79%), 3 females (21%) | 29 males (91%), 3 females (9%) | 12 males (100%) | 6 males (54.5%), 5 females (45.5%) | 3 females (100%) |
| Race, number (%) | 30 White (71%), 10 Black (24%), 1 Asian (2%), 1 Other (2%) | 11 White (79%), 3 Black (21%) | 23 White (72%), 9 Black (28%) | 9 White (75%), 2 Black (17%), 1 Asian (8%) | 10 White (91%), 1 Black (9%) | 2 White (67%), 1 Asian (33%) |

Compound 1 Single- and Multiple-Dose Pharmacokinetics in Healthy Volunteers

Compound 1 plasma concentrations reached peak levels at approximately 1 to 2 hours after oral dosing of the immediate release capsule formulation. Compound 1 plasma concentrations declined bi-exponentially afterwards with a terminal elimination $t_{1/2}$ of approximately 6 to 15 hours after single dosing (Table 21-B) and of 8 to 16 hours after multiple twice-daily dosing (Table 21-C). Compound 1 functional half-life, estimated from $C_{max}$ to $C_{trough}$ ratio at steady-state, was approximately 3 hours. After multiple dosing, there was a small but statistically significant (p<0.05) difference between Compound 1 pre-dose concentrations on Study Day 13 (13% lower) compared with Study Day 5. There was no statistically significant difference in for change in the dose-normalized $C_{max}$ values with dose. There was no trend for change in Compound 1 dose-normalized $AUC_\infty$ with doses over the 3 to 36 mg dose range (P>0.05); however, the dose-normalized $AUC_\infty$ following single 48 mg dose was 40% lower than that following 3 mg dose (p<0.05).

Following multiple dosing in healthy subjects, there was no statistically significant difference (p>0.05) in Compound 1 dose-normalized steady-state $C_{max}$, $C_{trough}$, or AUC for the 24 mg twice-daily regimen compared to the 3, 6, or 12 mg twice-daily regimens.

Overall, Compound 1 exposures appeared to be dose proportional particularly over the single dose range of 3 to 36 mg and the multiple dose range of 3 mg to 24 mg BID.

TABLE 21B

Pharmacokinetic parameters (mean ± standard deviation) of Compound 1 after administration of single doses of the immediate release formulation to healthy subjects

| Pharmacokinetic Parameters (Units) | 1 mg Cpd. 1 (N = 6) | 3 mg Cpd. 1 (N = 6) | 6 mg Cpd. 1 (N = 6) | 12 mg Cpd. 1 (N = 6) | 24 mg Cpd. 1 (N = 6) | 36 mg Cpd. 1 (N = 6) | 48 mg Cpd. 1 (N = 6) |
|---|---|---|---|---|---|---|---|
| $C_{max}$ (ng/mL) | 7.72 ± 2.36 | 25.0 ± 6.88 | 38.9 ± 9.96 | 82.9 ± 12.1 | 158 ± 18.4 | 277 ± 44.5 | 314 ± 81.9 |
| $T_{max}$ (h)[a] | 1.3 (1.0-2.0) | 1.0 (1.0-1.5) | 1.0 (1.0-1.5) | 1.3 (0.5-1.5) | 1.3 (1.0-1.5) | 0.8 (0.5-1.0) | 1.0 (0.5-1.0) |
| $t_{1/2}$ (h)[b] | — | 5.9 ± 2.4 | 11.0 ± 3.4 | 12.1 ± 7.4 | 14.5 ± 9.0 | 6.4 ± 4.0 | 12.2 ± 3.5 |
| $AUC_t$ (ng · h/mL) | 29.8 ± 5.78 | 102 ± 27.5 | 159 ± 37.5 | 329 ± 48.9 | 612 ± 78.6 | 909 ± 201 | 1030 ± 174 |
| $AUC_\infty$ (ng · h/mL) | — | 103 ± 27.6 | 160 ± 37.6 | 331 ± 49.8 | 615 ± 78.1 | 911 ± 202 | 1040 ± 174 |
| CL/F (L/h) | — | 31.3 ± 10.4 | 39.1 ± 9.06 | 37.0 ± 6.32 | 39.5 ± 4.92 | 41.1 ± 8.35 | 47.6 ± 8.97 |

[a]Median (range)
[b]Terminal elimination half-life, presented as harmonic meat ± pseudo-standard deviation

TABLE 21C

Steady-State (Day 14) Pharmacokinetic parameters (mean ± standard deviation) of Compound 1 following administration of multiple twice-daily oral doses of the immediate release formulation to healthy subjects

| PK Parameters (Units) | 3 mg BID (N = 8) | 6 mg BID (N = 8) | 12 mg BID (N = 8) | 24 mg BID (N = 8) |
|---|---|---|---|---|
| $C_{max}$ (ng/mL) | 18.5 ± 5.41 | 28.8 ± 3.67 | 57.6 ± 11.0 | 119 ± 16.9 |
| $T_{max}$ (h) | 1.5 (0.5-3.0) | 2.0 (1.5-3.0) | 2.3 (1.5-3.0) | 1.8 (1.5-2.0) |
| $AUC_{0-12}$ (ng · h/mL) | 78.3 ± 70.3 | 138 ± 16.7 | 271 ± 52.7 | 529 ± 62.6 |
| $C_{trough}$ (ng/mL) | 1.46 ± 0.50 | 2.29 ± 0.41 | 4.54 ± 1.55 | 9.50 ± 2.57 |
| $t_{1/2}$ (h)[a] | 15.7 ± 10.6 | 13.6 ± 8.5 | 7.6 ± 4.8 | 8.0 ± 4.2 |
| $t_{1/2}F$ (h)[b] | 3.2 ± 0.4 | 3.3 ± 0.3 | 3.2 ± 0.5 | 3.3 ± 0.4 |
| CL/F (L/h) | 40.7 ± 10.6 | 43.9 ± 5.4 | 45.5 ± 8.04 | 46.1 ± 6.44 |
| $CL_r$ (L/h) | 7.5 ± 2.34 | 8.1 ± 1.8 | 9.7 ± 2.3 | 8.6 ± 2.8 |
| $f_e$ (%) | 19 ± 5 | 19 ± 6 | 21 ± 4 | 19 ± 6 |
| $R_{ac}\,AUC_{0-12}$[c] | 1.1 (0.9-1.2) | 1.0 (0.9-1.2) | 1.0 (0.9-1.1) | 1.0 (0.8-1.3) |

[a]Terminal elimination half-life.
[b]Functional half-life calculated from $C_{max}$ to $C_{trough}$ ratio at steady state.
[c]Accumulation ratio for $AUC_{0-12}$.

Compound 1 Multiple-Dose Pharmacokinetics in Subjects with RA

In subjects with RA who were on stable doses of methotrexate, Compound 1 plasma concentrations reached peak levels at 1 to 2 hours after dosing (Table 21D). The mean terminal elimination half-life of Compound 1 ranged from approximately 10 to 14 hours, and the functional half-life was approximately 4 hours. The median accumulation ratio of Compound 1 after 26 days of twice-daily dosing ranged from 0.8 to 1.4. The median ratio of Compound 1 $C_{max}$ and $AUC_{0-12}$ when administered with methotrexate (on Study Day 29) to those when administered without methotrexate (Study Day 28) ranged from 0.9 to 1.2, indicating a lack of significant effect of methotrexate co-administration on Compound 1 pharmacokinetics. The ratio of Compound 1 exposure in subjects with rheumatoid arthritis to Compound 1 exposure in healthy subjects ranged from 1.1 (24 mg twice-daily dose) to 1.6 (6 mg twice-daily dose) for $AUC_{0-12}$ and from 1.2 (24 mg twice-daily dose) to 1.7 (6 mg twice-daily dose) for $C_{max}$.

TABLE 21D

Pharmacokinetic parameters (mean ± standard deviation) of Compound 1 following administration of multiple twice-daily oral doses to subjects with mild to moderate rheumatoid arthritis on stable doses of methotrexate

| PK Parameters (Units) | Compound 1 6 mg BID (N = 4) | | Compound 1 12 mg BID (N = 3) | | Compound 1 24 mg BID (N = 3) | |
|---|---|---|---|---|---|---|
| Study Day | Day 28 | Day 29 | Day 28 | Day 29 | Day 28 | Day 29 |
| $C_{max}$ (ng/mL) | 47.1 ± 7.47 | 42.4 ± 8.85 | 71.1 ± 14.8 | 60.8 ± 4.01 | 129 ± 39.0 | 154 ± 39.5 |
| $T_{max}$ (h) | 1.5 (1.0-2.0) | 2.0 (1.5-3.0) | 2.0 (1.5-2.0) | 2.0 (1.5-3.0) | 1.5 (1.5-4.0) | 1.0 (0.5-1.5) |
| $AUC_{0-12}$ (ng · h/mL) | 231 ± 48.5 | 215 ± 49.2 | 334 ± 49.4 | 338 ± 14.5 | 637 ± 143 | 665 ± 89.8 |
| $C_{trough}$ (ng/mL) | 5.81 ± 3.06 | 4.63 ± 3.48 | 5.41 ± 0.98 | 6.44 ± 1.09 | 15.3 ± 1.86 | 14.9 ± 4.37 |
| $t_{1/2}$ (h)[a] | — | 9.5 ± 3.6 | — | 14.4 ± 5.3 | — | 11.5 ± 7.6 |
| $t_{1/2}F$ (h)[b] | — | 3.5 ± 0.9 | — | 3.7 ± 0.2 | — | 3.6 ± 0.1 |
| CL/F (L/h) | 26.7 ± 4.96 | 29.0 ± 5.92 | 36.4 ± 5.44 | 35.6 ± 1.56 | 39.1 ± 9.79 | 36.5 ± 4.70 |
| $CL_r$ (L/h) | 6.94 ± 4.04 | 4.93 ± 2.41 | 6.27 ± 2.79 | 4.96 ± 3.34 | 6.31 ± 0.96 | 8.60 ± 1.30 |
| $f_e$ (%) | 25 ± 14 | 16 ± 5 | 17 ± 8 | 14 ± 10 | 17 ± 5 | 24 ± 2 |
| $R_{ac}\,AUC_{0-12}$[d] | 1.4 (1.0-1.8) | — | 1.2 (0.9-1.4) | — | 1.3 (1.2-1.4) | — |
| Day 29/Day 28 $AUC_{0-12}$ Ratio[c] | | 0.9 (0.9-1.0) | | 1.0 (0.9-1.1) | | 1.0 (0.9-1.2) |

[a]Terminal elimination half-life.
[b]Functional half-life calculated from Cmax to Ctrough ratio at steady state.
[c]Accumulation ratio for $AUC_{0-12}$.
Harmonic mean ± pseudo-standard deviation are presented for $t_{1/2}$ and $t_{1/2}F$.
Median and range (minimum to maximum) are presented for $T_{max}$, accumulation ratios, and Day 29/Day 28 ratios.
BID: twice-daily Effect of Compound 1 Co-Administration on Methotrexate Exposure Pharmacokinetic parameters of methotrexate when administered before (Study Day 1) and after administration of multiple doses of Compound 1 (Day 29) are summarized in Table 21E. Since methotrexate was administered weekly and has a short plasma half-life, no plasma accumulation was expected with repeated dosing and $AUC_\infty$ was calculated for both Days 1 and 29. The median ratio for methotrexate $AUC_\infty$ and $C_{max}$ when administered after multiple doses of Compound 1 (on Study Day 29) to that when administered without Compound 1 (on Study Day 1) ranged from 0.9 to 1.1 and from 0.8 to 1.2, respectively. There was no observed change in methotrexate dose-normalized $AUC_\infty$ when administered with or without Compound 1.

cebo, and between healthy subjects and subjects with RA on background treatment of methotrexate, though the number of subjects with RA was limited. There was no evidence of

TABLE 21E

Pharmacokinetic parameters (mean ± standard deviation) of methotrexate following administration to subjects with RA alone (Day 1) or concomitant with Compound 1 (Day 29)

| PK Parameters (Units) | Compound 1 6 mg BID Group (N = 4) | | Compound 1 12 mg BID Group (N = 3) | | Compound 1 24 mg BID Group (N = 3) | | Placebo (N = 4) | |
|---|---|---|---|---|---|---|---|---|
| | Methotrexate Dose (mg) | | | | | | | |
| | 16.3 ± 6.6 | | 14.2 ± 5.2 | | 14.2 ± 1.4 | | 17.5 ± 5.0 | |
| | Day 1 | Day 29 | Day 1 | Day 29 | Day 1 | Day 29 | Day 1 | Day 29 |
| $C_{max}$ (ng/mL) | 245 ± 63.6 | 228 ± 23.0 | 278 ± 44.0 | 255 ± 99.9 | 196 ± 58.6 | 256 ± 29.3 | 318 ± 138 | 354 ± 182 |
| $T_{max}$ (h) | 2.5 (1.5-6.0) | 1.8 (1.0-2.0) | 3.0 (2.0-3.0) | 2.5 (2.5-3.0) | 3.0 (0-3.0) | 2.5 (2.0-3.0) | 1.8 (1.5-3.0) | 1.8 (1.0-4.0) |
| $AUC_\infty$ (ng·h/mL) | 1470 ± 494 | 1490 ± 424 | 1670 ± 393 | 1780 ± 791 | 966 ± 365 | 1370 ± 324 | 1640 ± 470 | 1590 ± 458 |
| $t_{1/2}$ (h)[a] | 4.0 ± 2.6 | 4.7 ± 1.3 | 4.0 ± 0.3 | 4.2 ± 0.6 | 3.0 ± 1.1 | 3.1 ± 1.3 | 3.9 ± 0.5 | 3.8 ± 0.3 |
| CL/F (L/h) | 11.8 ± 6.43 | 10.9 ± 3.43 | 8.36 ± 1.28 | 8.14 ± 1.03 | 16.9 ± 8.89 | 10.6 ± 1.61 | 11.2 ± 3.81 | 11.3 ± 2.66 |
| $CL_r$ (L/h) | 6.63 ± 3.79 | 5.43 ± 2.02 | 6.13 ± 1.93 | 4.78 ± 2.28 | 7.46 ± 0.70 | 6.43 ± 0.75 | 4.32 ± 1.12 | 5.80 ± 1.08 |
| $f_e$ (%) | 58 ± 29 | 51 ± 20 | 74 ± 19 | 59 ± 26 | 54 ± 25 | 63 ± 4 | 45 ± 25 | 57 ± 26 |
| $AUC_\infty$ Ratio[b] | — | 1.0 (0.8-1.4) | — | 0.9 (0.9-1.3) | — | 1.1 (1.0-3.1) | — | 0.9 (0.8-1.2) |

[a]Terminal elimination half-life presented as harmonic mean ± pseudo-standard deviation.
[b]Ratio of methotrexate exposure ($AUC_\infty$) on Study Day 29 to that on Study Day 1; median and range (minimum to maximum) are presented.

Safety and Tolerability

Across all three evaluations, a total of 74 healthy subjects and 11 subjects with RA received Compound 1 and a total of 26 healthy subjects and 3 subjects with RA received placebo. There were no dose-limiting toxicities or safety concerns with Compound 1 from the single doses up to 48 mg or multiple doses up to 24 mg twice daily. Notably, the safety and tolerability profile of Compound 1 was comparable between subjects who received Compound 1 or placebo, and between healthy subjects and subjects with RA on background treatment of methotrexate, though the number of subjects with RA was limited. There was no evidence of a dose or time dependency for the incidence of adverse events in either healthy subjects or subjects with RA. There were no study discontinuations due to adverse events, no serious adverse events and no clinically significant changes in ECG parameters, or laboratory metrics in any of the subjects or treatment groups. The maximum tolerated dose of Compound 1 was not reached in the single or multiple dose studies. Adverse events that were reported by at least two subjects in Compound 1 or placebo groups in Study 1 or Study 2—Part 1 are presented in Table 21F.

TABLE 21F

Treatment-emergent adverse events reported by two or more healthy subjects administered Compound 1 or placebo in the single and multiple ascending dose evaluations

| | Single doses (Study 1) | | | | | | | |
|---|---|---|---|---|---|---|---|---|
| System Organ Class MedDRA Preferred Term | Placebo (N = 14) | 1 mg Compound 1 (N = 6) | 3 mg Compound 1 (N = 6) | 6 mg Compound 1 (N = 6) | 12 mg Compound 1 (N = 6) | 24 mg Compound 1 (N = 6) | 36 mg Compound 1 (N = 6) | 48 ng Compound 1 (N = 6) | Total Compound 1 (N = 42) |
| Any Adverse Event | 3 (21.4%) | 0 | 0 | 1 (16.7%) | 0 | 1 (16.7%) | 2 (33.3%) | 2 (33.3%) | 6 (14.3%) |
| Nervous System Disorders | | | | | | | | 0 | |
| Headache | 0 | 0 | 0 | 0 | 0 | 0 | 0 | 2 (33.3%) | 2 (4.8%) |
| Presyncope* | 0 | 0 | 0 | 1 (16.7%) | 0 | 1 (16.7%) | 0 | 0 | 2 (4.8%) |

| | Multiple twice-daily doses (Study 2 - Part 1) | | | | |
|---|---|---|---|---|---|
| System Organ Class MedDRA Preferred Term | Placebo (N = 12) | 3 mg Compound 1 (N = 8) | 6 mg Compound 1 (N = 8) | 12 mg Compound 1 (N = 8) | 24 mg Compound 1 (N = 8) | Total Compound 1 (n = 32) |
| Any Adverse Event Gastrointestinal Disorders | 7 (58.3%) | 2 (25.0%) | 2 (25.0%) | 3 (37.5%) | 4 (50.0%) | 11 (34.4%) |
| Abdominal Discomfort | 3 (25.0%) | 0 | 0 | 0 | 0 | 0 |
| Abdominal Pain | 0 | 0 | 1 (12.5%) | 0 | 1 (12.5%) | 2 (6.3%) |
| Diarrhoea | 1 (8.3%) | 0 | 1 (12.5%) | 1 (12.5%) | 0 | 2 (6.3%) |

TABLE 21F-continued

Treatment-emergent adverse events reported by two or more healthy subjects administered Compound 1 or placebo in the single and multiple ascending dose evaluations

| Infections and Infestations | | | | | | |
|---|---|---|---|---|---|---|
| Nasopharyngitis | 2 (16.7%) | 1 (12.5%) | 1 (12.5%) | 0 | 0 | 2 (6.3%) |
| Nervous System Disorders | | | | | | |
| Headache | 2 (16.7%) | 0 | 2 (25.0%) | 2 (25.0%) | 1 (12.5%) | 5 (15.6%) |

*The two cases of presyncope were associated with venipuncture.

In healthy subjects who were administered single doses of either Compound 1 (1, 3, 6, 12, 24, 36, and 48 mg) or placebo in Study 1, 14.3% (6/42) and 21.4% (3/14) of subjects, respectively, reported to have one or more treatment-emergent adverse events (TEAEs). All TEAEs were assessed as mild in severity. The adverse events reported by more than one subject who received Compound 1 were headache and presyncope (1 subject in 6 mg and 1 subject in 24 mg dose group) in association with venipuncture (see Table 21F).

In healthy subjects who were administered multiple doses of Compound 1 (3, 6, 12, and 24 mg BID) or placebo for 14 consecutive days in Study 2—Part 1, 34% (11/32) and 58% (7/12) of subjects, respectively, reported one or more TEAEs. The overall incidences of TEAEs were numerically higher at higher doses of Compound 1; 2 (25.0%), 2 (25.0%), 3 (37.5%) and 4 (50%) subjects in the 3 mg, 6 mg, 12 mg and 24 mg dose groups, respectively; however, these rates were lower than that was observed in the placebo group (58%). All TEAEs were reported as mild in severity. Four events occurred in at least two subjects who received Compound 1: headache, abdominal pain, diarrhea, and nasopharyngitis; three of these events also occurred in subjects who received placebo: headache, diarrhea and nasopharyngitis (Table 21F).

There were no clinically significant changes in any hematologic parameters after multiple-dose administration in healthy subjects for 14 days. With increasing doses of Compound 1, there were statistically significant downward trends in mean levels of hemoglobin, RBCs, WBCs and neutrophils; however, even at the 24 mg dose, the mean levels were within the normal reference range. The mean changes in reticulocyte counts with increasing dose of Compound 1 compared to placebo were not statistically significant, suggesting no evidence of a dose related effect on reticulocyte counts after 14 days of Compound 1 treatment. Total cholesterol, HDL-cholesterol, and LDL-cholesterol showed a statistically significant upward trend with increasing Compound 1 dose compared with placebo; however, the final mean values for these lipid parameters in the Compound 1 dose groups remained within the normal reference range.

Subjects with mild to moderate RA on stable background doses of methotrexate, in Study 2—Part 2, were administered multiple doses of Compound 1 (a total of 11 subjects) or placebo (a total of 3 subjects). Five subjects in the Compound 1 dose groups and two subjects in the placebo group experienced at least one TEAE. In the Compound 1 dose groups, 7 TEAEs were reported: nausea, vomiting, viral gastroenteritis, upper respiratory tract infection, post-traumatic neck syndrome, back pain, and insomnia. All TEAEs were reported by the investigators as mild or moderate in severity, and no adverse event was reported in more than one subject in any treatment group. There was no evidence of a dose relationship with any of these events. Notably, as these subjects with RA received a stable background dose of methotrexate, there were no changes in hepatobiliary metrics for those receiving Compound 1. There was also no evidence of a Compound 1 dose-related effect on renal function in these subjects with RA, as evaluated by serum creatinine and blood urea nitrogen values.

Discussion

Compound 1 was well-tolerated after single doses up to 48 mg and multiple twice daily doses up to 24 mg of Compound 1 immediate-release formulation. All adverse events occurred after single- or multiple-dose administrations were mild to moderate in nature with comparable frequency between subjects who received Compound 1 or placebo. No anemia, serious infections, or clinically significant changes in hematology, hepatobiliary or renal laboratory metrics was observed with 14 days of repeated Compound 1 dosing in healthy volunteers or 27 days of dosing in RA patients.

Compound 1 displayed multi-exponential plasma disposition with a functional half-life of 3 to 4 hours across the dose range of 3 to 24 mg twice daily of the immediate-release formulation in healthy volunteers and subjects with RA. The terminal elimination half-life of Compound 1 ranged from 6 to 16 hours across the different dose levels. However, given the multi-exponential disposition of Compound 1, the longer terminal half-life is less relevant clinically than the functional half-life (Dutta et al., *Clin. Drug Investig.*, 2006, Vol. 26(12), pp. 681-690; Sabin, *Pharm. Res.*, 2008, Vol. 25(12), pp. 2869-77). Consistent with a shorter functional half-life, there was no accumulation across the evaluated 3 to 24 mg twice-daily dose range. While there are no solid clinical data to suggest that extended exposure is needed for efficacy of JAK inhibitor (i.e. to determine whether efficacy is concentration driven or AUC driven), the pharmacokinetic profile of the immediate-release formulation of Compound 1 appears to be generally more suited for twice-daily dosing than for once-daily dosing.

Compound 1 displayed dose-proportional pharmacokinetics particularly over the 3 to 36 mg dose range, which encompasses the dose ranges evaluated in Phase 2b clinical trials in RA (3 to 18 mg BID and 24 mg QD), or that is currently being evaluated in Crohn's disease (3 to 24 mg BID).

It has been reported previously that the JAK inhibitors tofacitinib and filgotinib have higher exposures in subjects with RA than those in healthy volunteers (see FDA, "Clinical Pharmacology and Biopharmaceutics Review(s)—Tofacitinib", Application Number 203214Orig1s000, Center for Drug Evaluation and Research, 2011; Namour et al., *Clin. Pharmacokinet.*, 2015, Vol. 54, pp. 859-874). Compound 1's apparent oral clearance was 23% lower in subjects with RA (leading to approximately 30% higher exposure), on average across all dose groups, compared to healthy subjects. In general, older subjects are expected to have lower renal and metabolic capacity compared to younger subjects (Mangoni, *Br. J Clin. Pharmacol.*, 2004, Vol. 57(1), pp. 6-14). RA subjects who received multiple-doses of Compound 1 were 26 years older, on average, than the healthy subjects evaluated in Study 2 (Table 21A); therefore, age cannot be excluded as potential contributor to the apparently 30% higher exposure of Compound 1 in RA subjects than in healthy subjects.

Methotrexate remains the first line therapy for treatment of RA and is often used with biologic DMARDs or in combination with other csDMARDs (see Ma, et al., *Rheumatology* (Oxford), 2010, Vol. 49(1), pp. 91-8; Singh, et al., *Arthritis Care Res.* (Hoboken), 2012, Vol. 64(5), pp. 625-39; Smolen, et al., *Ann. Rheum. Dis.*, 2014, Vol. 73(3), pp. 492-509). Therefore, at least in a subset of the RA patients, it is expected that Compound 1 will be added to the first line therapy, methotrexate; thus, it was important to confirm a lack of any potential interaction between Compound 1 and methotrexate. The ratios of Compound 1 AUC and $C_{max}$ values when administered with methotrexate to those when administered alone indicate lack of significant effect of methotrexate on Compound 1 (Table 21D). Similarly, Compound 1 did not have any significant effect on methotrexate exposures (Table 21E). This was consistent with the observed safety and tolerability profiles in these two populations.

In summary, Compound 1 displayed favorable safety and tolerability profiles over single doses up to 48 mg and multiple doses up to 24 mg twice daily for 14 days in healthy subjects and for 27 days in subjects with RA. Compound 1 demonstrated a pharmacokinetic profile suitable for twice-daily dosing with the immediate release formulation. There was no pharmacokinetic interaction between methotrexate and Compound 1 and there was no accumulation of Compound 1 with repeated administration.

Example 32: Treatment of Moderately to Severely Active Rheumatoid Arthritis in Patients Who have Inadequately Responded to or are Intolerant to Anti-TNF Therapy The following example briefly describes the results of a Phase 2b, 12-week, randomized, double-blind, parallel-group, placebo-controlled study in which adult subjects with moderately to severely active rheumatoid arthritis (RA) who have inadequately responded to or who are intolerant to an anti-tumor necrosis factor (TNF) therapy were treated with Compound 1.

The study was conducted in accordance with the International Conference on Harmonisation guidelines, applicable regulations, and the principles of the Declaration of Helsinki. The study protocol was approved by an independent ethics committee or institutional review board. All patients provided written informed consent before participating in any study-related procedures.

Participants

Adult men and women aged 18 years or older, who had been diagnosed with RA and fulfilled either the 1987 revised American College of Rheumatology (ACR) classification criteria (Arnett et al, *Arthritis Rheum.*, 1988, Vol. 31(3), pp. 315-324) or the 2010 ACR/European League Against Rheumatism (EULAR) criteria (Smolen et al, *Ann. Rheum. Dis.*, 2010, Vol. 69(6), pp. 964-975) were enrolled in the study. Active RA was defined as subjects having ≥6 swollen joints (based on a 66-joint count); ≥6 tender joints (based on a 68-joint count); and high-sensitivity C-reactive protein (hsCRP)>upper limit of normal (ULN=5 mg/L) or seropositivity for both rheumatoid factor (RF) and anti-cyclic citrullinated peptide (CCP). Eligible subjects must have been treated with ≥1 anti-TNF biologic agent for ≥3 months but continued to experience active RA, or discontinued anti-TNF biologic therapy because of intolerance or toxicity. In addition, subjects with prior exposure to non-anti-TNF biologic therapy were allowed to enroll, as long as they had failed ≥1 anti-TNF biologic. All biologic therapies had to be washed out prior to randomization: ≥4 weeks for etanercept, ≥8 weeks for adalimumab, infliximab, certolizumab, and golimumab, >8 weeks for abatacept, >12 weeks for tocilizumab, and >1 year for rituximab. A stable dose of methotrexate (7.5-25 mg/week) was required throughout the study. Key exclusion criteria were prior exposure to a JAK inhibitor, or a need for any immunosuppressant other than methotrexate. Subjects with serum aspartate transaminase (AST) or alanine transaminase (ALT)>1.5×ULN or absolute neutrophil count (ANC)<1,200/µL or absolute lymphocytes count <750/µL at screening were excluded.

Study Design and Treatment

The study was a phase 2b, 12-week, randomized, double-blind, parallel-group, placebo-controlled study conducted at 123 sites, enrolling patients in the United States (176 patients, 64%) and Puerto Rico (11 patients, 4%); Australia and New Zealand (6 patients, 2%); Western Europe including Belgium, Spain and Great Britain (29 patients, 11%); Eastern Europe including Czech Republic, Hungary, Poland (54 patients, 20%).

Subjects were equally randomized to receive oral immediate-release doses of Compound 1 (immediate release capsules comprising Tartrate Hydrate) at 3 mg BID, 6 mg BID, 12 mg BID or 18 mg BID, or matching placebo BID, for 12 weeks. Randomization was performed centrally, according to a blocked randomization schedule, by investigators enrolling via an interactive voice response system. Subjects, caregivers, investigators, joint assessors, and the study team were blinded to the treatment administered. Placebo and Compound 1 capsules were identical in appearance. Subjects should have been taking an oral supplement of folic acid (or equivalent) from four weeks prior to baseline and throughout the study. Subjects were allowed to continue stable doses of methotrexate and non-steroidal anti-inflammatory drugs (NSAIDS), acetaminophen, or oral corticosteroids (equivalent to prednisone ≤10 mg).

Assessments

The primary efficacy endpoint was the proportion of subjects achieving an ACR20 response at Week 12. Secondary endpoints included the proportions of subjects achieving an ACR50/ACR70 response and the proportion of subjects achieving 28-joint count disease activity score based on C-reactive protein (DAS28(CRP))≤3.2, or <2.6, at Week 12. Among the other endpoints were the proportion of subjects achieving low disease activity (LDA) or clinical remission (CR) based on Clinical Disease Activity Index (CDAI) criteria (LDA, CDAI≤10; CR, ≤2.8); change in DAS28 (CRP), and change in the Health Assessment Questionnaire-Disability Index (HAQ-DI) (Anderson et al, *Arthritis Care Res.* (*Hoboken*), 2012, Vol. 64(5), pp. 640-647), including the proportion of subjects achieving minimal clinically important difference (MCID) of −0.22 (Strand et al, *Rheumatology* (*Oxford*), 2006, Vol. 45(12), pp. 1505-1513). A post hoc analysis was performed to determine the proportion of subjects who had a sustained ACR20 response, defined as achievement of the ACR20 criteria at every visit (at Weeks 2, 4, 6, 8 and 12).

Safety was evaluated at each scheduled visit during treatment and for 30 days after the last dose of study drug on the basis of AEs, serious AEs, vital signs, and laboratory tests (hematology, blood chemistry, and urinalysis). Adverse events were coded according to the Medical Dictionary for Regulatory Activities (MedDRA, version 17.1). Descriptions of AE severity and post-baseline laboratory changes were based on the Rheumatology Common Toxicity Criteria v.2.0, developed by the OMERACT Drug Safety Working Group (Woodworth et al., 2007, *J. Rheumatol., Vol.* 34(6), ppl. 1401-14).

Statistical Methods

All efficacy analyses were conducted in modified intent-to-treat population, which consisted of all randomized patients who received ≥1 dose of study drug. For ACR response rates, the last observation carried forward (LOCF) was the primary missing data imputation method and non-responder imputation (NRI) was also used to assess the robustness of the results. For continuous endpoints including DAS28 (CRP). LOCF missing data imputation was implemented; NRI is reported for binary endpoints. Binary endpoints including ACR response rates were analyzed using chi-square test with normal approximation when comparing each Compound 1 treatment group to placebo group. Continuous endpoints were analyzed using an Analysis of Covariance (ANCOVA) model with treatment group as a factor and baseline measurement as the covariate. The Multiple Comparison Procedure and Modeling (MCPMod) method was implemented to detect any non-flat dose-response relationship by evaluating several non-linear dose-response models at the same time. P-values were not corrected for multiple comparisons.

Assuming ACR20 response rates of 25% in the placebo group and 55% in any Compound 1 group, a sample size of 50 subjects per group (250 patients total) was estimated to provide at least 80% power to detect a 30% difference in response rates between the placebo group and a Compound 1 group when using a 1-sided test with an alpha level of 0.05.

Results

Subject Disposition and Baseline Characteristics

Figure 4:
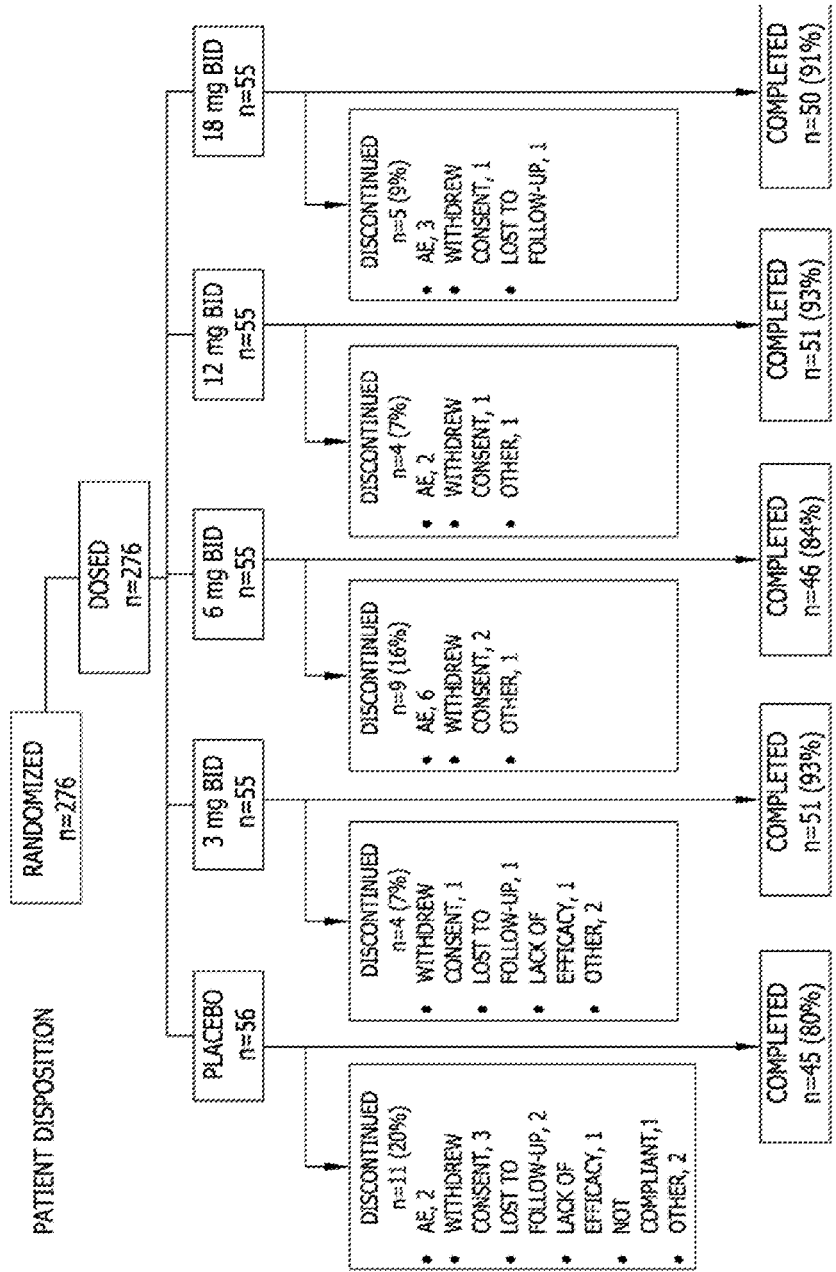
FIG. 4 shows the subject disposition for the study described in Example 55.

In total, 276 subjects were randomized; all received their intended treatment. The overall study completion rate was 88% (FIG. 4). Baseline subject characteristics and disease activity were generally similar among treatment groups (see Table 22A). The mean duration since RA diagnosis was 12 years. Seventy-two percent of subjects had prior exposure to only one anti-TNF, 28% to ≥2 anti-TNFs, and 20% of subjects were also exposed to non-anti-TNF biologics. At baseline, subjects had mean swollen and tender joint counts of 18 (out of 66 joints) and 28 (out of 68 joints), respectively; 60% subjects had an elevated hsCRP and mean DAS28(CRP) was 5.8.

TABLE 22A

Baseline Patient Characteristics and Disease Activity

| | | Compound 1 | | | |
|---|---|---|---|---|---|
| Characteristic | Placebo (n = 56) | 3 mg BID (n = 55) | 6 mg BID (n = 55) | 12 mg BID (n = 55) | 18 mg BID (n = 55) |
| Female, number (%) | 48 (86) | 43 (78) | 43 (78) | 44 (80) | 42 (76) |
| Age, years, mean (SD) | 58 (12) | 57 (13) | 56 (12) | 59 (11) | 57 (12) |
| Duration since RA diagnosis, years, mean (SD) | 12.1 (9.0) | 11.8 (9.4) | 12.3 (10.6) | 12.2 (10.2) | 10.9 (7.7) |
| RF positive, number (%) | 49 (88) | 43 (78) | 45 (82) | 45 (82) | 48 (87) |
| Anti-CCP positive, number (%) | 48 (86) | 45 (82) | 45 (82) | 45 (82) | 47 (86) |
| Used ≥1 prior anti-TNF agent, number (%) | 42 (76) | 39 (71) | 38 (70) | 38 (72) | 38 (69) |
| Used ≥2 prior anti-TNF agents, number (%) | 13 (24) | 16 (29) | 16 (30) | 15 (28) | 17 (31) |
| Used prior non-anti-TNF agents, number (%)* | 9 (16) | 10 (18) | 14 (26) | 14 (26) | 7 (13) |
| Disease activity | | | | | |
| TJC68, mean (SD) | 28 (15) | 28 (15) | 30 (16) | 26 (16) | 26 (15) |
| SJC66, mean (SD) | 19 (12) | 17 (10) | 17 (10) | 17 (10) | 18 (10) |
| HAQ-DI, mean (SD) | 1.6 (0.7) | 1.5 (0.7) | 1.6 (0.7) | 1.6 (0.6) | 1.5 (0.6) |
| DAS28 (CRP), mean (SD) | 5.8 (0.9) | 5.7 (0.9) | 5.9 (0.9) | 5.7 (0.9) | 5.8 (1.0) |
| CDAI, mean (SD) | 41 (12) | 40 (13) | 42 (12) | 40 (12) | 41 (14) |
| hsCRP, mg/L, mean (SD)‡ | 10.1 (13.2) | 11.4 (11.8) | 18.6 (27.4) | 14.4 (23.0) | 14.0 (15.1) |
| hsCRP >ULN,† n (%)‡ | 28 (50) | 35 (64) | 34 (62) | 33 (60) | 35 (64) |

Figure 1A:
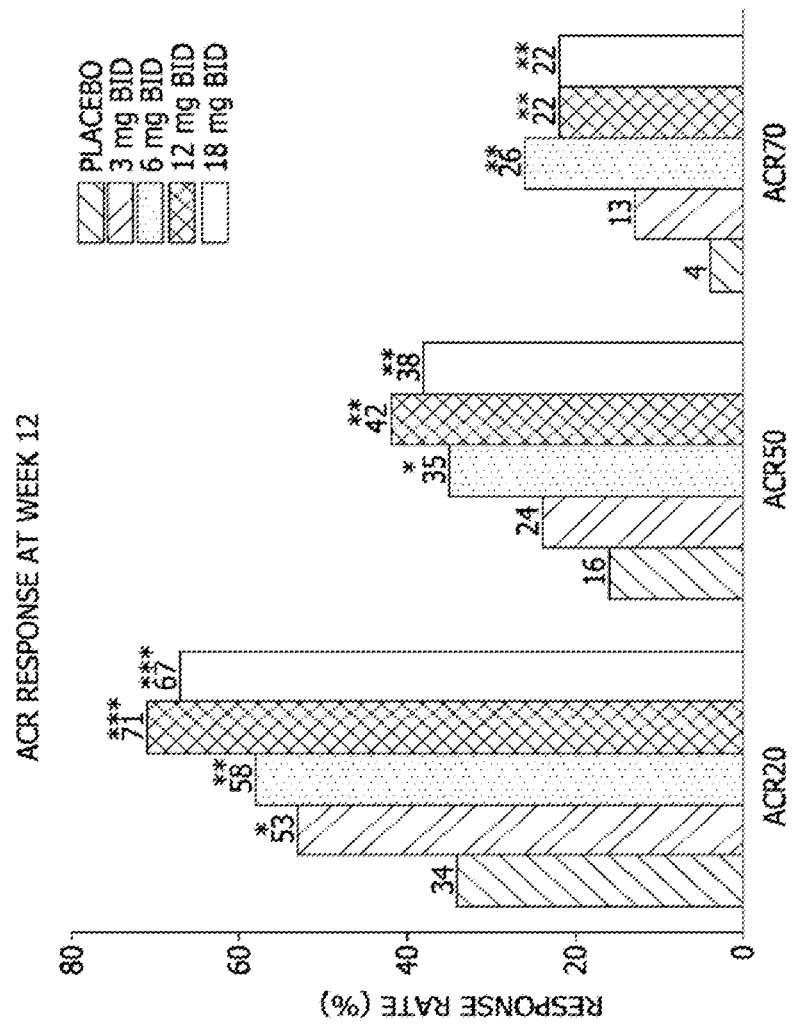
FIG. 1A shows the ACR20, ACR50, and ACR70 response rate at week 12 following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)).
Figure 1B:
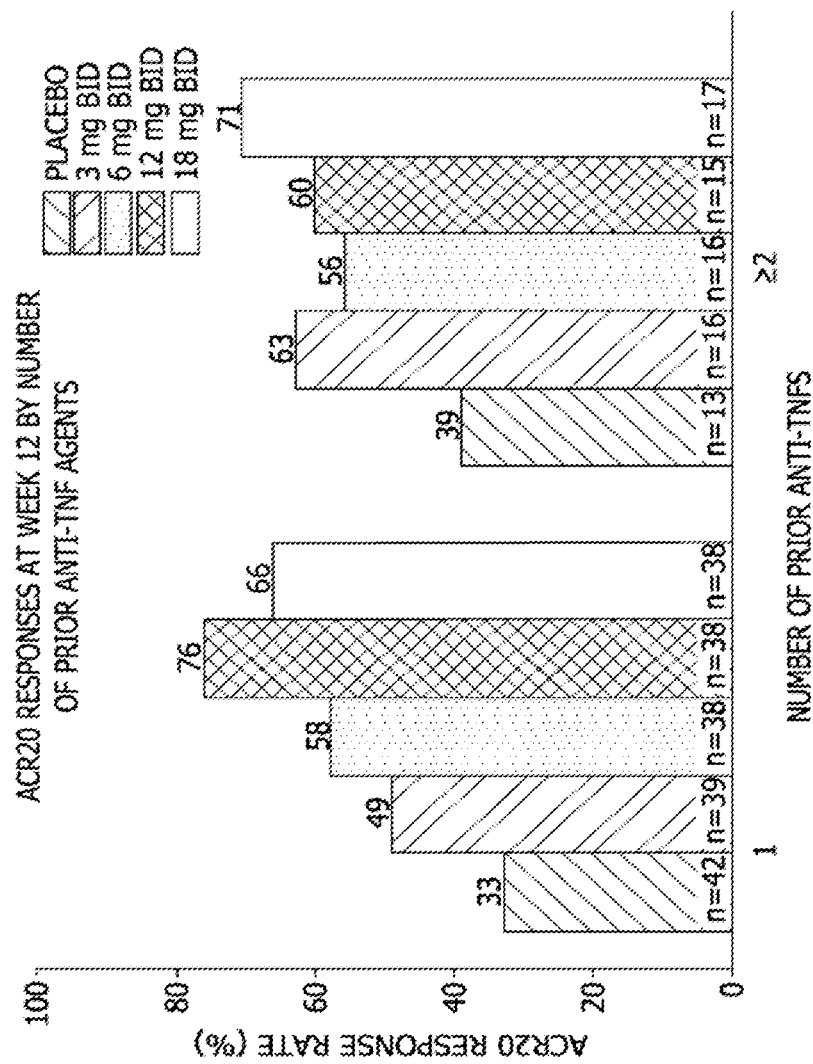
FIG. 1B shows the ACR20 response rate at week 12 in the same population, broken down by number of prior anti-TNF biologic agents.

Abbreviations:
BID-twice daily;
CDAI-Clinical Disease Activity Index;
DAS28 (CRP)-Disease Activity Score-28 joints using C-reactive protein;
HAQ-DI-Health Assessment Questionnaire-Disability index;
hsCRP-high-sensitivity C-reactive protein;
RA-rheumatoid arthritis;
SJC66-swollen joint count using 66 joints;
TJC68-tender joint count using 68 joints;
TNF-tumor necrosis factor;
ULN-upper limit of normal.
*Non-TNF biologic agents.
†ULN = 5 mg/L
‡Subjects with normal hsCRP could be enrolled as long as they were positive for rheumatoid factor and anti-cyclic citrullinated peptide.
Modified intent-to-treat population.
Percentages were calculated using non-missing values Efficacy The primary analysis based on LOCF revealed that an ACR20 response was achieved by 55.6% (P=0.033), 63.5% (P=0.004), 72.7% (P<0.001%), and 70.9% (P<0.001) in subjects treated with Compound 1 at 3, 6, 12, and 18 mg BID, respectively, compared with 35.2% in subjects who received placebo. Analysis based on NRI also demonstrated a statistically significant improvement in ACR20 response rate in subjects who received any dose of Compound 1 compared with those who received placebo (FIG. 1A). A significant dose-response relationship was observed for all doses of Compound 1 (P<0.01). The ACR20 response rates (NRI) at Week 12 were similar among patients who had received 1 versus >2 prior anti-TNFs (FIG. 36B). ACR50 and ACR70 response rates were significantly higher at Compound 1 doses of ≥6 mg BID versus placebo (FIG. 1A).

Figure 2B:
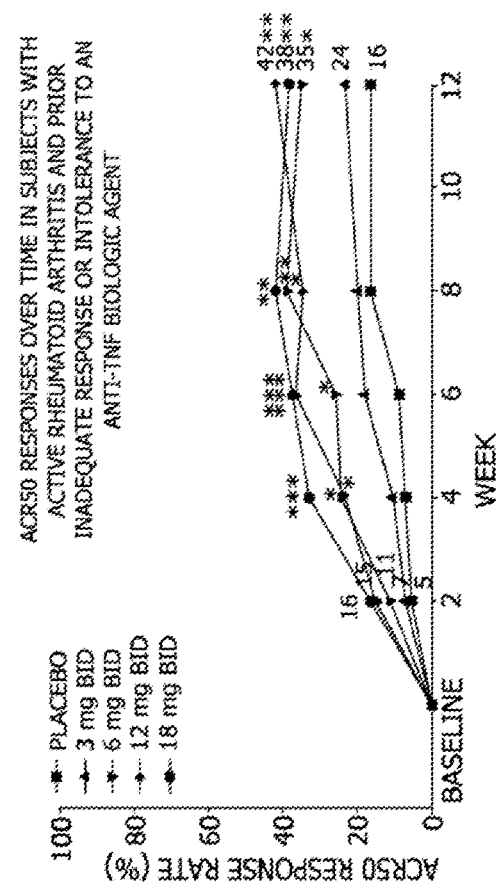
FIGS. 2A-2D show the ACR20 (FIG. 2A), ACR50 (FIG. 2B), and ACR70 (FIG. 2C) responses or DAS28 (CRP) mean change from baseline (FIG. 2D) over time following administration of placebo or various doses of Compound 1 to subjects with active rheumatoid arthritis and prior inadequate response or intolerance to an anti-TNF biologic agent (*P<0.05; P<0.01; *P<0.001 relative to placebo; modified intent-to-treat population (NRI)).
Figure 2A:
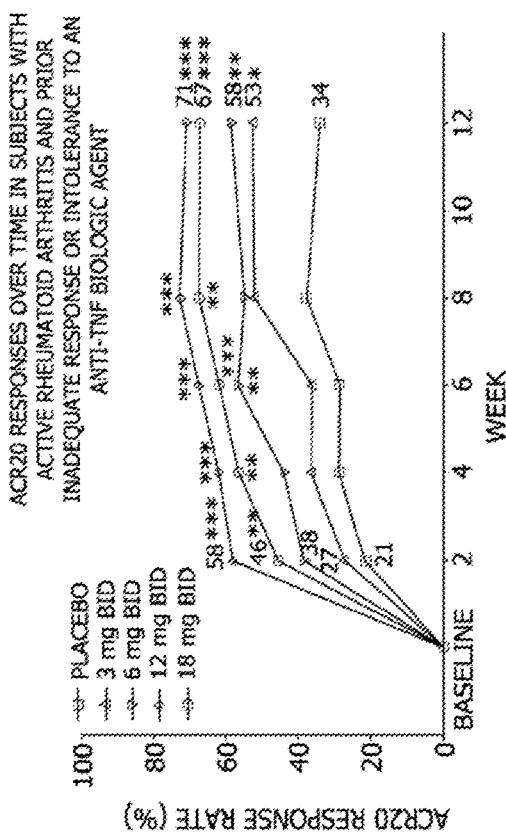
Figure 2C:
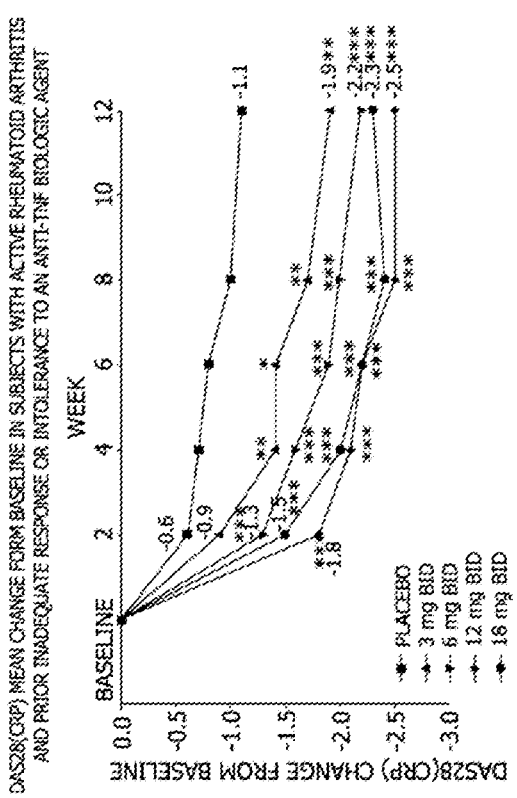
Figure 2D:
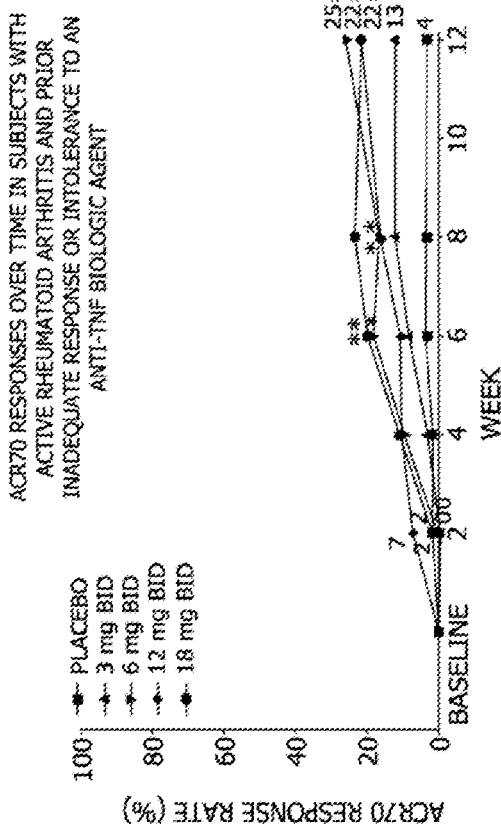

Significant differences in ACR20 response rates (NRI) were observed at the first post-baseline assessment (Week 2) in subjects treated with Compound 1 12 mg BID and 18 mg BID versus placebo (P≤0.007; FIG. 2A); the maximum response rate (71%) was observed with the 12 mg BID dose by Week 8 and plateaued thereafter. Starting at Week 4, there were significantly greater ACR50 response rates with Compound 1 doses ≥6 mg BID versus placebo; the maximum response rate (42%) was observed with the 18 mg BID dose by week 8 and plateaued thereafter (FIG. 2B). Improvements in ACR70 response rates better than placebo were observed starting at Week 6, with peak response of up to 25% at Week 12 (FIG. 2C). A sustained ACR20 response (at every visit between Week 2 through 12, NRI) was achieved by 13%, 22%, 40% and 27% of subjects in the Compound 1 3 mg, 6 mg, 12 mg and 18 mg BID groups respectively, versus 4% in the placebo group. Significant improvements in DAS28(CRP) (LOCF) occurred at the Week 2 assessment with Compound 1 at ≥6 mg BID versus placebo (P<0.001; FIG. 2D).

Figure 2E:
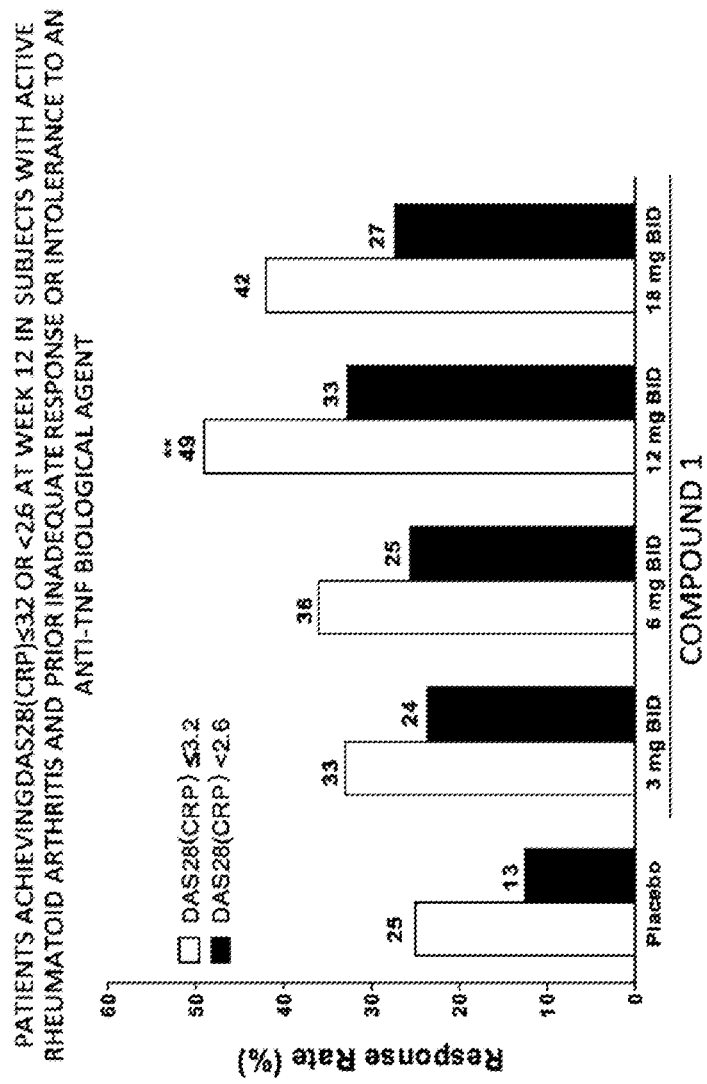
FIG. 2E shows the subjects achieving a DAS28(CRP) score of ≤3.2 or <2.6 at week 12 in the same population.
Figure 2F:
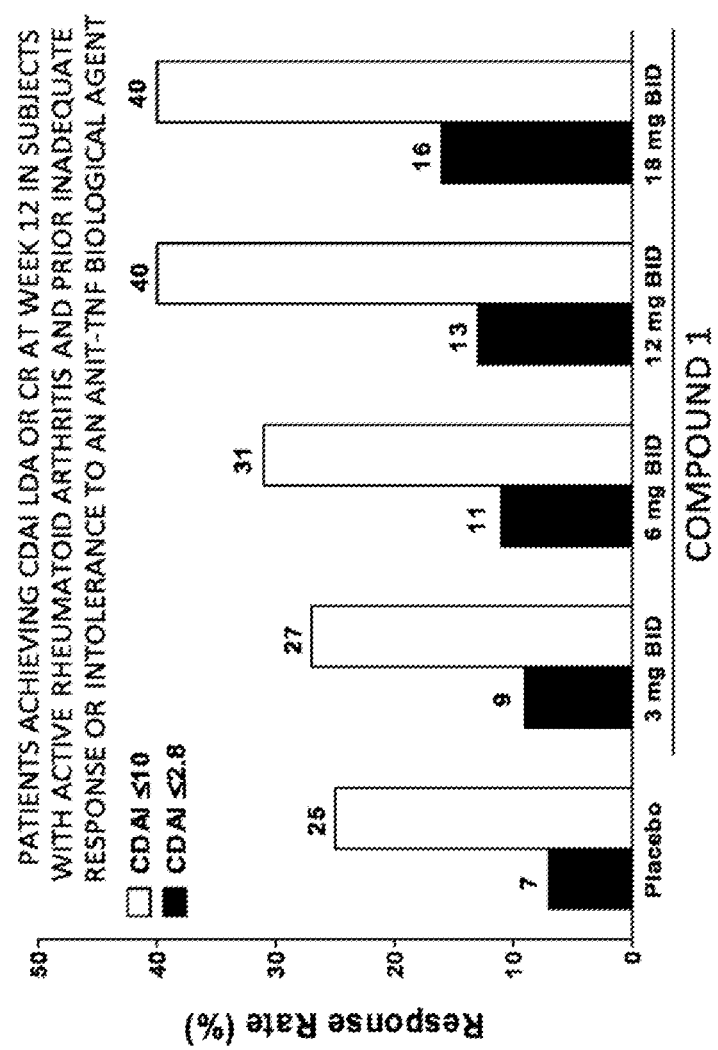
FIG. 2F shows the subjects achieving low disease activity (LDA) or clinical remission (CR) based on clinical disease activity index (CDAI) criteria (LDA is CDAI≤10; CR is CDAI≤2.8) at week 12 in the same population.

A higher percentage of subjects receiving Compound 1 (any dose) achieved DAS28(CRP)≤3.2 or <2.6, versus placebo at Week 12 (NRI, FIGS. 2E and 2F) with the difference being statistically significantly for the Compound 1 12 mg BID group (DAS28(CRP)≤3.2, 49%; DAS28(CRP)<2.6, 33%, P<0.01) compared with placebo (25% and 13%, respectively). Similarly, a higher percentage of patients treated with any dose of Compound 1 achieved CDAI LDA or CR criteria versus placebo at Week 12 (NRI, FIG. 2F). At Week 12, treatment with Compound 1 at 12 mg BID also resulted in statistically significant mean changes from baseline in individual components of the ACR score compared with placebo (Table 22B). In addition, a significantly greater proportion of patients achieved the MCID for HAQ-DI with Compound 1≥6 mg BID (58%-64%) as compared with placebo (44%).

TABLE 22B

Mean Changes From Baseline in ACR Components at Week 12

| ACR Component | Placebo (n = 55) | Compound 1 | | | |
| --- | --- | --- | --- | --- | --- |
| | | 3 mg BID (n = 54) | 6 mg BID (n = 53) | 12 mg BID (n = 55) | 18 mg BID (n = 55) |
| TJC68 | −9.3 | −13.4 | −15.7** | −16.8** | −15.1* |
| | (−12.5, −6.1) | (46.6, −10.1) | (−19.0, −12.5) | (−20.1, −13.6) | (−18.3, −11.9) |
| SJC66 | −6.4 | −9.5 | −9.2 | −10.0* | −9.2 |
| | (−8.7, −4.2) | (−11.8, −7.2) | (−11.4, −6.9) | (−12.3, −7.8) | (−11.5, −7.0) |
| Patient's assessment of pain | −16.5 | −24.7 | −31.4**,† | −36.3*** | −35.0*** |
| | (−23.5, −9.5) | (−31.8, −17.6) | (−38.6, −24.2) | (−43.3, −29.3) | (−42.0, −27.9) |
| PhGA | −29.6‡ | −33.8 | −37.5 | −43.5*** | −42.4** |
| | (−35.3, −23.8) | (−39.4, −28.1) | (−43.2, −31.7) | (−49.1, −37.9) | (−48.0, −36.8) |
| PtGA | −20.0 | −24.2 | −29.9† | −37.4*** | −33.5**,† |
| | (−27.0, −13.0) | (−31.3, −17.1) | (−37.1, −22.6) | (−44.4, −30.4) | (−40.6, −26.5) |
| HAQ-DI | −0.2 | −0.3 | −0.5**,† | −0.5* | −0.5**,† |
| | (−0.4, −0.1) | (−0.4, −0.1) | (−0.6, −0.3) | (−0.6, −0.3) | (−0.7, −0.4) |
| HAQ-DI ≤MCID,§ n (%), 95% CI | 24 (44), 31-57 | 27 (50), 37-63 | 30 (58), 44-71† | 35 (64), 51-76 | 34 (63), 50-76† |
| hsCRP, mg/L | −0.4 | −7.9* | −9.7** | −6.8* | −6.9* |
| | (−4.6, 3.9) | (−12.2, −3.6) | (−14.1, −5.4) | (−11.1, −2.6) | (−11.1, −2.6) |

Data are mean (95% CI), unless otherwise noted.
Abbreviations:
ACR-American College of Rheumatology;
BID-twice daily;
HAQ-DI-Health Assessment Questionnaire-Disability index;
hsCRP-high-sensitivity C-reactive protein;
LOCF-last observation carried forward;
MCID-minimal clinically important difference;
PhGA-physician's global assessment of disease activity;
PtGA-patient global assessment of disease activity;
RA-rheumatoid arthritis;
SJC66-swollen joint count using 66 joints;
TJC68-tender joint count using 68 joints.
*P < 0.05;
**P < 0.01;
***P < 0.001 relative to placebo.
†1 patient with missing data.
‡2 patients with missing data.
§MCID = −0.22.
Modified intent-to-treat population (LOCF).

Safety

The percentage of subjects with any treatment-emergent AEs was numerically higher in a dose-dependent manner for the Compound 1 6, 12 and 18 mg BID treatment groups compared with placebo (Table 22C). Most reported AEs were considered mild to moderate in severity. The most commonly observed AEs were headache, nausea, upper respiratory tract infection, and urinary tract infection. The incidences of serious AEs and severe AEs were low, without an apparent dose-response relationship (Table 22C). Five subjects in the Compound 1 dose groups reported seven serious AEs (3 mg BID; one subject each with pancreatitis and pulmonary embolism, 6 mg BID; one subject with pulmonary embolism and deep vein thrombosis, one patient with TIA and benign prostate hyperplasia, 18 mg BID dose; one subject acute respiratory failure). One subject on placebo experienced a serious AE of bronchiectasis. The overall infection rates were similar for the Compound 1 3—and 6 mg BID dose groups and placebo (20%, 22%, and 23%, respectively), but were higher in the Compound 1 12—and 18 mg BID dose groups (40% and 38%). No serious infections were reported in any of the Compound 1 treatment groups. Herpes zoster occurred in two subjects in the placebo group (4%) and three subjects who received Compound 1 (1%, one case each in the 3-, 12- and 18 mg BID groups; all were isolated to a single dermatome). The two reported events of hepatic disorders in the 18 mg BID dose group and one event in the placebo group were attributed to increased transaminases; none were serious. There was an adjudicated case of transient ischemic attack (left ventricular hypertrophy, classified as mild) in one subject in the Compound 1 6 mg BID group. One patient in the 6 mg BID group had one event each of basal cell carcinoma and squamous cell carcinoma. There were no opportunistic infections or deaths during the study period.

Dose-dependent increases in low-density lipoprotein cholesterol (LDL-C) and high-density lipoprotein cholesterol (HDL-C) were observed; however, the ratios of LDL-C/HDL-C remained the same through Week 12. Of the subjects with normal AST or ALT at baseline, 6-18% of patients on Compound 1 had elevated AST at least twice, and 4-11% had elevated ALT at least twice, versus 2% and 6% on placebo, respectively. The number of these subjects was higher in the higher dose groups. Most of the elevations were Grade 1 (for AST and ALT, ≥21.2-<1.6×ULN) and Grade 2 (1.6-3.0×ULN). One subject each (2%) in the Compound 1 3 mg BID and placebo group (2%) had a Grade 3 ALT elevation (3.0-8.0×ULN). Of the subjects with normal creatinine at baseline, 4-14% subjects on Compound 1 had elevated creatinine at least twice versus none in the placebo group. One subject in the 18 mg BID group had a Grade 3 elevation (≥1.9-53.0×ULN). The elevations did not result in discontinuation of any subject from the study.

Figure 3B:
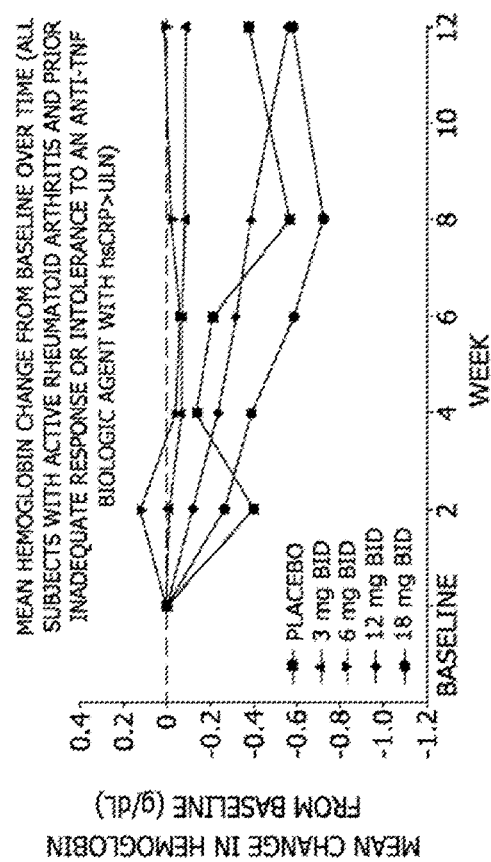
FIG. 3B shows the mean hemoglobin change from baseline over time in subjects with high-sensitivity C-reactive protein (hsCRP) greater than the upper limit of normal (ULN) (normal ranges for hemoglobin: 11.5-15.5 g/dL in females and 13.2-17.0 g/dL in males; ULN for hsCRP=5 mg/L).
Figure 3A:
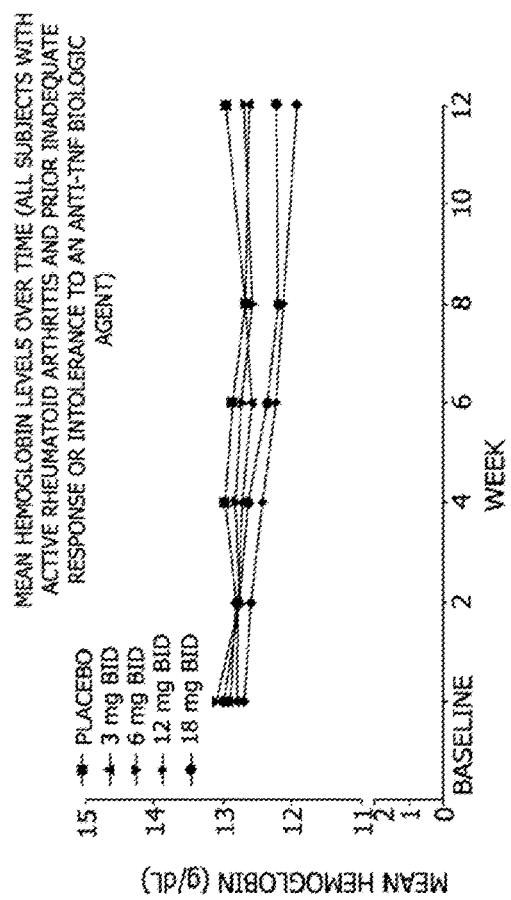
FIG. 3A shows the mean hemoglobin levels overtime for all subjects following administration of placebo or various doses of Compound 1 to subjects with active rheumatoid arthritis and prior inadequate response or intolerance to an anti-TNF biologic agent (safety population with observed data (no imputation of missing values)).

Decreases from baseline in mean hemoglobin levels were observed in a dose-dependent manner with Compound 1, although mean hemoglobin levels remained within the normal range across all dose groups during the study (FIG. 3A). Twenty-six out of 219 subjects (11.9%) in the Compound 1 groups had a Grade 2 decrease in hemoglobin (from 15-20 g/L); 14/219 subjects (6.4%) had a Grade 3 decrease (from 21-29 g/L); 8/219 subjects (3.7%) had a Grade 4 decrease (?30 g/L). The majority (79%) of these decreases were transient (only one occurrence) and one subject discontinued the study due to reported AE of low hemoglobin. However, in subjects with underlying systemic inflammation, as measured by elevated baseline hsCRP, treatment with Compound 1 at 3- or 6 mg BID resulted in mean increases from baseline in hemoglobin levels compared with placebo (FIG. 3B).

Decreases in mean circulating leukocytes, neutrophils (Table 22D) and natural killer (NK) cells were also observed, and one subject discontinued study drug due to leukopenia. Only NK cell reductions appeared to be dose-related. The mean percentage change in NK cells was +16.5±46.6 in the placebo group; a dose-dependent decrease was seen in subjects treated with Compound 1 (−15.8±25.3 in the 3 mg BID group, −18.3±47.4 in the 6 mg BID group, −28.0±37.3 in the 12 mg BID group, and −42.6±31.7 in the 18 mg BID group). At all doses of Compound 1, there was a transient mean increase in total lymphocytes, which returned to baseline level by Week 12, except in the 18 mg dose group. There were two subjects in the 18 mg dose group with Grade 4 lymphocyte reduction; one subject was reported to have vaginal and urinary tract infection, and the other herpes zoster. One subject had a Grade 4 neutrophil reduction, which was not associated with a serious infection.

TABLE 22C

Adverse Events Summary

| AE, n (%) | Placebo (n = 56) | Compound 1 | | | |
|---|---|---|---|---|---|
| | | 3 mg BID (n = 55) | 6 mg BID (n = 55) | 12 mg BID (n = 55) | 18 mg BID (n = 55) |
| Any AE | 25 (45) | 26 (47) | 31 (56) | 37 (67) | 39 (71) |
| Any serious AE | 1 (2) | 2 (4) | 2 (4) | 0 | 1 (2) |
| Any severe AE | 2 (4) | 1 (2) | 2 (4) | 2 (4) | 1 (2) |
| Any AE leading to discontinuation | 2 (4) | 0 | 6 (11) | 2 (4) | 3 (5) |
| Any death | 0 | 0 | 0 | 0 | 0 |
| AEs of special interest | | | | | |
| Infection | 13 (23) | 11 (20) | 12 (22) | 22 (40) | 21 (38) |
| Serious infection | 1 (2) | 0 | 0 | 0 | 0 |
| Cardiovascular event | 0 | 0 | 1 (2)† | 0 | 0 |
| Herpes zoster | 2 (4) | 1 (2) | 0 | 1 (2) | 1 (2) |
| Hepatic disorder* | 1 (2) | 0 | 0 | 0 | 2 (4) |
| Malignancy | 0 | 0 | 1 (2)‡ | 0 | 0 |

Abbreviations:
AE-adverse event;
BID-twice daily,
*AEs as reported by the investigator.
†The cardiovascular event was adjudicated as a transient ischemic attack.
‡One patient with basal cell and squamous cell carcinoma.

TABLE 22D

Mean Change Over Time in Select Hematology Parameters and Incidence of Patients With Abnormalities

| Abnormality, number (%) | Placebo (n = 56)* | Compound 1 | | | |
|---|---|---|---|---|---|
| | | 3 mg BID (n = 55)* | 6 mg BID (n = 55)* | 12 mg BID (n = 55) | 18 mg BID (n = 55) |
| Neutrophils × $10^9$/L | | | | | |
| Grade 2 (1.0-1.4) | 1 (2) | 0 | 3 (6) | 4 (7) | 7 (13) |
| Grade 3 (0.5-0.9) | 0 | 0 | 0 | 2 (4) | 1 (2) |
| Grade 4 (<0.5) | 0 | 0 | 0 | 1 (2) | 0 |

TABLE 22D-continued

Mean Change Over Time in Select Hematology Parameters and Incidence of Patients With Abnormalities

| | | Compound 1 | | | |
|---|---|---|---|---|---|
| Abnormality, number (%) | Placebo (n = 56)* | 3 mg BID (n = 55)* | 6 mg BID (n = 55)* | 12 mg BID (n = 55) | 18 mg BID (n = 55) |
| Lymphocytes × 10$^9$/L | | | | | |
| Grade 2 (1.0-1.4) | 18 (33) | 14 (26) | 19 (35) | 14 (25) | 26 (47) |
| Grade 3 (0.5-0.9) | 9 (16) | 8 (15) | 8 (15) | 11 (20) | 9 (16) |
| Grade 4 (<0.5) | 0 | 1 (2) | 1 (2) | 0 | 2 (4) |

BID-twice daily.
*1 subject with missing data.
Safety population.
Grading based on OMERACT Rheumatology Common Toxicity Criteria v.20

Discussion

In this study, a broad dose range of Compound 1 (dosed up to 18 mg BID) was tested to assess efficacy and safety in subjects with an inadequate response or intolerance to anti-TNF biologic therapies. At all doses, Compound 1 demonstrated rapid and robust efficacy as shown by significantly greater improvements in clinical and functional outcomes compared to placebo. The onset of improvement with Compound 1 treatment was rapid with up to 58% of subjects achieving an ACR20 response as early as 2 weeks after treatment. The proportion of ACR20 responders reached a maximum at 8 weeks and plateaued at 71% through Week 12. Improvements in ACR50 (up to 42%) and ACR70 (up to 25%) response rates in the Compound 1 groups also reached a maximum before Week 12. The speed of the response is in contrast to the 3-6 months observed for many biologic therapies (Bathon, et al., *The New England Journal of Medicine*, 200, Vol. 343(22), pp. 1586-93; Keystone, et al., *Arthritis and Rheumatism*, 2008, Vol. 58(11), pp. 3319-29; Keystone, et al., *Arthritis and Rheumatism*, 2004, Vol. 50(5), pp. 1400-11) and comparable with that observed for other JAK inhibitors, baricitinib and tofacitinib in TNF-IR patients. (Burmester, et al., *Lancet* (London. England), 2013, Vol. 381(9865), pp. 451-60; Genovese, et al., *European League Against Rheumatism*, 2015; 2015). In addition, the ACR20 response rate was comparable between subjects with two or more prior anti TNF therapies and those with only one prior anti-TNF. In general, the maximum efficacy was observed at the 12 mg BID dose.

Despite producing significant clinical improvement in different spectra of RA patients, there are safety concerns with JAK inhibitors, predominantly around impairing the body's ability to fight infections, viral reactivation, as well as altering hematopoietic homeostasis that could link to anemia. The most commonly reported adverse events with JAK inhibitors are infections, herpes zoster, pulmonary tuberculosis, cryptococcal pneumonia and pneumocystis pneumonitis (Fleischmann, et al., *Arthritis Rheumatol.*, 2015, Vol. 67(2), pp. 334-43; Genovese, et al., *Arthritis Rheumatol.*, 2016, Vol. 68(1), pp. 46-55). In addition, increases in total cholesterol, elevation of transaminase and serum creatinine, decreases in neutrophil counts and anemia are also observed. (Burmester, et al., *Lancet* (London, England), 2013, Vol. 381(9865), pp. 451-60; Genovese, et al., *Arthritis Rheumatol.*, 2016, Vol. 68(1), pp. 46-55; Keystone, et al., *Annals of the Rheumatic Diseases*, 2015, Vol. 1 74(2), pp. 33340).

In the current study, a broad range of doses of Compound 1 were tested to assess the selectivity of Compound 1 in vivo. Overall, Compound 1 demonstrated an acceptable safety and tolerability profile at all doses in this refractory RA population. There was no serious infection, although the proportion of overall infection rates was higher at the two highest doses of Compound 1 (12 mg and 18 mg BID). The most commonly observed infections with Compound 1 were bronchitis, upper respiratory, and urinary tract infections. The incidence of herpes zoster was similar in the placebo group (two subjects, 4%) and the Compound 1 treatment groups (three subjects, 1%), and all were non-disseminated.

At the 12 mg BID and 18 mg BID doses, there was a modest decrease in mean hemoglobin levels by Week 12, although the mean hemoglobin levels remained within the normal range. Notably, in subjects with elevated hsCRP at baseline, who were receiving 3 or 6 mg BID Compound 1, mean hemoglobin levels increased compared to placebo treatment, possibly due to a reduction of systemic inflammation while minimizing inhibitory effects on JAK2.

Circulating NK cells, which function as the critical mediator of host immunity against malignancy and infections, were measured as a pharmacodynamic readout of IL-15 inhibition. With increasing doses of Compound 1 there was a greater decrease in mean circulating NK cell counts. At the maximally efficacious dose, 12 mg BID, NK cells decreased by 28% from baseline, with proportionally smaller decreases in NK cells observed at lower doses. Given the fact that IL-15 signaling involves a heterodimer of JAK1 and JAK3, this was to be expected at higher doses of Compound 1. It is unclear how much each of the heterodimeric components (JAK1 and JAK3) contributes to the overall IL-15 signaling. However, it is possible that at higher exposure of Compound 1, the threshold for in-vivo selectivity for JAK1 compared to JAK3 is lowered in the context of the JAK1/JAK3 heterodimer. Of note, for tofacitinib at 5 mg BID, the reported median decrease in NK cells at week 24 was ~35%, with greater reduction at 10 mg BID or higher doses of tofacitinib (van Vollenhoven, et al., *Annals of the Rheumatic Diseases*, 2015, pp. 258-9; Addendum to Primary Clinical Review, NDA 203,214, Center for Drug Evaluation and Research). However, it is important to note that the significance of NK cell reduction, especially what is considered clinically meaningful reduction in NK cells in terms of predicting clinical events (i.e. onset of viral reactivation) is lacking. A significant association with the changes in nadir NK cells and treated infection rates with tofacitinib treatment was observed (van Vollenhoven, et al., *Annals of the Rheumatic Diseases*, 2015, pp. 258-9). No association of the reduced NK cells with clinical events was observed in the current study.

As reported with other JAK inhibitors, a dose-dependent elevation of low density lipoprotein cholesterol and high density lipoprotein cholesterol levels was observed with Compound 1, however, the ratio of LDL-C/HDL-C remained unchanged. For the other laboratory parameters of interest, i.e, serum transaminases, WBC, neutrophil, or lymphocytes, the mean changes were unremarkable and lacked apparent dose relationship, with only one subject discontinuing the study early due to leukopenia.

In summary, the results of the current study demonstrated safety and efficacy of a selective JAK1 inhibitor, Compound 1, in a difficult-to-treat population of RA patients who had an inadequate response or intolerance to anti-TNF biologic therapies.

Example 33: Treatment of Moderately to Severely Active Rheumatoid Arthritis in Patients Who have Inadequately Responded to Methotrexate The following example briefly describes the results of a Phase 2b, 12-week, randomized, double-blind, parallel-group, placebo-controlled study in which adult subjects with moderately to severely active rheumatoid arthritis (RA) who have inadequately responded to stable methotrexate therapy were treated with Compound 1.

Patients

Men and women aged ≥18 years with active RA and inadequate response to methotrexate were included in the study. Diagnosis of RA was based on the 1987 revised American College of Rheumatology (ACR) classification criteria (Arnett et al, *Arthritis Rheum.*, 1988, Vol. 31(3), pp. 315-324) or the 2010 ACR/European League Against Rheumatism (EULAR) criteria (Smolen et al, *Ann. Rheum. Dis.*, 2010, Vol. 69(6), pp. 964-975). Active RA was defined by minimum disease activity criteria of ≥6 swollen joints (based on 66 joint counts) at screening and baseline; ≥6 tender joints (based on 68 joint counts) at screening and baseline; and high-sensitivity C-reactive protein (hsCRP) greater than the upper limit of normal (ULN) or positive test results for both rheumatoid factor and anti-cyclic citrullinated peptide (CCP) at screening. Eligible patients had been receiving methotrexate for ≥3 months, with a stable prescription (7.5-25 mg/week) for ≥4 weeks before baseline. Stable doses of methotrexate were continued throughout the study. In addition, all patients were requested to take a dietary supplement of oral folic acid (or equivalent) from 4 weeks prior to baseline and throughout study participation. All other oral disease-modifying antirheumatic drugs (DMARDs) were discontinued before baseline for ≥5 times the mean terminal elimination half-life of the specific DMARD to ensure washout. High-potency opiates (e.g., oxycodone, methadone, morphine) were discontinued ≥4 weeks before baseline. All patients had a negative tuberculosis screening assessment or, if there was evidence of a latent tuberculosis infection, completed ≥2 weeks of tuberculosis prophylaxis or had documented completion of a full course of tuberculosis prophylaxis before baseline. Patients were allowed to receive nonsteroidal anti-inflammatory drugs, acetaminophen, oral/inhaled corticosteroids, and low-potency opiates. Patients were excluded if they had received JAK inhibitor therapy or any other investigational or approved biologic RA therapy.

Treatment

Patients were randomized in a 1:1:1:1:1:1 ratio in a double-blind manner to oral doses of Compound 1 (immediate release capsules comprising Tartrate Hydrate) 3 mg BID, 6 mg BID, 12 mg BID, 18 mg BID, or 24 mg QD (two 12 mg tablets administered at the same time), or placebo BID for 12 weeks. Patients were randomized using an interactive voice/web response system according to a blocked randomization schedule. Investigators, patients, and other study personnel were blinded to the treatment assignments throughout the study. To maintain blinding, the placebo and active treatments had an identical appearance. Patients were instructed to take their doses (6 capsules total, split into 2 batches of 3) at approximately the same times each day.

Assessments

The primary efficacy endpoint was a ≥20% improvement in ACR criteria (ACR20) at week 12. Other endpoints included ACR50 and ACR70 response rates; change in 28-joint Disease Activity Score using C-reactive protein (DAS28(CRP)); change in Clinical Disease Activity Index (CDAI); the proportion of patients achieving low disease activity (LDA) or clinical remission based on DAS28(CRP) and CDAI criteria; and change in the Health Assessment Questionnaire Disability Index (HAQ-DI). The minimal clinically important difference (MCID) on the HAQ-DI, which is a decrease of ≥0.22, (Strand et al, 2006) was also evaluated.

Safety was evaluated during treatment and for 30 days after the last dose of study drug on the basis of adverse events (AEs), vital signs, physical examinations, and laboratory tests. AEs were coded using the Medical Dictionary for Regulatory Activities (MeDRA), version 17.1.

Statistical Analyses

The per-protocol primary efficacy analysis was conducted in a modified intent-to-treat population, including all randomized patients who take at least 1 dose of study drug, with last observation carried forward (LOCF) imputation; data were also analyzed with nonresponder imputation (NRI). Statistical tests were 1-sided with a significance level of 0.05 for efficacy analyses and 2-sided with a significance level of 0.05 for all other analyses. A sample of 270 patients (45 per randomized treatment group) was targeted give 80% power to establish a real difference of 30% in the primary efficacy endpoint (ACR20 response rate at week 12), assuming the response rate would be 30% in the placebo group and 60% in at least 1 of the Compound 1 dose groups.

Results

Patients

Figure 5A:
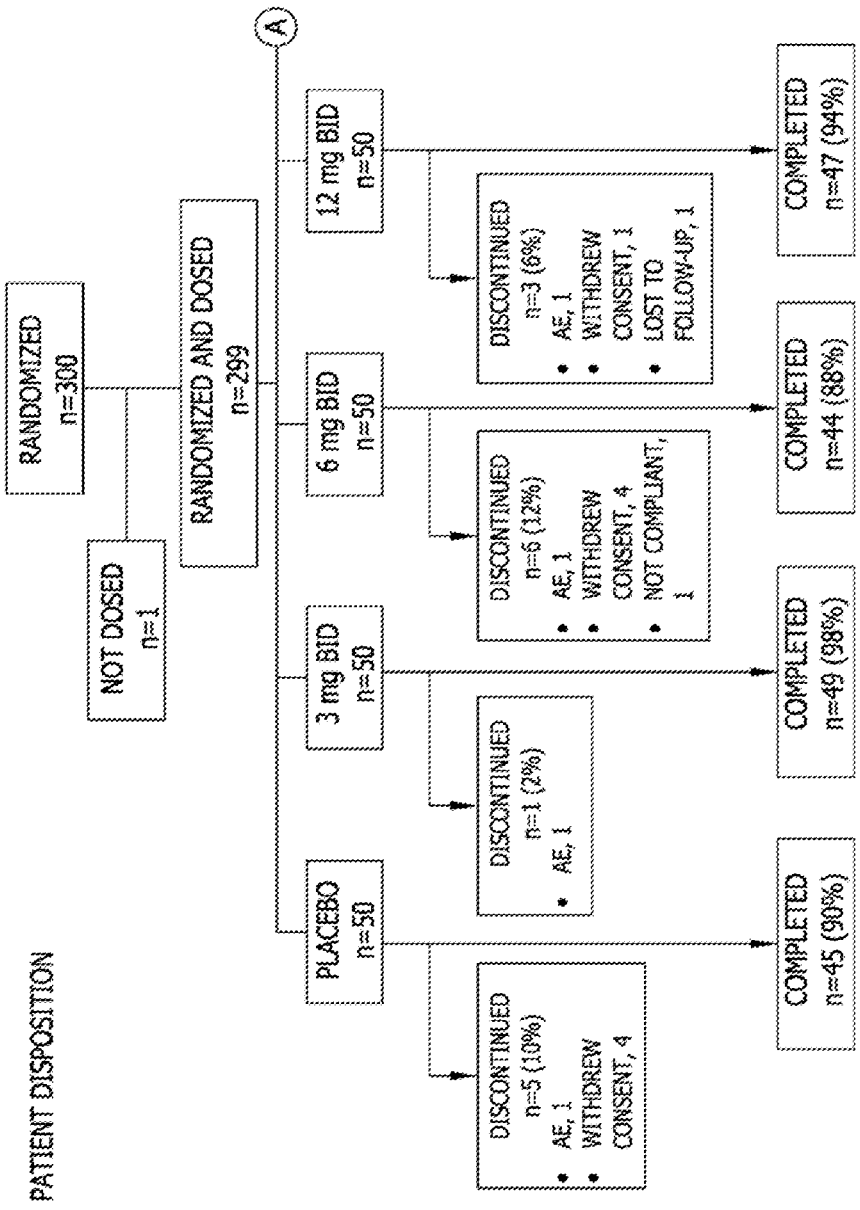
FIGS. 5A and 5B show the subject disposition for the study described in Example 56.
Figure 5B:
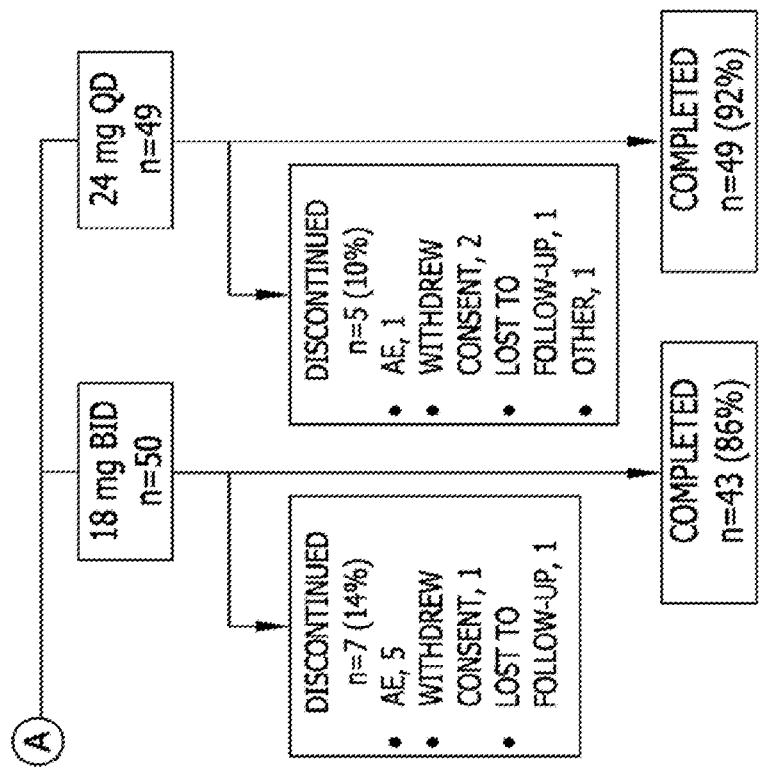

A total of 300 patients were randomized, and 299 received placebo (n=50) or Compound 1 3 mg BID (n=50), 6 mg BID (n=50), 12 mg BID (n=50), 18 mg BID (n=50) (or 24 mg QD (n=49). Overall, 91% of patients completed the study, with similar discontinuation rates across treatment groups and no apparent relationship between Compound 1 dose and discontinuation (FIGS. 5A and 5B). Demographic and clinical characteristics at baseline were balanced among treatment groups (Table 23A). Patients were from Eastern Europe (61%), Central/South America (18% Fe), the United States (10(8) Western Europe (8%), or other regions (4). Patients had a mean disease duration of 6.9 years and 17.7% had used 1 prior non-methotrexate DMARD. Of note, patients with normal hsCRP could be enrolled if they were positive for rheumatoid factor and anti-CCP antibody. Approximately 43% of patients had hsCRP values ≤ULN at baseline.

TABLE 23A

Baseline Characteristics and Disease Activity in Patients With Inadequate Response to Methotrexate

| | | Compound 1 | | | | |
|---|---|---|---|---|---|---|
| Characteristic | Placebo (n = 50) | 3 mg BID (n = 50) | 6 mg BID (n = 50) | 12 mg BID (n = 50) | 18 mg BID (n = 50) | 24 mg QD (n = 49) |
| Female, number (%) | 38 (76) | 40 (80) | 34 (68) | 41 (82) | 42 (84) | 42 (86) |
| Age, years, mean (SD) | 55 (12) | 53 (12) | 55 (12) | 56 (12) | 55 (14) | 56 (12) |

TABLE 23A-continued

Baseline Characteristics and Disease Activity in Patients With Inadequate Response to Methotrexate

| | | Compound 1 | | | | |
|---|---|---|---|---|---|---|
| Characteristic | Placebo (n = 50) | 3 mg BID (n = 50) | 6 mg BID (n = 50) | 12 mg BID (n = 50) | 18 mg BID (n = 50) | 24 mg QD (n = 49) |
| Years since RA diagnosis, mean (SD) | 5.9 (5.3) | 3.9 (3.8) | 7.0 (5.5) | 9.3 (8.6) | 7.3 (7.9) | 8.3 (7.1) |
| RF positive, number (%) | 41 (82) | 45 (90) | 46 (92) | 44 (88) | 41 (82) | 44 (90) |
| Anti-CCP positive, number (%) | 39 (78) | 40 (80) | 45 (90) | 43 (86) | 40 (80) | 45 (92) |
| Methotrexate dose, mg, mean (SD) | 16 (4) | 16 (4) | 16 (4) | 14 (4) | 15 (5) | 15 (4) |
| Prednisolone dose, mg, mean (SD) | 0 | | | 0 | 0 | 0 |
| ≥1 prior non-MTX DMARD, number (%) | 7 (14) | 6 (12) | 12 (24) | 11 (22) | 5 (10) | 12 (24) |
| 1 | 6 (12) | 4 (8) | 10 (20) | 9 (18) | 2 (4) | 8 (16) |
| 2 | 1 (2) | 2 (4) | 1 (2) | 1 (2) | 1 (2) | 3 (6) |
| ≥3 | 0 | 0 | 1 (2) | 1 (2) | 2 (4) | 1 (2) |
| Disease Activity | | | | | | |
| TJC68, mean (SD) | 29 (16) | 27 (15) | 28 (16) | 28 (13) | 27 (15) | 28 (16) |
| SJC66, mean (SD) | 19 (12) | 15 (8) | 19 (12) | 17 (11) | 17 (112) | 18 (13) |
| HAQ-DI, mean (SD) | 1.4 (0.7) | 1.3 (0.7) | 1.6 (0.7) | 1.5 (0.6) | 1.6 (0.6) | 1.5 (0.7) |
| DAS28 (CRP), mean (SD) | 5.6 (1.1) | 5.5 (1.1) | 5.8 (1.0) | 5.6 (0.9) | 5.7 (0.8) | 5.7 (1.0) |
| CDAI, mean (SD) | 40 (14) | 38 (13) | 43 (14) | 39 (12) | 40 (13) | 41 (13) |
| hsCRP, mg/L, mean (SD) | 15 (26) | 11 (15) | 17 (20) | 11 (15) | 13 (15) | 14 (16) |
| hsCRP > ULN,* number (%) | 27 (54) | 25 (50) | 31 (62) | 26 (52) | 28 (56) | 33 (67) |

Efficacy

Figure 6:
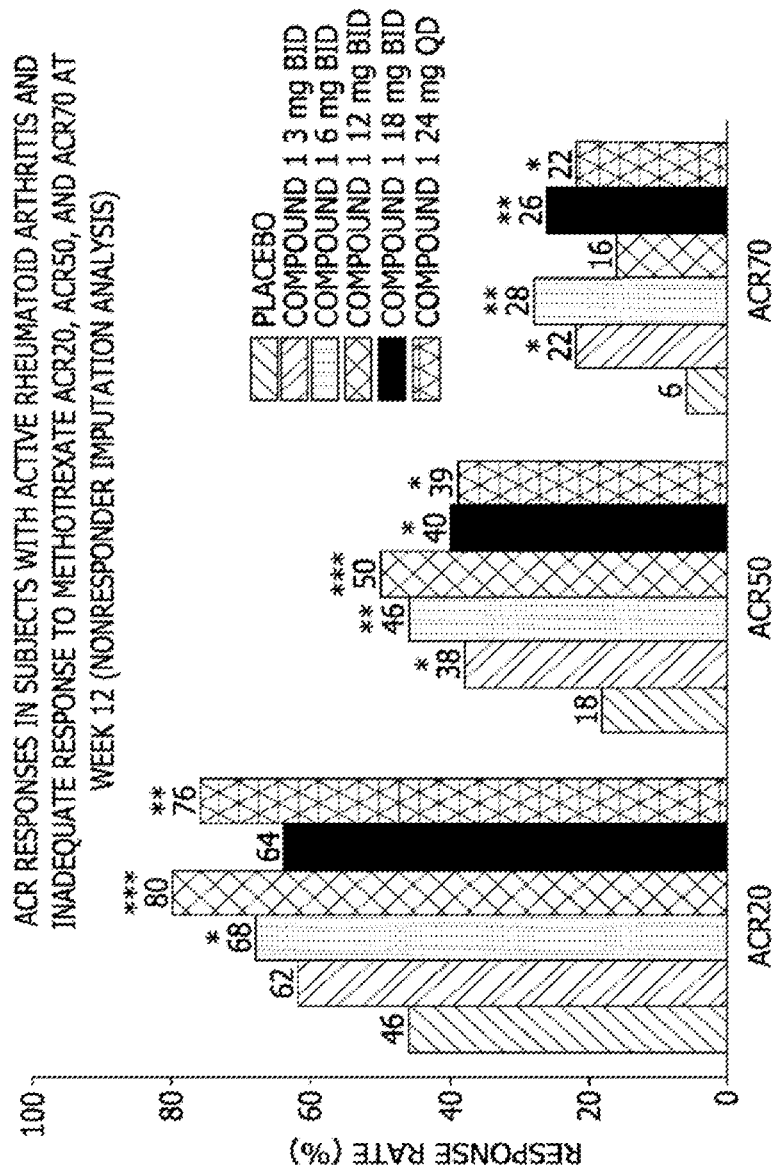
FIG. 6 shows the ACR20, ACR50, and ACR70 responses at week 12 following administration of placebo or various doses of Compound 1 to subjects with active rheumatoid arthritis and inadequate response to methotrexate (*P<0.05; P<0.01; *P<0.001 relative to placebo; modified intent-to-treat population with NRI of missing values).
Figure 7A:
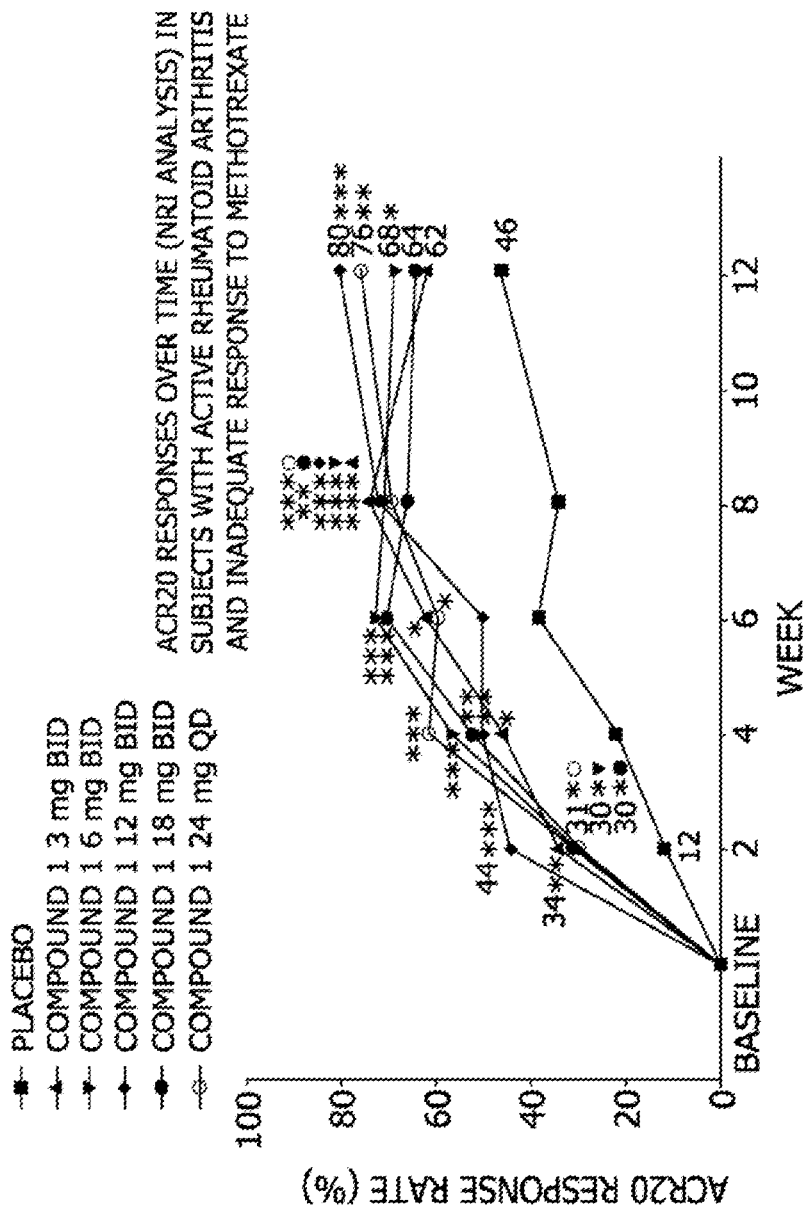
FIGS. 7A-7D show the ACR20 (FIG. 7A, NRI analysis), ACR50 (FIG. 7B, NRI analysis), and ACR70 (FIG. 7C, NRI analysis) responses or DAS28(CRP) mean change from baseline (FIG. 7D, observed cases) over time following administration of placebo or various doses of Compound 1 to subjects with active rheumatoid arthritis and inadequate response to methotrexate (*P<0.05; P<0.01; *P<0.001 relative to placebo; modified intent-to-treat population).
Figure 7B:
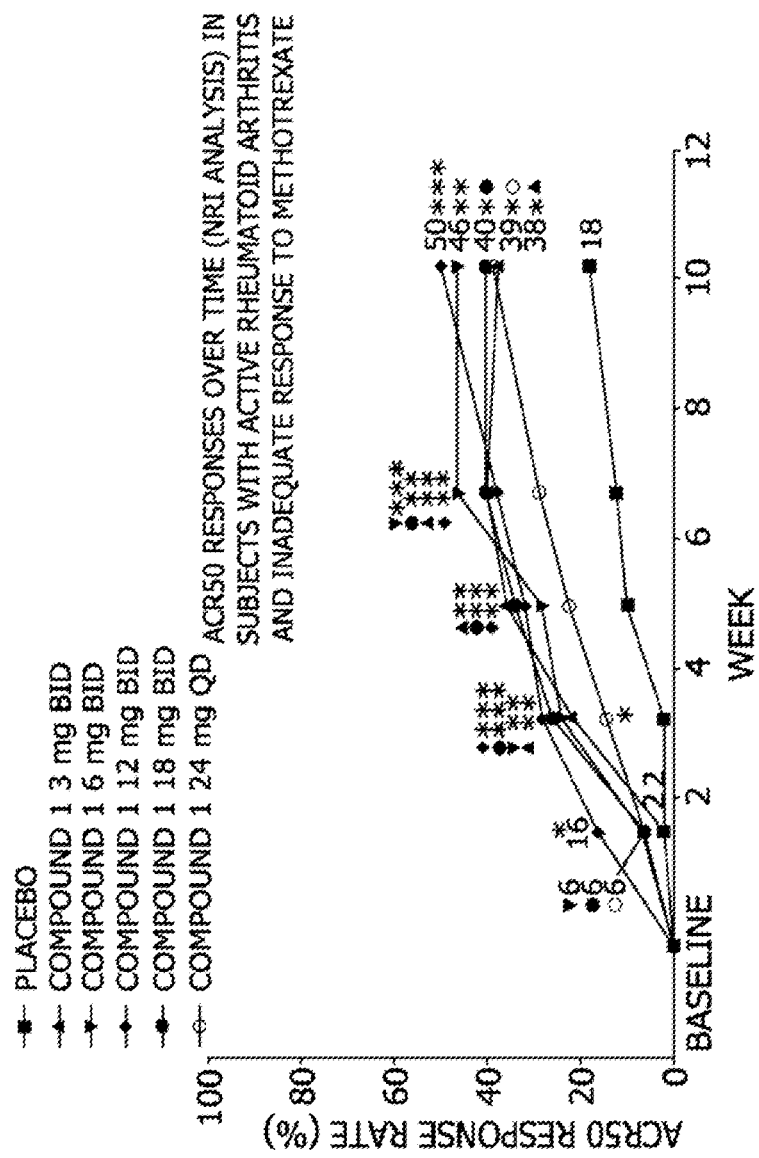
Figure 7C:
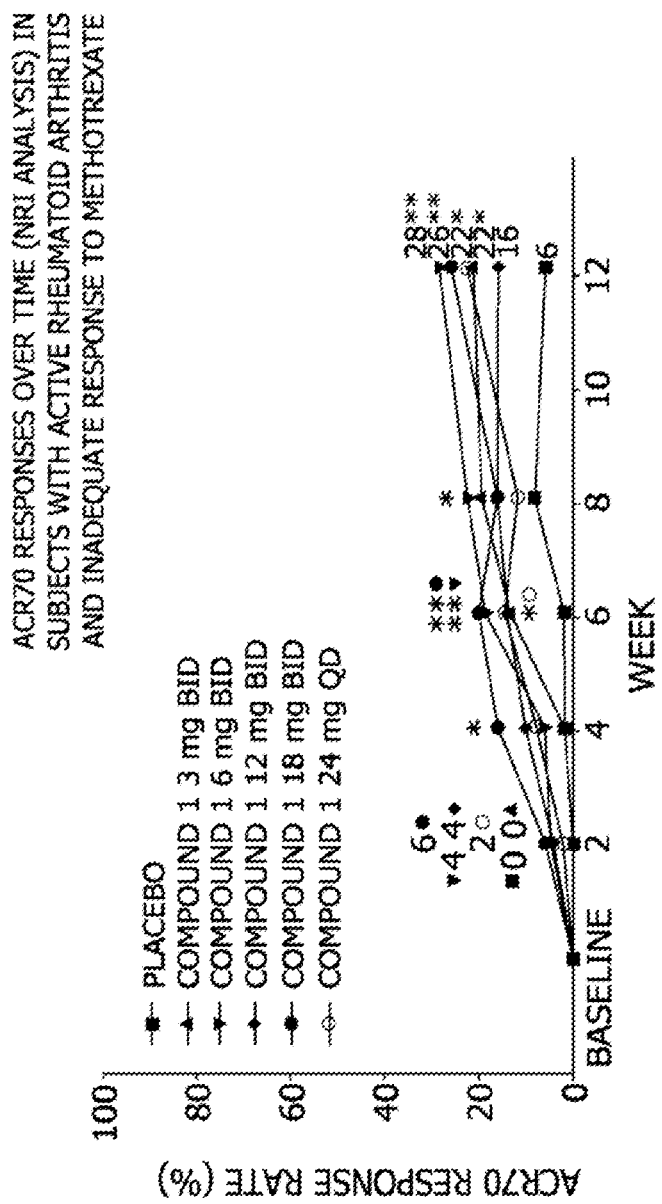
Figure 7D:
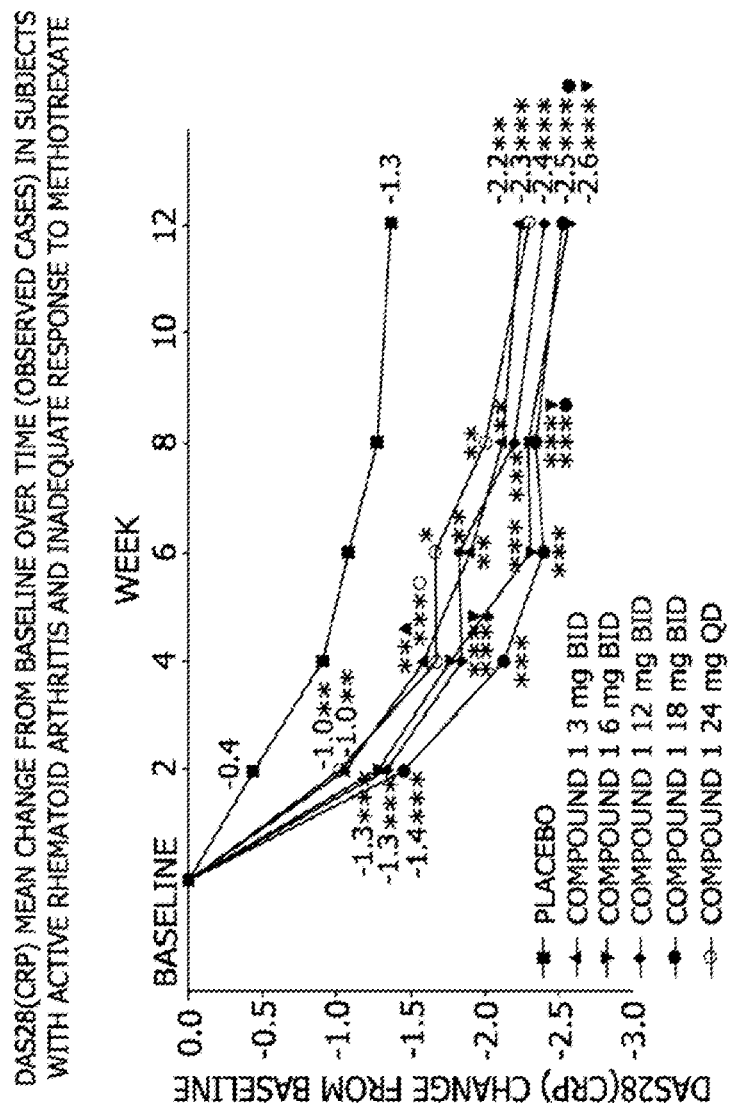

The primary per-protocol endpoint, ACR20 at week 12 (LOCF imputation), was met at every dose of Compound 1 except the lowest dose of 3 mg BID. The proportions of patients with ACR20 were 65% (P=0.153), 73% (P=0.18), 82% (P=0.001), 77% (P=0.008), and 82% (P=0.001) at 3 mg BID, 6 mg BID, 12 mg BID, 18 mg BID, and 24 mg QD, respectively, versus the placebo response rate (50/0). ACR20 responses (NRI) were significantly higher with Compound 1 at 6 mg BID (68%), 12 mg BID (80)%), and 24 mg QD (76%) versus placebo (46%; FIG. 6). Responses with more stringent criteria, i.e., ACR50 and ACR70, were achieved at week 12 by significantly higher percentages of patients who received Compound 1 versus placebo at all doses except 12 mg BID for ACR70 response (NRI; FIG. 6). ACR20 response rates increased over time with Compound 1 to reach mean maximum values at weeks 6 to 12 (FIG. 7A). ACR50 responses were significant from week 4 onward and plateaued at week 8 (FIG. 7B); ACR70 responses also appeared to plateau by week 8, with some further improvements up to week 12 (FIG. 7C). At the first assessment (week 2), ACR20 responses with Compound 1 ranged from 30% to 44% and were significantly higher at all doses in patients who received Compound 1 versus placebo (12%). Mean decreases in DAS28(CRP) improved over time from baseline, ranging from −2.2 to −2.6 with Compound 1 at week 12, and were significantly lower compared with placebo (−1.3) at all Compound 1 doses and every time point (FIG. 7D).

Figure 8A:
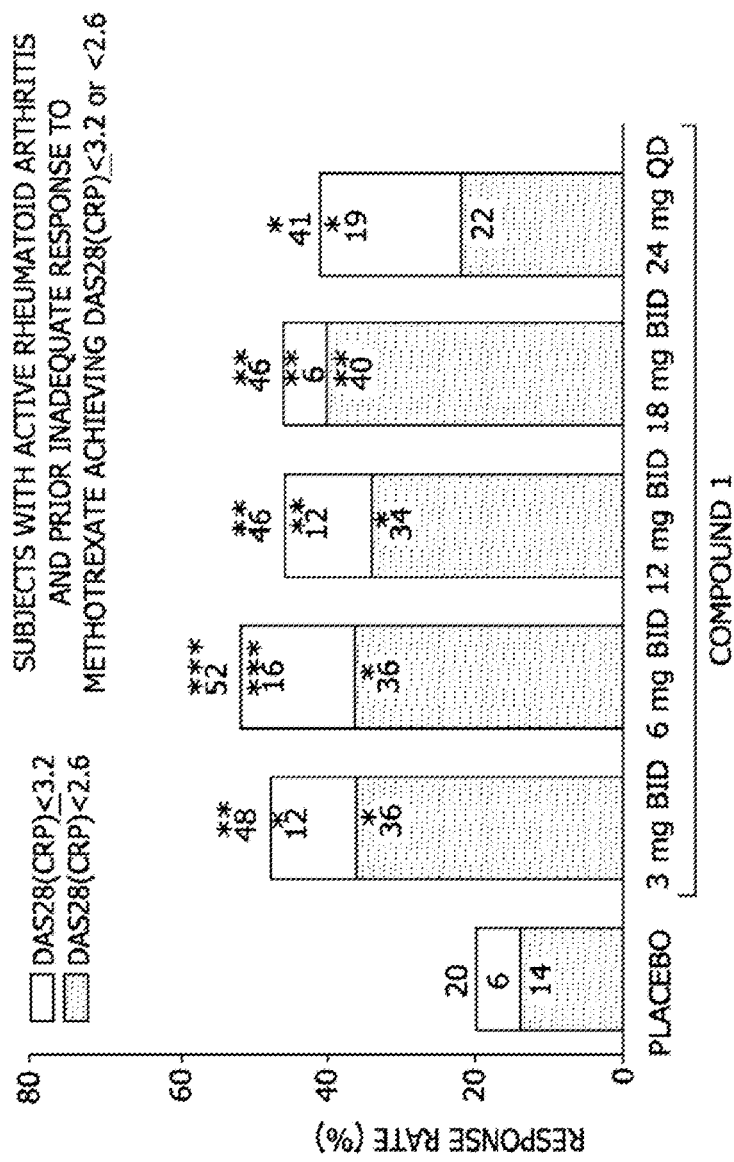
FIGS. 8A and 8B show subjects achieving a DAS28 (CRP) score of ≤3.2 or <2.6 (FIG. 8A) or CDAI of ≤10 or ≤2.8) at week 12 following administration of placebo or various doses of Compound 1 to subjects with active rheumatoid arthritis and inadequate response to methotrexate (*P<0.05; P<0.01; *P<0.001 relative to placebo; modified intent-to-treat population (NRI)). For FIGS. 8A and 8B, the bottom number indicates the percentage of subjects who achieved both cutoff values, the middle number indicates the percentage of subjects who achieved the less stringent cutoff but not the more stringent cutoff value, and the top number indicates the percentage of patients who achieved either cutoff value.
Figure 8B:
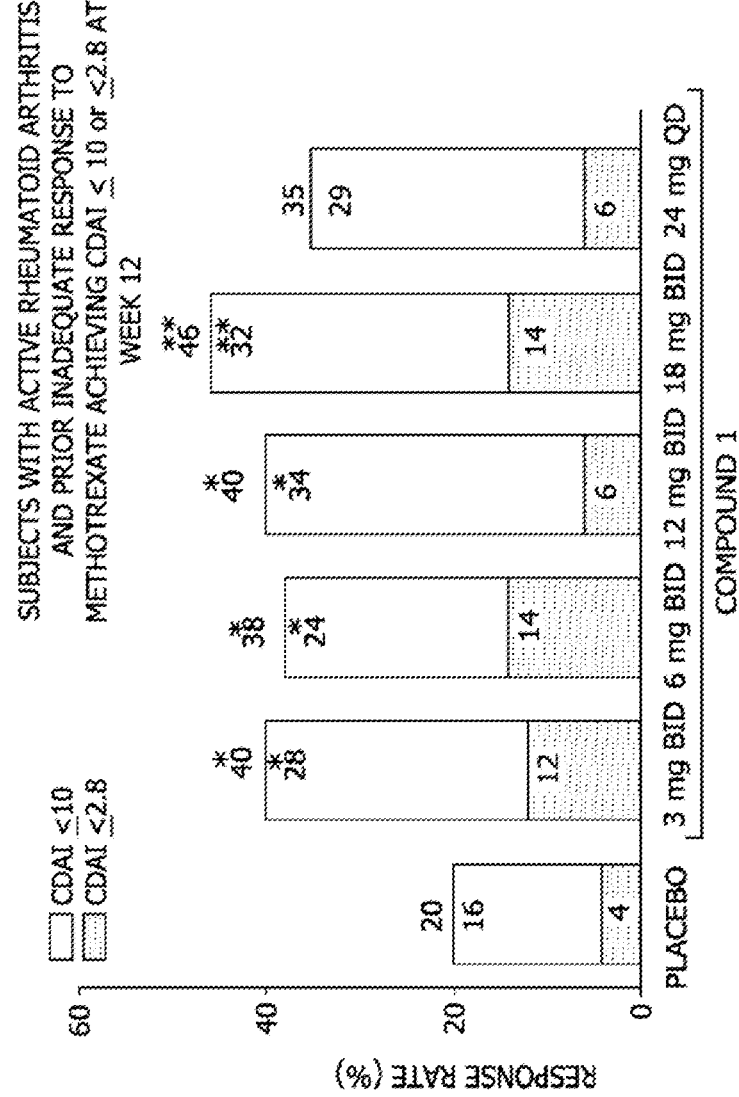

Higher percentages of patients who received Compound 1 achieved DAS28(CRP)≤3.2 or <2.6 compared with placebo. The DAS28(CRP)≤3.2 cutoff was achieved by a significantly higher percentage of patients (41%-52%) at all doses of Compound 1 compared with placebo (20%); the <2.6 cutoff was achieved by significantly higher proportions (34%-40%) with Compound 1 compared with placebo (14%) at all doses except 24 mg QD (22%; FIG. 8A). Similarly, CDAI<10 was achieved by a significantly higher percentage of patients (40%-46%) compared with placebo (20%) with Compound 1 at all doses except 24 mg QD (35%; FIG. 8B).

Improvements from baseline in ACR component scores were larger with Compound 1 compared with placebo, reaching statistical significance for most comparisons at doses of 6 mg BID and greater (Table 23B). Changes from baseline on the HAQ-DI at week 12 with Compound 1 ranged from −0.6 to −0.8 and were significantly greater than that seen with placebo (−0.4) for all but the Compound 1 24 mg QD dose (−0.6). Numerically, more patients in the Compound 1 dose groups ≥6 mg BID (69%-88%) met the MCID at week 12 compared with placebo (67%); the study was not powered for this analysis, and the comparisons versus placebo mostly were not statistically significant.

TABLE 23B

Mean Changes From Baseline in ACR Components at Week 12

| | | | Compound 1 | | | |
|---|---|---|---|---|---|---|
| ACR Component | Placebo (n = 50) | 3 mg BID (n = 50) | 6 mg BID (n = 50) | 12 mg BID (n = 50) | 18 mg BID (n = 50) | 24 mg QD (n = 49) |
| TJC68 | −14.4 | −15.9 | −19.2* | −19.2* | −17.4 | −18.9* |
| SJC66 | −9.9 | −12.1 | −11.9 | −12.7* | −13.2* | −13.1* |
| Patient's assessment of pain | −19.9 | −25.3 | −33.8** | −33.4** | −34.9** | −29.8* |
| Physician's global assessment of disease activity | −28.0 | −34.7 | −43.0*** | −45.6*** | −36.6* | −37.6* |
| Patient's global assessment of disease activity | −17.5 | −26.9 | −31.4** | −23.8 | −29.1* | −24.1 |
| HAQ-DI | −0.4 | −0.6* | −0.7** | −0.8*** | −0.6* | −0.6 |
| HAQ-DI ≤ MCID,§ number (%), 95% CI | 30 (67), 53-80 | 33 (67), 54-81 | 34 (69), 57-82 | 44 (88), 79-97 | 35 (74), 62-87 | 38 (78), 66-89 |
| hsCRP | −0.4 | −10.5*** | −8.8** | −8.9*** | −7.5** | −8.4*** |

Abbreviations:
ACR—American College of Rheumatology; BID—twice daily; HAQ-DI—Health Assessment Questionnaire Disability Index; hsCRP—high-sensitivity C-reactive protein; LOCF—last observation carried forward; MCID—minimal clinically important difference; QD—once daily; RA—rheumatoid arthritis; SJC66—swollen joint count using 66 joints; TJC68—tender joint count using 68 joints.
*$P < 0.05$; $P < 0.01$; *$P < 0.001$ relative to placebo.
§MCID = −0.22.
Modified intent-to-treat population with LOCF imputation of missing values.
95% CIs were calculated based on a normal approximation to the binomial distribution.

As can be seen from these results, Compound 1 had an early onset of action in subjects who have demonstrated a prior inadequate response to methotrexate. In particular. ACR20 response rates improved starting at week 2, with a maximum effect achieved as early as week 6, with continued improvement in some dose groups through week 12, ACR50 (maximum efficacy up to 50%) and ACR70 (maximum efficacy up to 28%) response rates also quickly plateaued by about week 8. Compound 1 showed a dose-dependent efficacy that seemed to reach a maximum at 12 mg BID.

Safety

The safety and tolerability profile of Compound 1 across doses was acceptable (Table 23C). Incidence of any AE was statistically significantly higher with Compound 1 overall versus placebo (45% vs 26%; P=0.012), with a trend of dose dependence. Among common AEs, those that occurred in ≥3% patients in any group were abdominal pain, abdominal pain upper, back pain, blood creatine phosphokinase increased, cough, diarrhea, dyslipidemia, dyspepsia, gastroenteritis, headache, herpes zoster, influenza, leukopenia, nasopharyngitis, upper respiratory tract infection, urinary tract infection, white blood cell count decreased, and wound. Most AEs in the Compound 1 treatment groups were mild or moderate in severity. Severe AEs occurred in 1 patient each with Compound 1 at 6 mg BID (lung cancer at posttreatment day 10 in a 79-year-old male patient with family and smoking histories; the patient died 3 months later), 12 mg BID (pyrexia), 18 mg BID (hyperbilirubinemia), and 24 mg QD (head injury). There were 2 serious AEs with Compound 1 that were considered possibly related to study drug: community-acquired pneumonia at 12 mg BID and syncope at 24 mg QD. Infections overall occurred in 20% of patients who received Compound 1 and 14% who received placebo, with no tendency towards higher rates at higher doses. Three herpes zoster infections, 1 with Compound 1 at 3 mg BID and 2 at 24 mg QD, involved 1 dermatome per patient. A patient in the Compound 1 6 mg BID group, aged 79 years and with a history of smoking, was diagnosed with lung cancer 10 days after stopping study treatment and died 3 months later.

At week 12, mean values for alanine aminotransferase (ALT) were significantly higher with Compound 1 18 mg BID than with placebo; mean values for aspartate aminotransferase (AST) were significantly higher than placebo with all Compound 1 doses >3 mg BID (Table 23D). However, grade 3/4 ALT or AST abnormalities during the study were sporadic, with no clear dose dependence (Table 23E). Creatinine and creatine phosphokinase levels were significantly higher in all Compound 1 dose groups compared with placebo. Compound 1 was associated with elevations in high-density and low-density lipoprotein cholesterol (HDL-C; LDL-C); HDL-C elevation was statistically significant at 6 mg BID, whereas LDL-C values were significantly higher than placebo for all Compound 1 doses; however, the ratios of LDL-C/HDL-C remained the same through week 12. There were no significant decreases in lymphocyte or neutrophil levels between placebo and Compound 1 dose groups by week 12. Grade 3 lymphocyte values occurred with placebo and all doses of Compound 1; grade 4 values occurred in 1 patient each with Compound 1 at 3 mg BID and 18 mg BID (Table 23E). Grade 3 neutrophil values occurred with Compound 1 at 12 mg BID (1 patient), 18 mg BID (3 patients), and 24 mg QD (1 patient). Natural killer (NK) cell percentages were significantly lower than placebo with Compound 1 doses ≥6 mg BID (Table 23D).

Figure 9A:
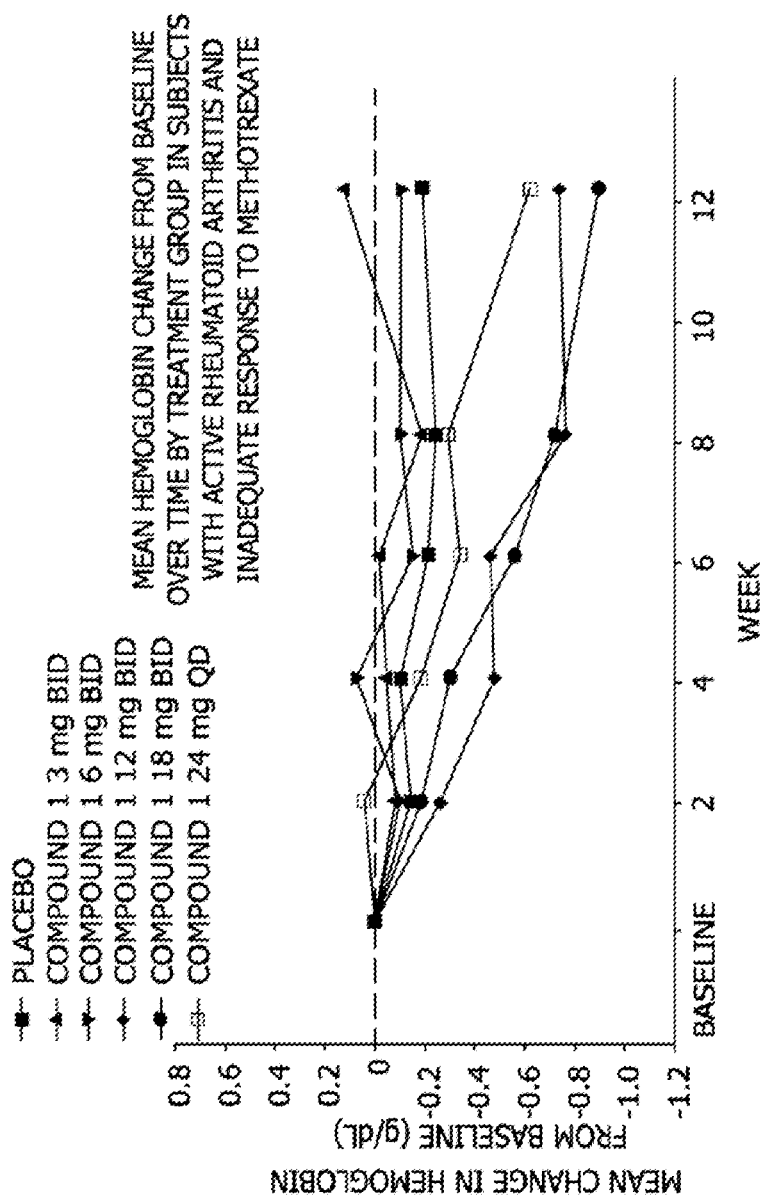
Figure 9B:
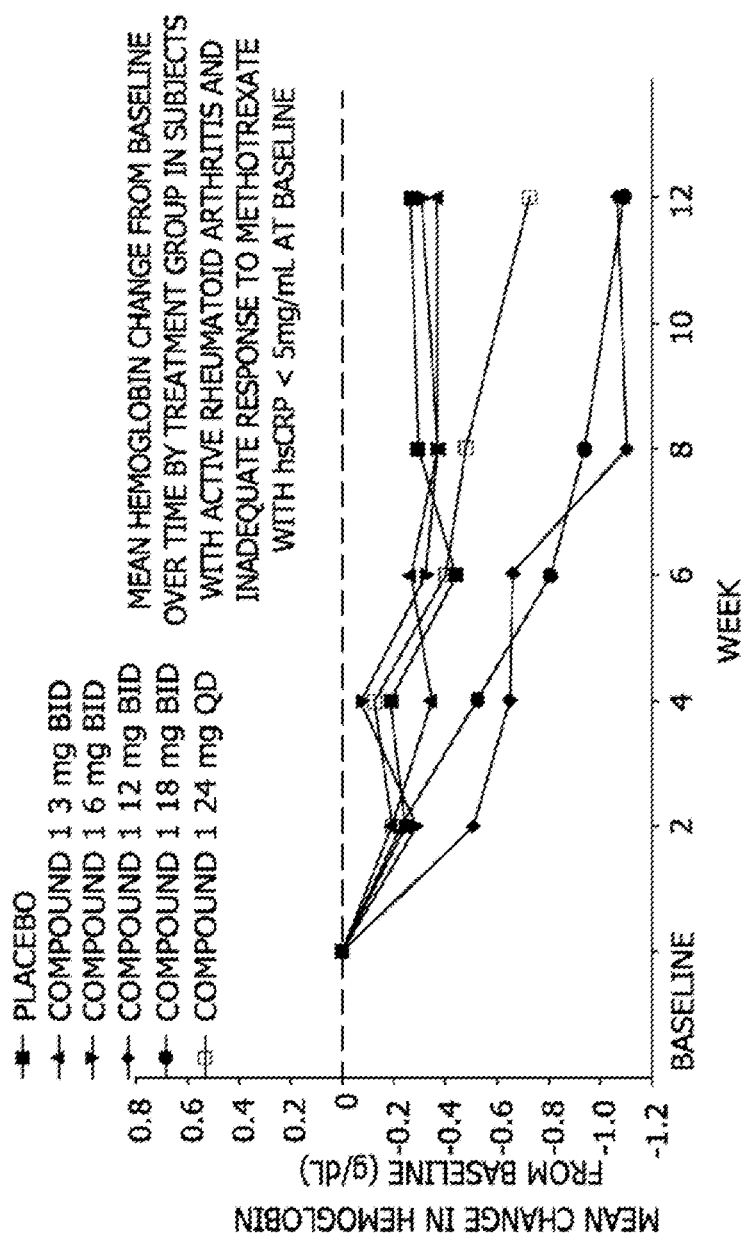

Mean changes in hemoglobin over time in all patients, patients with hsCRP values ≤5 mg/mL, and patients with hsCRP values >5 mg/mL are shown in FIGS. 9A-9C. Mean hemoglobin values remained stable or increased at lower doses, most notably in patients with elevated CRP at baseline. Dose-dependent decreases in hemoglobin were seen at higher doses without clinical impact.

TABLE 23C

Adverse Events Summary

| AE, Number (%) | Placebo (n = 50) | Compound 1 | | | | |
|---|---|---|---|---|---|---|
| | | 3 mg BID (n = 50) | 6 mg BID (n = 50) | 12 mg BID (n = 50) | 18 mg BID (n = 50) | 24 mg QD (n = 49) |
| *Overal AEs* | | | | | | |
| Any AE | 13 (26) | 19 (38) | 23 (46) | 29 (58) | 25 (50) | 17 (35) |
| Any AE possibly drug related* | 6 (12) | 5 (10) | 6 (12) | 17 (34) | 11 (22) | 5 (10) |
| Any serious AE | 0 | 0 | 2 (4) | 1 (2) | 3 (6) | 2 (4) |
| Any serious AE possibly drug related* | 0 | 0 | 0 | 1 (2) | 0 | 1 (2) |
| Any severe AE | 0 | 0 | 1 (2) | 1 (2) | 1 (2) | 1 (2) |
| Any AE leading to discontinuation | 1 (2) | 1 (2) | 1 (2) | 1 (2) | 5 (10) | 1 (2) |
| Any AE leading to death | 0 | 0 | 0 | 0 | 0 | 0 |
| *AEs ≥3% in any group* | | | | | | |
| Abdominal pain | 0 | 1 (2) | 1 (2) | 2 (4) | 0 | 1 (2) |
| Abdominal pain upper | 0 | 0 | 0 | 2 (4) | 1 (2) | 1 (2) |
| Back pain | 0 | 1 (2) | 3 (6) | 1 (2) | 0 | 1 (2) |
| Blood creatine phosphokinase increased | 0 | 0 | 0 | 3 (6) | 2 (4) | 1 (2) |
| Cough | 0 | 1 (2) | 1 (2) | 3 (6) | 1 (2) | 0 |
| Diarrhea | 0 | 0 | 1 (2) | 3 (6) | 1 (2) | 1 (2) |
| Dyslipidemia | 0 | 1 (2) | 0 | 3 (6) | 0 | 0 |
| Dyspepsia | 1 (2) | 0 | 0 | 0 | 2 (4) | 0 |
| Gastroenteritis | 0 | 2 (4) | 0 | 0 | 0 | 1 (2) |
| Headache | 1 (2) | 2 (4) | 1 (2) | 3 (6) | 0 | 1 (2) |
| Herpes zoster | 0 | 1 (2) | 0 | 0 | 0 | 2 (4) |
| Influenza | 0 | 0 | 0 | 4 (8) | 1 (2) | 0 |
| Leukopenia | 0 | 0 | 0 | 3 (6) | 1 (2) | 0 |
| Nasopharyngitis | 1 (2) | 1 (2) | 2 (4) | 4 (8) | 2 (4) | 3 (6) |
| Upper respiratory tract infection | 0 | 0 | 1 (2) | 1 (2) | 2 (4) | 0 |
| Urinary tract infection | 2 (4) | 2 (4) | 2 (4) | 2 (4) | 0 | 2 (4) |
| White blood cell count decreased | 0 | 0 | 1 (2) | 0 | 2 (4) | 0 |
| Wound | 0 | 0 | 2 (4) | 0 | 0 | 0 |
| *AEs of special interest* | | | | | | |
| Infection | 7 (14) | 10 (20) | 7 (14) | 12 (24) | 11 (22) | 9 (18) |
| Serious infection | 0 | 0 | 0 | 1 (2) | 0 | 0 |
| Cardiovascular event | 0 | 0 | 0 | 0 | 0 | 1 (2)* |
| Herpes zoster† | 0 | 1 (2) | 0 | 0 | 0 | 2 (4) |
| Hepatic disorder | 0 | 0 | 0 | 0 | 2 (4) | 0 |
| Malignancy | 0 | 0 | 1 (2)‡ | 0 | 0 | 0 |

Abbreviations:
AE—adverse event; BID—twice daily; QD—once daily.
*The cardiovascular event was a cerebrovascular accident and was adjudicated as an ischemic stroke.
†The events of herpes zoster involved 1 dermatome per patient.
‡Lung cancer at posttreatment day 10 in a 79-year-old male patient with family and smoking histories. The patient died 3 months later.

TABLE 23D

Mean Changes in Laboratory Values of Interest at Week 12

| Mean (SD) Value | Placebo (n = 50) | Compound 1 | | | | |
|---|---|---|---|---|---|---|
| | | 3 mg BID (n = 50) | 6 mg BID (n = 50) | 12 mg BID (n = 50) | 18 mg BID (n = 50) | 24 mg QD (n = 49) |
| ALT, U/L | −1.3 (15.4) | −1.1 (20.7) | 6.5 (10.0) | 7.0 (31.8) | 8.5 (18.5)* | 5.3 (20.7) |
| AST, U/L | −0.1 (8.4) | 1.9 (11.9) | 6.6 (5.5)** | 7.6 (14.3)** | 7.7 (11.3)** | 4.8 (10.9)* |
| HDL-C, mmol/L | 0.01 (0.21) | 0.12 (0.32) | 0.17 (0.26)* | 0.13 (0.30) | 0.13 (0.43) | 0.13 (0.33) |
| LDL-C, mmol/L | −0.05 (0.43) | 0.28 (0.82)* | 0.34 (0.71)* | 0.49 (0.93)** | 0.27 (0.83)* | 0.32 (0.62)** |
| Creatinine, μmol/L | −0.9 (7.9) | 2.0 (8.2)** | 4.9 (9.1)** | 4.3 (7.1)** | 4.6 (10.2)** | 5.4 (8.5)** |

TABLE 23D-continued

Mean Changes in Laboratory Values of Interest at Week 12

| | | Compound 1 | | | | |
|---|---|---|---|---|---|---|
| Mean (SD) Value | Placebo (n = 50) | 3 mg BID (n = 50) | 6 mg BID (n = 50) | 12 mg BID (n = 50) | 18 mg BID (n = 50) | 24 mg QD (n = 49) |
| Creatine phosphokinase, U/L | −7.7 (90.1) | 40.2 (46.5)* | 82.5 (80.6)** | 100.4 (126.5)** | 108.7 (140.2)** | 59.4 (94.0)** |
| Lymphocytes, ×10$^9$/L | −0.09 (0.50) | 0.12 (0.58) | 0.01 (0.79) | −0.08 (0.67) | −0.12 (0.53) | −0.13 (0.49) |
| Neutrophils, ×10$^9$/L | −0.5 (2.20) | −1.1 (2.13) | −0.9 (1.60) | −0.9 (1.90) | −0.9 (2.16) | −0.4 (1.99) |
| NK cells, CD3−/16−/56+, %† | −0.1 (4.46) | −1.3 (4.54) | −3.1 (4.09)** | −3.3 (4.67)** | −5.3 (4.24)** | −4.9 (5.12)** |

Abbreviations:
ALT—alanine aminotransferase; AST—aspartate aminotransferase; BID—twice daily; HDL-C—high-density lipoprotein cholesterol; LDL-C—low-density lipoprotein cholesterol; NK—natural killer; QD—once daily.
*P < 0.05; **P < 0.01 relative to placebo; P value for difference between treatment groups in baseline and mean change from baseline using a contrast within the one-way analysis of variance.
†Mean percentage change from baseline at week 12.

TABLE 23E

Incidence of Patients With Laboratory Abnormalities at Week 12

| | | Compound 1 | | | | |
|---|---|---|---|---|---|---|
| | Placebo (n = 50) | 3 mg BID (n = 50) | 6 mg BID (n = 50) | 12 mg BID (n = 50) | 18 mg BID (n = 50) | 24 mg QD (n = 49) |
| ALT, U/L | | | | | | |
| Grade 3 (3.0-8.0 × ULN) | 0 | 1 | 1 | 2 | 1 | 0 |
| Grade 4 (>8.0 × ULN) | 0 | 0 | 0 | 0 | 1 | 0 |
| AST, U/L | | | | | | |
| Grade 3 (3.0-8.0 × ULN) | 0 | 1 | 1 | 0 | 1 | 0 |
| Grade 4 (>8.0 × ULN) | 0 | 0 | 0 | 0 | 0 | 0 |
| Neutrophils × 10$^9$/L | | | | | | |
| Grade 3 (0.5-0.9) | 0 | 0 | 0 | 1 | 3 | 1 |
| Grade 4 (<0.5) | 0 | 0 | 0 | 0 | 0 | 0 |
| Lymphocytes, × 10$^9$/L | | | | | | |
| Grade 3 (0.5-0.9) | 7 | 8 | 13 | 16 | 17 | 15 |
| Grade 4 (<0.5) | 0 | 1 | 0 | 0 | 1 | 0 |

Abbreviations: ALT—alanine aminotransferase; AST—aspartate aminotransferase; BID—twice daily; QD—once daily; ULN—upper limit of normal.

As can be seen from these results, the safety and tolerability profile of Compound 1 was acceptable across doses.

Example 34: A Phase 2/3 Ankylosing Spondylitis Clinical Study (Select-Axis 1)

Figure 10:
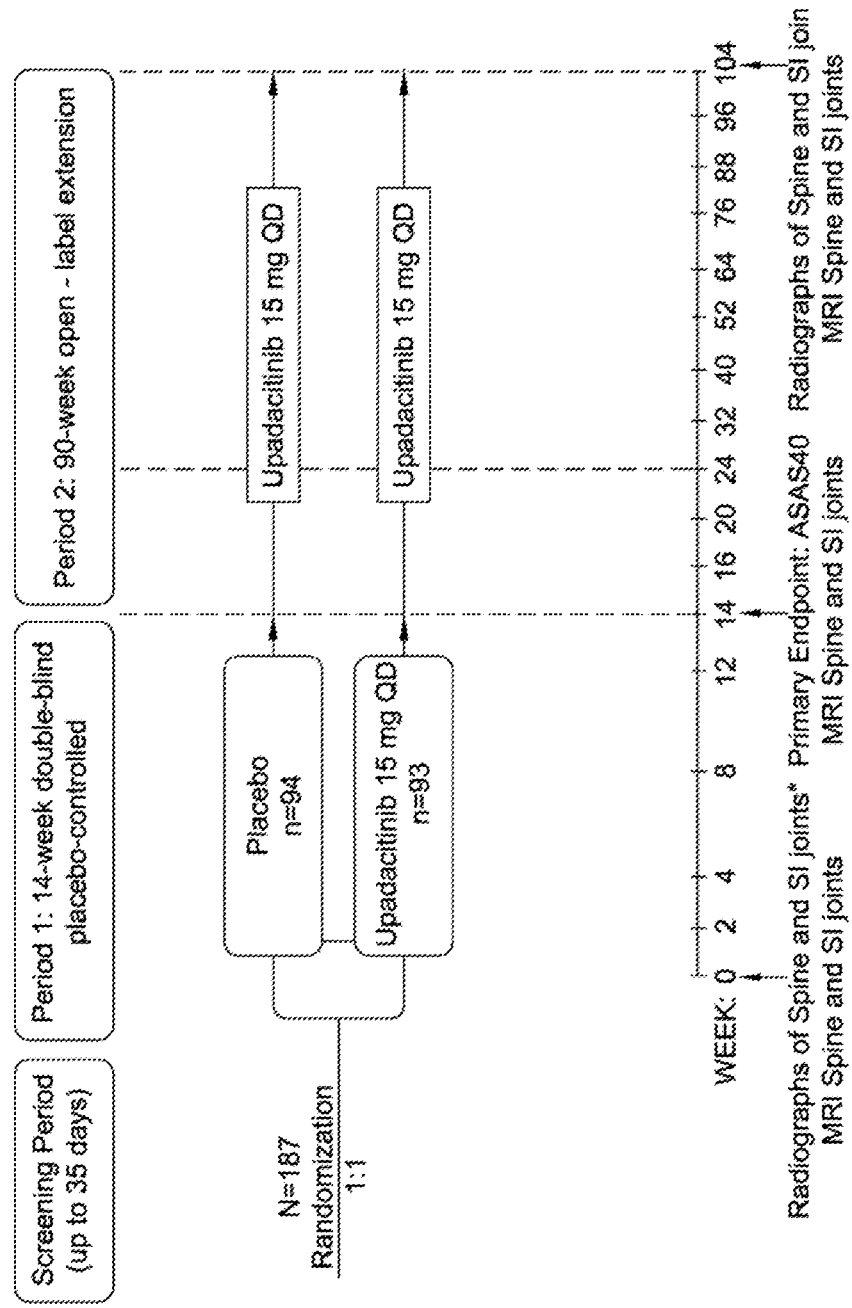
FIG. 10 depicts the Phase 2/3 Ankylosing Spondylitis (SELECT-AXIS 1) clinical study plan. Asterisk (*) indicates radiographs were conducted during the screening period. ASAS40=Assessment of SpondyloArthritis international Society 40% response. MRI=magnetic resonance imaging. QD=once daily. SI=sacroiliac.

SELECT-AXIS 1 is a multicentre, randomised, double-blind, parallel-group, placebo-controlled, Phase 2/3, two-period study of upadacitinib (FIG. 10). 15 mg upadacitinib refers to the 15 mg once-daily (QD) upadacitinib Extended Release (ER) Wet Granulated Tablets drug product as described herein are provided in the following Table 24A. The 15 mg upadacitinib ER tablet (or matching placebo) is taken orally once daily, beginning on Day 1 (Baseline), and should be taken at approximately the same time each day, with or without food.

TABLE 24A

Upadacitinib 15 mg Extended Release (ER) Tablets (Wet Granulated)

| Component | Function | Weight |
|---|---|---|
| Tablet Core Intragranular | | |
| Upadacitinib* | Drug substance | 15.4 |
| Microcrystalline cellulose (≥65% through 75 um screen) (Avicel PH 102) | Filler | 41.2 |
| Hypromellose 2208 | Control release polymer and binder | 4.9 |
| Purified water | Wetting agent | N/A |
| Extragranular | | |
| Microcrystalline cellulose (≥65% through 75 um screen) (Avicel PH 102) | Filler | 121.3 |

TABLE 24A-continued

Upadacitinib 15 mg Extended Release (ER) Tablets (Wet Granulated)

| Component | Function | Weight |
|---|---|---|
| Mannitol (Pearlitol 100 SD) | Filler | 100.6 |
| Tartaric acid powder | pH modifier | 96.0 |
| Hypromellose 2208 | Control release polymer | 91.1 |
| Colloidal Silicon Dioxide | Glidant | 7.4 |
| Magnesium Stearate | Lubricant | 7.2 |
| Film Coat | | |
| OPADRY II Yellow (PVA, TiO$_2$, PEG3350, Talc, Iron Oxide Yellow) | Film coat | 14.40 |
| Purified water** | Processing Aid | N/A |

*hemillydrate upadacitinib free base Form C as disclosed in WO2017066775 and WO 2018/165581 is used. 15 mg amount per tablet refers to the amount of anhydrous upadacitinib free base in the tablet;
**removed during processing.

Period 1 is the 14-week randomized, double-blind, parallel-group, placebo-controlled period designed to compare the safety and efficacy of upadacitinib free base 15 mg QD (once daily) versus placebo for the treatment of signs and symptoms of subjects with active AS who have had an inadequate response to at least two NSAIDs over an at least 4-week period in total at maximum recommended or tolerated doses or intolerance to or a contraindication for NSAIDs, and who are biologic Disease Modifying Anti-Rheumatic Drug (bDMARD)-naïve.

Period 2 is an open label long-term extension to evaluate the long-term safety, tolerability, and efficacy of upadacitinib free base 15 mg QD in subjects with AS who have completed Period 1.

X-rays of the pelvis were performed within the 35-day screening period to evaluate the SI joints to confirm the fulfillment of the modified New York Criteria for AS. X-rays of the spine were also performed within the 35-day screening period to assess for total spinal ankylosis; subjects with total spinal ankylosis were not eligible for this study. The x-rays of the spine and pelvis were not required during the Screening Period if the subject had a previous anteroposterior (AP) pelvis x-ray and lateral spine x-rays within 90 days of the Screening Period, provided that the x-rays are confirmed to be adequate for the required evaluations and are deemed acceptable by the central imaging vendor.

Subjects who met eligibility criteria were randomized in a 1:1 ratio to one of two treatment groups:
Group 1: Upadacitinib free base 15 mg QD, N=85 (Day 1 to Week 14)→Upadacitinib free base 15 mg QD (Week 14 and thereafter)
Group 2: Placebo, N=85 (Day 1 to Week 14)→Upadacitinib free base 15 mg QD (Week 14 and thereafter)

Starting at Week 16, subjects who did not achieve at least an ASAS 20 response at two consecutive visits had the option to add or modify doses of NSAIDs, acetaminophen/paracetamol, low potency opioid medications (tramadol or combination of acetaminophen and codeine or hydrocodone), and/or modify dose of MTX or SSZ at Week 20 or thereafter.

Starting at Week 24, subjects who still did not achieve at least an ASAS 20 response at two consecutive visits were discontinued from study drug treatment.

Subjects who completed the Week 14 visit (end of Period 1) entered the open-label long-term extension portion of the study, Period 2 (90 weeks). Subjects who were assigned to Upadacitinib in Period 1 continued to receive Upadacitinib free base 15 mg QD in an open-label manner. Subjects who were randomized to placebo at Baseline also received open-label upadacitinib free base 15 mg QD at Week 14.

Main Inclusion Criteria:
1 Male or female ≥18 years of age.
2 Subject with a clinical diagnosis of AS and meeting the modified New York Criteria for AS.
3 Subject must have baseline disease activity as defined by having a Bath Ankylosing Spondylitis Disease Activity Index (BASDAI) score ≥4 and a Patient's Assessment of Total Back Pain score (Total Back Pain score)≥4 based on a 0-10 Numeric Rating Scale (NRS) at the Screening and Baseline Visits.
4 Subject has had an inadequate response to at least two NSAIDs over an at least 4-week period in total at maximum recommended or tolerated doses, or subject has an intolerance to or contraindication for NSAIDs.
5 If entering the study on concomitant methotrexate (MTX), leflunomide, sulfasalazine (SSZ), and/or hydroxychloroquine, subject must be on a stable dose of MTX (≤25 mg/week) and/or SSZ (≤3 g/day) and/or hydroxychloroquine (≤400 mg/day) or leflunomide (≤20 mg/day) for at least 28 days prior to the Baseline Visit. A combination of up to two background conventional-synthetic disease modifying anti-rheumatic drugs (csDMARDs) is allowed EXCEPT the combination of MTX and leflunomide.
6 If entering the study on concomitant oral corticosteroids, subject must be on a stable dose of prednisone (≤10 mg/day), or oral corticosteroid equivalents, for at least 14 days prior to the Baseline Visit.
7 If entering the study on concomitant NSAIDs, tramadol, combination of acetaminophen and codeine or hydrocodone, and/or non-opioid analgesics, subject must be on stable dose(s) for at least 14 days prior to the Baseline Visit.

Main Exclusion Criteria:
1 Patients with total spinal ankylosis were ineligible.
2 Prior exposure to any Janus kinase (JAK) inhibitor (including but not limited to tofacitinib, baricitinib, and filgotinib).
3 Prior exposure to any biologic therapy with a potential therapeutic impact on spondyloarthritis (SpA).
4 Intra-articular joint injections, spinal/paraspinal injection(s), or parenteral administration of corticosteroids within 28 days prior to the Baseline Visit. Inhaled or topical corticosteroids are allowed.
5 Subject on any other DMARDs (other than those allowed), thalidomide, or apremilast within 28 days or five half-lives (whichever is longer) of the drug prior to the Baseline Visit.
6 Subject on opioid analgesics (except for combination acetaminophen/codeine or acetaminophen/hydrocodone which are allowed) or use of inhaled marijuana within 14 days prior to the Baseline Visit.
7 Subject has a history of inflammatory arthritis of different etiology other than axial SpA (including but not limited to rheumatoid arthritis [RA], psoriatic arthritis [PsA], mixed connective tissue disease, systemic lupus erythematosus, reactive arthritis, scleroderma, polymyositis, dermatomyositis, fibromyalgia), or any arthritis with onset prior to 17 years of age.

Primary Endpoint

The primary efficacy endpoint is ASAS 40 response at Week 14.

Key Secondary Endpoints

The key multiplicity adjusted secondary efficacy endpoints at Week 14 are:

1. Change from Baseline in Ankylosing Spondylitis Disease Activity Score (ASDAS(CRP));
2. Change from Baseline in MRI Spondyloarthritis Research Consortium of Canada (SPARCC) score (Spine);
3. Proportion of subjects with BASDAI 50 response (defined as 50% improvement in the Bath AS Disease Activity Index);
4. Change from Baseline in AS quality of life (ASQoL);
5. Proportion of subjects with ASAS partial remission (PR) (defined as an absolute score of ≤2 units for each of the four domains identified in ASAS 40);
6. Change from Baseline in BASFI;
7. Change from Baseline in BASMI$_{lin}$;
8. Change from Baseline in Maastricht Ankylosing Spondylitis Enthesitis Score (MASES) (i.e., for subjects with baseline enthesitis);
9. Change from Baseline in Work Productivity and Activity Impairment (WPAI) (the overall work impairment due to SpA);
10. Change from Baseline in ASAS HI.

Additional key secondary endpoints are:
11. ASAS 20 response at Week 14.
12. Change from Baseline in MRI SPARCC score (SI joints) at Week 14.

Additional endpoints are the following measurements assessed in subjects treated with upadacitinib versus placebo at scheduled time points other than those specified for the primary and key secondary variables:
1. Proportion of subjects with ASAS 20 response;
2. Proportion of subjects with ASAS 40 response;
3. Proportion of subjects with ASAS PR;
4. Proportion of subjects with ASAS 5/6 (20% improvement from Baseline in five out of the following six domains: BASFI, patient's assessment of total back pain, PtGA, inflammation [mean of Questions 5 and 6 of the BASDAI] lateral lumbar flexion from BASMI-lin, and high sensitivity CRP [hsCRP]);
5. Proportion of subjects with Inactive Disease based on ASDAS(CRP) and ASDAS(ESR) (ASDAS score <1.3);
6. Proportion of subjects with Major Improvement based on ASDAS(CRP) and ASDAS(ESR) (a change from Baseline ≤-2.0);
7. Proportion of subjects with Clinically Important Improvement based on ASDAS(CRP) and ASDAS (ESR) (a change from Baseline ≤-1.1);
8. Proportion of subjects with Resolution of dactylitis (i.e., for subjects with baseline presence of dactylitis);
9. Change from Baseline in ASAS HI;
10. Change from Baseline in ASDAS(CRP) and ASDAS (ESR) respectively;
11. Change from Baseline in AsQoL;
12. Change from Baseline in BASDAI;
13. Change from Baseline in BASFI;
14. Change from Baseline in BASMIlin;
15. Change from Baseline in CRP;
16. Change from Baseline in Total dactylitis count (i.e., for subjects with baseline presence of dactylitis);
17. Change from Baseline in FACIT-F;
18. Change from Baseline in 1SI;
19. Change from Baseline in MASES (i.e., for subjects with baseline MASES>0);
20. Change from Baseline in Modified Stoke Ankylosing Spondylitis Spine Score (mSASSS) score with conventional radiograph;
21. Change from Baseline in MRI SPARCC score of SI joints;
22. Change from Baseline in MRI SPARCC score of Spine;
23. Change from Baseline in Patient's Assessment of Total Back Pain NRS score 0-10;
24. Change from Baseline in Patient's Assessment of Nocturnal Back Pain NRS score 0-10;
25. Change from Baseline in Patient's Global Assessment of Pain NRS score 0-10;
26. Change from Baseline in Physician's Global Assessment of Disease Activity NRS score 0-10;
27. Change from Baseline in Inflammation (mean of Questions 5 and 6 of BASDAI NRS scores 0-10);
28. Change from Baseline in Patient's assessment of total back pain (BASDAI Question 2 NRS score 0-10);
29. Change from Baseline in Peripheral pain/swelling (BASDAI Question 3 NRS score 0-10);
30. Change from Baseline in Duration of morning stiffness (BASDAI Question 6 NRS score 0-10);
31. Change from Baseline in Patient's Global Assessment of Disease Activity NRS score 0-10;
32. Change from Baseline in TJC68 and SJC66;
33. Change from Baseline in WPAI (all 4 dimension scores);
34. Change from Baseline in Categories in ISI. See, e.g., Machado et al., *Ann Rheum Dis* (2018) 77: 1539-40; Maksymowych et al., *Arthritis Rheum* (2005) 53: 502-9.

Analysis Windows

For each protocol-specified study visit, a target study day will be identified to represent the corresponding visit along with a window around the target day. Windows will be selected in a non-overlapping fashion so that a collection date does not fall into multiple visit windows. If a subject has two or more actual visits in one visit window, the visit closest to the target day will be used for analysis. If two visits are equidistant from the target day, then the later visit will be used for analysis.

Statistical Analyses

The planned sample size of 170 for this study (with 1:1 randomisation ratio) was determined to provide ≥90% power for detecting a 26% difference in ASAS40 response rate (assuming a placebo ASAS40 response rate of 20%). Power and sample size calculations were performed at a two-sided significance level of 0-05 accounting for a 10% dropout rate. The full analysis set included all randomised patients who received at least one dose of study drug. The safety analysis set included all patients who received at least one dose of study drug. The SPARCC MRI assessment population was pre-specified in the statistical analysis plan (baseline included MRI data ≤3 days after first dose of study drug, and week 14 included MRI data up to first dose of Period 2 study drug; first dose in Period 2 was at week 14). A supplemental post hoc SPARCC MRI analysis was conducted to include all MRI data collected at nominal visits at baseline and week 14. Cumulative probability plots were generated to illustrate MRI SPARCC score changes on a patient level.

Figure 11:
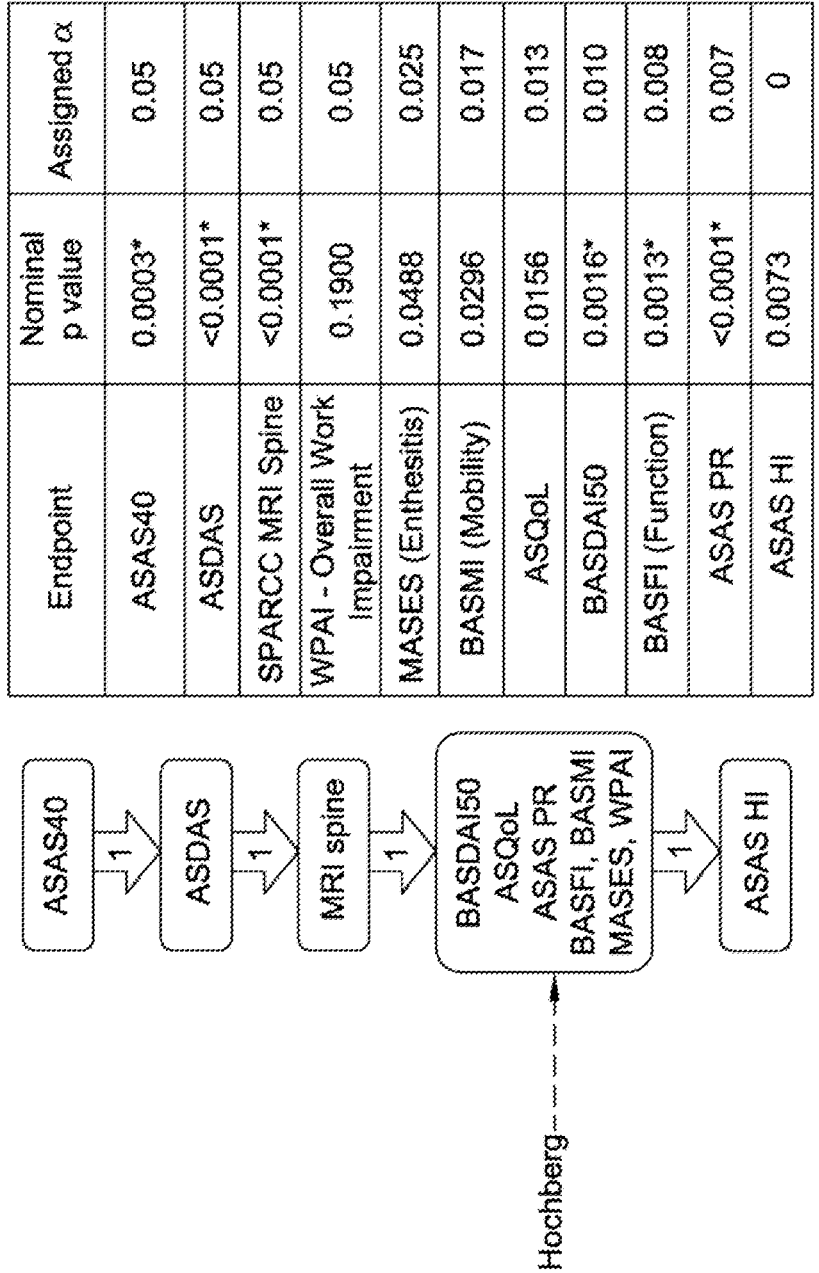
FIG. 11 depicts the multiplicity-controlled analysis used in the Phase 2/3 Ankylosing Spondylitis (SELECT-AXIS 1) clinical trial using the Hochberg Procedure. Asterisk (*) indicates result was statistically significant in multiplicity-controlled analysis, otherwise nominal p values are shown. The multiplicity-controlled endpoints are tested in a sequential manner with initially assigned α=0.05. Statistical significance (p<0.05) can be claimed for a lower ranked endpoint only if the previous endpoint in the sequence meets the requirements of statistical significance. ASAS HI can be evaluated only if the group of endpoints tested by Hochberg procedure are all statistically significant. Within the Hochberg procedure. BASDAI50. BASFI, and ASAS PR achieved the required statistical significance; however, WPAI, MASES, BASMI, and ASQoL did not meet the requirement of statistical significance, so ASAS HI was not tested. Per Hochberg procedure, all endpoints are tested using assigned α according to the magnitude of nominal p value starting from the largest one. If an endpoint is rejected, all endpoints with smaller p values are rejected. If an endpoint fails, then the procedure advances to the next endpoint. ASAS=Assessment of SpondyloArthritis International Society. ASAS40=ASAS 40% response. ASAS HI=ASAS Health Index. ASAS PR=ASAS Partial Remission, ASDAS=Ankylosing Spondylitis Disease Activity Score. ASQoL=Ankylosing Spondylitis Quality of Life. BASDAI50=50% improvement from baseline in Bath Ankylosing Spondylitis Disease Activity Index. BASFI=Bath Ankylosing Spondylitis Functional Index. BASMI=Bath Ankylosing Spondylitis Metrology Index. MASES=Maastricht Ankylosing Spondylitis Enthesitis Score. MRI=magnetic resonance imaging. QD=once daily. SPARCC=Spondyloarthritis Research Consortium of Canada. WPAI=Work Productivity and Activity Impairment.

In the full analysis set, the primary endpoint was compared between the upadacitinib and the placebo group using the Cochran-Mantel-Haenszel test, adjusting for the stratification factor of screening hsCRP level. Non-responder imputation was used for handling missing data. Similar analyses as for the primary endpoint were conducted for secondary efficacy binary endpoints. For continuous secondary efficacy endpoints, comparisons between the upadacitinib and the placebo group were performed using mixed model for repeated measures with treatment group, visit, and treatment-by-visit interaction as fixed effects and the corresponding baseline value and the stratification factor of screening hsCRP level as the covariates. In order to preserve the overall type I error rate at a-=0.05 level, a step-down approach was used to test the primary and multiplicity-controlled key secondary endpoints. The testing sequence includes a group of endpoints tested by the Hochberg procedure, including BASDAI50. ASQoL, ASAS PR, BASFI, BASMI, MASES, and WPAI (FIG. 11). See, e.g., Hochberg Y, Tamhane A C. Multiple comparison procedures: John Wiley & Sons, Inc., 1987.

Week 14 Results

Between Oct. 24, 2017, and Sep. 10, 2018, 395 patients were assessed for eligibility, and 187 were enrolled into the study. Of the 395 patients screened, 208 (52.7%) did not meet eligibility criteria and were excluded from the study (main reason for screening failure was not meeting the radiographic criterion of the modified New York criteria for AS). The remaining 187 patients who met eligibility criteria were randomised to placebo (n=94) or upadacitinib (n=93). Overall, 95.2% of patients completed Period 1 through week 14 on study drug (placebo, 8994 [94.7%]; upadacitinib, 89/93 [95.7%]); one patient in the placebo group discontinued study drug but completed Period 1 visits. The most common primary reason for study drug discontinuation by week 14 were adverse events in the placebo group (n=3 [3.2%]) and adverse events (n=2 [2.2%]) and withdrawal of consent (n=2 [2.2%]) in the upadacitinib group.

Mean age was 45.4 years, mean duration from onset of symptoms was 14.4 years, and mean duration since diagnosis was 6.9 years. Most patients were male (132 [70.6%]), were human leukocyte antigen (HLA) B27 positive (143 [76.5%]) and were receiving concomitant NSAIDs at baseline (150 [80.2%]). Baseline disease characteristics were generally balanced between the two groups. Key demographics and baseline characteristics of the patients are summarized in the below Table 24B.

TABLE 24B

Key demographics and baseline characteristics of patients

| Key Demographic and Baseline Characteristics Mean (SD) or a (%) | PLACEBO N = 94 | Upadacitinib 15 mg qd n = 93 |
|---|---|---|
| Male | 69 (73.4) | 63 (67.7) |
| Age (Yrs) | 44 (12.1) | 47 (12.8) |
| HLA-B27 Positive | 73 (77.7) | 70 (75.3) |
| White | 76 (80.9) | 79 (84.9) |
| Region | | |
| North America | 10 (10.6) | 9 (9.7) |
| South/Central America | 0 | 0 |
| Western Europe | 33 (35.1) | 30 (32.3) |
| Eastern Europe | 34 (36.2) | 36 (38.7) |
| Asia[a] | 14 (14.9) | 12 (12.9) |
| Other[b] | 3 (3.2) | 6 (6.5) |
| Duration of AS Diagnosis (Yrs) | 6.0 (6.79) | 7.8 (10.64) |
| Duration of AS Symptom (Yrs) | 14.0 (9.86) | 14.8 (11.64) |
| NSAID Use at Baseline | 80 (85.1) | 70 (75.3) |
| Prior NSAID Use | 94 (100) | 92 (98.9) |
| csDMARDs Use at Baseline | 17 (18.1) | 13 (14.0) |
| BASDAI | 6.5 (1.56) | 6.3 (1.76) |
| Total back pain (NRS 0-10) | 6.7 (1.78) | 6.8 (1.77) |
| Patient Global Assessment (NRS 0-10) | 6.8 (1.66) | 6.6 (1.81) |
| ASDAS (CRP) | 3.7 (0.74) | 3.5 (0.76) |
| BASFI (Function) | 5.5 (2.17) | 5.4 (2.36) |
| BASMI (Mobility) | 3.5 (1.48) | 3.7 (1.45) |
| Presence of Enthesitis (MASES > 0) | 55 (58.5) | 54 (58.1) |
| MASES Score[c] | 3.7 (2.71) | 3.9 (2.79) |
| MRI Spine SPARCC[d] | 11.9 (14.52) | 10.4 (14.36) |
| MRI Sacroiliac Joint SPARCC[d] | 5.4 (8.55) | 7.9 (10.91) |
| hsCRP at Screening (mg/L) | 11.7 (11.11) | 9.6 (12.57) |
| hsCRP > ULN at Screening | 68 (72.3) | 67 (72.0) |
| AS QoL | 10.3 (4.65) | 10.0 (5.27) |
| WPAI-Overall Work Impairment[e] | 53.3 (24.64) | 54.3 (28.10) |
| ASAS Health Index | 8.2 (3.84) | 8.6 (4.12) |

[a]South Korea and Japan.
[b]New Zealand and Australia.
[c]Summarized for subjects with presence of enthesitis at baseline.
[d]Summarized for subjects whose baseline MRI data up to 3 days post first dose of study drug.
[e]Summarized for subjects employed at baseline.

Figure 12A:
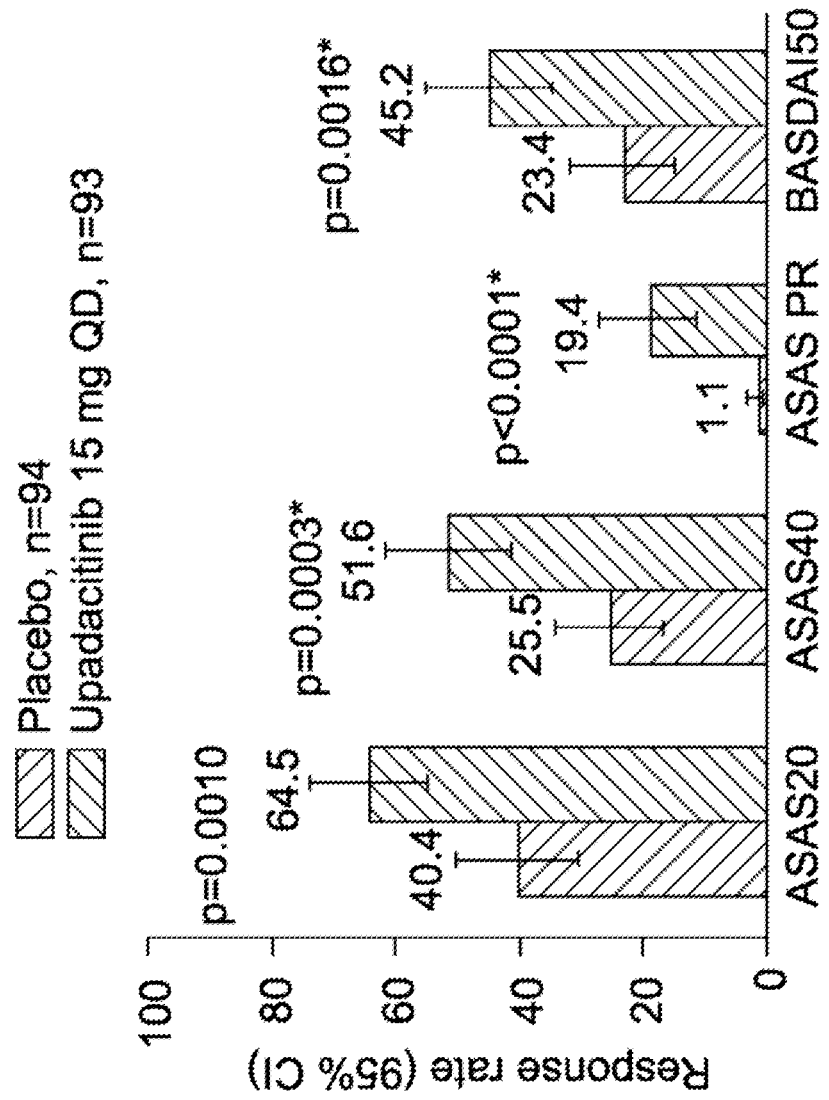
FIGS. 12A-12C and FIGS. 12D-12N, respectively depict the Week 14 results of the Phase 2/3 Ankylosing Spondylitis (SELECT-AXIS 1) clinical trial for key clinical efficacy endpoints, and time course of key endpoints up to and including Week 64.
Figure 12B:
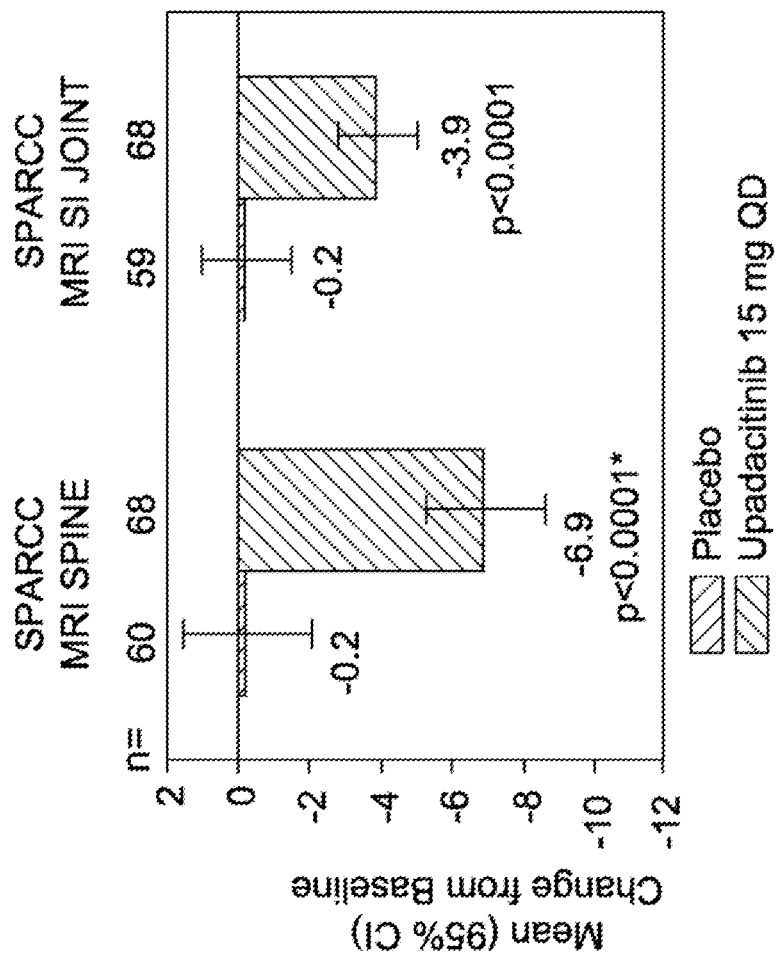
Figure 12C:
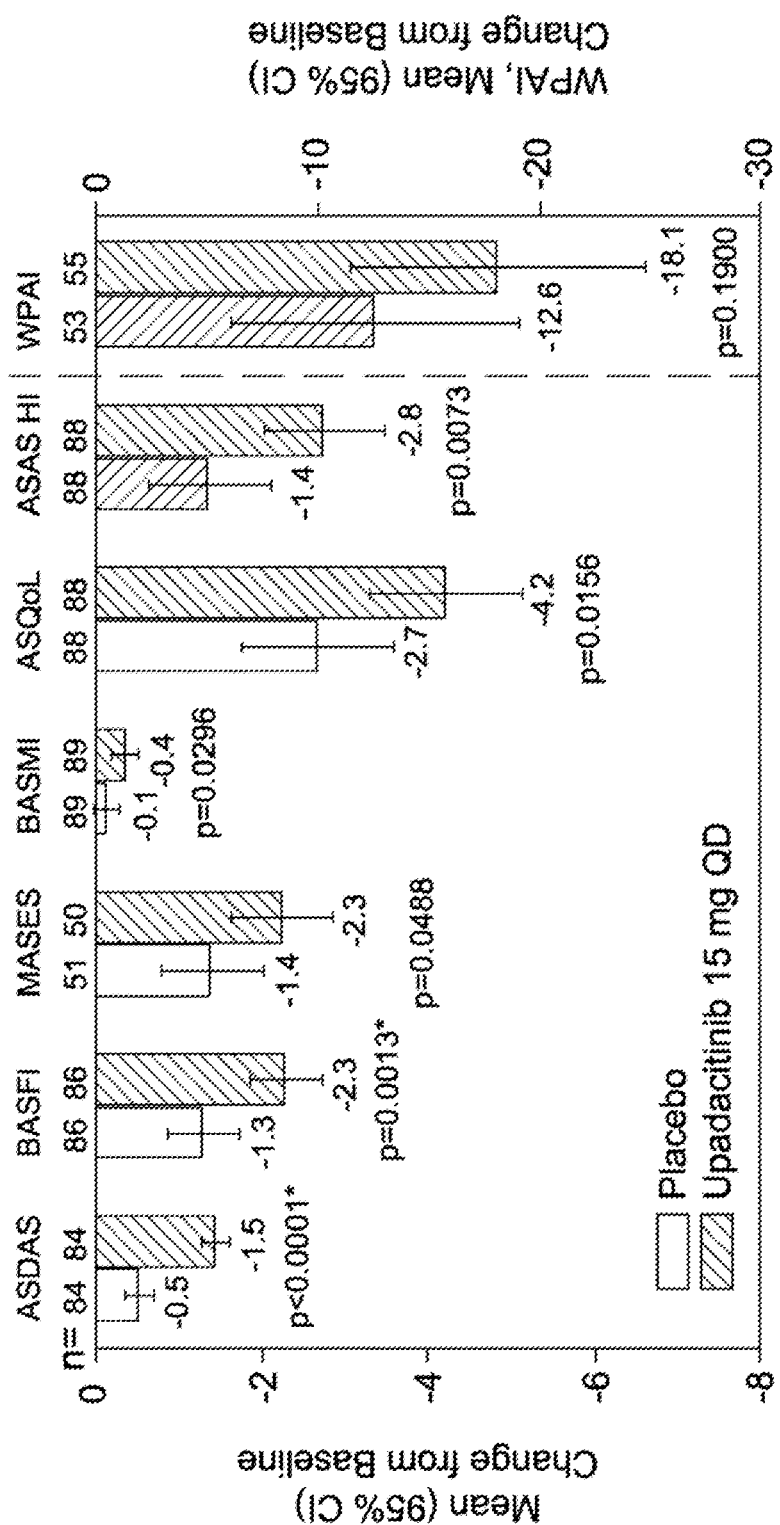

The study met its primary endpoint, with statistically significantly more patients treated with upadacitinib versus placebo achieving ASAS40 response at week 14 (48/93 [51.6%] vs 24/94 [25.5%]; p=0.0003) with a treatment difference (95% CI) of 26.1% (12.6-39.5%) (FIG. 12A). A significant difference for upadacitinib versus placebo in ASAS40 (FIG. 13A) and the mean change for each of its four individual domains (FIGS. 12B-12E) was observed as early as the first post-baseline visit (week 2), and this difference was maintained consistently through week 14, with week 14 achieving a statistically significant difference in the multiplicity-controlled analysis. Accounting for multiplicity adjustment, change from baseline to week 14 in ASDAS (CRP) (FIG. 12C). SPARCC MRI spine (FIG. 12B), and BASH (FIG. 12C) and proportion of patients who achieved BASDAI50 (FIG. 12A) and ASAS PR (FIG. 12A) were statistically significant for upadacitinib versus placebo. Upadacitinib versus placebo mean (95% CI) change from baseline to week 14 was −1.45 (−1.62 to −1.28) versus −0.54 (−0.71 to −0.37; treatment difference, −0.91 [−1.14 to −0.68, p<0.0001]) for ASDAS (CRP) and −2.29 (−2.73 to −1.85) versus −1.30 (−1.74 to −0.86; treatment difference, −1.00 [−1.60 to −0.39, p=0.0013]) for BASFI. BASDAI50 was achieved by 42/93 (45.2%) patients treated with upadacitinib versus 22/94 (23.4%) patients in the placebo group (treatment difference, 21.8% [8.5-35.0%; p=0.0016]) and ASAS PR was achieved by 18/93 (19.4%) patients in the upadacitinib group versus 1/94 (1.1%) in the placebo group (treatment difference, 18.3% [10.0-26.6%; p<0.001]).

For the other multiplicity-controlled key efficacy endpoints, statistical significance based on multiplicity adjustment was not met per the Hochberg procedure. Consistent improvement was observed in patients receiving upadacitinib versus placebo with nominal p values <0.05 for MASES (p=0.0488), BASMI (p=0.0296), ASQoL (p=0.0156), and ASAS HI (p=0.0073) at week 14, except for WPAI (FIG. 12C).

The additional key secondary efficacy endpoints. ASAS20 and SPARCC MRI SI joint score, also improved with upadacitinib versus placebo based on nominal p values (FIGS. 12A and 12B). ASAS20 was achieved by 60/93 (64.5%) patients treated with upadacitinib versus 38/94 (40.4%) of patients in the placebo group at week 14 (treatment difference, 24.1% [10.2-38.0%; p=0.0010]).

Figure 14:
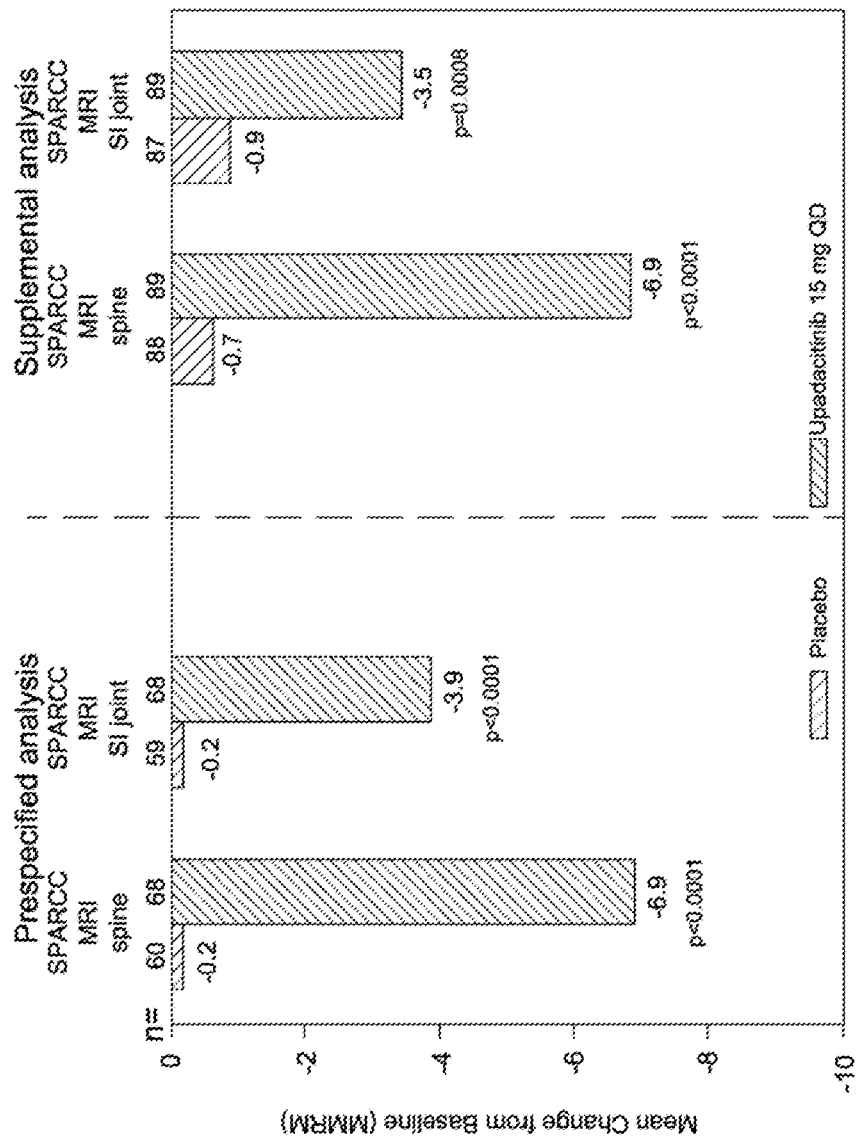
FIG. 14 depicts the pre-specified and supplemental SPARCC MRI Analysis of the Phase 2/3 Ankylosing Spondylitis (SELECT-AXIS 1) clinical trial. The SPARCC MRI assessment population was pre-specified in the statistical analysis plan (baseline included MRI data ≤3 days after first dose of study drug, and Week 14 included MRI data up to first dose of period 2 study drug). The supplemental SPARCC MRI analysis included all MRI data collected at nominal visits at baseline and Week 14, and confirmed the results of the primary SPARCC MRI analysis for both the spine and SI joints. MMRM=mixed model for repeated measures. MRI=magnetic resonance imaging. QD=once daily. SI=sacroiliac. SPARCC=Spondyloarthritis Research Consortium of Canada.
Figure 15B:
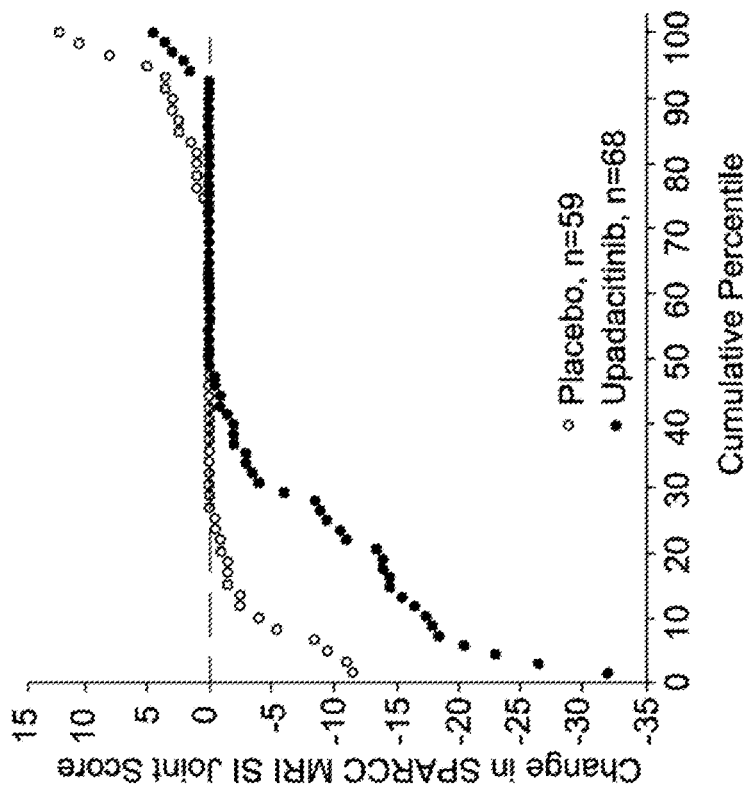
FIGS. 15A-15D depict the cumulative probability plots of change in SPARCC scores as described in FIG. 14 for the Phase 2/3 Ankylosing Spondylitis (SELECT-AXIS 1), demonstrating that the SPARCC MRI spine and SI joint scores improved from baseline to week 14 to a greater extent in patients receiving upadacitinib compared with placebo. Results for the primary MRI analyses (FIGS. 15A-15B) and supplemental MRI analyses (FIGS. 15C-15D) were consistent.
Figure 15A:
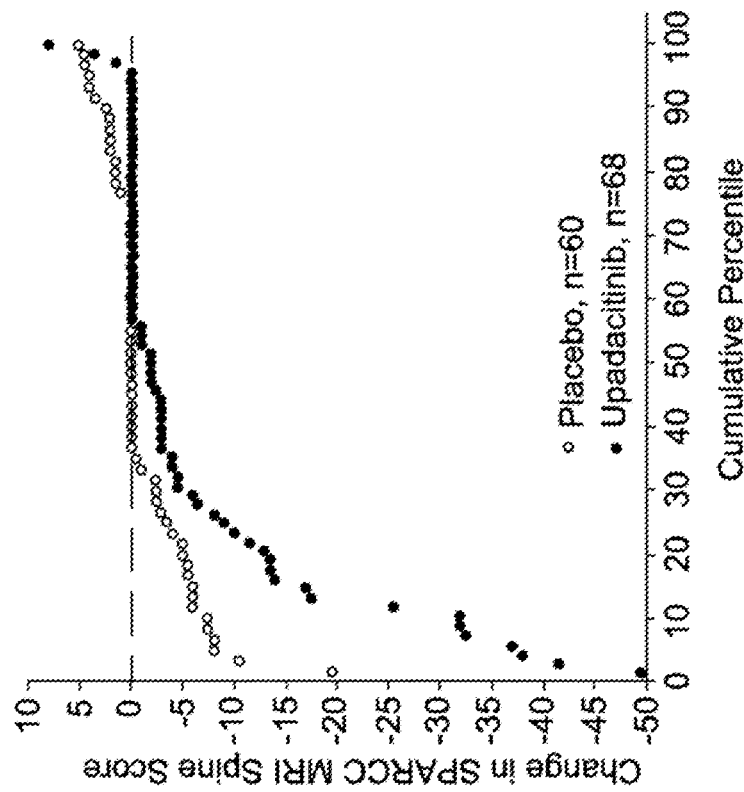
Figure 15C:
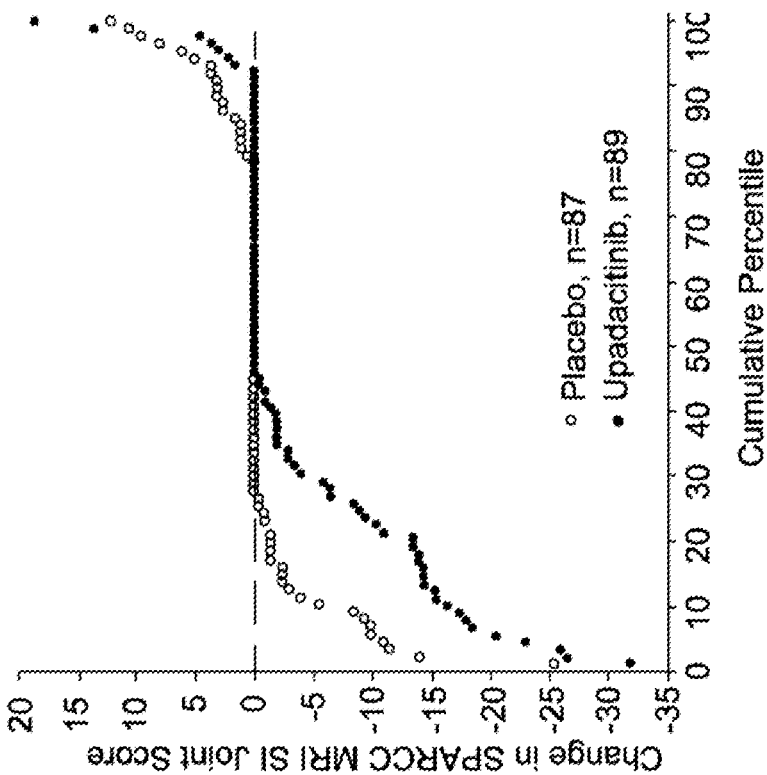
Figure 15D:
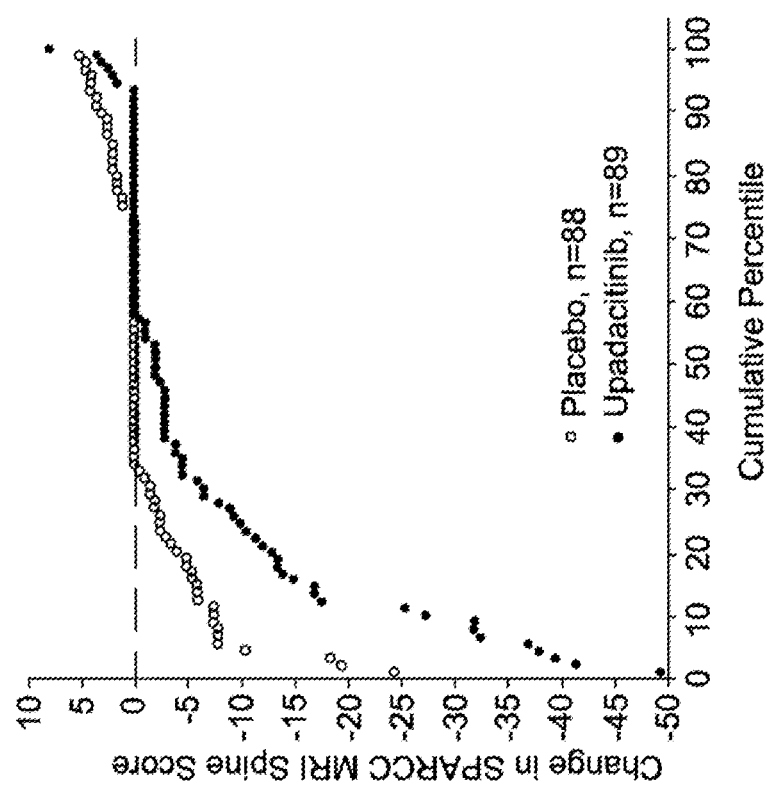

For the SPARCC MRI outcomes, change from baseline to week 14 in SPARCC MRI spine was −6.93 (−8.58 to −5.28) for upadacitinib versus −0.22 (−2.01 to 1.57) for placebo (treatment difference, −6.71 [−9.01 to −4.41; significant in multiplicity-controlled analysis, p<0.0001]) and change from baseline to week 14 in SPARCC MRI SI joint was −3.91 (−5.05 to −2.77) for upadacitinib versus −0.22 (−1.47 to −1.04) for placebo (treatment difference, −3.69 [−5.31 to −2.08; p<0.0001]; FIG. 12B). The supplemental MRI analysis conducted in all patients with available data confirmed the results of the primary SPARCC MRI analysis for both the spine and SI joints (FIG. 14). The cumulative probability plots of change in SPARCC scores demonstrated that SPARCC MRI spine and SI joint scores improved from baseline to week 14 to a greater extent in patients receiving upadacitinib compared with placebo; results for the primary MRI analyses (FIGS. 15A-15B) and supplemental MRI analyses (FIG. 15C-15D) were consistent. Table 24C below summarizes the primary and key secondary efficacy endpoints at Week 14. Table 24D below provides additional efficacy measurements at Week 14.

TABLE 24C

Primary and Key Secondary Efficacy Endpoints at Week 14[a]

| | Endpoint | PLACEBO N = 94 | Upadacitinib 15 mg qd N = 93 |
|---|---|---|---|
| Primary | ASAS40 | 25.5% | 51.6% |
| Multiplicity | ASDAS(CRP) | −0.54 | 1.45 |
| Adjusted | MRI Spine SPARCC[b] | −0.22 | −6.93 |
| Key | BASDAI50 | 23.4% | 45.2% |
| Secondary | AS QoL | −2.7 | −4.2 |
| | ASAS Partial Remission | 1.1% | 19.4% |
| | BASFI (Function) | −1.30 | −2.29 |
| | BASMI (Mobility) | −0.1 | −0.4 |
| | MASES (Enthesitis)[c] | −1.4 | −2.3 |
| | WPAI-Overall Work Impairment[d] | −12.6 | −18.1 |
| | ASAS Health Index | −1.4 | −2.8 |
| Other Key | ASAS20 | 40.4% | 64.5% |
| Secondary | MRI SI Joints SPARCC[c] | −0.22 | −3.91 |

Figure 16A:
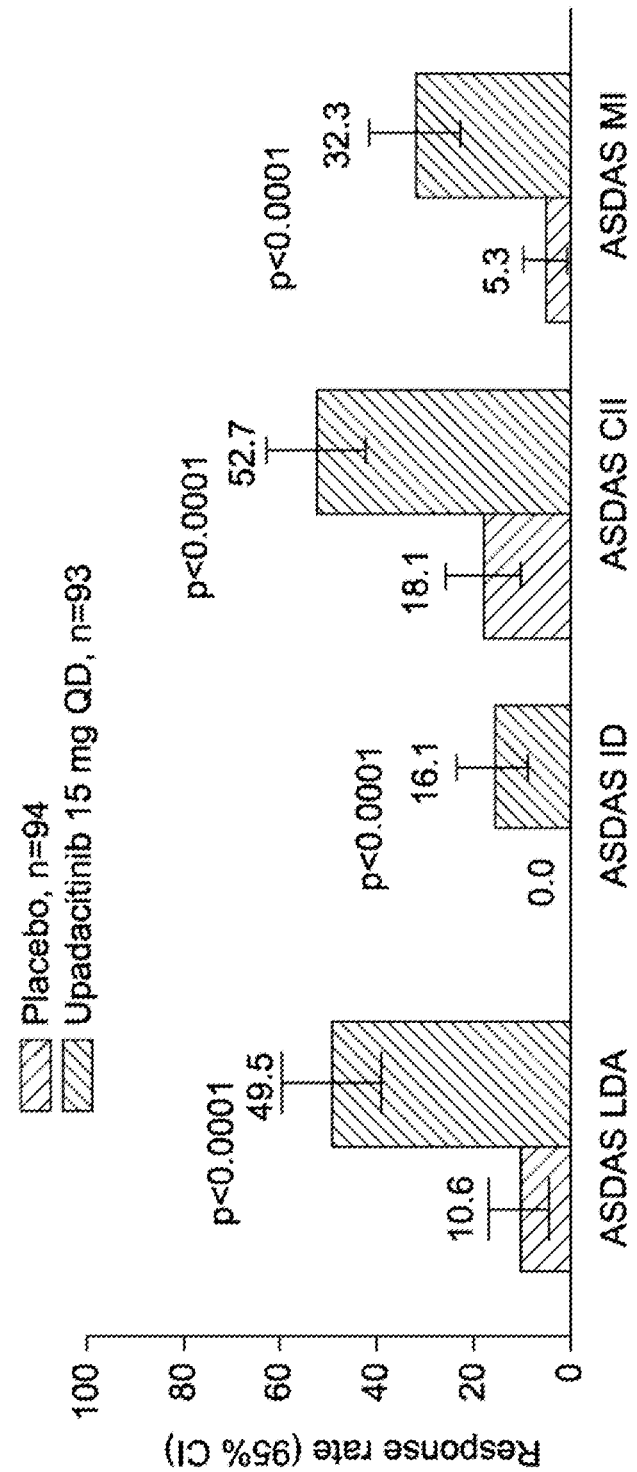
FIGS. 16A-16C depict the percentage of patients achieving ASDAS LDA, ASDAS ID, ASDAS CII, and ASDAS MI at Week 14 (FIG. 16A), Change From Baseline in Mean ASDAS Over Time (FIG. 16B), and ASDAS MI Over Time (FIG. 16C) in the Phase 2/3 Ankylosing Spondylitis (SELECT-AXIS 1) clinical trial. The proportions of patients who achieved ASDAS LDA, ASDAS ID. ASDAS CII, and ASDAS MI were greater (nominal p<0.000 1) for upadacitinib freebase versus placebo at Week 14 (FIG. 16A), ASDAS=Ankylosing Spondylitis Disease Activity Score. BL=baseline. CII=Clinically Important Improvement (≥1.1-point decrease from baseline). ID=Inactive Disease (score <1.3). LDA=low disease activity (<2.1). MI=Major Improvement (≥2-point decrease from baseline). MMRM=mixed model for repeated measures. NRI=non-responder imputation. QD=once daily.
Figure 16B:
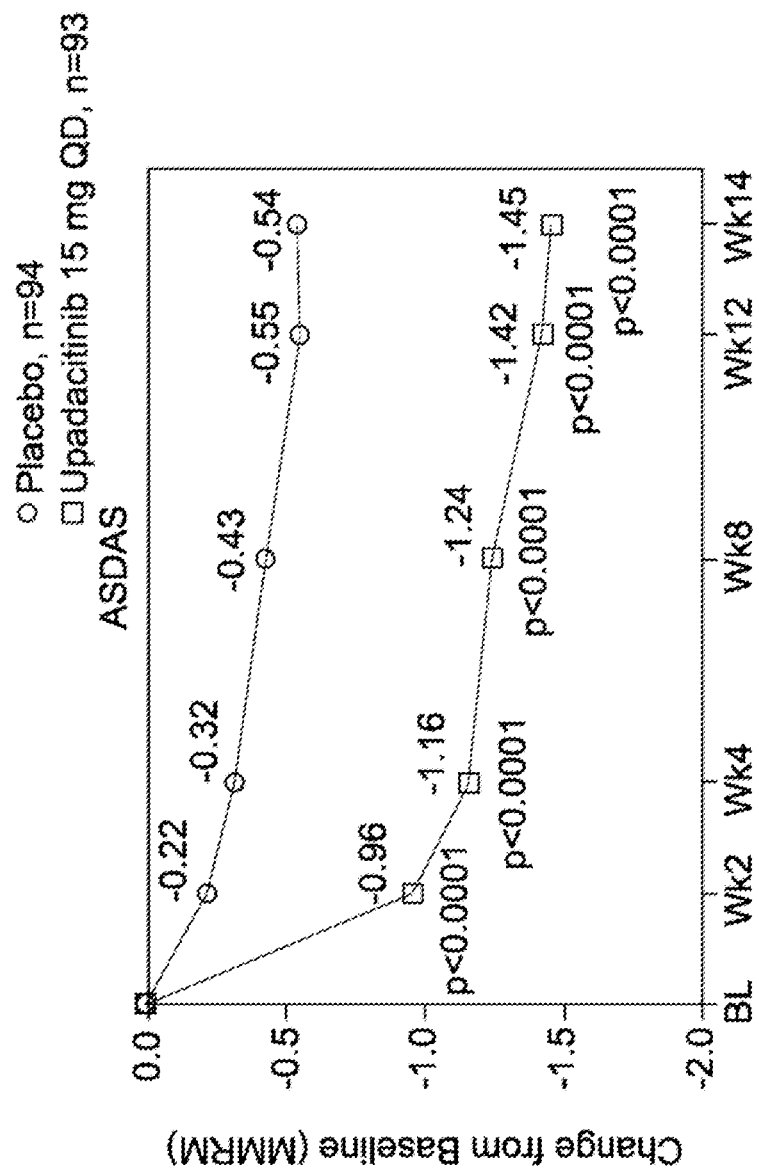
Figure 16C:
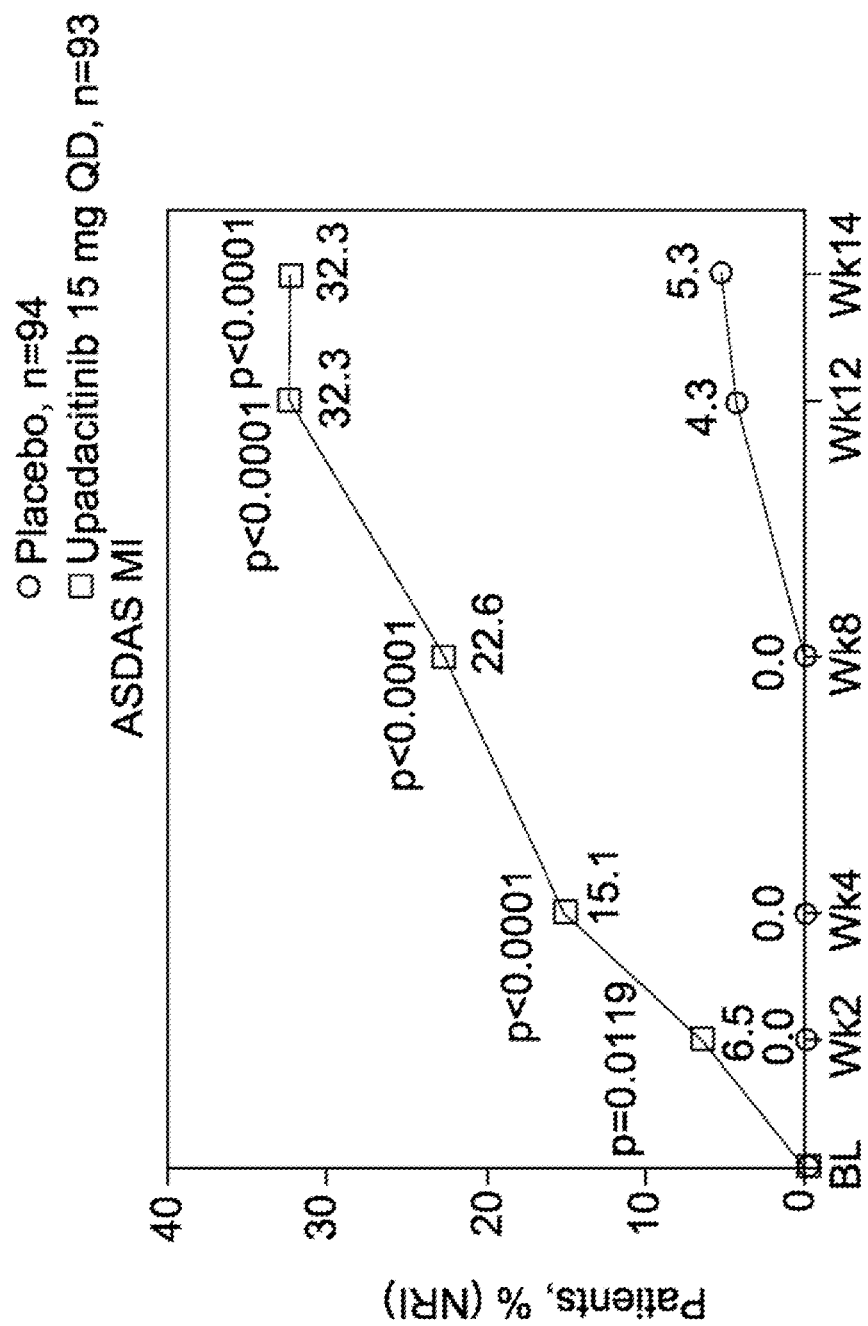
Figure 17B:
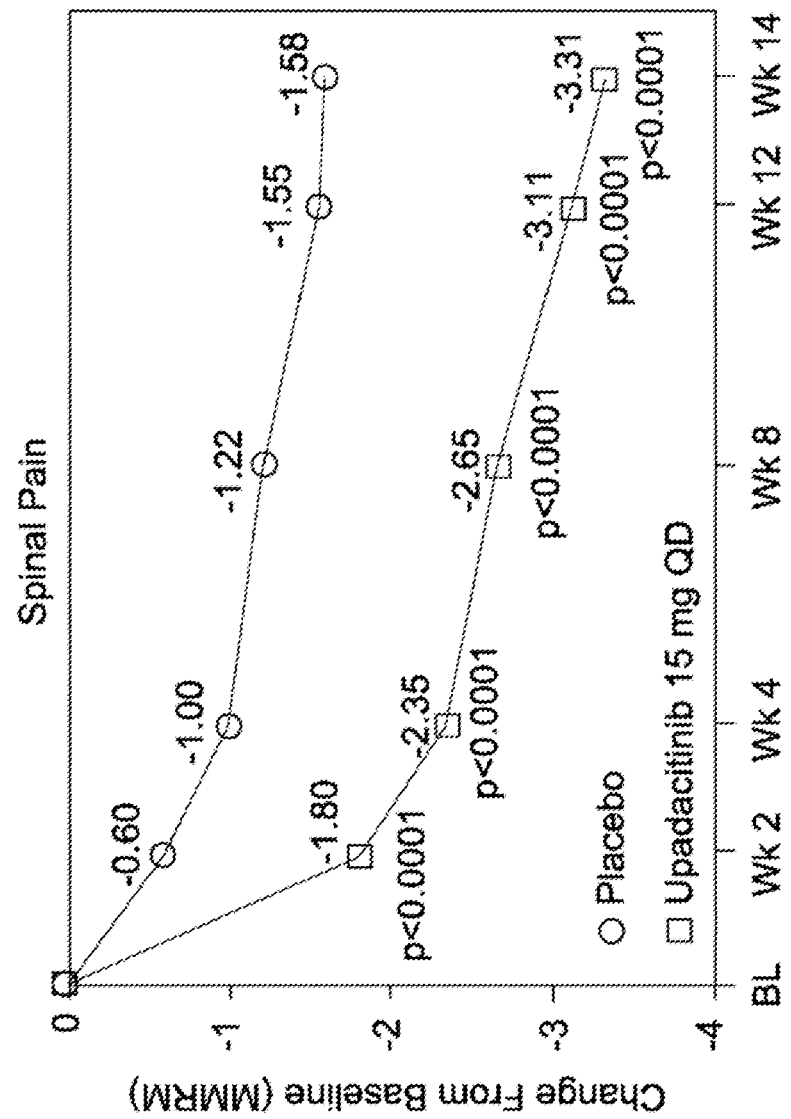
Figure 17C:
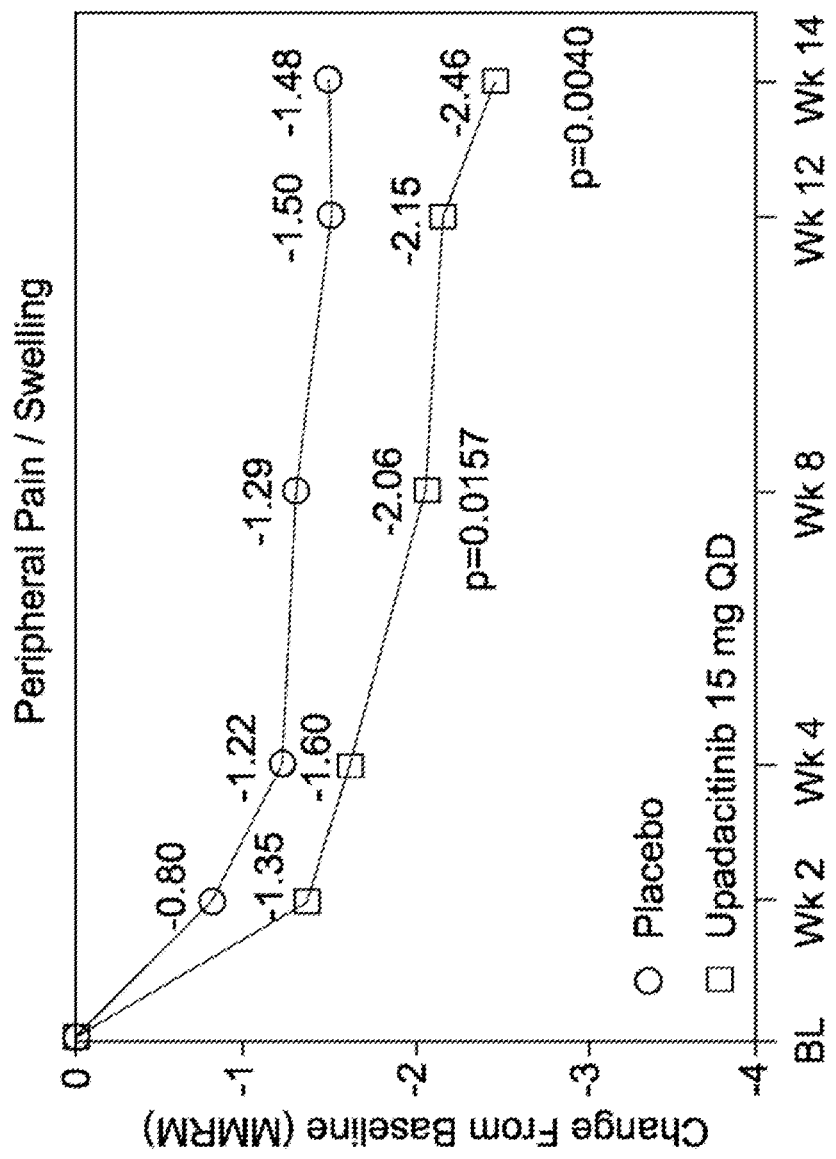
Figure 17D:
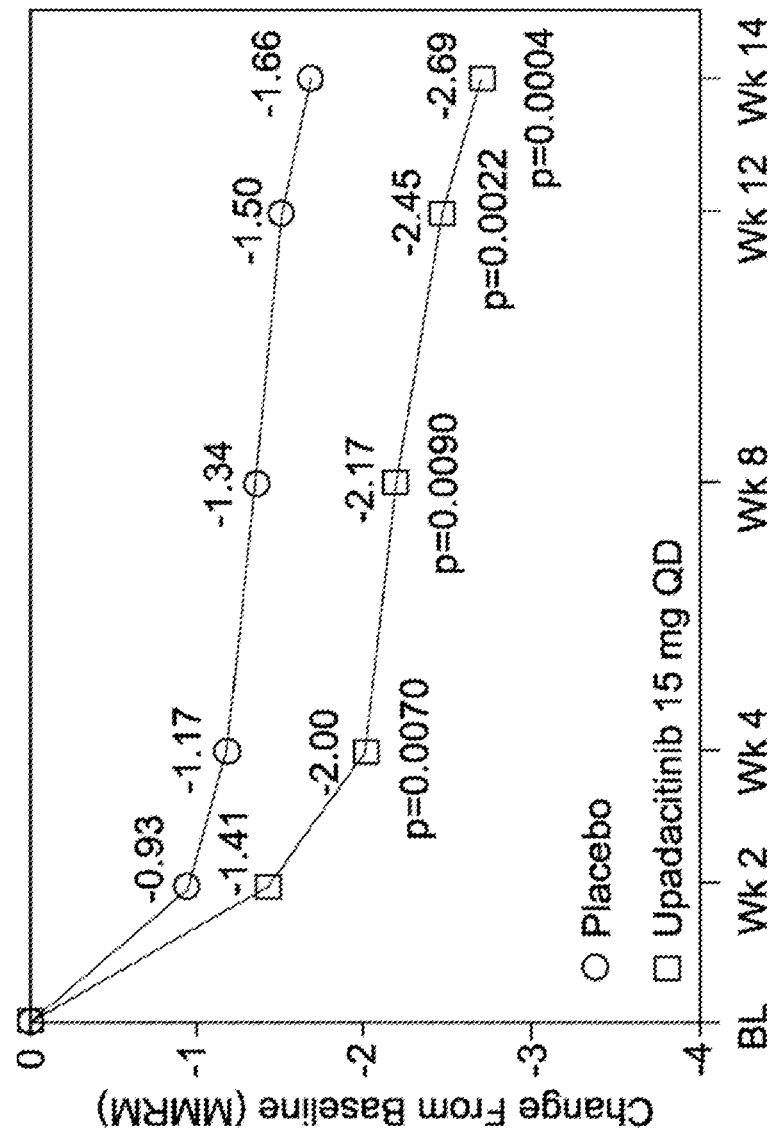

[a]Results for binary endpoints are based on NRI analysis. Analyses for all continuous endpoints are for the change from baseline value. Results for continuous endpoints are based on MMRM or ANCOVA analysis.
[b]Summarized for subjects whose baseline MRI data up to 3 days post first dose of study drug and week 14 data up to the first dose of period 2 study drug.
[c]Summarized for subjects with presence of enthesitis at baseline.
[d]Summarized for subjects employed at baseline The proportions of patients who achieved ASDAS LDA, ASDAS ID, ASDAS CII, and ASDAS MI were greater (nominal p<0.0001) for upadacitinib versus placebo at week 14 (FIG. 16A). These results are summarized in the below Table 24D. Improvement in the mean ASDAS (FIG. 161B) and the individual ASDAS components (FIGS. 17A-17D) was seen as early as week 2 with continued improvement up to week 14 with upadacitinib.

TABLE 24D

Additional Efficacy Measurements at Week 14

| Endpoint | PLACEBO (N = 94) | Upadaeitinib 15 mg qd (N = 93) |
|---|---|---|
| ASDAS ID | 0% | 16.1% |
| ASDAS LDA[a] | 10.6% | 49.5% |
| ASDAS MI | 5.3% | 32.3% |
| ASDAS CII | 18.1% | 52.7% |

[a]post-hoc analysis

Patients treated with the upadacitinib 15 mg QD dose showed greater improvement in back pain as assessed by the Total Back Pain component of ASAS response compared to placebo at Week 14. Improvement in the overall level of neck, back, or hip pain was demonstrated using BASDAI Question 2. Improvements were also demonstrated for peripheral pain and swelling (assessed by BASDAI question 3 on overall pain in joints other than in the neck, back, or hips) and nocturnal back pain. Improvements in total and nocturnal back pain were observed as early as Week 2.

No serious infections, herpes zoster, malignancy, venous thromboembolic events, or deaths were reported in Period 1. The proportion of patients with adverse events was higher in the upadacitinib group 58/93 (62.4%) versus placebo group 52/94 (55.3%). One serious adverse event in each group was reported during Period 1: cardiovascular disorder/circulation dysregulation in the placebo group (patient was not feeling well and was hospitalised but no significant findings were obtained) and worsening of spinal osteoarthritis in the upadacitinib group in a patient with a history of spondylosis and disc protrusion in the cervical spine. The proportion of patients with adverse events leading to discontinuation of study drug (upadacitinib, 2/93 [2.2%]; placebo, 3/94 [3.2%]) and infections (upadacitinib, 19/93 [20.4%]; placebo, 26/94 [27.7%]) was similar for both treatment groups. The most common adverse event in patients in the upadacitinib group was blood creatine phosphokinase (CPK), which increased (8/93 [8.6%] vs 2/94 [2.1%] patients in the placebo group), with four events (vs one with placebo) assessed by the investigator to be possibly related to study drug; all patients were asymptomatic with elevations <4×ULN, except for one patient in the placebo group with muscle pain and an increase to 4.3×ULN. Most of these events were reversible without study drug interruption (6/8 with upadacitinib, ½ with placebo). One patient in the upadacitinib group who already had grade 2 neutropenia at baseline experienced a mild adverse event of grade 2 neutropenia.

Seven patients reported hepatic disorder adverse events (upadacitinib, 5/93 [5.4%]; placebo, 2/94 [2.1%]); none resulted in study drug discontinuation, and all were asymptomatic alanine aminotransferase or aspartate aminotransferase increases, with associated elevations <2×ULN in 6/7 and an elevation <3×ULN in the remaining patient. No differences in mean haemoglobin levels were observed throughout the 14-week period in either group.

Increases from baseline to week 14 in low-density lipoprotein cholesterol (0.318 mmol/L) and high-density lipoprotein (HDL) cholesterol (0.263 mmol/L) were observed in the upadacitinib group versus the placebo group (−0.083 and 0.010 mmol/L, respectively); however, no changes in the total cholesterol/HDL ratio were observed (upadacitinib, −0.071 mmol/L; placebo, −0.083 mmol/L).

Week 14 Results Discussion

The SELECT-AXIS 1 is the first clinical trial of upadacitinib in AS and demonstrated consistent efficacy results supported by multiplicity-controlled endpoints. The study met its primary endpoint of ASAS40 response at week 14 (51.6% vs 25.5%) as well as several multiplicity-controlled secondary endpoints reflecting statistically significant improvement in disease activity (ASAS PR, BASDAI50, ASDAS), function (BASFI), and MRI outcomes (SPARCC MRI spine). The other multiplicity-controlled secondary endpoints did not meet significance in the multiplicity testing but demonstrated consistent improvements for ASQoL, BASMI, MASES, and ASAS HI, with upadacitinib versus placebo (nominal p<0.05), with the exception of WPAI.

A rapid onset of response to upadacitinib free base 15 mg QD treatment was observed for ASAS40 and ASDAS composite scores and their individual domains of disease activity (e.g., back pain, PtGA, morning stiffness, function, and serum markers of inflammation [hsCRP]), with responses observed as early as week 2 (first post-baseline visit) and consistently maintained through week 14. The results of upadacitinib on improving the signs and symptoms of AS are further confirmed by a significant reduction of active inflammation on MRI for both the spine and the SI joints.

In addition, outcomes related to clinically relevant treatment goals of remission or low disease activity, such as ASDAS ID or LDA, were also achieved, with 50% of patients reaching ASDAS LDA (difference vs placebo, 39%). See, e.g., Smolen et al., Ann Rheum Dis 2018; 77: 3-17. Of note, the placebo response rates for ASAS20 and ASAS40 in this study were similar to rates observed in recent clinical studies of AS; differences in ASAS40 response with upadacitinib versus placebo were p<0.05 (based on nominal p values) as early as week 2 and maintained throughout 14 weeks. See e.g., van der Heijde et al., Ann Rheum Dis 2017; 76: 1340-47; van der Heijde et al., Lancet 2018; 392: 2378-87; van der Heijde et al., Lancet 2018; 392: 2441-51; Landewe et al., Ann Rheum Dis 2014; 73: 3947. Interestingly, mean changes from baseline to week 14 in the MRI SPARCC scores for the spine and SI joints in the placebo group were quite small.

The study results are in line with findings from two Phase 2/3 JAK inhibitor studies in patients with active AS. See, e.g., van der Heijde et al., Ann Rheum Dis 2017; 76: 134047; van der Heijde et al., Lancet 2018; 392: 2378-87. Together with these findings, the SELECT-AXIS 1 results further support that JAK inhibitors could represent an effective treatment option for AS. Currently, only TNF-α and IL-17 inhibition have been proven to be effective in axSpA; but, these cytokines are not directly blocked by JAK inhibitors including upadacitinib. See. e.g., Furst and Louie, Arthritis Res Ther 2019; 21: 135. However, emerging data from upadacitinib RA studies suggest that selective inhibition of JAK1 may result in the secondary inhibition of additional pathways that do not depend on JAK 1 signalling, such as TNF-α and IL-12. See, e.g., Sornasse et al., Ann Rheum Dis 2019; 78: 365-66. Also, other JAK1-associated pathways, including IL-7 and IL-22, have been described in preclinical studies, but further research is needed to evaluate the mechanism of action of JAK inhibitors in axSpA. See, e.g., Veale et al., Rheumatology (Oxford) 2019; 58: 197-205; Gracey et al., Ann Rheum Dis 2016; 75: 2124-32.

The proportion of patients with adverse events was generally similar in the upadacitinib and placebo groups, and no new safety findings were observed compared with previous upadacitinib phase 3 RA studies. See, e.g., Burmester et al., Lancet 2018; 391: 2503-12; Genovese et al., Lancet 2018; 391: 2513-24; Fleischmann R, Pangan A L, Song I, et al. Upadacitinib versus placebo or adalimumab in patients with rheumatoid arthritis and an inadequate response to methotrexate: results of a phase 3, double-blind, randomized controlled trial. Arthritis Rheumatol 2019; doi: 10.1002/art.41032. [Epub ahead of print]; Cohen et al., Ann Rheum Dis (2019) 78. No serious infections, malignancies, anaemia, lymphopenia, herpes zoster, renal dysfunction, adjudicated major adverse cardiovascular events, venous thromboembolic events, or deaths were reported, and haemoglobin levels remained consistent throughout the study.

A higher proportion of patients in the upadacitinib group experienced adverse events of CPK elevation, all of which were asymptomatic and most were mild and reversible without study drug interruption. One patient in the placebo group experienced symptoms (muscle pain) in the setting of elevated CPK and permanently discontinued study drug. In the two previous JAK inhibitor studies, elevations in CPK were also observed. See e.g., van der Heijde et al., Ann Rheum Dis 2017; 76: 1340-47; van der Heijde et al., Lancet 2018; 392: 2378-87. Additional data are needed to better understand the safety profile of upadacitinib in axSpA.

JAK inhibitors, such as upadacitinib, could help address the unmet need in axSpA treatment given that only approximately half of bDMARD-naïve patients achieve an ASAS40 response and even less achieve remission with TNF or IL-17 inhibitor treatment. See, e.g., Sieper et al., Ann Rheum Dis 2017; 76: 571-92; Deodhar et al., Arthritis Rheumatol 2019; 71: 599-611; van der Heijde et al., Lancet 2018; 392: 2441-51; Landewe et al., Ann Rheum Dis 2014; 73: 3947; Lie E et al., Ann Rheum Dis 2011; 70: 157-63; Glintborg et al., Ann Rheum Dis 2013; 72: 1149-55. Furthermore, fewer patients are expected to achieve the treatment goal of sustained remission/LDA, and response rates are even lower in patients with AS who have not responded to bDMARD therapy. See, e.g., Sieper et al., Lancet 2017; 390: 73-84; Sieper et al., Ann Rheum Dis 2017; 76: 571-92; Deodhar et al., Arthritis Rheumatol 2019; 71: 599-611. Furthermore, some patients with axSpA may not be eligible for or might have contraindications common to IL-17 and TNF inhibitor therapy, such as allergic reactions and injection site pain, or specific to TNF inhibitors, such as congestive heart failure and concomitant demyelinating disease. See. e.g., Cortese et al., Mult Scler Relat Disord 2019; 35: 193-95. The use of IL-17 inhibitors is also not recommended for patients with concomitant inflammatory bowel disease. See, e.g., van der Heijde et al., Ann Rheum Dis 2017; 76: 978-91; Fragoulis et al., World J Gastroenterol 2019; 25: 2162-76. Because patients with AS are typically younger and may have more active lifestyles, a treatment option administered orally may be particularly important in this patient population. See e.g., Alten et al., Patient Prefer Adherence 2016; 10: 2217-28. Considering these unmet needs, the findings of the SELECT-AXIS 1 study, which demonstrated that upadacitinib treatment effects are within the range observed with bDMARDs and other JAK inhibitors in AS, support further investigation of upadacitinib for AS. See, e.g., Sieper et al., Ann Rheum Dis 2017; 76: 571-92; Deodhar et al., Arthritis Rheumatol 2019; 71: 599-611; van der Heijde et al., Ann Rheum Dis 2017; 76: 134047; van der Heijde et al., Lancet 2018; 392: 2378-87; van der Heijde et al., Lancet 2018; 392: 2441-51; Landewe et al., Ann Rheum Dis 2014; 73: 39-47.

This study is not without limitations. The focus on patients with AS who were bDMARD-naïve allowed for a focused evaluation of benefit and risk in a homogeneous population, but the safety and efficacy of upadacitinib in patients with AS who are bDMARD-IR or in patients with non-radiographic axSpA has not yet been evaluated, and further studies are needed in these patient populations. Furthermore, only one dose of upadacitinib was evaluated in this study, and thus there are no data to confirm whether a higher dose could have resulted in greater efficacy. Lastly, only 14-week, short-term data are reported here, but the long-term efficacy and safety of upadacitinib will be collected in the ongoing SELECT-AXIS 1 extension period for up to 2 years.

In conclusion, oral upadacitinib free base 15 mg QD significantly improved disease activity, function, and MRI-detected axial inflammation in patients with active AS after 14 weeks of treatment. The incidence of adverse events was similar with upadacitinib and placebo, and no new safety signals were observed compared with previous studies in RA. Overall, these results support the further investigation of upadacitinib for the treatment of AS/axSpA.

Year 1 Results

The phase 2/3 SELECT-AXIS 1 study included a randomized, placebo-controlled, 14-week period followed by 90-week open-label extension; reported here are data through week 64.

The study enrolled adults (≥18 years) with active AS who had an inadequate response to ≥2 non-steroidal anti-inflammatory drugs therapy (or intolerance to or contraindication for NSAIDs) and were biologic disease-modifying antirheumatic drugs naïve, and who met the modified New York criteria based on independent central reading of radiographs of the sacroiliac joints and who had active disease at baseline defined as Bath Ankylosing Spondylitis Disease Activity Index (BASDAI) score ≥4 and patient's assessment of back pain score ≥4 (numeric rating scale [NRS], 0-10) at screening and baseline visit. Patients receiving a stable dose of concomitant conventional synthetic disease-modifying antirheumatic drugs (DMARDs), oral glucocorticoids. NSAIDs and analgesics were eligible; patients with prior exposure to JAK inhibitors or biologic DMARDs with potential impact on spondyloarthritis were excluded. Of the 187 patients randomized to Period 1, 178 (continuous upadacitinib, n=89; placebo switch, n=89) completed week 14 on study drug and entered the open-label extension; 160 patients (continuous upadacitinib n=78 [83.9%]; placebo switch, n=82 [87.2%]) completed week 64. Lack of efficacy (n=10) and AEs (n=4) were the most common reasons for discontinuation of study drug between weeks 14 and 64. In the continuous upadacitinib and the placebo-to-upadacitinib switch groups, mean duration since AS symptom onset was 14.8 and 14.0 years, mean duration since diagnosis was 7.8 and 6.0 years, mean ASDAS was 3.5 and 3.7, and mean hsCRP levels were 9.6 and 11.4 mg/L, respectively. Concomitant medications included NSAIDs (76% and 86%), conventional synthetic DMARDs (14% and 18%), and glucocorticoids (6% and 13%, respectively).

Efficacy was assessed based on percentage of patients achieving ASAS20 response, ASAS40 response, ASAS partial remission, BASDAI50, and Ankylosing Spondylitis Disease Activity Score (ASDAS) inactive disease (ID; <1.3), low disease activity (LDA; <2.1), major improvement (MI; decrease from baseline ≥2.0), and clinically important improvement (CII; decrease from baseline ≥1.1) through 64 weeks. In addition, change from baseline in ASDAS based on C-reactive protein (ASDAS-CRP), Bath Ankylosing Spondylitis Functional Index (BASFI), and linear Bath Ankylosing Spondylitis Metrology Index (BASMI) through 64 weeks and Maastricht Ankylosing Spondylitis Enthesitis Score (MASES). Work Productivity and Activity Impairment (WPAI; on a scale of 0-100), ASAS Health Index (HI), and AS quality of life (ASQoL) through 52 were assessed.

ASAS20 and ASAS40 responses were defined as ≥20% or ≥40% improvement and an absolute improvement of ≥1 or ≥2 units (on an NRS scale of 0-10), respectively, from baseline in ≥3 of the following 4 domains (with no worsening of ≥20% and ≥1 unit or no worsening at all, respectively, in the remaining domain): Patient Global Assessment of disease activity (PtGA), patient assessment of back pain, BASFI, and inflammation defined as the mean of BASDAI questions 5 and 6 (severity and duration of morning stiffness). ASAS partial remission was defined as an absolute score of ≤2 units for each of the 4 domains identified for ASAS40 response, ASDAS-CRP consists of patient-reported outcomes about back pain (BASDAI item 2), peripheral pain/swelling (BASDAI item 3), duration of morning stiffness (BASDAI item 6), the PtGA, and CRP.

Figure 12D:
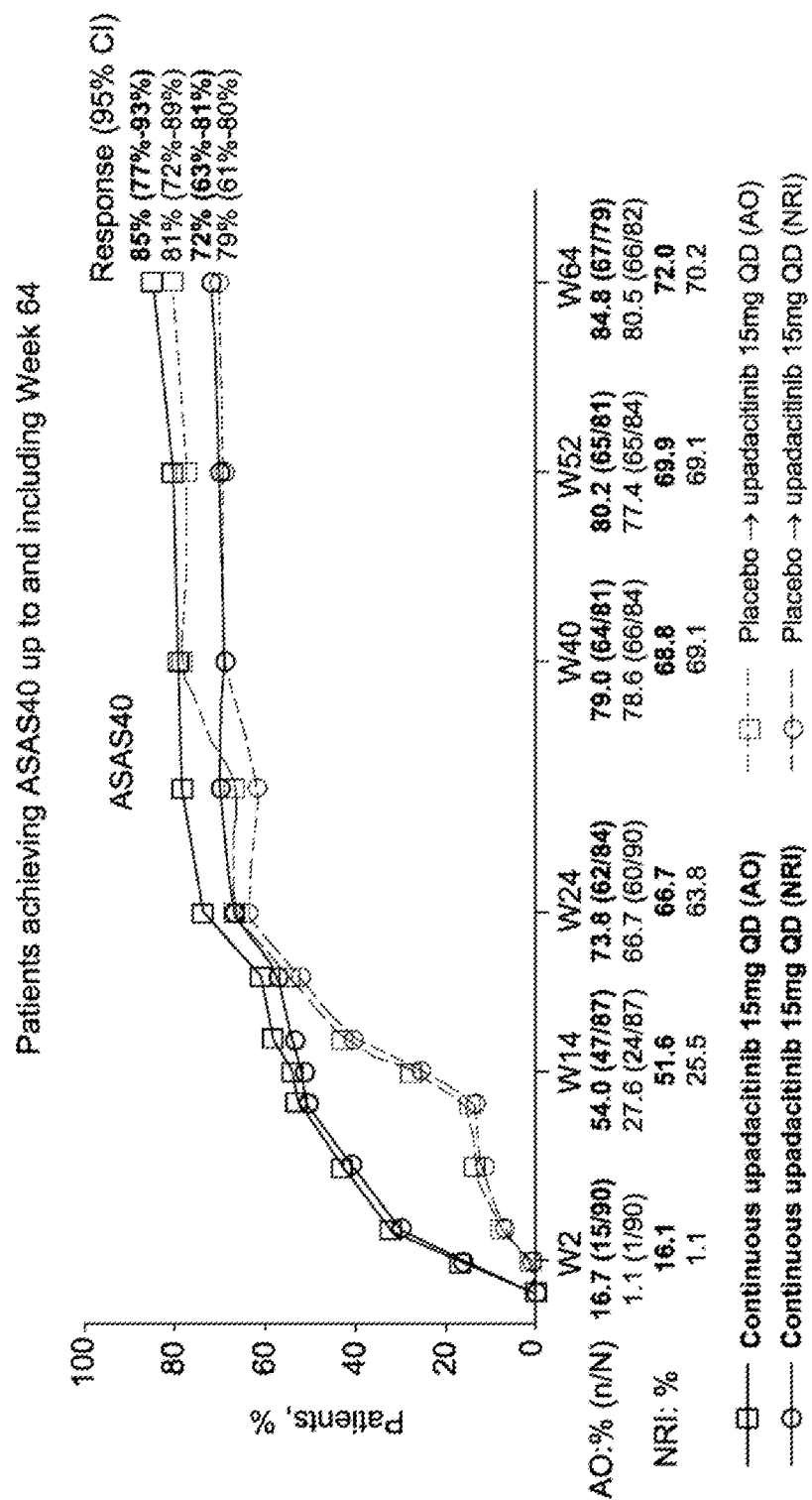
Figure 12E:
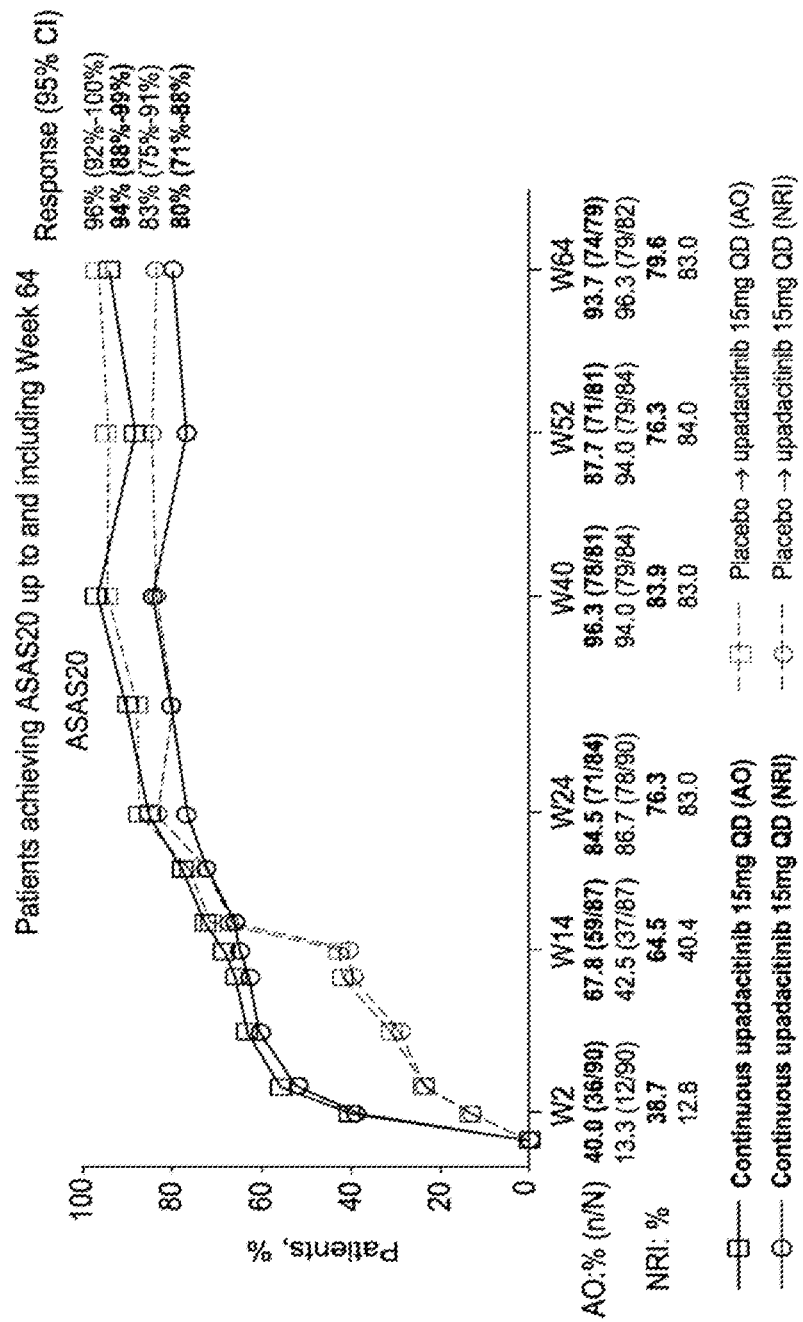
Figure 12F:
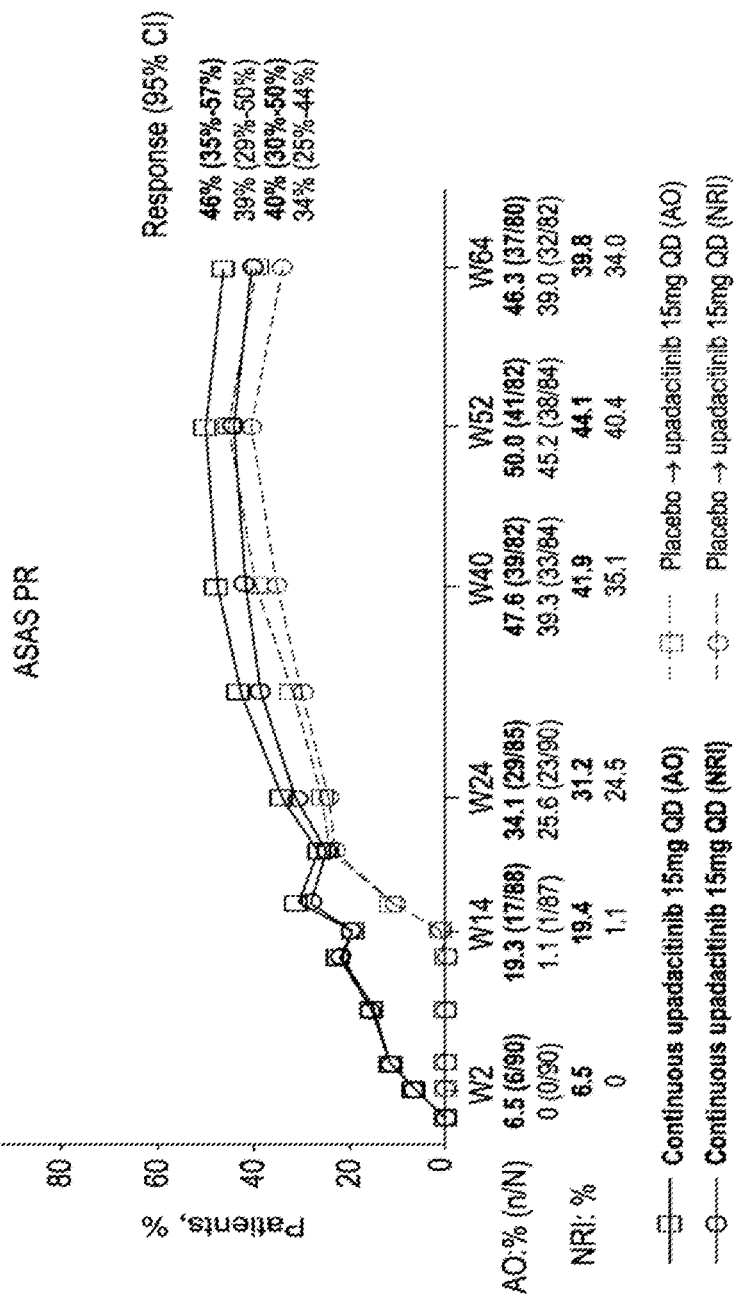
Figure 12G:
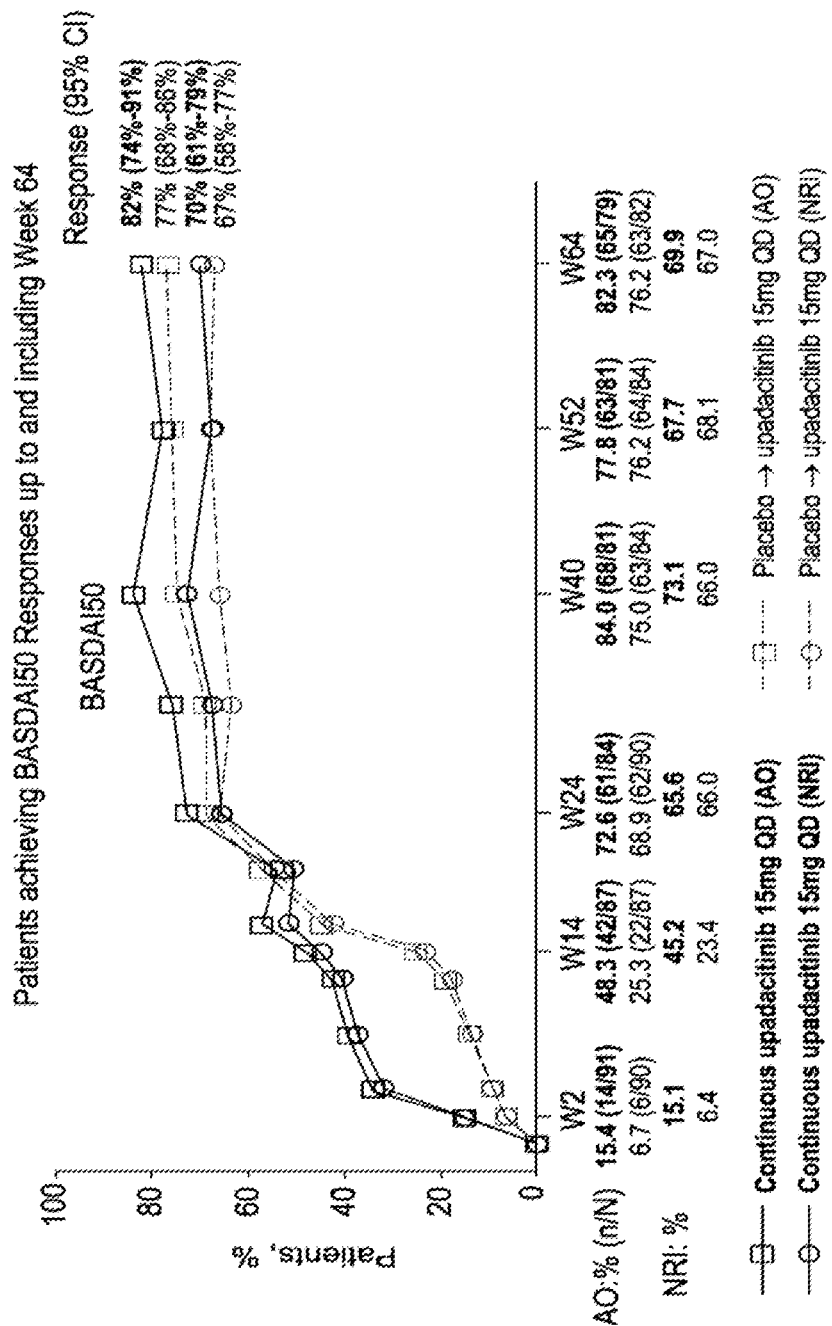
Figure 12H:
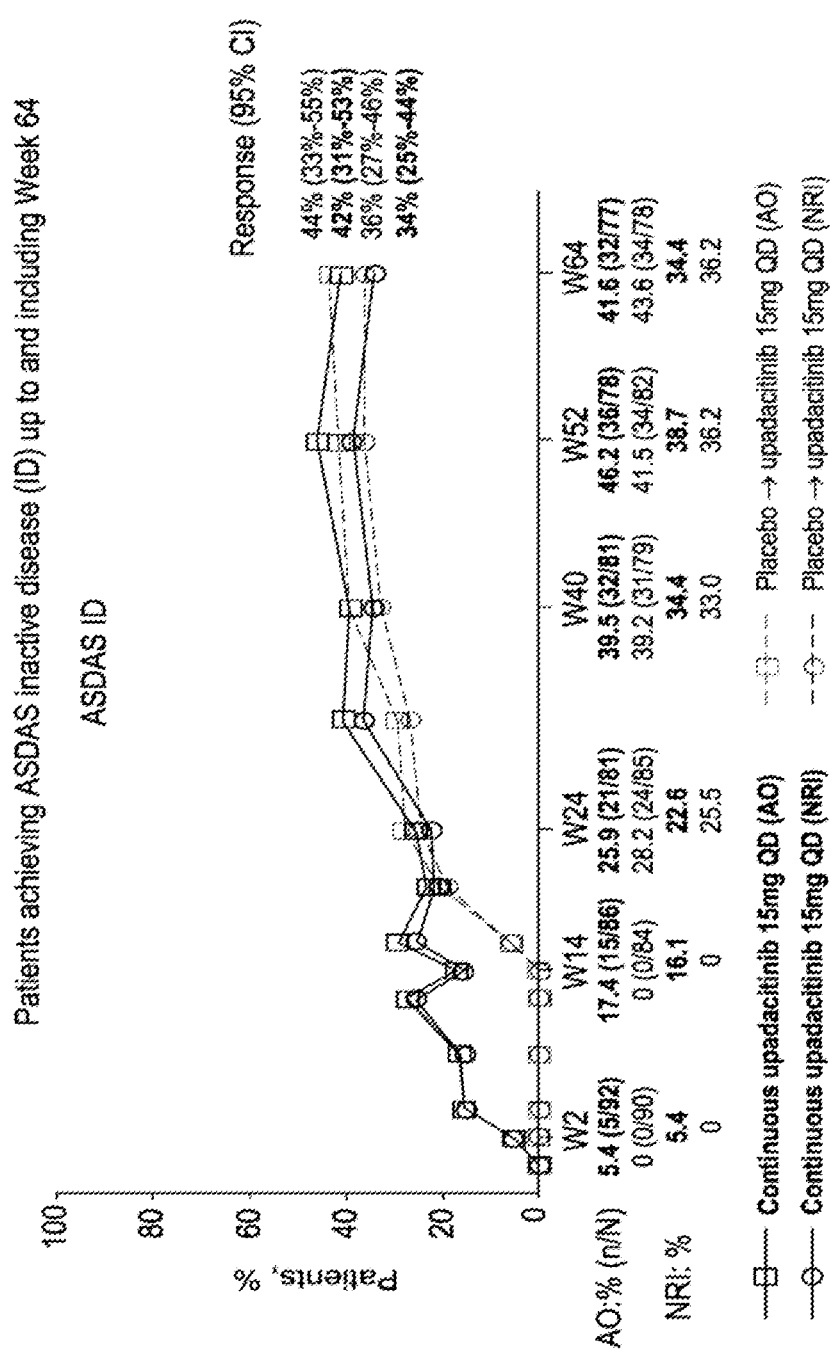
Figure 12I:
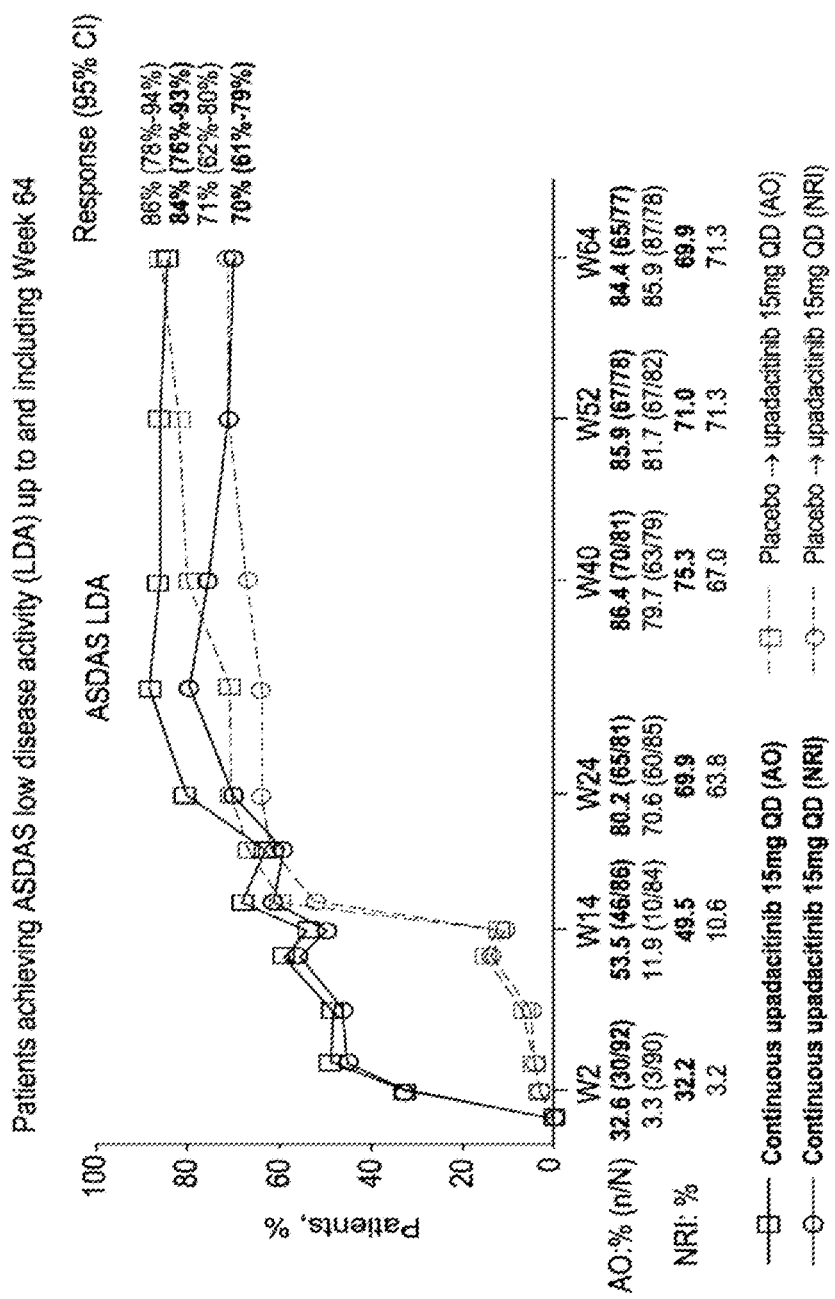
Figure 12J:
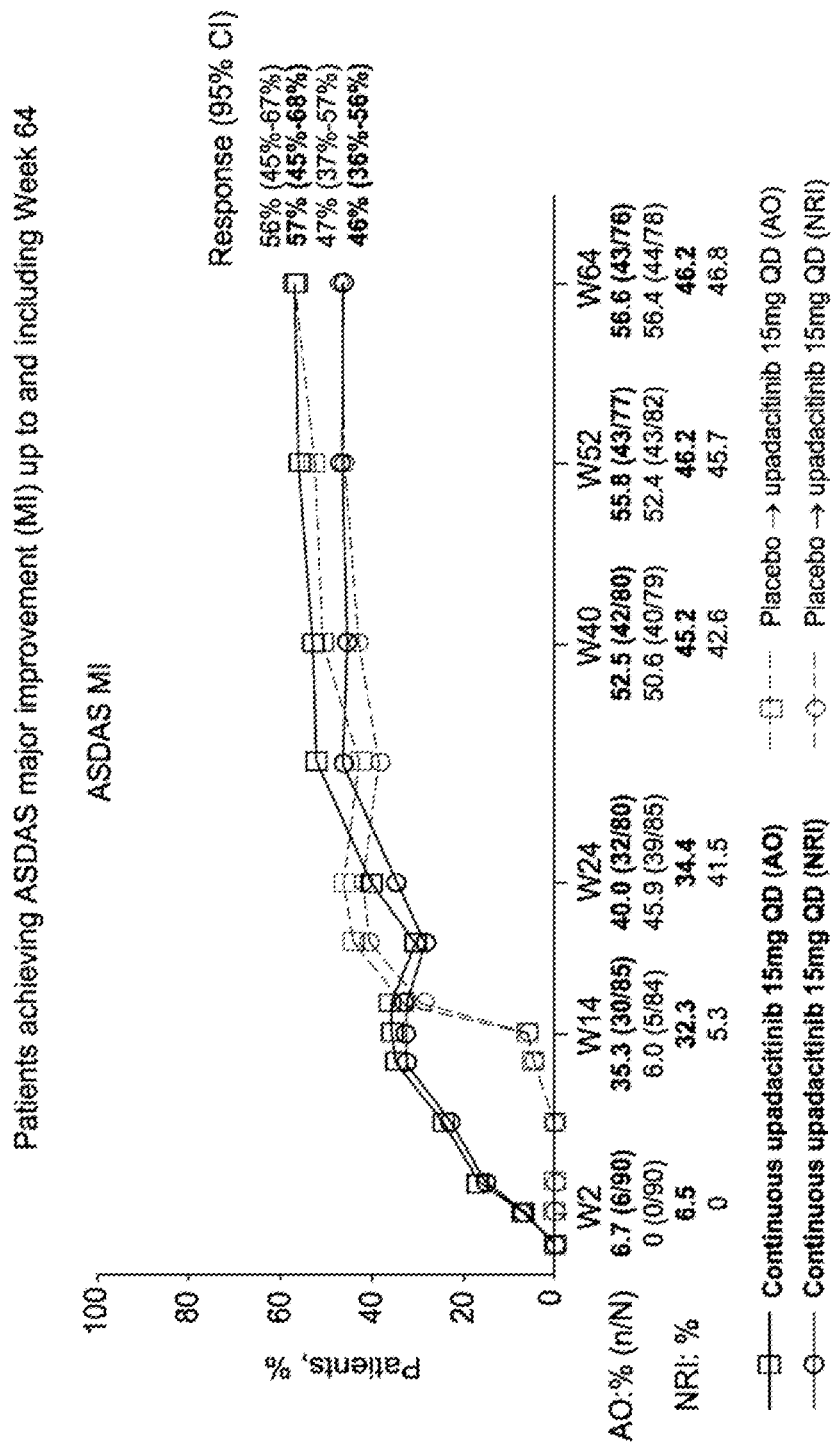
Figure 12K:
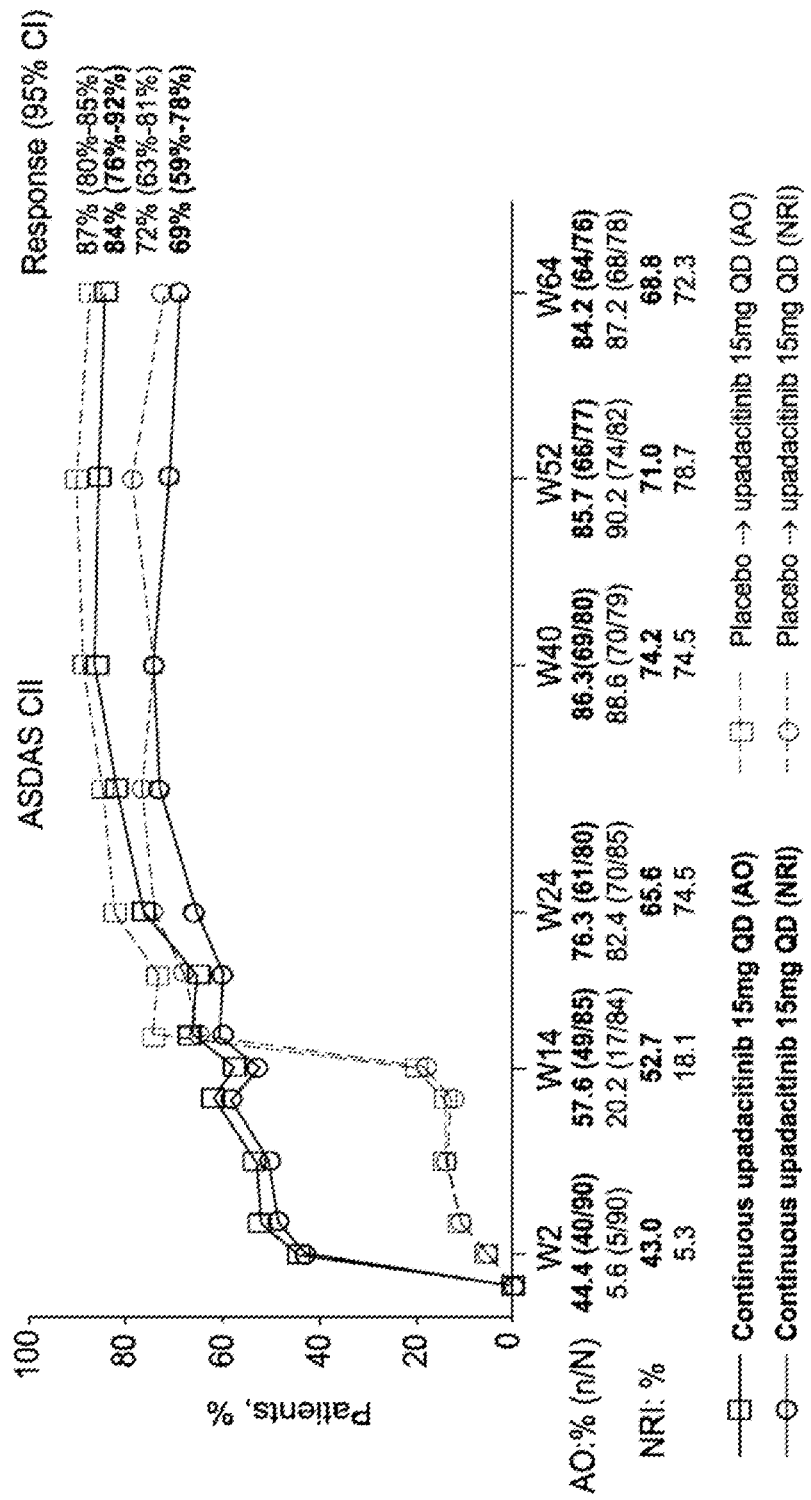
Figure 13A:
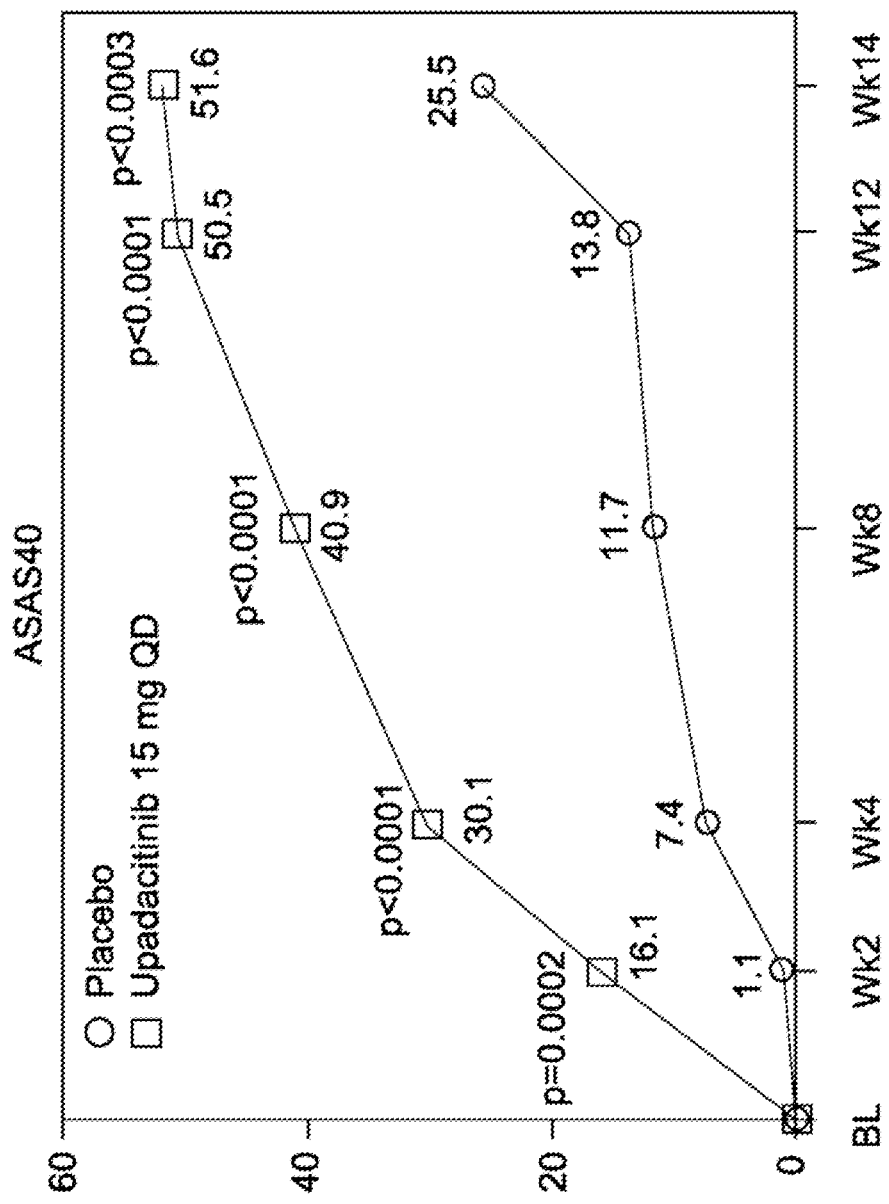
Figure 13C:
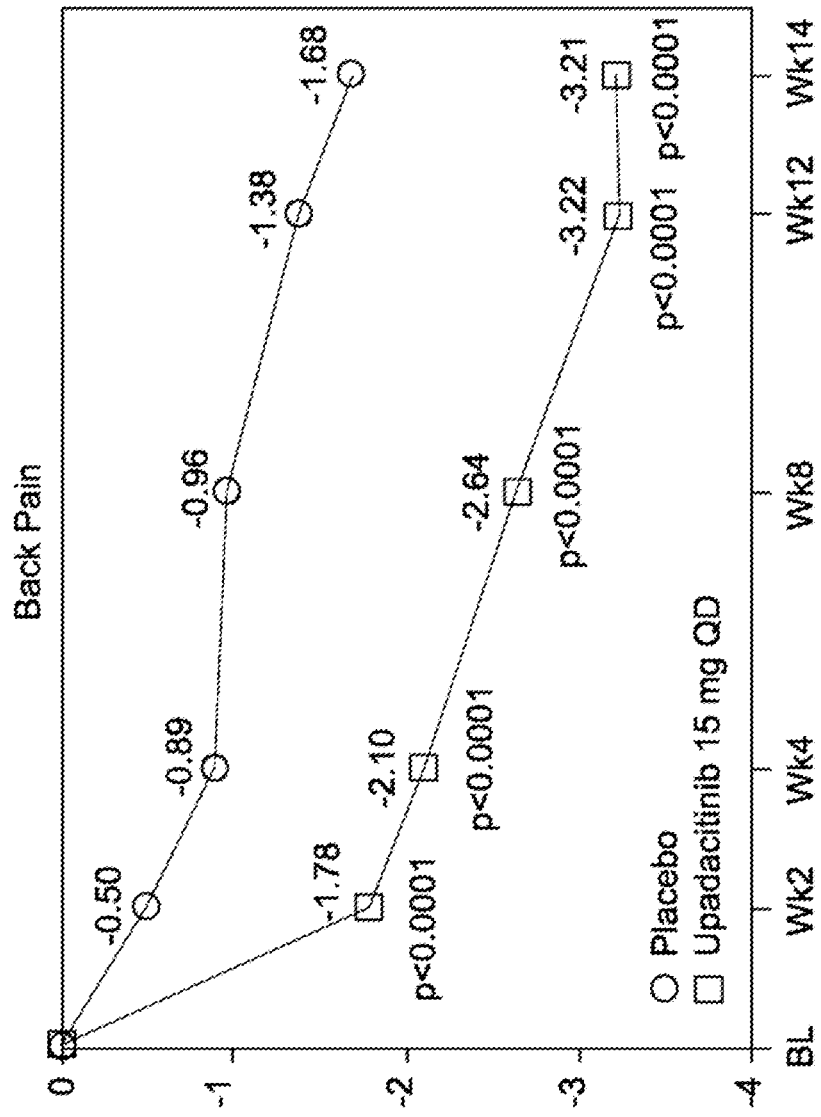
Figure 13D:
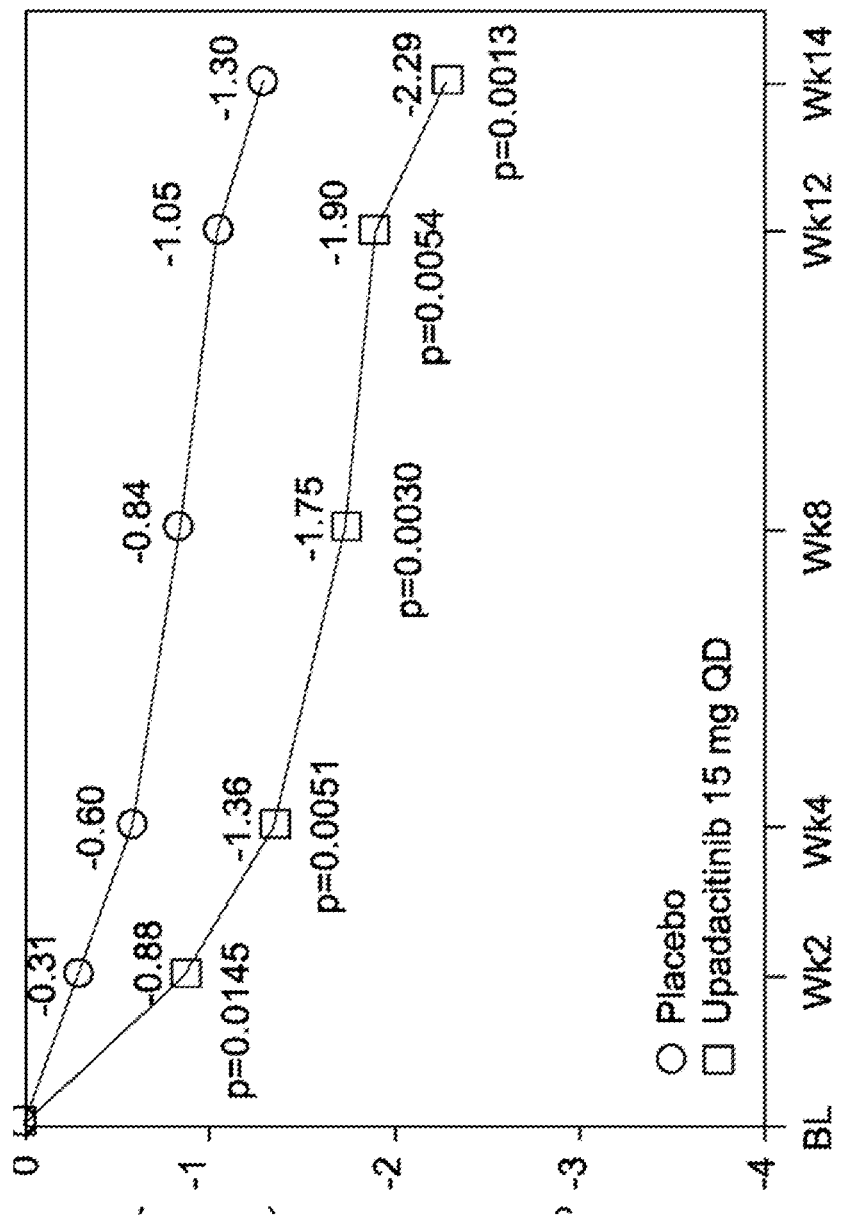
Figure 13E:
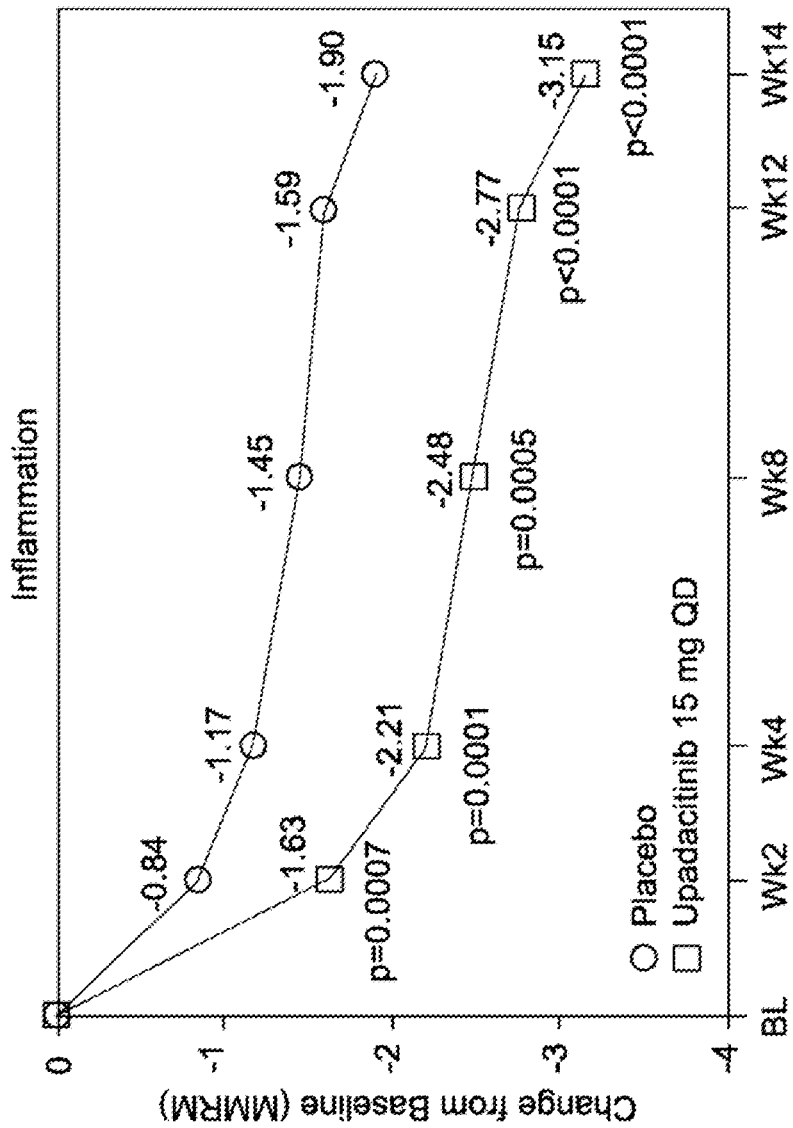

The percentage of patients achieving the primary efficacy endpoint of ASAS40 at week 14 continued to increase throughout the study in the continuous upadacitinib group: 85% (95% CI, 77%-93%) of patients achieved ASAS40 at week 64 in the as-observed analysis and 72% (63%-81%) in the NRI analysis (FIG. 12D). An analogous pattern of improvement was observed in the ASAS20 (94% [88%-99%] as-observed analysis and 80% [71%-88%] NRI analysis) (FIG. 12E), ASAS partial remission (46% [35%-57%] as-observed analysis and 40% [30%-50% NRI analysis) (FIG. 12F), and BASDAI50 endpoints (82% [74%-91%] as-observed analysis and 70% [61%-79%] NRI analysis) (FIG. 12G). Patients who switched from placebo to upadacitinib at week 14 showed a speed of onset and magnitude of responses comparable with patients who were initially randomized to upadacitinib (responses at week 64 were ASAS40: 81% [72%-89%] as-observed analysis and 70% [61%-80%] NRI analysis; ASAS20: 96% [92%-100%] as-observed analysis and 83% [75%-91%] NRI analysis; ASAS partial remission: 39% [29%-50] as-observed analysis and 34% [25%-44%] NRI analysis; and BASDAI50: (77% 168%-86%] as-observed analysis and 67% [58%-77%] NRI analysis). Likewise, the percentage of patients achieving ASDAS ID (FIG. 12H), ASDAS LDA (FIG. 12I), ASDAS MI (FIG. 12J), and ASDAS CII (FIG. 12K) continued to improve throughout the study in the continuous upadacitinib group; patients who switched to upadacitinib from placebo at week 14 showed a rapid onset of response for theses endpoints, with responses at week 64 similar to those observed in patients on continuous upadacitinib.

Mean changes from baseline to 1 year in disease activity (ASDAS), physical function (BASFI), patient assessment of pain and disease activity (PtGA), and inflammation (hsCRP) showed consistent improvement or sustained maintenance throughout the study in the continuous upadacitinib group; a similar magnitude of improvement was seen in the placebo-to-upadacitinib switch group after initiation of upadacitinib at week 14. Analogous patterns of improvement were shown in assessments of quality of life (ASQoL and ASAS HI), spinal mobility (BASMI), and enthesitis (MASES) over time, as well as in measurements of back pain, nocturnal back pain, BASDAI Q2 (back pain) and BASDAI Q5/6. Among patients who were employed at baseline, the mean (95% CI) WPAI overall work impairment score continued to improve throughout the study in the continuous upadacitinib group (from −20.5 [−27.1, −14.0] at week 14 to −35.6 [−43.2, −28.0] at week 52; as-observed analysis) and placebo-to-upadacitinib switch group (from −12.3 [−19.8, −4.8] at week 14 to −27.7 [−35.4, −20.0] at week 52).

Figure 12L:
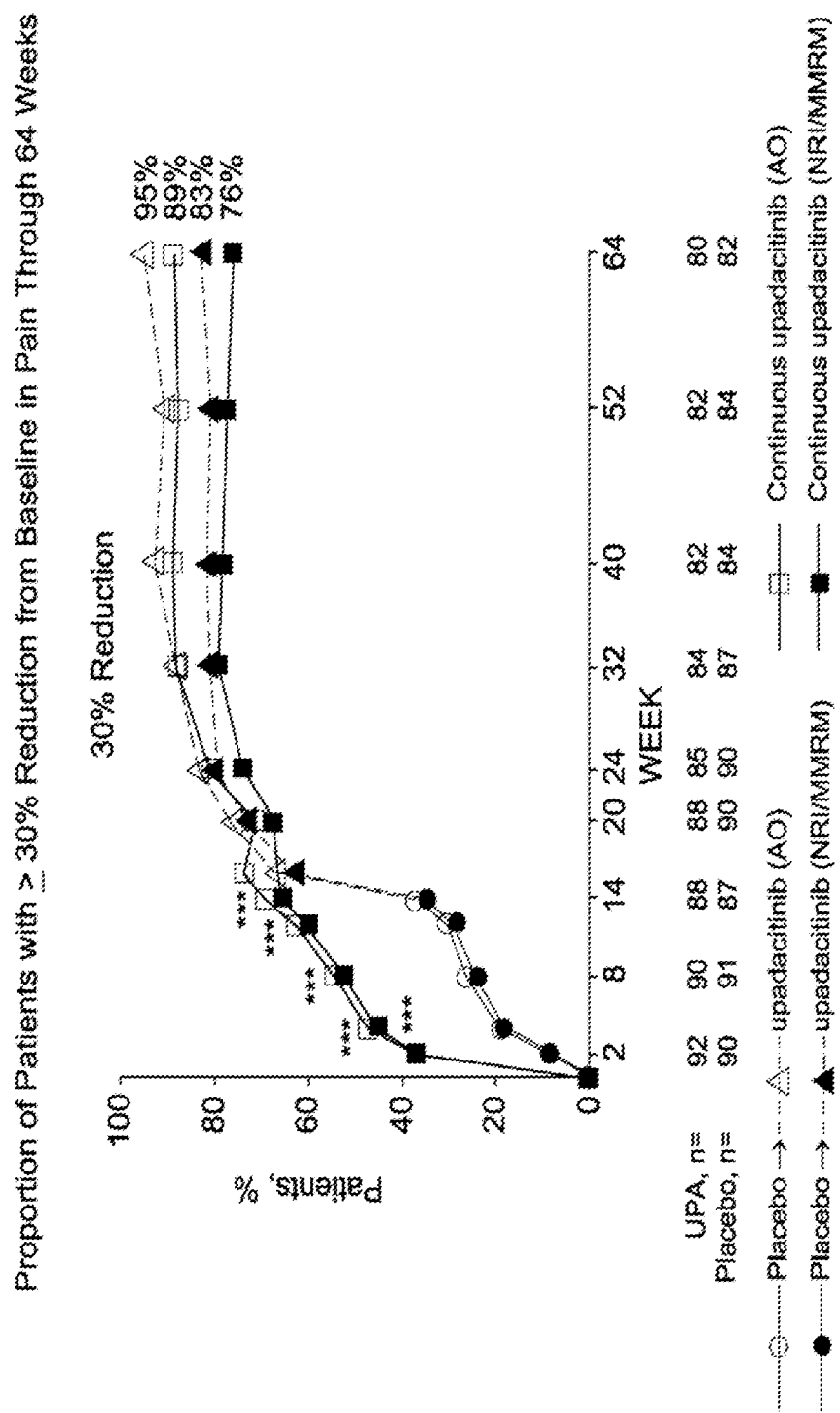
Figure 12M:
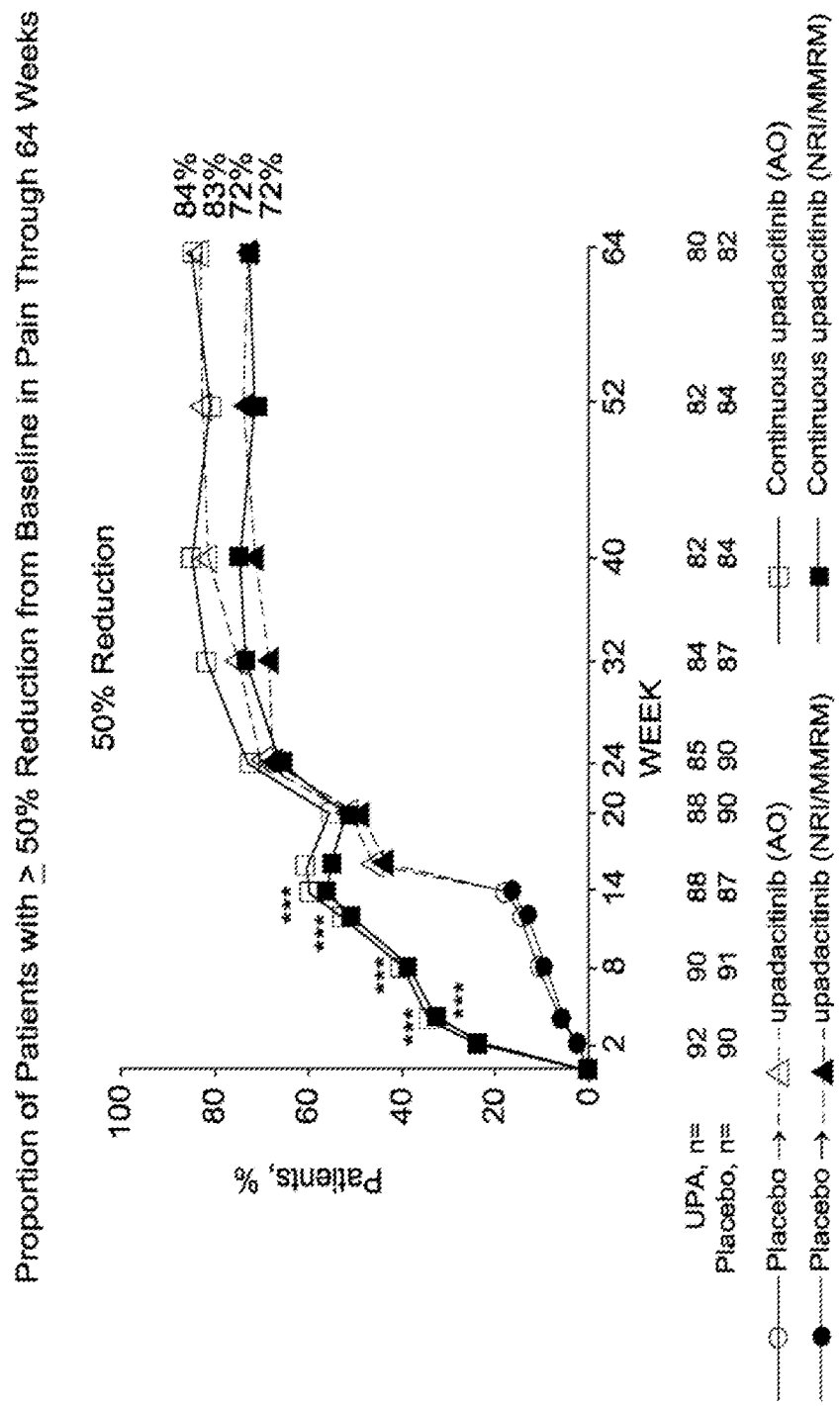
Figure 12N:
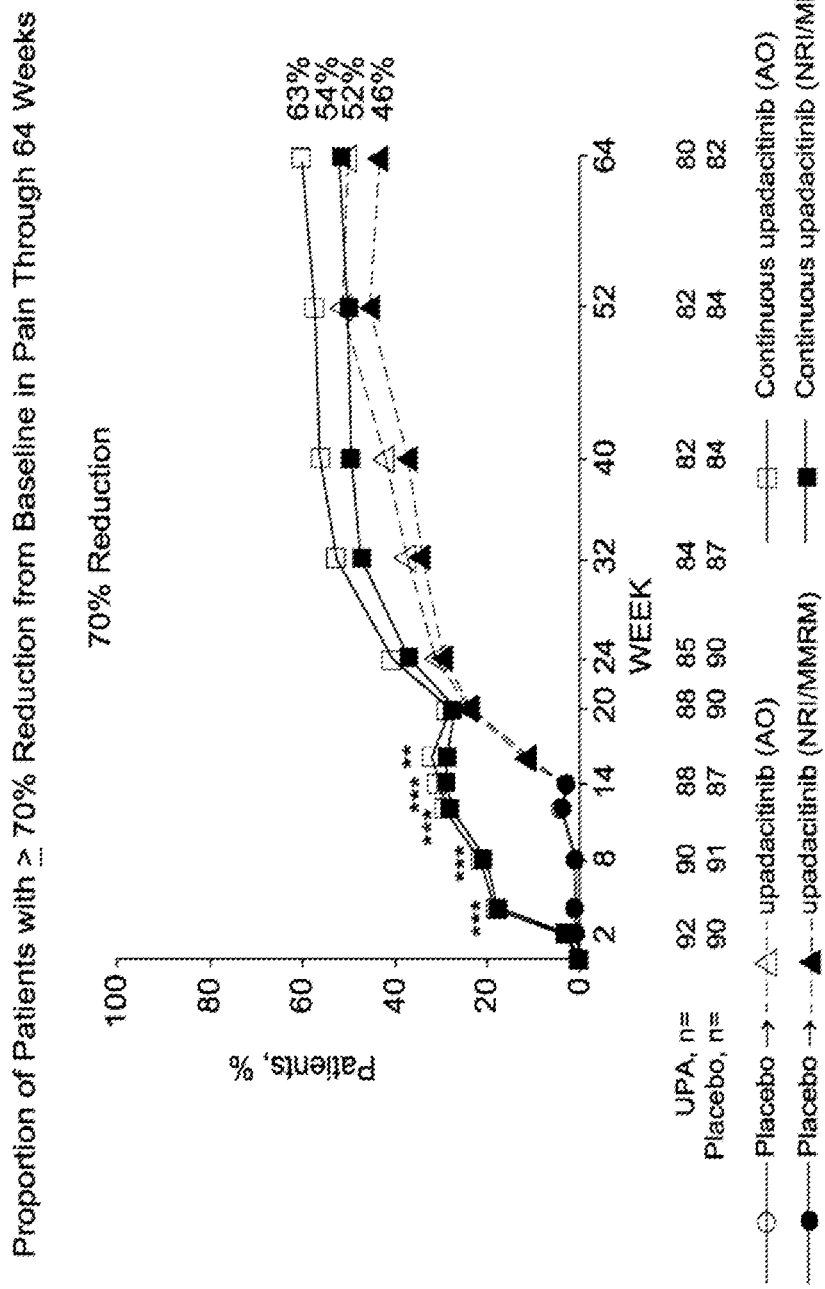

A significantly higher proportion of patients receiving upadacitinib versus placebo achieved ≥30% and ≥50% reduction in Patient's Global Assessment (PGA) of pain and back pain as early as week 2, and ≥70% reduction as early as week 4, and efficacy achieved was sustained thereafter. See, e.g., FIGS. 12L-12N. Patients who switched from placebo to open-label upadacitinib at week 14 generally reached the same level of pain reduction after week 14 as those initially randomized to upadacitinib.

Upadacitinib as a Promising Oral Therapy in AS and nr-AxSpA

SELECT-AXIS 1, the first study to report long-term data with a JAK inhibitor in AS, showed that upadacitinib 15 mg QD therapy led to sustained and consistent efficacy up to and including Week 64 in both NRI and as-observed analyses in patients with active AS who had an inadequate response to NSAIDs. Improvements were seen in disease activity measures (ASDAS, BASDAI, ASAS, and their components), inflammation (hsCRP), physical function (BASFI), quality of life (ASQoL, ASAS HI), and other aspects of disease (BASMI, MASES) with continuous upadacitinib therapy. In patients who switched from placebo to upadacitinib at week 14, a similar speed of onset and magnitude of efficacy response was observed up to and including Week 64 compared with those who received continuous upadacitinib starting at Week 0. Of note, approximately 40%-45% of patients receiving upadacitinib reached remission based on the more difficult to achieve endpoints ASAS partial remission (PR) or ASDAS inactive disease (ID) up to and including Week 64, and >80% were in a state of ASDAS low disease activity (LDA).

The below Table 24E provides placebo corrected data for upadacitinib at Week 14, biologics Ixekizumab and Adalimumab at Week 16, and JAK small molecule inhibitors Tofacitinib and Filgotinib at Week 12 for key primary and secondary endpoints. While this data is not a head to head comparison, the placebo corrected response calculated for upadacitinib for the more difficult to achieve endpoints ASAS PR, ASDAS ID, and ASDAS LDA shows decided promise over the efficacy demonstrated by the other two JAK small molecule inhibitors, with a remarkable efficacy only comparable to that demonstrated with the biologics. Furthermore, this efficacy, once achieved at Week 14, was sustained or improved overtime, with long term efficacy in these difficult to achieve endpoints (including ASDAS major improvement (MI) and ASDAS clinically important improvement (CII)), sustained or improved up to and including Week 64. Coupled with the fact that upadacitinib is well tolerated with no new or unexpected safety findings (particularly compared to the other JAK inhibitors), the data suggests upadacitinib will be a promising new safe oral therapy for AS patients, especially for those AS patients who have active disease and inadequate response to NSAIDs.

TABLE 24E

Placebo Corrected Responses (% response/placebo response, p value)

| | | Ixekiztunab vs. Adalimumab H2H Study | | | |
|---|---|---|---|---|---|
| Endpoint | Upadacitinib 15 mg QD Week 14 (naiive) | Ixekizumab Q4W Week 16 (TNF naiive) | ADA 40 mg EOW Week 16 (TNF naiive) | Tofacitinib 5 mg BID Week 12 (bDMARD-naiive) | Filgotinib 200 mg QD Week 12 (Mixed) |
| ASAS20 | 24.1% (64.5%/40.4%, p < 0.001) | 24% (64%/40%, p = 0.0015) | 19% (59%/40%, p = 0.0075) | 39.6% (80.8%/41.2%, p ≤ 0.001) | 36.2% (75.9%/39.7%, p < 0.0001) |
| ASAS40 | 26.1% (51.6%/25.5% p < 0.001*) | 30% (48%/18%, p < 0.0001,) | 18% (36%/18%, p = 0.0053) | 26.6% (46.2%/19.6%, p ≤ 0.01) | 18.9% (37.9%/19%, p = 0.0189) |
| BASDAI50 | 21.8% (45.2%/23.4%, p = 0.002*) | 25% (42%/17%, p = 0.0003) | 15% (32%/17%, p = 0.0119) | 18.8% (42.3%/23.5%, p ≤ 0.05) | NA |
| ASAS Partial Remisson (PR) | 18.3% (19.4%/1.1%, p < 0.001*) | NA | NA | 7.4% (19.2%/11.8%, NS) | 8.7% (12.1%/3.4%, p = 0.1028) |
| ASDAS Inactive Disease (ID) | 16.1% (16.1%/0%, p < 0.001) | 14% (16%/2%, p = 0.0074) | 14% (16%/2%, p = 0.0087) | 5.7% (13.5%/7.8%, NS) | 5% (5%/0%, p = 0.092) |
| ASDAS low disease activity (LDA) | 38.9% (49.5%/10.6%, p < 0.001) | 30% (43%/13%, p < 0.0001) | 25% (38%/13%, p = 0.0002) | 34.3% (53.9%/19.6%, p ≤ 0.001) | NA |

NS: non-significant; NA: not available; UPA p values are nominal, unless *significant after multiplicity-adjustment; Ixekizumab bDMARD-naïve AS COAST-V Study. Van der Heijde et al. Lancet 2018; 392: 2441-51; Tofacitinib study: van der Heijde D, et al. ARD 2017; 0: 1-8.; Filgotinib study: van der Heijde et al. Lancet 2018; 392: 2378-87.

Example 35: A Phase 3 Protocol in Subjects with Active Psoriatic Arthritis and a Previous Inadequate Response to at Least One Non-Biologic Disease Modifying Anti-Rheumatic Drug (DMARD) (SELECT-PSA1)

Figure 18:
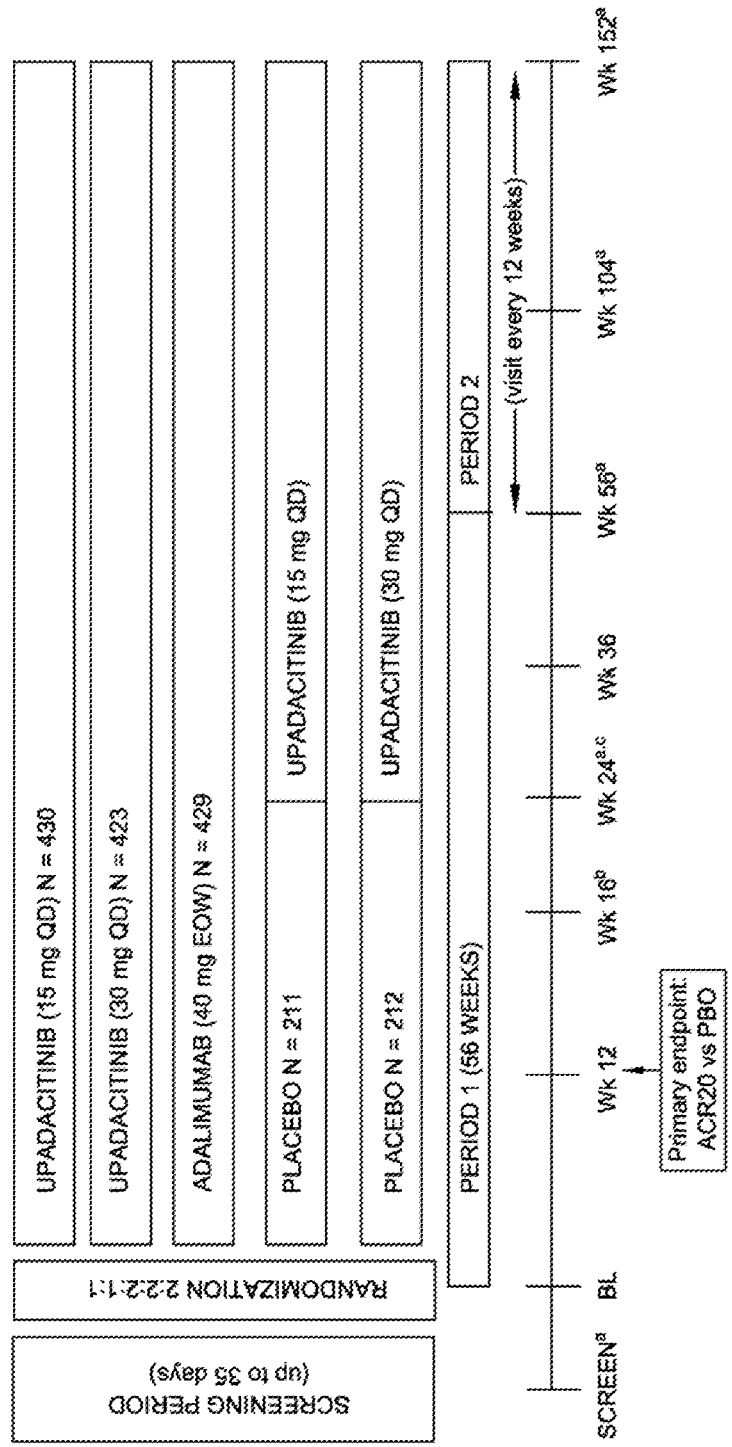
FIG. 18 depicts the Phase 3 Study design for SELECT-PSA1 in subjects with active PsA and a previous inadequate response to at least one non-biologic DMARD (PsA DMARD-IR), a. All subjects will receive x-rays of hands and feet at Screening, Week 24, Week 56, Week 104, and Week 152. b. At Week 16 rescue therapy will be offered to subjects classified as non-responders (defined as not achieving at least 20% improvement in either or both tender joint count (TJC) and swollen joint count (SJC) at both Week 12 and Week 16). c. At Week 24, all placebo subjects will switch to upadacitinib freebase 15 mg QD or 30 mg QD (1:1 ratio) regardless of response.

This is a Phase 3 multicenter study that includes to periods. The Study Design for SELECT-PSA1 is provided in FIG. 18. Period 1 is 56 weeks in duration and includes a 24-week randomized, double-blind, parallel-group, placebo-controlled and active comparator-controlled period followed by an additional 32 weeks of blinded, active comparator-controlled treatment (Weeks 24-56). Period 1 is designed to compare the safety, tolerability, and efficacy of upadacitinib free base 15 mg QD and 30 mag QD versus placebo and versus adalimumab 40 mg every other week (eow) in subjects with moderately to severely active PsA and have an inadequate response to non-biologic DMARDs (DMARD-R). Period is also designed to compare the efficacy of upadacitinib free base 15 mg QD and 30 mg QD versus placebo for the prevention of structural progression. Period 2 is an open-label (blinded until the last subject completes the last visit of Period 1), long-term extension of up to a total treatment duration of approximately 3 years to evaluate the safety, tolerability and efficacy of upadacitinib free base 15 mg QD and 30 mg QD in subjects with moderately to severely active PsA who have completed Period 1. 15 mg or 30 mg upadacitinib refers to the 15 mg and 30 mg once-daily (QD) upadacitinib drug product as described herein below (Table 25A).

TABLE 25A

Upadacitinib 15 and 30 mg Extended Release (ER) Tablets (Wet Granulated)

| Component | Function | 15 mg | 30 mg |
|---|---|---|---|
| Tablet Core Intragranular | | | |
| Upadacitinib* | Drug substance | 15.4 | 30.7 |
| Microcrystalline cellulose (≥65% through 75 um screen) (Avicel PH 102) | Filler | 41.2 | 82.4 |
| Hypromellose 2208 | Control release polymer and binder | 4.9 | 9.8 |
| Purified water | Wetting agent | N/A | N/A |
| Extragranular | | | |
| Microcrystalline cellulose (≥65% through 75 um screen) (Avicel PH 102) | Filler | 121.3 | 64.8 |
| Mannitol (Pearlitol 100 SD) | Filler | 100.6 | 100.6 |
| Tartaric acid powder | pH modifier | 96.0 | 96.0 |
| Hypromellose 2208 | Control release polymer | 91.1 | 86.2 |
| Colloidal Silicon Dioxide | Glidant | 2.4 | 2.4 |
| Magnesium Stearate | Lubricant | 7.2 | 7.2 |
| Film Coat | | | |
| OPADRY II Yellow (PVA, TiO$_2$, PEG-3350, Talc, Iron Oxide Yellow) | Film coat | 14.40 | 14.40 |
| Purified water** | Processing Aid | N/A | N/A |

*hemihydrate upadacitinib free base Form C as disclosed in WO2017066775 and WO 2018/165581 is used, 15 mg and 30 mg amount per tablet refers to the amount of anhydrous upadacitinib free base in the tablet;
**removed during processing, The study duration includes a 35-day screening period; a 56-week blinded period which includes 24 weeks of double-blind, placebo-controlled and active comparator controlled treatment followed by 32 weeks of active comparator controlled treatment (Period 1); a long-term extension period of up to a total treatment duration of approximately 3 years ([blinded until the last subject completes the last visit of Period 1] Period 2), a 30-day follow-up call or visit; and a 70-day follow-up call.

Subjects who met eligibility criteria were stratified by extent of psoriasis (≥3% body surface area [BSA] or <3% BSA), current use of at least 1 DMARD, presence of dactylitis, and presence of enthesitis, except for subjects from China and Japan, where randomization for each country was stratified by extent of psoriasis (≥3% body surface area [BSA] or <3% BSA) only, and then randomized in a 2:2:2:1:1 ratio to one of five treatment groups:

Group 1: upadacitinib 15 mg QD (N=430)
Group 2: upadacitinib free base 30 mg QD (N=423)
Group 3: adalimumab (ADA) (40 mg eow) (N=429)
Group 4: Placebo followed by upadacitinib free base 15 mg QD (N=211)
Group 5: Placebo followed by upadacitinib free base 30 mg QD (N=212)

No more than approximately 15% of subjects were enrolled with concomitant use of hydroxychloroquine, sulfasalazine, bucillamine, or iguratimod.

Subjects received both oral study drug QD (upadacitinib free base 15 mg, upadacitinib free base 30 mg, or matching placebo) and subcutaneous study drug cow (either ADA 40 mg or matching placebo) until all subjects completed Period 1 (Week 56) and sites and subjects are unblinded to study treatment.

Subjects who were assigned to placebo at Baseline were preassigned to receiving either upadacitinib free base 15 mg QD or upadacitinib free base 30 mg QD starting at Week 24 in a 1:1 ratio. Subjects who complete the Week 56 visit (end of Period 1) will enter the long-term extension portion of the study. Period 2 (total study duration up to approximately 3 years). Subjects will continue study treatment as assigned in Period 1. Subjects who are assigned to the upadacitinib free base 15 mg QD, upadacitinib free base 30 mg QD, or adalimumab 40 mg eow will continue to receive upadacitinib free base 15 mg QD, upadacitinib free base 30 mg QD, or adalimumab 40 mg cow, respectively, in a blinded manner. When the last subject completes the last visit of Period 1 (Week 56), study drug assignment in both periods will be unblinded to the sites, and subjects will be dispensed study drug in an open-label fashion until the completion of Period 2.

Subjects must have had inadequate response to ≥1 non-biologic DMARD (MTX, SSZ, LEF, apremilast, bucillamine or iguratimod) or an intolerance to or contraindication for DMARDs prior to the Screening visit. No background non-biologic DMARD therapy is required during participation in this study. For subjects who are on non-biologic DMARD therapy at baseline (MTX, SSZ. LEF, apremilast, hydroxychloroquine (HCQ), bucillamine or iguratimod), non-biologic DMARDs should have been started ≥12 weeks prior to the baseline visit, must be at stable dose for ≥4 weeks prior to the first dose of study drug and remain on a stable dose through Week 36 of the study; the non-biologic DMARD dose may be decreased only for safety reasons. In addition, all subjects taking MTX should take a dietary supplement of oral folic acid (or equivalent) throughout study participation.

At Week 16, rescue therapy will be offered to subjects classified as non-responders (defined as not achieving at least 20% improvement in either or both tender joint count (TJC) and swollen joint count (SJC) at both Week 12 and Week 16) as follows: 1) add or modify doses of non-biologic DMARDs, NSAIDs, acetaminophen/paracetamol, low potency opioid medications (tramadol or combination of acetaminophen and codeine or hydrocodone), oral corticosteroids and/or 2) receive 1 intra-articular, trigger point or tender point, intra-bursa, or intra-tendon sheath corticosteroid injection for 1 peripheral joint, 1 trigger point, 1 tender point, 1 bursa, or 1 enthesis (Rescue Therapy).

After the last subject completes the Week 24 study visit, an unblinded analysis will be conducted for the purpose of initial regulatory submission. To maintain integrity of the trial during the blinded 56-week period, study sites and subjects will remain blinded until all subjects have reached Week 56. A second unblinded analysis may be conducted for regulatory purposes after all subjects have completed Period 1. A final analysis will be conducted after all subjects have completed Period 2.

Primary and Secondary Endpoints

The primary efficacy endpoint is the proportion of subjects achieving American College of Rheumatology (ACR) 20% response rate at Week 12. The primary and secondary clinical endpoints for this study (SELECT-PSA1 clinical study; Example 35) and the SELECT-PSA2 clinical study (Example 36) are further described in Example 37.

Study Population

Patients with active psoriatic arthritis and a previous inadequate response to at least one non-biologic disease-modifying anti-rheumatic drug (non-biologic DMARD or DMARD).

Main Inclusion Criteria Include:
1. Adult male or female, ≥18 years old at Screening.
2. Clinical diagnosis of PsA with symptom onset at least 6 months prior to the Screening Visit and fulfillment of the Classification Criteria for PsA (CASPAR) criteria.
3. Subject has active disease at Baseline defined as ≥3 tender joints (based on 68 joint counts) and ≥3 swollen joints (based on 66 joint counts) at Screening and Baseline Visits.
4. Presence of either at Screening:
   ≥1 erosion on x-ray as determined by central imaging review or;
   hs-CRP>laboratory defined upper limit of normal (ULN).
5. Diagnosis of active plaque psoriasis or documented history of plaque psoriasis.
6. Subject has had an inadequate response (lack of efficacy after a minimum 12 week duration of therapy) to previous or current treatment with at least 1 non-biologic DMARD at maximally tolerated dose or up to dose defined in Inclusion Criterion 7 [(inadequate response to MTX is defined as ≥15 to ≤25 mg/week; or ≥10 mg/week in subjects who are intolerant of MTX at doses ≥12.5 mg/week after complete titration; for subjects in China. Taiwan, and Japan inadequate response to MTX is defined as ≥7.5 mg/week), SSZ, LEF, cyclosporine, apremilast, bucillamine or iguratimod)], or subject has an intolerance to or contraindication for DMARDs.
7. Subject who is on current treatment with concomitant non-biologic DMARDs at study entry must be on ≤2 non-biologic DMARDs (except the combination of MTX and leflunomide) at the following doses: MTX (≤25 mg/week), SSZ (≤3000 mg/day), leflunomide (LEF) (≤20 mg/day), apremilast (≤60 mg/day), HCQ (≤400 mg/day), bucillamine (≤300 mg/day) or iguratimod (≤50 mg/day) for ≥12 weeks and at stable dose for ≥4 weeks prior to the Baseline Visit. No other DMARDs are permitted during the study. Subjects who need to discontinue DMARDs prior to the Baseline Visit to comply with this inclusion criterion must follow the procedure specified below or at least five times the mean terminal elimination half-life of a drug:
   ≥8 weeks for LEF if no elimination procedure was followed, or adhere to an elimination procedure (i.e., 11 days with cholestyramine, or 30-day washout with activated charcoal or as per local label);
   ≥4 weeks for all others
8. Stable doses of non-steroidal anti-inflammatory drugs (NSAIDs), acetaminophen/paracetamol, low-potency opiates (tramadol or combination of acetaminophen and codeine or hydrocodone), oral corticosteroids (equivalent to prednisone ≤10 mg/day), or inhaled corticosteroids for stable medical conditions are allowed, but must have been at a stable dose for ≥1 week prior to the Baseline Visit.
9. Subjects must have discontinued all opiates (except for tramadol, or combination of acetaminophen and codeine or hydrocodone) at least 1 week and oral traditional Chinese medicine for at least 4 weeks prior to the first dose of study drug.
10. Where mandated by local requirements only, treatment with at least one of the following background medications is required: non-biologic DMARDs, NSAIDs, acetaminophen, low potency opiates (tramadol or combination of acetaminophen codeine or hydrocodone), or oral corticosteroids at doses.

Main Exclusion Criteria Include:
1. Prior exposure to any Janus Kinase (JAK) inhibitor (including but not limited to ruxolitinib, tofacitinib, baricitinib, and filgotinib).
2. Current treatment with >2 non-biologic DMARDs or use of DMARDs other than MTX, SSZ, LEF, apremilast, HCQ, bucillamine or iguratimod or use of MTX in combination with LEF at Baseline.
3. History of fibromyalgia, any arthritis with onset prior to age 17 years, or current diagnosis of inflammatory joint disease other than PsA (including, but not limited to rheumatoid arthritis, gout, overlap connective tissue diseases, scleroderma, polymyositis, dermatomyositis, systemic lupus erythrematosus). Prior history of reactive arthritis or axial spondyloarthritis including ankylosing spondylitis and non-radiographic axial spondyloarthritis is permitted if documentation of change in diagnosis to PsA or additional diagnosis of PsA is made. Prior history of fibromyalgia is permitted if documentation of change in diagnosis to PsA or documentation that the diagnosis of fibromyalgia was made incorrectly.

Analysis Windows

The following rules will be applied to assign actual subject visits to protocol-specified visits. For each protocol-specified study visit, a target study day will be identified to represent the corresponding visit along with a window around the target day. Windows will be selected in a non-overlapping fashion so that a collection date does not fall into multiple visit windows. If a subject has two or more actual visits in one visit window, the visit closest to the target day will be used for analysis. If two visits are equidistant from the target day, then the later visit will be used for analysis.

Results Up to and Including Week 24

As noted above, after the last subject completed the Week 24 study visit, an unblinded analysis was conducted for the purpose of initial regulatory submission.

The study met the primary endpoint ACR20 at Week 12. At week 12, the primary outcome of ACR20 response was achieved by 153 (36.2%) patients receiving placebo versus 303 (70.6%; difference: 34.5%; 95% CI: 28.2 to 40.7; P<0.001) receiving upadacitinib 15 mg and 332 (78.5%; difference: 42.3%; 95% CI: 36.3 to 48.3; P<0.001) receiving upadacitinib 30 mg; 279 (65.0%) patients receiving adalimumab achieved ACR20 response rates versus upadacitinib 15 mg (difference: 5.6%; 95% CI: −0.6 to 11.8) and 30 mg (difference: 13.5%; 95% CI: 7.5 to 19.4; P<0.001. Upadacitinib 30 mg was superior to adalimumab; the 15 mg dose was not superior to adalimumab, which prevented the testing of significance for secondary endpoints lower in the testing hierarchy. The efficacy of upadacitinib freebase 15 mg was demonstrated regardless of subgroups evaluated including baseline BMI, baseline hsCRP, and number of prior non-biologic DMARDs (≤1 or >1).

The study also showed statistical significance for the non-inferiority (NI) of ACR20 at Week 12 compared to adalimumab for both upadacitinib free base doses. After achieving the non-inferiority (NI) comparisons, superiority tests compared to adalimumab were conducted. Upadacitinib free base 30 mg showed superiority vs, adalimumab in ACR20 at Week 12.

The results for key secondary endpoints versus placebo were consistent with that of the primary endpoint. At week 12, treatment differences (95% CI) in ACR50 response versus placebo for upadacitinib 15 mg and 30 mg were 24.3% (18.7 to 29.9) and 38.5% (32.8 to 44.3), respectively and versus adalimumab were 0.0% (−6.5 to 6.5) and 14.2% (7.6 to 20.9), respectively. Treatment differences (95% CI) in ACR70 response versus placebo for upadacitinib 15 mg and 30 mg were 13.3% (9.5 to 17.0) and 22.9% (18.5 to 27.3), respectively and versus adalimumab were 1.9/6 (−2.9 to 6.6) and 11.5% (6.3 to 16.8), respectively. At week 24, the percentage of patients achieving ACR20/50/70 responses were in the same direction as the primary endpoint for both upadacitinib doses versus placebo and adalimumab; no clinical inferences can be drawn from these data. At week 24, the percentage of patients achieving Minimal Disease Activity (MDA) was significantly greater with both upadacitinib doses versus placebo (P<0.001 for both comparisons) and was in the same direction as the primary outcome versus adalimumab.

At week 16, a significantly greater percentage of patients achieved Psoriasis Area Severity Index of at least 75% (PASI 75) and Static Investigator Global Assessment of Psoriasis of 0 or 1 and at least a 2-point improvement from baseline (sIGA 0/1) response with both upadacitinib doses versus placebo (P<0.001 for each comparison). The percentage of patients achieving PASI 75 response was in the same direction as the primary endpoint for both upadacitinib doses versus adalimumab, and for sIGA 0/1 response with upadacitinib 30 mg; the percentage of sIGA 0/1 responders was not significantly different for upadacitinib 15 mg versus adalimumab. Greater improvement in patient-reported psoriasis symptoms, as measured by the Self-Assessment of Psoriasis Symptoms (SAPS), was also observed at Week 16 in patients treated with upadacitinib freebase 15 mg QD compared to placebo. Statistically greater efficacy was observed with each upadacitinib dose versus placebo for change from baseline in HAQ-DI, SF-36 PCS, and FACIT-F at week 12 (P<0.001 for each comparison). The proportion of HAQ-DI responders (≥0.35 improvement from baseline in HAQ-DI score) at Week 12 was 58% in patients receiving upadacitinib freebase 15 mg QD and 33% in patients receiving placebo.

Health-related quality of life was assessed by SF-36. Patients receiving upadacitinib freebase 15 mg QD experienced significantly greater improvement from baseline in the Physical Component Summary score compared to placebo at Week 12. Greater improvement was also observed in the Mental Component Summary score and all 8 domains of SF-36 (Physical Functioning, Bodily Pain, Vitality. Social Functioning, Role Physical. General Health, Role Emotional, and Mental Health) compared to placebo.

At week 24, significantly more upadacitinib-treated patients achieved resolution of enthesitis versus placebo (P<0.001 for each comparison); upadacitinib 15 mg was not significantly different to adalimumab for resolution of enthesitis and results with upadacitinib 30 mg were in the same direction as the primary endpoint. Rates for resolution of dactylitis are presented in the below Tables. The study also demonstrated significantly greater efficacy in PsA signs and symptoms as well as inhibition of radiographic progression compared to placebo. For example, at week 24, upadacitinib-treated patients exhibited significantly less radiographic progression versus placebo-treated patients as demonstrated by the change from baseline in modified total Sharp/van der Heijde Score (mTSS; P<0.001) (mTSS equivalent to SHS); mean progression was not different for upadacitinib and adalimumab. Statistically significant results were also achieved for both erosion and joint space narrowing scores for the 15 mg QD dosage. The proportion of patients with no radiographic progression (mTSS change ≤0) was higher with upadacitinib freebase 15 mg QD (93%) compared to placebo (89/6) at Week 24. These results are summarized below in the below Tables.

Figure 19A:
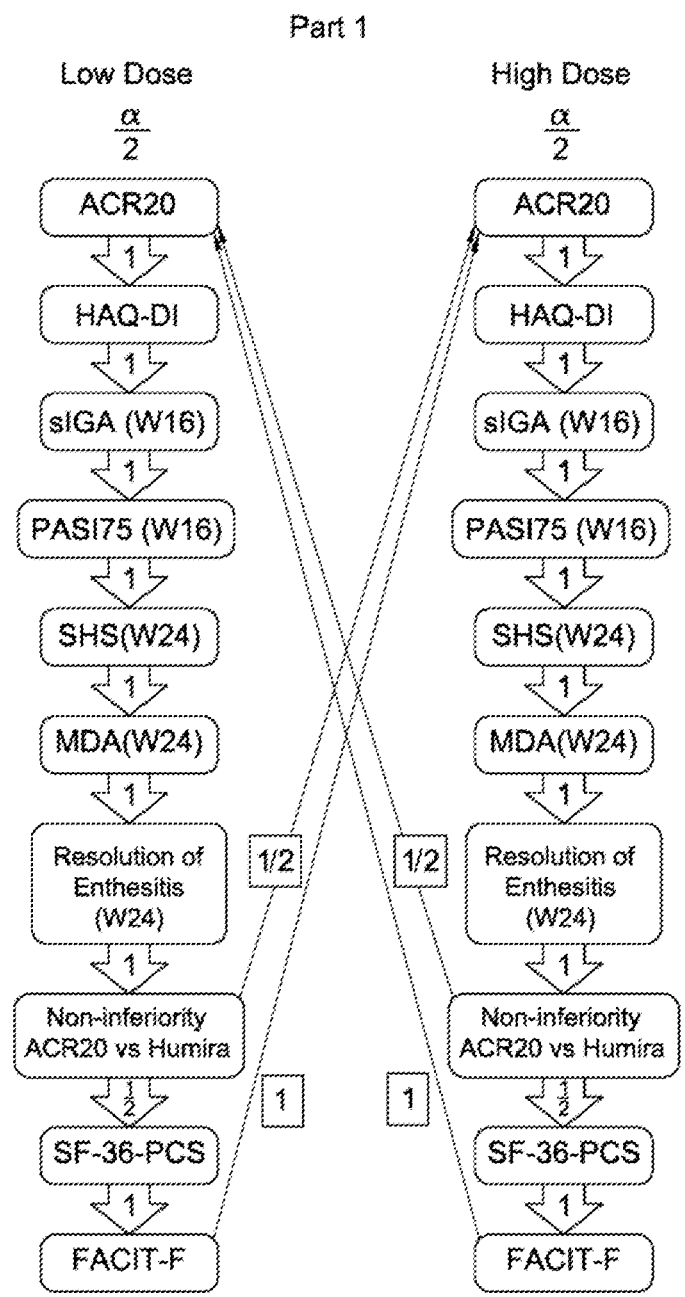
FIGS. 19A-19B depict the graphical testing procedure in the Phase 3 SELECT-PSA1 (PsA DMARD-IR) for the primary endpoint (ACR20 response at Week 12) and ranked secondary endpoints. The overall type I error rate was controlled at the 2-sided 0.05 level (including a 0.0001 α for the interim futility analysis).
Figure 19B:
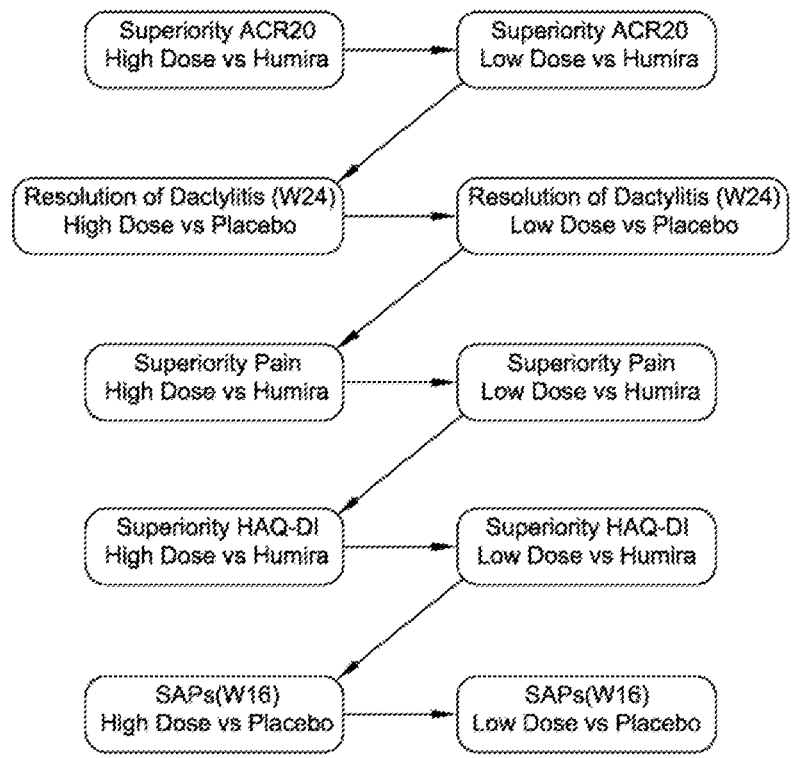
Figure 20A:
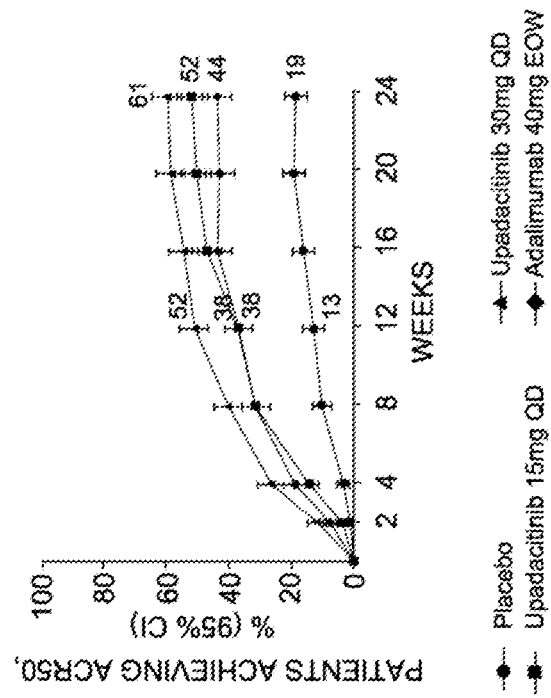
FIGS. 20A-20EE provide a summary of primary and key secondary efficacy results for the SELECT-PSA 1 (PsA DMARD-IR) Phase 3 clinical trial.
Figure 20B:
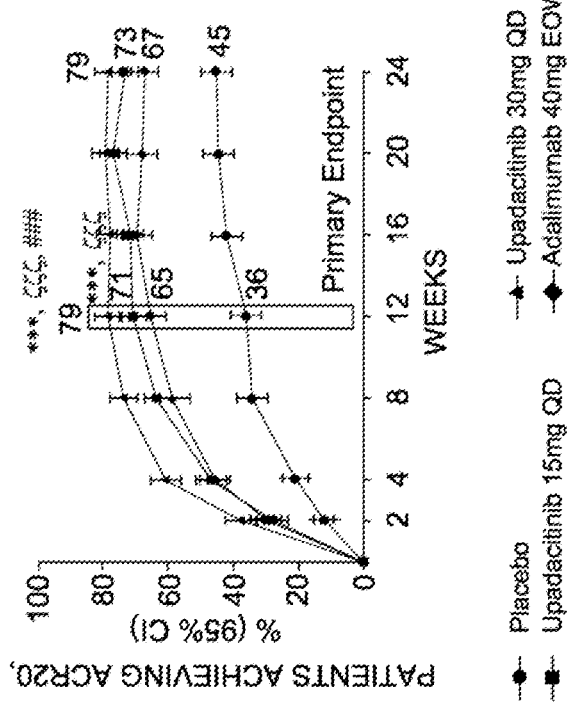
Figure 20C:
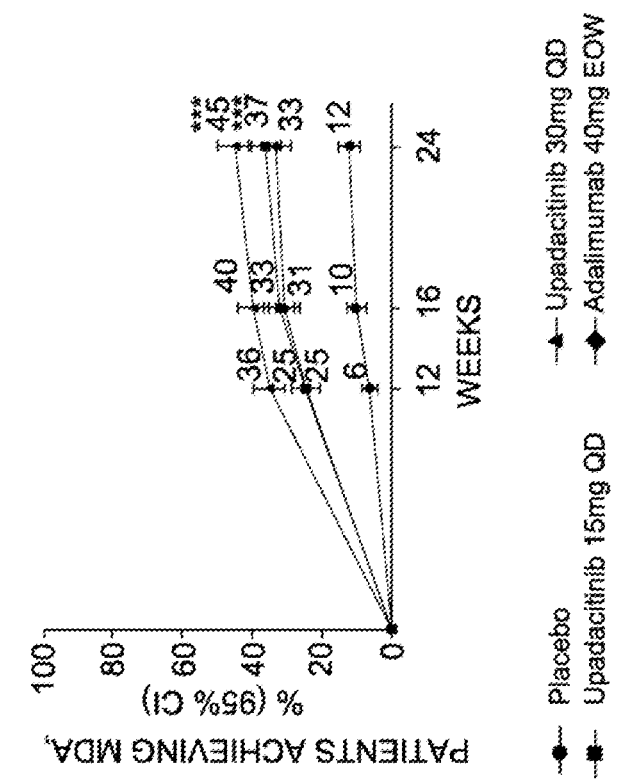
Figure 20D:
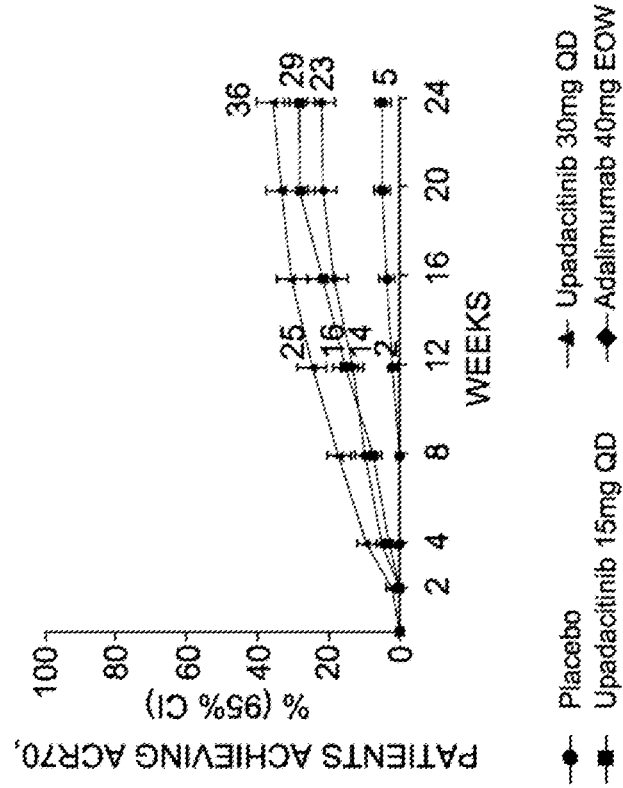
Figure 20E:
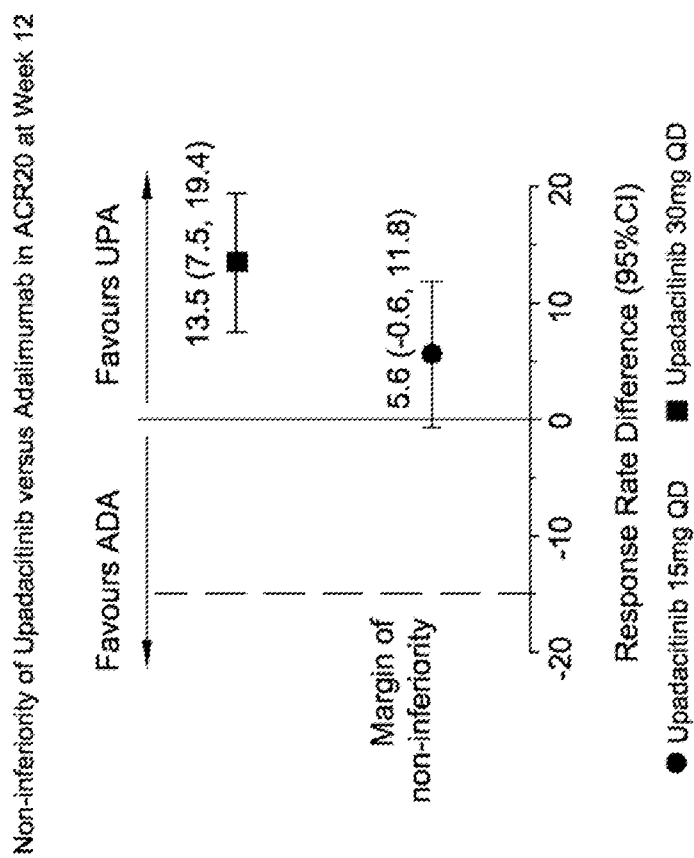
Figure 20F:
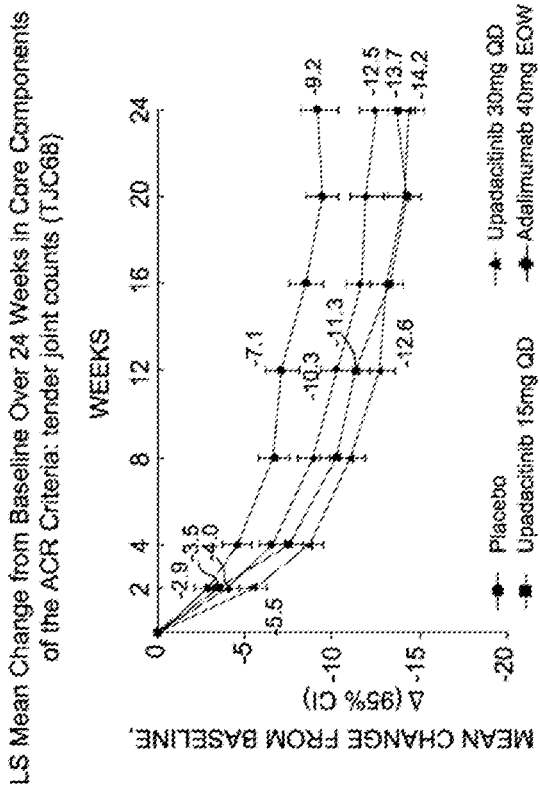
Figure 20G:
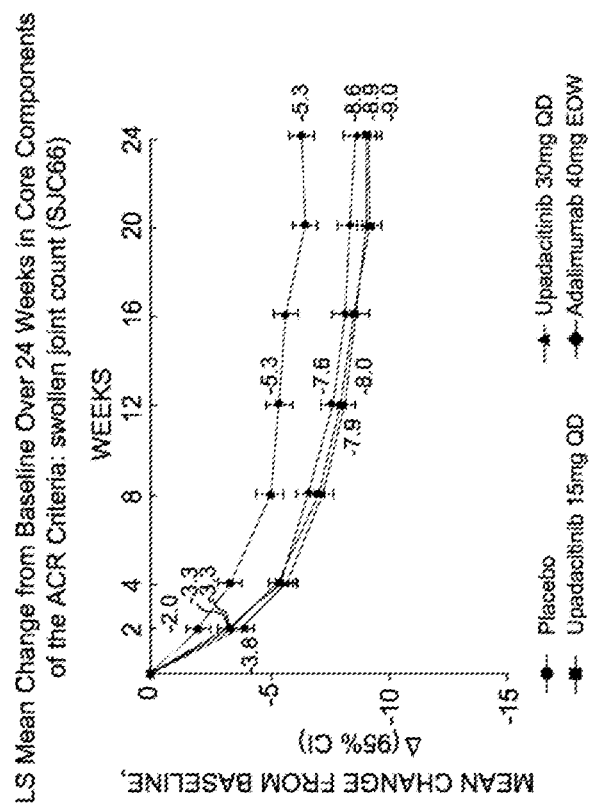
Figure 20H:
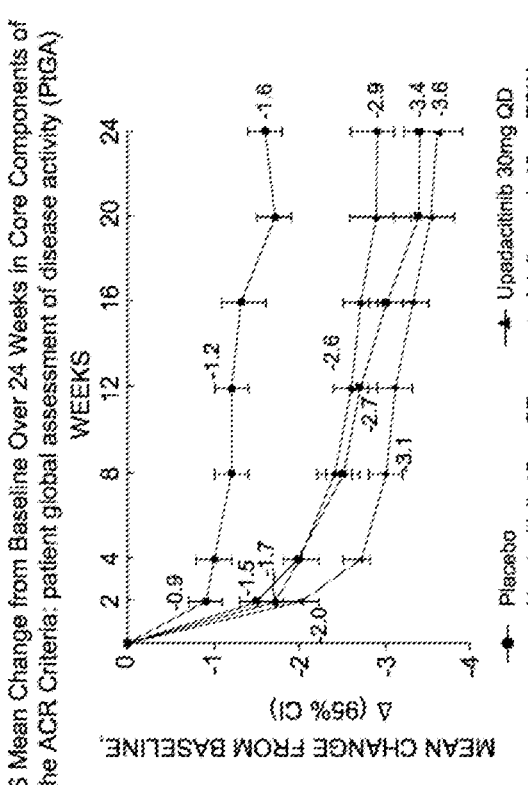
Figure 20I:
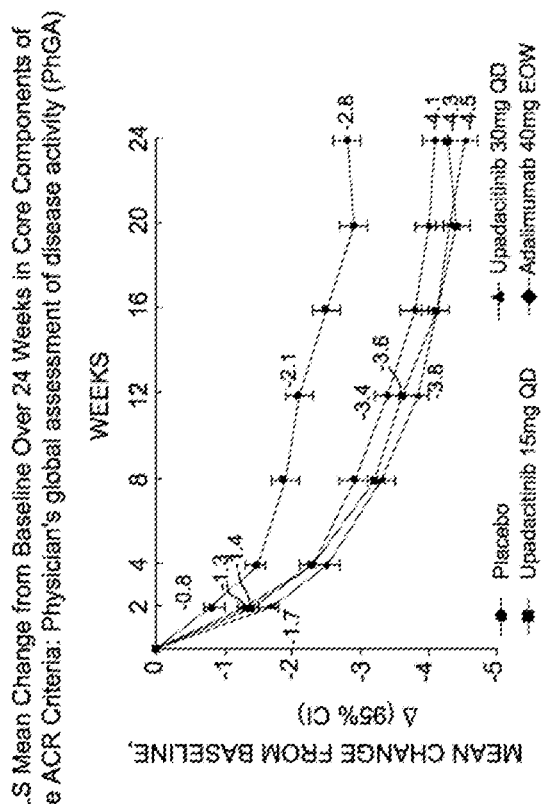
Figure 20K:
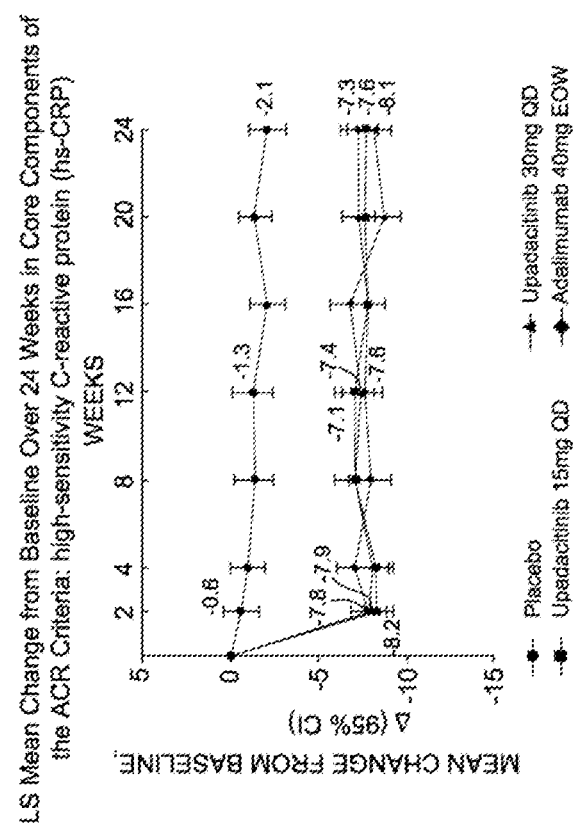
Figure 20J:
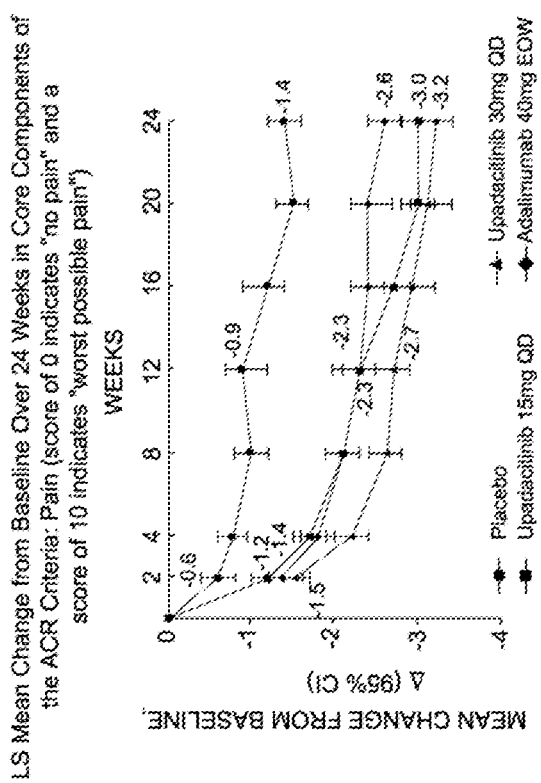
Figure 20M:
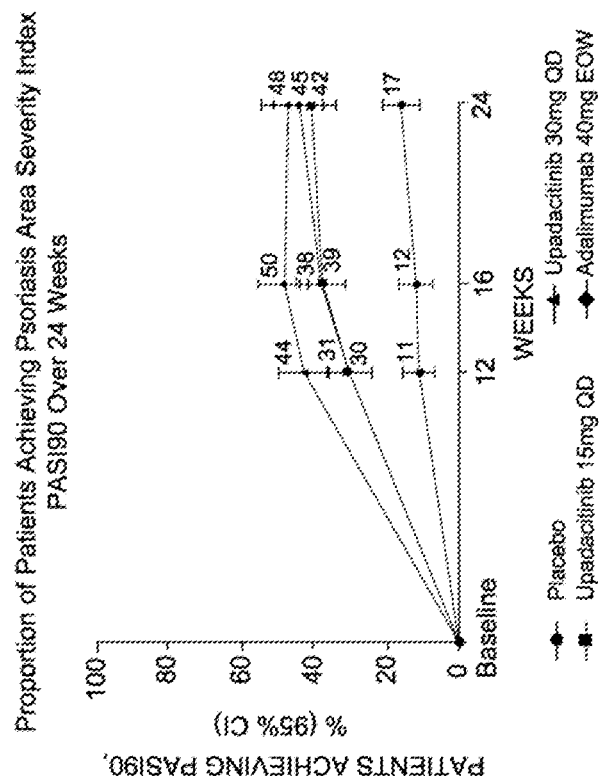
Figure 20L:
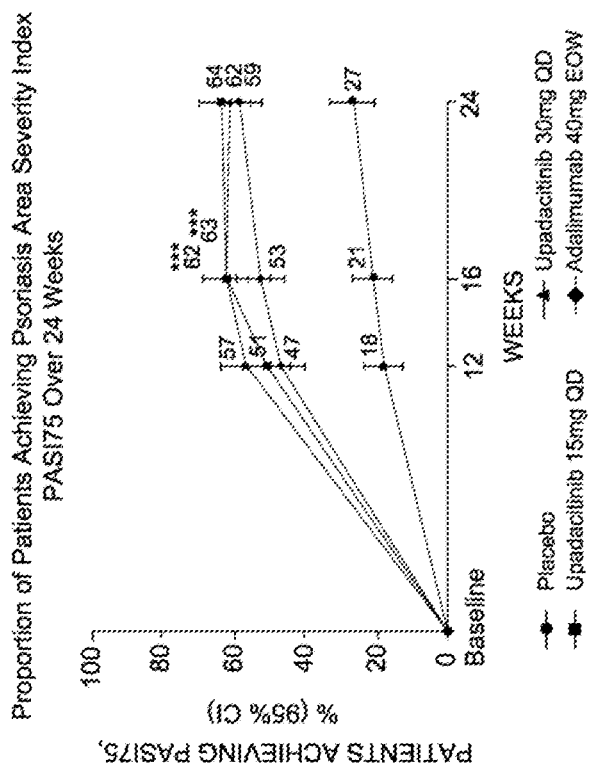
Figure 20O:
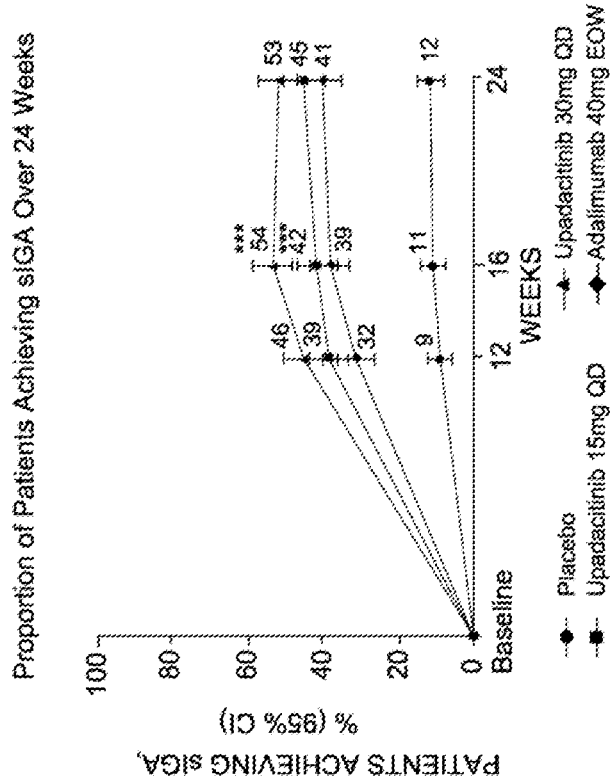
Figure 20N:
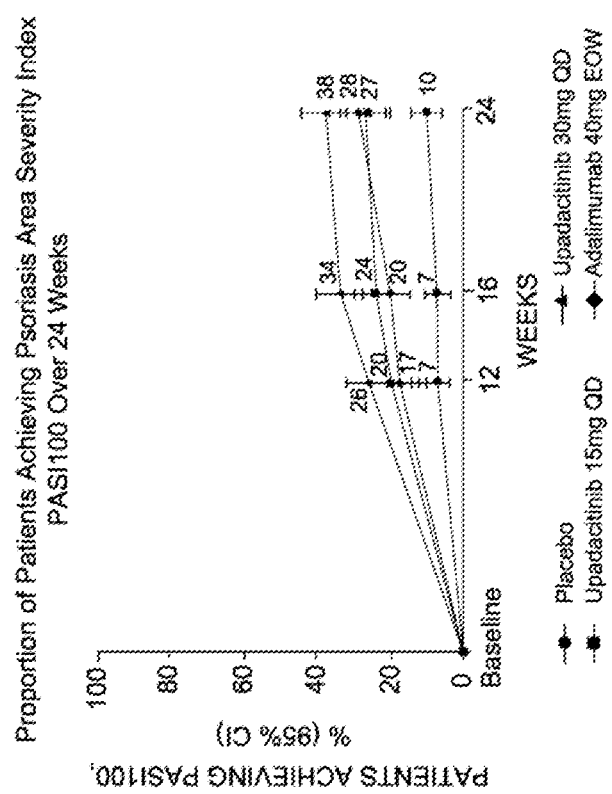
Figure 20Q:
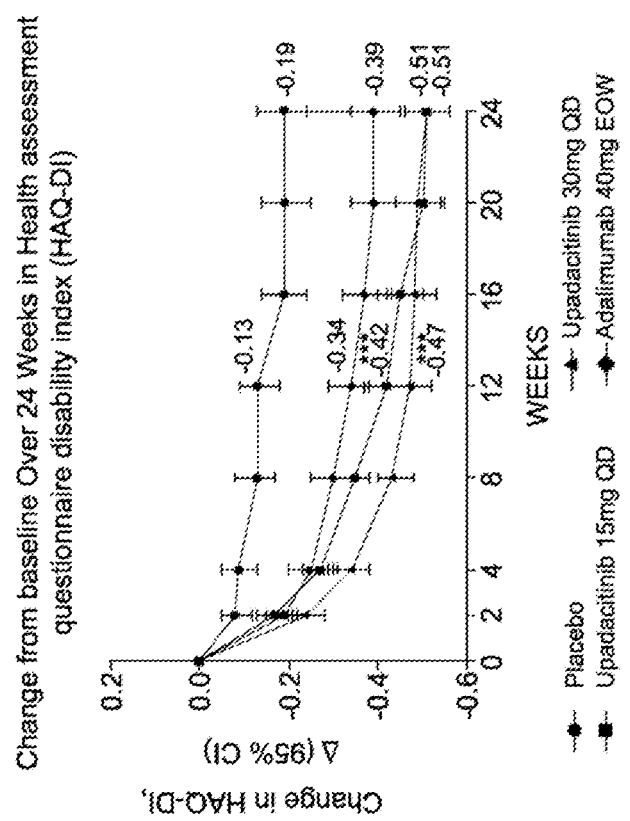
Figure 20P:
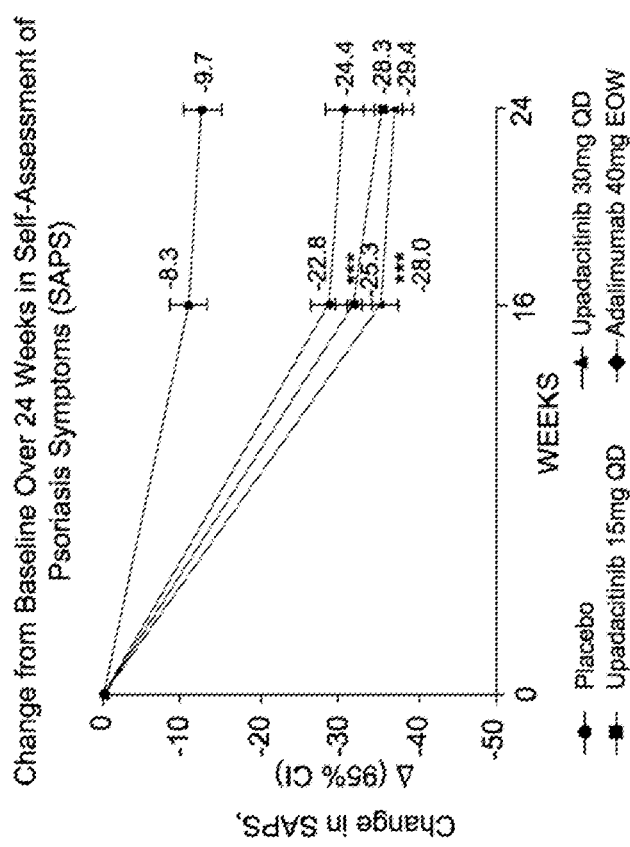
Figure 20S:
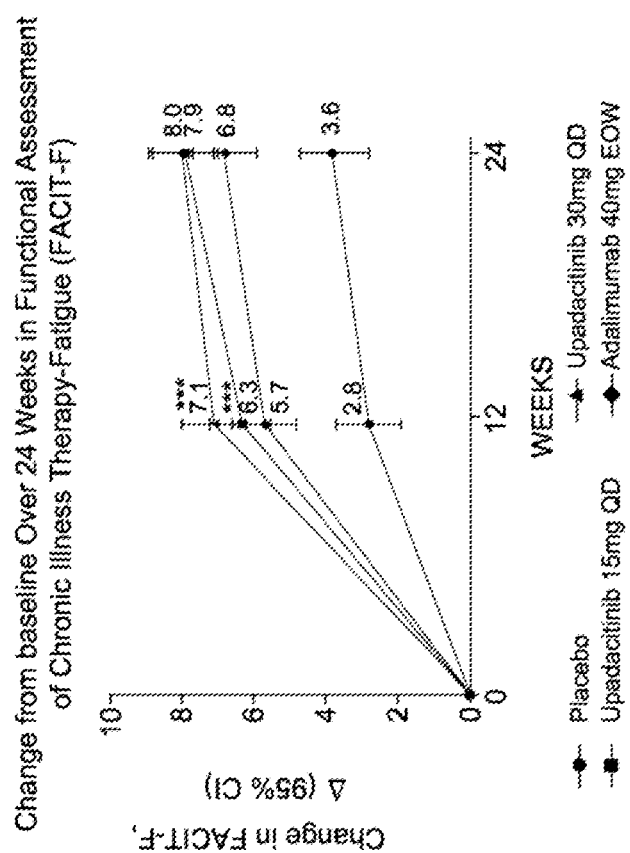
Figure 20R:
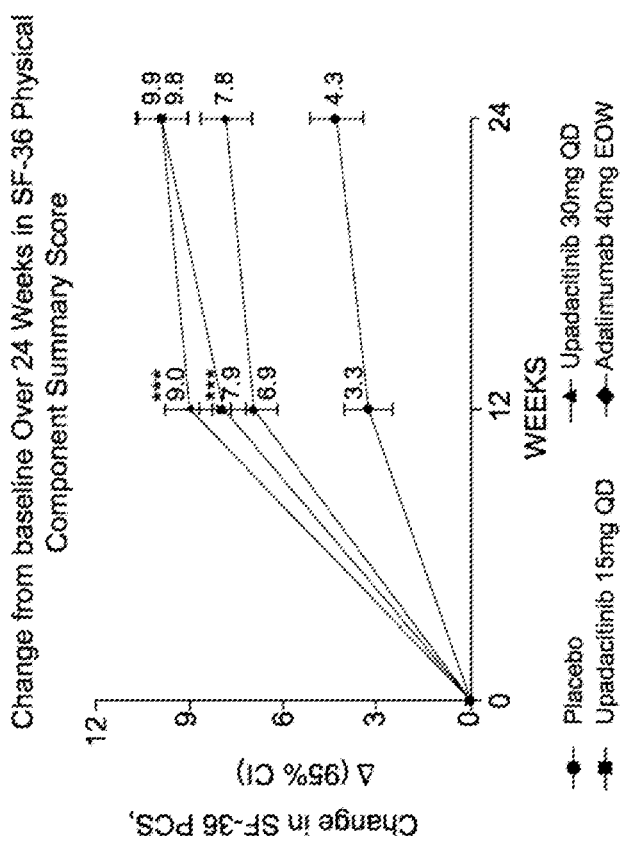
Figure 20U:
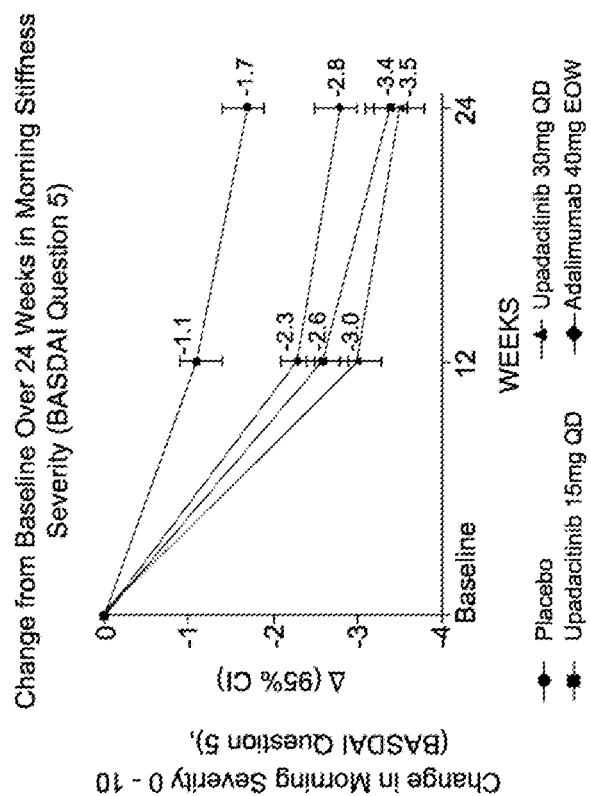
Figure 20T:
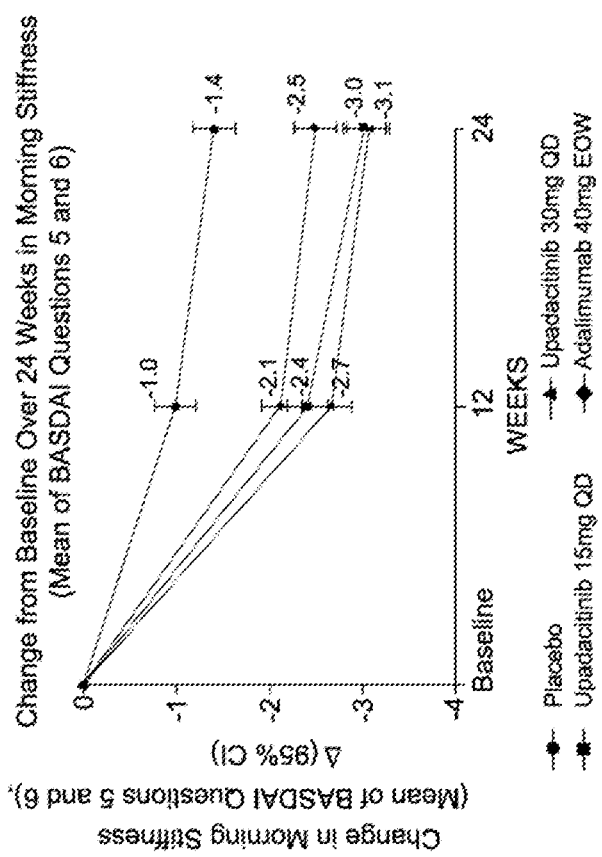
Figure 20V:
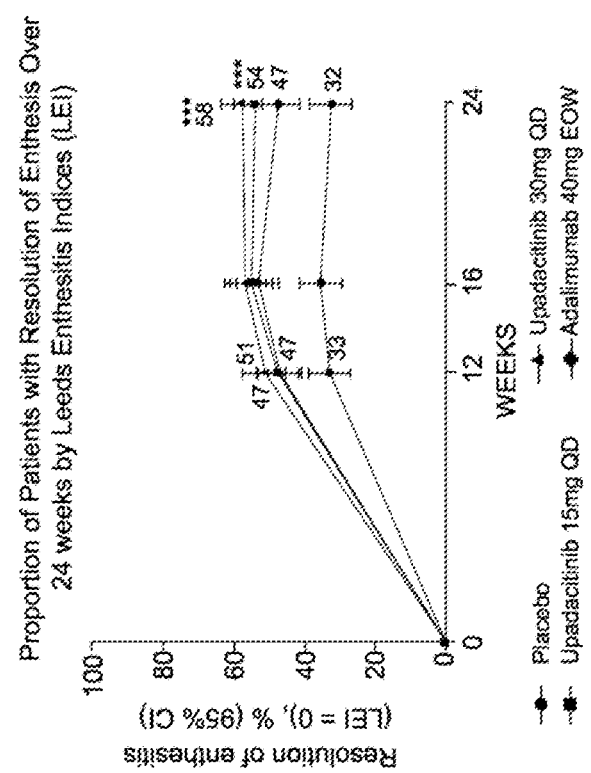
Figure 20W:
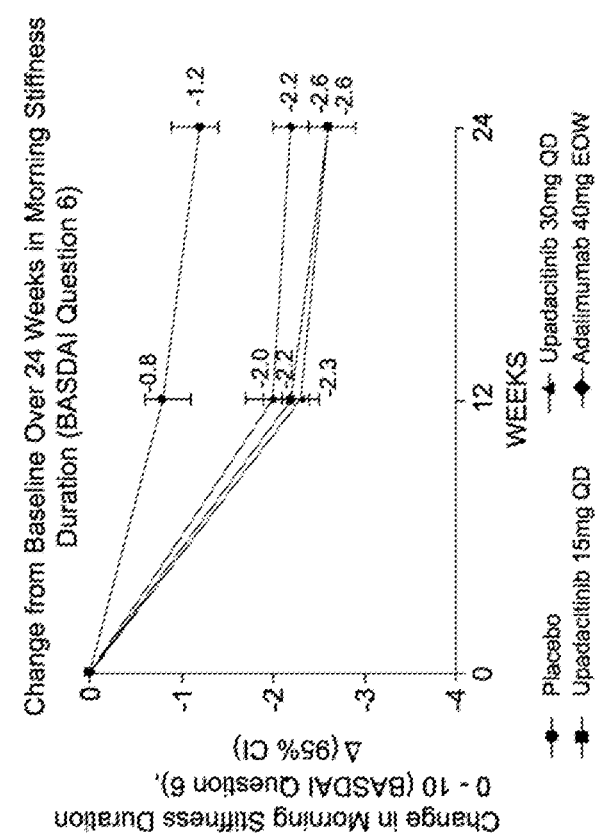
Figure 20Y:
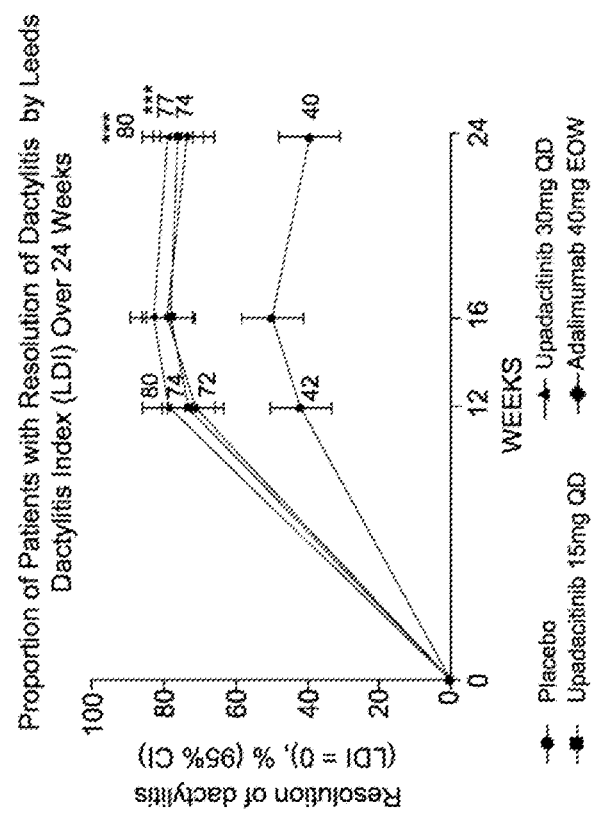
Figure 20X:
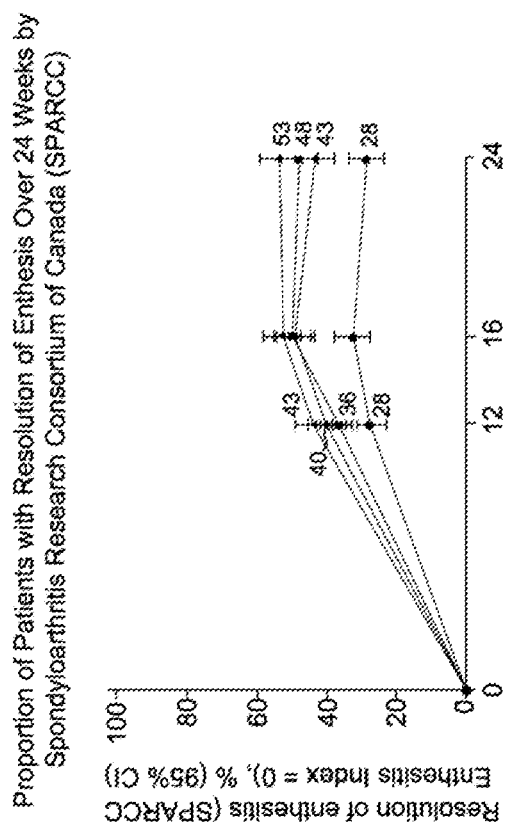

A summary of primary and key secondary efficacy results are presented in the below Tables (Parts 1 and 2). See also FIGS. 19A-19B for a listing of the ranked secondary endpoints. Parts 1 and 2. The time course of the ACR20 response and associated 95% confidence interval (CI) up to and including Week 24 is presented in FIG. 20A, and results for additional key secondary endpoints are presented in FIGS. 20B20BB. It was observed that this clinical efficacy achieved was sustained with continued daily dosing.

TABLE 25B

Demographics and Characteristics at Baseline

|  | Placebo N = 423 | Upadacitinib 15 mg QD N = 429 | Upadacitinib 30 mg QD N = 423 | Adalimumab 40 mg EOW N = 429 |
|---|---|---|---|---|
| Female, n (%) | 211 (49.9) | 238 (55.5) | 236 (55.8) | 222 (51.7) |
| Age (years) | 50.4 ± 12.2 | 51.6 ± 12.2 | 49.9 ± 12.4 | 51.4 ± 12.0 |
| White race, n (%) | 377 (89.1) | 386 (90.0) | 377 (89.1) | 375 (87.4) |
| BMI ≥25 kg/m², n (%) | 329 (77.8) | 342 (79.7) | 319 (75.4) | 334 (77.9) |
| Duration since PsA diagnosis (years) | 6.2 ± 7.0 | 6.2 ± 7.4 | 5.9 ± 6.4 | 5.9 ± 7.1 |
| Any non-biologic DMARD at baseline, n (%) | 347 (82.0) | 353 (82.3) | 346 (81.8) | 347 (80.9) |
| MTX alone | 267 (63.1) | 279 (65) | 268 (63.4) | 270 (62.9) |
| MTX + another non-biologic DMARD | 26 (6.1) | 20 (4.7) | 27 (6.4) | 16 (3.7) |
| Non-biologic DMARD other than MTX | 54 (12.8) | 54 (12.6) | 51 (12.1) | 61 (14.2) |
| Glucocorticoid use at baseline, n (%) | 70 (16.5) | 73 (17.0) | 71 (16.8) | 72 (16.8) |
| TJC68 | 20.4 ± 14.3 | 20.4 ± 14.7 | 19.4 ± 13.3 | 20.1 ± 13.8 |
| SJC66 | 11.0 ± 8.2 | 11.6 ± 9.3 | 10.6 ± 7.1 | 11.6 ± 8.8 |
| hs-CRP > ULN ᵃ, n (%) | 324 (76.6) | 324 (75.5) | 324 (76.6) | 308 (71.8) |
| HAQ-DI | 1.12 ± 0.6 | 1.15 ± 0.7 | 1.09 ± 0.6 | 1.12 ± 0.6 |
| Patient's Assessment of Pain (NRS 0-10) | 6.1 ± 2.1 | 6.7 ± 2.1 | 5.9 ± 2.1 | 6.0 ± 2.1 |
| BSA-psoriasis ≥3%, n (%) | 211 (49.9) | 214 (49.9) | 210 (49.6) | 211 (49.2) |
| PASI (for baseline BSA-psoriasis ≥3%) | 11.2 ± 11.4 | 9.78 ± 10.0 | 9.5 ± 8.8 | 9.4 ± 8.5 |

TABLE 25B-continued

Demographics and Characteristics at Baseline

|  | Placebo<br>N = 423 | Upadacitinib<br>15 mg QD<br>N = 429 | Upadacitinib<br>30 mg QD<br>N = 423 | Adalimumab<br>40 mg EOW<br>N = 429 |
|---|---|---|---|---|
| sIGA of Psoriasis score, n (%) | | | | |
| 0 | 24 (5.7) | 34 (7.9) | 21 (5.0) | 34 (7.9) |
| 1 | 86 (20.3) | 73 (17.0) | 78 (18.4) | 65 (15.2) |
| 2 | 167 (39.5) | 170 (39.6) | 173 (40.9) | 181 (42.2) |
| 3 | 119 (28.1) | 133 (31.0) | 128 (30.3) | 132 (30.8) |
| 4 | 27 (6.4) | 19 (4.4) | 23 (5.4) | 17 (4.0) |
| Presence of enthesitis (defined as LET >0), n (%) | 241 (57.0) | 270 (62.9) | 267 (63.1) | 265 (61.8) |
| Presence of dactylitis (defined as LDI >0), n (%) | 126 (29.8) | 136 (31.7) | 127 (30.0) | 127 (29.6) |

Values are mean ± SD unless noted.
[a]ULN >2.87 mg/L;
Permitted concomitant non-biologic DMARDs included: methotrexate, sulfasalazine, leflunomide, apremilast, hydroxychloroquine, bucillamine, and iguratimod.
BMI, body mass index;
BSA, body surface area;
DMARD, disease-modifying anti-rheumatic drug;
EOW, every other week;
HAQ-DI, Health Assessment Questionnaire-Disability Index;
hs-CRP, high-sensitivity C-reactive protein;
LDI, Leeds Dactylitis Index;
LEI, Leeds Enthesitis Index;
MTX, methotrexate;
NRS, numeric rating scale;
NSAID, nortsteroidal anti-inflammatory drug;
PASI, psoriasis area severity index;
PsA, psoriatic arthritis;
QD, once daily;
SD, standard deviation;
ULN, upper limit normal;
SD, standard deviation;
sIGA, Static Investigator Global Assessment of Psoriasis;
SJC, swollen joint count;
TJC, tender joint count.

TABLE 25C

Primary and Ranked Secondary Efficacy Endpoints-Part 1

| Summary Statistics<br>% or LS Mean (P-Value) | | Endpoint[a] | PLACEBO<br>N = 423 | ADA<br>40 MG EOW<br>N = 429 | UPA<br>15 MG QD<br>N = 429 | UPA<br>30 MG QD<br>N = 423 |
|---|---|---|---|---|---|---|
| Primary | | ACR20 (Wk12) | 36.2% | 65.0% | 70.6% (<0.0001*) | 78.5% (<0.0001*) |
| Ranked Secondary Endpoints (Part 1) | 1 | HAQ-DI (Wk12) | −0.14 | −0.34 | −0.42 (<0.0001*) | −0.47 (<0.0001) |
| | 2 | sIGA (Wk16)[b] | 10.9% | 38.5% | 41.9% (<0.0001 *) | 54.0% (<0.0001*) |
| | 3 | PASI 75 (Wk16)[c] | 21.3% | 53.1% | 62.6% (<0.0001*) | 62.4% (<0.0001*) |
| | 4 | SHS (mTSS) (Wk24) | 0.25 | 0.01 | −0.04 (0.0002*) | 0.03 (0.0069*) |
| | 5 | MDA (Wk24) | 12.3% | 33.3% | 36.6% (<0.0001*) | 45.4% (<0.0001*) |
| | 6 | Enthesitis Resolution (Wk 24)[d] | 32.4% | 47.2% | 53.7% (<0.0001*) | 57.7% (<0.0001*) |
| | 7 | ACR 20 NI vs ADA[e] (Wk12) | 36.2% | 65.0% | 70.6% (<0.0001*) | 78.5% (<0.0001*) |

TABLE 25C-continued

Primary and Ranked Secondary Efficacy Endpoints-Part 1

| Summary Statistics % or LS Mean (P-Value) | Endpoint[a] | PLACEBO N = 423 | ADA 40 MG EOW N = 429 | UPA 15 MG QD N = 429 | UPA 30 MG QD N = 423 |
|---|---|---|---|---|---|
| 8 | SF-36 PCS (Wk12) | 3.19 | 6.82 | 7.86 (<0.0001*) | 8.90 (<0.0001*) |
| 9 | FACIT-F (Wk12) | 2.8 | 5.7 | 6.3 (<0.0001*) | 7.1 (<0.0001*) |

Note:
The nominal p-values are provided in parentheses.

*Achieved statistical significance using graphical multiple testing procedure controlling the overall type I error rate at 2-sided 0.0499 level. Note that 0.0001 was spent at the interim futility analysis.

[a]Results for binary endpoints are based on NRI analysis. Results for MDA and enthesitis resolution at week 24 are based on non-responder imputation with additional rescue handling, where subjects rescued at Week 16 are imputed as non-responders. Results for continuous endpoints are based on MMRM model with fixed effects of treatment, visit, treatment-by-visit interaction, the stratification factor of current DMARD use (yes/no) and baseline measurement. Results for SHS are based on ANCOVA with linear extrapolation for missing data and rescue handling.

[b]Summarized for subjects with baseline sIGA ≥ 2; $N_{(pbo)}$ = 313, $N_{(ADA)}$ = 330, $N_{(upa15)}$ = 322, $N_{(upa30)}$ = 324.

[c]Summarized for subjects with baseline BSA affected by psoriasis ≥ 3%; N(pbo) = 211, N(ADA) = 211, N(upa15) = 214, N(upa30) = 210.

[d]Summaried for subjects with baseline LEI > 0; N(pbo) = 241, N(ADA) = 265, N(upa15) = 270, N(upa30) = 267.

[e]Non-inferiority test of upadacitinib vs adalimumab, perserving 50% of adlimumab effect.

TABLE 25D

Ranked Secondary Efficacy Endpoints in Part 2 and Other Key Secondary Endpoints

| Summary Statistics % or LS Mean (P-Value) | | Endpoint[a] | PLACEBO N = 423 | ADA 40 MG EOW N = 429 | UPA 15 MG QD N = 429 | UPA 30 MG QD N = 423 |
|---|---|---|---|---|---|---|
| Ranked Secondary Endpoints (Part 2) | 10 | ACR 20 Sup. vs ADA[b] (Wk12) | 36.2% | 65.0% | 70.6% (0.0815) | 78.5% (<0.0001*) |
| | 11 | Dactylitis Resolution (Wk24)[c] | 39.7% | 74.0% | 76.5% (<0.0001) | 79.5% (<0.0001) |
| | 12 | Pain Sup. vs ADA[b] (Wk12) | −0.9 | −2.3 | −2.3 (0.8970) | −2.7 (0.0028) |
| | 13 | HAQ-D1 Sup. vs ADA[b] (Wk12) | −0.14 | −0.34 | −0.42 (0.0162) | −0.47 (<0.0001) |
| | 14 | SAPS (Wk16) | −8.2 | −22.7 | −25.3 (<0.0001) | −28.1 (<0.0001) |
| Other Key Secondary | | ACR50 (Wk12) | 13.2% | 37.5% | 37.5% (<0.0001) | 51.8% (<0.0001) |
| | | ACR70 (Wk12) | 2.4% | 13.8% | 15.6% (<0.0001) | 25.3% (<0.0001) |
| | | ACR20 (Wk2) | 12.1% | 30.3% | 28.2% (<0.0001) | 38.3% (<0.0001) |

Note:
The nominal p-values are provided in parentheses.
*Statistical significance using graphical multiple testing procedure controlling overall type I error rate.
[a]Results for binary endpoints are based on NRI analysis. Results for dactylitis resolution at week 24 is based on non-responder imputation with additional rescue handling, where subjects rescued at Week 16 are imputed as non-responders. Results for continuous endpoints are based on MMRM model with fixed effects of treatment, visit, treatment-by-visit interaction, the stratification factor of current DMARD use (yes/no) and baseline measurement.
[b]Superiority test of upadacitinib vs. adalimumab.
[c]Summarized for subjects with baseline LDI > 0; N(pbo) = 126, N(ADA) = 127, N(upa15) = 136, N(upa30) = 127.

TABLE 25E

Additional Efficacy Endpoints for SELECT-PSA1: Summarized for subjects with baseline BSA affected by psoriasis ≥3%[a]

| Endpoint | PLACEBO N = 211 | ADA 40 MG EOW N = 211 | CPA 15 MG QD N = 214 | UPA 30 MG QD N = 210 |
|---|---|---|---|---|
| PASI 90 (Wk 16) | 12.3% | 38.9% | 38.3% (<0.0001) | 49.5% (<0.0001) |
| PASI 100 (Wk 16) | 7.1% | 19.9% | 23.8% | 33.8% (<0.0001) |

[a]Fall analysis set:
N (placebo) = 423, N(ADA) = 429, N(UPA15) = 429, N(UPA30) = 423.

Additional data for ACR20, ACR50, and ACR70 response at Week 24, and MDA, resolution of enthesitis (LEI=0), and resolution of dactylitis (LDI=0) at week 12 is set forth in the below Table 25F.

TABLE 25F

Additional Clinical Responses

| Endpoint | Placebo (N = 423) % | CPA 15 mg QD (N = 429) |
|---|---|---|
| ACR20 (Wk 24) | 45 | 73 |
| ACR50 (Wk 24) | 19 | 52 |
| ACR70 (Wk 24) | 5 | 29 |
| MDA (Wk 12) | 6 | 25 |
| Enthesitis resolution[a] (Wk 12) | 33 | 47 |
| Dactylitis resolution[b] (Wk 12) | 42 | 74 |

Patients who discontinued randomized treatment or were missing data at week of evaluation were imputed as non-responders in the analyses. For MDA, resolution of enthesitis; and resolution of dactylitis at Week 24, the subjects rescued at Week 16 were imputed as non-responders in the analyses.
[a]In patients with enthesitis at baseline (n = 241 and 270, respectively)
[b]In patients with dactylitis at baseline (n = 126 and 136)

Treatment with upadacitinib freebase 15 mg resulted in improvements in individual ACR components, including tender/painful and swollen joint counts, patient and physician global assessments of disease activity, HAQ-DI, pain assessment, and hsCRP compared to placebo. These results are shown in FIGS. 20F-20K and 20Q. Onset of efficacy was seen as early as Week 2 for ACR20 and its components.

Figure 20Z:
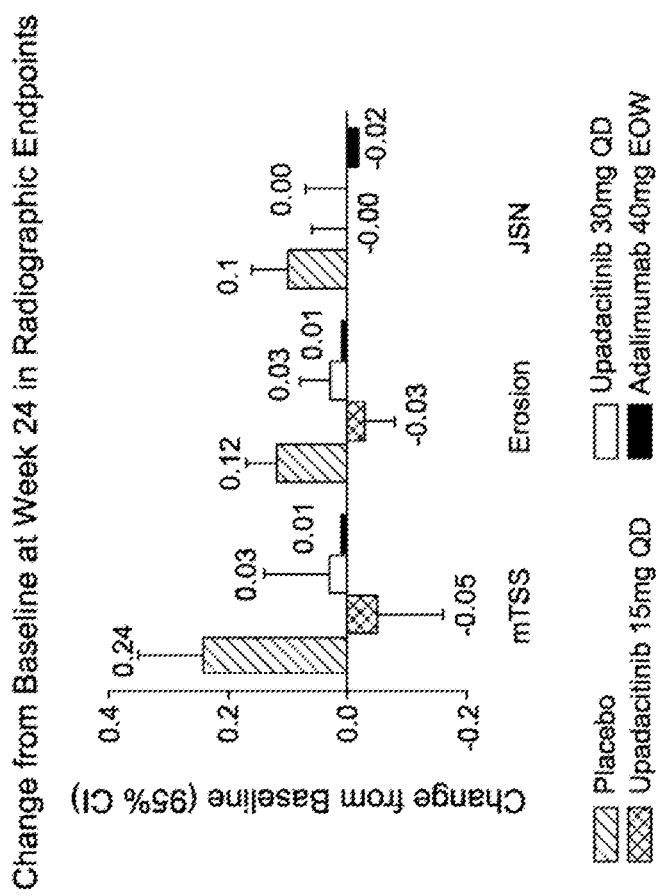
Figures 20A, 20B:
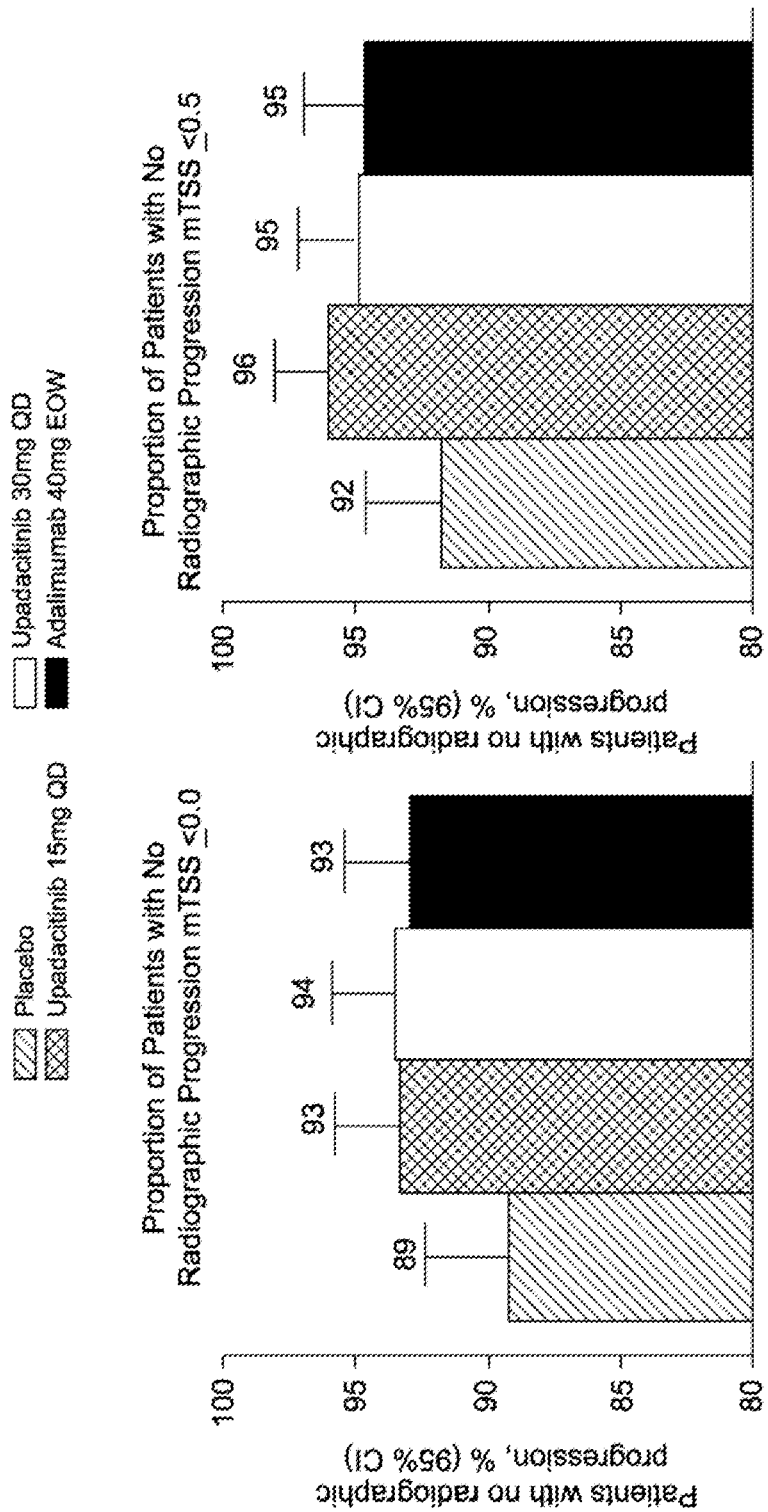
Figure 20C:
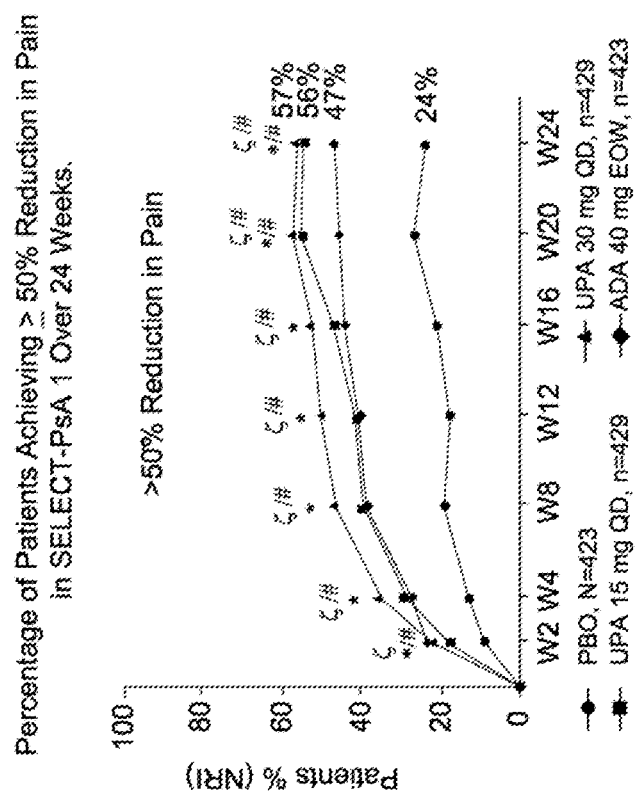
Figure 20D:
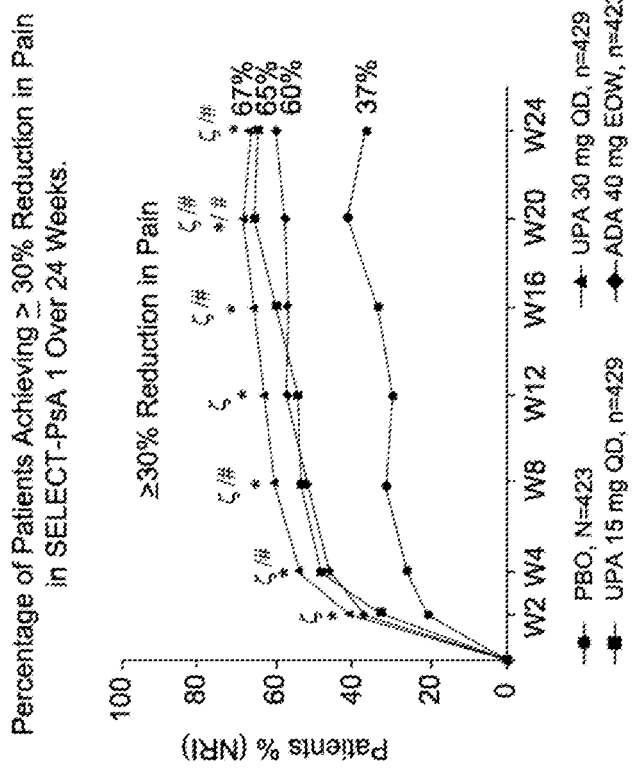
Figure 20E:
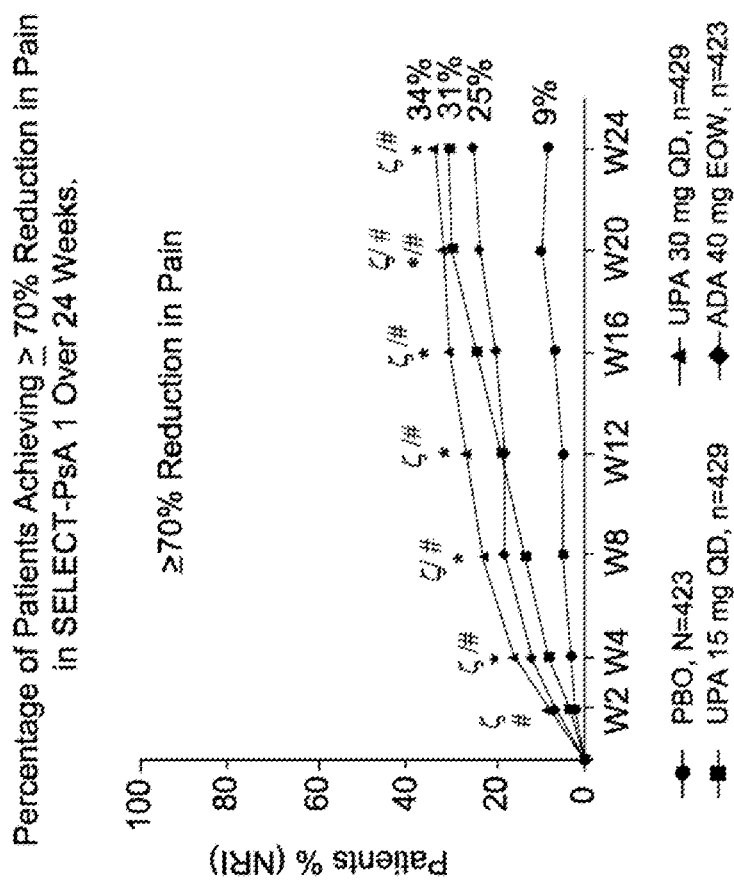

Inhibition of progression of structural damage was assessed radiographically and expressed as the change from baseline in modified Total Sharp Score (mTSS) and its components, the erosion score and the joint space narrowing score, at Week 24. Treatment with upadacitinib freebase 15 mg QD resulted in significantly greater inhibition of the progression of structural joint damage compared to placebo at Week 24. Statistically significant results were also achieved for both erosion and joint space narrowing scores. The proportion of patients with no radiographic progression (mTSS change ≤0) was higher with upadacitinib freebase 15 mg QD (93%) compared to placebo (89%) at Week 24. These results are summarized in FIG. 20Z.

The safety profile of upadacitinib in this trial was generally similar to the safety profile observed in other upadacitinib clinical trials. Through week 24, the rates of treatment-emergent adverse events and serious adverse events, including serious infections, were similar with placebo, adalimumab, and upadacitinib 15 mg but higher with upadacitinib 30 mg. The most common AE was upper respiratory tract infection. Rates of serious infections were 0.9%, 0.7%, 1.2%, and 2.6% with placebo, adalimumab, upadacitinib 15 mg and 30 mg, respectively. Up to week 24, treatment-emergent opportunistic infections included one event of candida urethritis with upadacitinib 15 mg, and one event each of Pneumocystis jirovecii pneumonia and cytomegalovirus with upadacitinib 30 mg. There were 3, 4, and 5 cases of herpes zoster reported with placebo and upadacitinib 15 mg and 30 mg, respectively. One malignancy occurred in each of the placebo and upadacitinib 15 mg arms, and 3 malignancies were reported in each of the upadacitinib 30 mg and adalimumab arms. No major adverse cardiovascular events (MACE) were reported with upadacitinib. One event of deep vein thrombosis was reported with placebo and 2 events with adalimumab; one event of pulmonary embolism was reported with upadacitinib 30 mg. One death, adjudicated to unknown cause, was reported with placebo.

Mean hemoglobin, neutrophil, lymphocyte, and platelet levels remained within normal limits from baseline through week 24 in all treatment arms. Adverse events of anemia and lymphopenia were reported at similar rates for upadacitinib 15 mg and placebo and more often with upadacitinib 30 mg. Adverse events of neutropenia were more common with upadacitinib compared to placebo. Overall, the frequency of Grade ≥3 laboratory abnormalities was ≤2.1%; most resolved without interruption in therapy. No patients had Grade 4 decreases in hematology parameters. One patient each reported isolated Grade 3 decrease in hemoglobin or platelets after discontinuation with upadacitinib 30 mg. The frequency of Grade 3 neutrophil and lymphocytes decreases was higher for upadacitinib 30 mg compared to other arms.

Hepatic disorder adverse events were reported in 3.8%, 15.6%, 9.1%, and 12.3% of the placebo, adalimumab, upadacitinib 15 mg and 30 mg groups, respectively. Most alanine aminotransferase (ALT) or aspartate aminotransferase (AST) increases were mild to moderate (Grade 2 or less). Grade 3 elevations in ALT occurred in 1.7%, 0.9%, 0.9%, and 1.2% with placebo, adalimumab, upadacitinib 15 mg and 30 mg, respectively. Grade 3 elevations in AST occurred in 0.5%, 0.2%, 0%, and 0.7% with placebo, adalimumab, and upadacitinib 15 mg and 30 mg, respectively. No Grade 4 elevations in ALT values were reported; 1 patient in the upadacitinib 30 mg group had a Grade 4 increase in AST at a single time point. No Hy's law cases were reported. Grade 3 or 4 increases in creatine phosphokinase (CPK) values were more common with upadacitinib and were reported in <2% of patients; no patients experienced rhabdomyolysis.

Mean increases in low-density lipoprotein cholesterol (LDL-C) and high-density lipoprotein cholesterol (HDL-C) were observed with upadacitinib in comparison to placebo. LDL-C:HDL-C and total cholesterol:HDL-C ratios did not change through week 24.

Upadacitinib as a Promising Oral Therapy for the Treatment of PsA

A review of the placebo corrected data for upadacitinib and the JAK small molecule inhibitor Tofacitinib (approved for the lower (5 mg BID) dose in the treatment of PsA) for key primary and secondary endpoints, while not a head to head comparison, suggests that upadacitinib 15 mg QD and 30 mg QD shows decided promise for the more difficult to achieve endpoints of minimal disease activity (MDA), as well as psoriasis endpoints PASI 75 or PASI 90, as well as certain ACR components (e.g., ACR20/50/70). It was observed that this clinical efficacy achieved was sustained with continued daily dosing (Table 25G)

TABLE 25G

| | Upadacitinib H2H Adalimumab Select PsA1 | | | Tofacitinib Opal | | Ixekizumamb | |
|---|---|---|---|---|---|---|---|
| | Upa 15 | Upa 30 | | Broaden | | Spirit P1 | |
| Endpoint | mg QD Week 12/16/24 | mg QD Week 12/16/24 | Adalimumab Week 12/24 | Tofa 5 mg BID Week 12 | Tofa 10 mg BID Week 12 | IXE 80 mg Q4W Week 24 | IXE 80 mg Q2W Week 24 |
| ACR20 | Week 12 34% (70.6%/36.2%, $p \leq 0.001$) | Week 12 42% (78.5%/36.2%, $p \leq 0.001$) | Week 12 29% (65%/36.2%) | 17% (50%/33%, $p \leq 0.05$) | 28% (61%/33%, $p \leq 0.001$) | 28% (57.9%/30.2%, $p \leq 0.001$) | 32% (62.1%/30.2%, $p \leq 0.001$) |
| ACR50 | Week 12 24% (37.5%/13.2%, $p \leq 0.001$) | Week 12 39% (51.8%/13.2%, $p \leq 0.001$) | Week 12 24% (37.5%/13.2%) | 18% (28%/10%, $p \leq 0.001$) | 30% (40%/10%, $p \leq 0.001$) | 25% (40.2%/15.1%, $p \leq 0.001$) | 32% (46.6%/15.1,% $p \leq 0.001$) |
| ACR70 | Week 12 13% (15.6%/2.4%, $p \leq 0.001$) | Week 12 23% (25.3%/2.4%, $p \leq 0.001$) | Week 12 11.4% (13.8%/2.4%) | 12% (17%/5%, $p \leq 0.01$) | 9% (14%/5%, $p \leq 0.05$) | 18% (23.4%/5.7%, $p \leq 0.001$) | 28% (34.0%/5.7%, $p \leq 0.001$) |
| MDA | Week 24 24% (36.6%/12.3%, $p \leq 0.001$) | Week 24 33% (45.4%/12.3%, $p \leq 0.001$) | Week 24 21% (33.3%/12.3%) | 19% (26%/7%) | 18% (25%/7%) | 15% (29.9%/15.1%, $p \leq 0.01$) | 26% (40.8%/15.1%, $p \leq 0.01$) |
| PASI 75 | Week 16 41% (62.6%/21.3%, $p \leq 0.001$) | Week 16 41% (62.4%/21.3%, $p \leq 0.001$) | Week 16 31.8% (53.1%/21.3%) | 28% (43%/15%, $p \leq 0.001$) | 29% (44%/15%, $p \leq 0.001$) | 61% (71.2 %/10.4%, $p \leq 0.001$) | 69% (79.9%/10.4%, $p \leq 0.001$) |
| PASI 90 | Week 16 26% (38.3%/12.3%, $p \leq 0.001$) | Week 16 37% (49.5%/12.3%, $p \leq 0.001$) | Week 16 17.6% (38.9%/21.3%) | 17% (27%/7%, $p \leq 0.01$) | 27% (27%/7%, $p \leq 0.001$) | 50% (56.2%/6%, $p \leq 0.001$) | 52% (67.8%/6%, $p \leq 0.001$) |

Tofacitinib study: Mease P et al. N Engl J Med 2017; 377: 1537-1550 (5 mg BID dose is approved in the United States for treatment of PsA; 10 mg BID dose is not approved in the United States); Ixekizumab study: Mease PJ et al. Ann Rheum Dis 2017; 76: 79-87.

Example 36: A Phase 3 Protocol in Subjects with Active Psoriatic Arthritis and a Previous Inadequate Response to at Least One Biologic Disease Modifying Anti-Rheumatic Drug (bDMARD) (Select PSA2)

Figure 21:
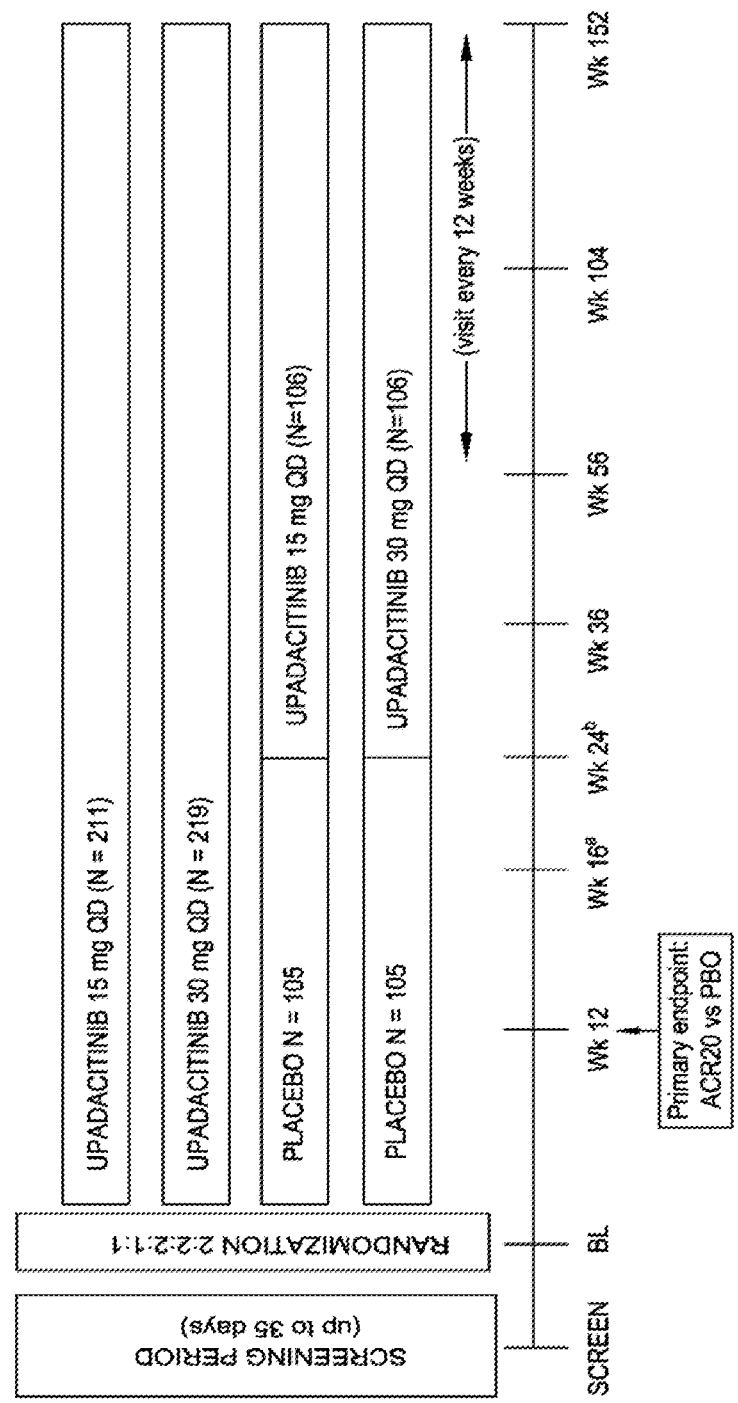
FIG. 21 depicts the Phase 3 Study design for SELECT-PSA2 in subjects with active PsA and a previous inadequate response to at least one bDMARD (PsA bDMARD-IR), a. At Week 16 rescue therapy will be offered to subjects classified as non-responders (defined as not achieving at least 20% improvement in either or both tender joint count (TJC) and swollen joint count (SJC) at both Week 12 and Week 16). b. At Week 24, all placebo subjects will switch to upadacitinib freebase 15 mg QD or 30 mg QD (1:1 ratio) regardless of response.

This is a Phase 3 multicenter study that includes two periods. The Phase 3 Study Design for SELECT-PSA2 is provided in FIG. 21. Period 1 is 56 weeks in duration and includes a 24-week randomized, double-blind, parallel-group, placebo-controlled period followed by an additional 32 weeks of blinded treatment (Weeks 24-56). Period 1 is designed to compare the safety, tolerability, and efficacy of upadacitinib free base 15 mg QD and 30 mg QD versus placebo in subjects with moderately to severely active PsA who have an inadequate response to at least one Biological Disease Modifying Anti-Rheumatic Drug (bDMARD) (PsA Bio-IR). Period 2 is an open label (blinded until the last subject completes the last visit of Period 1) long-term extension of up to a total treatment duration of approximately 3 years to evaluate the safety, tolerability and efficacy of upadacitinib free base 15 mg QD, and 30 mg QD, in subjects with PsA who have completed Period 1. 15 mg or 30 mg upadacitinib refers to the 15 mg and 30 mg once-daily (QD) upadacitinib drug product as described in Example 35.

The study duration includes a 35-day screening period; a 56-week blinded period which includes 24 weeks of double-blind, placebo-controlled treatment followed by 32 weeks of treatment blinded to dose of upadacitinib (Period 1); a long-term extension period of up to a total treatment duration of approximately 3 years ([blinded until the last subject completes the last visit of Period 1] Period 2); and a 30-day follow-up call or visit.

Subjects who met eligibility criteria were stratified by extent of psoriasis (≥3% body surface area [BSA] or <3% BSA), current use of at least 1 DMARD (yes or no), and number of prior failed (had an inadequate response to) biologic DMARDs (1 vs >1), except for subjects from Japan, for which randomization were stratified by extent of psoriasis (≥3% body surface area [BSA] or <3% BSA) only. Subjects were randomized in a 2:2:1:1 ratio to one of four treatment groups:

Group 1: upadacitinib free base 15 mg QD (N=211)
Group 2: upadacitinib free base 30 mg QD (N=219)
Group 3: Placebo followed by upadacitinib free base 15 mg QD (N=106)
Group 4: Placebo followed by upadacitinib free base 30 mg QD (N=106)

No more than approximately 40% of subjects were enrolled with <3% BSA extent of psoriasis and no more than approximately 30% of subjects were enrolled with prior failure of more than 1 biologic DMARD.

Subjects received oral study drug QD (upadacitinib free base 15 mg, upadacitinib free base 30 mg, or matching placebo) until the end of the study or until they discontinue study drug.

Subjects who were assigned to placebo at Baseline were preassigned to receiving either upadacitinib free base 15 mg QD or upadacitinib free base 30 mg QD starting at Week 24 in a 1:1 ratio. Subjects who completed the Week 56 visit (end of Period 1) entered the long-term extension portion of the study, Period 2 (total treatment up to approximately 3 years). Subjects continued study treatment as assigned in Period 1. Subjects continued to receive upadacitinib free base 15 mg QD or upadacitinib free base 30 mg QD, respectively, in a blinded manner until the last subject completed the last visit of Period 1 (Week 56), when study drug assignment in both periods will be unblinded to the sites, and subjects will be dispensed study drug in an open-label fashion until the completion of Period 2.

Subjects must have had inadequate response to >1 bDMARD prior to the Screening visit and must have discontinued all bDMARDs prior to the first dose of study drug. No background non-biologic DMARD therapy was required during participation in this study. For subjects who are on non-biologic DMARD therapy at baseline (methotrexate (MTX), sulfasalazine (SSZ), leflunomide (LEF), apremilast, hydroxychloroquine (HCQ), bucillamine or iguratimod), non-biologic DMARDs should have been started ≥12 weeks prior to baseline visit, must be at stable dose for ≥4 weeks prior to the first dose of study drug and remain at stable dose through Week 36 of the study; the non-biologic DMARD dose may be decreased only for safety reasons. In addition, all subjects taking MTX should take a dietary supplement of oral folic acid (or equivalent) throughout study participation.

At Week 16, rescue therapy will be offered to subjects classified as non-responders (defined as not achieving at least 20% improvement in either or both tender joint count (TJC) and swollen joint count (SJC) at both Week 12 and Week 16) as follows: 1) add or modify doses of non-biologic DMARDs, NSAIDs, acetaminophen/paracetamol, low potency opioid medications (tramadol or combination of acetaminophen and codeine or hydrocodone), oral corticosteroids and/or 2) receive 1 intra-articular, trigger point or tender point, intra-bursa, or intra-tendon sheath corticosteroid injection for 1 peripheral joint, 1 trigger point, 1 tender point, 1 bursa, or 1 enthesis (Rescue Therapy).

At Week 24, all subjects allocated to placebo at Baseline will be switched to blinded upadacitinib (randomized at baseline to either 15 mg QD or 30 mg QD) treatment regardless of clinical response.

After the last subject completes the Week 24 study visit, an unblinded analysis will be conducted for the purpose of initial regulatory submission. To maintain integrity of the trial during the blinded 56-week period study sites and subjects will remain blinded until all subjects have reached Week 56. A second unblinded analysis may be conducted for regulatory purposes after all subjects have completed Period 1. A final analysis will be conducted after all subjects have completed Period 2.

Primary and Secondary Endpoints

The primary efficacy endpoint is the proportion of subjects achieving American College of Rheumatology (ACR) 20% response rate at Week 12. The primary and secondary clinical endpoints for the SELECT-PSA1 clinical study (Example 35) and this study (SELECT-PSA2 clinical study; Example 36) are further described in Example 37.

Study Population

Patients with active psoriatic arthritis and a previous inadequate response to at least one biologic DMARD.

Inclusion Criteria Include:
6. Adult male or female, at least ≥18 years old at Screening.
7. Clinical diagnosis of PsA with symptom onset at least 6 months prior to the Screening Visit and fulfillment of the Classification Criteria for PsA (CASPAR).
8. Subject has active disease at Baseline defined as ≥3 tender joints (based on 68 joint counts) and ≥3 swollen joints (based on 66 joint counts) at Screening and Baseline Visits.
9. Diagnosis of active plaque psoriasis or documented history of plaque psoriasis.
10. Subject has had an inadequate response (lack of efficacy after a minimum 12-week duration of therapy) or intolerance to treatment with at least 1 bDMARD.
11. Subjects must have discontinued all bDMARDs prior to the first dose of study drug. Subjects who need to discontinue bDMARDs prior to the Baseline Visit to comply with this inclusion criterion must follow the procedure specified below or at least five times the mean terminal elimination half-life of a drug:
    ≥4 weeks for etanercept;
    ≥8 weeks for adalimumab, infliximab, certolizumab, golimumab, abatacept, tocilizumab, and ixekizumab;
    ≥16 weeks for secukinumab;
    ≥12 weeks for ustekinumab;
    ≥1 year for rituximab OR≥6 months if B cells have returned to pretreatment level or normal reference range (local lab) if pretreatment levels are not available.
12. Subject who is on current treatment with concomitant non-biologic DMARDs at study entry must be on s 2 non-biologic DMARDs (except the combination of MTX and leflunomide) at the following doses: MTX (≤25 mg/week), SSZ (≤3000 mg/day), leflunomide (LEF) (≤20 mg/day), apremilast (≤60 mg/day), HCQ (≤400 mg/day), bucillamine (≤300 mg/day) and iguratimod (≤50 mg/day) for ≥12 weeks and at stable dose for ≥4 weeks prior to the Baseline Visit. No other DMARDs are permitted during the study.
    Subjects who need to discontinue DMARDs prior to the Baseline Visit to comply with this inclusion criterion must follow the procedure specified below or at least five times the mean terminal elimination half-life of a drug:
    ≥8 weeks for LEF if no elimination procedure was followed, or adhere to an elimination procedure (i.e., 11 days with cholestyramine, or 30-day washout with activated charcoal or as per local label);
    ≥4 weeks for all others.
13. Stable doses of NSAIDs, acetaminophen/paracetamol, low-potency opiates (tramadol or combination of acetaminophen and codeine or hydrocodone), oral corticosteroids (equivalent to prednisone ≤10 mg/day), or inhaled corticosteroids for stable medical conditions are allowed, but must have been at a stable dose for ≥1 weeks prior to the Baseline Visit.
14. Subjects must have discontinued all opiates (except for tramadol or combination of acetaminophen and codeine or hydrocodone) at least 1 week and oral Traditional Chinese Medicine for at least 4 weeks prior to the first dose of study drug.

Exclusion Criteria Include:
1. Prior exposure to any Janus Kinase (JAK) inhibitor (including but not limited to ruxolitinib, tofacitinib, baricitinib, and filgotinib)
2. Current treatment with >2 non-biologic DMARDs or use of DMARDs other than MTX, SSZ, LEF, apremilast, HCQ, bucillamine or iguratimod or use of MTX in combination with LEF at Baseline
3. History of fibromyalgia, any arthritis with onset prior to age 17 years, or current diagnosis of inflammatory joint disease other than PsA (including, but not limited to rheumatoid arthritis, gout, overlap connective tissue diseases, scleroderma, polymyositis, dermatomyositis, systemic lupus erythematosus). Prior history of reactive arthritis or axial spondyloarthritis including ankylosing spondylitis and non-radiographic axial spondyloarthritis is permitted if documentation of change in diagnosis to PsA or additional diagnosis of PsA is made. Prior history of fibromyalgia is permitted if documentation of change in diagnosis to PsA or documentation that the diagnosis of fibromyalgia was made incorrectly.

Analysis Windows

For each protocol-specified study visit, a target study day will be identified to represent the corresponding visit along with a window around the target day. Windows will be selected in a non-overlapping fashion so that a collection date does not fall into multiple visit windows. If a subject has two or more actual visits in one visit window, the visit closest to the target day will be used for analysis. If two visits are equidistant from the target day, then the later visit will be used for analysis.

Results Up to and Including Week 24

As noted above, after the last subject completed the Week 24 study visit, an unblinded analysis was conducted for the purpose of initial regulatory submission.

A total of 642 subjects were randomized in this study, and 641 subjects received double-blind study treatment, out of which 591 (92.1%) completed study drug through Week 12, and 543 (84.6%) completed study drug through Week 24

The study met all primary and key secondary endpoints, with upadacitinib 15 mg QD and 30 mg QD demonstrating significantly greater efficacy in PsA compared with placebo. See the below Tables as well as FIGS. 22A-22BB. The time course of the primary endpoint ACR20 up to and including Week 24 is provided in FIG. 22A, and key secondary endpoints at ACR50, ACR70, and Proportion of Patients Achieving Minimal Disease Activity (MDA) Over 24 Weeks are provided in FIGS. 22B-22D. The time course of the change in baseline in Leeds Enthesitis Index (LEI) and subjects with resolution of enthesitis (LEI=0) up to and including Week 24 is presented in FIGS. 22E-22G. The time course of the change in baseline in Leeds Dactylitis Index (LDI) and subjects with resolution of dactylitis (LDI=0) up to and including Week 24 is presented in FIGS. 22H-22I. Data for other key secondary endpoints is provided in FIG. 21.

All p-values were statistically significant for both upadacitinib doses as compared to placebo (graphical multiple testing procedure controlling the overall type I error rate at the 0.05 level).

The primary analysis showed a significantly higher response rate in both upadacitinib treatment groups as compared to the placebo group for the primary endpoint. At week 12, significantly more patients achieved an ACR20 response in the upadacitinib 15 mg and 30 mg arms versus the placebo arm (56.9%, 63.8%, and 24.1%, respectively; p<0.001 for both upadacitinib arms versus placebo). By week 2, ACR20 response was achieved by more upadacitinib 15 mg- and 30 mg-treated patients (nominal p<0.001). The proportion of patients with ACR20 response continued to increase over time in both treatment groups with the plateau of response observed at week 12 for the upadacitinib 30 mg group, whereas the proportion of patients with ACR20 response in the upadacitinib 15 mg group increased through week 20, approximating the response rate in the 30 mg dose group by the end of the placebo-controlled period. Response rates for upadacitinib 15 mg and upadacitinib 30 mg were 44.9% and 64.8% in the subgroup of patients who had failed >1 biologic DMARD and 55.8% and 66.7% in the subgroup of patients that were on monotherapy; these responses were similar to results in the overall population. Additionally, improvements in ACR50 and ACR70 were observed with both upadacitinib doses versus placebo at week 12. From week 2 through week 24, improvement from baseline in all components of ACR response were observed with upadacitinib 15 mg or 30 mg versus placebo. The efficacy of upadacitinib freebase 15 mg was demonstrated regardless of subgroups evaluated including baseline BMI, baseline hsCRP, and number of prior non-biologic DMARDs (≤1 or >1).

The 15 mg and 30 mg doses of upadacitinib showed greater improvement versus placebo with respect to all key secondary endpoints. By week 12 and through week 24, improvement in psoriasis was observed with both upadacitinib doses versus placebo as measured by PASI 75/90/100 (at week 16, p<0.001 for PASI 75 and nominal p<0.001 for PASI 90/100; nominal p<0.001 for all the other time points) and sIGA 0/1 (p<0.001 at week 16; nominal p<0.001 for weeks 12 and 24). The changes from baseline in SAPS were greater for both upadacitinib arms versus placebo at weeks 16 (p<0.001) and 24 (nominal p<0.001). Improvements in physical function were observed in patients on both doses of upadacitinib versus placebo based on the mean change from baseline in HAQ-DI from week 2 through week 24 (p<0.001 at week 12) and SF-36 PCS at weeks 12 (p<0.001) and 24 (nominal p<0.001). The proportion of HAQ-DI responders (≥0.35 improvement from baseline in HAQ-DI score) at Week 12 was 45% in patients receiving upadacitinib freebase 15 mg QD and 27% in patients receiving placebo. Patients on both doses of upadacitinib reported improvements in fatigue as assessed by FACIT-F versus placebo at weeks 12 (p<0.001) and 24 (nominal p<0.001). Mean improvements from baseline in morning stiffness were observed at weeks 12 and 24 (nominal p<0.001). Resolution of enthesitis using both the LEI and the SPARCC enthesitis index and of dactylitis was reported in a higher proportion of patients on either dose of upadacitinib versus placebo from week 12 to week 24 (nominal p<0.001). A higher proportion of patients receiving either dose of upadacitinib achieved MDA through week 24 versus placebo (p<0001 at week 24 nominal p<0.001 for weeks 12 and 16). Mean changes from baseline in the DAPSA score were greater with both upadacitinib doses versus placebo through week 24 (nominal p<0.001 for all time points).

Health-related quality of life was assessed by SF-36. Patients receiving upadacitinib freebase 15 mg QD experienced significantly greater improvement from baseline in the Physical Component Summary score compared to placebo at Week 12. Greater improvement was also observed in the Mental Component Summary score and all 8 domains of SF-36 (Physical Functioning, Bodily Pain, Vitality, Social Functioning. Role Physical, General Health. Role Emotional, and Mental Health) compared to placebo.

TABLE 26A

Demographics and Characteristics at Baseline

|  | Placebo N = 212 | Upadatitinib 15 mg QD N = 211 | Upadacitinib 30 mg QD N = 218 |
| --- | --- | --- | --- |
| Female, n (%) | 120 (56.6) | 113 (53.6) | 115 (52.8) |
| Age (years) | 54.1 ± 11.5 | 53.0 ± 12.0 | 53.0 ± 11.9 |
| Race, n (%) |  |  |  |
| White | 186 (87.7) | 183 (86.7) | 196 (89.9) |
| Black or African American | 7 (3.3) | 5 (2.4) | 5 (2.3) |
| American Indian/Alaska Native | 0 | 3 (1.4) | 0 |

TABLE 26A-continued

Demographics and Characteristics at Baseline

|  | Placebo<br>N = 212 | Upadatitinib<br>15 mg QD<br>N = 211 | Upadacitinib<br>30 mg QD<br>N = 218 |
|---|---|---|---|
| Native Hawaiian or other Pacific Islander | 1 (0.5) | 1 (0.5) | 1 (0.5) |
| Asian | 17 (8.0) | 19 (9.0) | 16 (7.3) |
| Multiple | 1 (0.5) | 0 | 0 |
| Duration of PsA symptoms (years) | 14.6 ± 11.7 | 12.2 ± 8.8 | 13.3 ± 10.8 |
| Duration since PsA diagnosis (years) | 11.0 ± 10.3 | 9.6 ± 8.4 | 9.7 ± 8.7 |
| Number of prior failed biologic DMARDs, n (%) | | | |
| 0[a] | 18 (8.5) | 16 (7.6) | 17 (7.8) |
| 1 | 135 (63.7) | 126 (59.7) | 130 (59.6) |
| 2 | 35 (16.5) | 35 (16.6) | 46 (21.1) |
| ≥3 | 24 (11.3) | 34 (16.1) | 25 (11.5) |
| Monotherapy, n (%) | 112 (52.8) | 113 (53.6) | 120 (55.0) |
| Any non-biologic DMARD at baseline, n (%) | | | |
| MTX alone | 75 (35.4) | 74 (35.1) | 73 (33.5) |
| MTX + another non-biologic DMARD | 7 (3.3) | 6 (2.8) | 5 (2.3) |
| Non-biologic DMARD other than MTX | 18 (8.5) | 18 (8.5) | 20 (9.2) |
| MTX dose for patients with concomitant MTX alone at baseline (mg/week) | | | |
| Mean | 16.26 | 15.06 | 16.76 |
| Median | 17.50 | 15.00 | 17.50 |
| Steroid use at baseline, n (%) | 24 (11.3) | 22 (10.4) | 13 (6.0) |
| NSAID use at baseline, n (%) | 125 (59.0) | 124 (58.8) | 129 (59.2) |
| RF status positive, n (%) | 6 (2.8) | 11 (5.2) | 8 (3.7) |
| Anti-CCP status positive, n (%) | 10 (4.7) | 7 (3.3) | 5 (2.3) |
| TJC68 | 25.3 ± 17.6 | 24.9 ± 17.3 | 24.2 ± 15.9 |
| SJC66 | 12.0 ± 8.9 | 11.3 ± 8.2 | 12.9 ± 9.4 |
| hs-CRP > ULN[b] (mg/L), n (%) | 121 (57.1) | 126 (59.7) | 128 (58.7) |
| hs-CRP (mg/L) | 10.4 ± 18.5 | 11.2 ± 18.5 | 10.5 ± 17.2 |
| HAQ-DI | 1.23 ± 0.7 | 1.10 ± 0.6 | 1.19 ± 0.7 |
| Patient's assessment of pain (NRS 0-10) | 6.6 ± 2.1 | 6.4 ± 2.1 | 6.2 ± 2.2 |
| BSA-psoriasis ≥3%, n (%) | 131 (61.8) | 130 (61.6) | 131 (60.1) |
| PASI (for baseline BSA-Ps ≥3%) | 11.7 ± 11.4 | 10.1 ± 9.2 | 8.9 ± 9.1 |
| BSA-psoriasis >0%, n (%) | 198 (93.4) | 202 (95.7) | 202 (92.7) |
| BSA-psoriasis (for baseline >0%) | 12.8 ± 18.4 | 10.0 ± 15.7 | 10.0 ± 15.8 |
| sIGA of psoriasis score, n (%) | | | |
| 0 | 17 (8.0) | 9 (4.3) | 16 (7.3) |
| 1 | 32 (15.1) | 31 (14.7) | 38 (17.4) |
| 2 | 59 (27.8) | 82 (38.9) | 78 (35.8) |
| 3 | 88 (41.5) | 78 (37.0) | 77 (35.3) |
| 4 | 16 (7.5) | 11 (5.2) | 9 (4.1) |
| Presence of enthesitis LEI >0, n (%) | 144 (67.9) | 133 (63.0) | 152 (69.7) |
| SPARCC Enthesitis Index >0, n (%) | 173 (81.6) | 172 (81.5) | 179 (82.1) |

TABLE 26A-continued

Demographics and Characteristics at Baseline

|  | Placebo<br>N = 212 | Upadatitinib<br>15 mg QD<br>N = 211 | Upadacitinib<br>30 mg QD<br>N = 218 |
|---|---|---|---|
| Presence of dactylitis (defined as LDI >0), n (%) | 64 (30.2) | 55 (26.1) | 50 (22.9) |
| Morning stiffness score[c] | 5.8 ± 2.5 | 6.0 ± 2.5 | 5.7 ± 2.7 |

Values are mean ± SD unless noted.

[a]Patients with intolerance but not inadequate response to a biologic DMARD.

[b]ULN = 2.87 mg/L;

[c]Morning stiffness score is the mean of BASDAI questions 5 and 6;

[d]Based on investigator opinion.

Anti-CCP, anti-cyclic citrullinated peptide;

ASDAS, Ankylosing Spondylitis Disease Activity Score;

BASDAI, Bath Ankylosing Spondylitis Disease Activity Index;

BSA, body surface area;

DMARD, disease-modifying anti-rheumatic drug;

HAQ-DI, Health Assessment Questionnaire-Disability index;

hs-CRP, high-sensitivity C-reactive protein;

LDI, Leeds Dactylitis-Index;

LEI, Leeds Enthesitis Index;

MTX, methotrexate;

NRS, numeric rating scale;

NSAID, nonsteroidal anti-inflammatory drug;

PAST, Psoriasis Area Severity Index;

Ps, psoriasis;

PsA, psoriatic arthritis;

QD, once daily;

RE, rheumatoid factor;

ULN, upper limit normal;

SD, standard deviation;

sIGA, Static Investigator Global Assessment;

SJC, swollen joint count;

SPARCC, Spondyloarthritis Research Consortium of Canada;

TJC, tender joint count.

TABLE 26B

Primary and Key Secondary Efficacy Endpoints

| Summary Statistics<br>% or LS Mean<br>(P-Value) | Endpoint[a] | PLACEBO<br>N = 212 | UPA<br>15 MG QD<br>N = 211 | UPA<br>30 MG QD<br>N = 218 |
|---|---|---|---|---|
| Primary | ACR20 (Wk 12) | 24.1% | 56.9% (<0.0001*) | 63.8% (<0.0001*) |
| Ranked Key Secondary | 1. HAQ-DI (Wk 12) | −0.10 | −0.30 (<0.0001*) | −0.41 (<0.0001*) |
|  | 2. sIGA (Wk 16)[b] | 9.2% | 36.8% (<0.0001*) | 40.2% (<0.0001*) |
|  | 3. PASI 75 (Wk 16)[c] | 16.0% | 52.1% (<0.0001*) | 56.5% (<0.0001*) |
|  | 4. SF-36 PCS (Wk 12) | 1.62 | 5.2 (<0.0001*) | 7.1 (<0.0001*) |
|  | 5. FACIT-F (Wk 12) | 1.3 | 5.0 (<0.0001*) | 6.1 (<0.0001*) |
|  | 6. MDA (Wk 24) | 2.8% | 25.1% (<0.0001*) | 28.9% (<0.0001) |
|  | 7. SAPS (Wk 16) | −1.5 | −24.4 (<0.0001*) | −29.7 (<0.0001*) |

TABLE 26B-continued

Primary and Key Secondary Efficacy Endpoints

| Summary Statistics % or LS Mean (P-Value) | Endpoint[a] | PLACEBO N = 212 | UPA 15 MG QD N = 211 | UPA 30 MG QD N = 218 |
|---|---|---|---|---|
| Other Key Secondary | ACR50 (Wk 12) | 4.7% | 31.8% (<0.0001) | 37.6% (<0.0001) |
| | ACR70 (Wk 12) | 0.5% | 8.5% (<0.0001) | 16.5% (<0.0001) |
| | ACR20 (Wk 2) | 10.8% | 32.7% (<0.0001) | 33.5% (<0.0001) |

Note:
The nominal p-values are provided in parentheses.
*Statistical significance using graphical multiple testing procedure controlling overall type I error rate at the 0.05 level.
[a]Results for binary endpoints are based on NRI (net reclassification improvement) analysis. Results for minimal disease activity (MDA) at week 24 are based on non-responder imputation with additional rescue handling, where subjects rescued at Week 16 are imputed as non-responders. Results for continuous endpoints are based on mixed model for repeated measures (MMRM) model with fixed effects of treatment, visit, treatment-by-visit interaction, the stratification factor of current DMARD use (yes/no) and baseline measurement.
[b]Summarized for subjects with baseline sIGA ≥2.
[c]Summarized for subjects with baseline BSA affected by psoriasis ≥3%.

TABLE 26C

Additional Efficacy Endpoints for SELECT-PSA2: Summarized for subjects with baseline BSA affected by psoriasis ≥ 3%[a]

| Endpoint | PLACEBO N = 131 | UPA 15 MG QD N = 130 | UPA 30 MG QD N = 131 |
|---|---|---|---|
| PASI 90 (Wk 16) | 8.4% | 34.6% (<0.0001) | 45.0% (<0.0001) |
| PASI 00 (WK 16) | 6.1% | 25.4% (<0.0001) | 32.1% (<0.0001) |

[a]Full analysis set: N(PBO) = 212, N(UPA15) = 211, N(UPA30) = 218

TABLE 26D

Exploratory endpoints

| Endpoint | PLACEBO | UPA 15 MG QD | UPA 30 MG QD |
|---|---|---|---|
| Resolution of enthesitis at Week 12 (defined as LEI = 0) | 20.1% (N = 144) | 39.1% (<0.0001) (N = 133) | 48.0% (<0.0001) (N = 152) |
| Resolution of dactylitis at Week 12 (defined as LDI = 0) | 35.9% (N = 64) | 63.6% (<0.0001) (N = 55) | 76.0% (<0.0001) (N = 50) |

Additional data for ACR20, ACR50, and ACR70 response at Week 24, MDA at Week 12, and resolution of enthesitis (LEI=0), and resolution of dactylitis (LDI=0) at Week 24 is set forth in the below Table.

TABLE 26E

Additional Clinical Responses

| Endpoint | Placebo (N = 212) % | UPA 15 mg QD (N = 211) % |
|---|---|---|
| ACR20 (Wk 24) | 20 | 59 |
| ACR50 (Wk 24) | 9 | 38 |
| ACR70 (Wk 24) | 1 | 19 |
| MDA (Wk 12) | 4 | 17 |
| Enthesitis resolution[a] (Wk 24) | 15 | 43 |
| Dactylitis resolution[b] (Wk 24) | 28 | 58 |

Patients who discontinued randomized treatment or were missing data at week of evaluation were imputed as non-responders in the analyses. For MDA, resolution of enthesitis, and resolution of dactylitis at Week 24, the subjects rescued at Week 16 were imputed as non-responders in the analyses.
[a]In patients with enthesitis at baseline (n = 144 and 133, respectively)
[b]In patients with dactylitis at baseline (n = 64 and 55)

Treatment with upadacitinib freebase 15 mg QD resulted in improvements in individual ACR components, including tender/painful and swollen joint counts, patient and physician global assessments of disease activity, HAQ-DI, pain assessment, and hsCRP compared to placebo. These results are summarized in FIGS. 22N-22S and 22V. Onset of efficacy was seen as early as Week 2 for ACR20 and its components.

Through week 24, the rate of overall treatment-emergent AEs (TEAEs) was higher in the upadacitinib 30 mg arm and rates of serious AEs (SAEs) and TEAEs leading to discontinuation of trial drug were higher with both upadacitinib doses versus placebo.

The most commonly reported TEAEs were upper respiratory tract infection and nasopharyngitis in upadacitinib-treated patients. SAEs were reported in four (1.9%) patients on placebo, twelve (5.7%) on upadacitinib 15 mg, and eighteen (8.3%) on upadacitinib 30 mg. Serious infections occurred in one patient each (0.5%) on placebo and upadacitinib 15 mg and six (2.8%) patients on upadacitinib 30 mg. Pneumonia was the most frequently reported serious infection (one patient on upadacitinib 15 mg and three patients on upadacitinib 30 mg). Up to week 24, treatment-emergent opportunistic infections, excluding tuberculosis and herpes zoster, included one event each of candidiasis of the trachea and oropharyngeal candidiasis, both with upadacitinib 30 mg. Herpes zoster was reported in two, three, and eight patients in the placebo, upadacitinib 15 mg and 30 mg arms, respectively; none of the cases were serious. One patient on upadacitinib 15 mg and two patients on upadacitinib 30 mg had cutaneous disseminated herpes zoster. No cases of herpes zoster with central nervous system involvement were observed. Hepatic disorders were reported in three (1.4%) patients on placebo, four (1.9%) on upadacitinib 15 mg, and eighteen (8.3%) on upadacitinib 30 mg; most were asymptomatic liver enzyme elevations.

Malignancies were reported in three patients in each upadacitinib arm (upadacitinib 15 mg; one basal cell carcinoma, one prostate cancer, one rectal cancer; upadacitinib 30 mg: one rectal adenocarcinoma, one ovarian and endometrial cancer, and one basal cell carcinoma) and none in the placebo arm. The time to event onset for these malignant events was <6 months.

There were no adjudicated gastrointestinal perforations reported through week 24. One case of major adverse cardiovascular event (MACE; 0.5%, non-fatal myocardial infarction) and one case of venous thromboembolic event (VTE; 0.5%; pulmonary embolism) were reported in the upadacitinib 15 mg arm; both patients had at least one risk factor (e.g., obesity, hypertension, or hypercholesterolemia) for MACE or VTE, respectively. Over the 24-week period, one death was reported in the placebo arm related to a motor vehicle accident.

Generally, mean hemoglobin, neutrophil, lymphocyte, and platelet levels remained within normal limits from baseline through week 24 in all treatment arms. There were two patients with Grade 3 decreases in hemoglobin values in the upadacitinib 30 mg arm. Grade 3 decreases in neutrophils were reported in one patient on placebo (0.5%), two patients on upadacitinib 15 mg (1.0%), and four patients on upadacitinib 30 mg (1.8%). No patients had Grade 4 decreases in platelets, leukocytes, neutrophils, or lymphocytes.

Isolated Grade 3 increases in alanine aminotransferase or aspartate aminotransferase were observed in ≤1% of the patients among the treatment arms, and no Grade 4 increases were observed. No Hy's law cases were reported. Grade 3 increases in CPK values were reported in one (0.5%), one (0.5%), and five (2.3%) patients in the placebo, and upadacitinib 15 mg and 30 mg arms, respectively. Grade 4 increases in CPK values were reported in two patients with placebo and one patient with upadacitinib 15 mg. None led to discontinuation of trial drug and there were no events of rhabdomyolysis. Slight mean elevations in low-density lipoprotein cholesterol (LDL-C) and high-density lipoprotein cholesterol (HDL-C) were observed in the upadacitinib arms versus the placebo arm. The ratios of LDL-C:HDL-C and Total cholesterol:HDL-C generally remained constant through week 24.

Upadacitinib as a Promising Therapy for the Treatment of PsA

A review of the placebo corrected data for upadacitinib and the JAK small molecule inhibitor Tofacitinib (approved for the lower (5 mg BID) dose in the treatment of PsA) for key primary and secondary endpoints, while not a head to head comparison, suggests that upadacitinib 15 mg QD and 30 mg QD shows decided promise for the more difficult to achieve endpoints of minimal disease activity (MDA), as well as psoriasis endpoints PASI 75 or PASI 90, as well as certain ACR components (e.g., ACR2/50/70). Furthermore, it was observed that this efficacy, once achieved, was sustained or improved over time.

TABLE 26F

Placebo Corrected Responses (% response/placebo response)

| | Upadacitinib Select PsA2 | | Tofacitinib | | Ixekizumamb | |
| | Upa 15 mg | Upa 30 mg | Opal Beyond | | Spirit P2 | |
| Endpoint | QD Week 12/16/24 | QD Week 12/16/24 | Tofa 5 mg BID Week 12 | Tofa 10 mg BID Week 12 | IXE 80 mg Q4W Week 24 | IXE 80 mg Q2W Week 24 |
|---|---|---|---|---|---|---|
| ACR20 | Week 12 33% (56.9%/24.1%, p ≤ 0.001) | Week 12 40% (63.8%/24.1%, p ≤ 0.001) | 26% (50%/24%, p ≤ 0.001) | 23% (47%/24%, p ≤ 0.001) | 34% (53%/19%, p ≤ 0.001) | 29% (48%/19%, p ≤ 0.001) |
| ACR50 | Week 12 27% (31.8%/4.7%, p ≤ 0.001) | Week 12 37.6% (37.6%/4.7%, p ≤ 0.001) | 15% (30%/15%, p ≤ 0.01) | 13% (28%/15%, p ≤ 0.01) | 30% (35%/5%, p ≤ 0.001) | 28% (33%/5%, p ≤ 0.001) |
| ACR70 | Week 12 8% (8.5%/0.5%, p ≤ 0.001) | Week 12 16% (16.5%/0.5%, p ≤ 0.001) | 7% (17%/10%) | 4% (14%/10%) | 22% (22%/0%, p ≤ 0.001) | 12% (12%/0%, p ≤ 0.001) |
| PASI 75 | Week 16 36% (52%/16%, p ≤ 0.001) | Week 16 41% (57%/16%, p ≤ 0.001) | 7% (21%/14%) | 29% (43%/14%) | 41% (56%/15%, p ≤ 0.001) | 45% (60%/15%, p ≤ 0.001) |
| MDA | Week 24 22% (25%/3%, p ≤ 0.001) | Week 24 26% (29%/3%, p ≤ 0.001) | 8% (23%/15%) | 6% (21%/15%) | 25% (28%/3%, p ≤ 0.001) | 21% (24%/3%, p ≤ 0.001) |

Example 37: Select-PSA1 (Example 35) and Select-PSA2 (Example 36) Clinical Endpoints Primary Endpoints for PsA1 and PsA2 Studies The primary efficacy endpoint is the proportion of subjects achieving American College of Rheumatology (ACR) 20% response rate at Week 12, ACR20 response rate was determined based on a 20% or greater improvement in tender and swollen joint counts (TJC and SJC) and ≥3 of the 5 measures of Patient's Global Assessment of Pain (Pt Pain)

Numerical Rating Scale (NRS), Patient's Global Assessment (PtGA)-Disease Activity Numerical Rating Scale (NRS), Physician Global Assessment (PGA)-Disease Activity Numerical Rating Scale (NRS), Health Assessment Questionnaire—Disability Index (HAQ-D), or High-Sensitivity C Reactive Protein (hs-CRP).

Key Secondary Endpoints for PsA1 and PsA2 Studies

The key multiplicity adjusted secondary efficacy endpoints (each dose of upadacitinib versus placebo unless noted) are:

The proportion of subjects achieving Minimal Disease Activity (MDA) are determined based on subjects fulfilling 5 of 7 outcome measures: TJC≤1; SJC≤1; PASI≤1 or BSA-Ps≤3%; Patient's Global Assessment of Pain (Pt Pain) NRS≤1.5 (0-10 NRS); PtGA-Disease Activity NRS≤2 (0-10 NRS); HAQ-DI score ≤0.5; and LEI≤1. See. e.g., Coates L C, Kavanaugh A, Mease P J, et al; Group for Research and Assessment of Psoriasis and Psoriatic Arthritis (GRAPPA) 2015 treatment recommendations for psoriatic arthritis. Arthritis Rheumatol. 2016; 68(5):1060-71.

TABLE 27A

Study Key Endpoints

| | PsA-1 Study Key Secondary Endpoints | PsA-2 Study Key Secondary Endpoints |
|---|---|---|
| 1 | Change from baseline in Health Assessment Questionnaire-Disability Index (HAQ-DI) at Week 12; | Change from baseline in Health Assessment Questionnaire-Disability Index (HAQ-DI) at Week 12; |
| 2 | Proportion of subjects achieving a static Investigator Global Assessment (sIGA) of Psoriasis of 0 or 1 and at least a 2-point improvement from baseline at Week 16 (for subjects with baseline sIGA ≥ 2); | Proportion of subjects achieving a static Investigator Global Assessment (sIGA) of Psoriasis of 0 or 1 and at least a 2-point improvement from baseline at Week 16 (for subjects with baseline sIGA ≥ 2); |
| 3 | Psoriasis Area Severity Index (PASI) 75 response at Week 16 (for subjects with ≥3% Body Surface Area (BSA) psoriasis at baseline); | Psoriasis Area Severity Index (PASI) 75 response at Week 16 (for subjects with ≥3% Body Surface Area (BSA) psoriasis at baseline); |
| 4 | Change from baseline in Sharp/van der Heijde Score (SHS) at Week 24; | |
| 5 | Proportion of subjects achieving MDA (Minimal Disease Activity) at Week 24; | Proportion of subjects achieving MDA (Minimal Disease Activity) at Week 24; |
| 6 | Change from baseline in Leeds Enthesitis Index (LEI) at Week 24; | |
| 7 | Change from baseline in Leeds Dactylitis Index (LDI) at Week 24; | |
| 8 | American College of Rheumatology (ACR) 20 response rate at Week 12 (non-inferiority of upadacitinib vs adalimumab); | |
| 9 | Change from baseline in 36-item Short Form Health Survey (SF-36) at Week 12; | Change from baseline in 36-Item Short Form Health Survey (SF-36) at Week 12; |
| 10 | American College of Rheumatology (ACR) 20 response rate at Week 12 (superiority of upadacitinib vs. adalimumab); | |
| 11 | Change from baseline in Patient's Global Assessment of Pain Numerical Rating Scale (NRS) at Week 12 (superiority of upadacitinib vs. adalimumab); | |
| 12 | Change from baseline in Health Assessment Questionnaire-Disability Index (HAQ-DI) at Week 12 (superiority of upadacitinib vs. adalimumab); | |
| 13 | Change from baseline in Functional Assessment of Chronic Illness Therapy-Fatigue (FACIT-Fatigue) Questionnaire at Week 12; and | Change from baseline in Functional Assessment of Chronic Illness Therapy-Fatigue (FACIT-Fatigue) Questionnaire at Week 12.; and |
| 14 | Change from baseline in Self-Assessment of Psoriasis Symptoms (SAPS) Questionnaire at Week 16. | Change from baseline in Self-Assessment of Psoriasis Symptoms (SAPS) Questionnaire at Week 16 |

Additional key secondary efficacy endpoints (each dose of upadacitinib versus placebo) are:

TABLE 27B

Additional Key Secondary Efficacy Endpoints

| | PsA-1 Study Additional Key Secondary Endpoints | PsA-2 Study Additional Key Secondary Endpoints |
|---|---|---|
| 1 | ACR50/70 response at Week 12; | ACR50/70 response at Week 12; |
| 2 | ACR20 response at Week 2 | ACR20 response at Week 2 |

ACR20/50/70 response rates are determined based on 20%/50%/70% or greater improvement in TJC and SJC and ≥3 of the 5 measures of Patient's Global Assessment of Pain (Pt Pain) NRS, PtGA-Disease Activity NRS, PGA-Disease Activity NRS, HAQ-DI, or hs-CRP.

Additional Secondary Endpoints for PsA1 and PsA2 Studies

The following outcome measures were assessed in subjects treated with upadacitinib as compared to placebo and adalimumab at scheduled time points other than those specified for the primary and key secondary variables:

TABLE 27C

| Additional Secondary Endpoints | |
|---|---|
| PsA-1 Study Additional Secondary Endpoints | PsA-2 Study Additional Secondary Endpoints |
| 1. Proportion of subjects with no radiographic progression (defined as change from baseline in SHS ≤ 0); | |
| 2. Change from baseline in individual components of ACR response: (i) Change from baseline in Tender Joint Count (TJC) (0-68); (ii) Change from baseline in Swollen Joint Count (SJC) (0-66); (iii) Change from baseline in Physician Global Assessment (PGA)-Disease Activity Numerical Rating Scale (NRS); (iv) Change from baseline in Patient's Global Assessment (PtGA)-Disease Activity Numerical Rating Scale (NRS); (v) Change from baseline in Patient's Global Assessment of Pain Numerical Rating Scale (NRS); (vi) Change from baseline in Health Assessment Questionnaire-Disability index (HAQ-DI); (vii) Change from baseline in High-Sensitivity C Reactive Protein (hs-CRP); | Change from baseline in individual components of ACR response: (i) Change from baseline in Tender Joint Count (TJC) (0-68); (ii) Change from baseline in Swollen Joint Count (SJC) (0-66); (iii) Change from baseline in Physician Global Assessment (PGA)-Disease Activity Numerical Rating Scale (NRS); (iv) Change from baseline in Patient's Global Assessment (PtGA)-Disease Activity Numerical Rating Scale (NRS); (v) Change from baseline in Patient's Global Assessment of Pain Numerical Rating Scale (NRS); (vi) Change from baseline in Health Assessment Questionnaire-Disability Index (HAQ-DI); (vii) Change from baseline in High-Sensitivity C Reactive Protein (hs-CRP); |
| 3. ACR 20/50/70 response rates; | ACR 20/50/70 response rates; |
| 4. Change from baseline in Leeds Dactylitis Index (LDI); | Change from baseline in Leeds Dactylitis Index (LDI); |
| 5. Change from baseline in dactylitis count; | Change from baseline in dactylitis count; |
| 6. Proportion of subjects with resolution of dactylitis; | Proportion of subjects with resolution of dactylitis; |
| 7. Change from baseline in Leeds Enthesitis Index (LEI); | Change from baseline in Leeds Enthesitis Index (LEI); |
| 8. Proportion of subjects with resolution of enthesitis sites included in the Leeds Enthesitis Index (LEI); | Proportion of subjects with resolution of enthesitis sites included in the Leeds Enthesitis Index (LEI); |
| 9. Change from baseline in Spondyloarthritis Research Consortium of Canada (SPARCC) Enthesitis Index; | Change from baseline in Spondyloarthritis Research Consortium of Canada (SPARCC) Enthesitis Index; |
| 10. Proportion of subjects with resolution of enthesitis sites included in the Spondyloarthritis Research Consortium of Canada (SPARCC) Enthesitis Index; | Proportion of subjects with resolution of enthesitis sites included in the Spondyloarthritis Research Consortium of Canada (SPARCC) Enthesitis Index; |
| 11. Change from baseline in total enthesitis count; | Change from baseline in total enthesitis count; |
| 12. Proportion of subjects with resolution of enthesitis; | Proportion of subjects with resolution of enthesitis; |
| 13. PASI 75/90/100 response rates (for subjects with ≥3% Body Surface Area (BSA) psoriasis at baseline); | PASI 75/90/100 response rates (for subjects with ≥3% Body Surface Area (BSA) psoriasis at baseline); |
| 14. Proportion of subjects achieving a static Investigator Global Assessment of Psoriasis (sIGA) score of 0 or 1 and at least a 2-point improvement from baseline; | Proportion of subjects achieving a static Investigator Global Assessment of Psoriasis (sIGA) score of 0 or 1 and at least a 2-point improvement from baseline; |
| 15. BSA-Ps; | BSA-Ps. |
| 16. Change from baseline in Modified Psoriatic Arthritis Response Criteria (PsARC); | Change from baseline in Modified Psoriatic Arthritis Response Criteria (PsARC); |
| 17. Change from baseline in Disease Activity Score 28 (DAS28) (CRP); | Change from baseline in Disease Activity Score 28 (DAS28) (CRP); |
| 18. Change from baseline in DAS28 (ESR); | Change from baseline in DAS28 (ESR); |
| 19. Change from baseline in PsA Disease Activity Score (PASDAS); | Change from baseline in PsA Disease Activity Score (PASDAS); |
| 20. Change from baseline in Disease Activity In Psoriatic Arthritis (DAPSA) score; | Change from baseline in Disease Activity In Psoriatic Arthritis (DAPSA) score; |
| 21. Change from baseline in Short Form 36 (SF-36) Health Questionnaire; | Change from baseline in Short Form 36 (SF-36) Health Questionnaire; |
| 22. Change from baseline in Functional Assessment of Chronic Illness Therapy (FACIT)-Fatigue Questionnaire; | Change from baseline in Functional Assessment of Chronic Illness Therapy (FACIT)-Fatigue Questionnaire; |
| 23. Change from baseline in EuroQol-5-Dimensions-5-Levels (EQ-5D-5L) Questionnaire; | Change from baseline in EuroQol-5-Dimensions-5-Levels (EQ-5D-5L) Questionnaire; |

TABLE 27C-continued

Additional Secondary Endpoints

| PsA-1 Study Additional Secondary Endpoints | PsA-2 Study Additional Secondary Endpoints |
|---|---|
| 24 Change from baseline in Work Productivity and Activity Impairment (WPAI) Questionnaire; | Change from baseline in Work Productivity and Activity Impairment (WPM) Questionnaire; |
| 25 Change from baseline in Health Resource Utilization (HRU) Questionnaire; | Change from baseline in Health Resource Utilization (HRU) Questionnaire; |
| 26 Change from baseline in Self-Assessment of Psoriasis Symptoms (SAPS) Questionnaire; | Change from baseline in Self-Assessment of Psoriasis Symptoms (SAPS) Questionnaire; |
| 27 Change from baseline in Bath Ankylosing Spondylitis Disease Activity Index (BASDAI); | Change from baseline in Bath Ankylosing Spondylitis Disease Activity Index (BASDAI); |
| 28 Bath Ankylosing Spondylitis Disease Activity Index (BASDAI) 50 response rates; | Bath Ankylosing Spondylitis Disease Activity Index (BASDAI) 50 response rates; |
| 29 Change from baseline in Morning stiffness (mean of BASDAI Questions 5 and 6); | Change from baseline in Morning stiffness (mean of BASDAI Questions 5 and 6); |
| 30 Change from baseline in Ankylosing Spondylitis Disease Activity Score (ASDAS); | Change from baseline in Ankylosing Spondylitis Disease Activity Score (ASDAS); |
| 21 Proportion of subjects with Ankylosing Spondylitis Disease Activity Score (ASDAS) Inactive Disease; | Proportion of subjects with Ankylosing Spondylitis Disease Activity Score (ASDAS) Inactive Disease; |
| 32 Proportion of subjects with Ankylosing Spondylitis Disease Activity Score (ASDAS) Major Improvement; | Proportion of subjects with Ankylosing Spondylitis Disease Activity Score (ASDAS) Major Improvement; |
| 33 Proportion of subjects with Ankylosing Spondylitis Disease Activity Score (ASDAS) Clinically important Improvement; | Proportion of subjects with Ankylosing Spondylitis Disease Activity Score (ASDAS) Clinically Important Improvement; |
| 34 Proportion of subjects achieving a clinically meaningful improvement in Health Assessment Questionnaire-Disability Index (HAQ-DI) (≥0.35). | Proportion of subjects achieving a clinically meaningful improvement in Health Assessment Questionnaire-Disability Index (HAQ-DI) (≥0.35). |

Example 38: A Phase 3 Randomized, Placebo-Controlled, Double-Blind Program to Evaluate Efficacy and Safety of Upadacitinib in Adult Subjects with Axial Spondyloarthritis (Select Axis 2)

The safety and efficacy data from the Phase 2/3 study (as described in Examples 2) show a favorable benefit:risk profile for upadacitinib and support the continued investigation of upadacitinib in adult subjects with active axSpA who had an inadequate response to biologic disease-modifying anti-rheumatic drug therapy (bDMARD-IR) (Study 1) and in adult subjects with active nr-axSpA (Study 2).

The Phase 3 clinical study plan is set forth in FIG. 2.

Adult Subjects with Active Ankylosing Spondylitis (AS) Who had an Inadequate Response to Biologic Disease-Modifying Anti-Rheumatic Drug Therapy (bDMARD-IR) (Study 1)

To evaluate the safety, tolerability, and efficacy of upadacitinib compared with placebo on reduction of signs and symptoms in adult subjects with active ankylosing spondylitis (AS) who had an inadequate response to biologic disease-modifying anti-rheumatic drug therapy (bDMARD-IR).

Study 1 (main study) is comprised of a 35-day Screening Period; a 14-week randomized, double-blind, parallel-group, placebo-controlled period (the Double-Blind Period); a 90-week open-label, long-term extension period (the Open-Label Extension Period); and a 30-day Follow-Up Visit (F/U Visit). Group 1: upadacitinib free base 15 mg QD; Group 2: placebo QD. Subjects in the placebo group will be switched to upadacitinib free base 15 mg QD at Week 14 in the Open-Label Extension Period for Study 1.

Eligible subjects will be adult females and males who are at least 18 years of age at Screening with a clinical diagnosis of AS, meet the modified New York Criteria for AS, and are without total spinal ankylosis (Study 1, bDMARD-IR AS). Eligible study subjects must have a Bath Ankylosing Spondylitis Disease Activity Index score ≥4 and a Patient's Assessment of Total Back Pain score (Total Back Pain score)≥4 based on a 0-10 numerical rating scale at the Screening and Baseline Visits.

For Study 1 (bDMARD-IR AS), subjects with prior exposure to 1 biologic disease-modifying anti-rheumatic drug (bDMARD) (either 1 tumor necrosis factor [TNF] inhibitor or 1 interleukin [IL]-7 inhibitor) may be enrolled, and the subject must have discontinued the bDMARD due to either intolerance or lack of efficacy. Prior exposure to a $2^{nd}$ bDMARD is allowed for no more than 30% of subjects if the reason for discontinuation was not due to lack of efficacy. Subjects who have had lack of efficacy to both a TNF inhibitor and IL-17 inhibitor are not eligible.

Study 1 Primary Endpoint

The primary endpoint is the proportion of subjects achieving an ASAS40 response at Week 14. Secondary endpoints for Study 1 are described below.

Adult Subjects with Active Non-Radiographic Axial Spondyloarthritis (Nr-axSpA) (Study 2)

To evaluate the safety, tolerability, and efficacy of upadacitinib compared with placebo on reduction of signs and symptoms in adult subjects with active non-radiographic axial spondyloarthritis (nr-axSpA).

Study 2 (nr-axSpA) is comprised of a 35-day Screening Period; a 52-week randomized, double-blind, parallel-group, placebo-controlled period (the Double-Blind Period); a 52-week open-label, long-term extension period (the Open-Label Extension Period); and a 30-day F/U Visit. Group 1: upadacitinib free base 15 mg QD; Group 2: placebo QD.

Subjects in the placebo group will be switched to upadacitinib free base 15 mg QD at Week 52 in the Open-Label Extension Period for Study 2 (nr-axSpA).

Eligible subjects will be adult females and males who are at least 18 years of age at Screening with a clinical diagnosis of nr-axSpA fulfilling the 2009 ASAS classification criteria for axSpA but not meeting the radiologic criterion of the modified New York criteria for AS and have objective signs of active inflammation on magnetic resonance imaging of sacroiliac joints or based on high sensitivity C-reactive protein >upper limit of normal (Study 2, nr-axSpA). Eligible study subjects must have a Bath Ankylosing Spondylitis Disease Activity Index score ≥4 and a Patient's Assessment of Total Back Pain score (Total Back Pain score)≥4 based on a 0-10 numerical rating scale at the Screening and Baseline Visits. Subject must have objective signs of active inflammation on MRI of SI joints or hsCRP>ULN at screening.

For Study 2 (nr-axSpA), subjects with prior failure of nonsteroidal anti-inflammatory drugs (NSAIDs) may be enrolled, and prior treatment with at most 1 bDMARD (either 1 TNF inhibitor or 1 IL-17 inhibitor) is allowed in a subset of subjects (at least 25%, but not exceeding 35% of total enrolled subjects). Subjects with prior exposure to 1 bDMARD (either 1 tumor necrosis factor [TNF] inhibitor or 1 interleukin [IL]-17 inhibitor) may be enrolled, and the subject must have discontinued the bDMARD due to either intolerance or lack of efficacy. Prior exposure to a $2^{nd}$ bDMARD is allowed for no more than 30% of subjects if the reason for discontinuation was not due to lack of efficacy. Subjects who have had lack of efficacy to both a TNF inhibitor and IL-17 inhibitor are not eligible.

Study 2 Primary Endpoints

The primary endpoint for European Union [EU]/European Medicines Agency [EMA] regulatory purposes is the proportion of subjects achieving an ASAS40 response at Week 14.

The primary endpoint for US/Food and Drug Administration [FDA] regulatory purposes is the proportion of subjects achieving an ASAS40 response at Week 52.

Secondary endpoints for Study 2 are described below.

Study 1: bDMARD-IR AS Specific Criteria
1. Subject must have a clinical diagnosis of AS and subjects must meet the modified New York criteria for AS.
2. Subject must not have total spinal ankylosis.
3. Subjects with prior exposure to 1 bDMARD (either 1 tumor necrosis factor [TNF] inhibitor or 1 interleukin [IL]-17 inhibitor) may be enrolled, and the subject must have discontinued the bDMARD due to either intolerance or lack of efficacy. Prior exposure to a $2^{nd}$ bDMARD is allowed for no more than 30% of subjects if the reason for discontinuation was not due to lack of efficacy. Subjects who have had lack of efficacy to both a TNF inhibitor and IL-17 inhibitor are not eligible.

Study 2: nr-axSpA-Specific Criteria
1. Subject must have a clinical diagnosis of nr-axSpA fulfilling the 2009 ASAS classification criteria for axSpA but not meeting the radiologic criterion of the modified New York criteria for AS.
2. Subjects with or without prior exposure to a bDMARD may be enrolled.
   For the subset of subjects with prior bDMARD exposure (at least 25%, but not exceeding 35% of total enrolled subjects), prior treatment with at most 1 bDMARD (either 1 TNF inhibitor or 1 IL-17 inhibitor) is allowed, and the subject must have discontinued the bDMARD due to either intolerance or lack of efficacy. Subjects who have had lack of efficacy to both a TNF inhibitor and IL-17 inhibitor are not eligible.
3. Subject must have objective signs of active inflammation on MRI of SI joints or hsCRP>ULN at screening.

The Following Eligibility Criteria are Applicable for Study 1 and Study 2:
1. Subject must be an adult male or female, at least 18 years of age at Screening.
2. Subject must meet the following scores at Screening and Baseline Visits: BASDAI score ≥4 and Total Back Pain score ≥4 based on a 0-10 NRS.
3. Subject has had an inadequate response to at least 2 NSAIDs over an at least 4-week period in total at maximum recommended or tolerated doses, or subject has an intolerance to or contraindication for NSAIDs.
4. The washout period for bDMARDs prior to the first dose of study drug is specified below:
   ≥4 weeks for etanercept;
   ≥8 weeks for adalimumab, infliximab, certolizumab, golimumab, abatacept, tocilizumab, and ixekizumab;
   ≥12 weeks for ustekinumab;
   ≥16 weeks for secukinumab;
   ≥1 year for rituximab OR≥6 months if B cells have returned to pre-treatment level or normal reference range (central lab) if pre-treatment levels are not available;
   ≥12 weeks or at least 5 times the mean terminal elimination half-life, whichever is longer, for other bDMARDs.
5. If entering the study on the following concomitant csDMARDs (MTX (≤25 mg/week); or Sulfasalazine (SSZ) (≤3 g/day); or Hydroxychloroquine (≤400 mg/day); or Chloroquine (≤400 mg/day); or Leflunomide (≤20 mg/day); or Apremilast (≤60 mg/day)), subject must be on a stable dose as indicated below for at least 28 days prior to the Baseline Visit. A combination of up to 2 background csDMARDs is allowed EXCEPT the combination of methotrexate (MTX) and leflunomide.
6. If entering the study on concomitant oral corticosteroids, subject must be on a stable dose of prednisone (≤10 mg/day) or oral corticosteroid equivalent for at least 14 days prior to the Baseline Visit.
7. If entering the study on concomitant NSAIDs, tramadol, combination of acetaminophen/paracetamol and codeine or combination of acetaminophen/paracetamol and hydrocodone, and/or non-opioid analgesics, subject must be on stable dose(s) for at least 14 days prior to the Baseline Visit.
8. Subject must not have been exposed to any JAK inhibitor.
9. Subject must not have used the following prohibited concomitant treatments within the specified timeframe prior to Baseline Visit:
   Intra-articular joint injections, spinal/paraspinal injection(s), or parenteral administration of corticosteroids within 28 days prior to the Baseline Visit. Inhaled or topical corticosteroids are allowed;

Any other csDMARDs (other than those allowed per eligibility criterion), including thalidomide, within 28 days or 5 half-lives (whichever is longer) of the drug prior to the Baseline Visit;

Opioid analgesics (except for combination of acetaminophen/paracetamol and codeine or combination of acetaminophen/paracetamol and hydrocodone which are allowed) within 14 days prior to the Baseline Visit.

10. Subject must not have received a live vaccine within 28 days (or longer if required locally) prior to the first dose of study drug or have expected need of live vaccination during study participation including at least 30 days (or longer if required locally) after the last dose of study drug.

11. Subject must have no systemic use of known strong cytochrome P450 3A (CYP3A) inhibitors from Screening through the end of study drug administration or strong CYP3A inducers 30 days prior to study drug administration through the end of study drug administration. Subjects must not use herbal therapies or other traditional medicines with unknown effects on CYP3A from Screening through the end of study drug administration.

12. Subject must not have been treated with any investigational drug of chemical or biologic nature within a minimum of 30 days or 5 half-lives of the drug (whichever is longer) prior to the first dose of study drug or is currently enrolled in another interventional study.

13. Subject must not have a history of an allergic reaction or significant sensitivity to constituents of the study drug (and its excipients) and/or other products in the same class.

Study 1 and Study 2 Secondary Endpoints

The key multiplicity-controlled secondary endpoints at Week 14 are as follows:

TABLE 28A

| | Study 1 (active AS) | Study 2 (active nr-axSpA) |
|---|---|---|
| 1 | Change from Baseline in Ankylosing Spondylitis Disease Activity Score (ASDAS) at Week 14 | Change from Baseline in Ankylosing Spondylitis Disease Activity Score (ASDAS) at Week 14 |
| 2 | Change from Baseline in magnetic resonance imaging (MRI) Spondyloarthritis Research Consortium of Canada (SPARCC) score (spine) at Week 14 (MRI-Spine SPARCC) | Change from Baseline in magnetic resonance imaging (MRI) Spondyloarthritis Research Consortium of Canada (SPARCC) score (SI joints) at Week 14 (MRI-Joints SPARCC) |
| 3 | Proportion of subjects with ASAS partial remission (PR) (an absolute score of ≤ 2 units for each of the 4 domains identified in ASAS40) at Week 14 | Proportion of subjects with ASAS partial remission (PR) On absolute score of ≤ 2 units for each of the 4 domains identified in ASAS40) at Week 14 |
| 4 | Proportion of subjects with Bath Ankylosing Spondylitis Disease Activity Index (BASDAI) 50 response at Week 14 | Proportion of subjects with Bath Ankylosing Spondylitis Disease Activity Index (BASDAI) 50 response at Week 14 |
| 5 | Change from Baseline in Bath Ankylosing Spondylitis Functional Index (BASFI) at Week 14 (Function) | Change from Baseline in Bath Ankylosing at Spondylitis Functional Index (BASFI) at Week 14 (Function) |
| 6 | Change from Baseline in Ankylosing Spondylitis Quality of Life (ASQoL) at Week 14 | Change from Baseline in Ankylosing Spondylitis Quality of Life (ASQoL) at Week 14 |
| 7 | Change from Baseline in ASAS Health Index (HI) at Week 14 | Change from Baseline in ASAS Health Index (HI) at Week 14 |
| 8 | Change from Baseline in Maastricht Ankylosing Spondylitis Enthesitis Score (MASES) at Week 14 (Enthesitis) | Change from Baseline in Maastricht Ankylosing Spondylitis Enthesitis Score (MASES) at Week 14 (Enthesitis) |
| 9 | Change from Baseline in Linear Bath Ankylosing Spondylitis Metrology Index (BASMI$_{lin}$) at Week 14 (Mobility) | Change from Baseline in Linear Bath Ankylosing Spondylitis Metrology Index (BASMI$_{lin}$) at Week 14 (Mobility) |

Additional key secondary endpoints at Week 14 include:

TABLE 28B

| | Study 1 (active AS) | Study 2 (active nr-axSpA) |
|---|---|---|
| 1 | Proportion of subjects with ASAS20 response at Week 14 | Proportion of subjects with ASAS20 response at Week 14 |
| 2 | Change from Baseline in MRI SPARCC score (SI joints) at Week 14 | Change from Baseline in MRI SPARCC score (spine) at Week 14 |
| 3 | | Proportion of subjects rescued between Week 24 and Week 52 |

Additional Study 1 and Study 2 Endpoints

Additional endpoints are the following measurements assessed at time points other than those specified for the primary and key secondary variables are as follows:

TABLE 28C

| | Study 1 (active AS) | Study 2 (active nr-axSpA) |
|---|---|---|
| 1 | Proportion of subjects with ASAS20 response | Proportion of subjects with ASAS20 response |
| 2 | Proportion of subjects with ASAS40 response | Proportion of subjects with ASAS40 response |
| 3 | Proportion of subjects with ASAS PR | Proportion of subjects with ASAS PR |
| 4 | Proportion of subjects with ASDAS Inactive Disease (ASDAS score < 1.3) | Proportion of subjects with ASDAS Inactive Disease (ASDAS score < 1.3) |
| 5 | Proportion of subjects with ASDAS Low Disease (ASDAS score < 2.1) | Proportion of subjects with ASDAS Low Disease (ASDAS score < 2.1) |
| 6 | Proportion of subjects with ASDAS Major Improvement (a change from Baseline of ≤−2.0) | Proportion of subjects with ASDAS Major Improvement (a change from Baseline of ≤−2.0) |
| 7 | Proportion of subjects with ASDAS Clinically Important Improvement (a change from Baseline of ≤−1.1) | Proportion of subjects with ASDAS Clinically Important Improvement (a change from Baseline of ≤−1.1) |
| 8 | Proportion of subjects with Discontinuation of opioids among subjects with opioid use at Baseline | Proportion of subjects with Discontinuation of opioids among subjects with opioid use at Baseline |
| 9 | Change from Baseline in ASAS HI | Change from Baseline in ASAS HI |
| 10 | Change from Baseline in ASDAS | Change from Baseline in ASDAS |
| 11 | Change from Baseline in ASQoL | Change from Baseline in ASQoL |
| 12 | Change from Baseline in BASDAI and BASDAI Questions including mean of question 5 and 6 of the BASDAI | Change from Baseline in BASDAI and BASDAI Questions including mean of question 5 and 6 of the BASDAI |
| 13 | Change from Baseline in BASFI | Change from Baseline in BASFI |
| 14 | Change from Baseline in BASMIlin | Change from Baseline in $BASMI_{lin}$ |
| 15 | Change from Baseline in High sensitivity C-reactive protein (hsCRP) | Change from Baseline in hsCRP |
| 16 | Change from Baseline in Functional Assessment of Chronic Illness Therapy-Fatigue (FACIT-F) | Change from Baseline in FACIT-F |
| 17 | Change from Baseline in EuroQoL-5D-5L (EQ-5D-5L) | Change from Baseline in EQ-5D-5L |
| 18 | Change from Baseline in MASES | Change from Baseline in MASES |
| 19 | Change from Baseline in Modified Stoke Ankylosing Spondylitis Spine Score (mSASSS) with conventional radiograph | Change from Baseline in mSASSS with conventional radiograph |
| 20 | Change from Baseline in MRI SPARCC score of SI joints | Change from Baseline in MRI SPARCC score of SI joints |
| 21 | Change from Baseline in MRI SPARCC score of spine | Change from Baseline in MRI SPARCC score of spine |
| 22 | Change from Baseline in Patient's Assessment of Total Back Pain (Total Back Pain score); | Change from Baseline in Total Back Pain; |
| 23 | Change from Baseline in Patient's Assessment of Nocturnal Back Pain (Nocturnal Back Pain) | Change from Baseline in Nocturnal Back Pain |
| 24 | Change from Baseline in Patient's Global Assessment of Pain (Pain) | Change from Baseline in Pain; |
| 25 | Change from Baseline in Physician's Global Assessment of Disease Activity (PGA) | Change from Baseline in PGA; |
| 26 | Change from Baseline in Patient's Global Assessment of Disease Activity (PtGA) | Change from Baseline in PtGA |
| 27 | Change from Baseline in 36-Item Short Form Health Survey (SF-36) | Change from Baseline in SF-36 |
| 28 | Change from Baseline in Tender joint count (TJC) and swollen joint count (SJC); | Change from Baseline in TJC and SJC |
| 29 | Change from Baseline in Work Productivity and Activity Impairment (WPAI) | Change from Baseline in WPAI |
| 30 | Change from Baseline in Change of NSAID score | Change from Baseline in Change of NSAID score |
| 31 | Change from Baseline in Physical Activity Assessment (step count, physical activity, and spinal range of motion tasks) as measured by a wearable device (in countries where the digital health technology device is approved) | |

U.S. Patent Application Publication Nos. 2017/0129902 and 2021/0228575 are incorporated by reference in their entirety and for all purposes.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

The foregoing has been described of certain non-limiting embodiments of the present disclosure. Those of ordinary skill in the art will appreciate that various changes and modifications to this description may be made without departing from the spirit or scope of the present disclosure, as defined in the following claims.

What is claimed is:

1. A method of treating a human patient having active psoriatic arthritis, comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg.

2. The method of claim 1, wherein the patient is an adult patient.

3. The method of claim 1, wherein the patient has had an inadequate response or intolerance to one or more disease-modifying antirheumatic drugs.

4. The method of claim 1, wherein the patient has had an inadequate response or intolerance to methotrexate.

5. The method of claim 1, wherein the patient has had an inadequate response or intolerance to an anti-TNF biologic agent.

6. The method of claim 1, wherein the therapeutically effective amount of Compound 1 is administered as 15.4 mg of Freebase Hydrate Form C.

7. A method of treating a human patient having active psoriatic arthritis, comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg, and wherein the method results in an ACR70 response at 12 weeks after the first daily administration.

8. The method of claim 7, wherein the patient is an adult patient.

9. The method of claim 7, wherein the patient has had an inadequate response or intolerance to one or more disease-modifying antirheumatic drugs.

10. The method of claim 7, wherein the patient has had an inadequate response or intolerance to methotrexate.

11. The method of claim 7, wherein the patient has had an inadequate response or intolerance to an anti-TNF biologic agent.

12. The method of claim 7, wherein the therapeutically effective amount of Compound 1 is administered as 15.4 mg of Freebase Hydrate Form C.

13. A method of treating a human patient having active psoriatic arthritis, comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg, and wherein the method results in an ACR50 response at 12 weeks after the first daily administration.

14. The method of claim 13, wherein the patient is an adult patient.

15. The method of claim 13, wherein the patient has had an inadequate response or intolerance to one or more disease-modifying antirheumatic drugs.

16. The method of claim 13, wherein the patient has had an inadequate response or intolerance to methotrexate.

17. The method of claim 13, wherein the patient has had an inadequate response or intolerance to an anti-TNF biologic agent.

18. The method of claim 13, wherein the therapeutically effective amount of Compound 1 is administered as 15.4 mg of Freebase Hydrate Form C.

19. A method of treating a human patient having active psoriatic arthritis, comprising orally administering once daily to the patient a tablet comprising a therapeutically effective amount of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1), wherein the therapeutically effective amount is 15 mg, and wherein the method results in an ACR20 response at 12 weeks after the first daily administration.

20. The method of claim 19, wherein the patient is an adult patient.

21. The method of claim 19, wherein the patient has had an inadequate response or intolerance to one or more disease-modifying antirheumatic drugs.

22. The method of claim 19, wherein the patient has had an inadequate response or intolerance to methotrexate.

23. The method of claim 19, wherein the patient has had an inadequate response or intolerance to an anti-TNF biologic agent.

24. The method of claim 19, wherein the therapeutically effective amount of Compound 1 is administered as 15.4 mg of Freebase Hydrate Form C.

* * * * *